(12) United States Patent
Jin et al.

(10) Patent No.: US 11,541,051 B2
(45) Date of Patent: Jan. 3, 2023

(54) COMPOSITIONS AND METHODS FOR TREATING CDK4/6-MEDIATED CANCER

(71) Applicant: Icahn School of Medicine at Mount Sinai, New York, NY (US)

(72) Inventors: Jian Jin, New York, NY (US); Xiaobao Yang, New York, NY (US); Jing Liu, Oradell, NJ (US); Yan Xiong, New York, NY (US); Poulikos Poulikakos, New York, NY (US); Zoi Karoulia, New York, NY (US); Xuewei Wu, New York, NY (US); Tamer Ahmed, Edison, NJ (US)

(73) Assignee: Icahn School of Medicine at Mount Sinai, New York, NY (US)

( * ) Notice: Subject to any disclaimer, the term of this patent is extended or adjusted under 35 U.S.C. 154(b) by 0 days.

(21) Appl. No.: 16/467,888

(22) PCT Filed: Dec. 7, 2017

(86) PCT No.: PCT/US2017/065027
§ 371 (c)(1),
(2) Date: Jun. 7, 2019

(87) PCT Pub. No.: WO2018/106870
PCT Pub. Date: Jun. 14, 2018

(65) Prior Publication Data
US 2019/0336503 A1    Nov. 7, 2019

Related U.S. Application Data

(60) Provisional application No. 62/431,806, filed on Dec. 8, 2016.

(51) Int. Cl.
| | | |
|---|---|---|
| *A61K 31/506* | (2006.01) | |
| *A61K 31/519* | (2006.01) | |
| *A61K 45/06* | (2006.01) | |
| *A61K 47/55* | (2017.01) | |
| *A61P 35/00* | (2006.01) | |
| *C07D 471/04* | (2006.01) | |

(52) U.S. Cl.
CPC .......... *A61K 31/506* (2013.01); *A61K 31/519* (2013.01); *A61K 45/06* (2013.01); *A61K 47/55* (2017.08); *A61P 35/00* (2018.01)

(58) Field of Classification Search
CPC .... A61K 31/506; A61K 31/519; A61K 45/06; A61K 47/55; C07D 471/04; A61P 35/00
See application file for complete search history.

(56) References Cited

U.S. PATENT DOCUMENTS

| | | |
|---|---|---|
| 5,691,147 A | 10/1997 | Draetta et al. |
| 8,377,937 B2 | 2/2013 | Bencsik et al. |
| 8,648,096 B2 | 2/2014 | Muller et al. |
| 9,809,603 B1 | 11/2017 | Jacques |
| 9,822,094 B2 | 11/2017 | Man et al. |
| 2002/0098161 A1 | 7/2002 | Uhrich |
| 2004/0063773 A1 | 4/2004 | Tang et al. |
| 2011/0172107 A1 | 7/2011 | Katz et al. |
| 2011/0196150 A1 | 8/2011 | Man et al. |
| 2014/0031325 A1 | 1/2014 | Bartlett et al. |
| 2015/0119435 A1 | 4/2015 | Crews et al. |
| 2015/0274738 A1 | 10/2015 | Gray et al. |
| 2015/0291562 A1 | 10/2015 | Crew et al. |
| 2016/0045504 A1 | 2/2016 | Grembecka et al. |
| 2017/0008904 A1 | 1/2017 | Crew et al. |
| 2017/0114098 A1 | 4/2017 | Aivado et al. |
| 2017/0283807 A1 | 10/2017 | Mounir et al. |
| 2018/0072741 A1 | 3/2018 | Vechorkin et al. |
| 2018/0086767 A1 | 3/2018 | Fesik et al. |
| 2018/0134684 A1 | 5/2018 | Bradner et al. |
| 2018/0186800 A1 | 7/2018 | Yamamoto et al. |
| 2019/0092768 A1* | 3/2019 | Gray .................... C07D 471/04 |
| 2019/0255041 A1 | 8/2019 | Jin et al. |
| 2019/0367525 A1 | 12/2019 | Ioannidis et al. |
| 2020/0338070 A1 | 10/2020 | Jin et al. |
| 2020/0399266 A1 | 12/2020 | Jin et al. |
| 2021/0261538 A1 | 8/2021 | Jin et al. |
| 2021/0283261 A1 | 9/2021 | Jin et al. |
| 2021/0395244 A1 | 12/2021 | Jin et al. |
| 2022/0054488 A1 | 2/2022 | Jin et al. |

FOREIGN PATENT DOCUMENTS

| | | |
|---|---|---|
| CN | 102822165 | 12/2012 |
| CN | 104736569 | 6/2015 |
| CN | 105085620 | 11/2015 |
| CN | 108137507 | 6/2018 |
| CN | 109071552 | 12/2018 |
| CN | 109790143 | 5/2019 |
| CN | 112778303 | 5/2021 |
| JP | 2018-526430 | 9/2018 |

(Continued)

OTHER PUBLICATIONS

ISA/US, International Search Report for PCT/US2017/065027 (dated Mar. 6, 2018).
PubChem-CID-44631912, Create Date: Mar. 8, 2010, p. 4.
Neklesa et al., "Small-Molecule Hydrophobic Tagging Induced Degradation of Halo Tag Fusion Proteins," Nat. Chem Biol. 2012, vol. 7(8), pp. 538-543.
EP Extended European Search Report in International Appln. No. 17877800, dated Feb. 19, 2021.
Bondeson et al., "Catalytic in vivo protein knockdown by small-molecule PROTACs," Nature Chemical Biology, 2015, 11(8):611-617.
Buckley et al., "HaloPROTACS: use of small molecule PROTACs to induce degradation of HaloTag fusion proteins," Just Accepted Manuscript, ACS Chemical Biology, 2015, 10(8):1831-1837.

(Continued)

*Primary Examiner* — Brenda L Coleman
(74) *Attorney, Agent, or Firm* — Fish & Richardson P.C.

(57) ABSTRACT

Methods for designing heterobifunctional small molecules which selectively degrade/disrupt CDK4/6 and compositions and methods of using such degraders/disruptors to treat CDK4/6-mediated cancer are provided.

15 Claims, 23 Drawing Sheets
Specification includes a Sequence Listing.

(56) References Cited

FOREIGN PATENT DOCUMENTS

| | | |
|---|---|---|
| JP | 2019-514883 | 5/2020 |
| MX | 2018000471 | 4/2018 |
| MX | 2018000360 | 6/2018 |
| WO | WO 2008/109104 | 9/2008 |
| WO | WO 2014/100719 | 6/2014 |
| WO | WO 2015/101293 | 7/2015 |
| WO | WO 2015/104677 | 7/2015 |
| WO | WO 2015/192123 | 12/2015 |
| WO | WO 2016/073956 | 5/2016 |
| WO | WO 2016/105518 | 6/2016 |
| WO | WO 2016/106518 | 7/2016 |
| WO | WO 2016/115480 | 7/2016 |
| WO | WO 2016/149668 | 9/2016 |
| WO | WO 2016/174130 | 11/2016 |
| WO | WO 2017/011371 | 1/2017 |
| WO | WO 2017/011590 | 1/2017 |
| WO | WO 2017/147700 | 9/2017 |
| WO | WO 2017/147701 | 9/2017 |
| WO | WO 2017/185031 | 10/2017 |
| WO | WO 2017/197051 | 11/2017 |
| WO | WO 2017/197055 | 11/2017 |
| WO | WO 2018/106870 | 6/2018 |
| WO | WO 2018/117177 | 6/2018 |
| WO | WO 2019/222380 | 11/2019 |
| WO | WO 2019/246570 | 12/2019 |
| WO | WO 2020/252043 | 12/2020 |
| WO | WO 2021/021904 | 2/2021 |

OTHER PUBLICATIONS

Buckley et al., "Small-Molecule Control of Intracellular Protein Levels through Modulation of the Ubiquitin Proteasome System," Angewandte Chemie International Edition, 2014, 53(9):2312-2330.
Buckley et al., "Small-Molecule Inhibitors of the Interaction between the E3 Ligase VHL and HIF1α," Angewandte Chemie International Edition, 2012, 51(46):11463-11467.
Buckley et al., "Targeting the von Hippel—Lindau E3 ubiquitin ligase using small molecules to dismpt the VHL/HIF-1α interaction," Journal of the American Chemical Society, 2012, 134(10):4465-4468.
Burkhart et al., "Cellular mechanisms of tumour suppression by the retinoblastoma gene," Nature Reviews Cancer, 2008, 8(9):671-682.
Chamberlain et al., "Structure of the human Cereblon—DDB1—lenalidomide complex reveals basis for responsiveness to thalidomide analogs," Nature Structural & Molecular Biology, 2014, 21(9):803-809.
Finn et al., "The cyclin-dependent kinase 4/6 inhibitor palbociclib in combination with letrozole versus letrozole alone as first-line treatment of oestrogen receptor-positive, HER2-negative, advanced breast cancer (PALOMA-1/TRIO-18): a randomised phase 2 study," The Lancet Oncology, 2015, 16(1):25-35.
Fischer et al., "Structure of the DDB1—CRBN E3 ubiquitin ligase in complex with thalidomide," Nature, 2014, 512(7512):49-53.
Galdeano et al., "Structure-guided design and optimization of small molecules targeting the proteinprotein interaction between the von Hippel—Lindau (VHL) E3 ubiquitin ligase and the hypoxia inducible factor (HIF) alpha subunit with in vitro nanomolar affinities," Journal of Medicinal Chemistry, 2014, 57(20):8657-8663.
Hamilton et al., "Targeting CDK4/6 in patients with cancer," Cancer Treatment Reviews, 2016, 45:129-138.
Herrera-Abreu et al., "Early adaptation and acquired resistance to CDK4/6 inhibition in estrogen receptor—positive breast cancer," Cancer Research, 2016, 76(8):2301-2313.
Ito et al., "Identification of a primary target of thalidomide teratogenicity," Science, 2010, 327(5971):1345-5130.
Lai et al., "Modular PROTAC design for the degradation of oncogenic BCR-ABL," Angewandte Chemie International Edition, 2016, 55(2):807-810.
Lim et al., "CDK4/6 inhibitors: promising opportunities beyond breast cancer," Cancer Discovery, 2016, 6(7):697-699.

Lu et al., "Hijacking the E3 ubiquitin ligase cereblon to efficiently target BRD4," Chemistry & Biology, 2015, 22(6):755-763.
Matsushime et al., "Identification and properties of an atypical catalytic subunit (p34$^{PSK-J3}$/cdk4) for mammalian D type G1 cyclins," Cell, 1992, 71(2):323-334.
Meyerson et al., "Identification of G1 kinase activity for cdk6, a novel cyclin D partner," Molecular and Cellular Biology, 1994, 14(3):2077-2086.
Sherr et al., "Targeting CDK4 and CDK6: from discovery to therapy," Cancer Discovery, 2016, 6(4):353-367.
Turner et al., "Palbociclib in hormone-receptor-positive advanced breast cancer," New England Journal of Medicine, 2015, 373(3):209-219.
Winter et al., "Phthalimide conjugation as a strategy for in vivo target protein degradation," Science, 2015, 348(6241):1376-1381.
Xie et al., "Pharmacological targeting of the pseudokinase Her3," Nature Chemical Biology, 2014, 10(12):1006-1012.
Yu et al., "Requirement for CDK4 kinase function in breast cancer," Cancer Cell, 2006, 9(1):23-32.
Zengerle et al., "Selective small molecule induced degradation of the BET bromodomain protein BRD4," ACS Chemical Biology, 2015, 10(8): 1770-1777.
CN Office Action in Chinese Appln. No. 201780085879.6, dated Jan. 5, 2022, 18 pages (with English Translation).
Fei et al., "PROTAC and its Application in the Treatment of Cancer," Chemistry of Life, Aug. 2014, 34(4):549-554 (with English abstract).
JP Office Action in Japanese Appln. No. 2019-530811, dated Dec. 14, 2021, 4 pages (with English Translation).
Toure et al., "Small-Molecule PROTACS: New Approaches to Protein Degradation," Angewandte Chemie-International Edition, Feb. 2016, 55(6):1966-1973.
Abramovich et al., "Hox regulation of normal and leukemic hematopoietic stem cells," Curr. Opin. Hematol., Max 2005, 12(3):210-216
Addie et al., "Discovery of 4-Amino-N-[(1S)-1-(4-chlorophenyl)-3-hydroxypropyl]1-(7H-pyrrolo[2,3-d]pyrimidin-4-yl)piperidine-4-carboxamide (AZD5363), an Orally Bioavailable, Potent Inhibitor of Akt Kinases," J. Med. Chem, Mar. 2013, 56(5):2059-2073
Aguilar et al., "Discovery of 4-((3'R,4'S,5'R)-6''-Chloro-4'-(3-chloro-2-fluorophenyl)l'-ethyl-2''- oxodispiro [cyclohexane-1,2'-pyrrolidine-3',3''-indoline]-5'-carboxamido)bicyclo[2.2.2]octane-1-carboxylic Acid (AA-115/APG-115): A Potent and Orally Active Murine Double Minute 2 (MDMZ) Inhibitor in Clinical Development, Journal of Medicinal Chemistry, Mar. 2017, 60(7):2819-2839.
Alinari et al., "Selective inhibition of protein arginine methyltransferase 5 blocks initiation and maintenance of B-cell transformation," Blood, Apr. 2015, 125(16):2530-2543.
Alzabin et al., "Hematopoietic progenitor kinase 1 is a critical component of prostaglandin E2-mediated suppression of the antitumor immune response," Cancer Immunol. Immunother., 2010, 59:419-429.
Alzabin et al., "Hematopoietic Progenitor Kinase 1 Is a Negative Regulator of Dendritic Cell Activation," J Immunol, 2009, 182:6187-6194.
Anders et al., "Differential expression analysis for sequence count data," Genome Biol., 2010 11:R106.
Armstrong et al., "MLL translocations specify a distinct gene expression profile that distinguishes a unique leukemia," Nat Genet, Jan. 2002, 30:41-47.
Artinger et al., "An MLL-dependent network sustains hematopoiesis," Proc. Natl. Acad. Sci. USA, Jul. 2013, 110(29):12000-12005.
Asiaban et al., "Cell-Based Ligand Discovery for the ENL YEATS Domain," ACS Chem. Biol., Apr. 2020. 15(4):895-903.
AU Notice of Allowance in Australian Appln. No. 2017348322, dated Dec. 14, 2021, 3 pages.
AU Office Action in Australian Appln. No. 2017348322, dated Dec. 10, 2020, 7 pages.
AU Office Action in Australian Appln. No. 2017348322, dated Sep. 27, 2021, 2 pages.
Ayton et al., "Molecular mechanisms of leukemogenesis mediated by MLL fusion proteins," Oncogene. Oct. 2001. 20:5695-5707.

(56) References Cited

OTHER PUBLICATIONS

Bachman et al., "EZH2 Expression Is Associated With High Proliferation Rate and Aggressive Tumor Subgroups in Cutaneous Melanoma and Cancers of the Endometrium, Prostate, and Breast," J. Clin. Oncol., 2006, 24(2):268-273.
Bai et al., "Targeted degradation of BET proteins in triple-negative breast cancer," Cancer Res., May 1, 2017, 77(9):2476-2487.
Basiorka et al. "Lenalidomide Stabilizes the Erythropoietin Receptor by Inhibiting the E3 Ubiquitin Ligase RNF41," Cancer Res., Apr. 2016, 76:3531-3540.
Bennett et al., "The Role of Nuclear Receptor-Binding SET Domain Family Histone Lysine Methyltransferases in Cancer," Cold Spring Harb. Perspect. Med., Jun. 2017, 7(6):a026708.
Berge et al., "Pharmaceutical Salts," Journal of Pharmaceutical Science, 1997, 66:1-19.
Bilsland et al., "Behavioral and neurochemical alterations in mice deficient in anaplastic lymphoma kinase suggest therapeutic potential for psychiatric indications," Neuropsychopharmacology, 2008, 33:685-700.
Biondi et al., "Biological and therapeutic aspects of infant leukemia," Blood, Jul. 2000, 96:24-33.
Biswas et al., "Function of leukemogenic mixed lineage leukemia 1 (MLL) fusion proteins through distinct partner protein complexes," Proc. Natl. Acad. Sci. USA, Sep. 2011, 108(38): 15751-15756.
Bitoun et al., "The mixed-lineage leukemia fusion partner 10 AF4 stimulates RNA polymerase II transcriptional elongation and mediates coordinated chromatin remodeling," Human Molecular Genetics, Jan 2007, 16:92-106.
Blake et al., "Discovery and preclinical pharmacology of a selective ATP-competitive Akt inhibitor (GDC-0068) for the treatment of human tumors," J. Med. Chem., Sep. 2012, 55(18):8110-8127.
Bolshan et al., "Synthesis, optimization, and evaluation of novel small molecules as antagonists of WDR5-MLL interaction," ACS Medicinal Chemistry Letters, Mar. 2013, 4(3):353-357.
Bondeson et al., "Lessons in PROTAC design from selective degradation with a promiscuous warhead," Cell Chem. Biol., Jan. 2018, 25:78-87e5.
Bottcher et al., "Fragment-based discovery of a chemical probe for the PWWP1 domain of NSD3," Nat. Chem. Biol., Aug. 2019, 15:822-829.
Bourdi et a1, "Safety Assessment of Metarrestin in Dogs: A Clinical Candidate Targeting a Subnuclear Structure Unigue to Metastatic Cancer Cell," Regul. Toxicol. Pharmacol., Aug. 2020, 116:104716.
Bracken et al., "*EZH2*is downstream of the pRB-E2F pathway, essential for proliferation and amplified in cancer," EMBO J., 2003, 22(20)5323-5335.
Bradley et al., "EZHZ Inhibitor/Efficacy m Non-Hodgkin's Lymphoma Does Not Require Suppression of H3K27 Monomethylation," Chem. Biol., 2014, 21(11):1463-1475.
Brand et al., "Homolog-selective degradation as a strategy to probe the function of CDK6 in AML," Cell Chem. Biol., Feb. 2019, 26(2):300-306e9.
Brauer et al., "Building a better understanding of the intracellular tyrosine kinase PTK6—BRK by BRK," Biochim. Biophys. Acta., Aug. 2010, 1806:66-73.
Braun et al., "Coordinated Splicing of Regulatcry Detained Introns within Oncogenic Transcripts Creates an Exploitable Vulnerability in Malignant Glioma," Cancer Cell, Oct. 2017, 32(4):411-426.
Brooun et al., "Polycomb repressive complex 2 structure with inhibitor reveals a mechanism of activation and drug resistance," Nat. Commun, Apr. 28, 2016, 7:11384, 12 pages.
Browne et al., "Regulation of peptide-chain elongation in mammalian cells," Eur. J. Biochem, Nov. 2002, 269:5360-5368.
Burnet, "The concept of immunological surveillance," Progress Exp. Tumor Res., 1970, 13:1-27.
Burslem et al., "Small-molecule modulation of protein homeostasis," Chem. Rev., Aug. 2017, 117(17):11269-11301.
Burslem et al., "The advantages of targeted protein degradation over inhibition: An RTK case study," Cell Chem. Biol., Jan. 2018, 25:67-77e3.

Cai et al., "Subunit composition and substrate specificity of a MOF-containing histone acetyltransferase distinct from the male-specific lethal (MSL) complex," The Journal of Biological Chemistg, Feb. 2010, 285(7):4268-4272.
Cai et al, "ZFX Mediates Non-canonical Oncogenic Functions of the Androgen Receptor Splice Variant 7 in Castrate-Resistant Prostate Cancer," 2018, Mol. Cell 72, 341-354 e346.
Campbell et al., "EPZ011989, A Potent, Orally-Available EZH2 Inhibitor with Robust in Vivo Activity," ACS Med. Chem. Lett, 2015, 6(5):491-495.
Cao et al., "Regulation and functional role of eEF1AZ in pancreatic carcinoma," Biochem. Biophys. Res. Commun, 2009, 380(1):11-16.
Cao et al., "Role of Histone H3 Lysine 27 Methylation in Polycomb-Group Silencing," Science, 2002, 298(5595):1039-1043.
Cao et al, "Targeting MLL1 H3K4 methyltransferase activity in mixed-lineage leukemia," Molecular Cell. Jan. 2014, 53(2):247-261.
Capiouzzo et al., "Erlotinib as maintenance treatment in advanced non-small-cell lung cancer: a multicentre, randomised, placebo-controlled phase 3 study," Lancet Oncol., Jun. 2010, 11:521-529.
Cardenas et al., "Enantioselective Synthesis of Pyrrolopyrimidine Scaffolds through Cation-Directed Nucleophihc Aromatic Substitution," Org. Lett., Mar. 2018, 20:2037-2041.
Carugo et al., "In Vivo functional platform targeting patient-derived xenografts identifies WDR5-Myc association as a critical determinant of pancreatic cancer." Cell Reports, Jun. 2016, 16(1):133-147.
Castro et al., "Breast tumor kinase and extracellular signal-regulated kinase 5 mediate Met receptor signaling to cell migration in breast cancer cells," Breast Cancer Research, 2010, 12:R60, 15 pages.
Chang et al., "EZH2 promotes expansion of breast tumor initiating cells through/activation of RAF1-β-catenin signaling," Cancer Cell, 2011, 19(1):86-100.
Chan-Penebre et al, "A selective inhibitor of PRMT5 with *in vivo* and *in vitro*potency in MCL models," Nature Chemical Biology, Apr. 2015, 11:432-437.
Chan et al., "An Anatomical Site and Genetic-Base Prognostic Model for Patients With Nuclear Protein in Testis (NUT) Midline Carcinoma: Analysis of 124 Patients," JNCI Cancer Spectr 4, 2020, pk2094 2020.
Chawade et al., "Normalyzer: a tool for rapid evaluation of normalization methods for omics data sets," J. Proteome. Res., 2014, 13:3114-31202014.
Chen et al., "Design, synthesis, and initial evaluation of affinity-based small molecular probe for detection of WDR5," Bioorganic Chemisty, Feb. 2018, 76:380-385.
Chen et al., "Gene expression profiling of WDR5 regulated genes in bladder cancer," Genomics Data, Sep. 2015, 5:27-29.
Chen et al., "PTK6 promotes hepatocellular carcinoma cell proliferation and invasion," Am. J. Transl. Res., Oct. 2016, (10):4354-4361.
Chen et al., "Upregulated WDR5 promotes proliferation, self-renewal and chemoresistance in bladder cancer via mediating H3K4 trimethylation," Scientific Reports, Feb. 2015, 5: 12 pages.
Chi et al., "Covalent histone modifications--miswritten, misinterpreted and mis-erased in human cancers," Nat. Rev. Cancer, 2010, 10:457-469.
Choi et al., "EML4-ALK mutations in lung cancer that confer resistance to ALK inhibitors," N. Engl. J. Med, Oct. 2010, 363(18): 1734-1739.
Choi et al., "Identification of novel isoforms of the EML4-ALK transforming gene in non-small cell lung cancer," Cancer Res., Jul. 2008, 68(13):4971-4976.
Christott et al., "Discovery of a Selective Inhibitor for the YEATS Domains of ENL/AF9.," SLAS Discov., 2019, 24:133-141.
Chung et al., "CbX8 acts non-canonically with Wdr5 to promote mammary tumorigenesis," Cell Reports, Jul. 2016, 16(2):472-486.
Clinicaltrials.gov [online], "Metarrestin (ML-246) in Subjects with Metastatic Solid Tumors," Jan. 10, 2020, retrieved on Mar. 16, 2022, retrieved from URL<https://clinicaltrials.gov/ct2/show/NCT04222413>, 12 pages.
CN Office Action in Chinese Appln. No. 201780081246.8, dated Dec. 2, 2021, 18 pages (with English Translation).

(56) References Cited

OTHER PUBLICATIONS

CN Office Action in Chinese Appln. No. 201780081246.8, dated Jun. 4, 2021, 19 pages (with English Translation).
Corthay, "Does the immune system naturally protect against cancer?" Front. Immunol., May 2014, 5(197):1-8.
Cromm et al., "Addressing kinase-independent functions of Fak Via PROTAC-mediated degradation," J. Am. Chem. Soc., Nov. 2018, 140(49):17019-17026.
Cromm et al., "Targeted protein degradation: from chemical biology to drug discovery," Cell Chem. Biol, Sep. 2017, 24(9):1181-1190.
Czermin et al., "*Drosophila*enhancer of Zeste/ESC complexes have a histone H3 methyltransferase activity that marks chromosomal Polycomb sites," Cell, 2002, 111(2):185-196.
Dai et al., "WDR5 expression is prognostic of breast cancer outcome," PLoS One, Sep. 2015, 10: 15 pages.
Davies et al., "Monoacidic Inhibitors of the Kelch-like ECH-Associated Protein 1: Nuclear Factor Erythroid 2-Related Factor 2 (KEAP1:NRF2) Protein-Protein Interaction with High Cell Potency Identified by Fragment-Based Discovery," Journal of Medicinal Chemistry, Apr. 2016, 59(8):3991-4006.
Dawson et al., "Inhibition of BET recruitment to chromatin as an effective treatment for MLL-fusion leukaemia," Nature, 2011, 478:529-15 533.
Deng et al., "Protein arginine methyltransferase 5 functions as an epigenetic activator of the androgen receptor to promote prostate cancer cell growth," Oncogene, 2017, 36:1223-1231
Derry et al., "Altered localization and activity of the intracellular tyrosine kinase BRK/Sik in prostate tumor cells," Oncogene, Jul. 2003, 22:4212-4220.
Deshpande et al., "Chromatin modifications as therapeutic targets in MLL-rearranged leukemia," Trends Immunol., Nov. 2012, 33(11):563-570.
Dias et al., "Structural analysis of the KANSL1/WDR5/KANSL2 complex reveals that WDR5 is required for efficient assembly and chromatin targeting of the NSL complex," Genes & Development, May 2014, 28(9):929-942.
Douglass, Jr. et al., "A comprehensive mathematical model for three-body binding equilibria," J. Am. Chem. Soc., Apr. 2013, 135(16):6092-6099.
Du et al., "FOXC1, a target or pclycomb, inhibits metastasis of breast cancer cells," Breast Cancer Res. Treat., 2012, 131(1):65-73.
Duanmin et al., "eEF1A2 protein expression correlates with lymph node metastasis and decreased survival in pancreatic ductal adenocarcinoma," Hepatogastroenterology, Jun. 2013, 60(124):870-875.
Dumble et al., "Discovery of novel AKT inhibitors with enhanced anti-tumor effects in combination with the MEK inhibitor," PloS One, Jun. 2014, 9(6), 11 pages.
EA Office Action in Eurasian Appln. No. 201991071, dated Jun. 10, 2020, 4 pages (with English translation).
Ee et al, "An embryonic stem cell-specific NuRD complex functions through interaction with WDR5," Stem Cell Reports, Jun. 2017, 8(6): 9 pages.
EP Extended European Search Report in European Appln. No. 19757825.5, dated Jan. 26, 2022, 14 pages.
EP Extended European Search Report in European Appln. No. 19763958.6, dated Dec. 8, 2021, 12 pages.
EP Extended European Search Report in European Appln. No. 17863645.2, dated Aug. 6, 2020, 10 pages.
EP Extended European Search Report in European Appln. No. 19830269.7, dated Mar. 7, 2022, 6 pages.
EP Office Action in European Appln. No. 17863645.2, dated Apr. 6, 2021, 7 pages.
EP Office Action in European Appln. No. 17863645.2, dated Mar. 11, 2022, 5 pages.
EP Office Action in European Appln. No. 19821826.5, dated Jan. 13, 2022, 4 pages.
EP Partial Supplementary Search Report in European Appln. No. 19757825.5, dated Oct. 18, 2021, 16 pages.
Erb et al. (2017). Transcription control by the ENL YEATS domain in acute leukaemia. Nature 543, 270-274.
Fabian et al., "A small molecule-kinase interaction map for clinical kinase inhibitors," Nat. Biotechnol., Mar. 2005, 23(3):329-336.
Fan et al., "A Kinase Inhibitor Targeted to mTORC1 Drives Regression in Glioblastoma," Cancer Cell, Mar. 2017, 31(3):424-435.
Fan et al., "BAHCC1 binds H3K27me3 via a conserved BAH module to mediate gene silencing and oncogenesis," Nature genetics, 2020, 52:1384-1396.
fda.gov [online], "Data Standards Manual (Monographs)," Feb. 27, 2018, retrieved on Feb. 7, 2022, retrieved from URL <https://www.fda.gov/drugs/electronic-regulatory-submission-and- review/data-standards-manual-monographs>, 1 page.
fda.gov [online], "Development & Approval Process | Drugs," Oct. 28, 2019, retrieved on Feb. 4, 2022, retrieved from URL <https://www.fda.gov/drugs/development-approval-process-drugs>, 4 pages.
Ferguson et al., "Kinase inhibitors: the road ahead," Nat. Rev. Drug Discov., May 2018, 17:353-377.
Ferrando et al., "Gene expression signatures in *MLL*-rearranged T-lineage and B-precursor acute leukemias: dominance of *HOX*dysregilation," Blood, Jul. 2003, 102(1):262-268.
Frankowski et al., "Metarrestin, a perinucleolar compartment inhibitor, effectively suppresses metastasis," Science Translational Medicine, May 2018, 10(441), 13 pages.
Frost et al., "Potent and selective chemical probe of hypoxic signalling downstream of HIF-$\alpha$ hydroglation Via VHL inhibition," Nat. Commun., Nov. 2016, 7:13312, 12 pages.
Fujii et al., "MEKERK pathway regulates EZH2 overexpression in association with aggressive breast cancer subtypes," Oncogene, 2011, 30(39):4118-4128.
Fujii et al., "Enhancer of Zeste Homologue 2 (EZHZ) Down-regulates RUNX3 by Increasing Histone H3 Methxlation," J. Biol. Chem., 2008, 283(25):17324-17332.
Gadd et al., "A Children's Oncology Group and TARGET initiative exploring the genetic landscape of Wilms tumor," Nat. Genet., Oct. 2017, 49:1487-1494.
Gao et al., "ZLD1122, a novel EZH2 and EZH1 small molecular inhibitor, blocks H3K27 methylation and diffuse large B cell lymphoma cell growth," RSC Adv., 2016, 6:28512-28521.
Garapaty-Rao et al., "Identification of EZH2 and EZH1 small molecule inhibitors with selective impact on diffuse large B cell lymphoma cell growth." Chem. Biol. 2013. 20(11):1329-1339.
Garnar-Wortzel et al., "Chemical Inhibition of ENL/AF9 YEATS Domains in Acute Leukemia," ACS Central Science, Apr. 2021, 7(5):815-830.
Ge et al., "WDR5 high expression and its effect on tumorigenesis in leukemia," Oncotarget, Jun. 2016, 7(25):37740-37754.
Gehling et al., "Discovery, design, and synthesis of indole-based EZH2 inhibitors," Bioorg. Med. Chem. Lett. 2015. 25(17):3644-3649.
Genscript.com [online], "Gen Script Make Research Easy," available on or before Mar. 3, 2015, retrieved on Mar. 17, 2022, retrieved from URL<https://www.genscript.com/gRNAdatabase.html>.
Getlik et al., "Structure-based optimization of a small molecule antagonist of the interaction between WD repeat-containing protein 5 (WDR5) and mixed-lineage leukemia 1 (MLL1)," Journal of Medicinal Chemistry, Mar. 2016, 59(6):2478-2496.
Gillis et al., "Biochemical and biological characterization of lymphocyte regulatory molecules; V. Identification of an interleukin 2-producing human leukemia T cell line," The Journal of experimental medicine, Dec. 1980,152:1709-1719.
Github.com [online], "ProteiNorm," Jul. 27, 2020, retrieved on Mar. 17, 2022, retrieved from URL <https://github.com/ByrumLab/proteiNorm>, 3 page.
Github.com [online], "PreprocessCore," Oct. 26, 2021, retrieved on Mar. 17, 2022, retrieved from URL<Gihttps://github.com/bmbolstad/preprocessCore>, 1 pages.
Gluz et al., "Triplenegative breast cancer—current status and future directions," Ann. Oncol., 2009, 20(12):1913-1927.
Godin-Heymann et al., "The T790M 'gatekeeper' mutation in EGFR mediates resistance to low concentrations of an irreversible EGFR inhibitor," Mol. Cancer Ther., Apr. 2008, 7(4):874-879.

(56) References Cited

OTHER PUBLICATIONS

Gonzalez et al., "Downregulation of EZH2 decreases growth of estrogen receptor-negative invasive breast carcinoma and requires BRCA1," Oncogene, 2009, 28(6):843-853.
Gonzalez et al., "EZH2 expands breast stem cells through actixiation of NOTCH1 signaling," Proc. Natl. Acad. Sci. USA, 2014, 111(8):3098-3103.
Grabe et al., "C797S Resistance: The undruggable EGFR mutation in non-small cell lung cancer?" ACS Med. Chem. Lett., 2018, 9:779-782.
Grebien et al., "Pharmacological targeting of the Wdr5-MLL interaction in C/EBPα N-terminal leukemia," Nature Chemical Biology, Aug, 2015, 11(8): 11 pages.
Guarnaccia et al., "Moonlighting with WDR5: A cellular multitasker," Journal of Clinical Medicine, Feb. 2018, 7(2): 17 pages.
Gullà et al., "Protein arginine methyltransferase 5 has prognostic relevance and is a druggable target in multiple myeloma," Leukemia, 2018, 32:996-1002.
Haegebarth et al., "Protein tyrosine kinase 6 negatively regulates growth and promotes enterocyte differentiation in the small intestine," Mol. Cell Biol, Jul. 2006, 26:4949-4957.
Hallberg et al., "Mechanistic insight into ALK receptor tyrosine kinase in human cancer biology," Nature Reviews Cancer, Oct. 2013, 13:685-700.
Han et al., "Discovery of ARD-69 as a Highly Potent Proteolysis Targeting Chimera (PROTAC) Degrader of Androgen Receptor (AR) for the Treatment of Prostate Cancer," Journal of Medicinal Chemistry, Jan. 2019, 62:941-964.
Harvey et al. "Brk protects breast cancer cells from autophagic cell death induced by loss of anchorage," The American Journal of Pathology, Sep. 2009, 175:1226-1234.
Harvey et al., "Use of RNA interference to validate Brk as a novel therapeutic target in breast cancer: Brk promotes breast carcinoma cell proliferation," Oncogene, Aug. 2003, 22:5006-5010.
He et al., "HIV-1 Tat and Host AFF4 Recruit Two Transcription Elongatiori Factors into a Bifunctional Complex for Coordinated Activation of HIV-1 Transcription," Mol. Cell., May 2010, 38(3):428-438.
He et al., "Human Polymerase-Associated Factor complex (PAFc) connects the Super Elongation Complex (SEC) to RNA polymerase II on chromatin," Proc. Natl. Acad. Sci. USA, Sep. 2011, 108(36):E636-E645.
Heerding et al., "Identification of 4-(2-(4-amino-1,2,5-oxadiazol-3-yl)-1-ethyl-7-{[(3S)-3-piperidinylmethyl]oxy}-1$H$-imidazo[4,5-c-9 pyridin-4-yl)-2-methyl-3-butyn-2-ol (GSK690693), a novel inhibitor of AKT kinase," Journal of Medicinal Chemistry, Sep. 2008, 51(18):5663-5679.
Heidenreich et al., "Structure-Based Approach toward Identification of Inhibitory Fragments for Eleven-Nineteen-Leukemia Protein (ENL)." J. Med. Chem. Nov. 2018. 61(23):10929-10934.
Henning et al., "Degradation of Akt using-protein-catalyzed capture agent," Journal of Peptide Science, 2016, 22:196-200.
Herbet et al., "Gefitinib--a novel targeted approach to treating cancer," Nat. Rev. Cancer, Dec. 2004, 4:956-965.
Hernandez et al., "The Kinase Activity of Hematopoietic Progenitor Kinase 1 Is Essential for the Regulation of T Cell Function," Cell reports, Oct. 2018, 25:80-94.
Hess, "MLL: a histone methyltransferase disrupted in leukemia," Trends Mol. Med, Oct. 2004, 10(10):500-507.
Higa et al., "CUL4-DDB 1 ubiquitin ligase interacts with multiple WD40-repeat proteins and regulates histone methylation," Nature Cell Biology, Nov. 2006, 8(11):1277-1283.
Hirai et al., "MK-2206, an allosteric Akt inhibitor, enhances antitumor efficacy by standard chemotherapeutic agents or molecular targeted drugs *in vitro* and *in vivo*," Molecular Cancer Therapeutics. Jul. 2010. 9(7):1956-1967.
Hiroyuki et al., "The structure of bestatin," The Journal of Antibiotics, Jan. 1976, 29(1):100-101.
Hirsch et al., "Lung cancer: current therapies and new targeted treatments," Lancet, Jan. 2017, 389:299-311.

Holm et al., "Global H3K27 trimethylation and EZH2 abundance in breast tumor subtypes," Mol. Oncol., 2012, 6(5):494-506.
Hsu et al., "Recognition of histone acetylation by the GAS41 YEATS domain promotes H2A.Z deposition in non-small cell lung cancer," Genes Dev., 2018, 32:58-69.
Hu et al., "Human HPKI, a novel human hematopoietic progenitor kinase that activates the JNK/SAPK kinase cascade," Genes Dev., Sep. 1996, 10:225 1-2264.
Hu et al., "Small Molecule Inhibitors of Protein Arginine Methyltransferases," Expert Opinion Investigational Drugs, 2016, 25:335-358.
Huang et al., "A Chemoproteomic Approach to Query the Degradable Kinome Using a Multi-kinase Degader," Cell Chemical Biology, Jan. 2018, 25(1):88-99.
Huang et al., "Covalent inhibition of NSD1 histone methyltransferase," Nat. Chem. Biol, 2020, 16:1403-1410.
Huber et al., "Variance stabilization applied to microarray data calibration and to the quantification of differential expression," Bioinformatics, 2002, 18 Suppl 1:S96-104.
IN Office Action in Indian Appln. No. 201917020814, dated Jun. 23, 2021, 6 pages (with English Translation).
Irie et al., "PTK6 regulates IGF-1-induced anchorage-independent survival," PLoS One, Jul. 2010, 5(7):e11729.
Ito et al., "PTK6 Inhibition Suppresses Metastases of Triple-Negative Breast Cancer Via SNAIL—Dependent E-Cadherin regilation," Cancer Res., Aug. 2016, 76:4406-4417.
Ito et al., "PTK6 regulates growth and survival of endocrine therapy-resistant ER+ breast cancer cells," NPJ Breast Cancer, Nov. 2017, 3:45.
Iwahara et al., "Molecular characterization of ALK, a receptor tyrosine kinase expressed specifically in the nervous system," Oncogene, Jan. 30, 1997, 14:439-449.
Jakobsson et al., "The dual methyltransferase METTL13 targets N terminus and Lys55 of eEF1A and modulates codon-specific translation rates," Nature Communications, Aug. 2018, 15 pages.
Jiang et al., "Development of dual and selective degraders of cyclin-dependent kinases 4 and 6," Angew. Chem. Int. Ed. Engl., May 2019, 58(19):6321-6326.
Jiang et al., "Targeting BRK-Positive Breast Cancers with Small-Molecule Kinase Inhibitors," Cancer Res., Jan. 2017, 77:175-186.
Jiao et al., "Structural basis of histone H3K27 trimethylation by an active polycomb repressive complex 2," Science, 2015, 350(6258):aac4383.
Jin et al., "Targeting methyltransferase PRMT5 eliminates leukemia stem cells in chronic myelogenous leukemia," The Journal of Clinical Investigation, Oct. 2016, 126:3961-3980.
JP Office Action in Japanese Appln. No. 2019-522841, dated Oct. 5, 2021, 14 pages (with English Translation).
Jude et al., "Unique and independent roles for MLL in adult hematopoietic stem cells and progenitors," Cell Stem Cell, Sep. 2007, 1(3):324-337.
Justin et al., "Structural basis of oncogenic histone H3K27M inhibition of human polycomb repressive complex 2," Nat. Commun, 2016, 7:11316.
Kanda et al., "Protein arginine methyltransferase 5 is associated with malignant phenotype and peritoneal metastasis in gastric cancer," International Journal of Oncology, Jun. 2016, 49:1195-1202.
Kanis et al., "A small molecule inhibitor of the perinucleolar compartment, ML246, attenuates growth and spread of ovarian cancer," Gynecol. Oncol. Res. Pract., 2018, 5:7.
Kanis et al., "Metarrestin: A novel compound active against ovarian cancer," Gynecol Oncol., Oct. 2015, 139(1):190.
Kaniskan et al., "Inhibitors of Protein Methyltransferases and Demethylases," Chem. Rev., 2018, 118(3):989-1068.
Kaniskan et al., "Selective inhibitors of protein methyltransferases," Journal of Medicinal Chemistry, 2015, 58:1596-1629.
Karatas et al., "Discovery of a highly potent, cell-permeable macrocyclic peptidomimetic (MM-589) targeting the WD repeat domain 5 protein (WDR5)—mixed lineage leukemia (MLL) protein-protein interaction," Journal of Medicinal Chemistry, Jun. 2017, 60(12):4818-4839.

(56) References Cited

OTHER PUBLICATIONS

Khalyfa et al., "Characterization of elongation factor-1A (eEF1A-1) and eEF1A-2/S1 protein expression in normal and *wasted*mice,"Journal of Biological Chemistry, 2001, 276:22915-22922.

Kiefer et al., "HPK1, a hematopoietic protein kinase activating the SAPK/JNK pathway," EMBO J., Dec. 1996, 15(24):7013-7025.

Kim et al. "Targeted disruption of the EZHZ-EED complex inhibits EZH2-dependent cancer" Nature Chemical Biology, 2013, 9:643-650.

Kim et al., "Targeting EZH2 in cancer," Nat. Med., 2016, 22(2):128-134.

Kleer et al., "EZH2 is a marker of aggressive breast cancer and promotes neoplastic transformation of breast epithelial cells," PNAS, 2003, 100(20):11606-11611.

Klein et al., "Yaf9 subunit of the NuA4 and SWR1 complexes targets histone H3K27ac through its YEATS domain," Nucleic Acids Res., Jan. 2018, 46:421-430.

Knutson et al, "A selective inhibitor of EZH2 blocks H3K27 methylation and kills mutant lymphoma cells," Nat. Chem. Biol., 8(11):890-896 2012.

Knutson et al., "Durable tumor regression in genetically altered malignant rhabdoid tumors by inhibition of methyltransferase EZH2," Proc. Natl. Acad. Sci. USA, 2013, 110(19):7922-7927.

Kobayashi et al., "EGFR mutation and resistance of non-small-cell lung cancer to gefitinib," N. Engl. J. Med., Feb. 2005, 352(8):786-792.

Koivunen et al., "*EML4-ALK*fusion gene and efficacy of an ALK kinase inhibitor in lung cancer," Clinical Cancer Research, Jul. 1, 2008, 14(13):4275-4283.

Konze et al., "An Orally Bioavailable Chemical Probe of the Lysine Methyltransferases EZH2 and EZHI," ACS Chem. Biol., 2013, 8(6):1324-1334.

Krause et al., "Tyrosine kinases as targets for cancer therapy," N. Engl. J. Med., Jul. 2005, 353(2):172-187.

Krivtsov et al., "*MLL*translocations, histone modifications and leukaemia stem-cell development," Nat. Rev. Cancer, Nov. 2007, 7:823-833.

Kryukov et al., "*MTAP*deletion confers enhanced dependency on the PRMT5 arginine methyltransferase in cancer cells." Science. 2016. 351(6278):1214-1218.

Kuenzi et al., "Polypharmacology-based ceritinib repurposing using integrated functional proteomics," Nat. Chem. Biol., Dec. 2017, 13(12):1222-1231.

Kung et al., "Design and Synthesis of Pyridone-Containing 3,4-Dihydroisoquinoline-1(2H)-ones as a Novel Class of Enhancer of Zeste Homolog 2 (EZH2) Inhibitors," J. Med. Chem., 2016, 59(18):8306-8325.

Kuzmichev et al., "Histone methyltransferase activity associated with a human multiprotein complex containing the Enhancer of Zeste protein," Genes Dev., 2002, 16(22):2893-2905.

Kwak et al., "Anaplastic lymphoma kinase inhibition in non-small-cell lung cancer," New England Journal of Medicine, Oct. 28, 2010, 363(18):1693-1703.

Lai et al., "Induced protein degradation: an emerging drug discovery paradigm," Nat. Rev. Drug Discov., Feb. 2017, 16(2):101-114.

Lapierre et al., "Discovery of 3-(3-(4-(1-Aminocyclobutyl)phenyl)-5-phenyl-3H-imidazo[4,5-b]pyridin-2-yl)pyridin-2-amine (ARQ 092): An orally bioavailable, selective, and potent allosteIic AKT inhibitor," Journal of Medicinal Chemistry, 2016, 59:6455-6469.

Lebraud et al., "Protein Degradation by In-Cell Self-Assembly of Proteolysis Targeting Chimeras," ACS Central Science, 2016, 2:927-934.

Li et al., "AF9 YEATS donlain links histone acetylation to DOT1L-mediated H3K79 methylation," Cell, Oct. 2014, 159(3):558-571.

Li et al., "Discovery of MD-224 as a first-in-class, highly potent, and efficacious proteolysis targeting chimera Murine Double Minute 2 degrader capable of achieving complete and durable tumor regression," J. Med. Chem., 2019, 62(2):448-466.

Li et al., "Discovery of potent and noncovalent reversible EGFR kinase inhibitors of EGFR$^{L858R/T790M/C797S}$," ACS Med. Chem. Lett., Jun. 2019, 10(6):869-873.

Li et al., "High-affinity small molecular blockers of mixed lineage leukemia 1 (MLL1)-WDR5 interaction inhibit MILL1 complex H3K4 methyltransferase activity," European Journal of Medicinal Chemistry, Nov. 2016, 124:480-489.

Li et al., "Molecular Coupling of Histone Crotonylation and Active Transcription by AF9 YEATS Domain," Mol. Cell., Apr. 2016, 62(2):181-193.

Li et al., "RSEM: accurate transcript quantification from RNA-Seq data with or without a reference genome," Bmc Bioinformatics, 2011, 12:323.

Li et al., "Structure-based design and synthesis of small molecular inhibitors disturbing the interaction of MLL1-WDR5," European Journal of Medicinal Chemistry, Aug. 2016, 118:1-8.

Li et al., "Structure-guided development of YEATS domain inhibitors by targeting $\pi$-$\pi$-$\pi$ stacking," Nat. Chem. Biol., Dec. 2018, 14:1140-1149.

Li et al., "The OncoPPi network of cancer-focused protein-protein interactions to inform biological insights and therapeutic strategies," Nat. Commun., Feb. 2017, 8:14356.

Li et al., "Understanding histone H3 lysine 36 metliylation and its deregulation in disease," Cell. Mol. Life Sci., Aug. 2019, 76(15):2899-2916.

Li et al., "ZMYND11-MBTD1 induces leukemo genesis through hijacking NuA4/T IP60 acetyltransferase complex and a PWWP-mediated chromatin association mechanism," Nat. Commun., 2021, 12(1), 18 pages.

Lin et al., "AFF4, a component of the ELL/PTEFb elongation complex and a shared subunit of MLL chimeras, can link transcription elongation to leukemia," Mol. Cell., Feb. 2010, 37(3):429-437.

Lin et al., "Clinicopathologic features, patterns of recurrence, and survival among women with triple-negative breast cancer in the National Comprehensive Cancer Network," Cancer, 2012, 118(22):5463-5472.

Lin et al., "Targeting ALK: Precision Medicine Takes on Drug Resistance," Cancer Discovery, Feb. 2017, 7(2):137-155.

Ling et al., "Involvement of hematopoietic progenitor kinase 1 in T cell receptor signaling," The Journal of biological chemistry, Jun. 2001, 276: 18908-18914.

Liou et al., "HPK1 is activated by lymphocyte antigen receptors and negatively regulates AP-1," Immunity, Apr. 2000, 12(4):399-408.

Liu et al., "Calcineurin is a common target of cyclophilin-cyclosporin A and FKBP-FK506 complexes," Cell, Aug. 1991, 66(4):807-815.

Liu et al., "Critical role of kinase activity of hematopoietic progenitor kinase 1 in anti-tumor immune surveillance," PloS one, Mar. 2019, 14:e02 12670.

Liu et al., "METTL13 Methylation of eEF1A Increases Translational Output to Promote Tumorigenesis," Cell, Jan. 2019, 176:491-504.e421.

Liu et al., "Widening Synthesis Bottlenecks: Realization of Ultrafast and Continuous-Flow Synthesis of High-Silica Zeolite SSZ-13 for NOx Removal," Angew. Chem., May 4, 2015, 127(19):5775-5779.

Losada et al., "Binding of *eEF1A2*to the RNA-dependent protein kinase PKR modulates its activity and promotes tumour cell survival," British Journal of Cancer, Nov. 2018, 119(11):1410-1420.

Lu et al., "Epigenetic Perturbations by Arg882-Mutated DNMT3A Potentiate Aberrant Stem Cell Gene-Expression Program and Acute Leukemia Development," Cancer Cell, 2016, 30:92-107.

Lu et al., "Targeting EGFR$^{L858R/T790M}$and EGFR$^{L858R/T70M/C797S}$resistance mntations in NSCLC: Current developments in medicinal chemistry," Med. Res. Rev., Jan. 2018, 38(5):1550-1581.

Mahara et al., "HIFI-$\alpha$ activation underlies a functional switch in the paradoxical role of Ezh2/PRC2 in breast cancer," PNAS, 2016, 113(26):E3735-E3744.

Mahmoud et al., "Discovery of 4-anilino $\alpha$-carbolines as novel Brk inhibitors," Bioorganic & Medicinal Chemistry Letters, Apr. 2014, 24:1948-1951.

Majer et al., "A687V EZH2 is a gain-offunction mutation found in lymphoma patients," FEBS Lett., 2012, 586(19):3448-3451.

(56) References Cited

OTHER PUBLICATIONS

Maniaci et al., "Homo-PROTACs: bivalent small-molecule dimeiizers of the VHL E3 ubiquitin ligase to induce self-degradation," Nature Communication, Oct. 2017, 8, 14 pages.
Manning et al., "AKT/PKB signaling: navigating the network," Cell, Apr. 2017, 169(3):381-405.
Marjon et al., "*MTAP*Deletions in Cancer Create Vulnerability to Targeting of the MAT2A/PRMT5/RIOK1 Axis," Cell Reports, Apr. 2016, 15:574-587.
Marschalek, "MLL Leukemia and Future Treatment Strategies," Arch. Pharm. Chem. Life Sci, Apr. 2015, 348(4):221-228.
Mavrakis et al., "Disordered methionine metabolism in MTAP/CDKNZA-deleted cancers leads to dependence on PRMTS," Science, Feb. 2016, 351(6278):1208-1213.
Mcalpine et al., "Abstract 4857: Discovery of PF-06855800, a SAM competitive PRMT5 inhibitor with potent antitumor activity," American Association for Cancer Research Annual Meeting, 2018, 78(13 Supplement), 4 pages.
McCabe et al., "EZH2 inhibition as a therapeutic strategy for lymphoma with EZH2-activating mutations," Nature, 2012, 492(7427):108-112.
McCabe et al., "Mutation of A677 in histone methyltransferase EZH2 in human B-cell lymphoma promotes hypertrimethylation ofhistone H3 on lysine 27 (H3K27)," Proc. Natl. Acad. Sci. USA, 2012, 109(8):2989-2994.
Meyer et al., "New insights to the *MLL*recombinome of acute leukemias," Leukemia, Aug. 2009, 23:1490-1499.
Meyer et al., "The *MLL*recombinome of acute leukemias in 2013," Leukemia, Nov. 2013, 27:2165-2176.
Meyer et al., "The MLL recombinome of acute leukemias," Leukemia, May 2006, 20:777-784.
Mi et al, "YEATS2 links histone acetylation to tumorigenesis of non-small cell lung cancer," Nat. Commun., Oct. 2017, 8:1088, 14 pages.
Migliori et al., "Symmetric dimethylation of H3R2 is a newly identified histone mark that supports euchromatin maintenance," Nature Structural and Molecular Biology, Feb. 2012, 19(2):136-144.
Miller et al., "Compass: a complex of proteins associated with atrithoraX-related SET domain protein," Proceedings of the National Academy of Sciences, Nov. 2001, 98(23):12902-12907.
Mitchell et al., "Cloning and characterisation of cDNAs encoding a novel non-receptor tyrosine kinase, brk, expressed in human breast tumours," Oncogene, Aug. 1994, 9:2383-2390.
Mohan et al., "Licensed to elongate: a molecular mechanism for MLL-based leukaemogenesis," Nat. Rev. Cancer, Oct. 2010, 10:721-728.
Mohan et al., "Linking H3K79 trimethylation to Wnt signaling through a novel Dot1-containing complex (DotCom)," Genes Dev., 2010, 24:574-589.
Molander et al., "Efficient hydrolysis of organotrifluoroborates via silica gel and water," Journal of Organic Chemistry, Oct. 2009, 74(19):364-7369.
Morin et al., "Somatic mutations altering EZH2 (Y641) in follicular and diffuse large B-cell lvmphomas of germinal-center origin," Nat. Genet., 2010, 42(2):181-185.
Morris et al., "*ALK*, the chromosome 2 gene locus altered by the t(2;5) in non-Hodgkin's lymphoma, encodes a novel neural receptor tyrosine kinase that is highly related to leukocyte tyrosine kinase (LTK)," Oncogene, Mar. 8, 1997, 14:2175-2188.
Morris et al., "Fusion of a kinase gene, *ALK*, to a nucleolar protein gene, NPM, in non-Hodgkin's lymphoma," Science, Mar. 4, 1994, 263(5151):1281-1284.
Moustakim et al., "Discovery of an MLLT1/3 YEATS Domain Chemical Probe," Angew. Chem. Int. Ed. Engl., Dec. 2018, 57(50):16302-16307.
Mueller et al., "A role for the MLL fusion partner ENL in transcriptional elongation and chromatin modification," Blood, Dec. 2007, 110(13):4445-4454.
Mueller et al., "Misguided Transcriptional Elongation Causes Mixed Lineage Leukemia," Plos Biol, Nov. 2009, 7(11):e1000249, 15 pages.
Müller et al, "Histone methyltransferase activity of a Drosophila Poly comb group repressor complex," Cell, 2002, 111(2):197-208.
MX Office Action in Mexican Appln. No. MX/a/2019/004950, dated Aug. 6, 2021, 6 pages (with English translation).
MX Office Action in Mexican Appln. No. MX/a/2019/004950, dated Nov. 23, 2021, 8 pages (with English Translation).
Nadeem Abbas et al., "Advances in targeting the epidermal growth factor receptor pathway by synthetic products and its regulation by epigenetic modulators as a therapy for glioblastoma," Cells, Apr. 2019, 8:350, 22 pages.
Ni et al., "Structural Insights into Interaction Mechanisms of Alternative Piperazine-urea YEATS Domain Binders in MLLT1," ACS Med. Chem. Lett., Dec. 2019, 10(12):1661-1666.
Nicholson et al., "EGFR and cancer prognosis," Eur. J. Cancer, Sep. 2001, 37 (Supp. 4):9-15.
Noble et al., "Protein kinase inhibitors: insights into drug design from structure," Science, Mar. 2004, 303:1800-1805.
Odho et al., "Characterization of a novel WDRS-binding site that recruits RbBP5 through a conserved motif to enhance methylation of histone H3 lysine 4 by mixed lineage leukemia protein-1," Journal of Biological Chemistry, Oct. 2010, 285(43):32967-32976.
Ohoka et al, "In vivo knockdown of pathogenic proteins via specific and nongenetic inhibitor of apoptosis protein (IAP)-dependent protein erasers (SNIPERS)," Journal of Biological Chemistry, Mar. 2017, 292(11):4556-4570.
Okada et al, "hDOT1L links histone methylation to leukemogenesis," Cell, Apr. 2005, 121(2):167-178.
Okuhira et al, "Specific degradation of CRABP-II Via cIAP1-mediated ubiquitylation induced by hybrid molecules that crosslink cIAP1 and the target protein," FEBS Lett., Apr. 2011, 585(8):1147-1152.
Olson et al., "Pharmacological perturbation of CDK9 using selective CDK9 inhibition or degradation," Nat. Chem. Biol., Feb. 2018, 14:163-170.
Ono et al., "PTK6 promotes cancer migration and invasion in pancreatic cancer cells dependent on ERK signaling," PLoS One, 2014, 9:e96060.
Ostrander et al, "Brk/PTK6 signaling in normal and cancer cell models," Curr. Opin. Phannacol., 2010, 10:662-669.
Ottis et al., "Proteolysis-targeting chimeras: induced protein degradation as a therapeutic strategy," ACS Chem. Biol., Mar. 2017, 12(4):892-898.
Paez et al., "*EGFR*mutations in lung/cancer: correlation with clinical response to gefitinib therapy," Science, Jun. 2004, 304:1497-500.
Pao et al., "Acquired resistance of lung adenocarcinomas to gefitinib or erlotinib is associated with a second mutation in the EGFR kinase domain," PLoS Med., Feb. 2005, 2(3):e73.
Papazimas et al., "A General Strategy for the Preparation of Thalidomide-Conjugate Linkers," Synlett, Aug. 23, 2017, 28:2881-2885.
Park et al., "Discovery of EGF receptor inhibitors that are selective for the d746-750/T790M/C797S mutant through structure-based *de novo*design," Angew. Chem. Int. Ed., Jun. 2017, 56(26):7634-7638.
Park et al., "PTK6 inhibition promotes apoptosis of Lapatinib-resistant Her2+breast cancer cells by inducing Bim," Breast Cancer Res, 2015, 17:86.
Patel et al., "A conserved arginine-containing motif crucial for the assembly and enzymatic activity of the mixed lineage leukemia protein-I core complex," The Journal of Biological Chemistry, Nov. 2008, 283(47):32162-32175.
Patel et al., "Recent updates on third generation EGFR inhibitors and emergence of fourth generation EGFR inhibitors to combat C797S resistance," Eur. J. Med. Chem., Dec. 2017, 142:32-47.
Patel et al., "Structure of WDR5 bound to mixed lineage leukemia protein-I peptide," The Journal of Biological Chemistry, Nov. 2008, 283(47):32158-32161.
PCT International Preliminary Report on Patentability in International Appln No. PCT/US2018/063847 , dated Jun. 18, 2020, 8 pages.

(56) References Cited

OTHER PUBLICATIONS

PCT International Preliminary Report on Patentability in International Appln. No. PCT/US2019/019123, dated Aug. 27, 2020, 10 pages.
PCT International Preliminary Report on Patentability in International Appln. No. PCT/US2019/038560, dated Dec. 30, 2020, 9 pages.
PCT International Preliminary Report on Patentability in International Appln. No. PCT/US2019/040507, dated Jan. 5, 2021, 7 pages
PCT International Preliminary Report on Patentability in International Appln. No. PCT/US2020/031527, dated Nov. 2, 2021, 8 pages.
PCT International Search Report and Written Opinion in International Appln. No. PCT/US2017/058718, dated Jan. 28, 2018, 8 pages.
PCT International Search Report and Written Opinion in International Appln. No. PCT/US2018/063847, dated Mar. 27, 2019, 11 pages.
PCT International Search Report and Written Opinion in International Appln. No. PCT/US2019/019123, dated Jun. 20, 2019, 15 pages.
PCT International Search Report and Written Opinion in International Appln. No. PCT/US2019/021014, dated Jun. 27, 2019, 11 pages.
PCT International Search Report and Written Opinion in International Appln. No. PCT/US2019/038560, dated Oct. 10, 2019, 12 pages.
PCT International Search Report and Written Opinion in International Appln. No. PCT/US2019/040507, dated Nov. 12, 2019, 10 pages.
PCT International Search Report and Written Opinion in International Appln. No. PCT/US2020/031527, dated Sep. 14, 2020, 11 pages.
PCT International Search Report and Written Opinion in International Appln. No. PCT/US2021/055574, dated Feb. 25, 2022, 11 pages.
PCT Invitation to Pay Additional Fees in International Appln. No. PCT/US2019/019123, dated Apr. 8, 2019, 3 pages.
PCT Invitation to Pay Additional Fees in International Appln. No. PCT/US2019/021014, dated Apr. 22, 2019, 2 pages.
PCT Invitation to Pay Additional Fees in International Appln. No. PCT/US2019/038560, dated Aug. 14, 2019, 2 pages.
PCT Invitation to Pay Additional Fees in International Appln. No. PCT/US2021/055574, dated Dec. 22, 2021, 2 pages.
Pellegrino et al., "EEF1A2 inactivates p53 by way of PI3K/AKT/mTOR-dependent stabilization of MDM4 in henatocellular carcinoma." Henatology, May 2014, 59(5):1886-1899.
Peng et al, "Protein tyrosine kinase 6 promotes ERBB2-induced mammary gland tumorigenesis in the mouse," Cell Death Dis., 2015, 6:e1848.
Perlman et al., "*MLLT1*YEATS domain mutations in clinically distinctive Favourable Histology Wilms tumours," Nat. Commun., Dec. 2015, 6:10013, 10 pages.
Peters et al., "Alectinib versus Crizotinib in Untreated ALK Positive Non-Small-Cell Lung Cancer," New England Journal of Medicine, Aug. 31, 2017, 377(9):829-838.
Pettersson et al., "PROteolysis TArgeting Chimeras (PROTACs)—past, present and future," Drug Discov. Today Technol., Apr. 2019, 31:15-27.
Pieters et al., "A treatment protocol for infants younger than 1 year with acute lymphoblastic leukaemia (Interfant-99): an observational study and a multicentre randomised trial," Lancet, Jul. 2007, 370:240-250.
Prabhu et al., "Adapting AlphaLISA high throughput screen to discover a novel small-molecule inhibitor targeting protein arginine methyltransferase 5 in pancreatic and colorectal cancers," Oncotarget, May 2017, 8(25):39963-39977.
Prêtre et al., "Inhibition of Akt and other AGC kinases: A target for clinical cancer therapy?," Accepted Manuscript, Seminars in Cancer Biology, 2018, 48:70-77.

Pui et al., "Treating Childhood Acute Lymphoblastic Leukemia without Cranial Irradiation," N. Engl. J. Med., Jun. 2009, 360(26):2730-2741.
Pulford et al., "Detection of anaplastic lymphoma kinase (ALK) and nucleolar protein nucleophosmin (NPM)-ALK proteins in normal and neoplastic cells with the monoclonal antibody ALK1," Blood, Feb. 15, 1997, 89(4):1394-1404.
Qi et al., "Selective inhibition of Ezh2 by a small molecule inhibitor blocks tumor cells proliferation," Proc. Natl. Acad. Sci. USA, 2012, 109(52):21360-21365.
Quentmeier et al., "EZH2 Y641 mutations in follicular lymphoma," Leukemia, 2011, 25(4):726-729.
Raina et al., "PROTACinduced BET protein degradation as a therapy for castration-resistant prostate cancer," Proceedings of the National Academy of Sciences of the United States of America, Jun. 2016, 113(26):7124-7129.
Rao et al., "Hijacked in cancer: the KMT2 (MLL) family of methyltransferases," Nat. Rev. Cancer, Jun. 2015, 15:334-346.
Ren et al., "PHF19 promotes multiple myeloma tumorigenicity through PRC2 activation and broad H3K27me3 domain formation," Blood, 2019, 134:1176-1189.
Ren et al., "Polycomb protein EZH2 regulates tumor invasion Via the transcriptional repression of the metastasis suppressor RKIP in breast and prostate cancer," Cancer Res., 2012, 72(12):3091-3104.
Ribas et al., "Cancer immunotherapy using checkpoint blockade," Science (New York, NY), Mar. 2018, 359(6382):1350-1355.
Rikova et al., "Global survey of phosphotyrosine signaling identifies oncogenic kinases in lung cancer," Cell, Dec. 14, 2007, 131(6):1190-1203.
Ritchie et al., "*limma*powers differential expression analyses for RNA-sequencing and microarray studies," Nucleic Acids Res., 2015, 43(7):e47.
Rodrik-Outmezguine et al., "Overcomihg mTOR resistance mutations with a new-generation mTOR inhibitor," Nature, Jun. 2016, 534:272-276.
Roguev et al., "The *Saccharomyces cerevisiae*Set1 complex includes an ash2 homologue and methylates histone 3 lysine," The EMBO journal, Dec. 2001, 20(24):7137-7148.
Rosati et al., "*NUP98*is fused to the NSD3 gene in acute myeloid leukemia associated with t(8;11)(p. 11.2;p. 15)," Blood, 2002, 99:3857-3860.
Sakamoto et al., "Protacs: chimeric molecules that target proteins to the Skpl-Cullin-F box complex for ubiguitination and degradation," Proc. Natl. Acad. Sci. USA, Jul. 2001, 98(15):8554-8559.
Salami et al., "Waste disposal-An attractive strategy for cancer therapy," Science, Mar. 2017, 355:1163-1167.
Saura et al., "A first-in-human phase I study of the ATP-competitive AKT inhibitor ipatasertib demonstrates robust and safe targeting of AKT in patients with solid tumors," Cancer Discovery, Jan. 2017, 7(1):102-113.
Sauvageau et al., "Poly comb group proteins: multi-faceted regulators of somatic stem cells and cancer," Cell Stem Cell., 2010, 7(3):299-313.
Sawasdikosol et al., "Hematopoietic progenitor kinase 1 (HPKl) regulates prostaglandin $E_2$-induced fos gene transcription," Blood, May 2003, 101(9):3687-3689.
Sawasdikosol et al., "HPKl as a novel target fer cancer immunotherapy," Immunologic Research, Dec. 2012, 54(1-3):262-265.
Sawasdikosol et al., "Prostaglandin $E_2$activates HPK 1 kinase activity via a PKA-dependent pathway," The Journal of biological chemistry, Nov. 2007, 282(48):34693-34699.
Schapira et al., "Targeted protein degradation: expanding the toolbox," Nat. Rev. Drug Discov., Dec. 2019, 18(12):949-963.
Schmandt et al., "The BRK tyrosine kinase is expressed in high-grade serous carcinoma of the ovary," Cancer Biol. Ther., 2006, 5:1136-1141.
Schneider et al. "Characterization of EBV-genome negative 'null' and 'T' cell lines derived from children with acute lymphoblastic leukemia and leukemic transformed non-Hodgkin lymphoma," International Journal of Cancer, May 1977, 19(5): 621-626.
Schrarnm et al., "Novel BQCA- and TBPB-derived M1 receptor hybrid ligands: orthosteric carbachol differentially reggilates partial agonism," ChemMedChem, Jul. 2019, 14(14):1349-1358.

(56) References Cited

OTHER PUBLICATIONS

Senisterra et al., "Small-molecule inhibition of MLL activity by disruption of its interaction with WDR5," Biochemical Journal, Jan. 2013, 449(1):151-159.
Seshacharyulu et al., "Targeting the EGFR signaling pathway in cancer therapy," Expert Opin. Ther. Targets, Jan. 2012, 16:15-31.
Shanle et al., "Association of Taf14 with acetylated histone H3 directs gene transcription and the DNA damage response," Genes Dev., 2015, 29:1795-1800.
Sharma et al., "Epidermal growth factor receptor mutations in lung cancer," Nat. Rev. Cancer, Mar. 2007, 7:169-181.
Shaw et al., "Ceritinib in ALK-rearranged non-small-cell lung cancer," New England Journal of Medicine, Mar. 27, 2014, 370(13):1189-1197
Shen et al., "Identification of LEM-14 inhibitor of the oncoprotein NSD2," Biochem Biophys. Res. Commun., Jan. 2019, 508(1):102-108.
Shen et al., "NSD3-Short Is an Adaptor Protein that Couples BRD4 to the CHD8 Chromatin Remodeler," Mol. Cell., Dec. 2015, 60(6):847-859.
Shen et al., "Structure-based design of 5-methylpyrimidopyridone derivatives as new wild-type sparing inhibitors of the epidermal growth factor receptor triple mutant (EGFR$^{L858R/T790M/C797S}$)," J. Med. Chem, Jul. 2019, 62:7302-7308.
Shibata et al., "Development of protein degradation inducers of oncogenic BCR-ABL protein by conjugation of ABL kinase inhibitors and IAP ligands," Cancer Science, Aug. 2017, 108(8):1657-1666.
Shimizu et al., "The protein arginine methyltransferase 5 promotes malignant phenotype of hepatocellular carcinoma cells and is associated with adverse patient outcomes after curative hepatectomy," International Journal of Oncology, Jan. 2017, 50(2):381-386.
Shiota et al, "Hyperphosphorylation of a novel 80 kDa protein-tyrosine kinase similar to Ltk in a human 40 Ki-1 lymphoma cell line, AMS3." Oncogene, Jun. 1994. 9(6):1567-1574.
Shui et al., "Hematopoietic progenitor kinase 1 negatively regulates T-cell receptor signaling and T cell-mediated immune responses," Nature Immunology, Jan. 2007, 8(1):84-91.
Slany, "When epigenetics kills: MLL fusion proteins in leukemia," Hematol. Oncol., Mar. 2005, 23:1-9.
Sneeringer et al., "Coordinated activities of wild-type plus mutant EZH2 dIive tumor-associated hypertrimethylation oflysine 27 on histone H3 (H3K27) in human B-cell lymphomas," Proc. Natl. Acad. Sci. USA, Dec. 7, 2010, 107(49):20980-20985.
Soda et al., "Identification of the transforming EML4-ALK fusion gene in non-small-cell lung cancer," Nature, Aug. 2, 2007,448z561-566.
Solomon et al., "First-line crizotinib versus chemotherapy in ALK-positive lung cancer," New England Journal of Medicine, Dec. 4, 2014, 371(23):2167-2177.
Song et al., "Selective inhibition of EZH2 by ZLD1039 blocks H3K27methylation and leads to potent anti-tumor activity in breast cancer," Sci. Rep., 2016, 6:20864.
Song et al., "WDR5 interacts with mixed lineage leukemia (MLL) protein Via the histone HJ-binding pocket," The Journal of Biological Chemistry, Dec. 2008, 283(50):35258-35264.
Soucy et al., "An inhibitor of NEDD8-activating enzyme as a new approach to treat cancer," Nature, Apr. 2009, 458:732-736.
Subrarnanian et al., "Gene set enrichment analysis: a knowledge-based approach for interpreting genome-wide expression profiles," Proc. Natl. Acad. Sci. USA, Sep. 2005, 102(43):15545-15550.
Suda et al., "The structure of bestatin," The Journal of Antibiotic, Jan. 1976, 29(1):100-101
Sun et al., "Discovery of AMG 232, a potent, selective, and orally bioavailable MDM2-p53 inhibitor in clinical development," Journal of Medicinal Chemistry, Feb. 2014, 57(4):1454-1472.
Sun et al., "PROTAC-induced BTK degradation as a novel therapy for mutated BTK C481S induced ibrutinib-resistant B-cell malignancies," Cell Research, Jul. 2018, 28(7):779-781.

Sun et al., "Up-regulated WDR5 promotes gastric cancer formation by induced cyclin D1 expression," Journal of Cellular Biochemistry, Apr. 2018, 119(4): 28 pages.
Sun et al., "WDR5 supports an N-Myc transcriptional complex that drives a protumorigenic gene expression signature in neuroblastoma," Cancer Research, Dec. 2015 75(23):5143-5154.
Tahirovic et al., "Discovery of N-alkylpiperazine side chain based CXCR4 antagonists with improved drug-like properties," ACS Med. Chem. Lett., May 2018, 9(5):446-451.
Takeuchi et al., "KIF5B-ALK, a novel fusion oncokinase identified by an immunohistochemistry—based diagnostic system for ALK-positive lung cancer," Clinical Cancer Research, May 1, 2009, 15(9):3143-3149.
Tan et al., "A kinase-independent role for EGF receptor in autophagy initiation," Cell, Jan. 2015, 160(1-2):145-160.
Tan et al., "Next-generation epidermal growth factor receptor tyrosine kinase inhibitors in epidermal growth factor receptor -mutant non-small cell lung cancer," Lung Cancer, Mar. 2016, 93:59-68.
Tan et al., "PBK/AKT-mediated upregulation of WDR5 promotes colorectal cancer metastasis by directly targeting ZNF407," Cell Death and Disease, Mar. 2017 , 8(3): 12 pages.
Taniguchi et al., "Silencing of Kruppel-like factor 2 by the histone methyltransferase EZH2 in human cancer," Oncogene, 2012, 31(15):1988-1994.
Tarighat et al., "The dualepigenetic role of PRMT5 in acute myeloid leukemia: gene activation and repression via histone arginine methylation," Leukemia, Nov. 2016, 30:789-799.
Thomas et al., "Interaction with WDR5 promotes target gene recognition and tumorigenesis by MYC," Molecular Cell, May 2015, 58(3):440-452.
Thomas et al., "The MYC-WDR5 nexus and cancer," Cancer Research, Oct. 2015, 75(19):4012-4015.
Thress et al., "Acquired EGFR C797S mutation mediates resistance to AZD9291 in non-small cell lung cancer harboring EGFR T790M," Nat. Med., May 2015, 21:560-562.
Trievel et al., "WDR5, a complexed protein," Nature Structural & Molecular Biology, Jul. 2009, 16(7):678-680.
Turner-Ivey et al., "Development of mammary hyperplasia, dysplasia, and invasive ductal carcinoma in transgenic mice expressing the 8p11 amplicon oncogene NSD3," Breast Cancer Res. Treat., Jul. 2017, 164(2):349-358.
Varamballiyet et al., "The polycomb group protein EZH2 is involved in progression of prostate cancer," Nature, 2002, 419(6907):624-629.
Varfolomeev et al., "IAP antagonists induce autoubiquitination of c-IAPs, NF-κB activation, and TNFα-dependent apoptosis," Cell, Nov. 2007, 131(4):669-681.
Vassilev et al., "In Vivo activation of the p53 pathway by small-molecule antagonists of MDM2," Science, Feb. 2004, 303(5659):844-848.
Verma et al., "Identification of Potent, Selective, Cell-Active Inhibitors of the Histone Lysine Methyltransferase EZH2," ACS Med. Chem. Lett., 2012, 3(12):1091-1096.
Vivanco et al., "A kinase-independent function of AKT promotes cancer cell suwival," eLIFE, 2014, 3:e03751.
Vu et al., "Discovery of RG7112: a small-molecule MDM2 inhibitor in clinical development," ACS Medicinal Chemis Letters, May 2013, 4(5):466-469.
Wakeling, "Use of pure antioestrogens to ehicidate the mode of action of oestrogens," Biochemical Pharmacology, May 1995, 49(11):1545-1549.
Wan et al., "ENL links histone aeetylation to oncogenic gene expression in acute myeloid leukaemia," Nature, Mar. 2017, 543:265-269.
Wan et al., "Impaired cell fate through gain-of-function mutations in a chromatin reader," Nature, Jan. 2020, 577:121-126.
Wang et al., "EAI045: The fourth-generation EGFR inhibitor overcoming T790M and C797S resistance," Cancer Lett., Jan. 2017, 385:51-54.
Wang et al., "MapSplice: accurate mapping of RNA-seq reads for splice junction discovery," Nucleic Acids Res., 2010, 38:e178.

(56) References Cited

OTHER PUBLICATIONS

Wang et al., "NUP98-NSD1 links H3K36 methylation to Hox-A gene activation and leukaemogenesis," Nat. Cell. Biol, Jul. 2007, 9(7):804-812.
Wang et al., "Polycomb genes, miRNA, and their deregulation in B-cell malignancies," Blood, 2015, 125(8): 1217-1225.
Wei et al., "Protein arginine methylation of non-histone proteins and its role in diseases," Cell Cycle, 2014, 13(1):32-41.
Weisberg et al., "Smac mimetics: implications for enhancement of targeted therapies in leukemia," Leukemia, Dec. 2010, 24:2100-2109.
Weiss et al., "Anaplastic lymphoma kinase and leukocyte tyrosine kinase: functions and genetic interactions in learning, memory and adult neurogenesis," Pharmacology, Biochemistry and Behavior, Jan. 2012, 100(3):566-574.
Weiss et al., "The role of T3 surface molecules in the activation of human T cells: a two-stimulus requirement for IL 2 production reflects events occurring at a pre-translational level," Journal of Immunology, Aug. 1984, 133(1):123-128.
Wieduwilt et al., "The epidermal growth factor receptor family: biology driving targeted therapeutics," Cell. Mol. Life Sci., May 2008, 65(10): 1566-1584.
Wood et al., "Lack of the t(2;5) or other mutations resulting in expression of anaplastic lymphoma kinase catalytic domain in CD30+ primary cutaneous lymphoproliferative disorders and Hodgkin's disease," Blood, Sep. 1, 1996, 88(5):1765-1770.
Wu et al., "Overexpression of WD repeat domain 5 associates with aggressive clinicopathological features and unfavorable prognosis in head neck squamous cell carcinoma," International Association of Oral Pathologists and the American Academy of Oral Pathology, Apr. 2018, 47(5): 27 pages.
Xie et al., "WDR5 positively regulates p53 stability by inhibiting p53 ubiquitination," Biochemical and Biophvsical Research Communications, May 2017, 487(2):333-338.
Xu et al., "eEF1A2 promotes cell migration, invasion and metastasis in pancreatic cancer by upregulating MMP-9 expression through Akt activation," Clin. Exp. Metastasis, May 2013, 30(7):933-944.
Xu et al, "Selective inhibition of EZH2 and EZH1 enzymatic activity by a small molecule suppresses *MLL*-rearranged leukemia," Blood, Jan. 2015, 125:346-357.
Xu et al., "Targeting EZH2 and PRC2 dependence as novel anti-cancer therapy," Exp. Hematol., 2015, 43(8):698-712.
Yang et al., "Structure-Activity Relationship Studies for Enhancer of Zeste Homologue 2 (EZH2) and Enhancer of Zeste Homologie 1 (EZH1) Inhibitors," J. Med. Chem., 2016, 59(16):7617-7633.
Yokoyama et al., "A Higher-Order Complex Containing AF4 and ENL Family Proteins with P-TEFb Facilitates Oncogenic and Physiologic MLL-Dependent Transcription," Cancer Cell, Feb. 2010, 17(2):198-212.
You et al., "Discovery of an AKT degrader with prolonged inhibition of downstream signaling," Cell Chemical Biology, 2020, 27(1):66-73.
Yu et al., "Altered *Hox* Expression and Segmental Identity in *Mll*-Mutant Mice," Nature, Nov. 1995, 378:505-508.
Yu et al., "Targeting AKT1-E17K and the PI3K/AKT pathway with an allosteiic AKT inhibitor, ARQ 092," PLOS One, Oct. 2015, 10(10):e0140479.
Yun et al., "The T790M mutation in EGFR kinase causes drug resistance by increasing the affinity for ATP." Proc. Natl. Acad. Sci. USA. Feb. 2008. 105(6):2070-2075.
Zeng et al., "Discovery of novel imidazo[1,2-a]pyrazin-8-amines as Brk/PTK6 inhibitors," Bioorg. Med. Chem. Lett., Oct. 2011, 21(19):5870-5875.
Zhang et al., "Proteolysis targeting chimeras (PROTACS) of anaplastic lymphoma linase (ALK)," Eur. J. Med. Chem., May 2018, 151:304-314.
Zhang et al., "Structural Insights into Histone Crotonyl-Lysine Recognition by the AF9 YEATS Domain," Structure, Sep. 2016, 24(9): 1606-1612.
Zhao et al. "PROTACs suppression cf CDK4/6, crucial kinases for cell cycle regulation in cancer," Chem. Commun. (Camb)., 2019, 55:2704-2707.
Zhao et al., "The language of chromatin modification in human cancers," Nat. Rev. Cancer, Jul. 2021, 21:413-430.
Zheng et al., "PTK6 activation at the membrane regulates epithelial-mesenchymal transition in prostate cancer," Cancer Res, Sep. 2013, 73(17):5426-5437.
Zhou et al., "Discovery of a Small-Molecule Degrader of Bromodomain and Extra-Terminal (BET) Proteins with Picomolar Cellular Potencies and Capable of Achieving Tumor Regression," Journal of Medicinal Chemistry, 2018, 61(2):462-481.
Zuber et al., "RNAi screen identifies Brd4 as a therapeutic target in acute myeloid leukaemia," Nature, 2011, 478:524-528.
EP Extended European Search Report in European Appln. No. 19821826.5, dated May 3, 2022, 10 pages.
Fisher et al., "Targeted protein degradation and the enzymology of degraders," Current Opinion in Chemical Biology, 2018, 44:47-55.
EP Office Action in European Appln. No. 17877800.7, dated May 24, 2022, 6 pages.
CN Office Action in Chinese Appln. No. 201780085879.6, dated Jun. 27, 2022, 15 pages (with English Translation).
JP Office Action in Japanese Appln. No. 2019-522841, dated Jul. 12, 2022, 8 pages (with English Translation).
PCT International Search Report and Written Opinion in International Appln. No. PCT/US2022/013225, dated Jun. 6, 2022, 24 pages.

\* cited by examiner

COMPOSITIONS AND METHODS FOR TREATING CDK4/6-MEDIATED CANCER

TECHNICAL FIELD

This disclosure relates to bivalent compounds (e.g., bi-functional small molecule compounds) which selectively degrade and/or disrupt cyclin-dependent kinase (CDK) 4 and/or 6, compositions comprising one or more of the bivalent compounds, and to methods of use thereof for the treatment of CDK4/6-mediated cancer in a subject in need thereof. The disclosure also relates to methods for designing such bivalent compounds.

BACKGROUND OF THE INVENTION

Cyclin-dependent kinase 4 (CDK4, also known as CMM3 and PSK-J3) (Matsushime et al., 1992) and cyclin-dependent kinase 6 (CDK6, also known as MCPH12 and PLSTIRE) (Meyerson and Harlow, 1994) are related serine/threonine kinases (referred to together as "CDK4/6") that play a critical role in the cyclin D/CDK4/6/Rb/E2F signaling pathway ("CDK4/6/Rb signaling") (Sherr et al., 2016). CDK4/6/Rb signaling mediates physiological cell cycle progression and cell proliferation. Dephosphorylated Rb binds transcription factors of the E2F family, thus preventing transition through the S phase. CDK4 and CDK6 promote cell cycle progression by phosphorylating Rb. Phosphorylation of Rb allows E2F to dissociate from Rb and promote transition through the S phase of the cell cycle (Burkhart and Sage, 2008).

Multiple types of cancer, including breast cancer, have been found to depend on aberrant activation of CDK4/6/Rb signaling for their progression ("CDK4/6-mediated cancer") (Yu et al., 2006; Hamilton and Infante, 2016; Lim et al., 2016). Conventional cancer treatments include surgery, radiation therapy, chemotherapy (e.g., gemcitabine HCl and temozolomide, a cytotoxic DNA alkylating agent), hormonal therapy, targeted antibody therapy, and combinations thereof. Among women, breast cancer has a considerably higher incident rate (43.3 per 100,000) than any other cancer. In North America, breast cancer is one of the leading causes of cancer death among women (about 15%), only second to lung cancer.

Significant effort has been spent on developing therapeutics capable of inhibiting the activity of CDK4/6. Three CDK4/6 inhibitors (palbociclib (PD-0332991; Pfizer), abemaciclib (LY2835219; Lilly), and ribociclib (LEE011; Novartis)) have been approved. All three compounds have shown preclinical activity in a range of tumor models, dependent on the expression of intact Rb in the tumor. Recently, three additional CDK4/6 inhibitors, trilaciclib (G1T28), G1T38, and SHR6390, have entered phase I clinical trials.

Clinical results have shown that patients with estrogen receptor (ER) positive (ER+) breast tumors show remarkable responses and increased progression-free survival when treated with CDK4/6 inhibitors coupled with endocrine therapy (i.e., treatment with one or more aromatase inhibitors or ER antagonists) (Finn et al., 2015; Turner et al., 2015). Despite the initial response to such treatments, however, the majority of these patients eventually develop resistance to such treatment within 14-28 months (Finn et al., 2015). Preliminary data suggest that such acquired resistance can arise from failure of inhibitor to suppress CDK4/6/Rb signaling or from loss of Rb (Herrera-Abreu et al., 2016). Overall, the clinical efficacy of CDK4/6 inhibitor monotherapy (i.e., CDK4/6 treatment alone without endocrine or other therapy) appears to be modest (Sherr et al., 2016). Toxicity can limit the administration of these inhibitors at a concentration high enough to sufficiently inhibit Rb phosphorylation in the tumor.

SUMMARY

The present disclosure relates generally to bivalent compounds (e.g., bi-functional small molecule compounds) which selectively degrade and/or disrupt CDK4/6, and to methods for the treatment of CDK4/6-mediated cancer (i.e., a cancer that overexpresses CDK4, CDK6 or both; cancer which depends on CDK4, CDK6, or both activity; or cancer having elevated levels of CDK4, CDK6, or both, activity relative to a wild-type tissue of the same species and tissue type). It is important to note, because the CDK4/6 degraders/disruptors have dual functions (enzyme inhibition plus protein degradation/disruption), the bivalent compounds disclosed/claimed here can be significantly more effective therapeutic agents than current CDK4/6 inhibitors, which inhibit the enzymatic activity of CDK4/6 but do not affect CDK4/6 protein levels. The present disclosure further provides methods for identifying CDK4/6 degraders/disruptors as described herein.

More specifically, the present disclosure provides a bivalent compound including a cyclin-dependent kinase 4/6 (CDK4/6) ligand conjugated to a degradation/disruption tag.

In an aspect, the CDK4/6 degraders/disruptors have the form "PI-linker-EL" as shown below:

Formula I

wherein PI comprises a CDK4/6 ligand (e.g., a CDK4/6 inhibitor) and EL comprises a degradation/disruption tag (e.g., E3 ligase ligand). Exemplary CDK4/6 ligands (PI) and exemplary degradation/disruption tags (EL) are disclosed herein.

For example, PI can include, but is not limited to:

Formula II

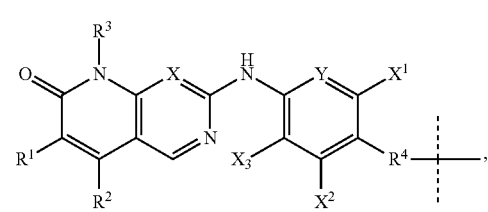

wherein $X^1$, $X^2$, and $X^3$ are independently hydrogen, halogen, C1-C8 alkyl, C1-C8 alkoxy, C1-C8 alkoxyalkyl, $NR^5R^6$, CN, $NO_2$, $COR^5$, $CO_2R^5$, $CONR^5R^6$, or $NR^5COR^6$;

$R^1$ and $R^4$ are independently hydrogen, halogen, C1-C8 alkyl, C1-C8 alkoxy, C1-C8 alkoxyalkyl, C1-C8 haloalkyl, C1-C8 hydroxyalkyl, C3-C7 cycloalkyl, C3-C7 heterocyclyl, C2-C8 alkenyl, C2-C8 alkynyl, $OR^5$, $SR^5$, $NR^5R^6$, CN, $NO_2$, $(CR^5R^6)mNR^7R^8$, $(CR^5R^6)mC(O)R^7$, $COR^5$, $CO_2R^5$, $CONR^5R^6$, $NR^5COR^6$, $NR^5SOR^6$, $NR^5SO_2R^6$, $SOR^5$, $SO_2R^5$, $SO_2NR^5R^6$, $(CR^5R^6)$m-aryl, or $(CR^5R^6)$m-heteroaryl, wherein m is 0-8;

$R^2$ is hydrogen, halogen, C1-C8 alkyl, C1-C8 alkoxy, C3-C7 cycloalkyl, or C3-C7 heterocyclyl;

$R^3$ is hydrogen, aryl, C1-C8 alkyl, C1-C8 alkoxy, C3-C7 cycloalkyl, or C3-C7 heterocyclyl;

$R^5$, $R^6$, $R^7$, $R^8$ are independently hydrogen, C1-C8 alkyl, C2-C8 alkenyl, C2-C8 alkynyl, arylalkyl, cycloalkyl, heterocycloalkyl, aryl, heteroaryl, or heteroarylalkyl;

optionally, $R^1$ and $R^2$; $R^5$ and $R^6$; or $R^7$ and $R^8$ independently form 4-8 membered alkyl or heterocyclyl rings; and X and Y are independently $CR^5R^6$ or N.

For example, PI can include:

Formula III wherein $R^1$ is independently hydrogen, C1-C8 alkyl, C1-C8 alkoxyalkyl, C1-C8 haloalkyl, C1-C8 hydroxyalkyl, C3-C7 cycloalkyl, C3-C7 heterocyclyl, C2-C8 alkenyl, or C2-C8 alkynyl;

$R^2$ is hydrogen, C1-C3 alkyl, or cyclopropyl;

$R^3$, $R^4$, and $R^5$ are independently hydrogen, halogen, C1-C8 alkyl, C1-C8 alkoxy, C3-C7 cycloalkyl, or C3-C7 heterocyclyl;

$R^6$ is hydrogen, halogen, C1-C8 alkyl, C1-C8 alkoxy, C1-C8 alkoxyalkyl, C1-C8 haloalkyl, C1-C8 hydroxyalkyl, C3-C7 cycloalkyl, C3-C7 heterocyclyl, C2-C8 alkenyl, C2-C8 alkynyl, $OR^7$, $SR^7$, $NR^7R^8$, CN, $NO_2$, $(CR^7R^8)$ $mNR^9R^{10}$, $(CR^7R^8)mC(O)R^9$, $COR^7$, $CO_2R^7$, $CONR^7R^8$, $NR^7COR^8$, $NR^7SOR^8$, $NR^7SO_2R^8$, $SOR^7$, $SO_2R^7$, $SO_2NR^7R^8$, $(CR^7R^8)$m-aryl, or $(CR^7R^8)$m-heteroaryl, wherein m is 0-8;

$R^7$, $R^8$, $R^9$, $R^{10}$ are independently hydrogen, C1-C8 alkyl, C2-C8 alkenyl, C2-C8 alkynyl, arylalkyl, cycloalkyl, heterocycloalkyl, aryl, heteroaryl, or heteroarylalkyl;

optionally, $R^7$ and $R^8$; $R^9$ and $R^{10}$ independently form 4-8 membered alkyl or heterocyclyl rings; and X and Y are independently $CR^7R^8$ or N.

For example, PI can include:

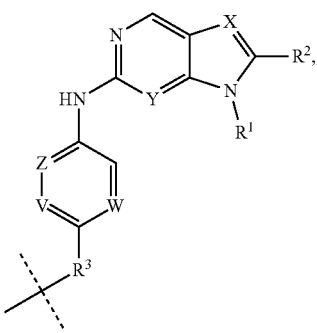

Formula IV wherein $R^1$ is independently hydrogen, C1-C8 alkyl, C1-C8 alkoxyalkyl, C1-C8 haloalkyl, C1-C8 hydroxyalkyl, C3-C7 cycloalkyl, C3-C7 heterocyclyl, C2-C8 alkenyl, or C2-C8 alkynyl;

$R^2$ is hydrogen, C1-C8 alkyl, C1-C8 alkoxyalkyl, C1-C8 haloalkyl, C1-C8 hydroxyalkyl, C3-C7 cycloalkyl, C3-C7 heterocyclyl, C2-C8 alkenyl, C2-C8 alkynyl, CN, $COR^4$, $CO_2R^4$, or $CONR^4R^5$;

$R^3$ is hydrogen, halogen, C1-C8 alkyl, C1-C8 alkoxy, C1-C8 alkoxyalkyl, C1-C8 haloalkyl, C1-C8 hydroxyalkyl, C3-C7 cycloalkyl, C3-C7 heterocyclyl, C2-C8 alkenyl, C2-C8 alkynyl, $OR^4$, $SR^4$, $NR^4R^5$, CN, $NO_2$, $(CR^4R^5)$ $mNR^6R^7$, $(CR^4R^5)mC(O)R^6$, $COR^4$, $CO_2R^4$, $CONR^4R^5$, $NR^4COR^5$, $NR^4SOR^5$, $NR^4SO_2R^5$, $SOR^4$, $SO_2R^4$, $SO_2NR^4R^5$, $(CR^4R^5)$m-aryl, or $(CR^4R^5)$m-heteroaryl, wherein m is 0-8;

$R^4$, $R^5$, $R^6$, $R^7$ are independently hydrogen, C1-C8 alkyl, C2-C8 alkenyl, C2-C8 alkynyl, arylalkyl, cycloalkyl, heterocycloalkyl, aryl, heteroaryl, or heteroarylalkyl;

optionally, $R^1$ and $R^2$; $R^4$ and $R^5$; $R^6$ and $R^7$ independently form 4-8 membered alkyl or heterocyclyl rings; and V, W, X, Y, and Z are independently $CR^4R^5$ or N.

For example, PI can include:

Formula VI wherein $R^1$ and $R^2$ are independently hydrogen, C1-C8 alkyl, C1-C8 alkoxyalkyl, C1-C8 haloalkyl, C1-C8 hydroxyalkyl, C3-C7 cycloalkyl, C3-C7 heterocyclyl, C2-C8 alkenyl, or C2-C8 alkynyl;

$R^3$ is hydrogen, C1-C6 alkyl, C1-C6 alkoxyalkyl, C1-C6 haloalkyl, C1-C6 hydroxyalkyl, C3-C6 cycloalkyl, C3-C6 heterocyclyl, C2-C6 alkenyl, or C2-C6 alkynyl;

$R^4$ is hydrogen, halogen, C1-C8 alkyl, C1-C8 alkoxy, C1-C8 alkoxyalkyl, C1-C8 haloalkyl, C1-C8 hydroxyalkyl, C3-C7 cycloalkyl, C3-C7 heterocyclyl, C2-C8 alkenyl, C2-C8 alkynyl, $OR^5$, $SR^5$, $NR^5R^6$, CN, $NO_2$, $(CR^5R^6)$ mNR$^7$R$^8$, (CR$^5$R$^6$)mC(O)R$^7$, COR$^5$, CO$_2$R$^5$, CONR$^5$R$^6$, NR$^5$COR$^6$, NR$^5$SOR$^6$, NR$^5$SO$_2$R$^6$, SOR$^5$, SO$_2$R$^5$, SO$_2$NR$^5$R$^6$, (CR$^5$R$^6$)m-aryl, or (CR$^5$R$^6$)m-heteroaryl, wherein m is 0-8;

n is independently 0-4;

optionally, R$^1$ and R$^2$; R$^5$ and R$^6$; R$^7$ and R$^8$ independently form 4-8 membered alkyl or heterocyclyl rings; and V, W, X, Y, and Z are independently CR$^5$R$^6$ or N.

The CDK4/6 ligand can be a CDK4/6 inhibitor, such as, e.g., abemaciclib, palbociclib, ribociclib, trilaciclib (G1T28), G1T38, SHR6390, and/or analogs thereof.

In some aspects, the CDK4/6 ligand can be, e.g.,

I

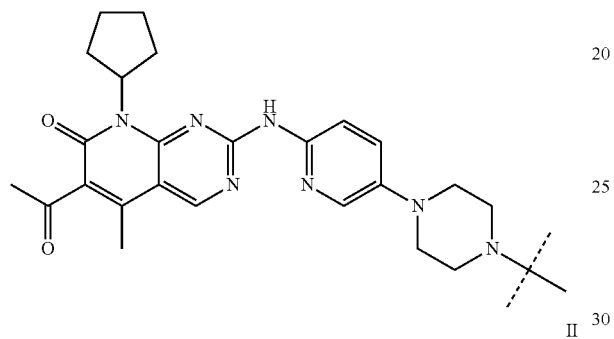

II

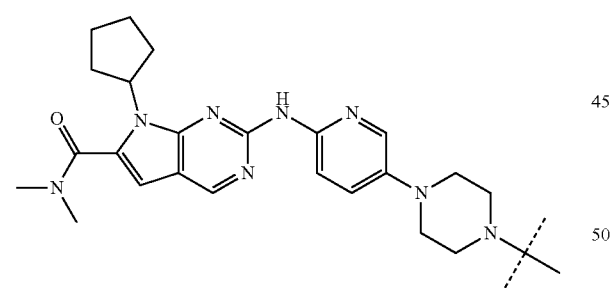

III

IV

The CDK4/6 ligand can be bound to CDK4/6.

EL includes, but is not limited to:

Formula VII

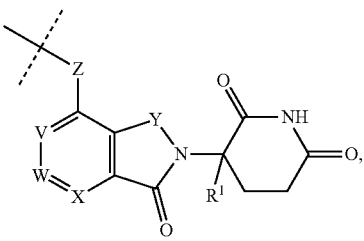

Formula VIII

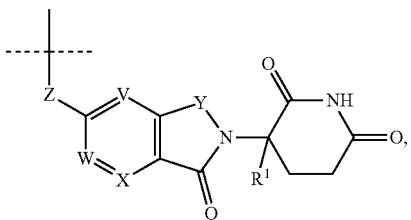

Formula IX

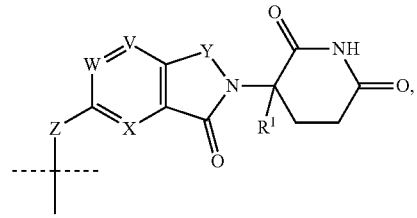

Formula XI

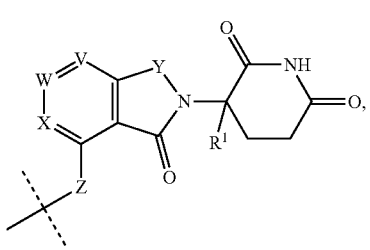

wherein V, W, X are independently CR$^2$ or N;

Y is CO or CH$_2$;

Z is CH$_2$, NH, or O;

R$^1$ is hydrogen, methyl, or fluoro; and

R$^2$ is hydrogen, halogen, or C1-C5 alkyl.

For example, EL can include:

Formula XII

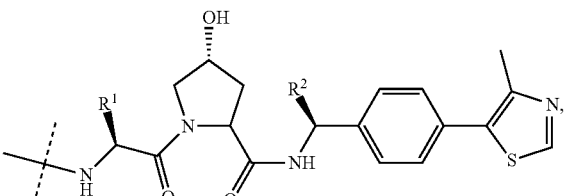

wherein R$^1$ and R$^2$ are independently hydrogen, C1-C8 alkyl, C1-C8 alkoxyalkyl, C1-C8 haloalkyl, C1-C8 hydroxyalkyl, C3-C7 cycloalkyl, C3-C7 heterocyclyl, C2-C8 alkenyl, or C2-C8 alkynyl.

For example, EL can include:

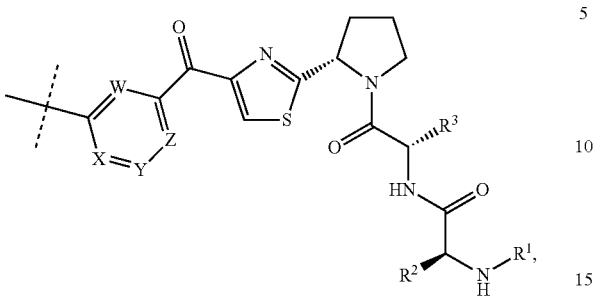

Formula XIII wherein R¹, R², R³ and R⁴ are independently hydrogen, C1-C8 alkyl, C1-C8 alkoxyalkyl, C1-C8 haloalkyl, C1-C8 hydroxyalkyl, C3-C7 cycloalkyl, C3-C7 heterocyclyl, C2-C8 alkenyl, or C2-C8 alkynyl; and V, W, X, Z are independently CR⁴ or N.

In some aspects, the degradation/disruption tag can be, e.g., pomalidomide, thalidomide, lenalidomide, VHL-1, adamantane, 1-((4,4,5,5,5-pentafluoropentyl)sulfinyl) nonane, nutlin-3a, RG7112, RG7338, AMG 232, AA-115, bestatin, MV-1, LCL161, and/or analogs thereof.

In some aspects, the degradation/disruption tag can be, e.g.,

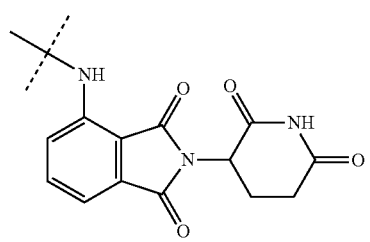

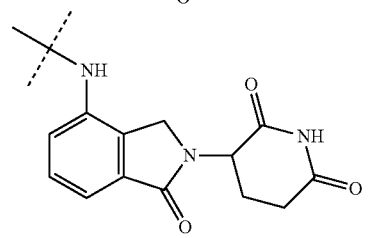

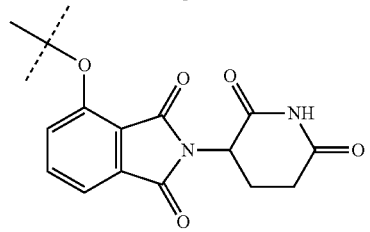

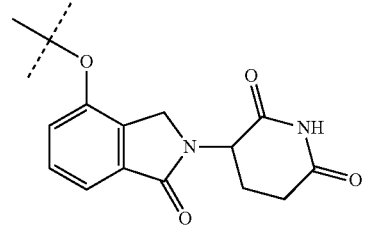

-continued

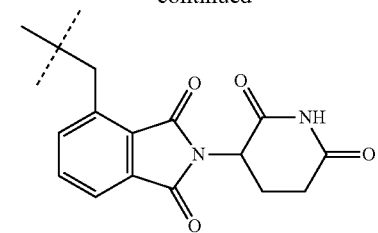

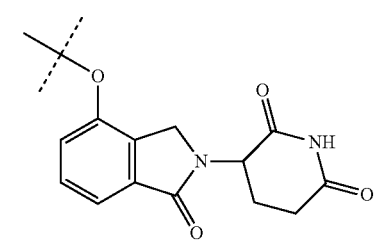

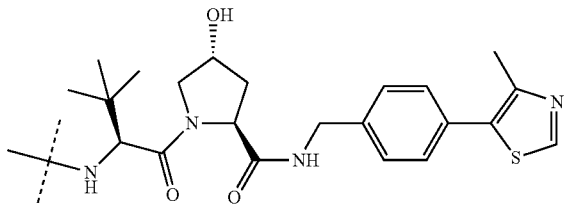

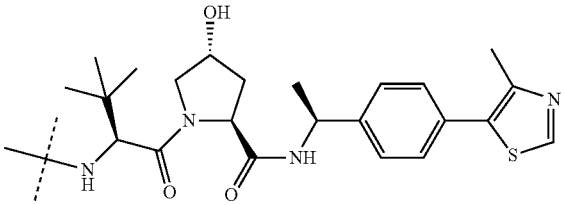

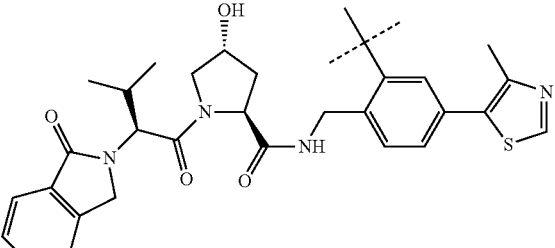

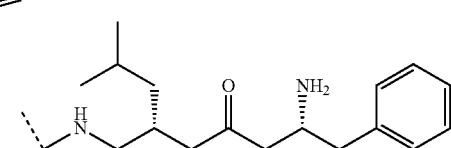

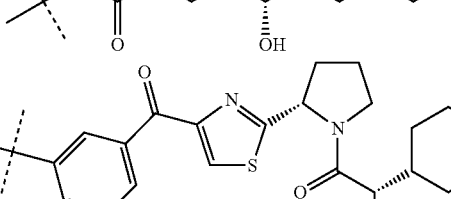

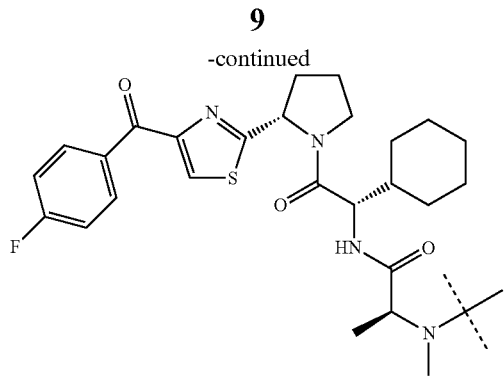

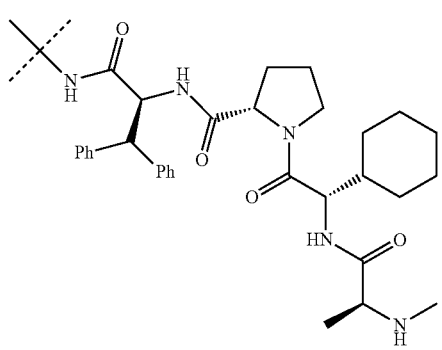

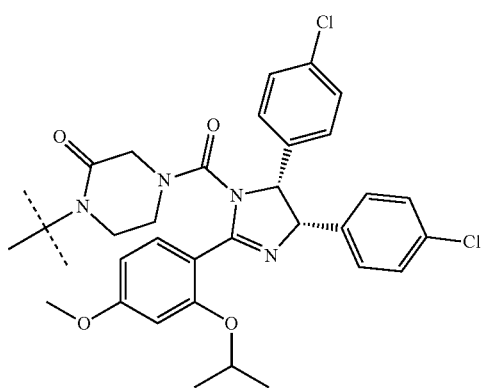

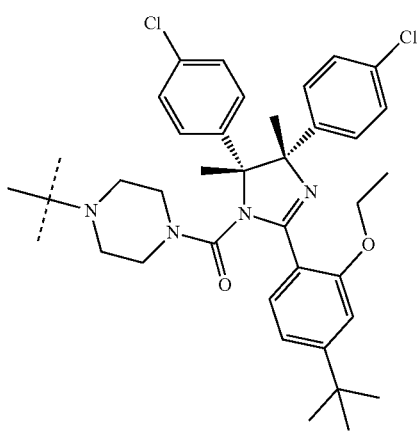

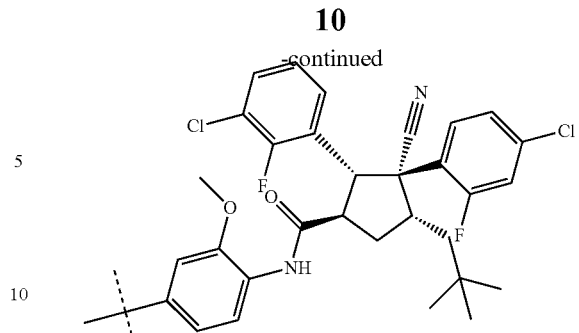

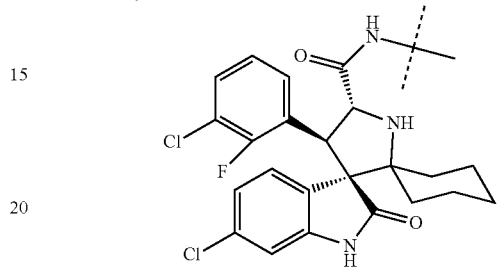

(left to right, then top to bottom, starting with Formula XIV at the top left corner and ending with Formula XXX at the bottom right corner).

In some aspects, the degradation/disruption tag can bind to a ubiquitin ligase (e.g., an E3 ligase such as a cereblon E3 ligase, a VHL E3 ligase, a MDM2 ligase, a TRIM21 ligase, a TRIM24 ligase, and/or a IAP ligase) and/or serve as a hydrophobic group that leads to CDK4 or CDK6 protein misfolding.

In any of the above-described compounds, the CDK4/6 ligand can be conjugated to the degradation/disruption tag through a linker. The linker can include, for example, acyclic or cyclic saturated or unsaturated carbon, ethylene glycol, amide, amino, ether, urea, carbamate, aromatic, heteroaromatic, heterocyclic and/or carbonyl containing groups with different lengths.

In some embodiments, the linker can be a moiety of:

Formula A wherein X is C=O or $CH_2$,
Y is C=O or $CH_2$, and
n is 0-15;

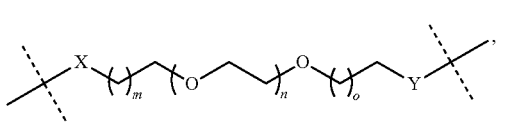

Formula B wherein X is C=O or $CH_2$,
Y is C=O or $CH_2$,
m is 0-15,
n is 0-6, and
o is 0-15; or

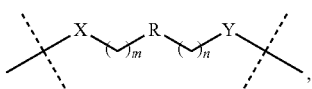

Formula C wherein
X is C=O or CH$_2$,
Y is C=O or CH$_2$,
R is —CH$_2$—, —CF$_2$—, —CH(C$_{1-3}$ alkyl)-, —C(C$_{1-3}$ alkyl)(C$_{1-3}$ alkyl)-, —CH=CH—, —C(C$_{1-3}$ alkyl)=C(C$_{1-3}$ alkyl)-, —C≡C—, —O—, —NH—, —N(C$_{1-3}$ alkyl)-, —C(O)NH—, —C(O)N(C$_{1-3}$ alkyl)-, a 3-13 membered ring, a 3-13 membered fused ring, a 3-13 membered bridged ring, and/or a 3-13 membered spiro ring,
m is 0-15, and
n is 0-15.

In some embodiments of Formula C, R is a 3-13 membered ring, a 3-13 membered fused ring, a 3-13 membered bridged ring, and/or a 3-13 membered spiro ring, one or more of which can contain one or more heteroatoms.

In some embodiments of Formula C, R has a structure of

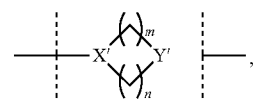

Formula V

X' = N or CH
Y' = N or CH
m = 0-5
n = 0-5

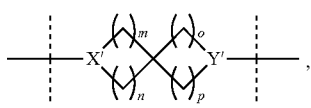

Formula W

X' = N or CH
Y' = N or CH
m = 0-5
n = 0-5
o = 0-5
p = 0-5

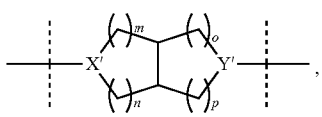

Formula X

X' = N or CH
Y' = N or CH
m = 0-5
n = 0-5
o = 0-5
p = 0-5

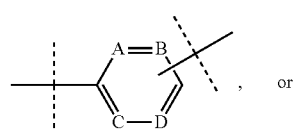

Formula Y

A = CH, C(C$_{1-3}$ alkyl), or N
B = CH, C(C$_{1-3}$ alkyl), or N
C = CH, C(C$_{1-3}$ alkyl), or N
D = CH, C(C$_{1-3}$ alkyl), or N or

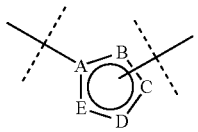

Formula Z

A = C, CH, C(C$_{1-3}$ alkyl), N, NH, N(C$_{1-3}$ alkyl), O, S
B = C, CH, C(C$_{1-3}$ alkyl), N, NH, N(C$_{1-3}$ alkyl), O, S
C = C, CH, C(C$_{1-3}$ alkyl), N, NH, N(C$_{1-3}$ alkyl), O, S
D = C, CH, C(C$_{1-3}$ alkyl), N, NH, N(C$_{1-3}$ alkyl), O, S In some aspects, the bivalent compound is a compound selected from XY028-082, XY028-003, XY028-004, XY028-005, XY019-098, XY028-006, XY028-007, XY028-008, XY028-009, XY028-085, XY028-084, XY028-083, XY028-132, XY028-133, XY019-106, XY028-162, XY028-163, XY028-002, XY028-114, XY028-097, XY019-108, XY028-105, XY028-106, XY028-140, XY028-141, XY028-142, XY028-143, XY028-144, XY028-145, YX26-56, YX26-66, YX26-58, YX30-108, YX30-107, YX30-85, YX30-86, YX30-117, YX30-118, YX30-126, YX30-125, XY028-186, YX33-29, YX33-31, YX33-74, YX33-94, YX33-108, YX33-96, YX33-97, YX33-109, YX33-110, YX33-112, YX33-123, YX35-48, YX39-47, YX39-48, YX39-56, YX39-65, YX39-74, YX39-123, YX39-124, YX39-147, YX44-18, YX44-19, YX44-22, YX44-46, YX44-48, YX44-78, YS36-95, YS36-60, YS36-61, YS36-62, YS36-63, YS36-64, YS36-65, YS36-66, YS36-67, YS36-68, YS36-69, YS36-70, YS36-71, and compound examples 80-135, or analogs thereof.

In some aspects, the document provides a method of treating a cyclin-dependent kinase 4/6 (CDK4/6)-mediated cancer, the method including administering to a subject in need thereof with a CDK4/6-mediated cancer one or more bivalent compounds including a CDK4/6 ligand conjugated to a degradation/disruption tag. The CDK4/6-mediated cancer may be a cancer which overexpresses cyclin-dependent kinase 4 (CDK4) and/or cyclin-dependent kinase 6 (CDK6) relative to a wild-type tissue of the same species and tissue type. The CDK4/6-mediated cancer can have elevated CDK4 and/or CDK6 enzymatic activity relative to a wild-type tissue of the same species and tissue type. Non-limiting examples of CDK4/6-mediated cancer include mesothelioma, hepatocellular cancer, central nervous system neoplasm, lung cancer, bone cancer, pancreatic cancer, skin cancer, head and neck cancer, melanoma, ovarian cancer, colon cancer, rectal cancer, anal cancer, stomach cancer, gastrointestinal cancer, breast cancer (e.g., estrogen receptor positive (ER+) breast cancer), uterine cancer, fallopian tube cancer, endometrial cancer, cervical cancer, vaginal cancer, vulvar cancer, esophageal cancer, gastrointestinal cancer, endocrine cancer, thyroid cancer, parathyroid cancer, adrenal cancer, soft tissue sarcoma, urethral cancer, penile cancer, prostate cancer, testicular cancer, leukemia, lymphoma, bladder cancer, renal cell cancer, brain stem glioma, pituitary cancer, adrenocortical cancer, gallbladder cancer, multiple myeloma, cholangiocarcinoma, fibrosarcoma, neuroblastoma, and/or retinoblastoma. The CDK4/6-mediated cancer can be a relapsed cancer. The CDK4/6-mediated cancer can have been refractory to one or more previous treatments.

In any of the above-described methods, the bivalent compounds can be XY028-082, XY028-003, XY028-004, XY028-005, XY019-098, XY028-006, XY028-007, XY028-008, XY028-009, XY028-085, XY028-084, XY028-083, XY028-132, XY028-133, XY019-106, XY028-162, XY028-163, XY028-002, XY028-114, XY028-097, XY019-108, XY028-105, XY028-106, XY028-140, XY028-141, XY028-142, XY028-143, XY028-144, XY028-145, YX26-56, YX26-66, YX26-58, YX30-108, YX30-107, YX30-85, YX30-86, YX30-117, YX30-118, YX30-126, YX30-125, XY028-186, YX33-29, YX33-31, YX33-74, YX33-94, YX33-108, YX33-96, YX33-97, YX33-109, YX33-110, YX33-112, YX33-123, YX35-48, YX39-47, YX39-48, YX39-56, YX39-65, YX39-74, YX39-123, YX39-124, YX39-147, YX44-18, YX44-19, YX44-22, YX44-46, YX44-48, YX44-78, YS36-95, YS36-60, YS36-61, YS36-62, YS36-63, YS36-64, YS36-65, YS36-66, YS36-67, YS36-68, YS36-69, YS36-70, YS36-71, and compound examples 80-135, or analogs thereof.

In some embodiments of the disclosed methods, the bivalent compounds can be administered, e.g., orally, parenterally, intradermally, subcutaneously, topically, and/or rectally.

Any of the above-described methods can further include treating the subject with one or more additional therapeutic regimens for treating cancer. The one or more additional therapeutic regimens for treating cancer can be, e.g., one or more of surgery, chemotherapy, radiation therapy, hormone therapy, or immunotherapy.

The document additionally provides a method for identifying a bivalent compound which mediates degradation/disruption of CDK4 and/or CDK6, the method including providing a heterobifunctional test compound including a CDK4/6 ligand conjugated to a degradation/disruption tag, contacting the heterobifunctional test compound with a cell (e.g., a cancer cell such as a CDK4/6-mediated cancer cell) including a ubiquitin ligase and at least one of CDK4 and CDK6. The method can include determining whether CDK4 or CDK6 levels decrease in the cell, and (i) identifying the heterobifunctional test compound as a bivalent compound which mediates degradation/reduction of CDK4 if CDK4 levels decrease in the cell and CDK6 levels do not decrease in the cell, (ii) identifying the heterobifunctional test compound as a bivalent compound which mediates degradation/reduction of CDK6 if CDK6 levels decrease in the cell and CDK4 levels do not decrease in the cell, or (iii) identifying the heterobifunctional test compound as a bivalent compound which mediates degradation/reduction of CDK4 and CDK6 if both CDK4 and CDK6 levels decrease in the cell.

As used herein, the terms "about" and "approximately" are defined as being within plus or minus 10% of a given value or state, preferably within plus or minus 5% of said value or state.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DETAILED DESCRIPTION

Figure 1:
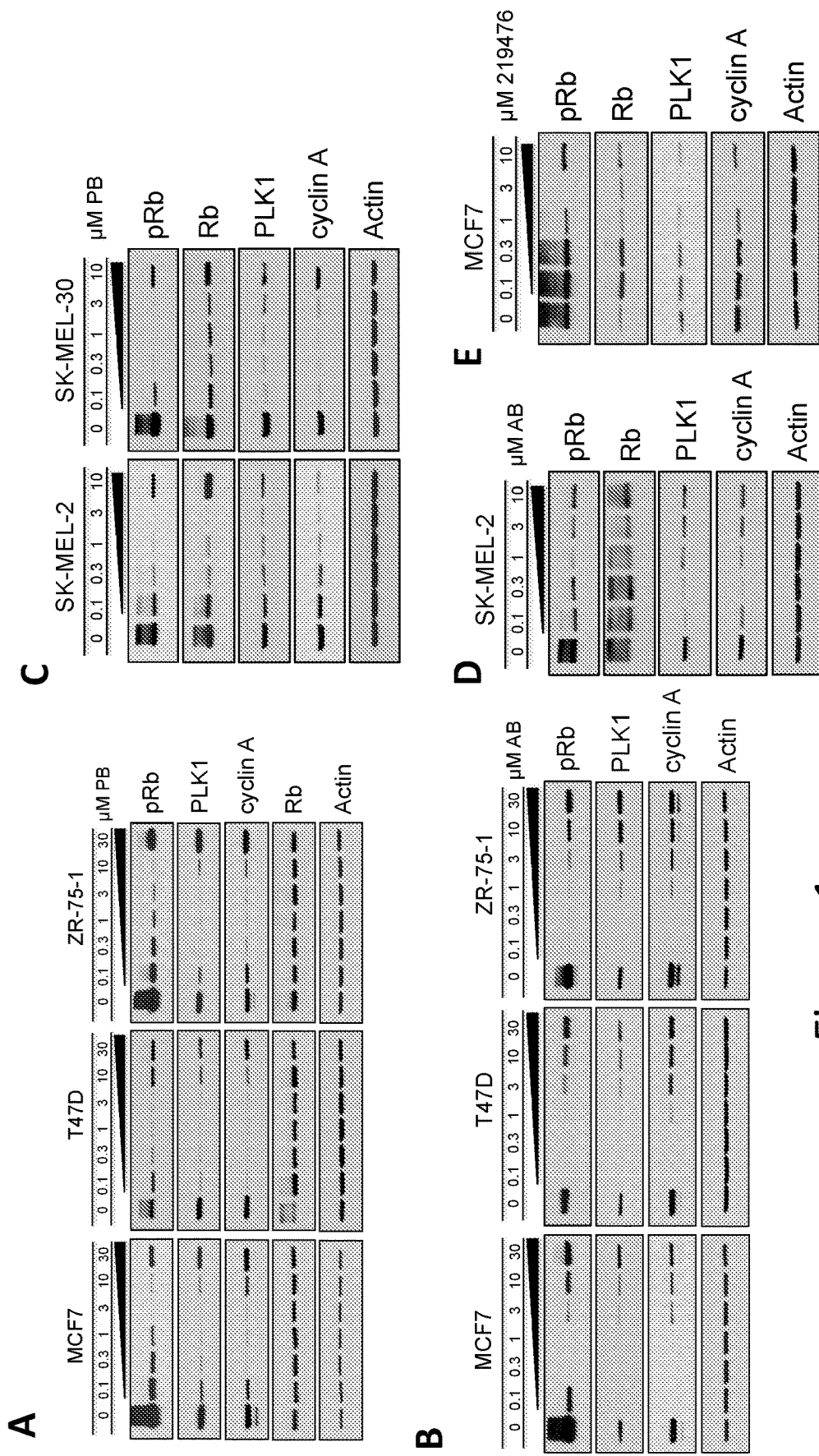
FIG. 1 is a series of Western blots showing the effect of various CDK4/6 inhibitors on CDK4/6 activity (as evidenced by Rb phosphorylation (pRb level)) and expression of Rb/E2F downstream targets PLK1 and cyclin A at different concentrations. palbociclib (PB)-treated breast cancer cells (A); abemaciclib (AB)-treated breast cancer cells (B); PB-treated melanoma cells (C); AB-treated melanoma cells (D); 219476-treated breast cancer cells (E).

The present disclosure is based, in part, on the discovery that novel heterobifunctional small molecules which selectively degrade CDK4, CDK6, or both CDK4 and CDK6 ("PROteolysis TArgeting Chimeras" or "PROTACs") are useful in the treatment of CDK4/6-mediated cancers, particularly estrogen receptor (ER) positive (ER+) breast cancer.

Successful strategies for selective degradation/disruption of the target protein induced by a small molecule include recruiting an E3 ubiquitin ligase and mimicking protein misfolding with a hydrophobic tag (Buckley and Crews, 2014). PROTACs are bivalent inhibitors with one moiety that binds an E3 ubiquitin ligase and another moiety that binds the protein target of interest (Buckley and Crews, 2014). The induced proximity leads to ubiquitination of the target followed by their degradation at proteasome. Two types of high affinity small-molecule E3 ligase ligands have been identified/developed: immunomodulatory drugs (IMiDs) such as thalidomide and pomalidomide, which bind cereblon (CRBN or CRL4CRBN), a component of a cullin-RING ubiquitin ligase (CRL) complex (Ito et al., 2010; Chamberlain et al., 2014; Fischer et al., 2014; Bondeson et al., 2015; Winter et al., 2015); and VHL-1, a hydroxyproline-containing ligand, which binds van Hippel-Lindau protein (VHL or CRL2VHL), a component of another CRL complex (Buckley et al., 2012; Buckley et al., 2012; Galdeano et al., 2014; Bondeson et al., 2015; Zengerle et al., 2015). The PROTAC technology has been successfully applied to degradation of multiple targets (Bondeson et al., 2015; Buckley et al., 2015; Lu et al., 2015; Winter et al., 2015; Zengerle et al., 2015; Lai et al., 2016), but not to degradation of CDK4/6. In addition, a hydrophobic tagging approach, which utilizes a bulky and hydrophobic adamantyl group, has been developed to mimic protein misfolding, leading to the degradation of the target protein by proteasome (Buckley and Crews, 2014). This approach has also been successfully applied to selective degradation of the pseudokinase Her3 (Xie et al., 2014), but not to degradation of CDK4/6.

As discussed in the following examples, this disclosure provides specific examples of novel CDK4/6 degraders/disruptors, and examined the effect of exemplary degraders/disruptors in inhibiting/disrupting CDK4/6 activity, suppressing CDK4/6 expression, and inhibiting cancer cell proliferation. The results indicated that these novel small molecules can be beneficial in treating cancer, especially breast cancer, melanoma, and lung cancer.

A number of selective small-molecule CDK4/6 catalytic inhibitors, such as palbociclib, abemaciclib, ribociclib, trilaciclib (G1T28), G1T38, and SHR6390, have recently been discovered. Some of these inhibitors have been in clinical trials for treating ER+ breast cancer. However, these inhibitors have exhibited very limited success when administered alone; rather, they must be co-administered with a second therapy such as endocrine therapy, causing increased off-target effects and toxicity. Further, even when co-administered with a second therapy, the majority of patients treated in the trials have developed resistance as early as 14 months.

Surprisingly, it was discovered that in addition to toxicity issues, CDK4/6 inhibitors weren't even able to suppress CDK4/6 activity when they were administered at high concentrations (Example 5, FIG. 1). In fact, there was a positive correlation between palbociclib or abemaciclib concentration and expression of the Rb/E2F downstream targets PLK1 and cyclin A (Example 6, FIGS. 2 and 3), and a corresponding inverse correlation between inhibitor concentration and suppression of cell cycle progression (Example 7, FIG. 4). It was found that this was because, although CDK4/6 inhibitors are able to inhibit the activity of CDK4 and CDK6, the inhibitors actually (unexpectedly) upregulate the expression of both CDK4 and CDK6, with a positive correlation between inhibitor concentration and CDK4/6 expression (Example 8, FIG. 5). CDK4/6 inhibitors don't upregulate the expression of CDK4 and CDK6 at the mRNA level (Example 8, FIGS. 6 and 7); rather, the inhibitors protect CDK4/6 from degradation by blocking them from ubiquitination (Example 9, FIG. 8). Consistent with the above results, increased CDK4/6 expression was associated with decreased CDK4/6 inhibitor efficacy (Example 10, FIG. 9). This indicates that CDK4/6 inhibitors only have a narrow window of activity and suggests that if cancer cells develop resistance to the inhibitors, inhibitor dosage cannot simply be increased to overcome the resistance.

Current drugs targeting CDK4/6 generally focus on inhibition of its catalytic function. Here, a different approach was taken: to develop compounds that directly and selectively target not only the catalytic function of CDK4/6, but also their level of expression at the protein level. Strategies for inducing protein degradation include recruiting E3 ubiquitin ligases, mimicking protein misfolding with hydrophobic tags, and inhibiting chaperones. For example, a thalidomide-JQ1 bivalent compound has been used to hijack the cereblon E3 ligase, inducing highly selective BET protein degradation in vitro and in vivo and resulting in a demonstrated delay in leukemia progression in mice (Winter et al., 2015). Similarly, BET protein degradation has also been induced via another E3 ligase, VHL (Zengerle et al., 2015). Partial degradation of Her3 has been induced using an adamantane-modified compound (Xie et al., 2014). Such an approach, based on the use of bivalent small molecule compounds, permits more flexible regulation of protein expression in vitro and in vivo compared with techniques such as gene knockout or shRNA knockdown. Unlike gene knockout or shRNA knockdown, a small molecule approach further provides an opportunity to study dose and time dependency in a disease model through varying the concentrations and frequencies of administration of the relevant small molecule.

PROTACs

In some aspects, the present disclosure provides bivalent compounds, also referred to herein as PROTACs, comprising a CDK4/6 ligand (or targeting moiety) conjugated to a degradation tag. Linkage of the CDK4/6 ligand to the degradation tag can be direct, or indirect via a linker.

As used herein, the terms "cyclin-dependent kinase 4/6 (CDK4/6) ligand" or "CDK4/6 ligand" or "CDK4/6 targeting moiety" are to be construed broadly, and encompass a wide variety of molecules ranging from small molecules to large proteins that associates with or binds to CDK4, CDK6, or both CDK4 and CDK6. The CDK4/6 ligand or targeting moiety can be, for example, a small molecule compound (i.e., a molecule of molecular weight less than about 1.5 kilodaltons (kDa)), a peptide or polypeptide, nucleic acid or oligonucleotide, carbohydrate such as oligosaccharides, or an antibody or fragment thereof.

The CDK4/6 ligand or targeting moiety can be a CDK4/6 inhibitor (e.g., abemaciclib, palbociclib, ribociclib, trilaciclib (G1T28), G1T38, SHR6390, and analogs thereof) which is capable of interfering with the enzymatic activity of CDK4, CDK6, or both CDK4 and CDK6. As used herein, an "inhibitor" refers to an agent that restrains, retards, or otherwise causes inhibition of a physiological, chemical or enzymatic action or function. An inhibitor can cause an at least 5% decrease in enzyme activity. An inhibitor can also or alternately refer to a drug, compound, or agent that prevents or reduces the expression, transcription, or translation of a gene or protein. An inhibitor can reduce or prevent the function of a protein, e.g., by binding to or activating/inactivating another protein or receptor.

Exemplary CDK4/6 ligands include, but are not limited to, the compounds shown below.

I

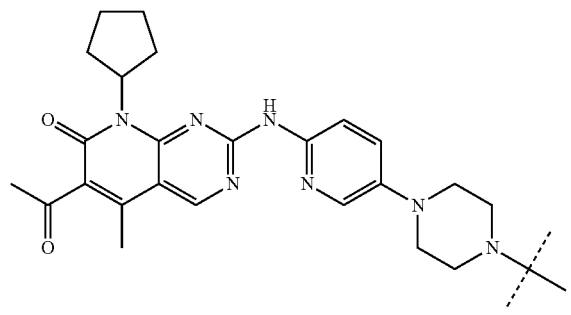

II

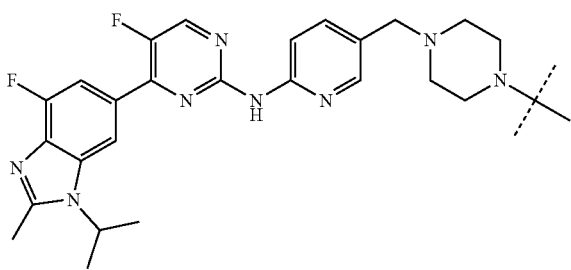

III

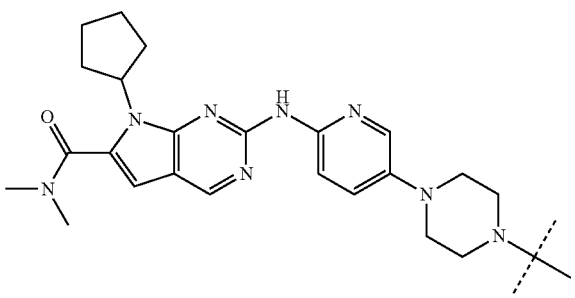

-continued

IV

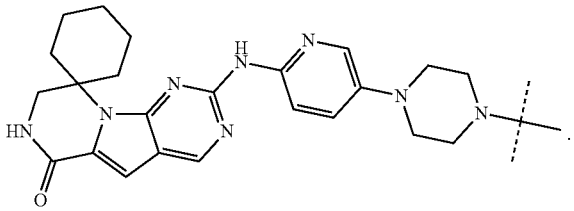

As used herein, the term "degradation/disruption tag" refers to a compound which associates with or binds to a ubiquitin ligase for recruitment of the corresponding ubiquitination machinery to CDK4, CDK6, or both CDK4 and CDK6 or induces CDK4, CDK6, or both CDK4 and CDK6 protein misfolding and subsequent degradation at the proteasome or loss of function.

In some aspects, the degradation/disruption tags of the present disclosure include, e.g., thalidomide, pomalidomide, lenalidomide, VHL-1, adamantane, 1-((4,4,5,5,5-pentafluoropentyl)sulfinyl)nonane, nutlin-3a, RG7112, RG7338, AMG 232, AA-115, bestatin, MV-1, LCL161, and/or analogs thereof.

As used herein, a "linker" is a bond, molecule, or group of molecules that binds two separate entities to one another. Linkers can provide for optimal spacing of the two entities. The term "linker" in some aspects refers to any agent or molecule that bridges the CDK4/6 ligand to the degradation/disruption tag. One of ordinary skill in the art recognizes that sites on the CDK4/6 ligand or the degradation/disruption tag, which are not necessary for the function of the PROTACs of the present disclosure, are ideal sites for attaching a linker, provided that the linker, once attached to the conjugate of the present disclosures, does not interfere with the function of the PROTAC, i.e., its ability to target CDK4/6 and recruit a ubiquitin ligase.

The length of the linker of the bivalent compound can be adjusted to minimize the molecular weight of the disruptors/degraders and avoid the clash of the CDK4/6 ligand or targeting moiety with the ubiquitin ligase or induce CDK4/6 misfolding by the hydrophobic tag at the same time.

In some embodiments, the degradation/disruption tags of the present disclosure include, for example, thalidomide, pomalidomide, lenalidomide, VHL-1, adamantane, 1-((4,4,5,5,5-pentafluoropentyl)sulfinyl)nonane, nutlin-3a, RG7112, RG7338, AMG 232, AA-115, bestatin, MV-1, LCL161, and analogs thereof. The degradation/disruption tags can be attached to each portion of interest in the structure of a CDK4/6 ligand or targeting moiety (e.g., abemaciclib, palbociclib, ribociclib, trilaciclib (G1T28), G1T38, or SHR6390) with linkers of different types and lengths in order to generate effective bivalent compounds. In particular, attaching thalidomide to either portion of the molecule can recruit the cereblon E3 ligase to CDK4/6 without causing destructive steric interactions with the CDK4/6/HSP90/CDC37 complex.

The bivalent compounds disclosed herein can selectively affect CDK4/6-mediated cancer cells (e.g., ER+ cells) compared to WT cells (i.e., a CDK4/6 degrader disruptor able to kill or inhibit the growth of a CDK4/6-mediated cancer cell while also having a relatively low ability to lyse or inhibit the growth of a WT cell), e.g., possess a $GI_{50}$ for one or more CDK4/6-mediated cancer cells more than 1.5-fold lower, more than 2-fold lower, more than 2.5-fold lower, more than 3-fold lower, more than 4-fold lower, more than 5-fold lower, more than 6-fold lower, more than 7-fold lower, more than 8-fold lower, more than 9-fold lower, more than 10-fold lower, more than 15-fold lower, or more than 20-fold lower than its $GI_{50}$ for one or more WT cells, e.g., WT cells of the same species and tissue type as the CDK4/6-mediated cancer cells.

Additional bivalent compounds (i.e., CDK4/6 degraders/disruptors) can be developed using the principles and methods disclosed herein. For example, other linkers, degradation tags, and CDK4/6 binding/inhibiting moieties (not limited to abemaciclib, palbociclib, ribociclib, trilaciclib (G1T28), G1T38, and SHR6390) can be synthesized and tested. Non-limiting examples of CDK4/6 disruptors/degraders (e.g., bivalent compounds) are shown in Table 1 (below). The left portion of the CDK4/6 disruptors/degraders bind to CDK4/6 (as abemaciclib, palbociclib, ribociclib, trilaciclib (G1T28), G1T38, and SHR6390 do), and the right portion recruits for the ubiquitination machinery to CDK4/6, which induces the poly-ubiquitination and degradation of CDK4 and CDK6, or induces CDK4/6 misfolding and subsequent loss of function or degradation at the proteasome.

Non-limiting examples of bivalent compounds are set forth in Table 1, below.

TABLE 1

| Cpd. Example Number | Cpd. Code | Structure | Chemical Name |
|---|---|---|---|
| 1 | XY028-082 | 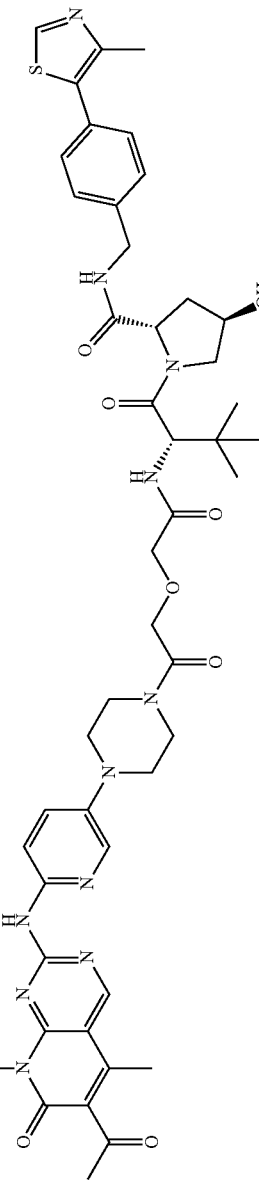 | (2S,4R)-1-((S)-2-(2-(2-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-2-oxoethoxy)acetamido)-3,3-dimethylbutanoyl)-4-hydroxy-N-(4-(4-methylthiazol-5-yl)benzyl)pyrrolidine-2-carboxamide |
| 2 | XY028-003 | 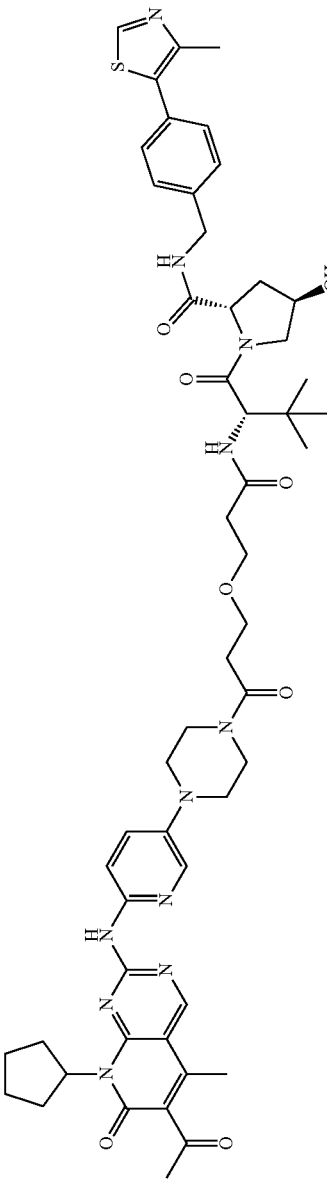 | (2S,4R)-1-((S)-2-(3-(3-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-3-oxopropoxy)propanamido)-3,3-dimethylbutanoyl)-4-hydroxy-N-(4-(4-methylthiazol-5-yl)benzyl)pyrrolidine-2-carboxamide |

TABLE 1-continued
| Cpd. Example Number | Cpd. Code | Structure | Chemical Name |
|---|---|---|---|
| 3 | XY028-004 | 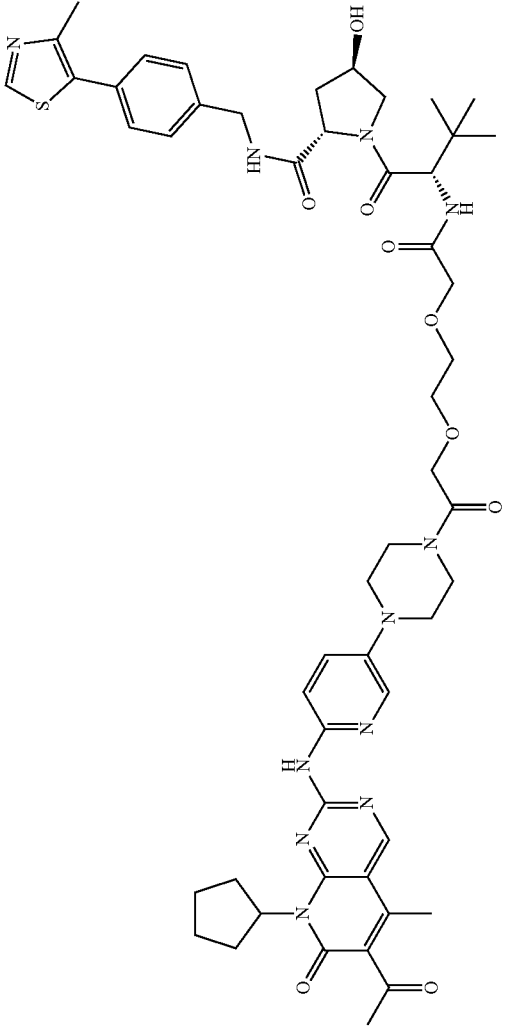 | (2S,4R)-1-((S)-2-(2-(2-(2-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-2-oxoethoxy)ethoxy)acetamido)-3,3-dimethylbutanoyl)-4-hydroxy-N-(4-(4-methylthiazol-5-yl)benzyl)pyrrolidine-2-carboxamide |

TABLE 1-continued

| Cpd. Example Number | Cpd. Code | Structure | Chemical Name |
|---|---|---|---|
| 4 | XY028-005 | 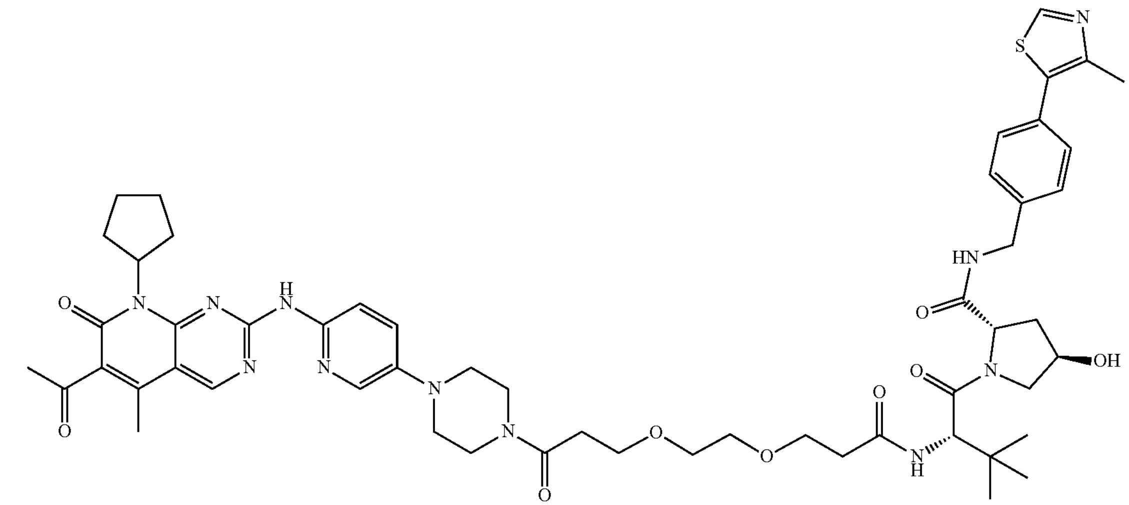 [SMILES: CC(=O)c1c(C)c2cnc(Nc3ccc(N4CCN(C(=O)CCOCCOCCC(=O)N[C@H](C(=O)N5C[C@H](O)C[C@H]5C(=O)NCc5ccc(-c6scnc6C)cc5)C(C)(C)C)CC4)cn3)nc2n(C2CCCC2)c1=O] | (2S,4R)-1-((S)-2-(3-(2-(3-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-3-oxopropoxy)ethoxy)propanamido)-3,3-dimethylbutanoyl)-4-hydroxy-N-(4-(4-methylthiazol-5-yl)benzyl)pyrrolidine-2-carboxamide |
| 5 | XY019-098 | 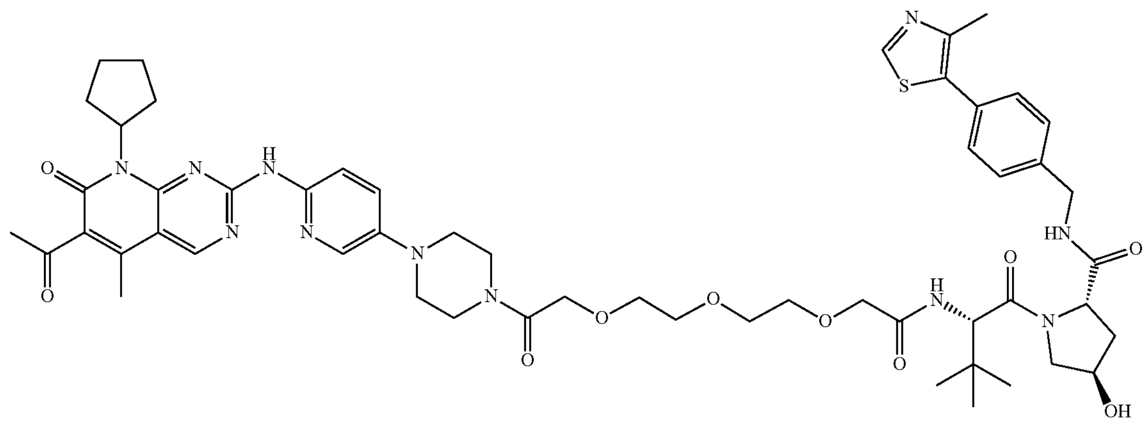 [SMILES: CC(=O)c1c(C)c2cnc(Nc3ccc(N4CCN(C(=O)COCCOCCOCC(=O)N[C@H](C(=O)N5C[C@H](O)C[C@H]5C(=O)NCc5ccc(-c6scnc6C)cc5)C(C)(C)C)CC4)cn3)nc2n(C2CCCC2)c1=O] | (2S,4R)-1-((S)-14-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-2-(tert-butyl)-4,14-dioxo-6,9,12-trioxa-3-azatetradecanoyl)-4-hydroxy-N-(4-(4-methylthiazol-5-yl)benzyl)pyrrolidine-2-carboxamide |

| Cpd. Example Number | Cpd. Code | Structure | Chemical Name |
|---|---|---|---|
| 6 | XY028-006 | 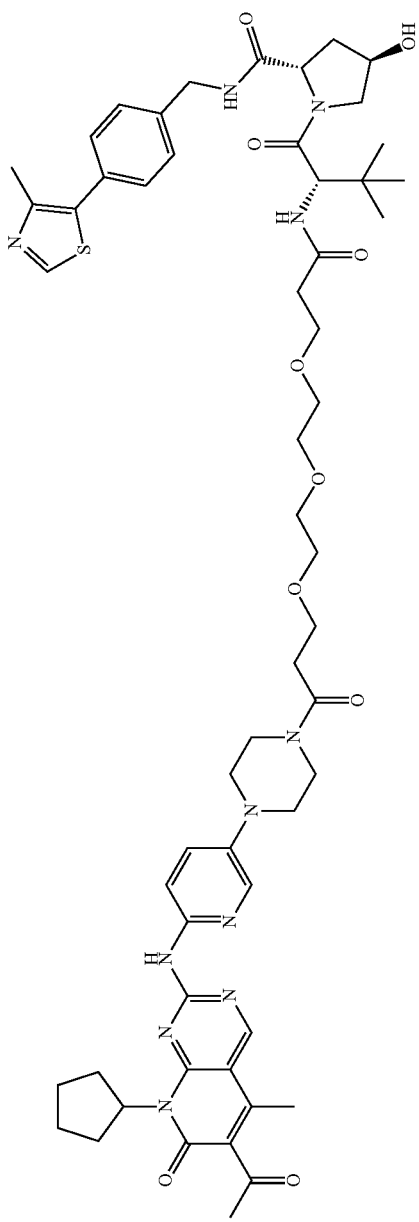 | (2S,4R)-1-((S)-16-(4-(6-((6-acetyl-8-cyclopentyl-5-methyl-7-oxo-7,8-dihydropyrido[2,3-d]pyrimidin-2-yl)aminopyridin-3-yl)piperazin-1-yl)-2-(tert-butyl)-4,16-dioxo-7,10,13-trioxa-3-azahexadecanoyl)-4-hydroxy-N-(4-(4-methylthiazol-5-yl)benzyl)pyrrolidine-2-carboxamide |
| 7 | XY028-007 | 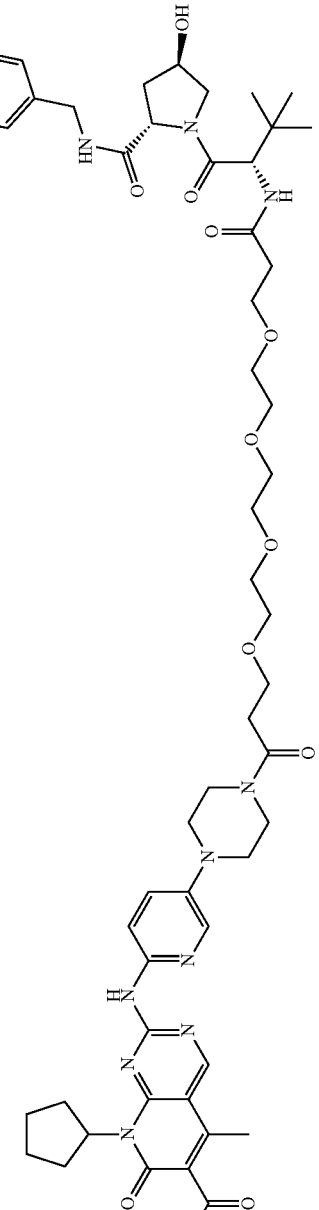 | (2S,4R)-1-((S)-19-(4-(6-((6-acetyl-8-cyclopentyl-5-methyl-7-oxo-7,8-dihydropyrido[2,3-d]pyrimidin-2-yl)aminopyridin-3-yl)piperazin-1-yl)-2-(tert-butyl)-4,19-dioxo-7,10,13,16-tetraoxa-3-azanonadecanoyl)-4-hydroxy-N-(4-(4-methylthiazol-5-yl)benzyl)pyrrolidine-2-carboxamide |

TABLE 1-continued

| Cpd. Example Number | Cpd. Code | Structure | Chemical Name |
|---|---|---|---|
| 8 | XY028-008 | 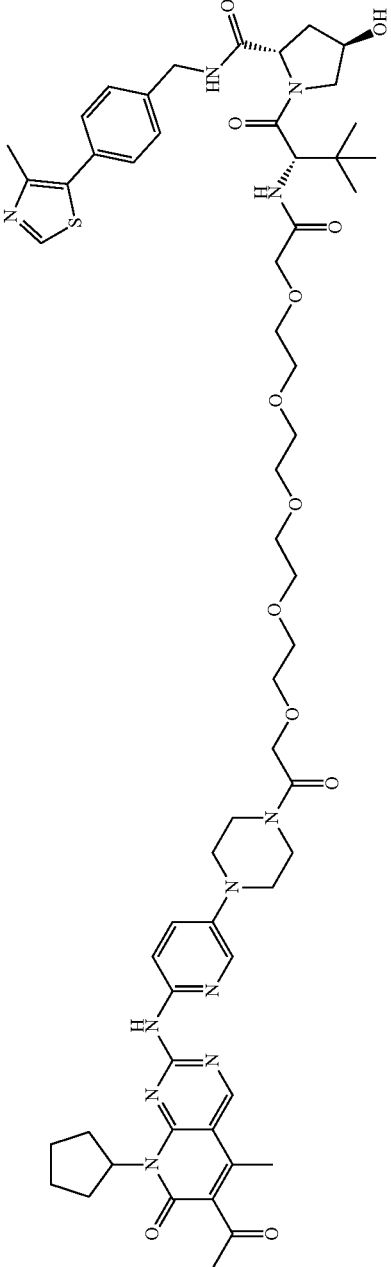 | (2S,4R)-1-((S)-20-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-2-(tert-butyl)-4,20-dioxo-6,9,12,15,18-pentaoxa-3-azaicosanoyl)-4-hydroxy-N-(4-(4-methylthiazol-5-yl)benzyl)pyrrolidine-2-carboxamide |
| 9 | XY028-009 | 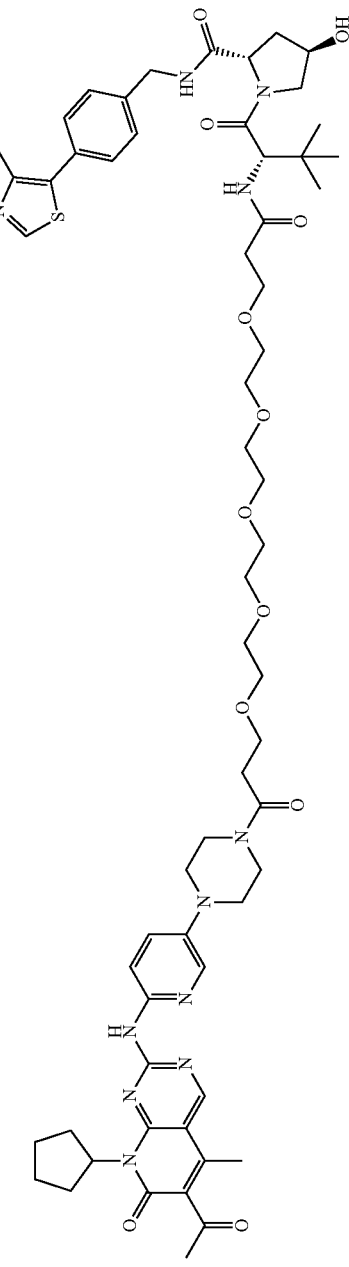 | (2S,4R)-1-((S)-22-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-2-(tert-butyl)-4,22-dioxo-7,10,13,16,19-pentaoxa-3-azadocosanoyl)-4-hydroxy-N-(4-(4-methylthiazol-5-yl)benzyl)pyrrolidine-2-carboxamide |

TABLE 1-continued

| Cpd. Example Number | Cpd. Code | Structure | Chemical Name |
|---|---|---|---|
| 10 | XY028-085 | 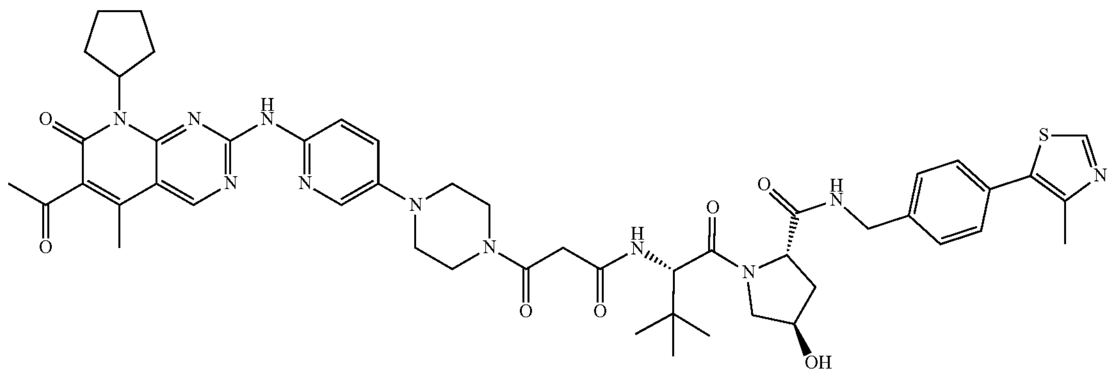 [SMILES: CC(=O)c1c(C)c2cnc(Nc3ccc(N4CCN(C(=O)CC(=O)N[C@H](C(=O)N5C[C@H](O)C[C@H]5C(=O)NCc5ccc(-c6scnc6C)cc5)C(C)(C)C)CC4)cn3)nc2n(C2CCCC2)c1=O] | (2S,4R)-1-((S)-2-(3-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-3-oxopropanamido)-3,3-dimethylbutanoyl)-4-hydroxy-N-(4-(4-methylthiazol-5-yl)benzyl)pyrrolidine-2-carboxamide |
| 11 | XY028-084 | 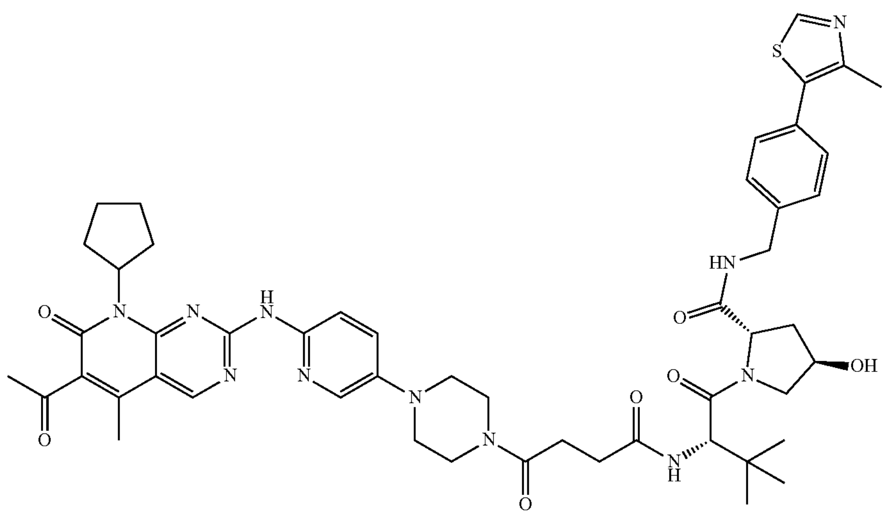 [SMILES: CC(=O)c1c(C)c2cnc(Nc3ccc(N4CCN(C(=O)CCC(=O)N[C@H](C(=O)N5C[C@H](O)C[C@H]5C(=O)NCc5ccc(-c6scnc6C)cc5)C(C)(C)C)CC4)cn3)nc2n(C2CCCC2)c1=O] | (2S,4R)-1-((S)-2-(4-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-4-oxobutanamido)-3,3-dimethylbutanoyl)-4-hydroxy-N-(4-(4-methylthiazol-5-yl)benzyl)pyrrolidine-2-carboxamide |

TABLE 1-continued

| Cpd. Example Number | Cpd. Code | Structure | Chemical Name |
|---|---|---|---|
| 12 | XY028-083 | 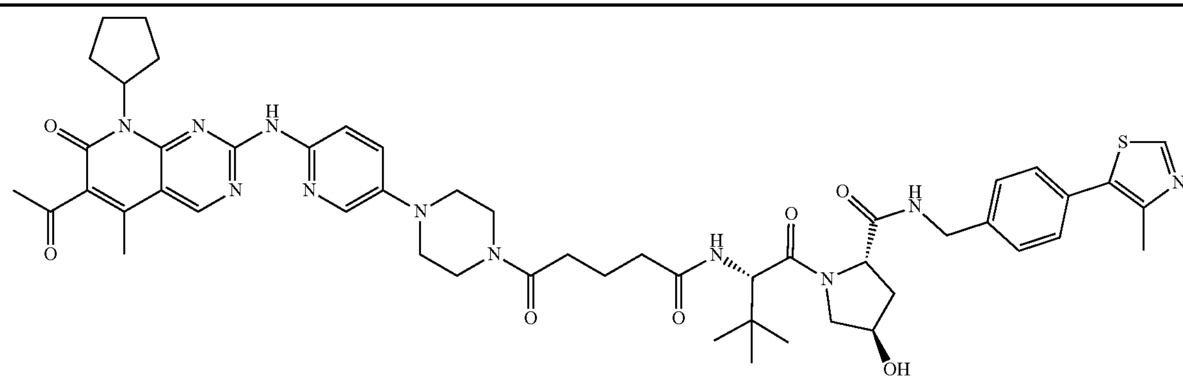 | (2S,4R)-1-((S)-2-(5-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-5-oxopentanamido)-3,3-dimethylbutanoyl)-4-hydroxy-N-(4-(4-methylthiazol-5-yl)benzyl)pyrrolidine-2-carboxamide |
| 13 | XY028-132 | 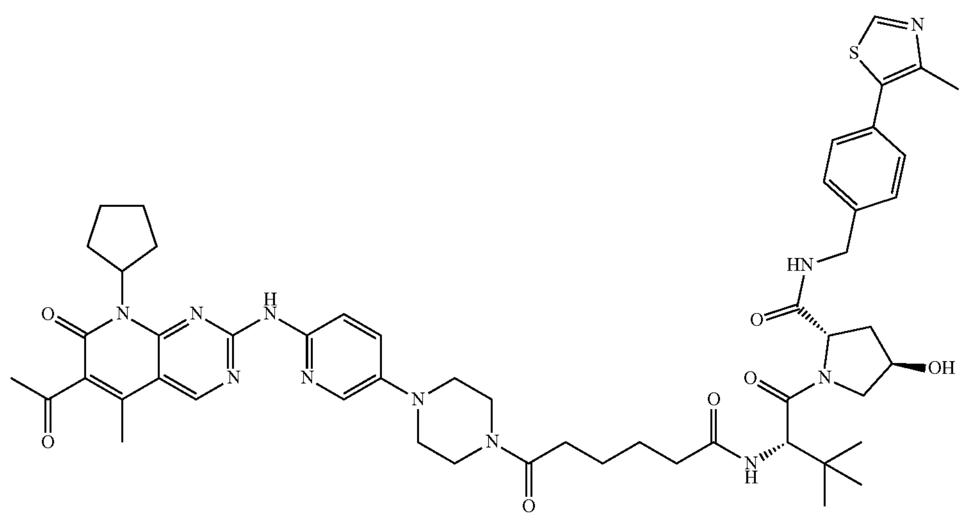 [SMILES: CC(=O)c1c(C)c2cnc(Nc3ccc(N4CCN(C(=O)CCCCC(=O)N[C@H](C(=O)N5C[C@H](O)C[C@H]5C(=O)NCc5ccc(-c6scnc6C)cc5)C(C)(C)C)CC4)cn3)nc2n(C2CCCC2)c1=O] | (2S,4R)-1-((S)-2-(6-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-6-oxohexanamido)-3,3-dimethylbutanoyl)-4-hydroxy-N-(4-(4-methylthiazol-5-yl)benzyl)pyrrolidine-2-carboxamide |

TABLE 1-continued

| Cpd. Example Number | Cpd. Code | Structure | Chemical Name |
|---|---|---|---|
| 14 | XY028-133 | 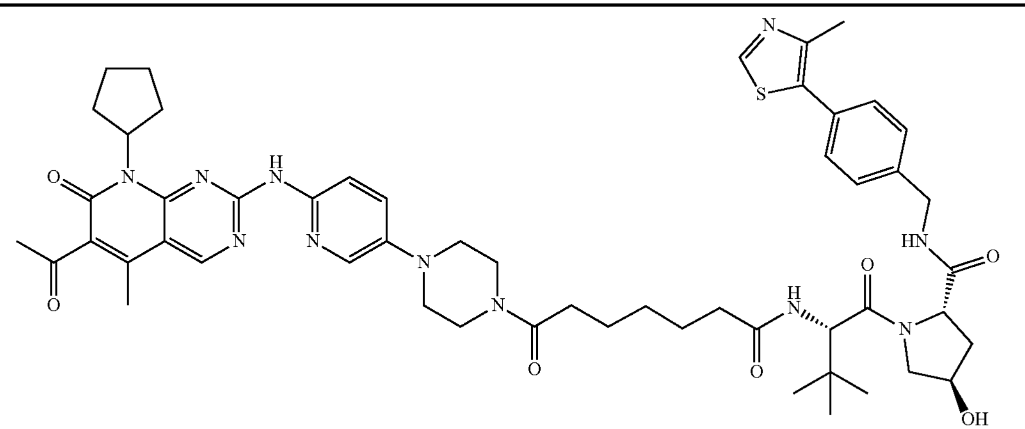 | (2S,4R)-1-((S)-2-(7-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-7-oxoheptanamido)-3,3-dimethylbutanoyl)-4-hydroxy-N-(4-(4-methylthiazol-5-yl)benzyl)pyrrolidine-2-carboxamide |
| 15 | XY019-106 | 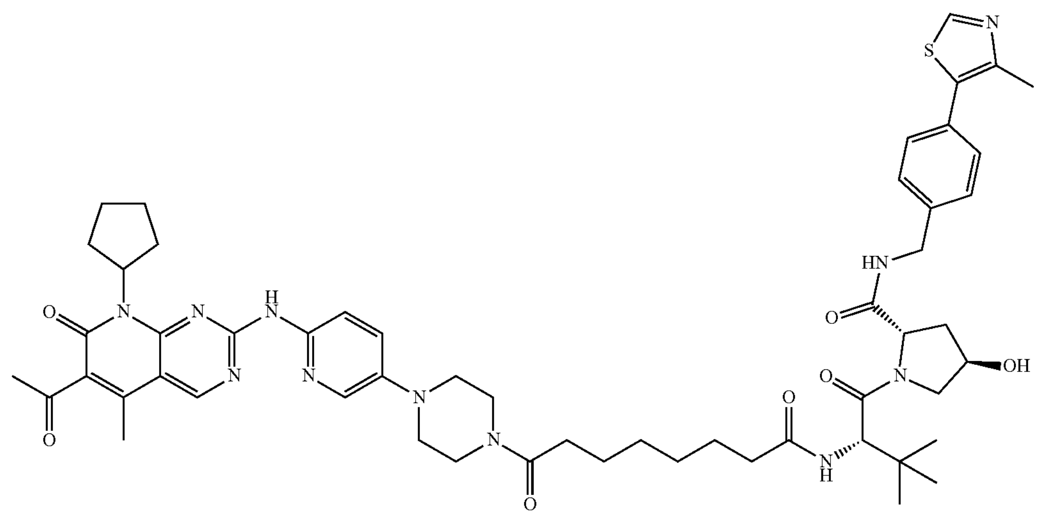 [SMILES: CC(=O)c1c(C)c2cnc(Nc3ccc(N4CCN(C(=O)CCCCCCC(=O)N[C@H](C(=O)N5C[C@H](O)C[C@H]5C(=O)NCc5ccc(-c6scnc6C)cc5)C(C)(C)C)CC4)cn3)nc2n(C2CCCC2)c1=O] | (2S,4R)-1-((S)-2-(8-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-8-oxooctanamido)-3,3-dimethylbutanoyl)-4-hydroxy-N-(4-(4-methylthiazol-5-yl)benzyl)pyrrolidine-2-carboxamide |

TABLE 1-continued

| Cpd. Example Number | Cpd. Code | Structure | Chemical Name |
|---|---|---|---|
| 16 | XY028-162 | 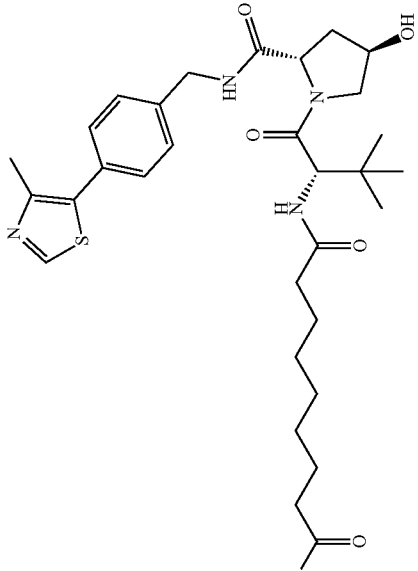 | (2S,4R)-1-((S)-2-(9-(4-(6-((6-acetyl-8-cyclopentyl-5-methyl-7-oxo-7,8-dihydropyrido[2,3-d]pyrimidin-2-yl)aminopyridin-3-yl)piperazin-1-yl)-9-oxononanamido)-3,3-dimethylbutanoyl)-4-hydroxy-N-(4-(4-methylthiazol-5-yl)benzyl)pyrrolidine-2-carboxamide |
| 17 | XY028-163 | 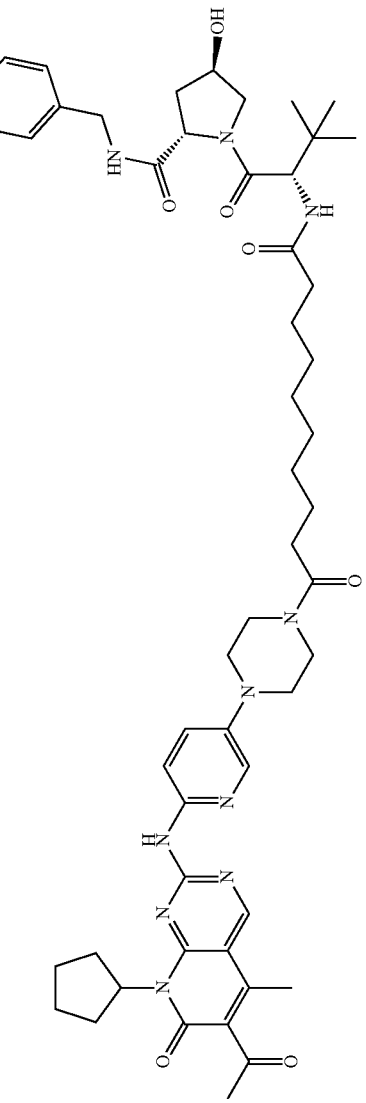 | (2S,4R)-1-((S)-2-(10-(4-(6-((6-acetyl-8-cyclopentyl-5-methyl-7-oxo-7,8-dihydropyrido[2,3-d]pyrimidin-2-yl)aminopyridin-3-yl)piperazin-1-yl)-10-oxodecanamido)-3,3-dimethylbutanoyl)-4-hydroxy-N-(4-(4-methylthiazol-5-yl)benzyl)pyrrolidine-2-carboxamide |

TABLE 1-continued

| Cpd. Example Number | Cpd. Code | Structure | Chemical Name |
|---|---|---|---|
| 18 | XY028-002 | 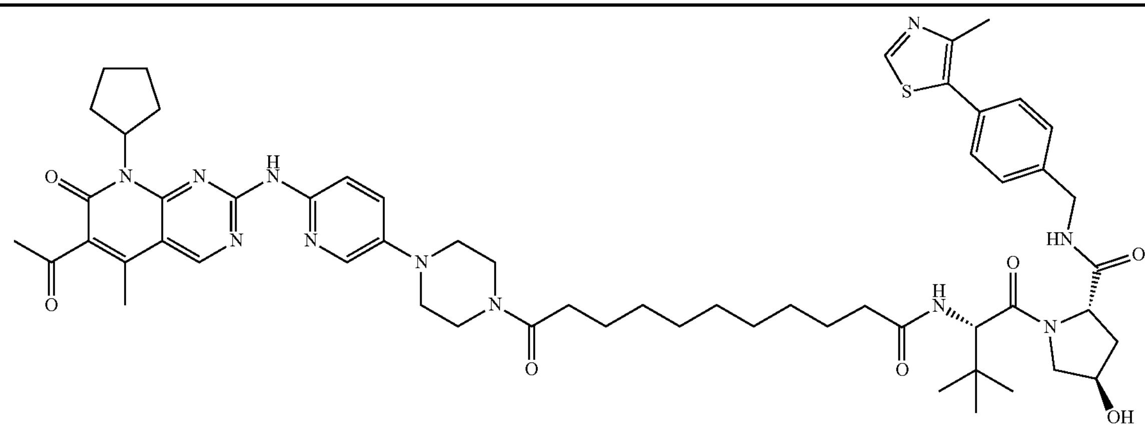 | (2S,4R)-1-((S)-2-(11-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-11-oxoundecanamido)-3,3-dimethylbutanoyl)-4-hydroxy-N-(4-(4-methylthiazol-5-yl)benzyl)pyrrolidine-2-carboxamide |
| 19 | XY028-114 | 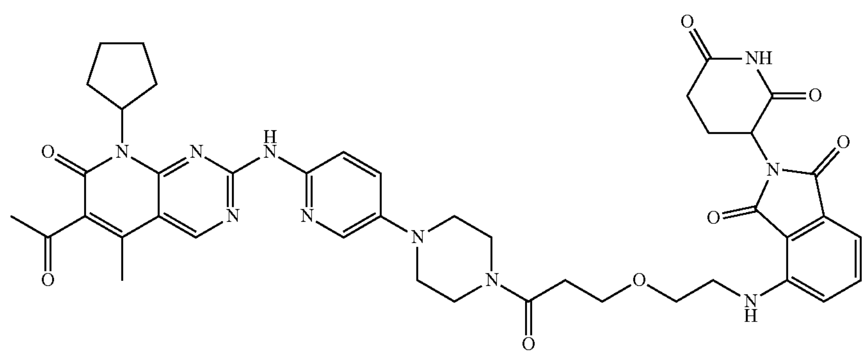 [SMILES: CC(=O)c1c(C)c2cnc(Nc3ccc(N4CCN(C(=O)CCOCCNc5cccc6c5C(=O)N(C5CCC(=O)NC5=O)C6=O)CC4)cn3)nc2n(C2CCCC2)c1=O] | 4-((2-(3-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-3-oxopropoxy)ethyl)amino)-2-(2,6-dioxopiperidin-3-yl)isoindoline-1,3-dione |

TABLE 1-continued

| Cpd. Example Number | Cpd. Code | Structure | Chemical Name |
|---|---|---|---|
| 20 | XY028-097 | 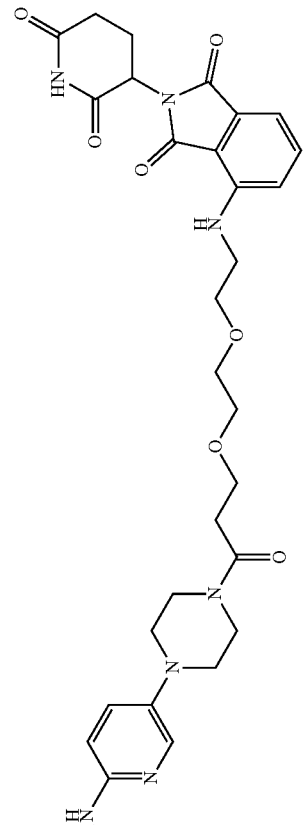 | 4-((2-(3-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-3-oxopropoxy)ethoxy)amino)-2-(2,6-dioxopiperidin-3-yl)isoindoline-1,3-dione |
| 21 | XY019-108 | 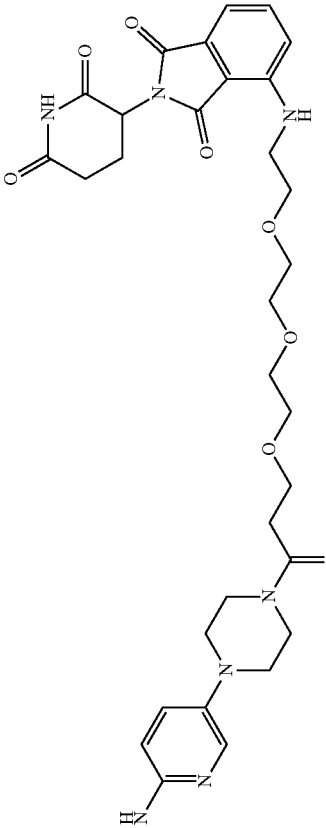 | 4-((2-(2-(2-(3-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-3-oxopropoxy)ethoxy)ethoxy)ethyl)amino)-2-(2,6-dioxopiperidin-3-yl)isoindoline-1,3-dione |

TABLE 1-continued

| Cpd. Example Number | Cpd. Code | Structure | Chemical Name |
|---|---|---|---|
| 22 | XY028-105 | 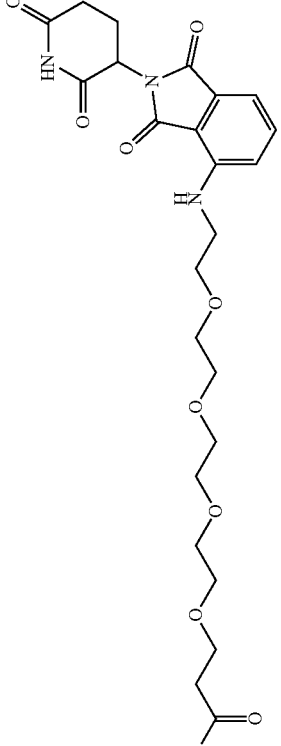 | 4-((15-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-15-oxo-3,6,9,12-tetraoxapentadecyl)amino)-2-(2,6-dioxopiperidin-3-yl)isoindoline-1,3-dione |
| 23 | XY028-106 | 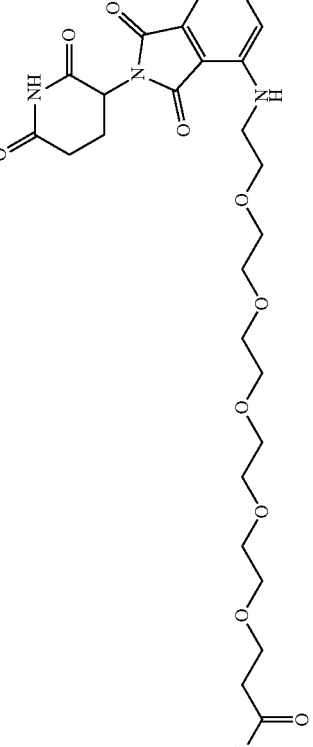 | 4-((18-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-18-oxo-3,6,9,12,15-pentaoxaoctadecyl)amino)-2-(2,6-dioxopiperidin-3-yl)isoindoline-1,3-dione |

TABLE 1-continued

| Cpd. Example Number | Cpd. Code | Structure | Chemical Name |
|---|---|---|---|
| 24 | XY028-140 | 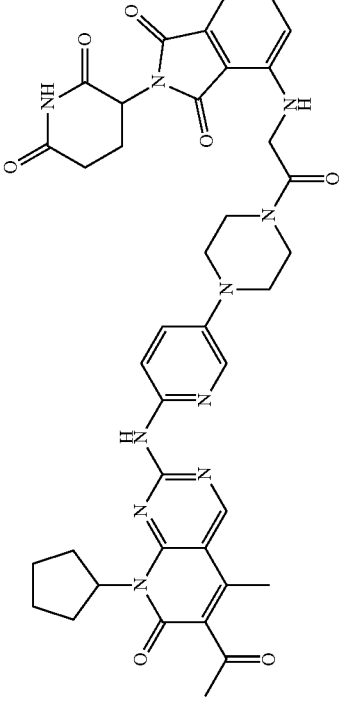 | 4-((2-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-2-oxoethyl)amino)-2-(2,6-dioxopiperidin-3-yl)isoindoline-1,3-dione |
| 25 | XY028-141 | 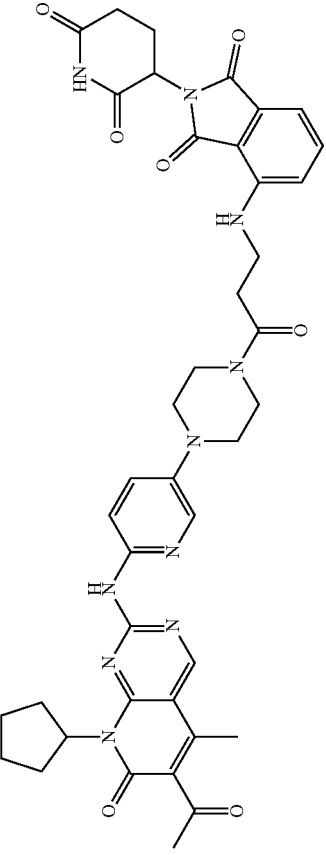 | 4-((3-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-3-oxopropyl)amino)-2-(2,6-dioxopiperidin-3-yl)isoindoline-1,3-dione |

TABLE 1-continued

| Cpd. Example Number | Cpd. Code | Structure | Chemical Name |
|---|---|---|---|
| 26 | XY028-142 | 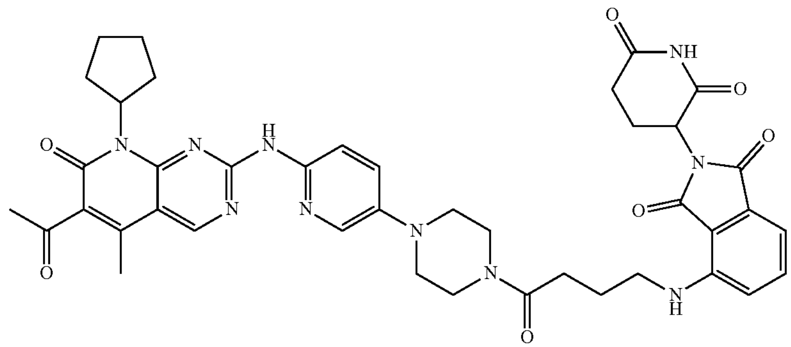 [SMILES: CC(=O)c1c(C)c2cnc(Nc3ccc(N4CCN(C(=O)CCCNc5cccc6c5C(=O)N(C5CCC(=O)NC5=O)C6=O)CC4)cn3)nc2n(C2CCCC2)c1=O] | 4-((4-(4-(6-((6-acetyl-8-cyclopentyl-5-methyl-7-oxo-7,8-dihydropyrido[2,3-d]pyrimidin-2-yl)aminopyridin-3-yl)piperazin-1-yl)-4-oxobutyl)amino)-2-(2,6-dioxopiperidin-3-yl)isoindoline-1,3-dione |
| 27 | XY028-143 | 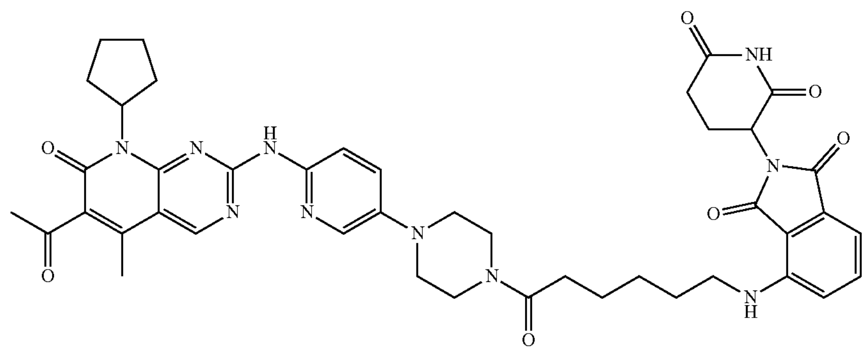 | 4-((6-(4-(6-((6-acetyl-8-cyclopentyl-5-methyl-7-oxo-7,8-dihydropyrido[2,3-d]pyrimidin-2-yl)aminopyridin-3-yl)piperazin-1-yl)-6-oxohexyl)amino)-2-(2,6-dioxopiperidin-3-yl)isoindoline-1,3-dione |

TABLE 1-continued

| Cpd. Example Number | Cpd. Code | Structure | Chemical Name |
|---|---|---|---|
| 28 | XY028-144 | 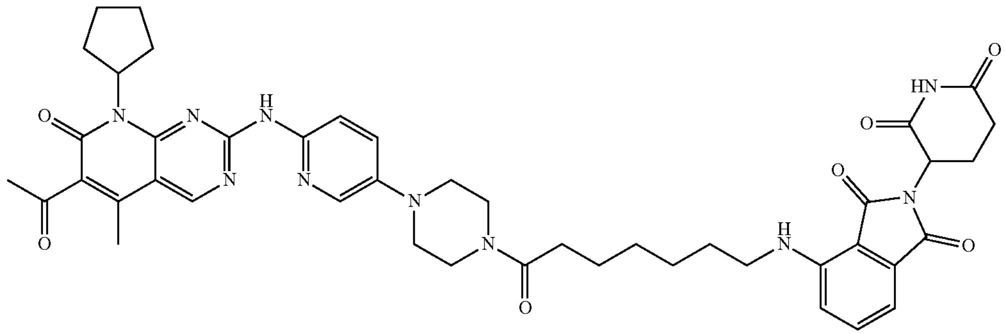 [SMILES: CC(=O)c1c(C)c2cnc(Nc3ccc(N4CCN(C(=O)CCCCCCNc5cccc6c5C(=O)N(C5CCC(=O)NC5=O)C6=O)CC4)cn3)nc2n(C2CCCC2)c1=O] | 4-((7-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-7-oxoheptyl)amino)-2-(2,6-dioxopiperidin-3-yl)isoindoline-1,3-dione |
| 29 | XY028-145 | 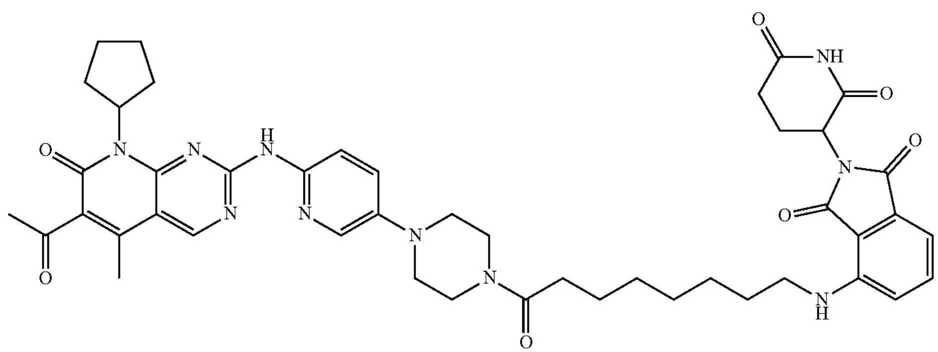 [SMILES: CC(=O)c1c(C)c2cnc(Nc3ccc(N4CCN(C(=O)CCCCCCCNc5cccc6c5C(=O)N(C5CCC(=O)NC5=O)C6=O)CC4)cn3)nc2n(C2CCCC2)c1=O] | 4-((8-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-8-oxooctyl)amino)-2-(2,6-dioxopiperidin-3-yl)isoindoline-1,3-dione |

TABLE 1-continued

| Cpd. Example Number | Cpd. Code | Structure | Chemical Name |
|---|---|---|---|
| 30 | YX26-56 | 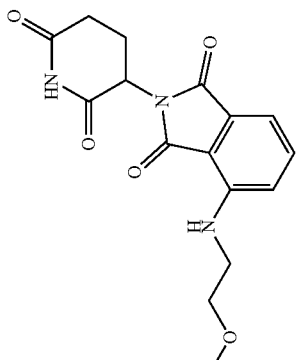 | 2-(2,6-dioxopiperidin-3-yl)-4-((2-(2-(2-(3-(4-((6-((5-fluoro-4-(4-fluoro-1-isopropyl-2-methyl-1H-benzo[d]imidazol-6-yl)pyrimidin-2-yl)amino)pyridin-3-yl)methyl)piperazin-1-yl)-3-oxopropoxy)ethoxy)ethoxy)ethyl)amino)isoindoline-1,3-dione |
| 31 | YX26-66 | 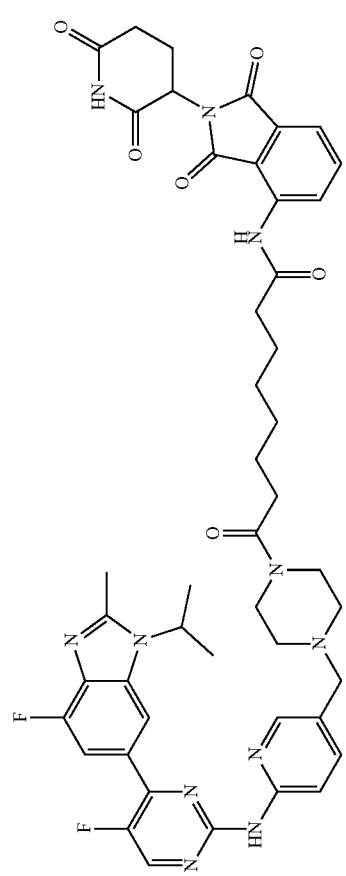 | N-(2-(2,6-dioxopiperidin-3-yl)-1,3-dioxoisoindolin-4-yl)-8-(4-((6-((5-fluoro-4-(4-fluoro-1-isopropyl-2-methyl-1H-benzo[d]imidazol-6-yl)pyrimidin-2-yl)amino)pyridin-3-yl)methyl)piperazin-1-yl)-8-oxooctanamide |

TABLE 1-continued

| Cpd. Example Number | Cpd. Code | Structure | Chemical Name |
|---|---|---|---|
| 32 | YX26-58 | 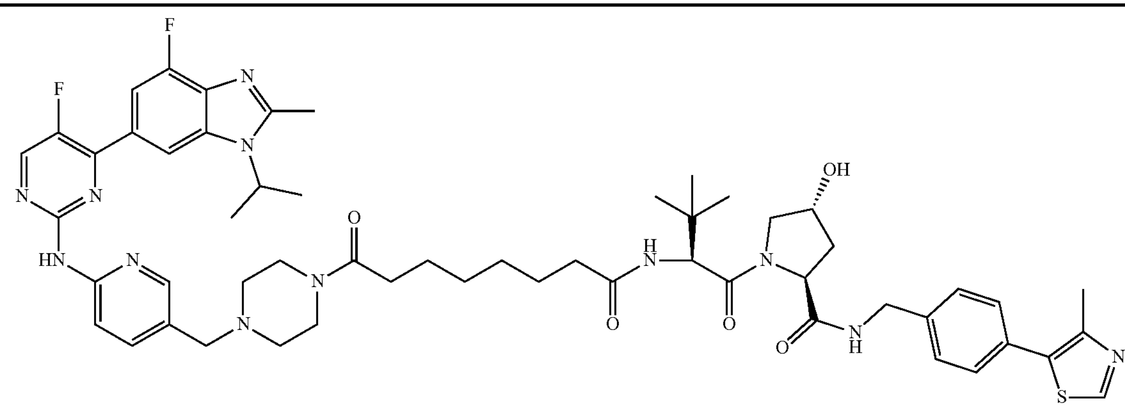 | (2S,4R)-1-((S)-2-(8-(4-((6-((5-fluoro-4-(4-fluoro-1-isopropyl-2-methyl-1H-benzo[d]imidazol-6-yl)pyrimidin-2-yl)amino)pyridin-3-yl)methyl)piperazin-1-yl)-8-oxooctanamido)-3,3-dimethylbutanoyl)-4-hydroxy-N-(4-(4-methylthiazol-5-yl)benzyl)pyrrolidine-2-carboxamide |
| 33 | YX30-108 | 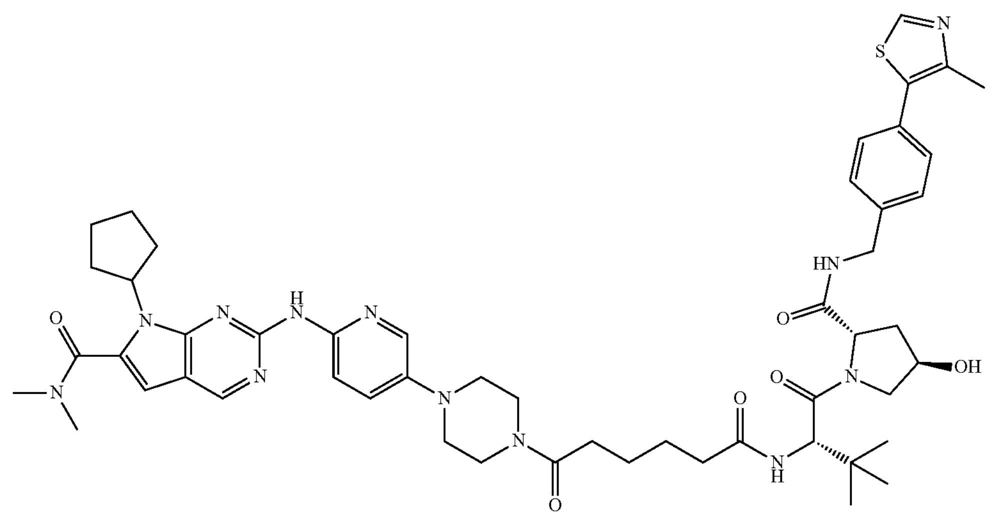 | 7-cyclopentyl-2-((5-(4-(6-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-6-oxohexanoyl)piperazin-1-yl)pyridin-2-yl)amino)-N,N-dimethyl-7H-pyrrolo[2,3-d]pyrimidine-6-carboxamide |

TABLE 1-continued

| Cpd. Example Number | Cpd. Code | Structure | Chemical Name |
|---|---|---|---|
| 34 | YX30-107 | 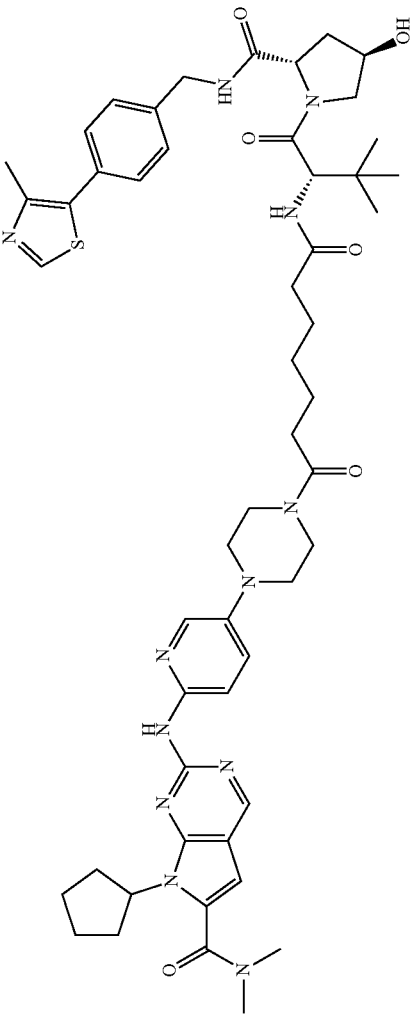 | 7-cyclopentyl-2-((5-(4-(7-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-7-oxoheptanoyl)piperazin-1-yl)pyridin-2-yl)amino)-N,N-dimethyl-7H-pyrrolo[2,3-d]pyrimidine-6-carboxamide |
| 35 | YX30-85 | 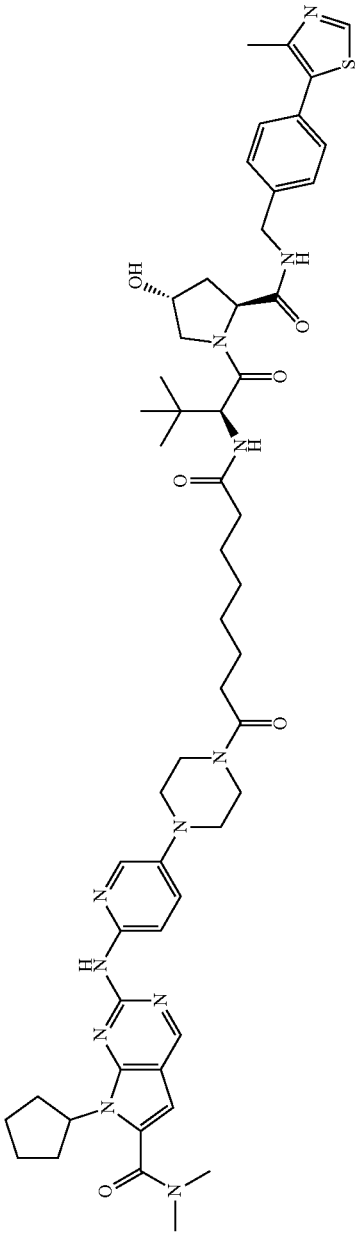 | 7-cyclopentyl-2-((5-(4-(8-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-8-oxooctanoyl)piperazin-1-yl)pyridin-2-yl)amino)-N,N-dimethyl-7H-pyrrolo[2,3-d]pyrimidine-6-carboxamide |

TABLE 1-continued

| Cpd. Example Number | Cpd. Code | Structure | Chemical Name |
|---|---|---|---|
| 36 | YX30-86 | 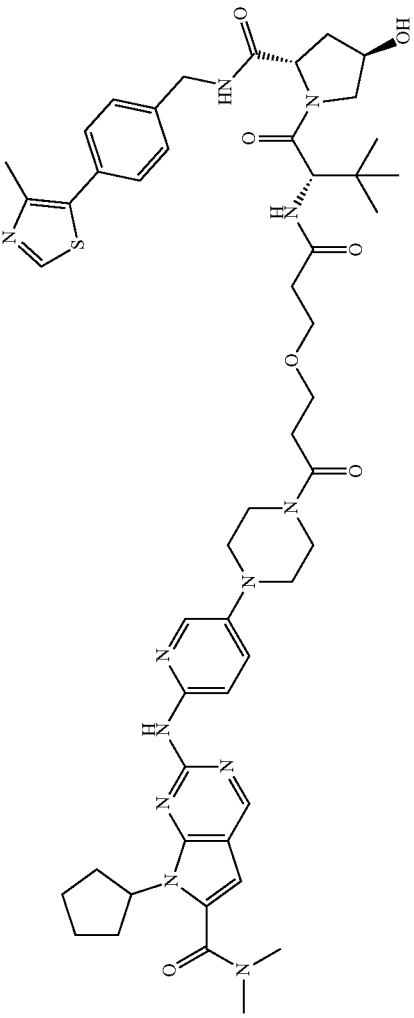 | 7-cyclopentyl-2-((5-(4-(3-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-3-oxopropoxy)propanoyl)piperazin-1-yl)pyridin-2-yl)amino)-N,N-dimethyl-7H-pyrrolo[2,3-d]pyrimidine-6-carboxamide |
| 37 | YX30-117 | 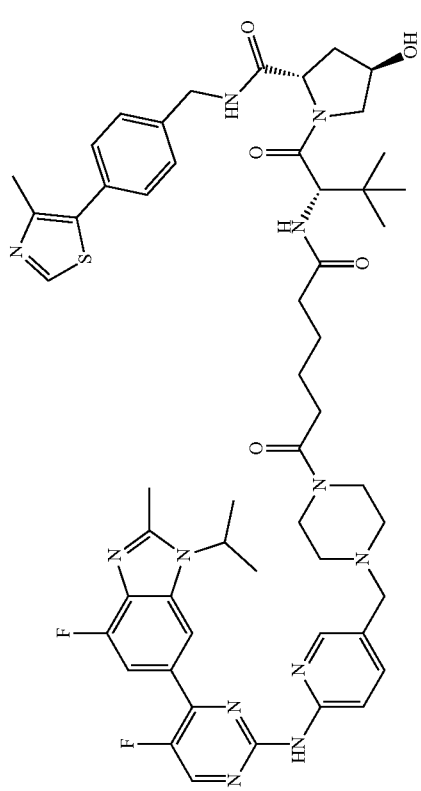 | (2S,4R)-1-((S)-2-(6-(4-((6-((5-fluoro-4-(4-fluoro-1-isopropyl-2-methyl-1H-benzo[d]imidazol-6-yl)pyrimidin-2-yl)amino)pyridin-3-yl)methyl)piperazin-1-yl)-6-oxohexanamido)-3,3-dimethylbutanoyl)-4-hydroxy-N-(4-(4-methylthiazol-5-yl)benzyl)pyrrolidine-2-carboxamide |

TABLE 1-continued

| Cpd. Example Number | Cpd. Code | Structure | Chemical Name |
|---|---|---|---|
| 38 | YX30-118 | 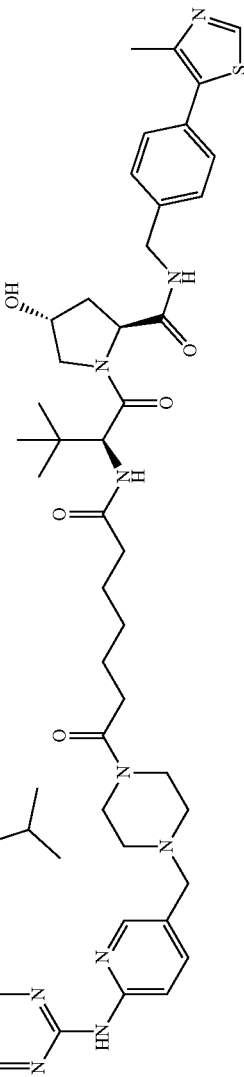 | (2S,4R)-1-((S)-2-(7-(4-((6-((5-fluoro-4-(4-fluoro-1-isopropyl-2-methyl-1H-benzo[d]imidazol-6-yl)pyrimidin-2-yl)amino)pyridin-3-yl)methyl)piperazin-1-yl)-7-oxoheptanamido)-3,3-dimethylbutanoyl)-4-hydroxy-N-(4-(4-methylthiazol-5-yl)benzyl)pyrrolidine-2-carboxamide |
| 39 | YX30-126 | 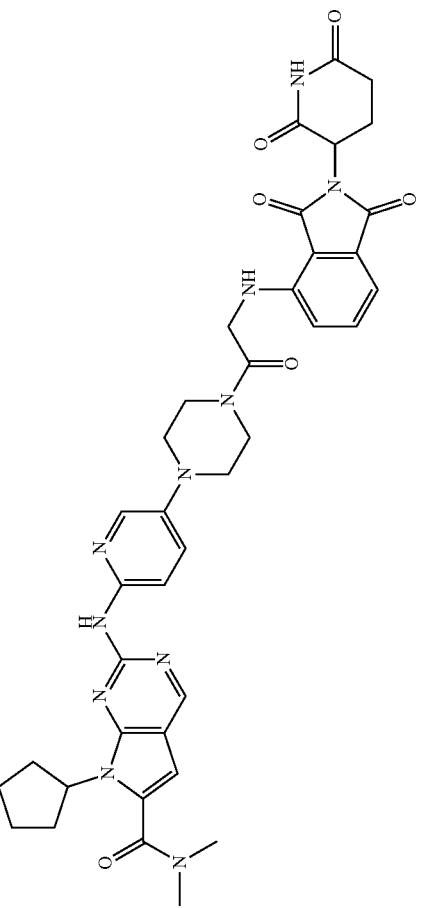 | 7-cyclopentyl-2-((5-(4-((2-(2,6-dioxopiperidin-3-yl)-1,3-dioxoisoindolin-4-yl)glycyl)piperazin-1-yl)pyridin-2-yl)amino)-N,N-dimethyl-7H-pyrrolo[2,3-d]pyrimidine-6-carboxamide |

TABLE 1-continued

| Cpd. Example Number | Cpd. Code | Structure | Chemical Name |
|---|---|---|---|
| 40 | YX30-125 | 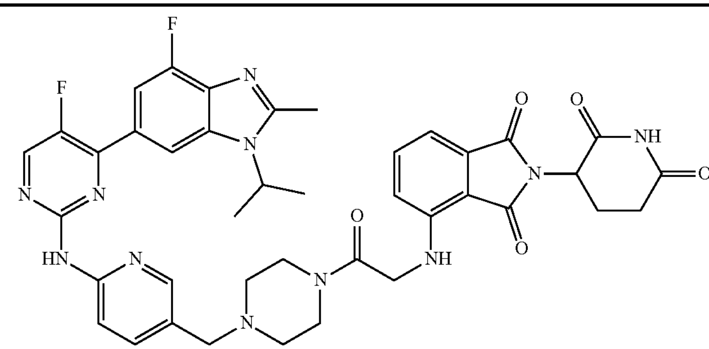 | 2-(2,6-dioxopiperidin-3-yl)-4-((2-(4-((6-((5-fluoro-4-(4-fluoro-1-isopropyl-2-methyl-1H-benzo[d]imidazol-6-yl)pyrimidin-2-yl)amino)pyridin-3-yl)methyl)piperazin-1-yl)-2-oxoethyl)amino)isoindoline-1,3-dione |
| 41 | XY028-186 | 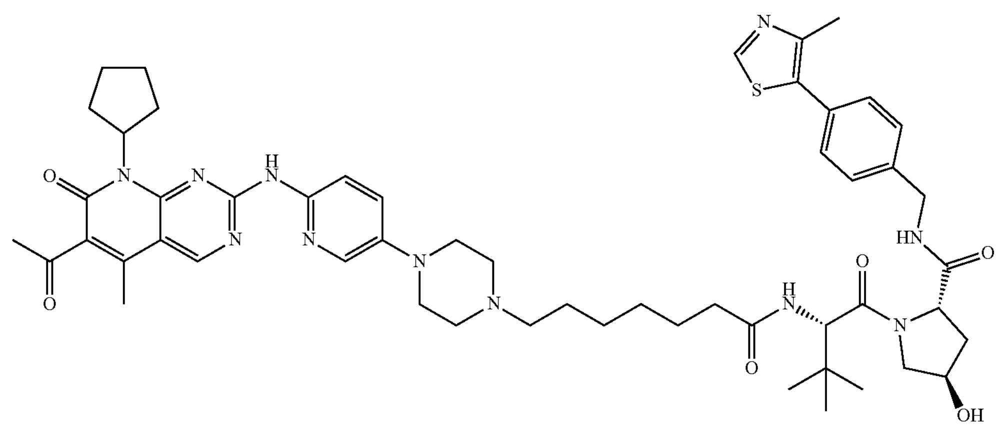 [SMILES: CC(=O)c1c(C)c2cnc(Nc3ccc(N4CCN(CCCCCCC(=O)N[C@H](C(=O)N5C[C@H](O)C[C@H]5C(=O)NCc5ccc(-c6scnc6C)cc5)C(C)(C)C)CC4)cn3)nc2n(C2CCCC2)c1=O] | (2S,4R)-1-((S)-2-(7-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)heptanamido)-3,3-dimethylbutanoyl)-4-hydroxy-N-(4-(4-methylthiazol-5-yl)benzyl)pyrrolidine-2-carboxamide |

TABLE 1-continued

| Cpd. Example Number | Cpd. Code | Structure | Chemical Name |
|---|---|---|---|
| 42 | YX33-29 | 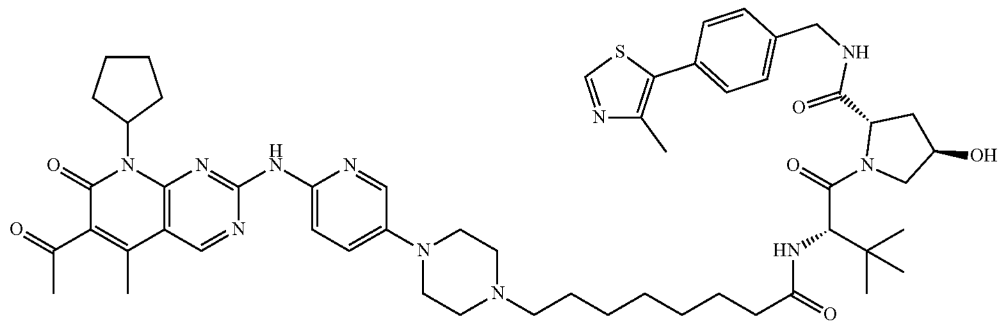 [SMILES: CC(=O)c1c(C)c2cnc(Nc3ccc(N4CCN(CCCCCCCC(=O)N[C@H](C(=O)N5C[C@H](O)C[C@H]5C(=O)NCc5ccc(-c6scnc6C)cc5)C(C)(C)C)CC4)cn3)nc2n(C2CCCC2)c1=O] | (2S,4R)-1-((S)-2-(8-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)octanamido)-3,3-dimethylbutanoyl)-4-hydroxy-N-(4-(4-methylthiazol-5-yl)benzyl)pyrrolidine-2-carboxamide |
| 43 | YX33-31 | 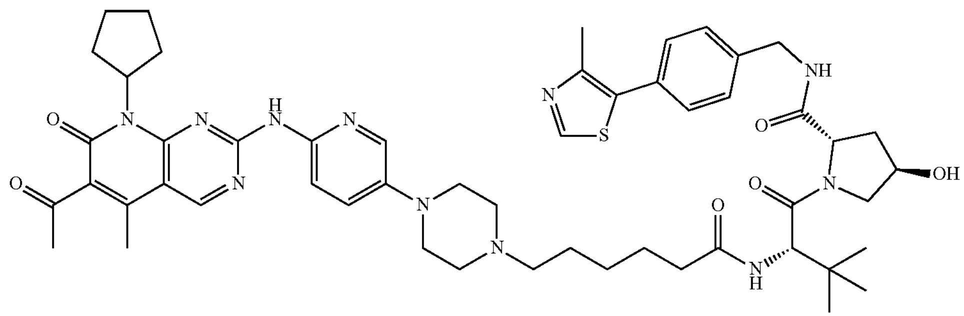 [SMILES: CC(=O)c1c(C)c2cnc(Nc3ccc(N4CCN(CCCCCC(=O)N[C@H](C(=O)N5C[C@H](O)C[C@H]5C(=O)NCc5ccc(-c6scnc6C)cc5)C(C)(C)C)CC4)cn3)nc2n(C2CCCC2)c1=O] | (2S,4R)-1-((S)-2-(6-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)hexanamido)-3,3-dimethylbutanoyl)-4-hydroxy-N-(4-(4-methylthiazol-5-yl)benzyl)pyrrolidine-2-carboxamide |
| 44 | YX33-74 | 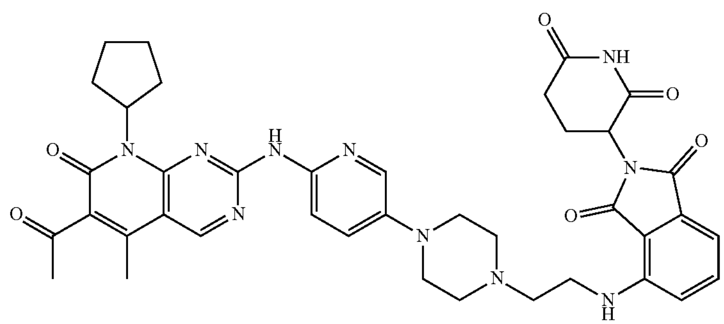 [SMILES: CC(=O)c1c(C)c2cnc(Nc3ccc(N4CCN(CCNc5cccc6c5C(=O)N(C5CCC(=O)NC5=O)C6=O)CC4)cn3)nc2n(C2CCCC2)c1=O] | 4-((2-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)ethyl)amino)-2-(2,6-dioxopiperidin-3-yl)isoindoline-1,3-dione |

TABLE 1-continued

| Cpd. Example Number | Cpd. Code | Structure | Chemical Name |
|---|---|---|---|
| 45 | YX33-94 | 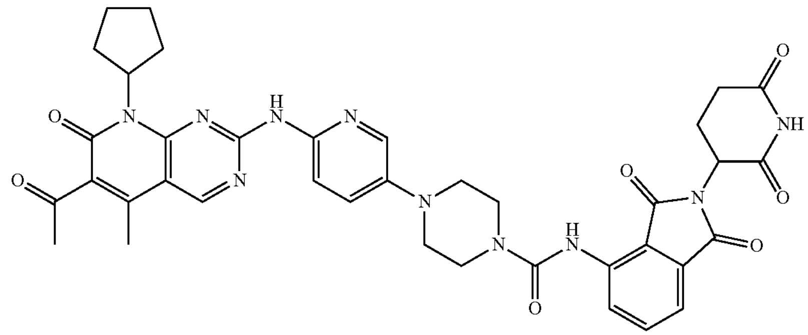 [SMILES: CC(=O)c1c(C)c2cnc(Nc3ccc(N4CCN(C(=O)Nc5cccc6c5C(=O)N(C5CCC(=O)NC5=O)C6=O)CC4)cn3)nc2n(C2CCCC2)c1=O] | 4-(6-(((6-acetyl-8-cyclopentyl-5-methyl-7-oxo-7,8-dihydropyrido[2,3-d]pyrimidin-2-yl)amino)pyridin-3-yl)-N-(2-(2,6-dioxopiperidin-3-yl)-1,3-dioxoisoindolin-4-yl)piperazine-1-carboxamide |
| 46 | YX33-108 | 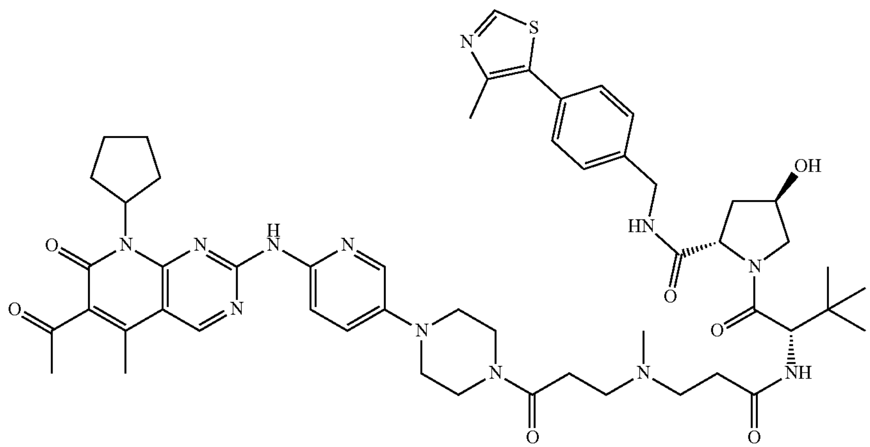 [SMILES: CC(=O)c1c(C)c2cnc(Nc3ccc(N4CCN(C(=O)CCN(C)CCC(=O)N[C@H](C(=O)N5C[C@H](O)C[C@H]5C(=O)NCc5ccc(-c6scnc6C)cc5)C(C)(C)C)CC4)cn3)nc2n(C2CCCC2)c1=O] | (2S,4R)-1-((S)-2-(3-(4-(6-(((6-acetyl-8-cyclopentyl-5-methyl-7-oxo-7,8-dihydropyrido[2,3-d]pyrimidin-2-yl)amino)pyridin-3-yl)piperazin-1-yl)-3-oxopropyl)(methyl)amino)propanamido)-3,3-dimethylbutanoyl)-4-hydroxy-N-(4-(4-methylthiazol-5-yl)benzyl)pyrrolidine-2-carboxamide |

TABLE 1-continued

| Cpd. Example Number | Cpd. Code | Structure | Chemical Name |
|---|---|---|---|
| 47 | YX33-96 | 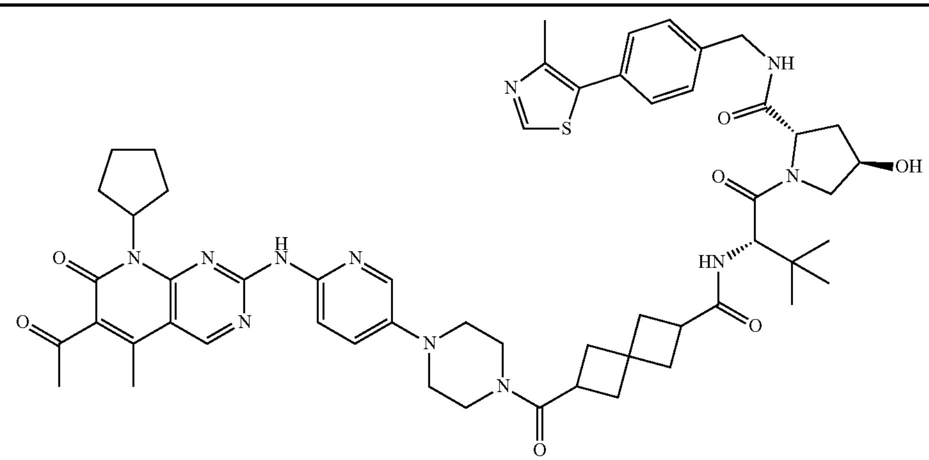 | (2S,4R)-1-((S)-2-(6-(4-(6-((6-acetyl-8-cyclopentyl-5-methyl-7-oxo-7,8-dihydropyrido[2,3-d]pyrimidin-2-yl)aminopyridin-3-yl)piperazine-1-carbonyl)spiro[3.3]heptane-2-carboxamido)-3,3-dimethylbutanoyl)-4-hydroxy-N-(4-(4-methylthiazol-5-yl)benzyl)pyrrolidine-2-carboxamide |
| 48 | YX33-97 | 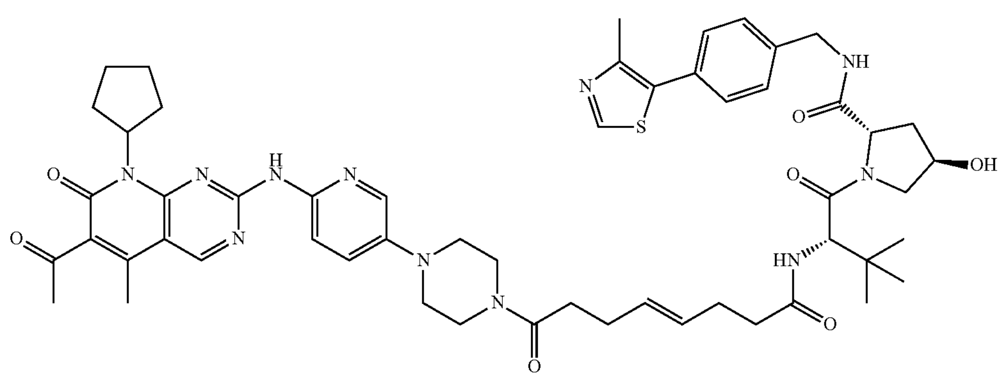 [SMILES: CC(=O)c1c(C)c2cnc(Nc3ccc(N4CCN(C(=O)CC/C=C/CCC(=O)N[C@H](C(=O)N5C[C@H](O)C[C@H]5C(=O)NCc5ccc(-c6scnc6C)cc5)C(C)(C)C)CC4)cn3)nc2n(C2CCCC2)c1=O] | (2S,4R)-1-((S)-2-((E)-8-(4-(6-((6-acetyl-8-cyclopentyl-5-methyl-7-oxo-7,8-dihydropyrido[2,3-d]pyrimidin-2-yl)aminopyridin-3-yl)piperazin-1-yl)-8-oxooct-4-enamido)-3,3-dimethylbutanoyl)-4-hydroxy-N-(4-(4-methylthiazol-5-yl)benzyl)pyrrolidine-2-carboxamide |

TABLE 1-continued

| Cpd. Example Number | Cpd. Code | Structure | Chemical Name |
|---|---|---|---|
| 49 | YX33-109 | 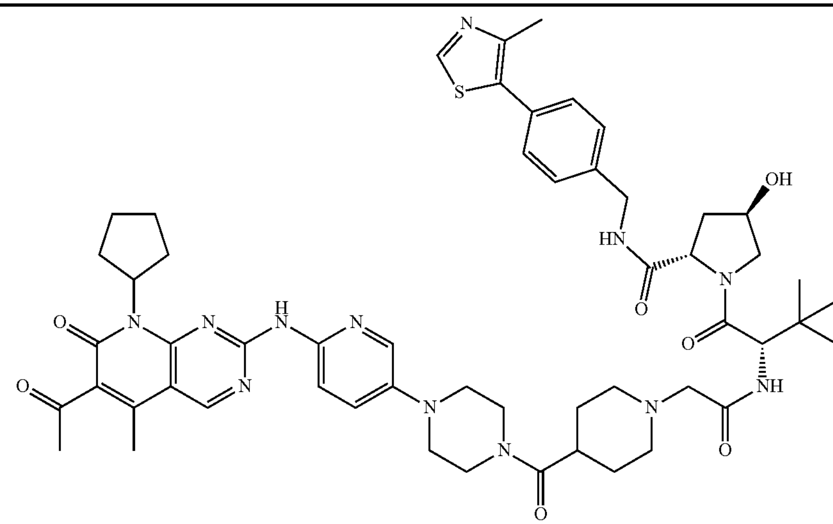 | (2S,4R)-1-((S)-2-(2-(4-(6-((6-acetyl-8-cyclopentyl-5-methyl-7-oxo-7,8-dihydropyrido[2,3-d]pyrimidin-2-yl)aminopyridin-3-yl)piperazine-1-carbonyl)piperidin-1-yl)acetamido)-3,3-dimethylbutanoyl)-4-hydroxy-N-(4-(4-methylthiazol-5-yl)benzyl)pyrrolidine-2-carboxamide |
| 50 | YX33-110 | 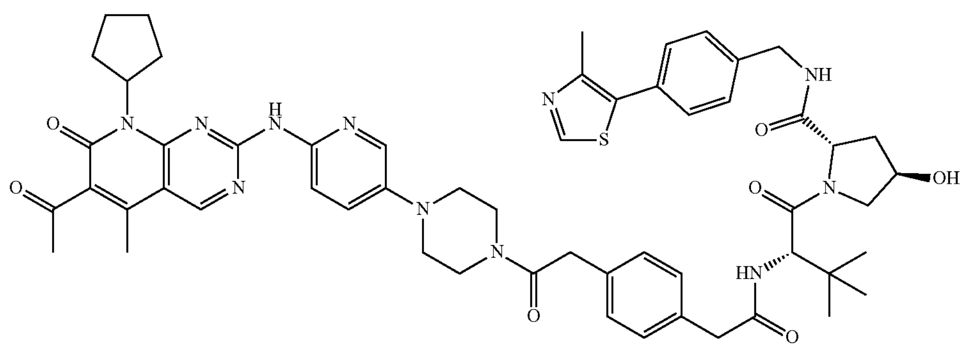 [SMILES: CC(=O)c1c(C)c2cnc(Nc3ccc(N4CCN(C(=O)Cc5ccc(CC(=O)N[C@H](C(=O)N6C[C@H](O)C[C@H]6C(=O)NCc6ccc(-c7scnc7C)cc6)C(C)(C)C)cc5)CC4)cn3)nc2n(C2CCCC2)c1=O] | (2S,4R)-1-((S)-2-(2-(4-(2-(4-(6-((6-acetyl-8-cyclopentyl-5-methyl-7-oxo-7,8-dihydropyrido[2,3-d]pyrimidin-2-yl)aminopyridin-3-yl)piperazin-1-yl)-2-oxoethyl)phenyl)acetamido)-3,3-dimethylbutanoyl)-4-hydroxy-N-(4-(4-methylthiazol-5-yl)benzyl)pyrrolidine-2-carboxamide |

TABLE 1-continued

| Cpd. Example Number | Cpd. Code | Structure | Chemical Name |
|---|---|---|---|
| 51 | YX33-122 | 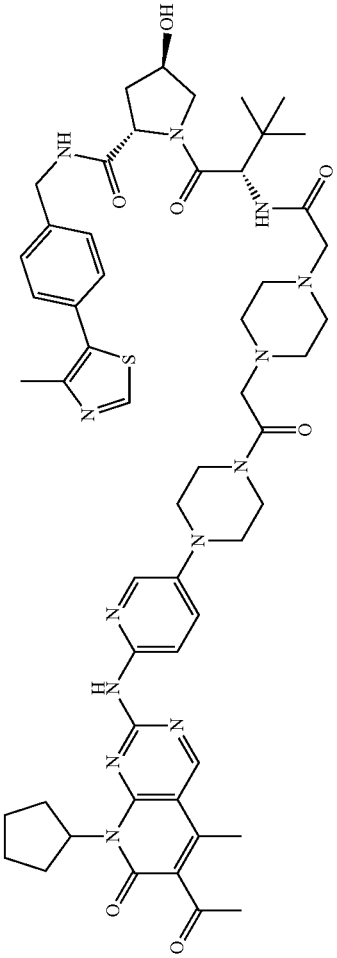 | (2S,4R)-1-((S)-2-(2-(4-(2-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-2-oxoethyl)piperazin-1-yl)acetamido)-3,3-dimethylbutanoyl)-4-hydroxy-N-(4-(4-methylthiazol-5-yl)benzyl)pyrrolidine-2-carboxamide |
| 52 | YX33-123 | 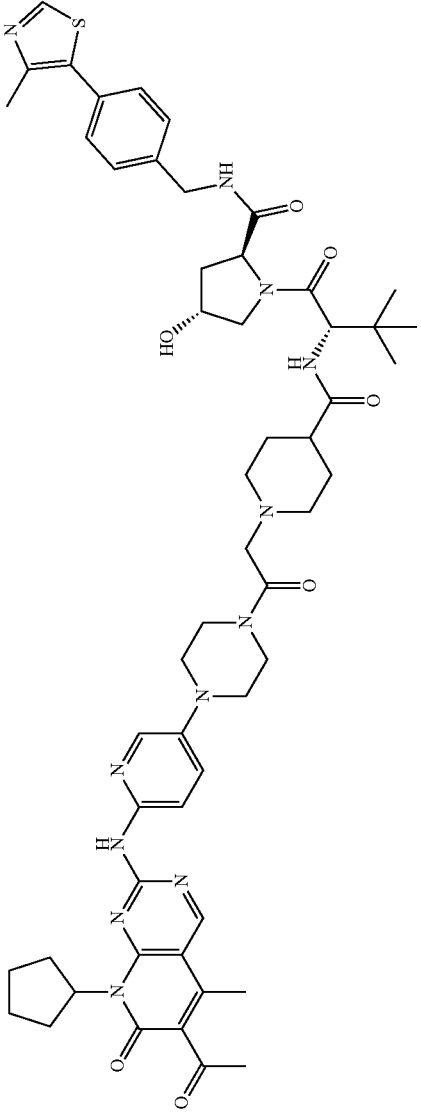 | 1-(2-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-2-oxoethyl)-N-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)piperidine-4-carboxamide |

TABLE 1-continued

| Cpd. Example Number | Cpd. Code | Structure | Chemical Name |
|---|---|---|---|
| 53 | YX35-48 | 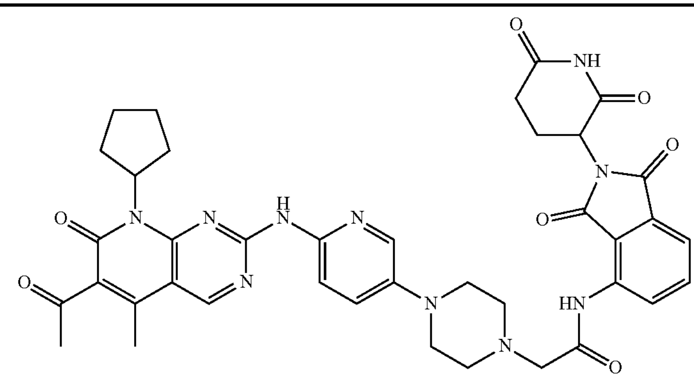 | 2-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-N-(2-(2,6-dioxopiperidin-3-yl)-1,3-dioxoisoindolin-4-yl)acetamide |
| 54 | YX39-47 | 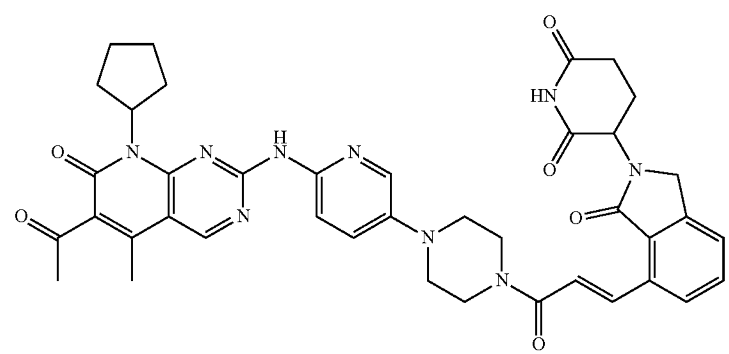 [SMILES: CC(=O)c1c(C)c2cnc(Nc3ccc(N4CCN(C(=O)/C=C/c5cccc6c5C(=O)N(C5CCC(=O)NC5=O)C6)CC4)cn3)nc2n(C2CCCC2)c1=O] | (E)-3-(7-(3-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-3-oxoprop-1-en-1-yl)-1-oxoisoindolin-2-yl)piperidine-2,6-dione |

TABLE 1-continued

| Cpd. Example Number | Cpd. Code | Structure | Chemical Name |
|---|---|---|---|
| 55 | YX39-48 | 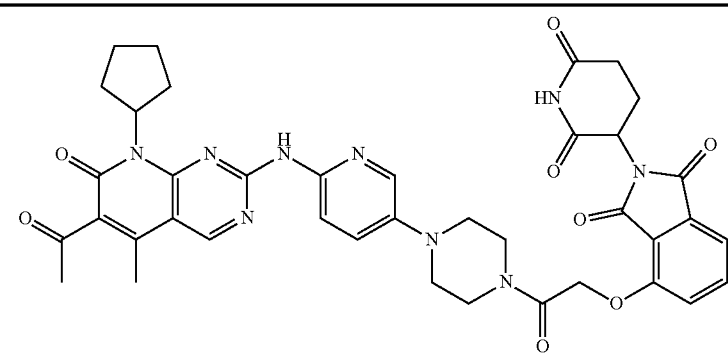 | 4-(2-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-2-oxoethoxy)-2-(2,6-dioxopiperidin-3-yl)isoindoline-1,3-dione |
| 56 | YX39-56 | 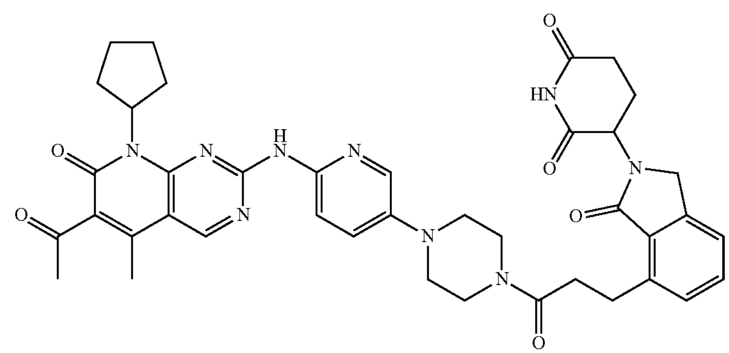 [SMILES: CC(=O)c1c(C)c2cnc(Nc3ccc(N4CCN(C(=O)CCc5cccc6c5C(=O)N(C5CCC(=O)NC5=O)C6)CC4)cn3)nc2n(C2CCCC2)c1=O] | 3-(7-(3-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-3-oxopropyl)-1-oxoisoindolin-2-yl)piperidine-2,6-dione |

TABLE 1-continued

| Cpd. Example Number | Cpd. Code | Structure | Chemical Name |
|---|---|---|---|
| 57 | YX39-65 | 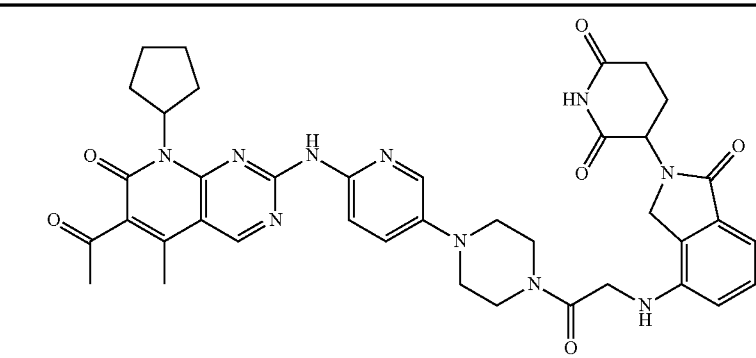 | 3-(4-((2-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-2-oxoethyl)amino)-1-oxoisoindolin-2-yl)piperidine-2,6-dione |
| 58 | YX39-74 | 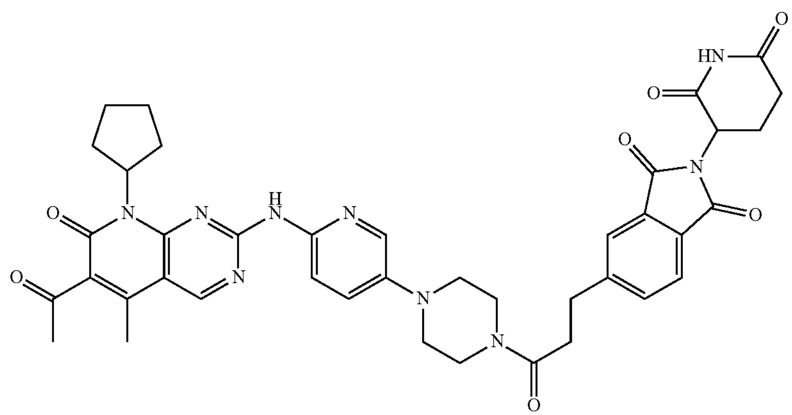 [SMILES: CC(=O)c1c(C)c2cnc(Nc3ccc(N4CCN(C(=O)CCc5ccc6c(c5)C(=O)N(C5CCC(=O)NC5=O)C6=O)CC4)cn3)nc2n(C2CCCC2)c1=O] | 5-(3-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-3-oxopropyl)-2-(2,6-dioxopiperidin-3-yl)isoindoline-1,3-dione |

TABLE 1-continued

| Cpd. Example Number | Cpd. Code | Structure | Chemical Name |
|---|---|---|---|
| 59 | YX39-123 | 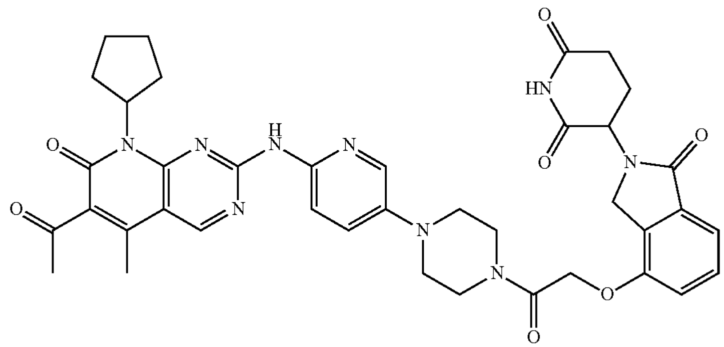 [SMILES: CC(=O)c1c(C)c2cnc(Nc3ccc(N4CCN(C(=O)COc5cccc6c5CN(C5CCC(=O)NC5=O)C6=O)CC4)cn3)nc2n(C2CCCC2)c1=O] | 3-(4-(2-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-2-oxoethoxy)-1-oxoisoindolin-2-yl)piperidine-2,6-dione |
| 60 | YX39-124 | 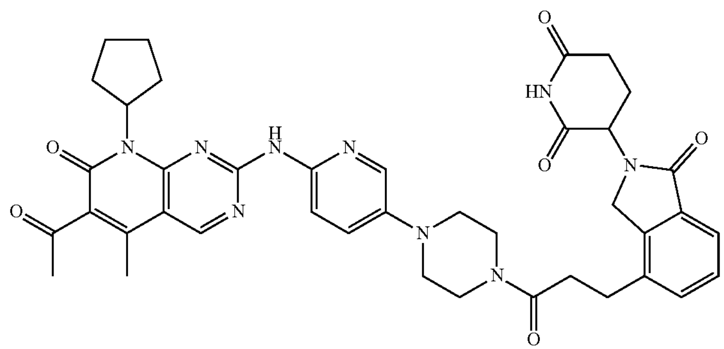 [SMILES: CC(=O)c1c(C)c2cnc(Nc3ccc(N4CCN(C(=O)CCc5cccc6c5CN(C5CCC(=O)NC5=O)C6=O)CC4)cn3)nc2n(C2CCCC2)c1=O] | 3-(4-(3-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-3-oxopropyl)-1-oxoisoindolin-2-yl)piperidine-2,6-dione |

TABLE 1-continued

| Cpd. Example Number | Cpd. Code | Structure | Chemical Name |
|---|---|---|---|
| 61 | YX39-147 | 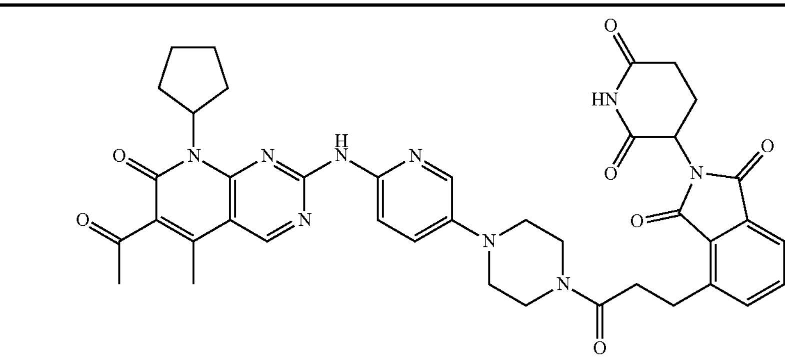 | 4-(3-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-3-oxopropyl)-2-(2,6-dioxopiperidin-3-yl)isoindoline-1,3-dione |
| 62 | YX44-18 | 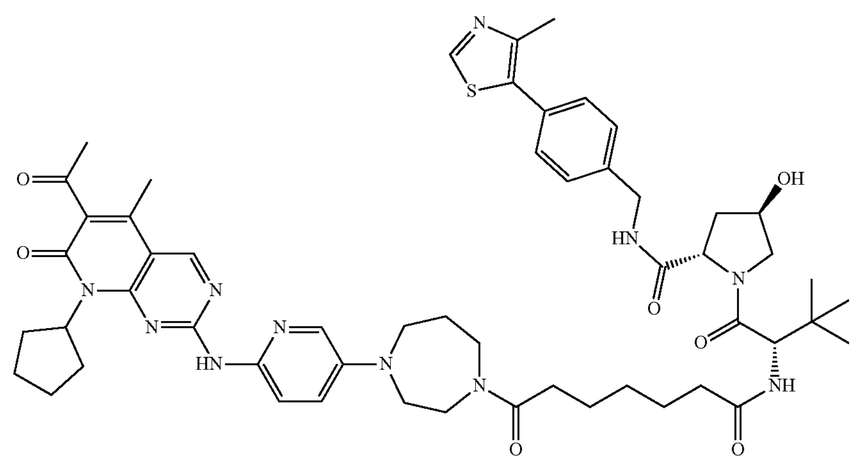 [SMILES: CC(=O)c1c(C)c2cnc(Nc3ccc(N4CCCN(C(=O)CCCCCC(=O)N[C@H](C(=O)N5C[C@H](O)C[C@H]5C(=O)NCc5ccc(-c6scnc6C)cc5)C(C)(C)C)CC4)cn3)nc2n(C2CCCC2)c1=O] | (2S,4R)-1-((S)-2-(7-(4-(6-((6-acetyl-8-cyclopentyl-5-methyl-7-oxo-7,8-dihydropyrido[2,3-d]pyrimidin-2-yl)amino)pyridin-3-yl)-1,4-diazepan-1-yl)-7-oxoheptanamido)-3,3-dimethylbutanoyl)-4-hydroxy-N-(4-(4-methylthiazol-5-yl)benzyl)pyrrolidine-2-carboxamide |

TABLE 1-continued

| Cpd. Example Number | Cpd. Code | Structure | Chemical Name |
|---|---|---|---|
| 63 | YX44-19 | 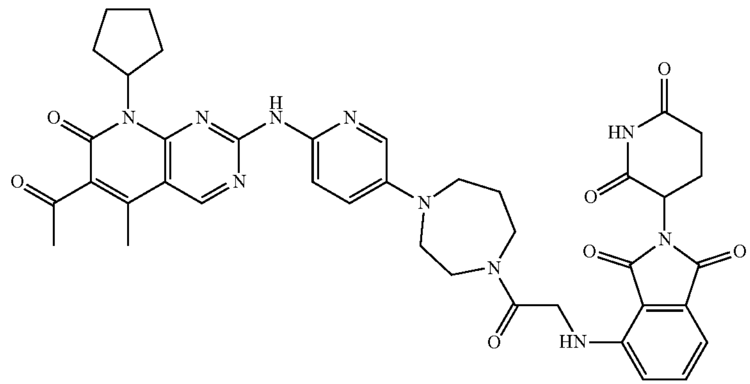 [SMILES: CC(=O)c1c(C)c2cnc(Nc3ccc(N4CCCN(C(=O)CNc5cccc6c5C(=O)N(C5CCC(=O)NC5=O)C6=O)CC4)cn3)nc2n(C2CCCC2)c1=O] | 4-((2-(4-(6-(((6-acetyl-8-cyclopentyl-5-methyl-7-oxo-7,8-dihydropyrido[2,3-d]pyrimidin-2-yl)amino)pyridin-3-yl)-1,4-diazepan-1-yl)-2-oxoethyl)amino)-2-(2,6-dioxopiperidin-3-yl)isoindoline-1,3-dione |
| 64 | YX44-22 | 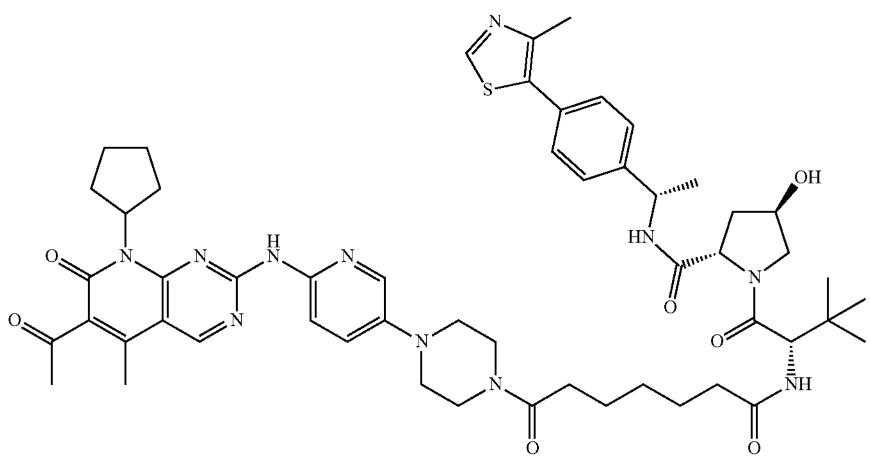 [SMILES: CC(=O)c1c(C)c2cnc(Nc3ccc(N4CCN(C(=O)CCCCCC(=O)N[C@H](C(=O)N5C[C@H](O)C[C@H]5C(=O)N[C@@H](C)c5ccc(-c6scnc6C)cc5)C(C)(C)C)CC4)cn3)nc2n(C2CCCC2)c1=O] | (2S,4R)-1-((S)-2-(7-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-7-oxoheptanamido)-3,3-dimethylbutanoyl)-4-hydroxy-N-((S)-1-(4-(4-methylthiazol-5-yl)phenyl)ethyl)pyrrolidine-2-carboxamide |

TABLE 1-continued

| Cpd. Example Number | Cpd. Code | Structure | Chemical Name |
|---|---|---|---|
| 65 | YX44-46 | 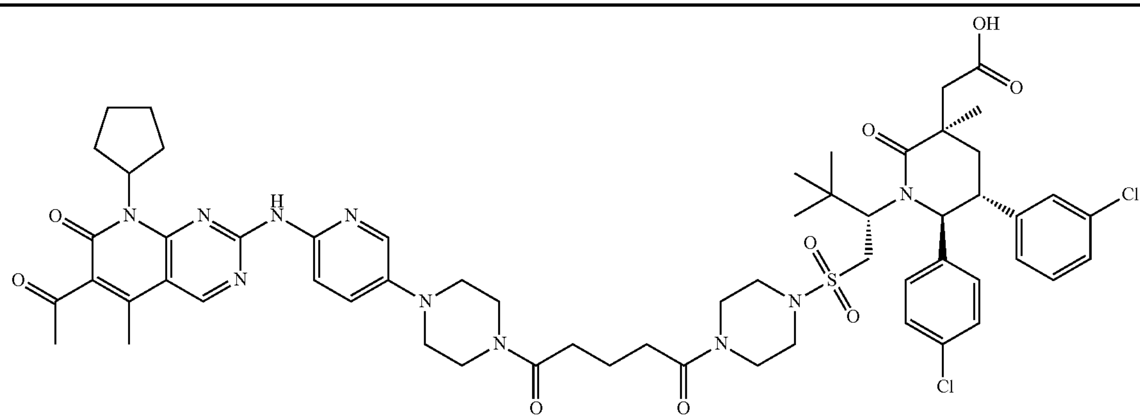 | 2-((3R,5R,6S)-1-((S)-1-((4-(5-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-5-oxopentanoyl)piperazin-1-yl)sulfonyl)-3,3-dimethylbutan-2-yl)-5-(3-chlorophenyl)-6-(4-chlorophenyl)-3-methyl-2-oxopiperidin-3-yl)acetic acid |
| 66 | YX44-48 | 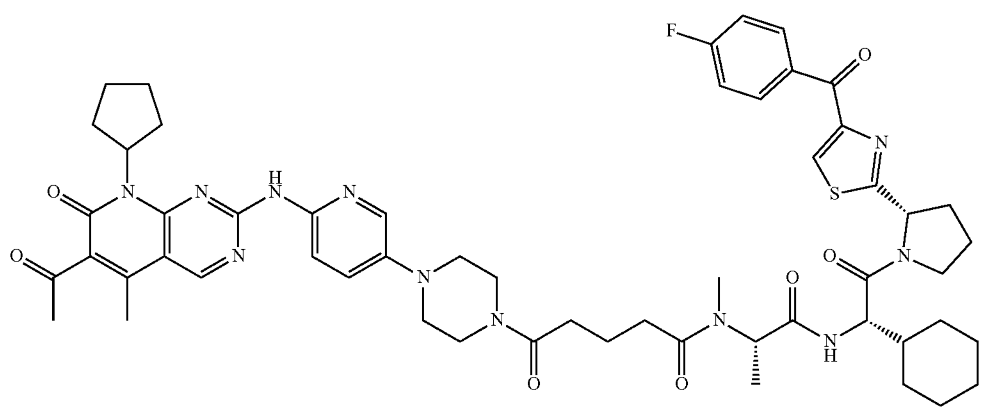 [SMILES: CC(=O)c1c(C)c2cnc(Nc3ccc(N4CCN(C(=O)CCCC(=O)N(C)[C@@H](C)C(=O)N[C@H](C(=O)N5CCC[C@H]5c5nc(C(=O)c6ccc(F)cc6)cs5)C5CCCCC5)CC4)cn3)nc2n(C2CCCC2)c1=O] | 5-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-N-((S)-1-(((S)-1-cyclohexyl-2-((S)-2-(4-(4-fluorobenzoyl)thiazol-2-yl)pyrrolidin-1-yl)-2-oxoethyl)amino)-1-oxopropan-2-yl)-N-methyl-5-oxopentanamide |

| Cpd. Example Number | Cpd. Code | Structure | Chemical Name |
|---|---|---|---|
| 67 | YS36-95 | 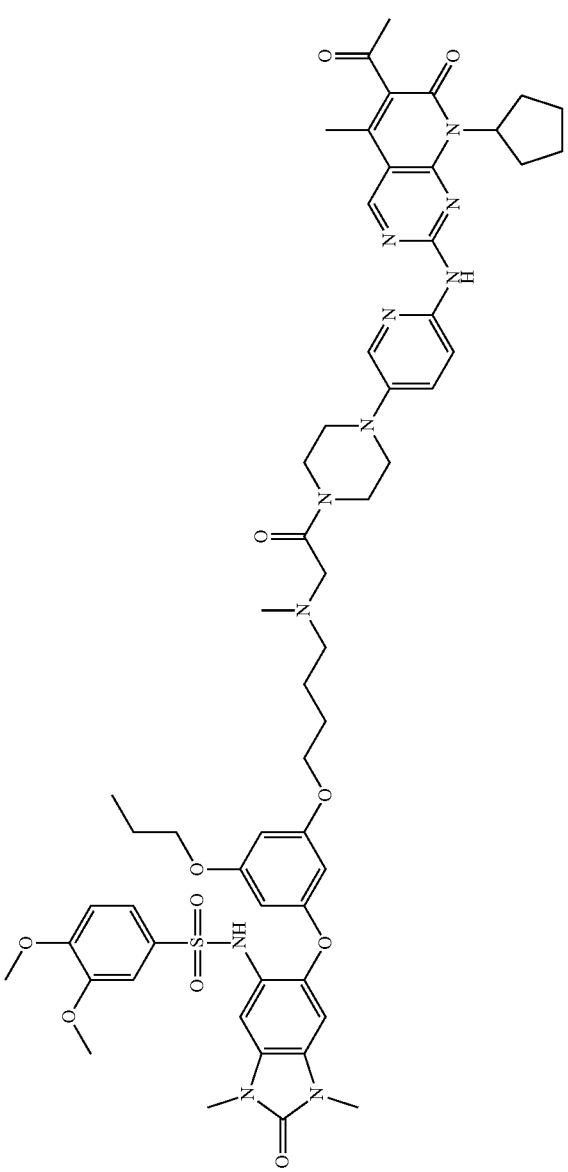 | N-(6-(3-(4-((2-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-2-oxoethyl)(methyl)amino)butoxy)-5-propoxyphenoxy)-1,3-dimethyl-2-oxo-2,3-dihydro-1H-benzo[d]imidazol-5-yl)-3,4-dimethoxybenzenesulfonamide |
| 68 | YS36-60 | 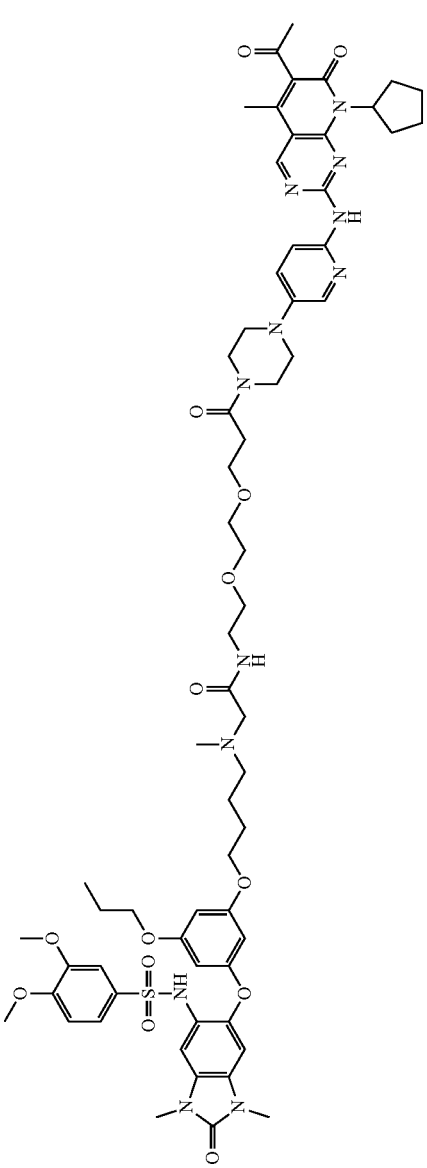 | N-(2-(2-(3-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-3-oxopropoxy)ethoxy)ethyl)-2-((4-(3-((3,4-dimethoxyphenyl)sulfonamido)-1,3-dimethyl-2-oxo-2,3-dihydro-1H-benzo[d]imidazol-5-yl)oxy)-5-propoxyphenoxy)butyl)(methyl)amino)acetamide |

TABLE 1-continued

| Cpd. Example Number | Cpd. Code | Structure | Chemical Name |
|---|---|---|---|
| 69 | YS36-61 | 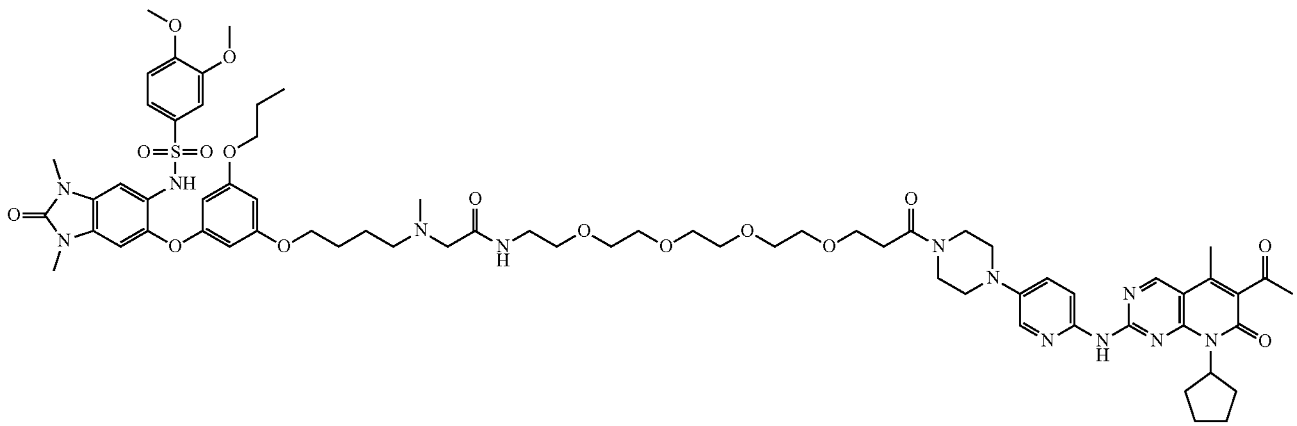 [SMILES: CCCOc1cc(OCCCCN(C)CC(=O)NCCOCCOCCOCCOCCC(=O)N2CCN(c3ccc(Nc4ncc5c(C)c(C(C)=O)c(=O)n(C6CCCC6)c5n4)nc3)CC2)cc(Oc2cc3c(cc2NS(=O)(=O)c2ccc(OC)c(OC)c2)n(C)c(=O)n3C)c1] | N-(15-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-15-oxo-3,6,9,12-tetraoxapentadecyl)-2-((4-(3-((6-((3,4-dimethoxyphenyl)sulfonamido)-1,3-dimethyl-2-oxo-2,3-dihydro-1H-benzo[d]imidazol-5-yl)oxy)-5-propoxyphenoxy)butyl)(methyl)amino)acetamide |
| 70 | YS36-62 | 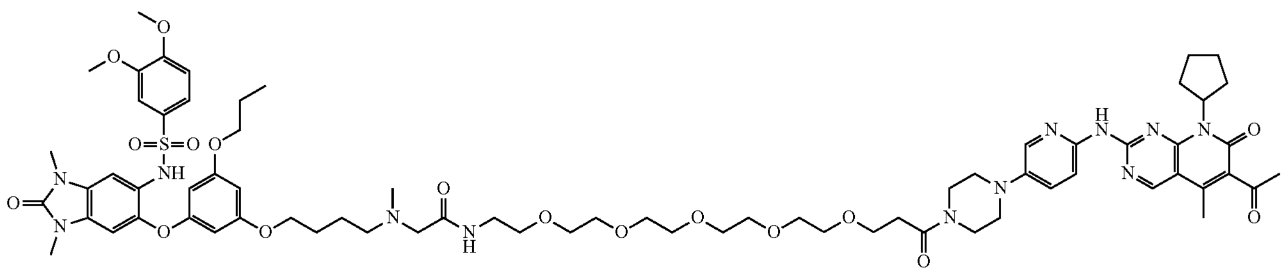 [SMILES: CCCOc1cc(OCCCCN(C)CC(=O)NCCOCCOCCOCCOCCOCCC(=O)N2CCN(c3ccc(Nc4ncc5c(C)c(C(C)=O)c(=O)n(C6CCCC6)c5n4)nc3)CC2)cc(Oc2cc3c(cc2NS(=O)(=O)c2ccc(OC)c(OC)c2)n(C)c(=O)n3C)c1] | N-(18-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-18-oxo-3,6,9,12,15-pentaoxaoctadecyl)-2-((4-(3-((6-((3,4-dimethoxyphenyl)sulfonamido)-1,3-dimethyl-2-oxo-2,3-dihydro-1H-benzo[d]imidazol-5-yl)oxy)-5-propoxyphenoxy)butyl)(methyl)amino)acetamide |

TABLE 1-continued

| Cpd. Example Number | Cpd. Code | Structure | Chemical Name |
|---|---|---|---|
| 71 | YS36-63 | 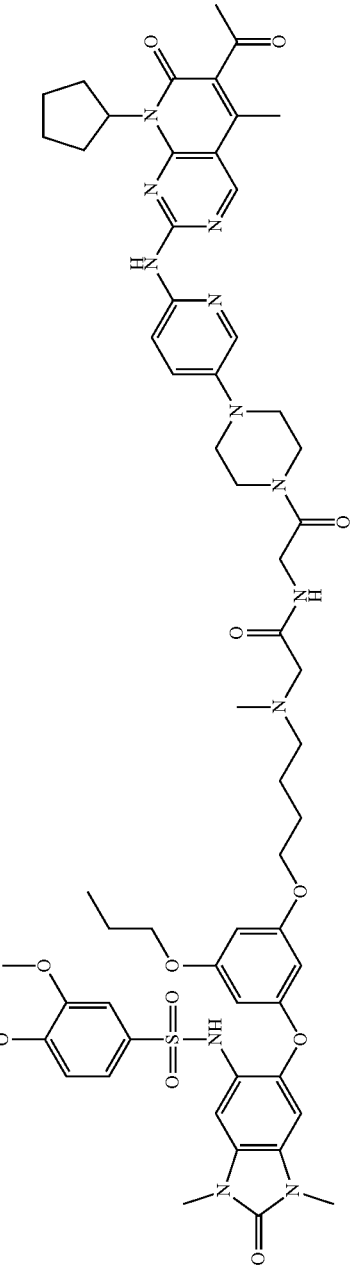 | N-(2-(4-(6-(((6-acetyl-8-cyclopentyl-5-methyl-7-oxo-7,8-dihydropyrido[2,3-d]pyrimidin-2-yl)amino)pyridin-3-yl)piperazin-1-yl)-2-oxoethyl)-2-((4-(3-((6-((3,4-dimethoxyphenyl)sulfonamido)-1,3-dimethyl-2-oxo-2,3-dihydro-1H-benzo[d]imidazol-5-yl)oxy)-5-propoxyphenoxy)butyl)(methyl)amino)acetamide |
| 72 | YS36-64 | 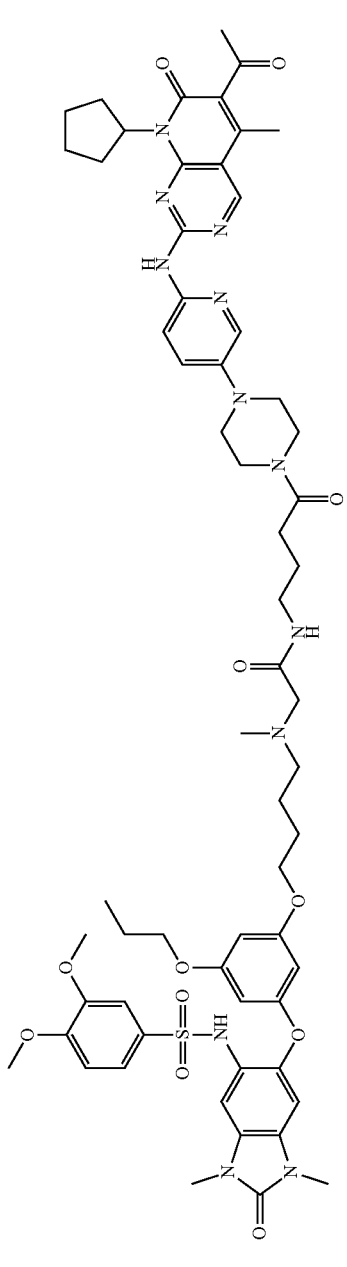 | N-(4-(4-(6-(((6-acetyl-8-cyclopentyl-5-methyl-7-oxo-7,8-dihydropyrido[2,3-d]pyrimidin-2-yl)amino)pyridin-3-yl)piperazin-1-yl)-4-oxobutyl)-2-((4-(3-((6-((3,4-dimethoxyphenyl)sulfonamido)-1,3-dimethyl-2-oxo-2,3-dihydro-1H-benzo[d]imidazol-5-yl)oxy)-5-propoxyphenoxy)butyl)(methyl)amino)acetamide |

TABLE 1-continued

| Cpd. Example Number | Cpd. Code | Structure | Chemical Name |
|---|---|---|---|
| 73 | YS36-65 | 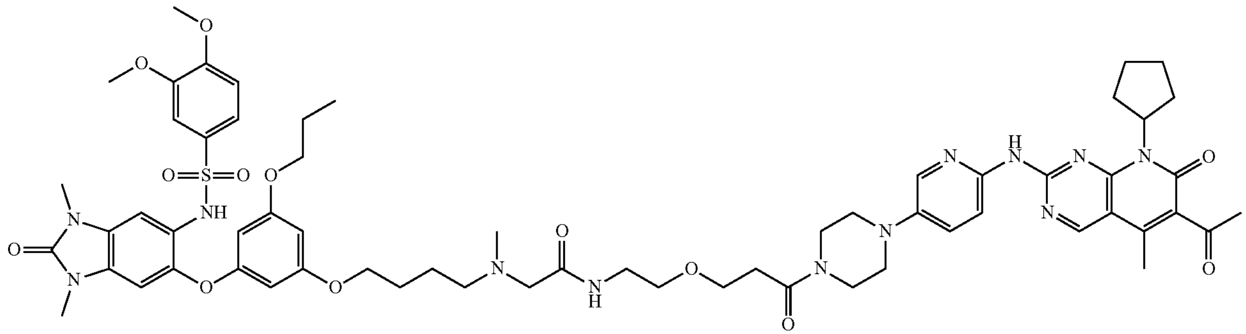 [SMILES: CCCOc1cc(OCCCCN(C)CC(=O)NCCOCCC(=O)N2CCN(c3ccc(Nc4ncc5c(C)c(C(C)=O)c(=O)n(C6CCCC6)c5n4)nc3)CC2)cc(Oc2cc3c(cc2NS(=O)(=O)c2ccc(OC)c(OC)c2)n(C)c(=O)n3C)c1] | N-(2-(3-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-3-oxopropoxy)ethyl)-2-((4-(3-((6-((3,4-dimethoxyphenyl)sulfonamido)-1,3-dimethyl-2-oxo-2,3-dihydro-1H-benzo[d]imidazol-5-yl)oxy)-5-propoxyphenoxy)butyl)(methyl)amino)acetamide |
| 74 | YS36-66 | 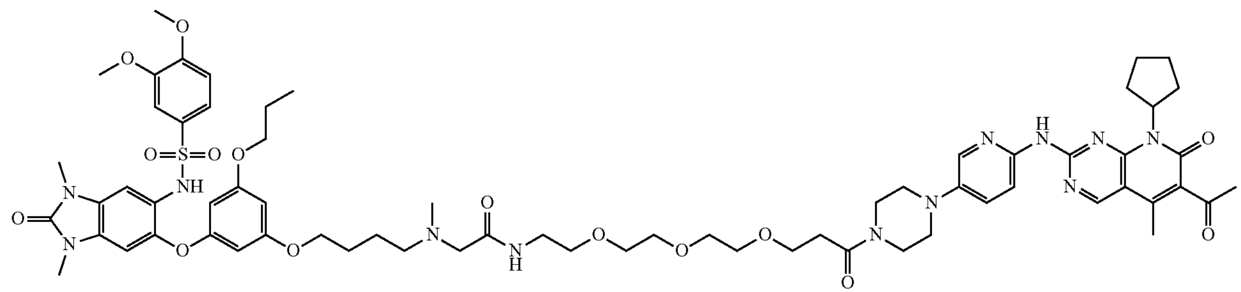 [SMILES: CCCOc1cc(OCCCCN(C)CC(=O)NCCOCCOCCOCCC(=O)N2CCN(c3ccc(Nc4ncc5c(C)c(C(C)=O)c(=O)n(C6CCCC6)c5n4)nc3)CC2)cc(Oc2cc3c(cc2NS(=O)(=O)c2ccc(OC)c(OC)c2)n(C)c(=O)n3C)c1] | N-(2-(2-(3-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-3-oxopropoxy)ethoxy)ethyl)-2-((4-(3-((6-((3,4-dimethoxyphenyl)sulfonamido)-1,3-dimethyl-2-oxo-2,3-dihydro-1H-benzo[d]imidazol-5-yl)oxy)-5-propoxyphenoxy)butyl)(methyl)amino)acetamide |

TABLE 1-continued
| Cpd. Example Number | Cpd. Code | Structure | Chemical Name |
|---|---|---|---|
| 75 | YS36-67 | 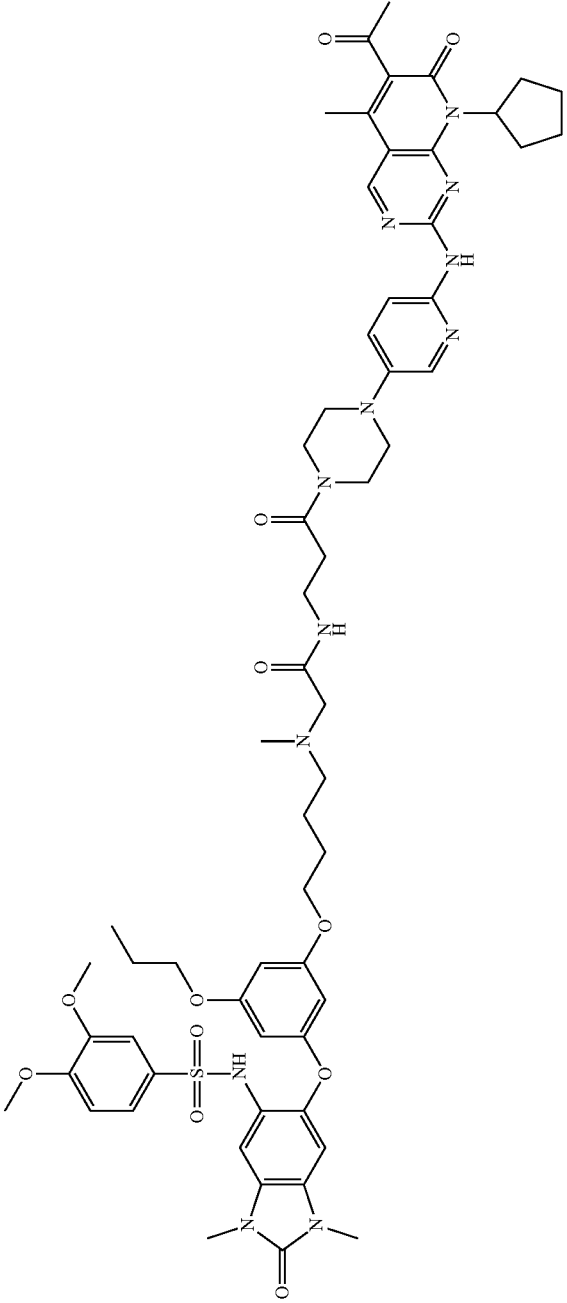 | N-(3-(4-(6-((6-acetyl-8-cyclopentyl-5-methyl-7-oxo-7,8-dihydropyrido[2,3-d]pyrimidin-2-yl)aminopyridin-3-yl)piperazin-1-yl)-3-oxopropyl)-2-((4-(3-((6-((3,4-dimethoxy-phenyl)sulfonamido)-1,3-dimethyl-2-oxo-2,3-dihydro-1H-benzo[d]imidazol-5-yl)oxy)-5-propoxyphenoxy)butyl)(methyl)amino)acetamide |

TABLE 1-continued

| Cpd. Example Number | Cpd. Code | Structure | Chemical Name |
|---|---|---|---|
| 76 | YS36-68 | 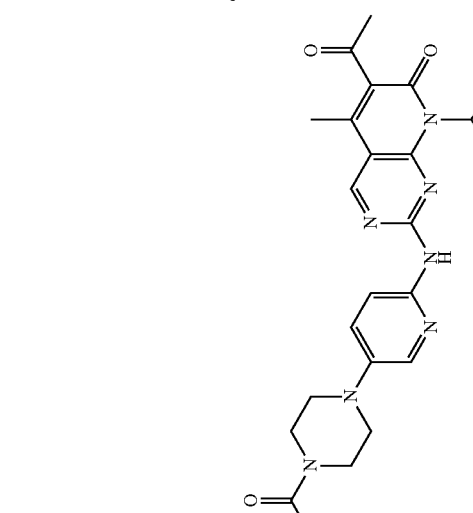 | N-(5-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-5-oxopentyl)-2-((4-(3-((6-((3,4-dimethoxyphenyl)sulfonamido)-1,3-dimethyl-2-oxo-2,3-dihydro-1H-benzo[d]imidazol-5-yl)oxy)-5-propoxyphenoxy)butyl)(methyl)amino)acetamide |
| 77 | YS36-69 | 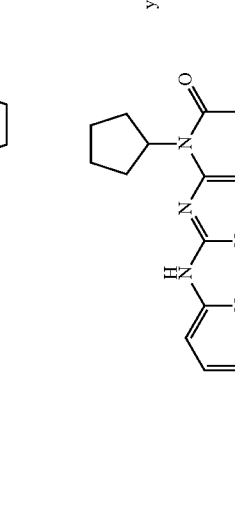 | N-(6-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-6-oxohexyl)-2-((4-(3-((6-((3,4-dimethoxyphenyl)sulfonamido)-1,3-dimethyl-2-oxo-2,3-dihydro-1H-benzo[d]imidazol-5-yl)oxy)-5-propoxyphenoxy)butyl)(methyl)amino)acetamide |

TABLE 1-continued

| Cpd. Example Number | Cpd. Code | Structure | Chemical Name |
|---|---|---|---|
| 78 | YS36-70 | 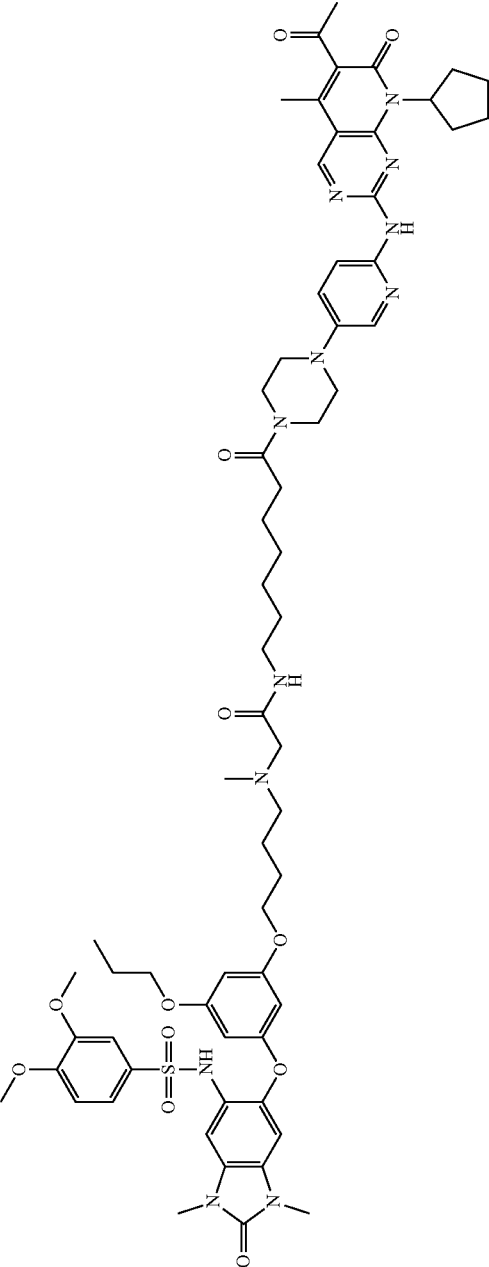 | N-(7-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-7-oxoheptyl)-2-((4-(3-((6-((3,4-dimethoxyphenyl)sulfonamido)-1,3-dimethyl-2-oxo-2,3-dihydro-1H-benzo[d]imidazol-5-yl)oxy)-5-propoxyphenoxy)butyl)(methyl)amino)acetamide |
| 79 | YS36-71 | 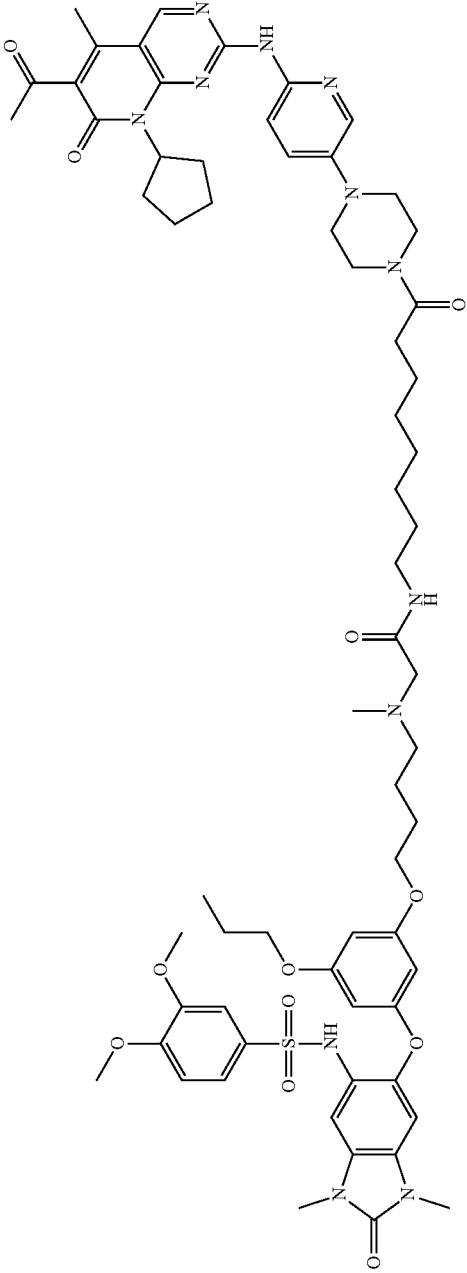 | N-(8-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-8-oxooctyl)-2-((4-(3-((6-((3,4-dimethoxyphenyl)sulfonamido)-1,3-dimethyl-2-oxo-2,3-dihydro-1H-benzo[d]imidazol-5-yl)oxy)-5-propoxyphenoxy)butyl)(methyl)amino)acetamide |

| Cpd. Example Number | Cpd. Code | Structure | Chemical Name |
|---|---|---|---|
| 80 | | 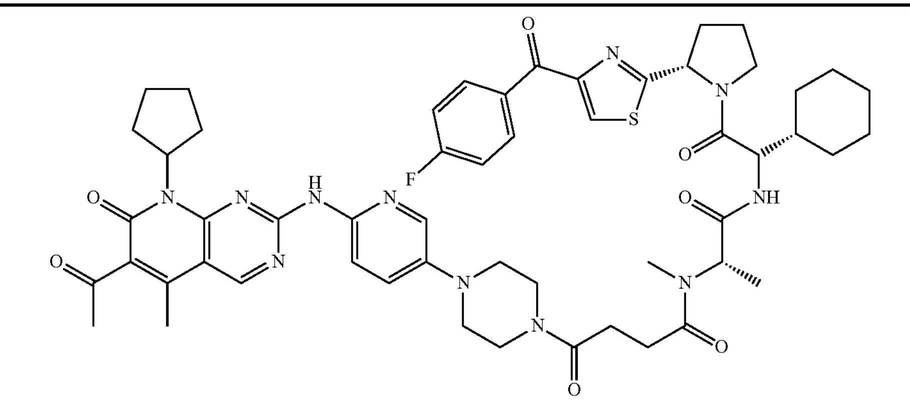 | 4-(4-(6-((6-acetyl-8-cyclopentyl-5-methyl-7-oxo-7,8-dihydropyrido[2,3-d]pyrimidin-2-yl)aminopyridin-3-yl)piperazin-1-yl)-N-((S)-1-(((S)-1-cyclohexyl-2-((S)-2-(4-fluorobenzoyl)thiazol-2-yl)pyrrolidin-1-yl)-2-oxoethyl)amino)-1-oxopropan-2-yl)-N-methyl-4-oxobutanamide |
| 81 | | 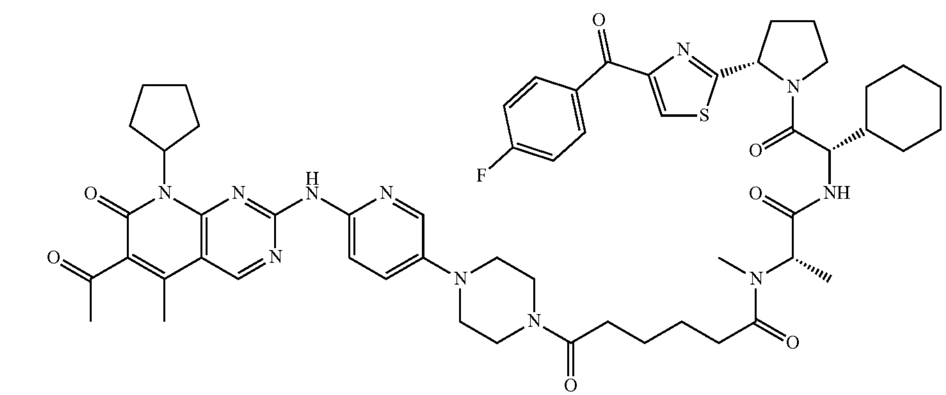 [SMILES: CC(=O)c1c(C)c2cnc(Nc3ccc(N4CCN(C(=O)CCCCC(=O)N(C)[C@@H](C)C(=O)N[C@H](C(=O)N5CCC[C@H]5c5nc(C(=O)c6ccc(F)cc6)cs5)C5CCCCC5)CC4)cn3)nc2n(C2CCCC2)c1=O] | 6-(4-(6-((6-acetyl-8-cyclopentyl-5-methyl-7-oxo-7,8-dihydropyrido[2,3-d]pyrimidin-2-yl)aminopyridin-3-yl)piperazin-1-yl)-N-((S)-1-(((S)-1-cyclohexyl-2-((S)-2-(4-fluorobenzoyl)thiazol-2-yl)pyrrolidin-1-yl)-2-oxoethyl)amino)-1-oxopropan-2-yl)-N-methyl-6-oxohexanamide |

| Cpd. Example Number | Cpd. Code | Structure | Chemical Name |
|---|---|---|---|
| 82 | | 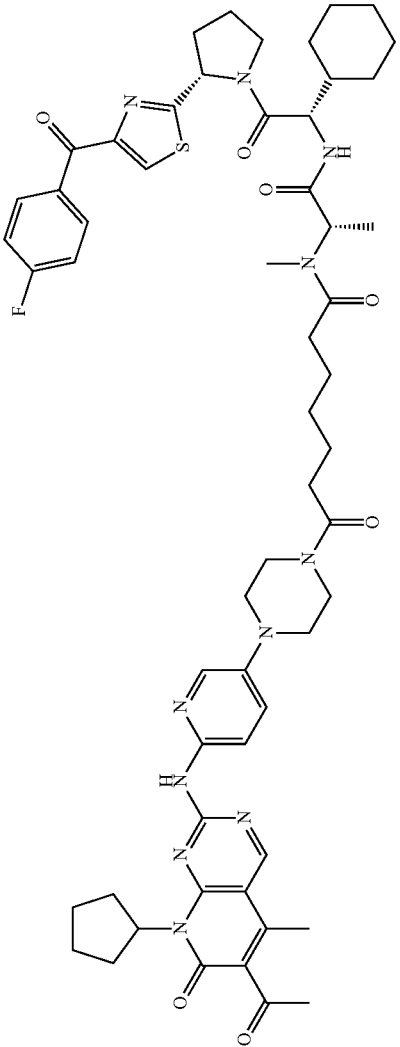 | 7-(4-(6-((6-acetyl-8-cyclopentyl-5-methyl-7-oxo-7,8-dihydropyrido[2,3-d]pyrimidin-2-yl)aminopyridin-3-yl)piperazin-1-yl)-N-((S)-1-(((S)-1-cyclohexyl-2-((S)-2-(4-fluorobenzoyl)thiazol-2-yl)pyrrolidin-1-yl)-2-oxoethyl)amino)-1-oxopropan-2-yl)-N-methyl-7-oxoheptanamide |
| 83 | | 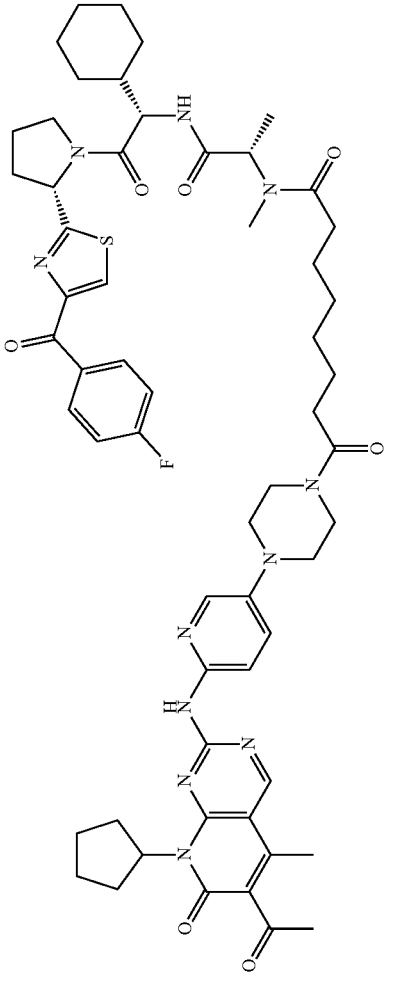 | 8-(4-(6-((6-acetyl-8-cyclopentyl-5-methyl-7-oxo-7,8-dihydropyrido[2,3-d]pyrimidin-2-yl)aminopyridin-3-yl)piperazin-1-yl)-N-((S)-1-(((S)-1-cyclohexyl-2-((S)-2-(4-fluorobenzoyl)thiazol-2-yl)pyrrolidin-1-yl)-2-oxoethyl)amino)-1-oxopropan-2-yl)-N-methyl-8-oxooctanamide |

TABLE 1-continued

| Cpd. Example Number | Cpd. Code | Structure | Chemical Name |
|---|---|---|---|
| 84 | | 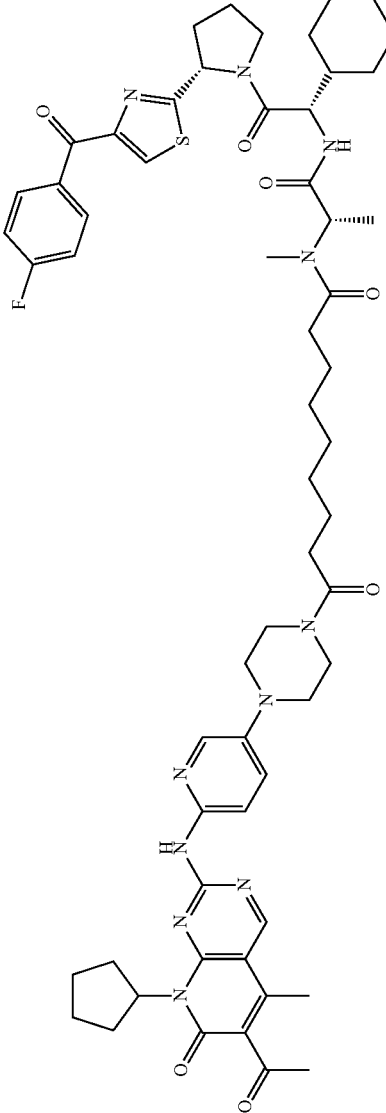 | 9-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-N-((S)-1-(((S)-1-cyclohexyl-2-((S)-2-(4-(4-fluorobenzoyl)thiazol-2-yl)pyrrolidin-1-yl)-2-oxoethyl)amino)-1-oxopropan-2-yl)-N-methyl-9-oxononanamide |
| 85 | | 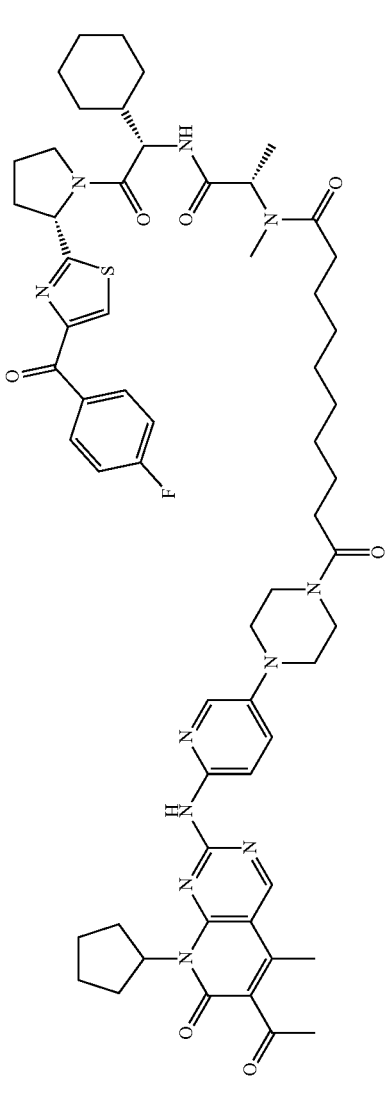 | 10-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-N-((S)-1-(((S)-1-cyclohexyl-2-((S)-2-(4-(4-fluorobenzoyl)thiazol-2-yl)pyrrolidin-1-yl)-2-oxoethyl)amino)-1-oxopropan-2-yl)-N-methyl-10-oxodecanamide |

TABLE 1-continued

| Cpd. Example Number | Cpd. Code | Structure | Chemical Name |
|---|---|---|---|
| 86 | | 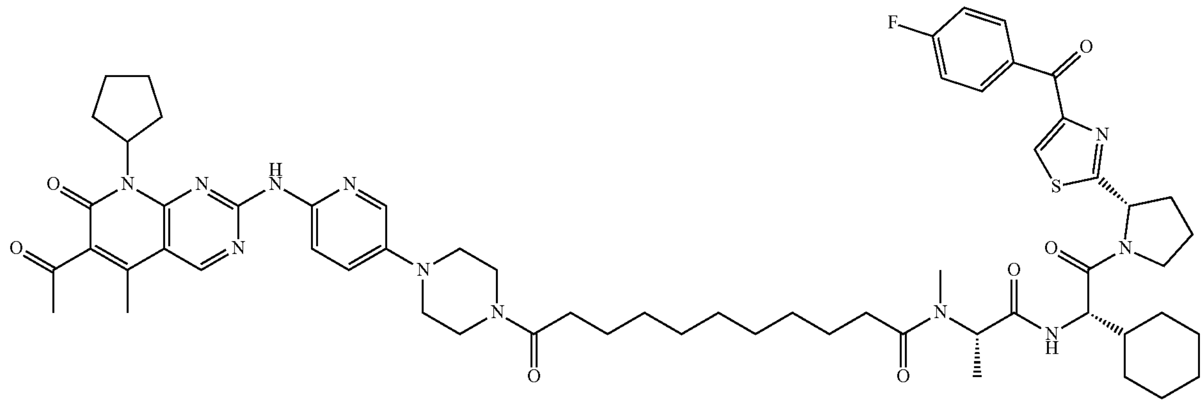 [SMILES: CC(=O)c1c(C)c2cnc(Nc3ccc(N4CCN(C(=O)CCCCCCCCCC(=O)N(C)[C@@H](C)C(=O)N[C@H](C(=O)N5CCC[C@H]5c5nc(C(=O)c6ccc(F)cc6)cs5)C5CCCCC5)CC4)cn3)nc2n(C2CCCC2)c1=O] | 11-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-N-((S)-1-(((S)-1-cyclohexyl-2-((S)-2-(4-fluorobenzoyl)thiazol-2-yl)pyrrolidin-1-yl)-2-oxoethyl)amino)-1-oxopropan-2-yl)-N-methyl-11-oxoundecanamide |
| 87 | | 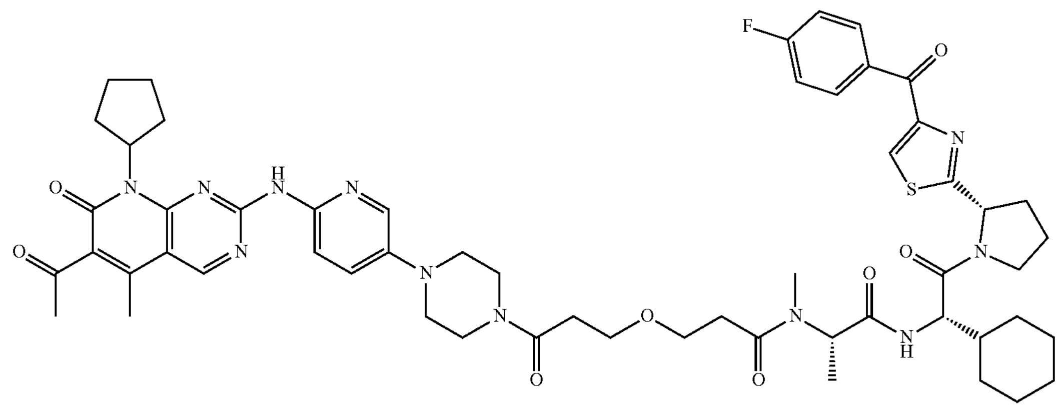 [SMILES: CC(=O)c1c(C)c2cnc(Nc3ccc(N4CCN(C(=O)CCOCCC(=O)N(C)[C@@H](C)C(=O)N[C@H](C(=O)N5CCC[C@H]5c5nc(C(=O)c6ccc(F)cc6)cs5)C5CCCCC5)CC4)cn3)nc2n(C2CCCC2)c1=O] | 3-(3-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-3-oxopropoxy)-N-((S)-1-(((S)-1-cyclohexyl-2-((S)-2-(4-fluorobenzoyl)thiazol-2-yl)pyrrolidin-1-yl)-2-oxoethyl)amino)-1-oxopropan-2-yl)-N-methylpropanamide |

TABLE 1-continued

| Cpd. Example Number | Cpd. Code | Structure | Chemical Name |
|---|---|---|---|
| 88 | | 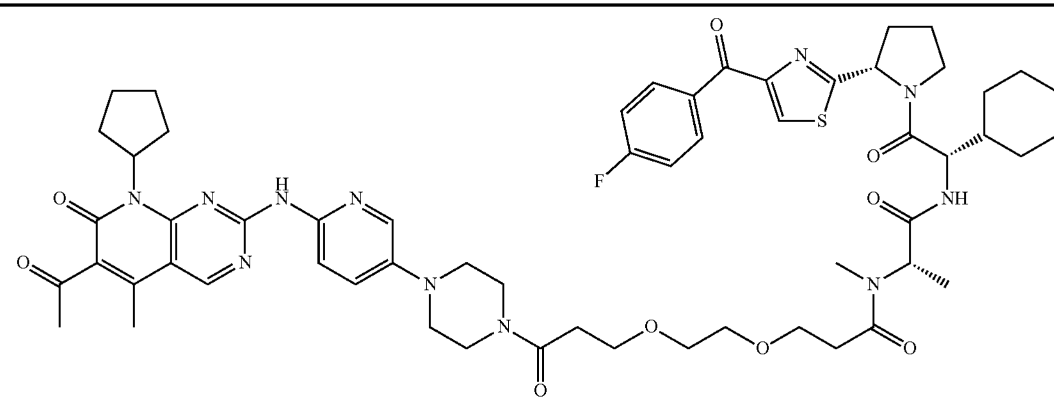 | 3-(2-(3-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-3-oxopropoxy)ethoxy)-N-((S)-1-(((S)-1-cyclohexyl-2-((S)-2-(4-(4-fluorobenzoyl)thiazol-2-yl)pyrrolidin-1-yl)-2-oxoethyl)amino)-1-oxopropan-2-yl)-N-methylpropanamide |
| 89 | | 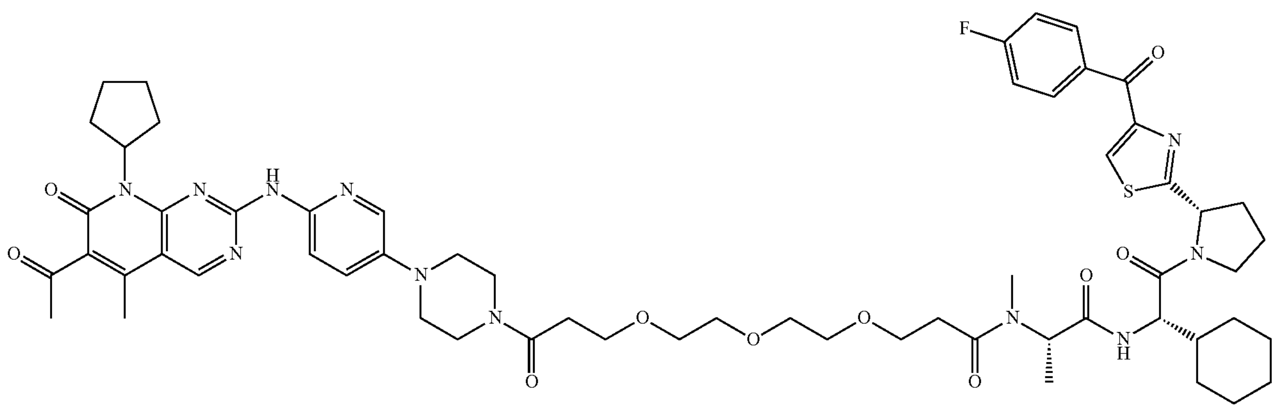 [SMILES: CC(=O)c1c(C)c2cnc(Nc3ccc(N4CCN(C(=O)CCOCCOCCOCCC(=O)N(C)[C@@H](C)C(=O)N[C@H](C(=O)N5CCC[C@H]5c5nc(C(=O)c6ccc(F)cc6)cs5)C5CCCCC5)CC4)cn3)nc2n(C2CCCC2)c1=O] | 3-(2-(2-(3-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-3-oxopropoxy)ethoxy)ethoxy)-N-((S)-1-(((S)-1-cyclohexyl-2-((S)-2-(4-(4-fluorobenzoyl)thiazol-2-yl)pyrrolidin-1-yl)-2-oxoethyl)amino)-1-oxopropan-2-yl)-N-methylpropanamide |

TABLE 1-continued

| Cpd. Example Number | Cpd. Code | Structure | Chemical Name |
|---|---|---|---|
| 90 | | 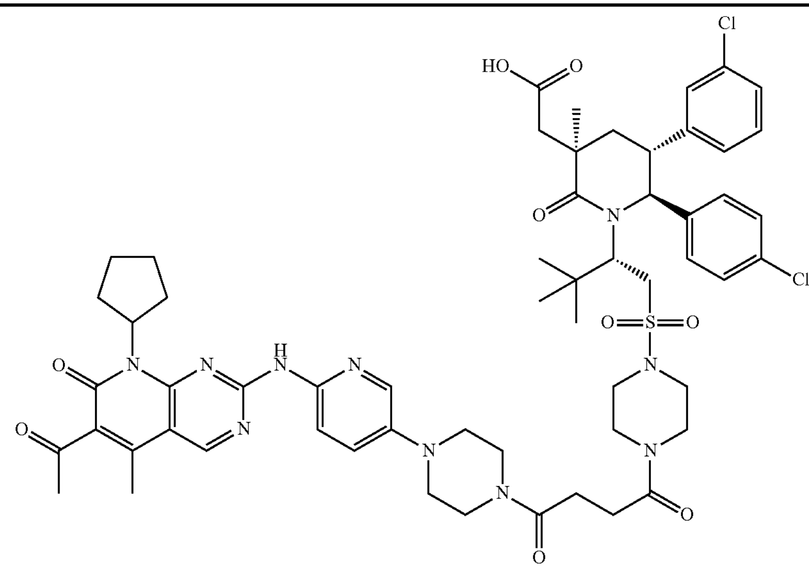 | 2-((3R,5R,6S)-1-((S)-1-((4-(4-(4-(6-acetyl-8-cyclopentyl-5-methyl-7-oxo-7,8-dihydropyrido[2,3-d]pyrimidin-2-yl)amino)pyridin-3-yl)piperazin-1-yl)-4-oxobutanoyl)piperazin-1-yl)sulfonyl)-3,3-dimethylbutan-2-yl)-5-(3-chlorophenyl)-6-(4-chlorophenyl)-3-methyl-2-oxopiperidin-3-yl)acetic acid |

TABLE 1-continued

| Cpd. Example Number | Cpd. Code | Structure | Chemical Name |
|---|---|---|---|
| 91 | | 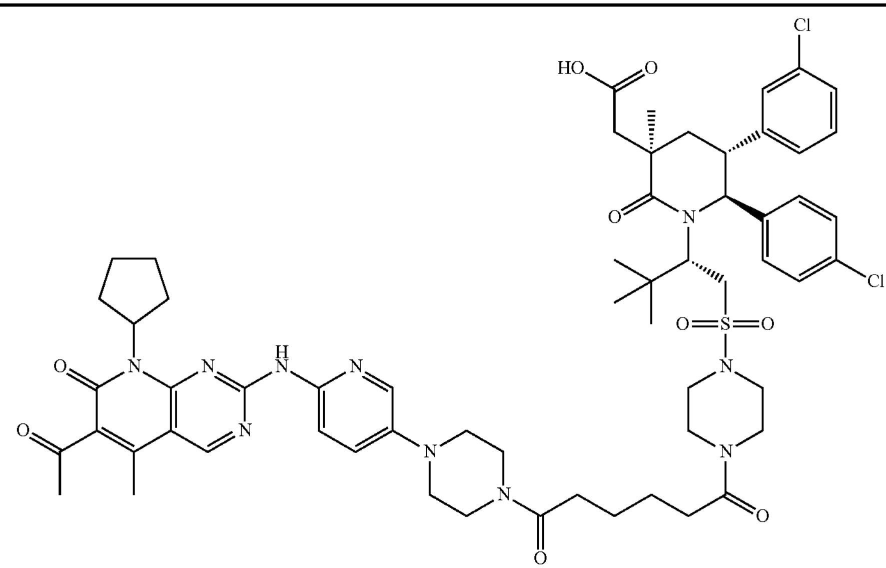 | 2-((3R,5R,6S)-1-((S)-1-((4-(6-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-6-oxohexanoyl)piperazin-1-yl)sulfonyl)-3,3-dimethylbutan-2-yl)-5-(3-chlorophenyl)-6-(4-chlorophenyl)-3-methyl-2-oxopiperidin-3-yl)acetic acid |
| 92 | | 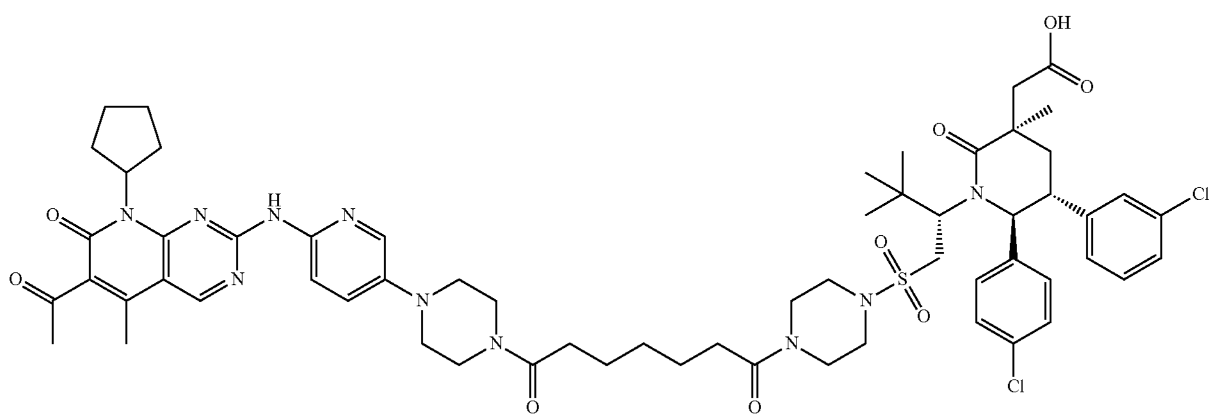 | 2-((3R,5R,6S)-1-((S)-1-((4-(7-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-7-oxoheptanoyl)piperazin-1-yl)sulfonyl)-3,3-dimethylbutan-2-yl)-5-(3-chlorophenyl)-6-(4-chlorophenyl)-3-methyl-2-oxopiperidin-3-yl)acetic acid |

TABLE 1-continued

| Cpd. Example Number | Cpd. Code | Structure | Chemical Name |
|---|---|---|---|
| 93 | | 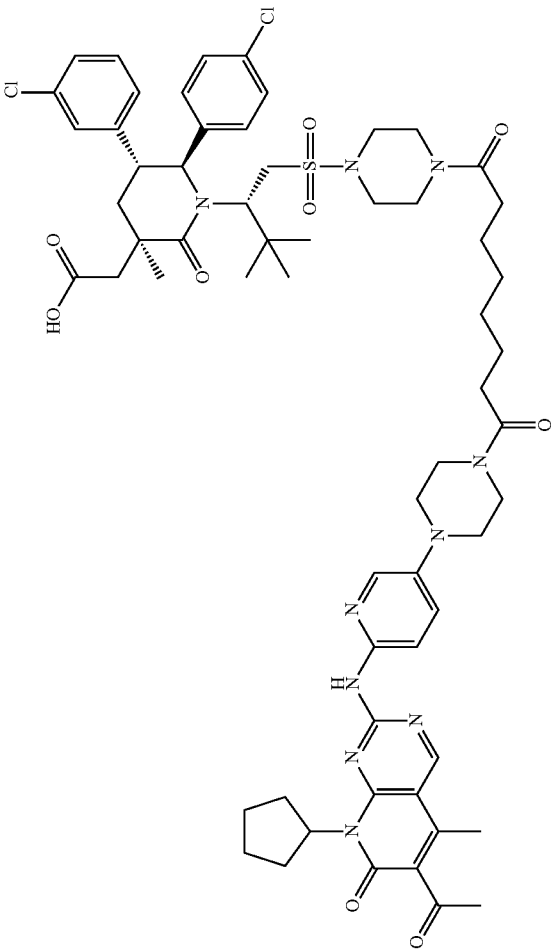 | 2-((3R,5R,6S)-1-((S)-1-((4-(8-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-8-oxooctanoyl)piperazin-1-yl)sulfonyl)-3,3-dimethylbutan-2-yl)-5-(3-chlorophenyl)-6-(4-chlorophenyl)-3-methyl-2-oxopiperidin-3-yl)acetic acid |
| 94 | | 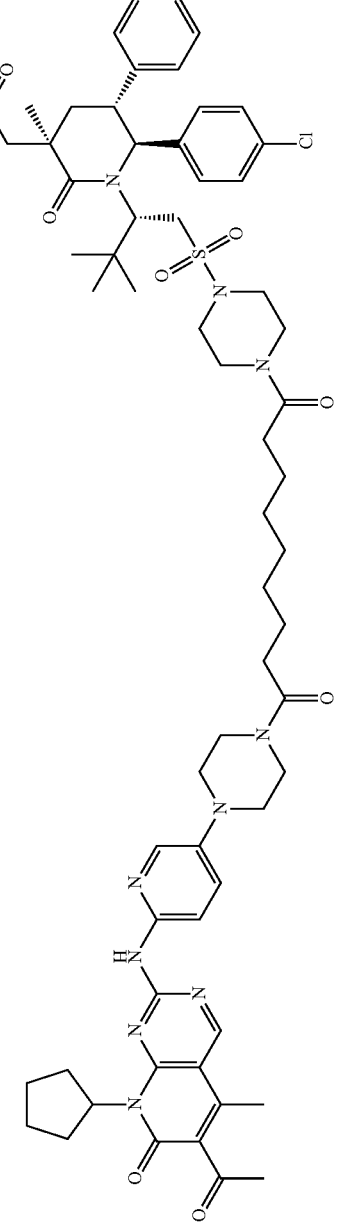 | 2-((3R,5R,6S)-1-((S)-1-((4-(9-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-9-oxononanoyl)piperazin-1-yl)sulfonyl)-3,3-dimethylbutan-2-yl)-5-(3-chlorophenyl)-6-(4-chlorophenyl)-3-methyl-2-oxopiperidin-3-yl)acetic acid |

TABLE 1-continued

| Cpd. Example Number | Cpd. Code | Structure | Chemical Name |
|---|---|---|---|
| 95 | | 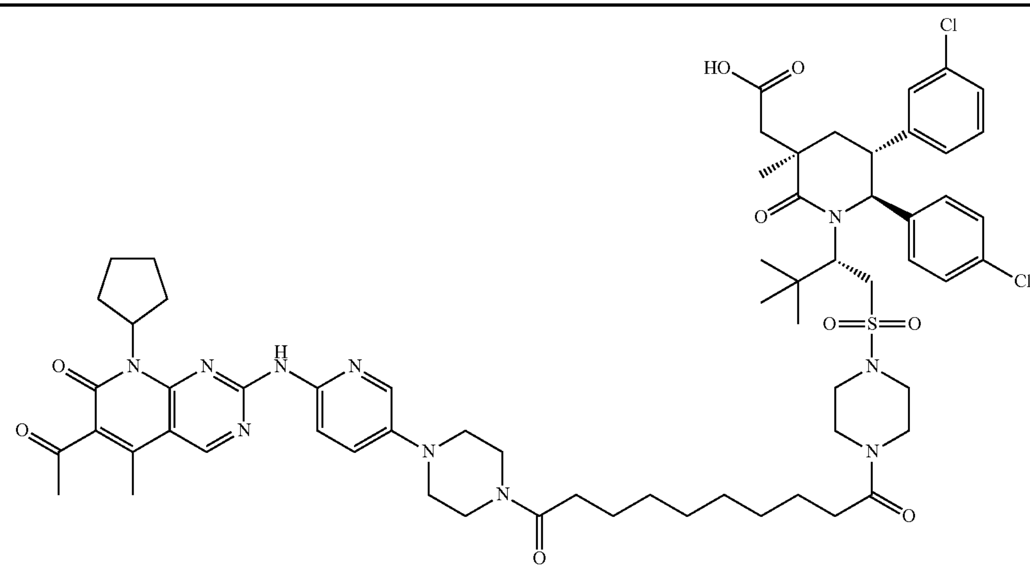 | 2-((3R,5R,6S)-1-((S)-1-((4-(10-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-10-oxodecanoyl)piperazin-1-yl)sulfonyl)-3,3-dimethylbutan-2-yl)-5-(3-chlorophenyl)-6-(4-chlorophenyl)-3-methyl-2-oxopiperidin-3-yl)acetic acid |
| 96 | | 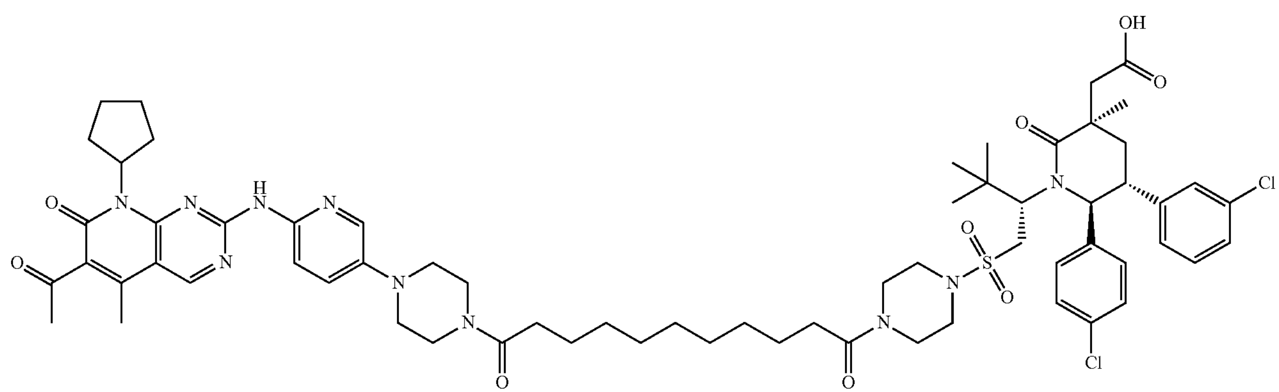 [SMILES: CC(=O)c1c(C)c2cnc(Nc3ccc(N4CCN(C(=O)CCCCCCCCCC(=O)N5CCN(S(=O)(=O)C[C@@H](N6C(=O)[C@@](C)(CC(=O)O)C[C@H](c7cccc(Cl)c7)[C@H]6c6ccc(Cl)cc6)C(C)(C)C)CC5)CC4)cn3)nc2n(C2CCCC2)c1=O] | 2-((3R,5R,6S)-1-((S)-1-((4-(11-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-11-oxoundecanoyl)piperazin-1-yl)sulfonyl)-3,3-dimethylbutan-2-yl)-5-(3-chlorophenyl)-6-(4-chlorophenyl)-3-methyl-2-oxopiperidin-3-yl)acetic acid |

TABLE 1-continued

| Cpd. Example Number | Cpd. Code | Structure | Chemical Name |
|---|---|---|---|
| 97 | | 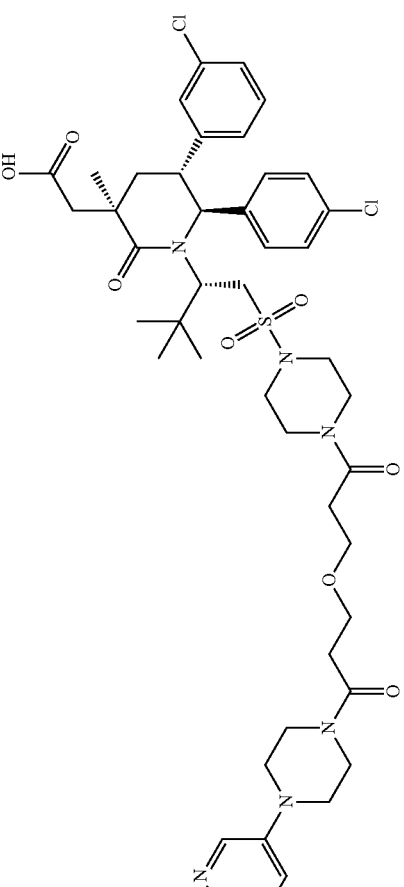 | 2-((3R,5R,6S)-1-((S)-1-((4-(3-(3-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-3-oxopropoxy)propanoyl)piperazin-1-yl)sulfonyl)-3,3-dimethylbutan-2-yl)-5-(3-chlorophenyl)-6-(4-chlorophenyl)-3-methyl-2-oxopiperidin-3-yl)acetic acid |
| 98 | | 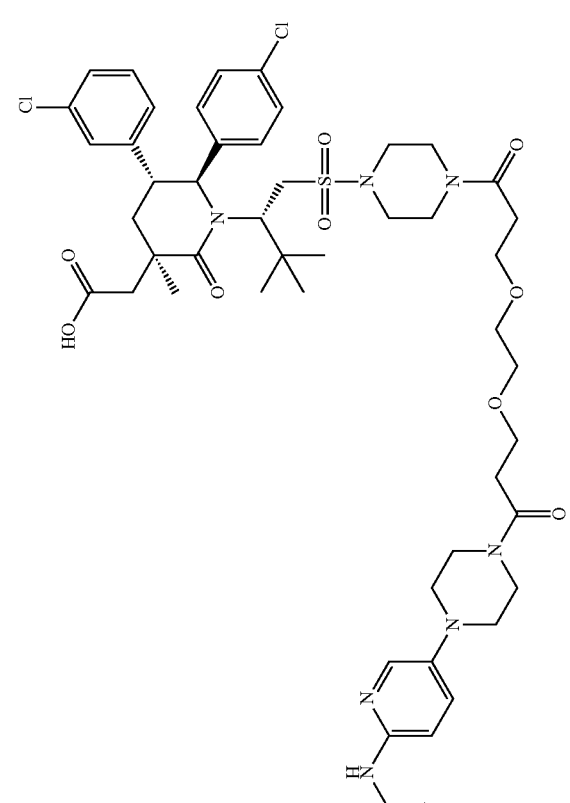 | 2-((3R,5R,6S)-1-((S)-1-((4-(3-(2-(3-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-3-oxopropoxy)ethoxy)propanoyl)piperazin-1-yl)sulfonyl)-3,3-dimethylbutan-2-yl)-5-(3-chlorophenyl)-6-(4-chlorophenyl)-3-methyl-2-oxopiperidin-3-yl)acetic acid |

TABLE 1-continued

| Cpd. Example Number | Cpd. Code | Structure | Chemical Name |
|---|---|---|---|
| 99 | | 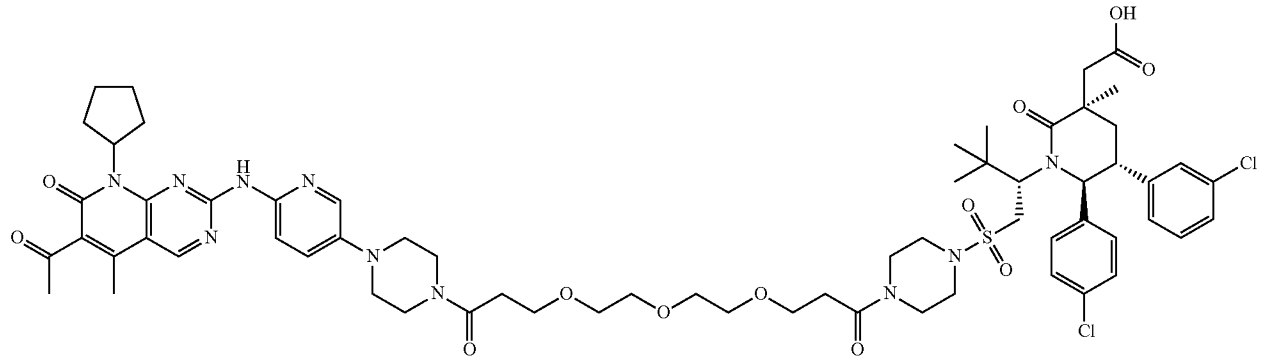 [SMILES: CC(=O)c1c(C)c2cnc(Nc3ccc(N4CCN(C(=O)CCOCCOCCOCCC(=O)N5CCN(S(=O)(=O)C[C@@H](N6C(=O)[C@@](C)(CC(=O)O)C[C@H](c7cccc(Cl)c7)[C@H]6c6ccc(Cl)cc6)C(C)(C)C)CC5)CC4)cn3)nc2n(C2CCCC2)c1=O] | 2-((3R,5R,6S)-1-((S)-1-((4-(3-(2-(2-(3-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-3-oxopropoxy)ethoxy)ethoxy)propanoyl)piperazin-1-yl)sulfonyl)-3,3-dimethylbutan-2-yl)-5-(3-chlorophenyl)-6-(4-chlorophenyl)-3-methyl-2-oxopiperidin-3-yl)acetic acid |
| 100 | | 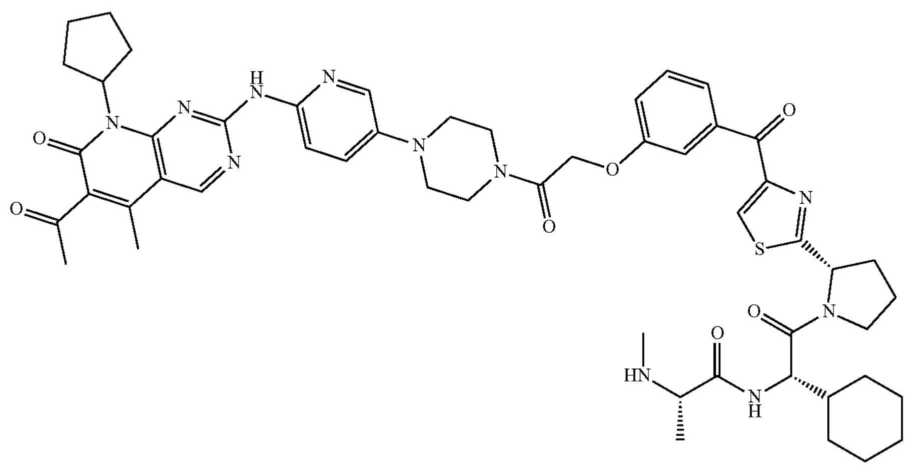 [SMILES: CN[C@@H](C)C(=O)N[C@H](C(=O)N1CCC[C@H]1c1nc(C(=O)c2cccc(OCC(=O)N3CCN(c4ccc(Nc5ncc6c(C)c(C(C)=O)c(=O)n(C7CCCC7)c6n5)nc4)CC3)c2)cs1)C1CCCCC1] | (S)-N-((S)-2-((S)-2-(4-(3-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-2-oxoethoxy)benzoyl)thiazol-2-yl)pyrrolidin-1-yl)-1-cyclohexyl-2-oxoethyl)-2-(methylamino)propanamide |

TABLE 1-continued

| Cpd. Example Number | Cpd. Code | Structure | Chemical Name |
|---|---|---|---|
| 101 | | 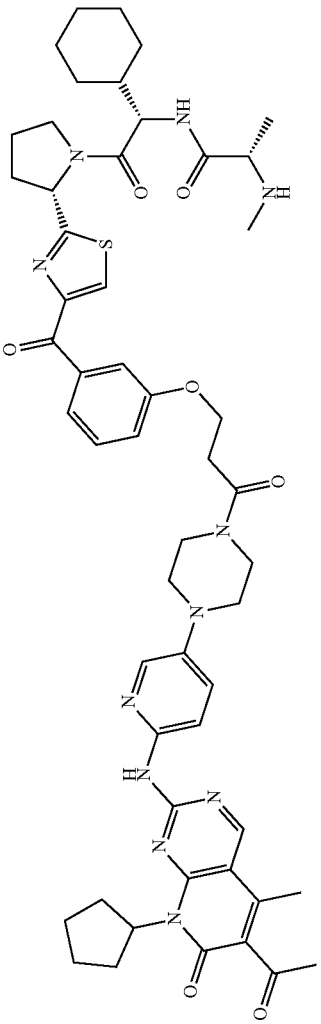 | (S)-N-((S)-2-((S)-2-(4-(3-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-3-oxopropoxy)benzoyl)thiazol-2-yl)pyrrolidin-1-yl)-1-cyclohexyl-2-oxoethyl)-2-(methylamino)propanamide |
| 102 | | 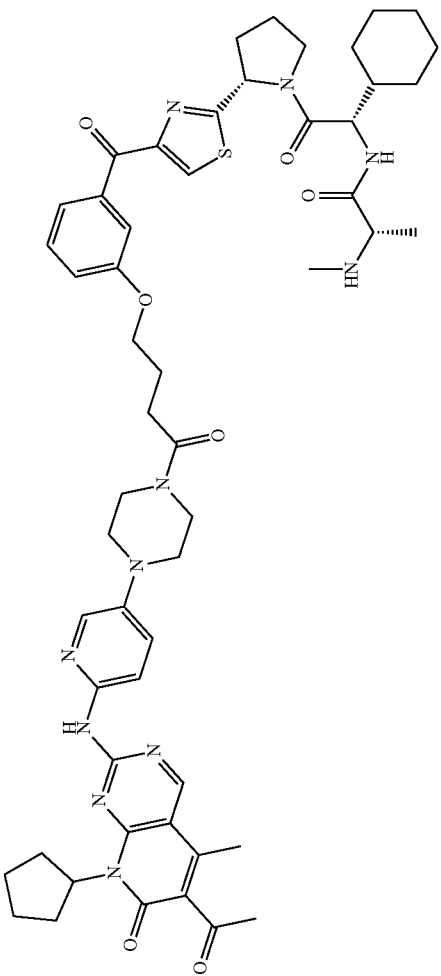 | (S)-N-((S)-2-((S)-2-(4-(3-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-4-oxobutoxy)benzoyl)thiazol-2-yl)pyrrolidin-1-yl)-1-cyclohexyl-2-oxoethyl)-2-(methylamino)propanamide |

TABLE 1-continued

| Cpd. Example Number | Cpd. Code | Structure | Chemical Name |
|---|---|---|---|
| 103 | | 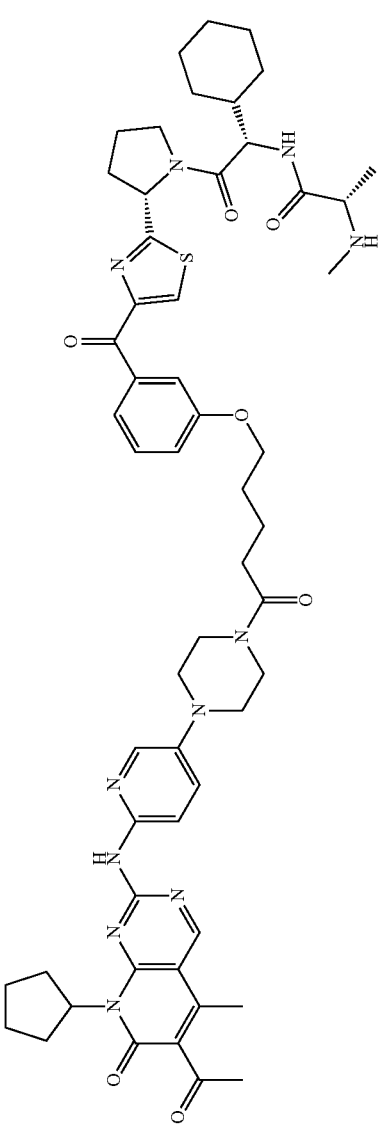 | (S)-N-((S)-2-((S)-2-(4-(3-((5-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-5-oxopentyl)oxy)benzoyl)thiazol-2-yl)pyrrolidin-1-yl)-1-cyclohexyl-2-oxoethyl)-2-(methylamino)propanamide |
| 104 | | 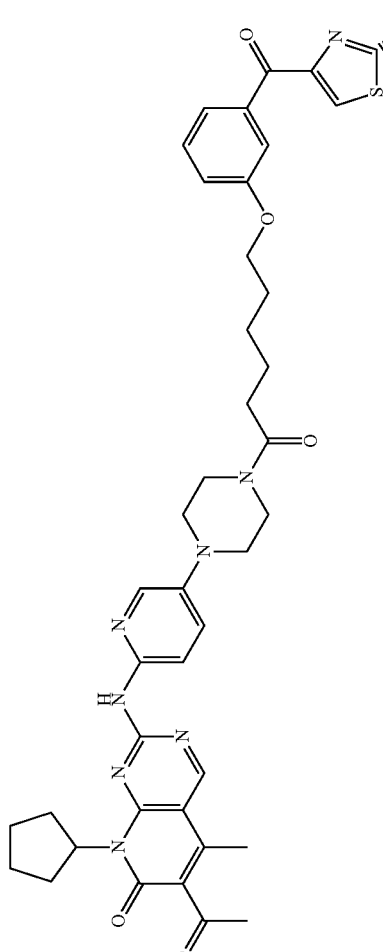 | (S)-N-((S)-2-((S)-2-(4-(3-((6-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-6-oxohexyl)oxy)benzoyl)thiazol-2-yl)pyrrolidin-1-yl)-1-cyclohexyl-2-oxoethyl)-2-(methylamino)propanamide |

| Cpd. Example Number | Cpd. Code | Structure | Chemical Name |
|---|---|---|---|
| 105 | | 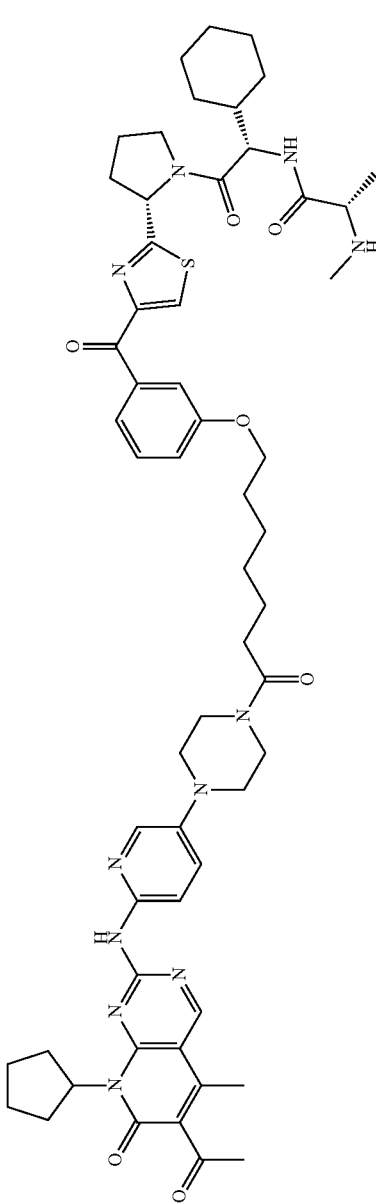 | (S)-N-((S)-2-((S)-2-(4-(3-((7-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-7-oxoheptyl)oxy)benzoyl)thiazol-2-yl)pyrrolidin-1-yl)-1-cyclohexyl-2-oxoethyl)-2-(methylamino)propanamide |

TABLE 1-continued

| Cpd. Example Number | Cpd. Code | Structure | Chemical Name |
|---|---|---|---|
| 106 | | 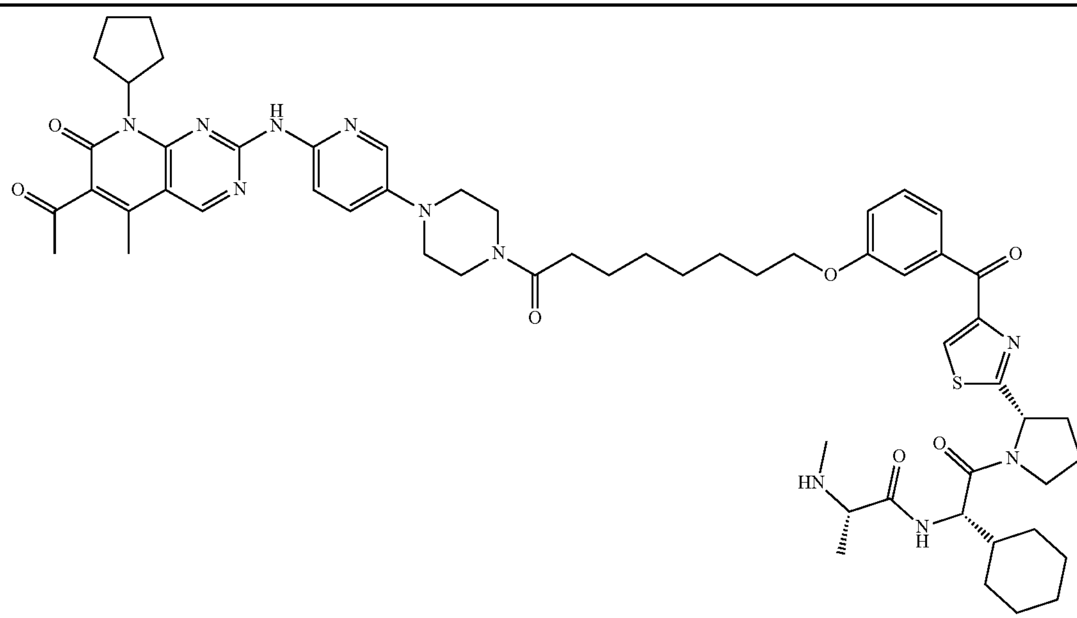 | (S)-N-((S)-2-((S)-2-(4-(3-((8-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-8-oxooctyl)oxy)benzoyl)thiazol-2-yl)pyrrolidin-1-yl)-1-cyclohexyl-2-oxoethyl)-2-(methylamino)propanamide |
| 107 | | 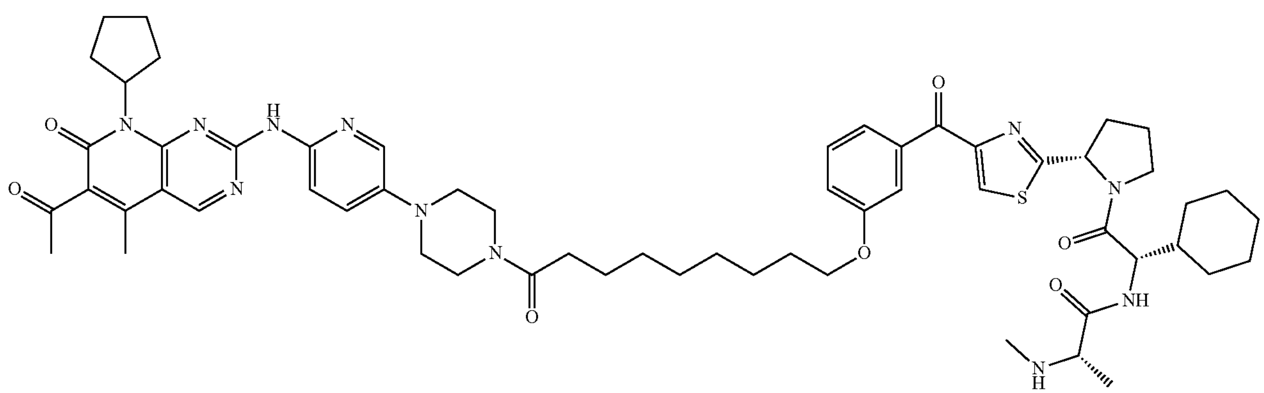 [SMILES: CN[C@@H](C)C(=O)N[C@H](C(=O)N1CCC[C@H]1c1nc(C(=O)c2cccc(OCCCCCCCCC(=O)N3CCN(c4ccc(Nc5ncc6c(C)c(C(C)=O)c(=O)n(C7CCCC7)c6n5)nc4)CC3)c2)cs1)C1CCCCC1] | (S)-N-((S)-2-((S)-2-(4-(3-((9-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-9-oxononyl)oxy)benzoyl)thiazol-2-yl)pyrrolidin-1-yl)-1-cyclohexyl-2-oxoethyl)-2-(methylamino)propanamide |

TABLE 1-continued
| Cpd. Example Number | Cpd. Code | Structure | Chemical Name |
|---|---|---|---|
| 108 | | 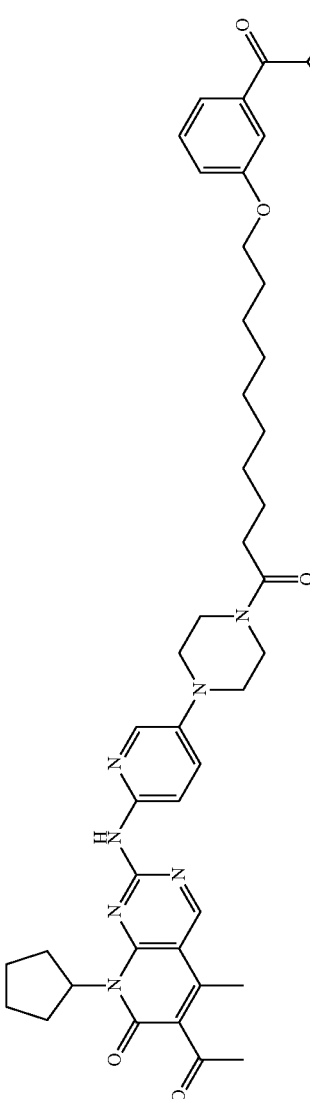 | (S)-N-((S)-2-((S)-2-(4-(3-((10-(4-(6-(((6-acetyl-8-cyclopentyl-5-methyl-7-oxo-7,8-dihydropyrido[2,3-d]pyrimidin-2-yl)amino)pyridin-3-yl)piperazin-1-yl)-10-oxodecyl)oxy)benzoyl)thiazol-2-yl)pyrrolidin-1-yl)-1-cyclohexyl-2-oxoethyl)-2-(methylamino)propanamide |

TABLE 1-continued

| Cpd. Example Number | Cpd. Code | Structure | Chemical Name |
|---|---|---|---|
| 109 | | 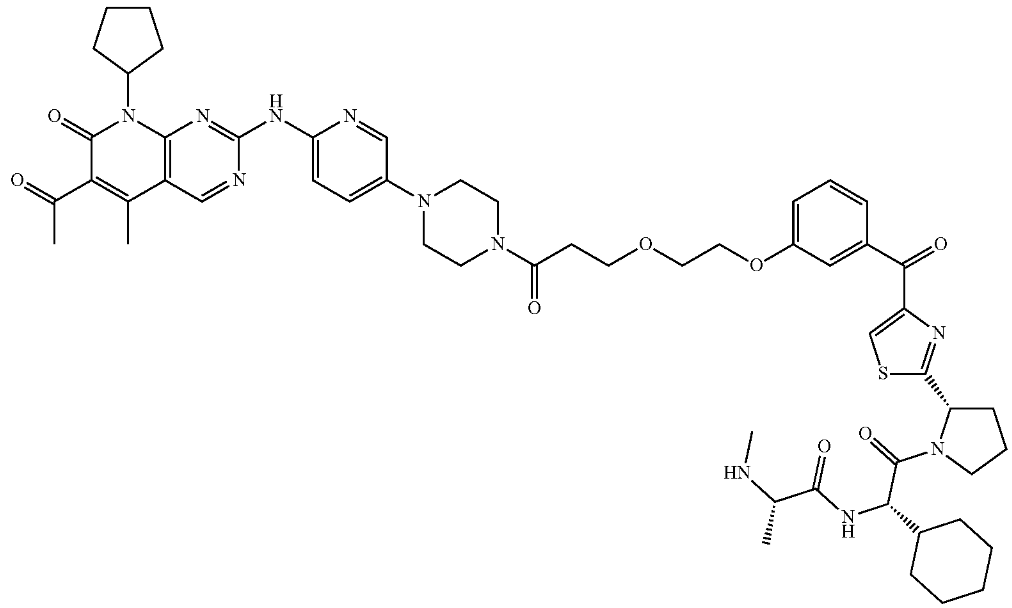 [SMILES: CN[C@@H](C)C(=O)N[C@H](C(=O)N1CCC[C@H]1c1nc(C(=O)c2cccc(OCCOCCC(=O)N3CCN(c4ccc(Nc5ncc6c(C)c(C(C)=O)c(=O)n(C7CCCC7)c6n5)nc4)CC3)c2)cs1)C1CCCCC1] | (S)-N-((S)-2-((S)-2-(4-(3-(2-(3-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-3-oxopropoxy)ethoxy)benzoyl)thiazol-2-yl)pyrrolidin-1-yl)-1-cyclohexyl-2-oxoethyl)-2-(methylamino)propanamide |
| 110 | | 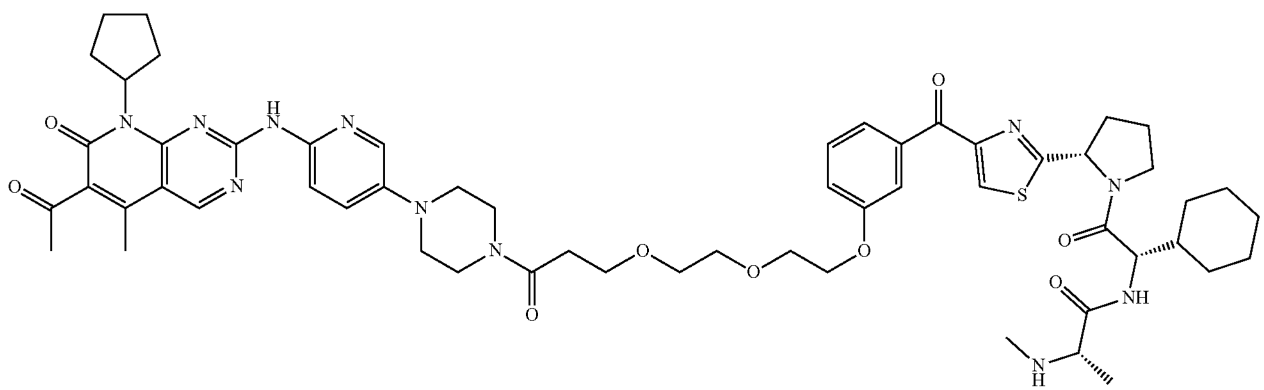 [SMILES: CN[C@@H](C)C(=O)N[C@H](C(=O)N1CCC[C@H]1c1nc(C(=O)c2cccc(OCCOCCOCCC(=O)N3CCN(c4ccc(Nc5ncc6c(C)c(C(C)=O)c(=O)n(C7CCCC7)c6n5)nc4)CC3)c2)cs1)C1CCCCC1] | (S)-N-((S)-2-((S)-2-(4-(3-(2-(2-(3-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-3-oxopropoxy)ethoxy)ethoxy)benzoyl)thiazol-2-yl)pyrrolidin-1-yl)-1-cyclohexyl-2-oxoethyl)-2-(methylamino)propanamide |

TABLE 1-continued

| Cpd. Example Number | Cpd. Code | Structure | Chemical Name |
|---|---|---|---|
| 111 | | 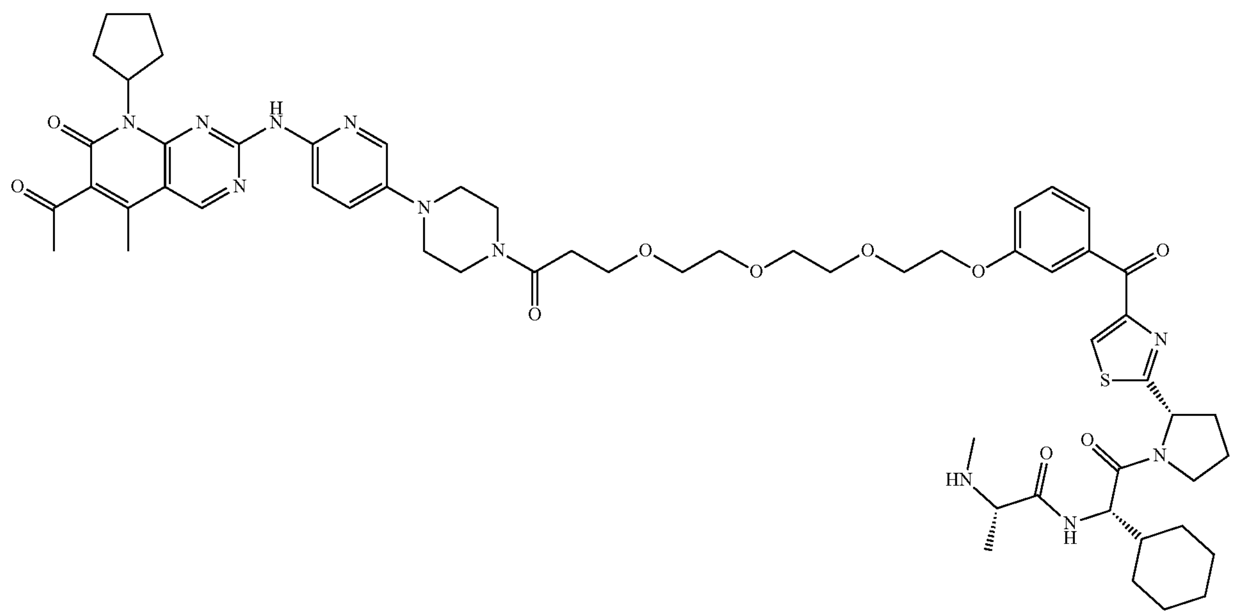 [SMILES: CN[C@@H](C)C(=O)N[C@H](C(=O)N1CCC[C@H]1c1nc(C(=O)c2cccc(OCCOCCOCCOCCC(=O)N3CCN(c4ccc(Nc5ncc6c(C)c(C(C)=O)c(=O)n(C7CCCC7)c6n5)nc4)CC3)c2)cs1)C1CCCCC1] | (S)-N-((S)-2-((S)-2-(4-(3-(2-(2-(2-(3-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-3-oxopropoxy)ethoxy)ethoxy)ethoxy)benzoyl)thiazol-2-yl)pyrrolidin-1-yl)-1-cyclohexyl-2-oxoethyl)-2-(methylamino)propanamide |

TABLE 1-continued

| Cpd. Example Number | Cpd. Code | Structure | Chemical Name |
|---|---|---|---|
| 112 | | 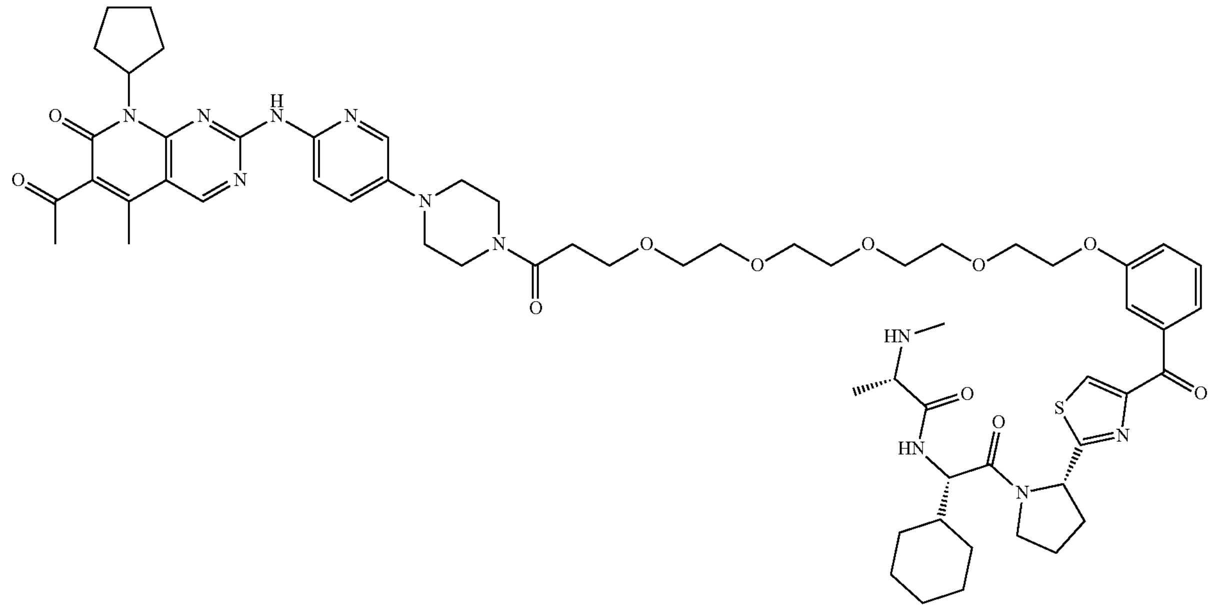 [SMILES: CN[C@@H](C)C(=O)N[C@H](C(=O)N1CCC[C@H]1c1nc(C(=O)c2cccc(OCCOCCOCCOCCOCCC(=O)N3CCN(c4ccc(Nc5ncc6c(C)c(C(C)=O)c(=O)n(C7CCCC7)c6n5)nc4)CC3)c2)cs1)C1CCCCC1] | (S)-N-((S)-2-((S)-2-(4-(3-((15-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-15-oxo-3,6,9,12-tetraoxapentadecyl)oxy)benzoyl)thiazol-2-yl)pyrrolidin-1-yl)-1-cyclohexyl-2-oxoethyl)-2-(methylamino)propanamide |
| 113 | | 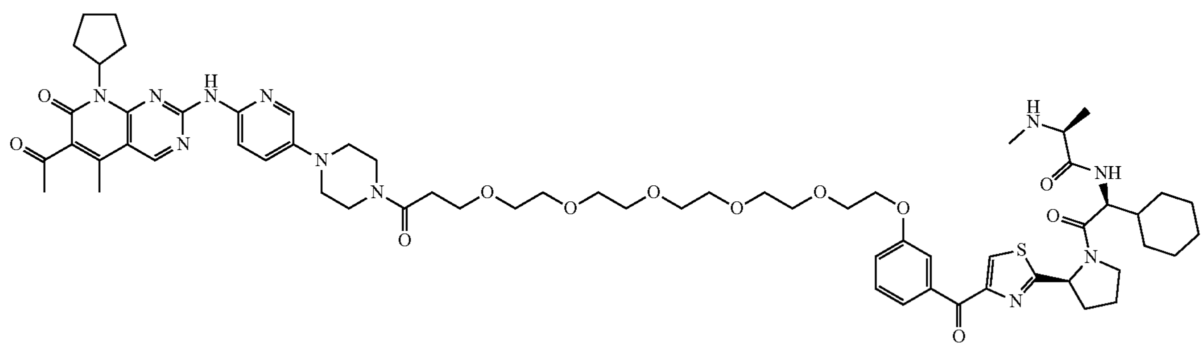 [SMILES: CN[C@@H](C)C(=O)N[C@H](C(=O)N1CCC[C@H]1c1nc(C(=O)c2cccc(OCCOCCOCCOCCOCCOCCC(=O)N3CCN(c4ccc(Nc5ncc6c(C)c(C(C)=O)c(=O)n(C7CCCC7)c6n5)nc4)CC3)c2)cs1)C1CCCCC1] | (S)-N-((S)-2-((S)-2-(4-(3-((18-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-18-oxo-3,6,9,12,15-pentaoxaoctadecyl)oxy)benzoyl)thiazol-2-yl)pyrrolidin-1-yl)-1-cyclohexyl-2-oxoethyl)-2-(methylamino)propanamide |

TABLE 1-continued

| Cpd. Example Number | Cpd. Code | Structure | Chemical Name |
|---|---|---|---|
| 114 | | 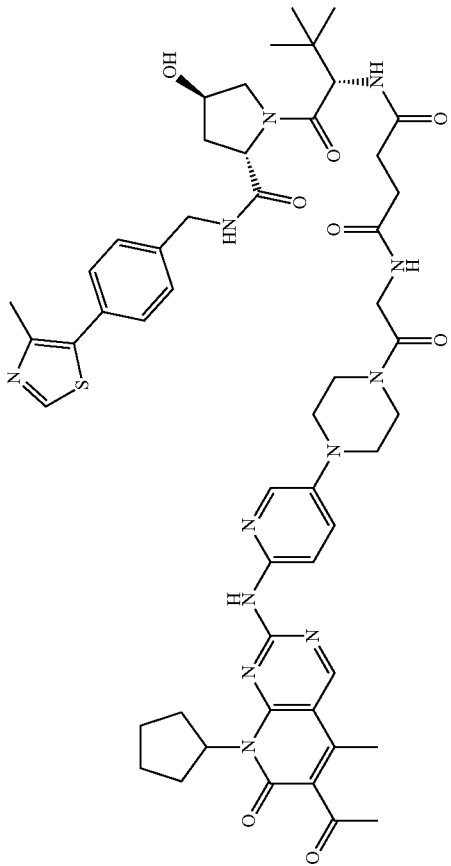 | N¹-(2-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-2-oxoethyl)-N⁴-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)succinamide |
| 115 | | 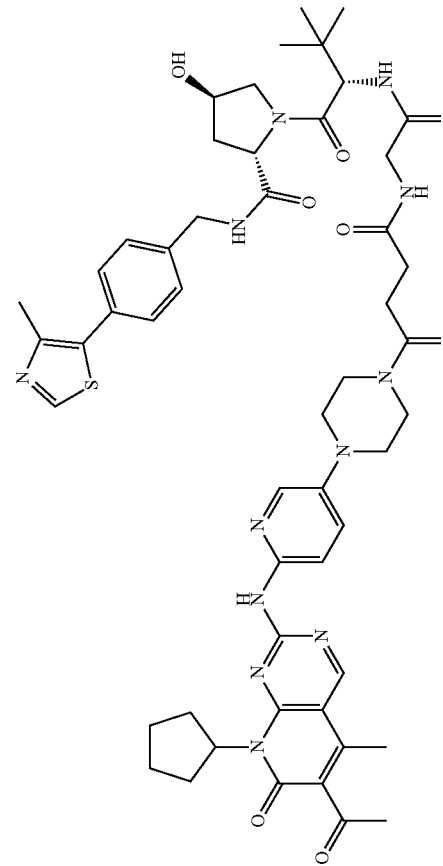 | (2S,4R)-1-((S)-2-(2-(4-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-4-oxobutanamido)acetamido)-3,3-dimethylbutanoyl)-4-hydroxy-N-(4-(4-methylthiazol-5-yl)benzyl)pyrrolidine-2-carboxamide |

TABLE 1-continued

| Cpd. Example Number | Cpd. Code | Structure | Chemical Name |
|---|---|---|---|
| 116 | | 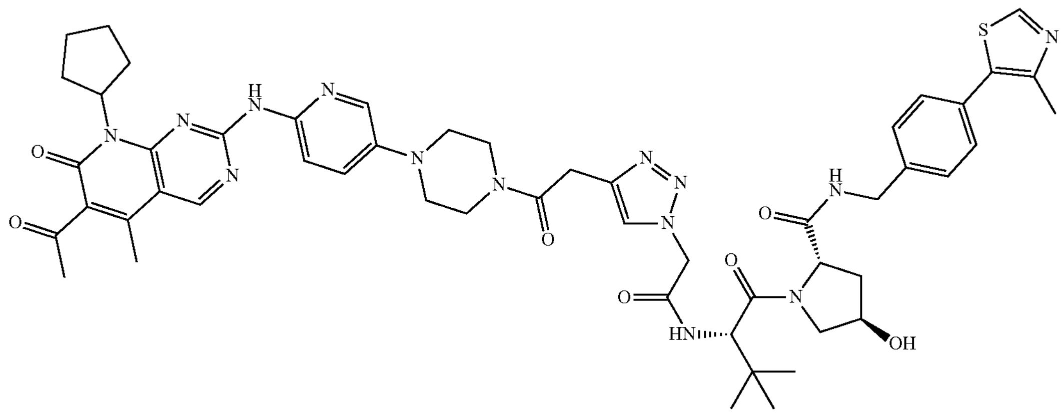 [SMILES: CC(=O)c1c(C)c2cnc(Nc3ccc(N4CCN(C(=O)Cc5cn(CC(=O)N[C@H](C(=O)N6C[C@H](O)C[C@H]6C(=O)NCc6ccc(-c7scnc7C)cc6)C(C)(C)C)nn5)CC4)cn3)nc2n(C2CCCC2)c1=O] | (2S,4R)-1-((S)-2-(2-(4-(2-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-2-oxoethyl)-1H-1,2,3-triazol-1-yl)acetamido)-3,3-dimethylbutanoyl)-4-hydroxy-N-(4-(4-methylthiazol-5-yl)benzyl)pyrrolidine-2-carboxamide |
| 117 | | 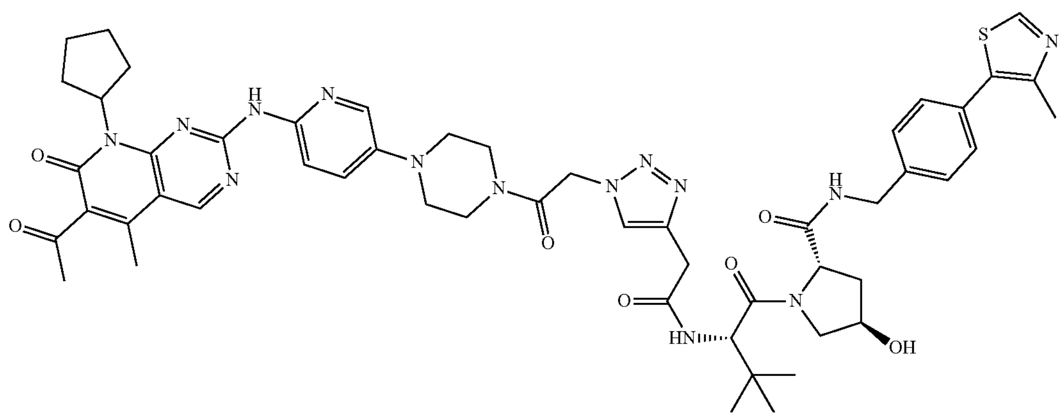 [SMILES: CC(=O)c1c(C)c2cnc(Nc3ccc(N4CCN(C(=O)Cn5cc(CC(=O)N[C@H](C(=O)N6C[C@H](O)C[C@H]6C(=O)NCc6ccc(-c7scnc7C)cc6)C(C)(C)C)nn5)CC4)cn3)nc2n(C2CCCC2)c1=O] | (2S,4R)-1-((S)-2-(2-(1-(2-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-2-oxoethyl)-1H-1,2,3-triazol-4-yl)acetamido)-3,3-dimethylbutanoyl)-4-hydroxy-N-(4-(4-methylthiazol-5-yl)benzyl)pyrrolidine-2-carboxamide |

TABLE 1-continued

| Cpd. Example Number | Cpd. Code | Structure | Chemical Name |
|---|---|---|---|
| 118 | | 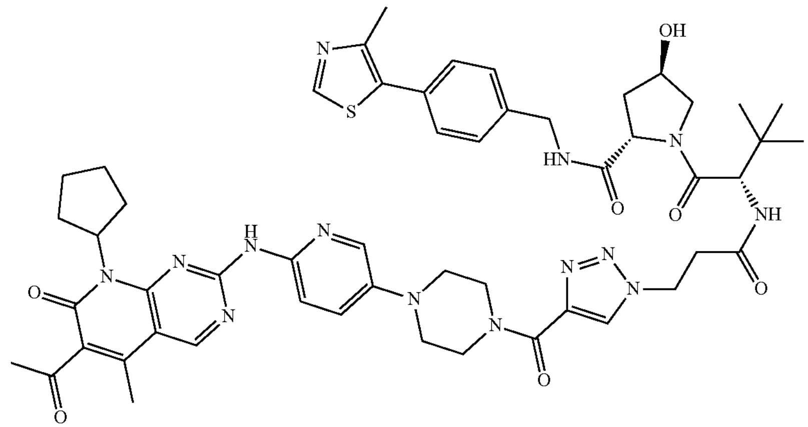 [SMILES: CC(=O)c1c(C)c2cnc(Nc3ccc(N4CCN(C(=O)c5cn(CCC(=O)N[C@H](C(=O)N6C[C@H](O)C[C@H]6C(=O)NCc6ccc(-c7scnc7C)cc6)C(C)(C)C)nn5)CC4)cn3)nc2n(C2CCCC2)c1=O] | (2S,4R)-1-((S)-2-(3-(4-(4-(6-((6-acetyl-8-cyclopentyl-5-methyl-7-oxo-7,8-dihydropyrido[2,3-d]pyrimidin-2-yl)amino)pyridin-3-yl)piperazine-1-carbonyl)-1H-1,2,3-triazol-1-yl)propanamido)-3,3-dimethylbutanoyl)-4-hydroxy-N-(4-(4-methylthiazol-5-yl)benzyl)pyrrolidine-2-carboxamide |
| 119 | | 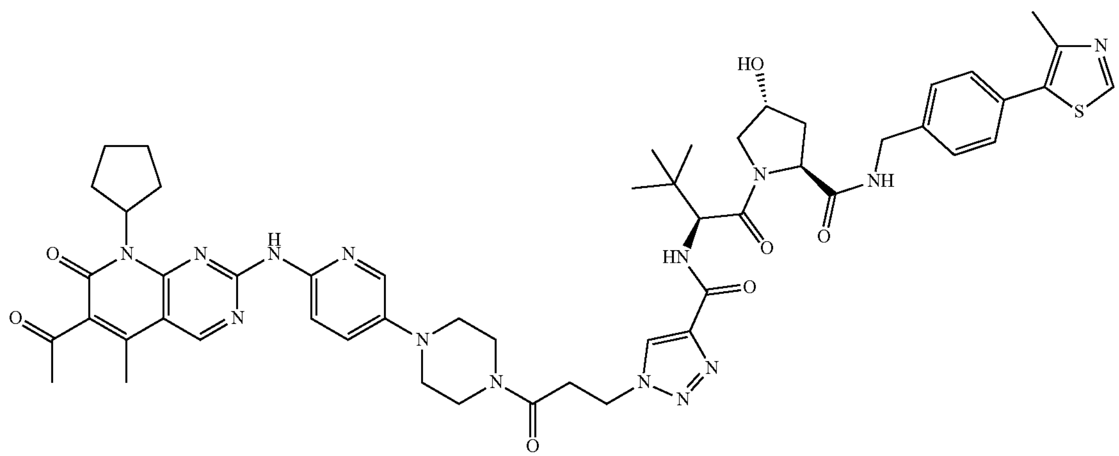 [SMILES: CC(=O)c1c(C)c2cnc(Nc3ccc(N4CCN(C(=O)CCn5cc(C(=O)N[C@H](C(=O)N6C[C@H](O)C[C@H]6C(=O)NCc6ccc(-c7scnc7C)cc6)C(C)(C)C)nn5)CC4)cn3)nc2n(C2CCCC2)c1=O] | 1-(3-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-3-oxopropyl)-N-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-1H-1,2,3-triazole-4-carboxamide |

TABLE 1-continued

| Cpd. Example Number | Cpd. Code | Structure | Chemical Name |
|---|---|---|---|
| 120 | | 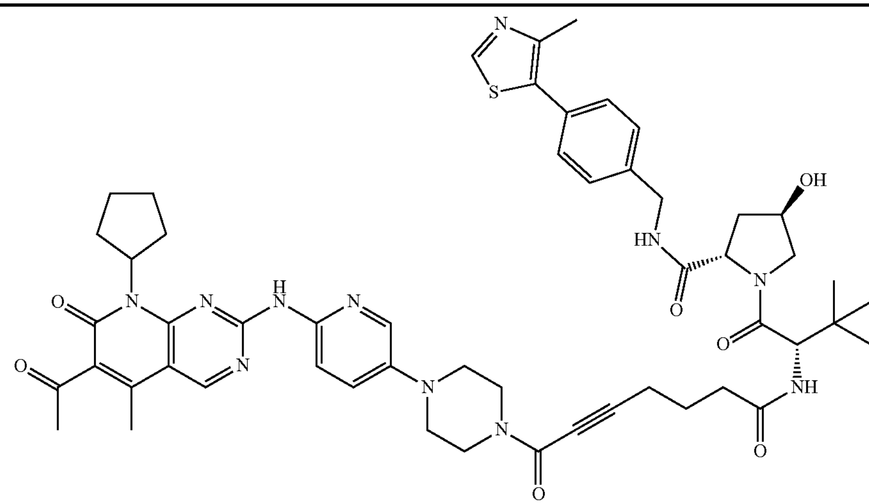 | (2S,4R)-1-((S)-2-(7-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-7-oxohept-5-ynamido)-3,3-dimethylbutanoyl)-4-hydroxy-N-(4-(4-methylthiazol-5-yl)benzyl)pyrrolidine-2-carboxamide |
| 121 | | 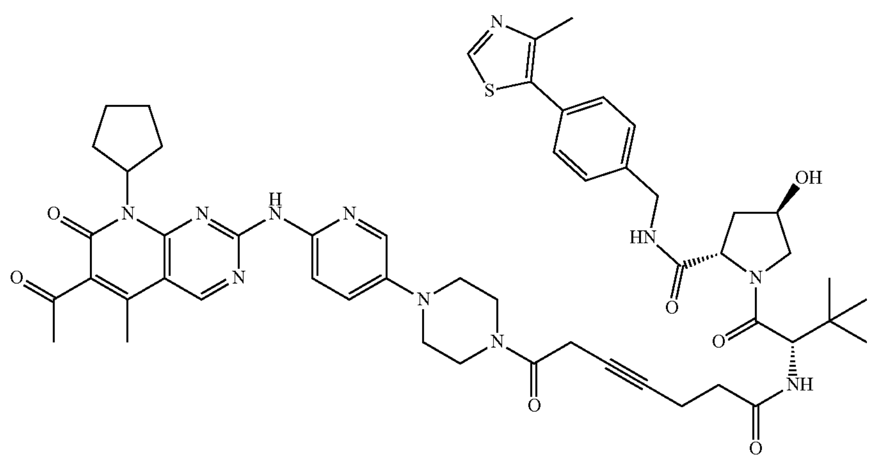 [SMILES: CC(=O)c1c(C)c2cnc(Nc3ccc(N4CCN(C(=O)CC#CCCC(=O)N[C@H](C(=O)N5C[C@H](O)C[C@H]5C(=O)NCc5ccc(-c6scnc6C)cc5)C(C)(C)C)CC4)cn3)nc2n(C2CCCC2)c1=O] | (2S,4R)-1-((S)-2-(7-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-7-oxohept-4-ynamido)-3,3-dimethylbutanoyl)-4-hydroxy-N-(4-(4-methylthiazol-5-yl)benzyl)pyrrolidine-2-carboxamide |

TABLE 1-continued

| Cpd. Example Number | Cpd. Code | Structure | Chemical Name |
|---|---|---|---|
| 122 | | 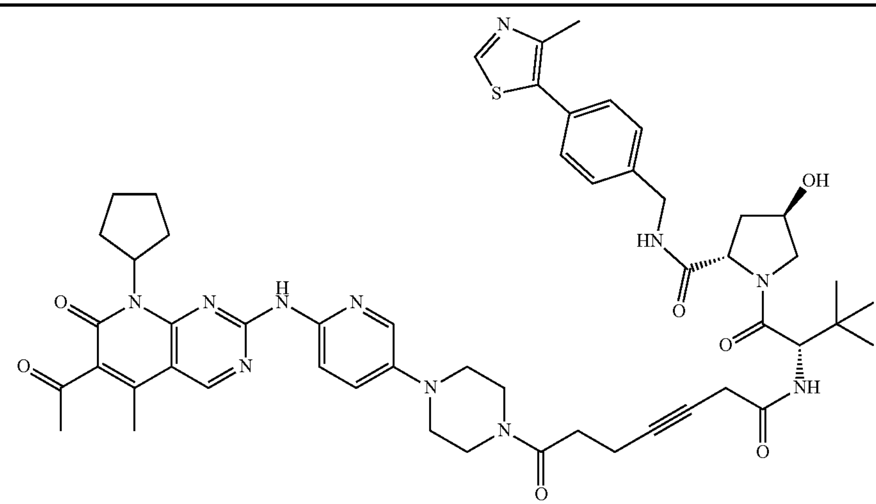 | (2S,4R)-1-((S)-2-(7-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-7-oxohept-3-ynamido)-3,3-dimethylbutanoyl)-4-hydroxy-N-(4-(4-methylthiazol-5-yl)benzyl)pyrrolidine-2-carboxamide |
| 123 | | 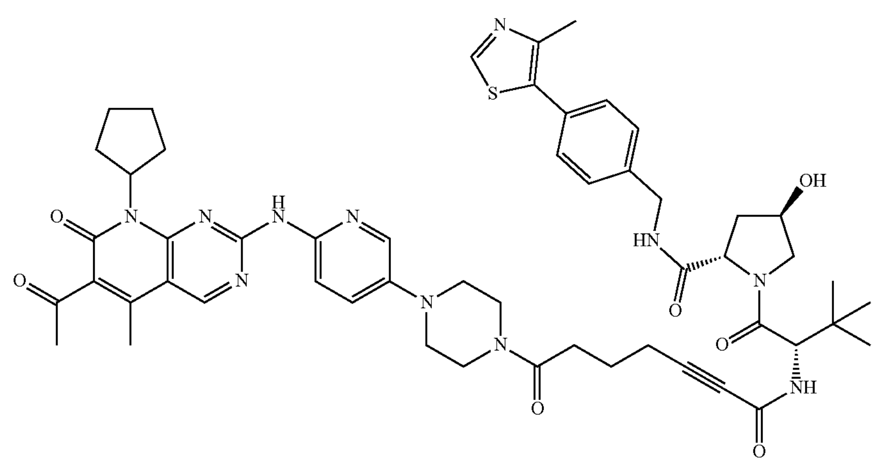 [SMILES: CC(=O)c1c(C)c2cnc(Nc3ccc(N4CCN(C(=O)CCCC#CC(=O)N[C@H](C(=O)N5C[C@H](O)C[C@H]5C(=O)NCc5ccc(-c6scnc6C)cc5)C(C)(C)C)CC4)cn3)nc2n(C2CCCC2)c1=O] | (2S,4R)-1-((S)-2-(7-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-7-oxohept-2-ynamido)-3,3-dimethylbutanoyl)-4-hydroxy-N-(4-(4-methylthiazol-5-yl)benzyl)pyrrolidine-2-carboxamide |

TABLE 1-continued

| Cpd. Example Number | Cpd. Code | Structure | Chemical Name |
|---|---|---|---|
| 124 | | 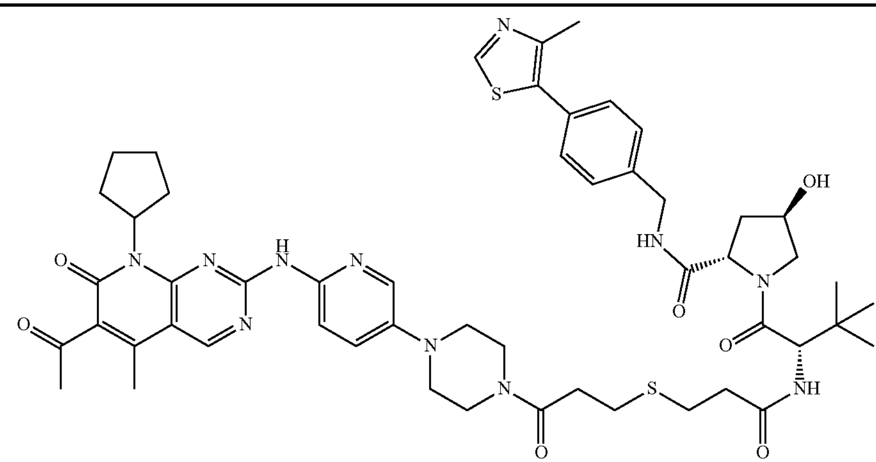 | (2S,4R)-1-((S)-2-(3-((3-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-3-oxopropyl)thio)propanamido)-3,3-dimethylbutanoyl)-4-hydroxy-N-(4-(4-methylthiazol-5-yl)benzyl)pyrrolidine-2-carboxamide |
| 125 | | 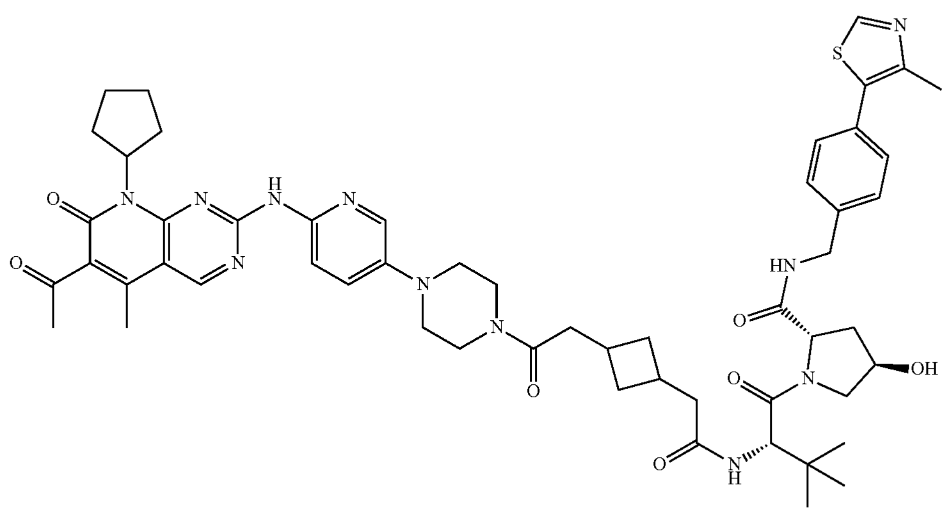 [SMILES: CC(=O)c1c(C)c2cnc(Nc3ccc(N4CCN(C(=O)CC5CC(CC(=O)N[C@H](C(=O)N6C[C@H](O)C[C@H]6C(=O)NCc6ccc(-c7scnc7C)cc6)C(C)(C)C)C5)CC4)cn3)nc2n(C2CCCC2)c1=O] | (2S,4R)-1-((S)-2-(2-(3-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-2-oxoethyl)cyclobutyl)acetamido)-3,3-dimethylbutanoyl)-4-hydroxy-N-(4-(4-methylthiazol-5-yl)benzyl)pyrrolidine-2-carboxamide |

| Cpd. Example Number | Cpd. Code | Structure | Chemical Name |
|---|---|---|---|
| 126 | YX44-78 | 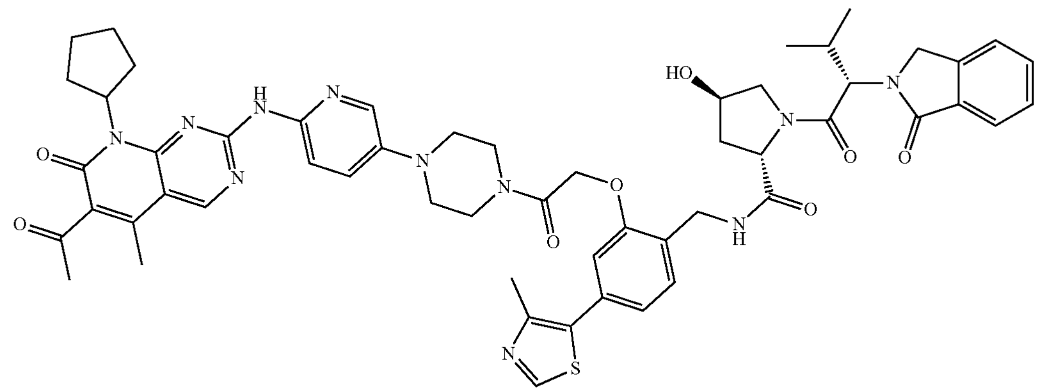 [SMILES: CC(=O)c1c(C)c2cnc(Nc3ccc(N4CCN(C(=O)COc5cc(-c6scnc6C)ccc5CNC(=O)[C@@H]5C[C@@H](O)CN5C(=O)[C@H](C(C)C)N5Cc6ccccc6C5=O)CC4)cn3)nc2n(C2CCCC2)c1=O] | (2S,4R)-N-(2-(2-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-2-oxoethoxy)-4-(4-methylthiazol-5-yl)benzyl)-4-hydroxy-1-((S)-3-methyl-2-(1-oxoisoindolin-2-yl)butanoyl)pyrrolidine-2-carboxamide |
| 127 | | 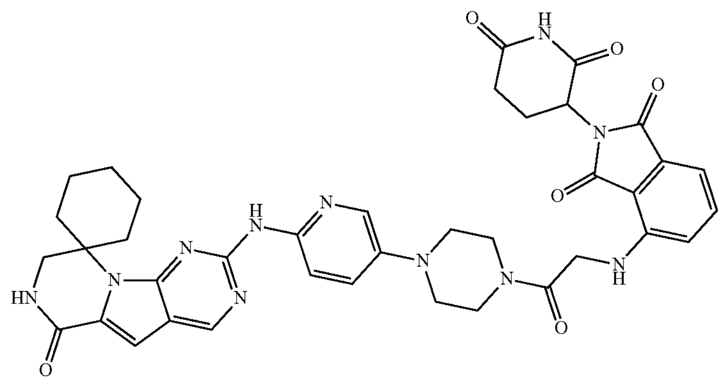 [SMILES: O=C1CCC(N2C(=O)c3cccc(NCC(=O)N4CCN(c5ccc(Nc6ncc7cc8n(c7n6)C6(CCCCC6)CNC8=O)nc5)CC4)c3C2=O)C(=O)N1] | 2-(2,6-dioxopiperidin-3-yl)-4-(((2-oxo-2-(4-(6-((6'-oxo-7',8'-dihydro-6'H-spiro[cyclohexane-1,9'-pyrazino[1',2':1,5]pyrrolo[2,3-d]pyrimidin]-2'-yl)amino)pyridin-3-yl)piperazin-1-yl)ethyl)amino)isoindoline-1,3-dione |

TABLE 1-continued

| Cpd. Example Number | Cpd. Code | Structure | Chemical Name |
|---|---|---|---|
| 128 | | 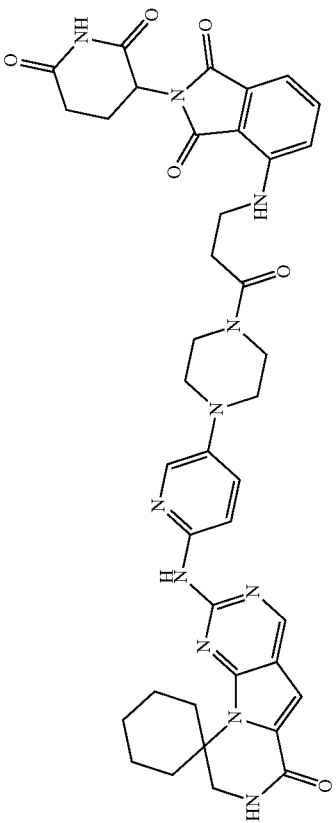 | 2-(2,6-dioxopiperidin-3-yl)-4-(((3-oxo-3-(4-(6-((6-oxo-7,8-dihydro-6H-spiro[cyclohexane-1,9'-pyrazino[1',2':1,5]pyrrolo[2,3-d]pyrimidin]-2'-yl)amino)pyridin-3-yl)piperazin-1-yl)propyl)amino)isoindoline-1,3-dione |
| 129 | | 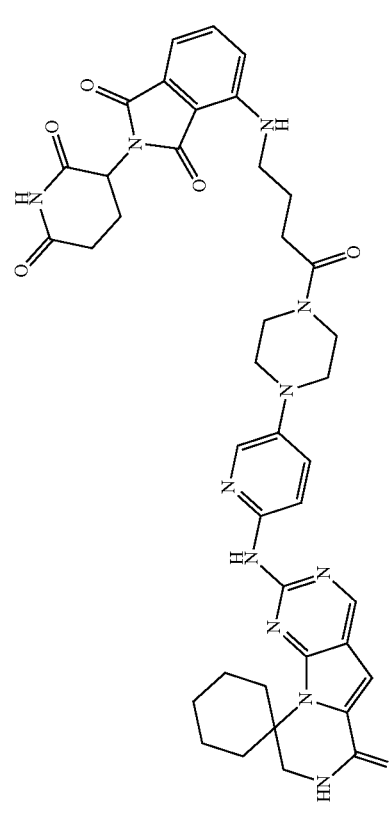 | 2-(2,6-dioxopiperidin-3-yl)-4-((4-oxo-4-(6-((6-oxo-7,8-dihydro-6H-spiro[cyclohexane-1,9'-pyrazino[1',2':1,5]pyrrolo[2,3-d]pyrimidin]-2'-yl)amino)pyridin-3-yl)piperazin-1-yl)butyl)amino)isoindoline-1,3-dione |

TABLE 1-continued

| Cpd. Example Number | Cpd. Code | Structure | Chemical Name |
|---|---|---|---|
| 130 | | 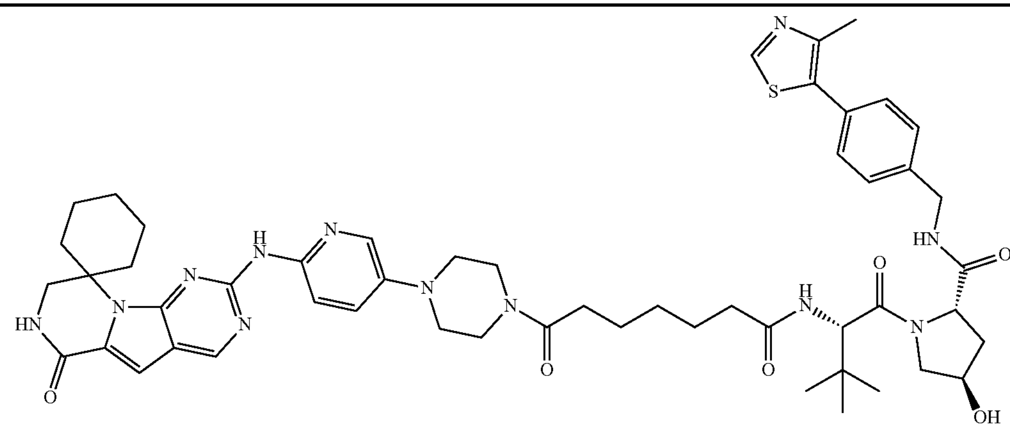 | (2S,4R)-1-((S)-3,3-dimethyl-2-(7-oxo-7-(4-(6-((6'-oxo-7',8'-dihydro-6'H-spiro[cyclohexane-1,9'-pyrazino[1',2':1,5]pyrrolo[2,3-d]pyrimidin]-2'-yl)amino)pyridin-3-yl)piperazin-1-yl)heptanamidobutanoyl)-4-hydroxy-N-(4-(4-methylthiazol-5-yl)benzyl)pyrrolidine-2-carboxamide |
| 131 | | 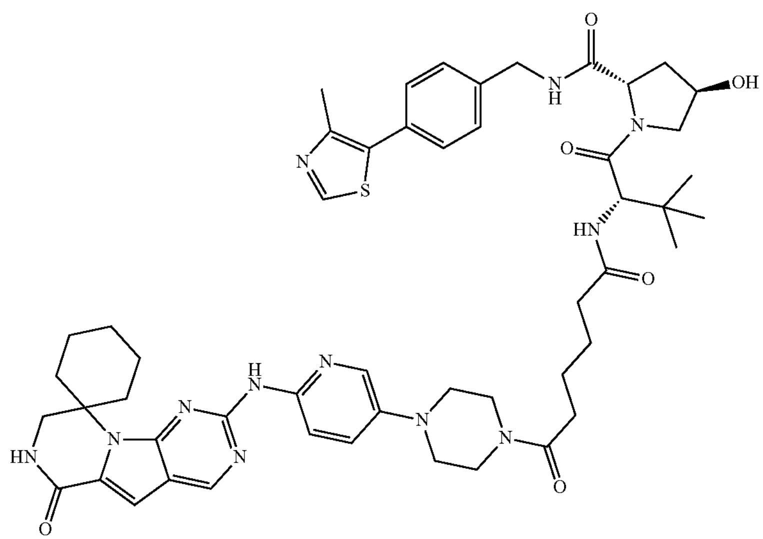 [SMILES: Cc1ncsc1-c1ccc(CNC(=O)[C@@H]2C[C@@H](O)CN2C(=O)[C@@H](NC(=O)CCCCC(=O)N2CCN(c3ccc(Nc4ncc5cc6n(c5n4)C4(CCCCC4)CNC6=O)nc3)CC2)C(C)(C)C)cc1] | (2S,4R)-1-((S)-3,3-dimethyl-2-(6-oxo-6-(4-(6-((6'-oxo-7',8'-dihydro-6'H-spiro[cyclohexane-1,9'-pyrazino[1',2':1,5]pyrrolo[2,3-d]pyrimidin]-2'-yl)amino)pyridin-3-yl)piperazin-1-yl)hexanamidobutanoyl)-4-hydroxy-N-(4-(4-methylthiazol-5-yl)benzyl)pyrrolidine-2-carboxamide |

TABLE 1-continued

| Cpd. Example Number | Cpd. Code | Structure | Chemical Name |
|---|---|---|---|
| 132 | | 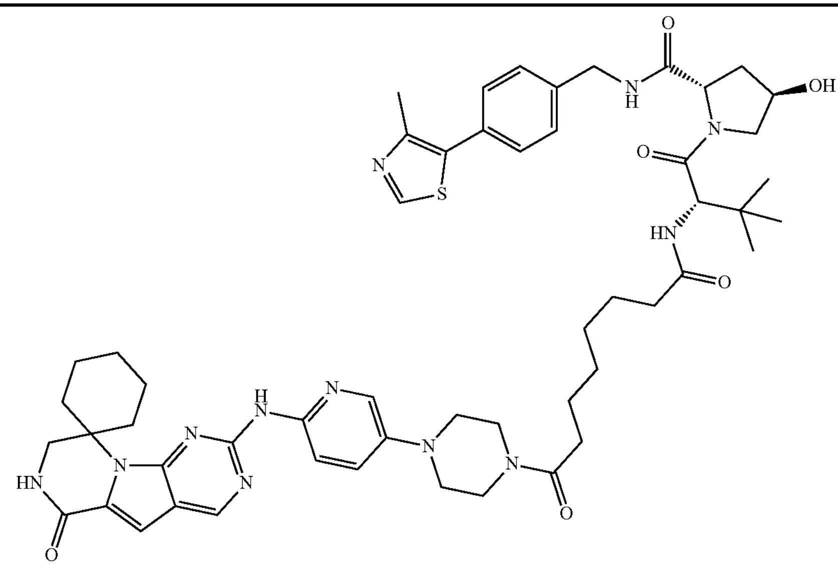 | (2S,4R)-1-((S)-3,3-dimethyl-2-(8-oxo-8-(4-(6-((6'-oxo-7',8'-dihydro-6H-spiro[cyclohexane-1,9'-pyrazino[1',2':1,5]pyrrolo[2,3-d]pyrimidin]-2'-yl)amino)pyridin-3-yl)piperazin-1-yl)octanamido)butanoyl)-4-hydroxy-N-(4-(4-methylthiazol-5-yl)benzyl)pyrrolidine-2-carboxamide |
| 133 | | 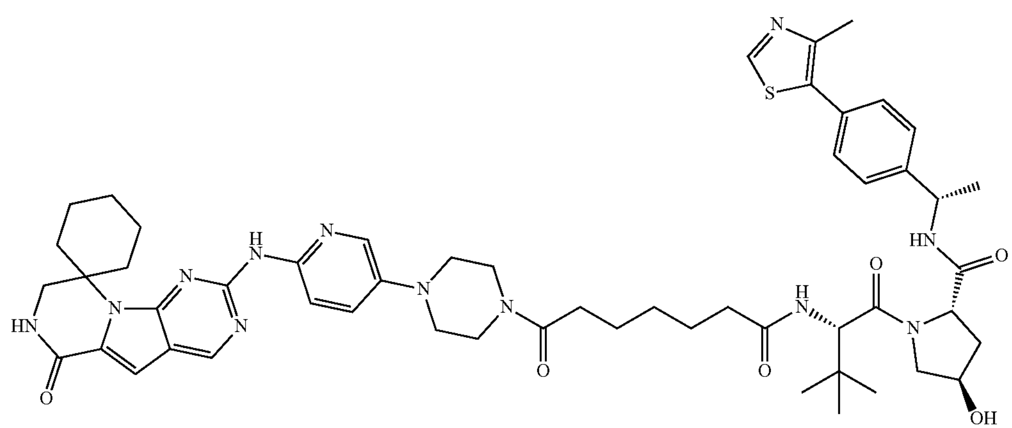 [SMILES: Cc1ncsc1-c1ccc([C@H](C)NC(=O)[C@@H]2C[C@@H](O)CN2C(=O)[C@@H](NC(=O)CCCCCC(=O)N2CCN(c3ccc(Nc4ncc5cc6n(c5n4)C4(CCCCC4)CNC6=O)nc3)CC2)C(C)(C)C)cc1] | (2S,4R)-1-((S)-3,3-dimethyl-2-(7-oxo-7-(4-(6-((6'-oxo-7',8'-dihydro-6H-spiro[cyclohexane-1,9'-pyrazino[1',2':1,5]pyrrolo[2,3-d]pyrimidin]-2'-yl)amino)pyridin-3-yl)piperazin-1-yl)heptanamido)butanoyl)-4-hydroxy-N-((S)-1-(4-(4-methylthiazol-5-yl)phenyl)ethyl)pyrrolidine-2-carboxamide |

TABLE 1-continued
| Cpd. Example Number | Cpd. Code | Structure | Chemical Name |
|---|---|---|---|
| 134 | | 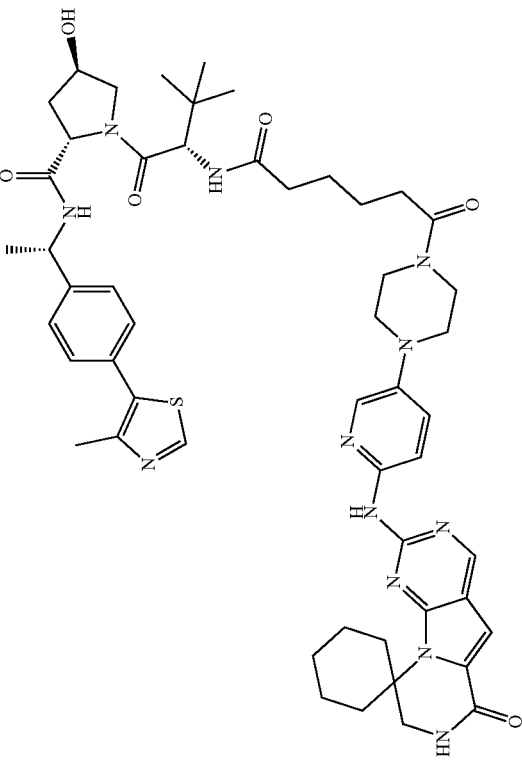 | (2S,4R)-1-((S)-3,3-dimethyl-2-(6-oxo-6-(4-(6-((6'-oxo-7',8'-dihydro-6'H-spiro[cyclohexane-1,9'-pyrazino[1',2':1,5]pyrrolo[2,3-d]pyrimidin]-2'-yl)aminopyridin-3-yl)piperazin-1-yl)hexanamido)butanoyl)-4-hydroxy-N-((S)-1-(4-(4-methylthiazol-5-yl)phenyl)ethyl)pyrrolidine-2-carboxamide |

TABLE 1-continued
| Cpd. Example Number | Cpd. Code | Structure | Chemical Name |
|---|---|---|---|
| 135 | | 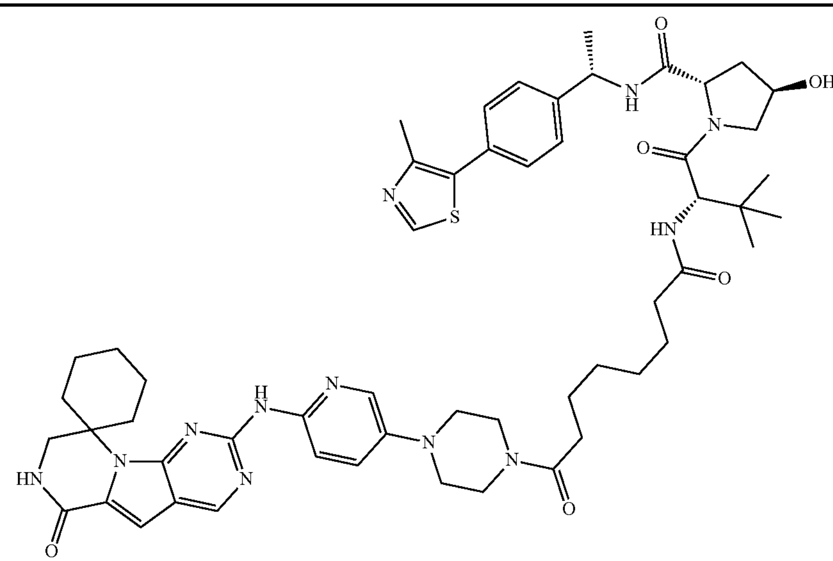 | (2S,4R)-1-((S)-3,3-dimethyl-2-(8-oxo-8-(4-(6-((6'-oxo-7',8'-dihydro-6'H-spiro[cyclohexane-1,9'-pyrazino[1',2':1,5]pyrrolo[2,3-d]pyrimidin]-2'-yl)aminopyridin-3-yl)piperazin-1-yl)octanamido)butanoyl)-4-hydroxy-N-((S)-1-(4-(4-methylthiazol-5-yl)phenyl)ethyl)pyrrolidine-2-carboxamide |

In an aspect, the CDK4/6 degraders/disruptors have the form "PI-linker-EL" as shown below:

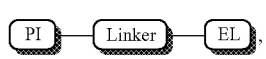

Formula I wherein PI comprises a CDK4/6 ligand (e.g., a CDK4/6 inhibitor) and EL comprises a degradation/disruption tag (e.g., E3 ligase ligand). Exemplary CDK4/6 ligands (PI) and exemplary degradation/disruption tags (EL) are disclosed herein.

For example, PI can include, but is not limited to:

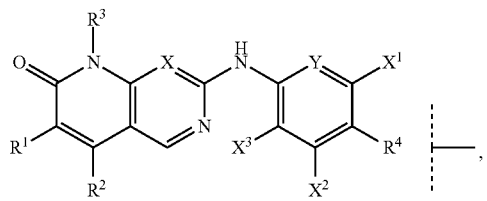

Formula II wherein $X^1$, $X^2$, and $X^3$ are independently hydrogen, halogen, C1-C8 alkyl, C1-C8 alkoxy, C1-C8 alkoxyalkyl, $NR^5R^6$, CN, $NO_2$, $COR^5$, $CO_2R^5$, $CONR^5R^6$, or $NR^5COR^6$;

$R^1$ and $R^4$ are independently hydrogen, halogen, C1-C8 alkyl, C1-C8 alkoxy, C1-C8 alkoxyalkyl, C1-C8 haloalkyl, C1-C8 hydroxyalkyl, C3-C7 cycloalkyl, C3-C7 heterocyclyl, C2-C8 alkenyl, C2-C8 alkynyl, $OR^5$, $SR^5$, $NR^5R^6$, CN, $NO_2$, $(CR^5R^6)mNR^7R^8$, $(CR^5R^6)mC(O)R^7$, $COR^5$, $CO_2R^5$, $CONR^5R^6$, $NR^5COR^6$, $NR^5SOR^6$, $NR^5SO_2R^6$, $SOR^5$, $SO_2R^5$, $SO_2NR^5R^6$, $(CR^5R^6)$m-aryl, or $(CR^5R^6)$m-heteroaryl, wherein m is 0-8;

$R^2$ is hydrogen, halogen, C1-C8 alkyl, C1-C8 alkoxy, C3-C7 cycloalkyl, or C3-C7 heterocyclyl;

$R^3$ is hydrogen, aryl, C1-C8 alkyl, C1-C8 alkoxy, C3-C7 cycloalkyl, or C3-C7 heterocyclyl;

$R^5$, $R^6$, $R^7$, $R^8$ are independently hydrogen, C1-C8 alkyl, C2-C8 alkenyl, C2-C8 alkynyl, arylalkyl, cycloalkyl, heterocycloalkyl, aryl, heteroaryl, or heteroarylalkyl;

optionally, $R^1$ and $R^2$; $R^5$ and $R^6$; or $R^7$ and $R^8$ independently form 4-8 membered alkyl or heterocyclyl rings; and X and Y are independently $CR^5R^6$ or N.

For example, PI can include:

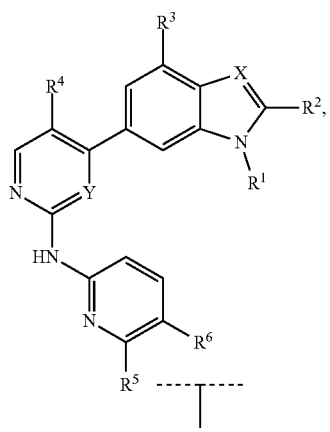

Formula III wherein $R^1$ is independently hydrogen, C1-C8 alkyl, C1-C8 alkoxyalkyl, C1-C8 haloalkyl, C1-C8 hydroxyalkyl, C3-C7 cycloalkyl, C3-C7 heterocyclyl, C2-C8 alkenyl, or C2-C8 alkynyl;

$R^2$ is hydrogen, C1-C3 alkyl, or cyclopropyl;

$R^3$, $R^4$, and $R^5$ are independently hydrogen, halogen, C1-C8 alkyl, C1-C8 alkoxy, C3-C7 cycloalkyl, or C3-C7 heterocyclyl;

$R^6$ is hydrogen, halogen, C1-C8 alkyl, C1-C8 alkoxy, C1-C8 alkoxyalkyl, C1-C8 haloalkyl, C1-C8 hydroxyalkyl, C3-C7 cycloalkyl, C3-C7 heterocyclyl, C2-C8 alkenyl, C2-C8 alkynyl, $OR^7$, $SR^7$, $NR^7R^8$, CN, $NO_2$, $(CR^7R^8)mNR^9R^{10}$, $(CR^7R^8)mC(O)R^9$, $COR^7$, $CO_2R^7$, $CONR^7R^8$, $NR^7COR^8$, $NR^7SOR^8$, $NR^7SO_2R^8$, $SOR^7$, $SO_2R^7$, $SO_2NR^7R^8$, $(CR^7R^8)$m-aryl, or $(CR^7R^8)$m-heteroaryl, wherein m is 0-8;

$R^7$, $R^8$, $R^9$, $R^{10}$ are independently hydrogen, C1-C8 alkyl, C2-C8 alkenyl, C2-C8 alkynyl, arylalkyl, cycloalkyl, heterocycloalkyl, aryl, heteroaryl, or heteroarylalkyl;

optionally, $R^7$ and $R^8$; $R^9$ and $R^{10}$ independently form 4-8 membered alkyl or heterocyclyl rings; and X and Y are independently $CR^7R^8$ or N.

For example, PI can include:

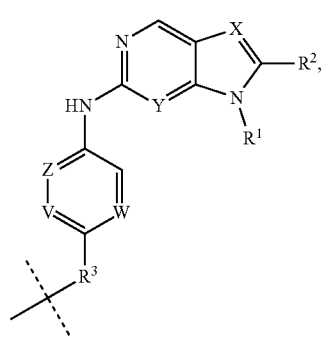

Formula IV wherein $R^1$ is independently hydrogen, C1-C8 alkyl, C1-C8 alkoxyalkyl, C1-C8 haloalkyl, C1-C8 hydroxyalkyl, C3-C7 cycloalkyl, C3-C7 heterocyclyl, C2-C8 alkenyl, or C2-C8 alkynyl;

$R^2$ is hydrogen, C1-C8 alkyl, C1-C8 alkoxyalkyl, C1-C8 haloalkyl, C1-C8 hydroxyalkyl, C3-C7 cycloalkyl, C3-C7 heterocyclyl, C2-C8 alkenyl, C2-C8 alkynyl, CN, $COR^4$, $CO_2R^4$, or $CONR^4R^5$;

$R^3$ is hydrogen, halogen, C1-C8 alkyl, C1-C8 alkoxy, C1-C8 alkoxyalkyl, C1-C8 haloalkyl, C1-C8 hydroxyalkyl, C3-C7 cycloalkyl, C3-C7 heterocyclyl, C2-C8 alkenyl, C2-C8 alkynyl, $OR^4$, $SR^4$, $NR^4R^5$, CN, $NO_2$, $(CR^4R^5)mNR^6R^7$, $(CR^4R^5)mC(O)R^6$, $COR^4$, $CO_2R^4$, $CONR^4R^5$, $NR^4COR^5$, $NR^4SOR^5$, $NR^4SO_2R^5$, $SOR^4$, $SO_2R^4$, $SO_2NR^4R^5$, $(CR^4R^5)$m-aryl, or $(CR^4R^5)$m-heteroaryl, wherein m is 0-8;

$R^4$, $R^5$, $R^6$, $R^7$ are independently hydrogen, C1-C8 alkyl, C2-C8 alkenyl, C2-C8 alkynyl, arylalkyl, cycloalkyl, heterocycloalkyl, aryl, heteroaryl, or heteroarylalkyl;

optionally, $R^1$ and $R^2$; $R^4$ and $R^5$; $R^6$ and $R^7$ independently form 4-8 membered alkyl or heterocyclyl rings; and V, W, X, Y, and Z are independently $CR^4R^5$ or N.

For example, PI can include:

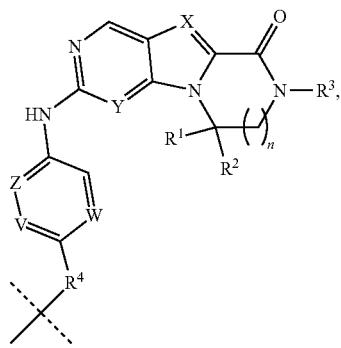

Formula VI wherein $R^1$ and $R^2$ are independently hydrogen, C1-C8 alkyl, C1-C8 alkoxyalkyl, C1-C8 haloalkyl, C1-C8 hydroxyalkyl, C3-C7 cycloalkyl, C3-C7 heterocyclyl, C2-C8 alkenyl, or C2-C8 alkynyl;

$R^3$ is hydrogen, C1-C6 alkyl, C1-C6 alkoxyalkyl, C1-C6 haloalkyl, C1-C6 hydroxyalkyl, C3-C6 cycloalkyl, C3-C6 heterocyclyl, C2-C6 alkenyl, or C2-C6 alkynyl;

$R^4$ is hydrogen, halogen, C1-C8 alkyl, C1-C8 alkoxy, C1-C8 alkoxyalkyl, C1-C8 haloalkyl, C1-C8 hydroxyalkyl, C3-C7 cycloalkyl, C3-C7 heterocyclyl, C2-C8 alkenyl, C2-C8 alkynyl, $OR^5$, $SR^5$, $NR^5R^6$, CN, $NO_2$, $(CR^5R^6)mNR^7R^8$, $(CR^5R^6)mC(O)R^7$, $COR^5$, $CO_2R^5$, $CONR^5R^6$, $NR^5COR^6$, $NR^5SOR^6$, $NR^5SO_2R^6$, $SOR^5$, $SO_2R^5$, $SO_2NR^5R^6$, $(CR^5R^6)$m-aryl, or $(CR^5R^6)$m-heteroaryl, wherein m is 0-8;

n is 0-4;

optionally, $R^1$ and $R^2$; $R^5$ and $R^6$; $R^7$ and $R^8$ independently form 4-8 membered alkyl or heterocyclyl rings; and V, W, X, Y, and Z are independently $CR^5R^6$ or N.

The CDK4/6 ligand can be a CDK4/6 inhibitor, such as, for example, abemaciclib, palbociclib, ribociclib, trilaciclib (G1T28), G1T38, SHR6390, and/or analogs thereof.

In some aspects, the CDK4/6 ligand can be, e.g.,

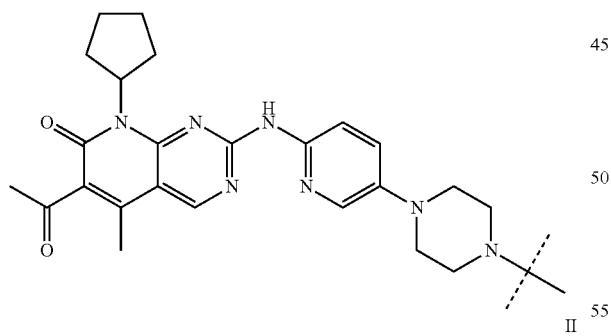

I

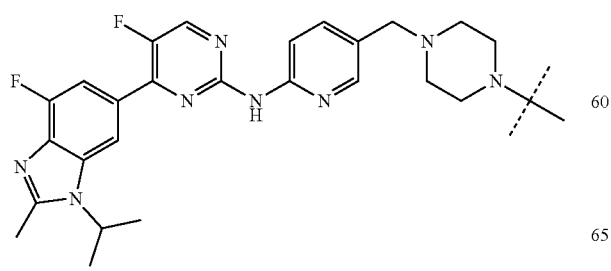

II

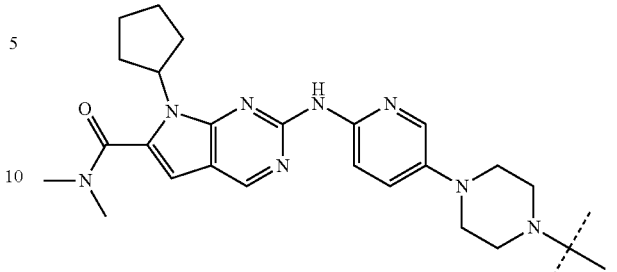

III

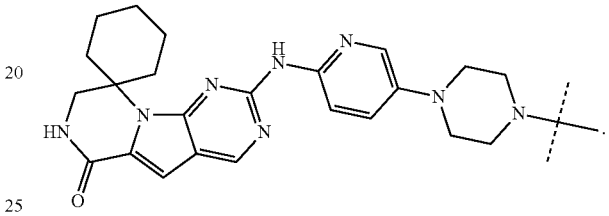

IV

The CDK4/6 ligand can be bound to CDK4/6.

EL includes, but is not limited to:

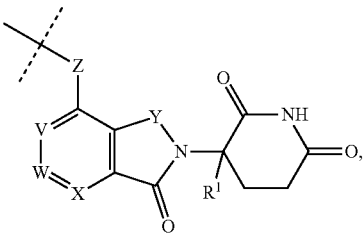

Formula VII

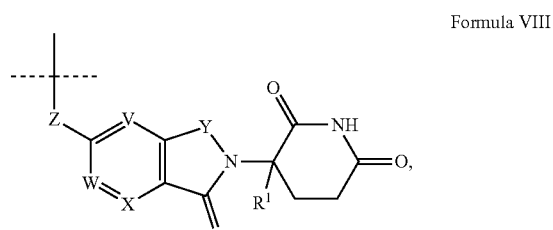

Formula VIII

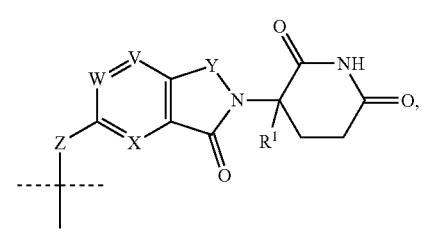

Formula IX

-continued

Formula XI

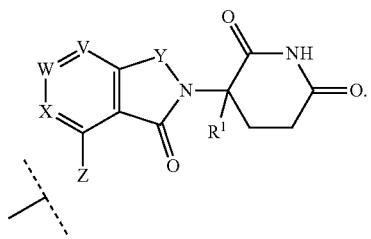

wherein V, W, X are independently $CR^2$ or N;
Y is CO or $CH_2$;
Z is $CH_2$, NH, or O;
$R^1$ is hydrogen, methyl, or fluoro; and
$R^2$ is hydrogen, halogen, or C1-C5 alkyl.
For example, EL can include:

Formula XII

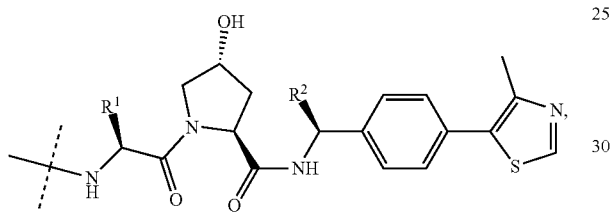

wherein $R^1$ and $R^2$ are independently hydrogen, C1-C8 alkyl, C1-C8 alkoxyalkyl, C1-C8 haloalkyl, C1-C8 hydroxyalkyl, C3-C7 cycloalkyl, C3-C7 heterocyclyl, C2-C8 alkenyl, or C2-C8 alkynyl.
For example, EL can include:

Formula XIII

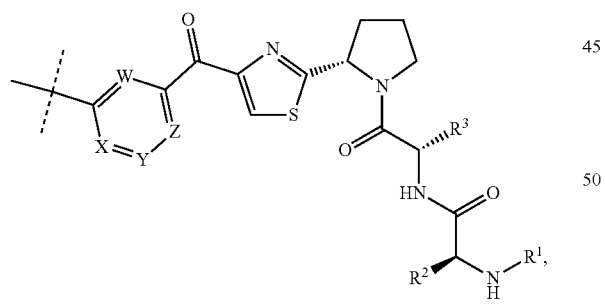

wherein $R^1$, $R^2$, $R^3$ and $R^4$ are independently hydrogen, C1-C8 alkyl, C1-C8 alkoxyalkyl, C1-C8 haloalkyl, C1-C8 hydroxyalkyl, C3-C7 cycloalkyl, C3-C7 heterocyclyl, C2-C8 alkenyl, or C2-C8 alkynyl; and
V, W, X, Z are independently $CR^4$ or N.

In some aspects, the degradation/disruption tag can be, for example, pomalidomide, thalidomide, lenalidomide, VHL-1, adamantane, 1-((4,4,5,5,5-pentafluoropentyl)sulfinyl) nonane, nutlin-3a, RG7112, RG7338, AMG 232, AA-115, bestatin, MV-1, LCL161, and/or analogs thereof.

In some aspects, the degradation/disruption tag can be, e.g.,

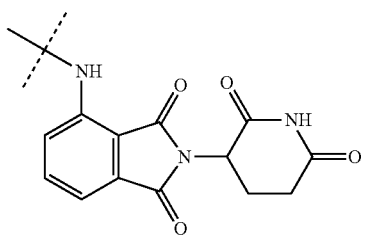

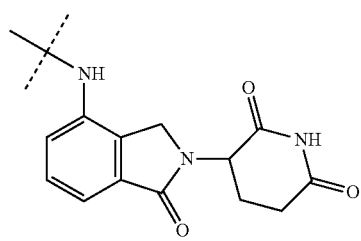

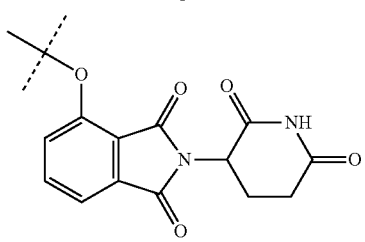

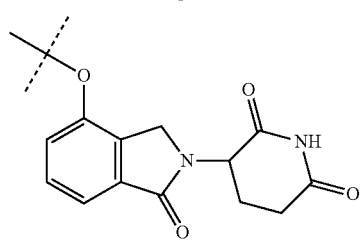

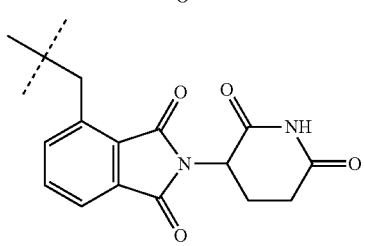

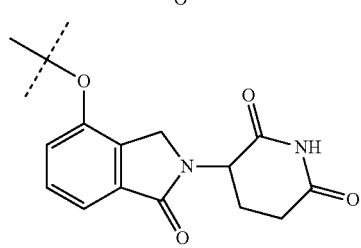

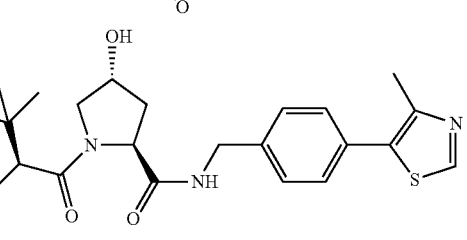

169
-continued

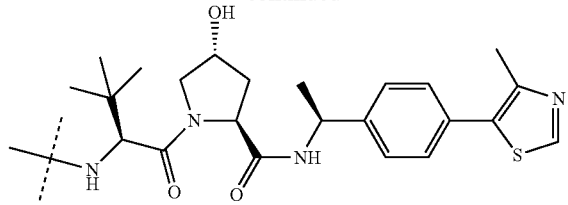

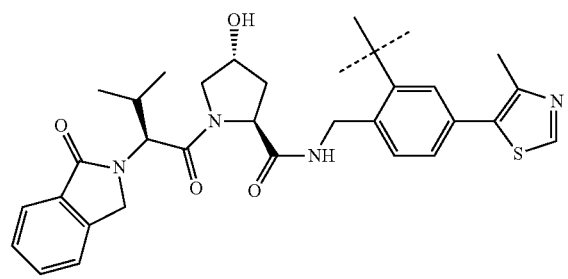

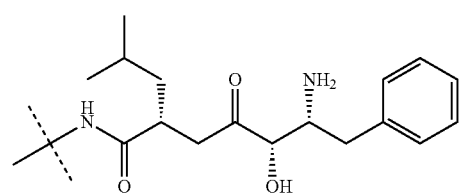

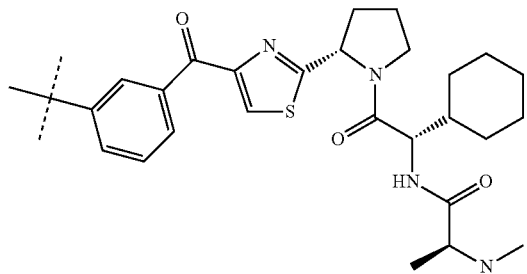

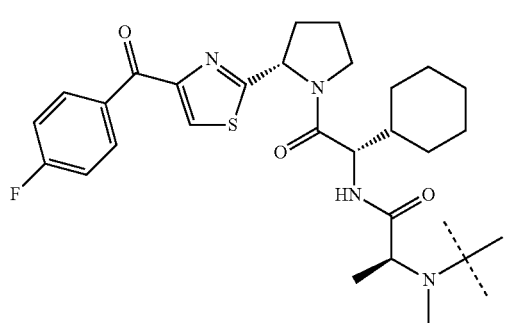

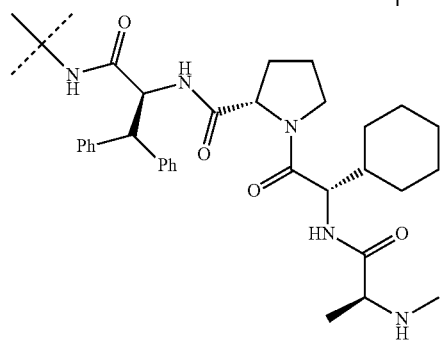

170
-continued

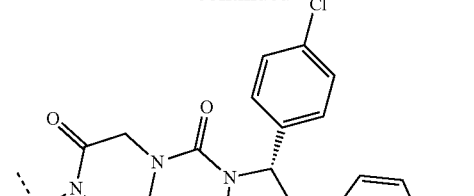

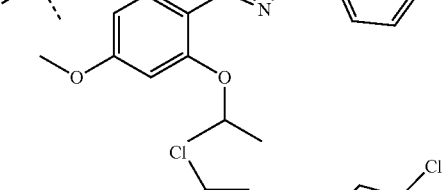

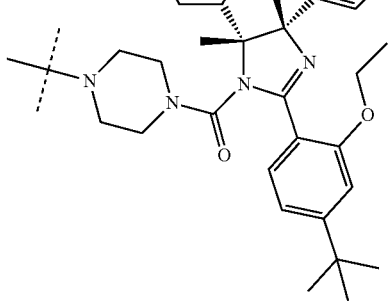

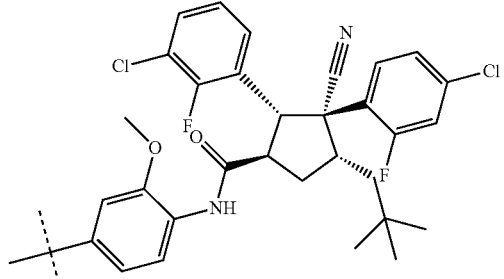

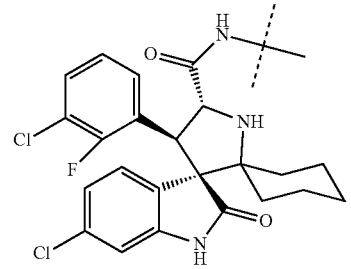

(left to right, then top to bottom, starting with Formula XIV at the top left corner and ending with Formula XXX at the bottom right corner).

In some aspects, the degradation/disruption tag can bind to a ubiquitin ligase, such as, for example, an E3 ligase. Exemplary E3 ligases include, for example, a cereblon E3 ligase, a VHL E3 ligase, a MDM2 ligase, a TRIM21 ligase, a TRIM24 ligase, and/or a IAP ligase. In some aspects, the degradation/disruption tag can serve as a hydrophobic group that leads to CDK4 or CDK6 protein misfolding.

In any of the above-described compounds, the CDK4/6 ligand can be conjugated to the degradation/disruption tag through a linker. The linker can include, for example, acyclic or cyclic saturated or unsaturated carbon, ethylene glycol, amide, amino, ether, urea, carbamate, aromatic, heteroaromatic, heterocyclic and/or carbonyl containing groups with different lengths.

In some embodiments, the linker can be a moiety of:

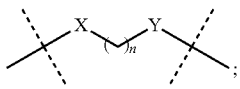

Formula A wherein X is C═O or CH₂,
Y is C═O or CH₂, and
n is 0-15

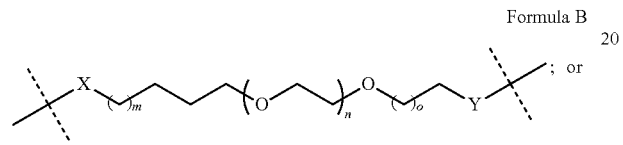

Formula B wherein X is C═O or CH₂,
Y is C═O or CH₂,
m is 0-15
n is 0-6, and
o is 0-15

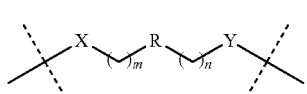

Formula C wherein X is C═O or CH₂,
Y is C═O or CH₂,
R is ─CH₂─, ─CF₂─, ─CH(C₁₋₃ alkyl)─,
─C(C₁₋₃ alkyl)C(C₁₋₃ alkyl)─, ─CH═CH─,
─C(C₁₋₃ alkyl)═C(C₁₋₃ alkyl)─, ─C═C─,
─O─, ─NH─, ─N(C₁₋₃ alkyl)─,
─C(O)NH─, ─C(O)N(C₁₋₃ alkyl)─,
a 3-13 membered ring, a 3-13 membered fused ring, a 3-13 membered bridged ring, and/or a 3-13 membered spiro ring,
m is 0-15, and
n is 0-15

In some embodiments of Formula C, R is a 3-13 membered ring, a 3-13 membered fused ring, a 3-13 membered bridged ring, and/or a 3-13 membered spiro ring, one or more of which can contain one or more heteroatoms.

In some embodiments of Formula C, R has a structure of

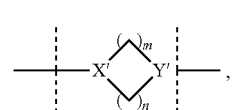

Formula V

X′ = N or CH
Y′ = N or CH
m = 0-5
n = 0-5

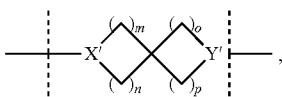

Formula W

X′ = N or CH
Y′ = N or CH
m = 0-5
n = 0-5
o = 0-5
p = 0-5

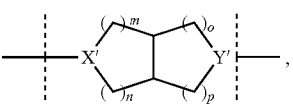

Formula X

X′ = N or CH
Y′ = N or CH
m = 0-5
n = 0-5
o = 0-5
p = 0-5

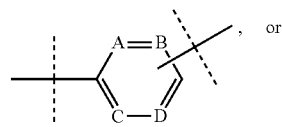

Formula Y

A = CH, C(C₁₋₃ alkyl), or N
B = CH, C(C₁₋₃ alkyl), or N
C = CH, C(C₁₋₃ alkyl), or N
D = CH, C(C₁₋₃ alkyl), or N

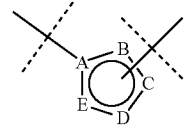

Formula Z

A = C, CH, C(C₁₋₃ alkyl), N, NH, N(C₁₋₃ alkyl), O, S
B = C, CH, C(C₁₋₃ alkyl), N, NH, N(C₁₋₃ alkyl), O, S
C = C, CH, C(C₁₋₃ alkyl), N, NH, N(C₁₋₃ alkyl), O, S
D = C, CH, C(C₁₋₃ alkyl), N, NH, N(C₁₋₃ alkyl), O, S Synthesis and Testing of Bivalent Compounds The binding affinity of novel synthesized bivalent compounds (i.e., CDK4/6 degraders/disruptors) can be assessed using standard biophysical assays known in the art (e.g., ITC). Cellular assays can then be used to assess the bivalent compound's ability to induce CDK4/6 degradation and inhibit cancer cell proliferation. Besides evaluating bivalent compound's induced changes in the protein expression of CDK4/6, CDK4/6 enzymatic activity can also be assessed. Multiple cycles of designs, syntheses, and biological tests can be performed. Promising bivalent compounds can then be further optimized using methods known in the art to improve their pharmacokinetic/pharmacodynamic properties (e.g., absorption, distribution, metabolism, and excretion (ADME) properties). Assays suitable for use in any or all of these steps are known in the art, and include, for example, Western blotting, quantitative mass spectrometry (MS) analysis, flow cytometry, enzymatic inhibition, isothermal titration calorimetry (ITC), surface plasmon resonance (SPR), cell growth inhibition and xenograft and PDX models. Suitable cell lines for use in any or all of these steps are known in the art and include, for example, breast cancer cell lines (e.g., ER+ breast cancer cell lines such as MCF7, T47D, and ZR-75-1) and melanoma cell lines (e.g., A375, SK-MEL-2, SK-MEL-30, and WM1382).

By way of non-limiting example, detailed synthesis protocols are described in the Examples for specific exemplary CDK4/6 degraders/disruptors.

Pharmaceutically acceptable isotopic variations of the compounds disclosed herein are contemplated and can be synthesized using conventional methods known in the art or methods corresponding to those described in the Examples (substituting appropriate reagents with appropriate isotopic variations of those reagents). Specifically, an isotopic variation is a compound in which at least one atom is replaced by an atom having the same atomic number, but an atomic mass different from the atomic mass usually found in nature. Useful isotopes are known in the art and include, for example, isotopes of hydrogen, carbon, nitrogen, oxygen, phosphorus, sulfur, fluorine, and chlorine. Exemplary isotopes thus include, for example, $^2$H, $^3$H, $^{13}$C, $^{14}$C, $^{15}$N, $^{17}$O, $^{18}$O, $^{32}$P, $^{35}$S, $^{18}$F, and $^{36}$Cl.

Isotopic variations (e.g., isotopic variations containing $^2$H) can provide therapeutic advantages resulting from greater metabolic stability, e.g., increased in vivo half-life or reduced dosage requirements. In addition, certain isotopic variations (particularly those containing a radioactive isotope) can be used in drug or substrate tissue distribution studies. The radioactive isotopes tritium ($^3$H) and carbon-14 ($^{14}$C) are particularly useful for this purpose in view of their ease of incorporation and ready means of detection.

Pharmaceutically acceptable solvates of the compounds disclosed herein are contemplated. A solvate can be generated, by substituting a solvent used to crystallize a compound disclosed herein with an isotopic variation (e.g., $D_2O$ in place of $H_2O$, $d_6$-acetone in place of acetone, or $d_6$-DMSO in place of DMSO).

Pharmaceutically acceptable fluorinated variations of the compounds disclosed herein are contemplated and can be synthesized using conventional methods known in the art or methods corresponding to those described in the Examples (substituting appropriate reagents with appropriate fluorinated variations of those reagents). Specifically, a fluorinated variation is a compound in which at least one hydrogen atom is replaced by a fluoro atom. Fluorinated variations can provide therapeutic advantages resulting from greater metabolic stability, e.g., increased in vivo half-life or reduced dosage requirements.

Characterization of Exemplary CDK4/6 Degraders/Disruptors

Specific exemplary abemaciclib-, ribociclib-, and palbociclib-based CDK4/6 degraders/disruptors were characterized in various different breast cancer and melanoma cells (Examples 12 and 13, FIGS. 10-23). XY019-098, XY019-106, XY028-003, XY019-108, XY028-132, XY028-133, YX26-66, XY028-140, XY028-144, YX039-48, YX039-124, YX039-123, YX039-147, YX039-56, and YX039-65 in particular were found to be especially effective in suppressing both CDK4/6 expression and CDK4/6 activity. This efficacy in suppressing CDK4/6 expression and CDK4/6 activity correlated with efficacy in inhibiting cancer cell proliferation.

Pharmaceutical Compositions

In some aspects, the compositions and methods described herein include the manufacture and use of pharmaceutical compositions and medicaments that include one or more bivalent compounds as disclosed herein. Also included are the pharmaceutical compositions themselves.

In some aspects, the compositions disclosed herein can include other compounds, drugs, or agents used for the treatment of cancer. For example, in some instances, pharmaceutical compositions disclosed herein can be combined with one or more (e.g., one, two, three, four, five, or less than ten) compounds. Such additional compounds can include, for example, conventional chemotherapeutic agents known in the art (e.g., gemcitabine HCl and temozolomide). When co-administered, CDK4/6 degraders/disruptors disclosed herein can operate in conjunction with conventional chemotherapeutic agents to produce mechanistically additive or synergistic therapeutic effects.

In some aspects, the pH of the compositions disclosed herein can be adjusted with pharmaceutically acceptable acids, bases, or buffers to enhance the stability of the CDK4/6 degraders/disruptor or its delivery form.

Pharmaceutical compositions typically include a pharmaceutically acceptable carrier, adjuvant, or vehicle. As used herein, the phrase "pharmaceutically acceptable" refers to molecular entities and compositions that are generally believed to be physiologically tolerable and do not typically produce an allergic or similar untoward reaction, such as gastric upset, dizziness and the like, when administered to a human. A pharmaceutically acceptable carrier, adjuvant, or vehicle is a composition that can be administered to a patient, together with a compound of the invention, and which does not destroy the pharmacological activity thereof and is nontoxic when administered in doses sufficient to deliver a therapeutic amount of the compound. Exemplary conventional nontoxic pharmaceutically acceptable carriers, adjuvants, and vehicles include saline, solvents, dispersion media, coatings, antibacterial and antifungal agents, isotonic and absorption delaying agents, and the like, compatible with pharmaceutical administration.

In particular, pharmaceutically acceptable carriers, adjuvants, and vehicles that can be used in the pharmaceutical compositions of this invention include, but are not limited to, ion exchangers, alumina, aluminum stearate, lecithin, self-emulsifying drug delivery systems (SEDDS) such as d-α-tocopherol polyethylene glycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin, may also be advantageously used to enhance delivery of compounds of the formulae described herein.

As used herein, the CDK4/6 degraders/disruptors disclosed herein are defined to include pharmaceutically acceptable derivatives or prodrugs thereof. A "pharmaceutically acceptable derivative" means any pharmaceutically acceptable salt, solvate, or prodrug, e.g., carbamate, ester, phosphate ester, salt of an ester, or other derivative of a compound or agent disclosed herein, which upon administration to a recipient is capable of providing (directly or indirectly) a compound described herein, or an active metabolite or residue thereof. Particularly favored derivatives and prodrugs are those that increase the bioavailability of the compounds disclosed herein when such compounds are administered to a mammal (e.g., by allowing an orally administered compound to be more readily absorbed into the blood) or which enhance delivery of the parent compound to a biological compartment (e.g., the brain or lymphatic system) relative to the parent species. Preferred prodrugs include derivatives where a group that enhances aqueous solubility or active transport through the gut membrane is appended to the structure of formulae described herein. Such derivatives are recognizable to those skilled in the art without undue experimentation. Nevertheless, reference is made to the teaching of Burger's Medicinal Chemistry and Drug Discovery, 5$^{th}$ Edition, Vol. 1: Principles and Practice, which is incorporated herein by reference to the extent of teaching such derivatives.

The CDK4/6 degraders/disruptors disclosed herein include pure enantiomers, mixtures of enantiomers, pure diastereoisomers, mixtures of diastereoisomers, diastereoisomeric racemates, mixtures of diastereoisomeric racemates and the meso-form and pharmaceutically acceptable salts, solvent complexes, morphological forms, or deuterated derivative thereof.

In particular, pharmaceutically acceptable salts of the CDK4/6 degraders/disruptors disclosed herein include, for example, those derived from pharmaceutically acceptable inorganic and organic acids and bases. Examples of suitable acid salts include acetate, adipate, benzoate, benzenesulfonate, butyrate, citrate, digluconate, dodecylsulfate, formate, fumarate, glycolate, hemisulfate, heptanoate, hexanoate, hydrochloride, hydrobromide, hydroiodide, lactate, maleate, malonate, methanesulfonate, 2-naphthalenesulfonate, nicotinate, nitrate, palmoate, phosphate, picrate, pivalate, propionate, salicylate, succinate, sulfate, tartrate, tosylate, trifluoromethylsulfonate, and undecanoate. Salts derived from appropriate bases include, for example, alkali metal (e.g., sodium), alkaline earth metal (e.g., magnesium), ammonium and N-(alkyl)4+ salts. The invention also envisions the quaternization of any basic nitrogen-containing groups of the CDK4/6 degraders/disruptors disclosed herein. Water or oil-soluble or dispersible products can be obtained by such quaternization.

In some aspects, the pharmaceutical compositions disclosed herein can include an effective amount of one or more CDK4/6 degraders/disruptors. The terms "effective amount" and "effective to treat," as used herein, refer to an amount or a concentration of one or more compounds or a pharmaceutical composition described herein utilized for a period of time (including acute or chronic administration and periodic or continuous administration) that is effective within the context of its administration for causing an intended effect or physiological outcome (e.g., treatment or prevention of cell growth, cell proliferation, or cancer). In some aspects, pharmaceutical compositions can further include one or more additional compounds, drugs, or agents used for the treatment of cancer (e.g., conventional chemotherapeutic agents) in amounts effective for causing an intended effect or physiological outcome (e.g., treatment or prevention of cell growth, cell proliferation, or cancer).

In some aspects, the pharmaceutical compositions disclosed herein can be formulated for sale in the United States, import into the United States, or export from the United States.

Administration of Pharmaceutical Compositions

The pharmaceutical compositions disclosed herein can be formulated or adapted for administration to a subject via any route, for example, any route approved by the Food and Drug Administration (FDA). Exemplary methods are described in the FDA Data Standards Manual (DSM) (available at http://www.fda.gov/Drugs/DevelopmentApprovalProcess/FormsSubmissionRequirements/ElectronicSubmissions/DataStandardsManualmonographs). In particular, the pharmaceutical compositions can be formulated for and administered via oral, parenteral, or transdermal delivery. The term "parenteral" as used herein includes subcutaneous, intracutaneous, intravenous, intramuscular, intraperitoneal, intra-articular, intra-arterial, intrasynovial, intrasternal, intrathecal, intralesional, and intracranial injection or infusion techniques.

For example, the pharmaceutical compositions disclosed herein can be administered, for example, topically, rectally, nasally (e.g., by inhalation spray or nebulizer), buccally, vaginally, subdermally (e.g., by injection or via an implanted reservoir), or ophthalmically.

For example, pharmaceutical compositions of this invention can be orally administered in any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions or emulsions are administered orally, the active ingredient may be suspended or dissolved in an oily phase is combined with emulsifying or suspending agents. If desired, certain sweetening, flavoring, or coloring agents can be added.

For example, the pharmaceutical compositions of this invention can be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax, and polyethylene glycols.

For example, the pharmaceutical compositions of this invention can be administered by nasal aerosol or inhalation. Such compositions are prepared according to techniques well-known in the art of pharmaceutical formulation and can be prepared as solutions in saline, employing benzyl alcohol or other suitable preservatives, absorption promoters to enhance bioavailability, fluorocarbons, or other solubilizing or dispersing agents known in the art.

For example, the pharmaceutical compositions of this invention can be administered by injection (e.g., as a solution or powder). Such compositions can be formulated according to techniques known in the art using suitable dispersing or wetting agents (such as, for example, Tween 80) and suspending agents. The sterile injectable preparation may also be a sterile injectable solution or suspension in a non-toxic parenterally acceptable diluent or solvent, e.g., as a solution in 1,3-butanediol. Among the acceptable vehicles and solvents that may be employed are mannitol, water, Ringer's solution, and isotonic sodium chloride solution. In addition, sterile, fixed oils are conventionally employed as a solvent or suspending medium. For this purpose, any bland fixed oil can be employed, including synthetic mono- or diglycerides. Fatty acids, such as oleic acid and its glyceride derivatives are useful in the preparation of injectables, as are natural pharmaceutically-acceptable oils, e.g., olive oil or castor oil, especially in their polyoxyethylated versions. These oil solutions or suspensions can also contain a long-chain alcohol diluent or dispersant, or carboxymethyl cellulose or similar dispersing agents which are commonly used in the formulation of pharmaceutically acceptable dosage forms such as emulsions and or suspensions. Other commonly used surfactants such as Tweens, Spans, or other similar emulsifying agents or bioavailability enhancers which are commonly used in the manufacture of pharmaceutically acceptable solid, liquid, or other dosage forms can also be used for the purposes of formulation.

In some aspects, an effective dose of a pharmaceutical composition of this invention can include, but is not limited to about 0.00001, 0.0001, 0.001, 0.01, 0.02, 0.03, 0.04, 0.05, 0.06, 0.07, 0.08, 0.09, 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1, 1.25, 1.5, 1.75, 2, 2.5, 3, 4, 5, 6, 7, 8, 9, 10, 15, 20, 30, 40, 50, 60, 70, 80, 90, 100, 200, 300, 400, 500, 600, 700, 800, 900, 1000, 2500, 5000, or 10000 mg/kg/day, or according to the requirements of the particular pharmaceutical composition.

When the pharmaceutical compositions disclosed herein include a combination of a compound of the formulae described herein (e.g., a CDK4/6 degraders/disruptors) and one or more additional compounds (e.g., one or more additional compounds, drugs, or agents used for the treatment of cancer or any other condition or disease, including conditions or diseases known to be associated with or caused by cancer), both the compound and the additional compound should be present at dosage levels of between about 1 to 100%, and more preferably between about 5 to 95% of the dosage normally administered in a monotherapy regimen. The additional agents can be administered separately, as part of a multiple dose regimen, from the compounds of this invention. Alternatively, those agents can be part of a single dosage form, mixed together with the compounds of this invention in a single composition.

In some aspects, the pharmaceutical compositions disclosed herein can be included in a container, pack, or dispenser together with instructions for administration.

Methods of Treatment

The methods disclosed herein contemplate administration of an effective amount of a compound or composition to achieve the desired or stated effect. Typically, the compounds or compositions of the invention will be administered from about 1 to about 6 times per day or, alternately or in addition, as a continuous infusion. Such administration can be used as a chronic or acute therapy. The amount of active ingredient that can be combined with the carrier materials to produce a single dosage form will vary depending upon the host treated and the particular mode of administration. A typical preparation will contain from about 5% to about 95% active compound (w/w). Alternatively, such preparations can contain from about 20% to about 80% active compound.

In some aspects, the present disclosure provides methods for using a composition comprising a CDK4/6 degrader/disruptor, including pharmaceutical compositions (indicated below as 'X') disclosed herein in the following methods:

Substance X for use as a medicament in the treatment of one or more diseases or conditions disclosed herein (e.g., cancer, referred to in the following examples as 'Y'). Use of substance X for the manufacture of a medicament for the treatment of Y; and substance X for use in the treatment of Y.

In some aspects, the methods disclosed include the administration of a therapeutically effective amount of one or more of the compounds or compositions described herein to a subject (e.g., a mammalian subject, e.g., a human subject) who is in need of, or who has been determined to be in need of, such treatment. In some aspects, the methods disclosed include selecting a subject and administering to the subject an effective amount of one or more of the compounds or compositions described herein, and optionally repeating administration as required for the prevention or treatment of cancer.

In some aspects, subject selection can include obtaining a sample from a subject (e.g., a candidate subject) and testing the sample for an indication that the subject is suitable for selection. In some aspects, the subject can be confirmed or identified, e.g. by a health care professional, as having had or having a condition or disease. In some aspects, suitable subjects include, for example, subjects who have or had a condition or disease but that resolved the disease or an aspect thereof, present reduced symptoms of disease (e.g., relative to other subjects (e.g., the majority of subjects) with the same condition or disease), or that survive for extended periods of time with the condition or disease (e.g., relative to other subjects (e.g., the majority of subjects) with the same condition or disease), e.g., in an asymptomatic state (e.g., relative to other subjects (e.g., the majority of subjects) with the same condition or disease). In some aspects, exhibition of a positive immune response towards a condition or disease can be made from patient records, family history, or detecting an indication of a positive immune response. In some aspects, multiple parties can be included in subject selection. For example, a first party can obtain a sample from a candidate subject and a second party can test the sample. In some aspects, subjects can be selected or referred by a medical practitioner (e.g., a general practitioner). In some aspects, subject selection can include obtaining a sample from a selected subject and storing the sample or using the in the methods disclosed herein. Samples can include, e.g., cells or populations of cells.

In some aspects, methods of treatment can include a single administration, multiple administrations, and repeating administration of one or more compounds disclosed herein as required for the prevention or treatment of the disease or condition from which the subject is suffering (e.g., a CDK4/6-mediated cancer, e.g., ER+ breast cancer). In some aspects, methods of treatment can include assessing a level of disease in the subject prior to treatment, during treatment, or after treatment. In some aspects, treatment can continue until a decrease in the level of disease in the subject is detected.

The term "subject," as used herein, refers to any animal. In some instances, the subject is a mammal. In some instances, the term "subject," as used herein, refers to a human (e.g., a man, a woman, or a child).

The terms "administer," "administering," or "administration," as used herein, refer to implanting, ingesting, injecting, inhaling, or otherwise absorbing a compound or composition, regardless of form. For example, the methods disclosed herein include administration of an effective amount of a compound or composition to achieve the desired or stated effect.

The terms "treat", "treating," or "treatment," as used herein, refer to partially or completely alleviating, inhibiting, ameliorating, or relieving the disease or condition from which the subject is suffering. This means any manner in which one or more of the symptoms of a disease or disorder (e.g., cancer) are ameliorated or otherwise beneficially altered. As used herein, amelioration of the symptoms of a particular disorder (e.g., cancer) refers to any lessening, whether permanent or temporary, lasting or transient that can be attributed to or associated with treatment by the compositions and methods of the present invention. In some embodiments, treatment can promote or result in, for example, a decrease in the number of tumor cells (e.g., in a subject) relative to the number of tumor cells prior to treatment; a decrease in the viability (e.g., the average/mean viability) of tumor cells (e.g., in a subject) relative to the viability of tumor cells prior to treatment; a decrease in the rate of growth of tumor cells; a decrease in the rate of local or distant tumor metastasis; or reductions in one or more symptoms associated with one or more tumors in a subject relative to the subject's symptoms prior to treatment.

As used herein, the term "treating cancer" means causing a partial or complete decrease in the rate of growth of a tumor, and/or in the size of the tumor and/or in the rate of local or distant tumor metastasis, and/or the overall tumor burden in a subject, and/or any decrease in tumor survival, in the presence of a degrader/disruptor (e.g., an CDK4/6 degrader/disruptor) described herein.

The terms "prevent," "preventing," and "prevention," as used herein, shall refer to a decrease in the occurrence of a disease or decrease in the risk of acquiring a disease or its associated symptoms in a subject. The prevention may be complete, e.g., the total absence of disease or pathological cells in a subject. The prevention may also be partial, such that the occurrence of the disease or pathological cells in a subject is less than, occurs later than, or develops more slowly than that which would have occurred without the present invention.

Exemplary CDK4/6-mediated cancers that can be treated with CDK4/6 degraders/disruptors include, for example, solid tumors (e.g., breast cancer (e.g., ER+ breast cancer) and prostate cancer), leukemia (e.g., acute lymphoblastic leukemia, acute myeloid leukemia, chronic lymphocytic leukemia, chronic myelogenous leukemia, hairy cell leukemia, and myeloid leukemia), lymphoma (e.g., Burkitt's lymphoma, cutaneous T-cell lymphoma, diffuse large B-cell lymphoma (DLBCL), follicular lymphoma (FL), Hodgkin's lymphoma, mantel cell lymphoma, and non-Hodgkin's lymphoma (NHL)), adrenocortical cancer, AIDS-related cancer, anal cancer, astrocytoma, basal cell carcinoma, skin cancer (non-melanoma), bile duct cancer, bladder cancer, bone cancer (e.g., fibrosarcoma/osteosarcoma/malignant fibrous histiocytoma), brain tumor (e.g., cerebral astrocytoma, ependymoma, glioma, medulloblastoma, and supratentorial primitive neuroectodermal tumors (PNETs)), brainstem glioma, bronchial adenomas/carcinoids, carcinoid tumors, central nervous system neoplasms, cervical cancer, cholangiocarcinoma, chronic myeloproliferative disorder, colon cancer, endometrial cancer, esophageal cancer, melanoma (e.g., cutaneous or intraocular), gallbladder cancer, gastrointestinal cancer (e.g., colorectal, duodenal, and gastric (stomach) cancer), germ cell tumors, head and neck cancer, hepatocellular (liver) cancer, hypopharyngeal cancer, islet cell carcinoma, Kaposi's sarcoma, kidney (renal cell) cancer, laryngeal cancer, lip and oral cavity cancer, lung cancer (small cell and non-small cell), Merkel cell carcinoma, mesothelioma, endocrine cancer (e.g., multiple endocrine neoplasia syndrome), multiple myeloma/plasma cell neoplasm mycosis fungoides, myelodysplastic syndrome, myeloproliferative disorders, nasal cavity and paranasal sinus cancer, nasopharyngeal cancer, neuroblastoma, oropharyngeal cancer, ovarian cancer, pancreatic cancer, parathyroid cancer, penile cancer, pituitary cancer, pleuropulmonary blastoma, rectal cancer, retinoblastoma, rhabdomyosarcoma, salivary gland cancer, Ewing sarcoma, soft tissue sarcoma, Sezary syndrome, squamous cell carcinoma, squamous neck cancer, synovial sarcoma, testicular cancer, thymoma, thymic carcinoma, thyroid cancer, transitional cell cancer, trophoblastic tumors, urethral cancer, uterine cancer, fallopian tube cancer, vaginal cancer, visual pathway and hypothalamic glioma, vulvar cancer, Waldenstrom's macroglobulinemia, and Wilms' tumor.

As used herein, the term "preventing a disease" (e.g., preventing cancer) in a subject means for example, to stop the development of one or more symptoms of a disease in a subject before they occur or are detectable, e.g., by the patient or the patient's doctor. Preferably, the disease (e.g., cancer) does not develop at all, i.e., no symptoms of the disease are detectable. However, it can also result in delaying or slowing of the development of one or more symptoms of the disease. Alternatively, or in addition, it can result in the decreasing of the severity of one or more subsequently developed symptoms.

Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

An effective amount can be administered in one or more administrations, applications or dosages. A therapeutically effective amount of a therapeutic compound (i.e., an effective dosage) depends on the therapeutic compounds selected. Moreover, treatment of a subject with a therapeutically effective amount of the compounds or compositions described herein can include a single treatment or a series of treatments. For example, effective amounts can be administered at least once. The compositions can be administered one from one or more times per day to one or more times per week; including once every other day. The skilled artisan will appreciate that certain factors can influence the dosage and timing required to effectively treat a subject, including but not limited to the severity of the disease or disorder, previous treatments, the general health or age of the subject, and other diseases present.

Following administration, the subject can be evaluated to detect, assess, or determine their level of disease. In some instances, treatment can continue until a change (e.g., reduction) in the level of disease in the subject is detected. Upon improvement of a patient's condition (e.g., a change (e.g., decrease) in the level of disease in the subject), a maintenance dose of a compound, or composition disclosed herein can be administered, if necessary. Subsequently, the dosage or frequency of administration, or both, can be reduced, e.g., as a function of the symptoms, to a level at which the improved condition is retained. Patients may, however, require intermittent treatment on a long-term basis upon any recurrence of disease symptoms.

EXAMPLES

Example 1

Procedures for the Synthesis of VHL-1 Alkyl Linkers

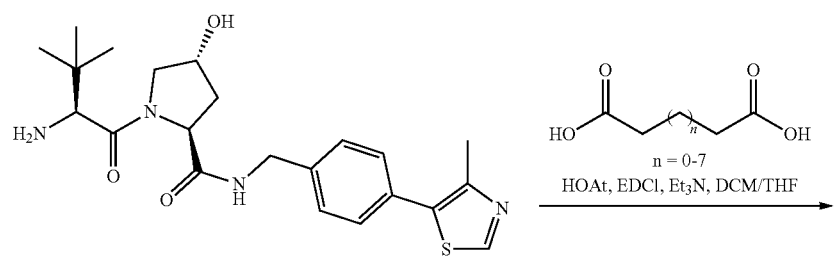

-continued

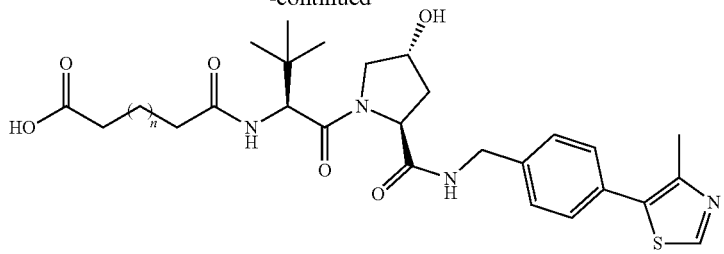

To a solution of diacid (10 mmol) in DCM/THF (1:1, 200 ml) was added VHL-1 (2 mmol), triethylamine (1 ml, 7.1 mmol), HOAt (300 mg, 2.2 mmol), and EDCI (420 mg, 2.2 mmol) sequentially at 0° C. The resulting solution was stirred for 2 h at 0° C., before being warmed to room temperature (RT). After stirring overnight at RT, the reaction was quenched with water. After concentration under reduced pressure, the resulting residue was purified by reverse-phase chromatography to yield the desired product.

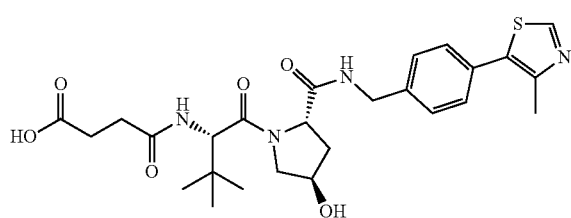 [SMILES: Cc1ncsc1-c1ccc(CNC(=O)[C@@H]2C[C@@H](O)CN2C(=O)[C@@H](NC(=O)CCC(=O)O)C(C)(C)C)cc1]

Linker 1: 4-(((S)-1-((2S,4R)-4-Hydroxy-2-((4-(4-methylthiazol-5-yl)benzyl)carbamoyl) pyrrolidin-1-yl)-3,3-dimethyl-1-oxobutan-2-yl)amino)-4-oxobutanoic acid (810 mg, 85%) as white solid. $^1$H NMR (600 MHz CD$_3$OD) δ 9.10 (s, 1H), 7.51 (d, J=7.8 Hz, 2H), 7.44 (d, J=8.4 Hz, 2H), 4.64 (s, 1H), 4.60-4.49 (m, 3H), 4.39 (d, J=15.6 Hz, 1H), 3.91 (d, J=10.8 Hz, 1H), 3.82 (dd, J=9.6, 3.6 Hz, 1H), 2.67-2.55 (m, 4H), 2.52 (s, 3H), 2.25-2.22 (m, 1H), 2.12-2.07 (m, 1H), 1.06 (s, 9H). HRMS (ESI-TOF) m/z: [M+H]$^+$ calculated for C$_{26}$H$_{35}$N$_4$O$_6$S, 531.2272, found 531.2280.

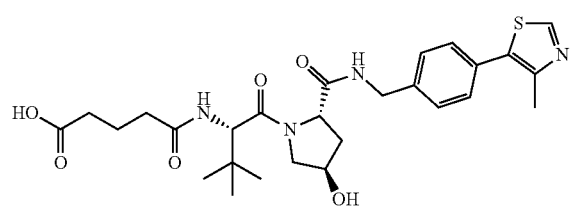 [SMILES: Cc1ncsc1-c1ccc(CNC(=O)[C@@H]2C[C@@H](O)CN2C(=O)[C@@H](NC(=O)CCCC(=O)O)C(C)(C)C)cc1]

Linker 2: 5-(((S)-1-((2S,4R)-4-Hydroxy-2-((4-(4-methylthiazol-5-yl)benzyl)carbamoyl) pyrrolidin-1-yl)-3,3-dimethyl-1-oxobutan-2-yl)amino)-5-oxopentanoic acid (230 mg, 43%) as white solid. $^1$H NMR (600 MHz CD$_3$OD) δ 9.14 (s, 1H), 7.51 (d, J=9.0 Hz, 2H), 7.46 (d, J=8.4 Hz, 2H), 4.65 (s, 1H), 4.60-4.57 (m, 1H), 4.56 (d, J=15.6 Hz, 1H), 4.53-4.50 (m, 1H), 4.38 (d, J=15.6 Hz, 1H), 3.94 (d, J=11.4 Hz, 1H), 3.82 (dd, J=11.4, 3.6 Hz, 1H), 2.52 (s, 3H), 2.40-2.30 (m, 4H), 2.26-2.22 (m, 1H), 2.12-2.08 (m, 1H), 1.91 (t, J=7.8 Hz, 2H), 1.06 (s, 9H). HRMS (ESI-TOF) m/z: [M+H]$^+$ calculated for C$_{27}$H$_{37}$N$_4$O$_6$S, 545.2428, found 545.2432.

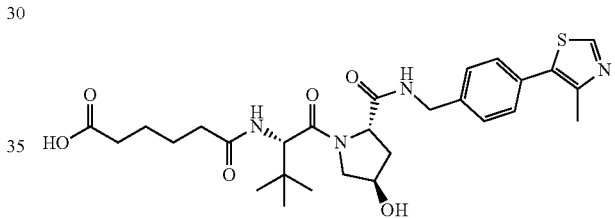

Linker 3: 6-(((S)-1-((2S,4R)-4-Hydroxy-2-((4-(4-methylthiazol-5-yl)benzyl)carbamoyl) pyrrolidin-1-yl)-3,3-dimethyl-1-oxobutan-2-yl)amino)-6-oxohexanoic acid (700 mg, 63%) as white solid. $^1$H NMR (600 MHz CD$_3$OD) δ 9.12 (s, 1H), 7.51 (d, J=9.0 Hz, 2H), 7.46 (d, J=8.4 Hz, 2H), 4.65 (s, 1H), 4.60-4.55 (m, 2H), 4.53-4.50 (m, 1H), 4.38 (d, J=16.8 Hz, 1H), 3.93 (d, J=10.8 Hz, 1H), 3.82 (dd, J=11.4, 3.6 Hz, 1H), 2.52 (s, 3H), 2.38-2.21 (m, 5H), 2.12-2.08 (m, 1H), 1.71-1.62 (m, 4H), 1.06 (s, 9H). HRMS (ESI-TOF) m/z: [M+H]$^+$ calculated for C$_{28}$H$_{39}$N$_4$O$_6$S, 559.2585, found 559.2605.

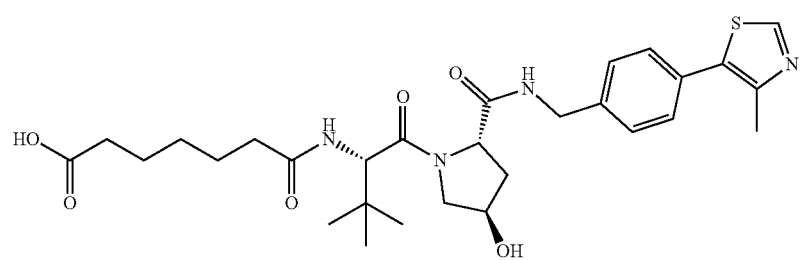

Linker 4: 7-(((S)-1-((2S,4R)-4-Hydroxy-2-((4-(4-methylthiazol-5-yl)benzyl)carbamoyl) pyrrolidin-1-yl)-3,3-dimethyl-1-oxobutan-2-yl)amino)-7-oxoheptanoic acid (810 mg, 79%) as white solid. $^1$H NMR (600 MHz CD$_3$OD) δ 8.98 (s, 1H), 7.50 (d, J=8.4 Hz, 2H), 7.44 (d, J=9.0 Hz, 2H), 4.65 (s, 1H), 4.60-4.49 (m, 3H), 4.38 (d, J=15.6 Hz, 1H), 3.93 (d, J=10.8 Hz, 1H), 3.82 (dd, J=11.4, 3.6 Hz, 1H), 2.51 (s, 3H), 2.35-2.22 (m, 5H), 2.13-2.08 (m, 1H), 1.68-1.59 (m, 4H), 1.42-1.34 (m, 2H), 1.06 (s, 9H). HRMS (ESI-TOF) m/z: [M+H]$^+$ calculated for C$_{29}$H$_{41}$N$_4$O$_6$S, 573.2741, found 573.2754.

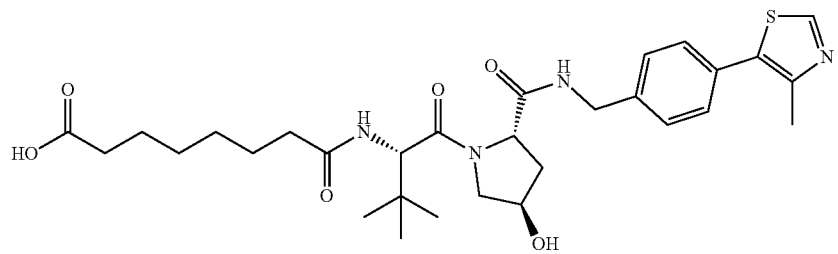 [SMILES: Cc1ncsc1-c1ccc(CNC(=O)[C@@H]2C[C@@H](O)CN2C(=O)[C@@H](NC(=O)CCCCCCC(=O)O)C(C)(C)C)cc1]

Linker 5: 8-(((S)-1-((2S,4R)-4-Hydroxy-2-((4-(4-methylthiazol-5-yl)benzyl)carbamoyl) pyrrolidin-1-yl)-3,3-dimethyl-1-oxobutan-2-yl)amino)-8-oxooctanoic acid (980 mg, 78%) as white solid. $^1$H NMR (600 MHz, CD$_3$OD) δ 8.94 (s, 1H), 7.47 (d, J=8.1 Hz, 2H), 7.42 (d, J=8.2 Hz, 2H), 4.63 (s, 1H), 4.59-4.47 (m, 3H), 4.35 (d, J=15.4 Hz, 1H), 3.90 (d, J=11.0 Hz, 1H), 3.80 (dd, J=10.9, 3.9 Hz, 1H), 2.48 (s, 3H), 2.32-2.17 (m, 5H), 2.08 (ddd, J=13.3, 9.1, 4.5 Hz, 1H), 1.67-1.55 (m, 4H), 1.40-1.28 (m, 4H), 1.03 (s, 9H). HRMS (ESI-TOF) m/z: [M+H]$^+$ calculated for C$_{30}$H$_{43}$N$_4$O$_6$S, 587.2898; found: 587.2903.

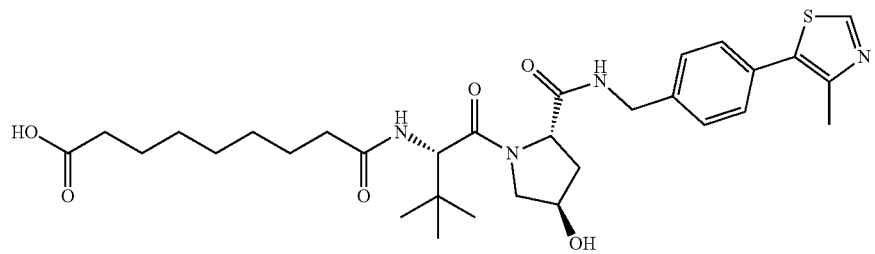 [SMILES: Cc1ncsc1-c1ccc(CNC(=O)[C@@H]2C[C@@H](O)CN2C(=O)[C@@H](NC(=O)CCCCCCCC(=O)O)C(C)(C)C)cc1]

Linker 6: 9-(((S)-1-((2S,4R)-4-Hydroxy-2-((4-(4-methylthiazol-5-yl)benzyl)carbamoyl) pyrrolidin-1-yl)-3,3-dimethyl-1-oxobutan-2-yl)amino)-9-oxononanoic acid (750 mg, 66%) as white solid. $^1$H NMR (600 MHz CD$_3$OD) δ 9.09 (s, 1H), 7.51 (d, J=9.0 Hz, 2H), 7.46 (d, J=8.4 Hz, 2H), 4.66 (s, 1H), 4.61-4.50 (m, 3H), 4.38 (d, J=15.6 Hz, 11H), 3.93 (d, J=10.8 Hz, 1H), 3.82 (dd, J=11.4, 3.6 Hz, 1H), 2.52 (s, 3H), 2.36-2.22 (m, 5H), 2.12-2.07 (m, 1H), 1.68-1.59 (m, 4H), 1.40-1.34 (m, 8H), 1.06 (s, 9H); HPLC 98%; t$_R$=4.24 min; HRMS (TOF) calculated for C$_{31}$H$_{45}$N$_4$O$_6$S [M+H]$^+$, 601.3054, found 601.3064.

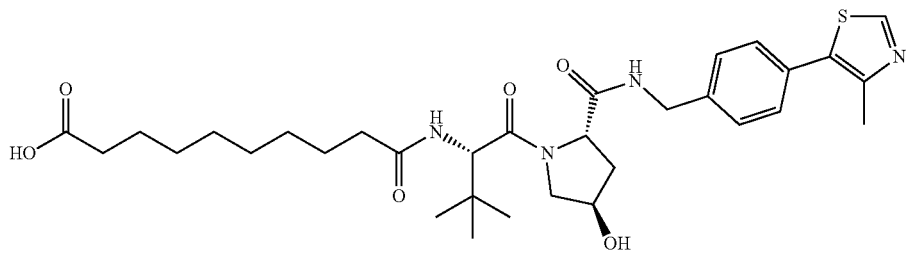 [SMILES: Cc1ncsc1-c1ccc(CNC(=O)[C@@H]2C[C@@H](O)CN2C(=O)[C@@H](NC(=O)CCCCCCCCC(=O)O)C(C)(C)C)cc1]

Linker 7: 10-(((S)-1-((2S,4R)-4-Hydroxy-2-((4-(4-methylthiazol-5-yl)benzyl)carbamoyl) pyrrolidin-1-yl)-3,3-dimethyl-1-oxobutan-2-yl)amino)-10-oxodecanoic acid (900 mg, 73%) as white solid. $^1$H NMR (600 MHz CD$_3$OD) δ 8.98 (s, 1H), 7.50 (d, J=8.4 Hz, 2H), 7.45 (d, J=9.0 Hz, 2H), 4.66 (s, 1H), 4.61-4.50 (m, 3H), 4.38 (d, J=14.4 Hz, 11H), 3.93 (d, J=10.8 Hz, 1H), 3.83 (dd, J=11.4, 3.6 Hz, 1H), 2.51 (s, 3H), 2.35-2.22 (m, 5H), 2.13-2.08 (m, 1H), 1.66-1.58 (m, 4H), 1.38-1.32 (m, 10H), 1.06 (s, 9H). HRMS(TOF) calculated for C$_{32}$H$_{47}$N$_4$O$_6$S [M+H]$^+$, 615.3211, found 615.3224.

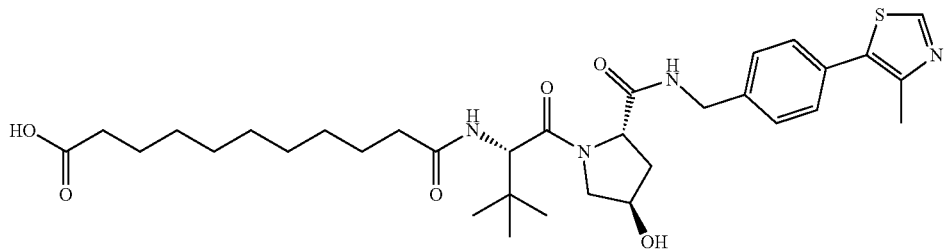 [SMILES: Cc1ncsc1-c1ccc(CNC(=O)[C@@H]2C[C@@H](O)CN2C(=O)[C@@H](NC(=O)CCCCCCCCCC(=O)O)C(C)(C)C)cc1]

Linker 8: 11-(((S)-1-((2S,4R)-4-Hydroxy-2-((4-(4-methylthiazol-5-yl)benzyl)carbamoyl) pyrrolidin-1-yl)-3,3-dimethyl-1-oxobutan-2-yl)amino)-11-oxoundecanoic acid (930 mg, 78%) as white solid. $^1$H NMR (600 MHz CD$_3$OD) δ 8.95 (s, 1H), 7.49 (d, J=8.4 Hz, 2H), 7.44 (d, J=7.8 Hz, 2H), 4.66 (s, 1H), 4.61-4.50 (m, 3H), 4.38 (d, J=15.6 Hz, 1H), 3.93 (d, J=9.6 Hz, 1H), 3.82 (dd, J=11.4, 3.6 Hz, 1H), 2.50 (s, 3H), 2.35-2.21 (m, 5H), 2.12-2.07 (m, 1H), 1.66-1.57 (m, 4H), 1.37-1.29 (m, 12H), 1.06 (s, 9H). HRMS (ESI-TOF) calculated for C$_{33}$H$_{49}$N$_4$O$_6$S, 629.3367, found 629.3368.

Example 2

Procedures for the Synthesis of VHL-1 PEG Linkers

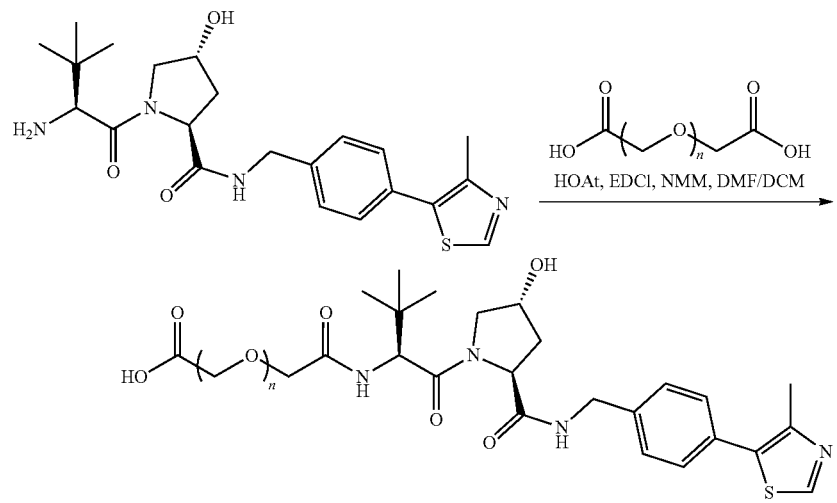

To a solution of diacid (4 mmol) in DMF (10 ml) and DCM (250 ml) was added NMM (10 mmol), VHL-1 (2 mmol), HOAt (2.4 mmol), and EDCI (2.4 mmol) at 0° C. The resulting reaction solution was stirred at 0° C. for 6 h and then at RT overnight. The progress of the reaction was monitored by LC/MS. After VHL-1 was totally consumed, the reaction was concentrated and the resulting residue was purified by reverse-phase chromatography to yield the product.

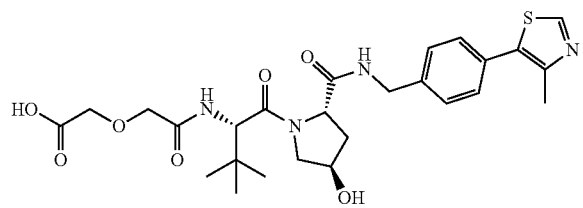 [SMILES: Cc1ncsc1-c1ccc(CNC(=O)[C@@H]2C[C@@H](O)CN2C(=O)[C@@H](NC(=O)COCC(=O)O)C(C)(C)C)cc1]

Linker 9: 2-(2-(((S)-1-((2S,4R)-4-Hydroxy-2-((4-(4-methylthiazol-5-yl)benzyl)carbamoyl) pyrrolidin-1-yl)-3,3-dimethyl-1-oxobutan-2-yl)amino)-2-oxoethoxy)acetic acid (810 mg, 69%) as white solid. $^1$H NMR (600 MHz, CD$_3$OD) δ 8.97 (s, 1H), 7.47 (d, J=8.2 Hz, 2H), 7.43 (d, J=8.1 Hz, 2H), 4.69 (s, 1H), 4.60-4.47 (m, 3H), 4.36 (d, J=15.5 Hz, 1H), 4.27-4.17 (m, 2H), 4.16-4.07 (m, 2H), 3.89 (d, J=11.0 Hz, 1H), 3.81 (dd, J=11.0, 3.8 Hz, 1H), 2.48 (s, 3H), 2.22 (dd, J=13.1, 7.6 Hz, 1H), 2.08 (ddd, J=13.3, 9.2, 4.5 Hz, 1H), 1.05 (s, 9H). HRMS (ESI-TOF) m/z: [M+H]$^+$ calculated for C$_{26}$H$_{35}$N$_4$O$_7$S, 547.2221; found: 547.2230.

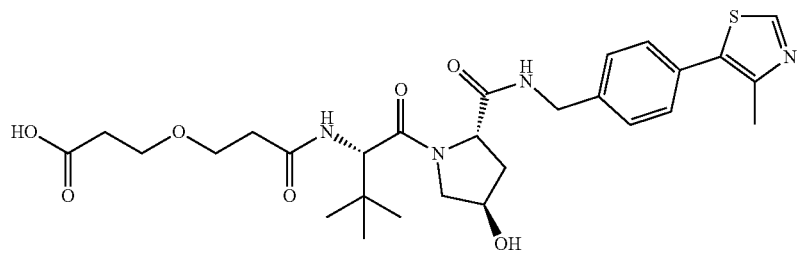

Linker 10: 3-(3-(((S)-1-((2S,4R)-4-Hydroxy-2-((4-(4-methylthiazol-5-yl)benzyl)carbamoyl) pyrrolidin-1-yl)-3,3-dimethyl-1-oxobutan-2-yl)amino)-3-oxopropoxy)propanoic acid (450 mg, 63%) as white solid. $^1$H NMR (600 MHz, CD$_3$OD) δ 9.00 (s, 1H), 7.45 (d, J=22.1 Hz, 4H), 4.64 (s, 1H), 4.61-4.44 (m, 3H), 4.36 (d, J=15.4 Hz, 1H), 3.84 (dd, J=57.3, 10.5 Hz, 2H), 3.75-3.56 (m, 4H), 2.60-2.39 (m, 7H), 2.24-2.17 (m, 1H), 2.11-2.03 (m, 1H), 1.03 (s, 9H). HRMS (ESI-TOF) m/z: [M+H]$^+$ calculated for C28H$_{39}$N$_4$O$_7$S, 575.2534; found: 575.2543.

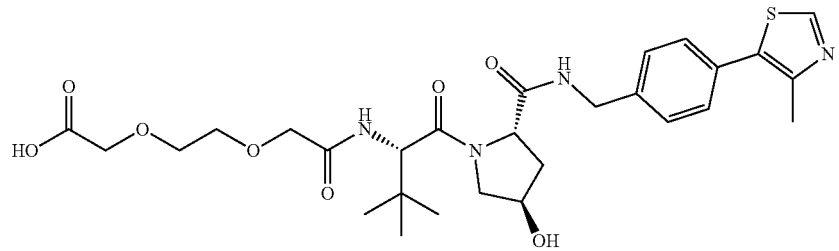 [SMILES: Cc1ncsc1-c1ccc(CNC(=O)[C@@H]2C[C@@H](O)CN2C(=O)[C@@H](NC(=O)COCCOCC(=O)O)C(C)(C)C)cc1]

Linker 11: 2-(2-(2-(((S)-1-((2S,4R)-4-Hydroxy-2-((4-(4-methylthiazol-5-yl)benzyl) carbamoyl)pyrrolidin-1-yl)-3,3-dimethyl-1-oxobutan-2-yl)amino)-2-oxoethoxy)ethoxy)acetic acid (680 mg, 54%) as white solid. $^1$H NMR (600 MHz, CD$_3$OD) δ 9.05 (s, 1H), 7.48 (d, J=8.1 Hz, 2H), 7.44 (d, J=8.2 Hz, 2H), 4.69 (s, 1H), 4.56 (dd, J=18.6, 12.1 Hz, 2H), 4.50 (s, 1H), 4.36 (d, J=15.5 Hz, 1H), 4.21 (d, J=16.8 Hz, 1H), 4.13 (d, J=16.9 Hz, 1H), 4.08 (d, J=15.6 Hz, 1H), 4.04 (d, J=15.7 Hz, 1H), 3.88 (d, J=11.0 Hz, 1H), 3.83-3.69 (m, 5H), 2.49 (s, 3H), 2.25-2.19 (m, 1H), 2.08 (ddd, J=13.3, 9.2, 4.4 Hz, 1H), 1.04 (s, 9H). HRMS (ESI-TOF) m/z: [M+H]$^+$ calculated for C$_{28}$H$_{39}$N$_4$O$_8$S, 591.2483; found: 591.2477.

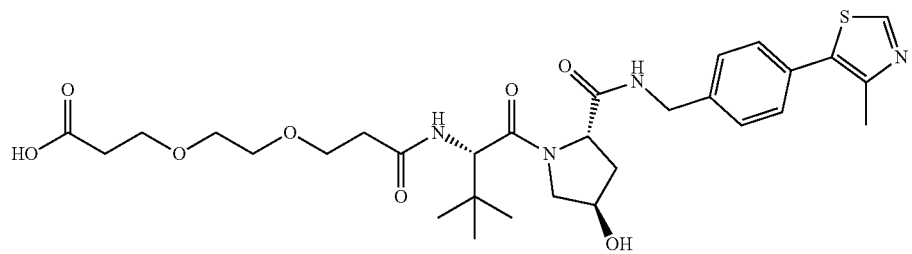 [SMILES: Cc1ncsc1-c1ccc(CNC(=O)[C@@H]2C[C@@H](O)CN2C(=O)[C@@H](NC(=O)CCOCCOCCC(=O)O)C(C)(C)C)cc1]

Linker 12: 3-(2-(3-(((S)-1-((2S,4R)-4-Hydroxy-2-((4-(4-methylthiazol-5-yl)benzyl) carbamoyl)pyrrolidin-1-yl)-3,3-dimethyl-1-oxobutan-2-yl)amino)-3-oxopropoxy)ethoxy) propanoic acid (680 mg, 64%) as white solid. $^1$H NMR (600 MHz, CD$_3$OD) δ 8.98 (d, J=20.1 Hz, 1H), 7.48 (d, J=8.0 Hz, 2H), 7.43 (d, J=8.1 Hz, 2H), 4.64 (s, 1H), 4.59-4.51 (m, 2H), 4.49 (s, 1H), 4.35 (d, J=15.5 Hz, 1H), 3.89 (d, J=11.0 Hz, 1H), 3.80 (dd, J=10.9, 3.8 Hz, 1H), 3.76-3.67 (m, 4H), 3.63-3.55 (m, 4H), 2.60-2.43 (m, 7H), 2.21 (dd, J=13.1, 7.6 Hz, 1H), 2.08 (ddd, J=13.2, 9.1, 4.5 Hz, 1H), 1.04 (s, 9H). HRMS (ESI-TOF) m/z: [M+H]$^+$ calculated for C$_{30}$H$_{43}$N$_4$O$_8$S, 619.2796; found: 619.2800.

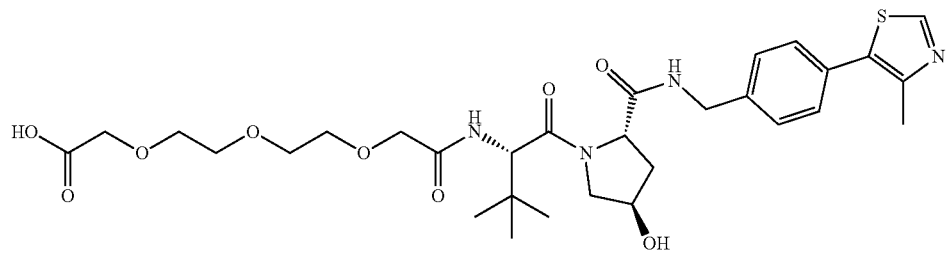 [SMILES: Cc1ncsc1-c1ccc(CNC(=O)[C@@H]2C[C@@H](O)CN2C(=O)[C@@H](NC(=O)COCCOCCOCC(=O)O)C(C)(C)C)cc1]

Linker 13: (S)-13-((2S,4R)-4-Hydroxy-2-((4-(4-methylthiazol-5-yl)benzyl)carbamoyl) pyrrolidine-1-carbonyl)-14,14-dimethyl-11-oxo-3,6,9-trioxa-12-azapentadecanoic acid (880 mg, 54%) as white solid. $^1$H NMR (600 MHz, CD$_3$OD) δ 9.05 (s, 1H), 7.48 (d, J=8.2 Hz, 2H), 7.44 (d, J=8.3 Hz, 2H), 4.69 (s, 1H), 4.60-4.51 (m, 2H), 4.50 (s, 1H), 4.36 (d, J=15.5 Hz, 1H), 4.10 (s, 1H), 4.07 (d, J=15.6 Hz, 1H), 4.03 (d, J=15.6 Hz, 1H), 3.87 (d, J=11.0 Hz, 1H), 3.80 (dd, J=11.0, 3.8 Hz, 1H), 3.76-3.64 (m, 9H), 2.50 (s, 3H), 2.22 (dd, J=13.1, 7.6 Hz, 1H), 2.08 (ddd, J=13.3, 9.2, 4.4 Hz, 1H), 1.04 (s, 9H). HRMS (ESI-TOF) m/z: [M+H]$^+$ calculated for C$_{30}$H$_{43}$N$_4$O$_9$S, 635.2745; found: 635.2751.

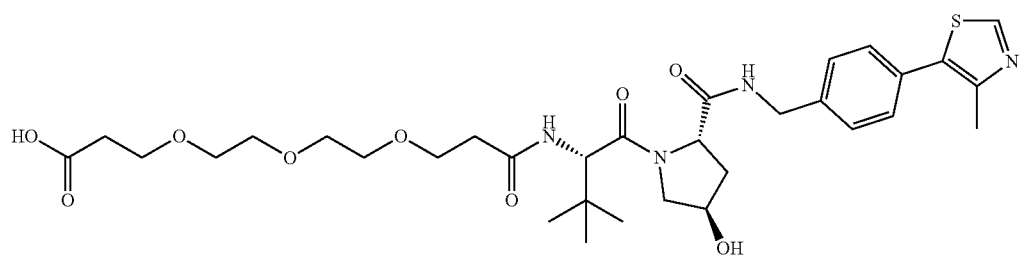 [SMILES: Cc1ncsc1-c1ccc(CNC(=O)[C@@H]2C[C@@H](O)CN2C(=O)[C@@H](NC(=O)CCOCCOCCOCCC(=O)O)C(C)(C)C)cc1]

Linker 14: (S)-15-((2S,4R)-4-Hydroxy-2-((4-(4-methylthiazol-5-yl)benzyl)carbamoyl) pyrrolidine-1-carbonyl)-16,16-dimethyl-13-oxo-4,7,10-trioxa-14-azaheptadecanoic acid (677 mg, 57%) as white solid. $^1$H NMR (600 MHz, CD$_3$OD) δ 8.95 (s, 1H), 7.47 (d, J=8.1 Hz, 2H), 7.42 (d, J=8.1 Hz, 2H), 4.65 (s, 1H), 4.59-4.51 (m, 2H), 4.49 (s, 1H), 4.35 (d, J=15.5 Hz, 1H), 3.89 (d, J=11.1 Hz, 1H), 3.80 (dd, J=10.9, 3.9 Hz, 1H), 3.76-3.67 (m, 4H), 3.66-3.54 (m, 8H), 2.60-2.50 (m, 3H), 2.50-2.43 (m, 4H), 2.21 (dd, J=13.1, 7.6 Hz, 1H), 2.08 (ddd, J=13.3, 9.1, 4.5 Hz, 1H), 1.04 (s, 9H). HRMS (ESI-TOF) m/z: [M+H]$^+$ calculated for C$_{32}$H$_{47}$N$_4$O$_9$S, 663.3058; found: 663.3059.

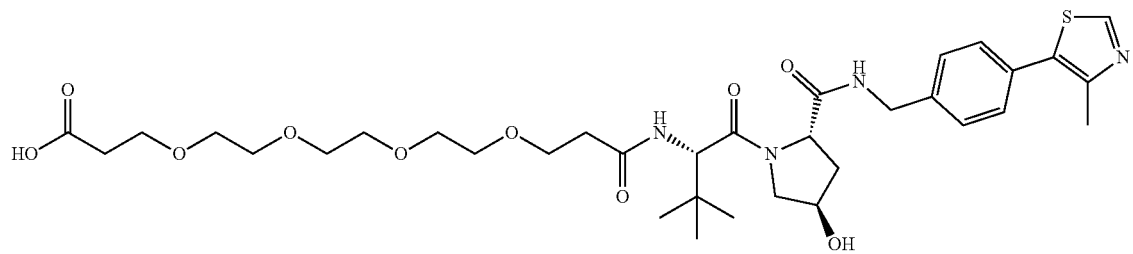 [SMILES: Cc1ncsc1-c1ccc(CNC(=O)[C@@H]2C[C@@H](O)CN2C(=O)[C@@H](NC(=O)CCOCCOCCOCCOCCC(=O)O)C(C)(C)C)cc1]

Linker 15: (S)-18-((2S,4R)-4-Hydroxy-2-((4-(4-methylthiazol-5-yl)benzyl)carbamoyl) pyrrolidine-1-carbonyl)-19,19-dimethyl-16-oxo-4,7,10,13-tetraoxa-17-azaicosanoic acid (590 mg, 65%) as white solid. $^1$H NMR (600 MHz, CD$_3$OD) δ 8.99 (s, 1H), 7.48 (d, J=8.1 Hz, 2H), 7.42 (d, J=8.2 Hz, 2H), 4.65 (s, 1H), 4.59-4.51 (m, 2H), 4.49 (s, 1H), 4.35 (d, J=15.5 Hz, 1H), 3.89 (d, J=11.0 Hz, 1H), 3.80 (dd, J=10.9, 3.8 Hz, 1H), 3.77-3.67 (m, 4H), 3.67-3.54 (m, 12H), 2.61-2.43 (m, 7H), 2.21 (dd, J=13.0, 7.6 Hz, 1H), 2.08 (ddd, J=13.2, 9.1, 4.4 Hz, 1H), 1.04 (s, 9H). HRMS (ESI-TOF) m/z: [M+H]$^+$ calculated for C$_{34}$H$_{51}$N$_4$O$_{10}$S, 707.3320; found: 707.3321.

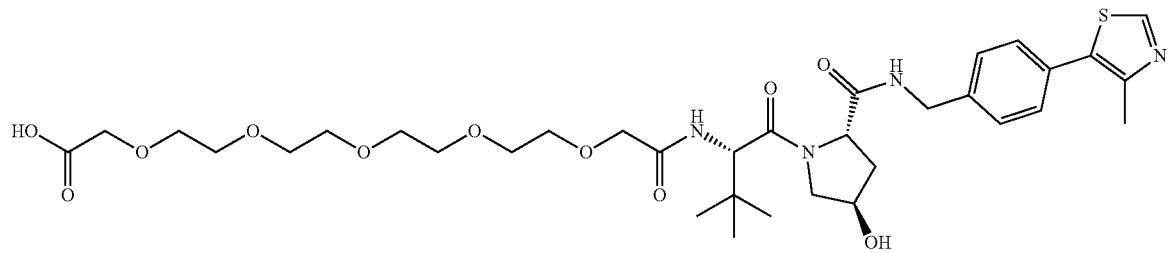 [SMILES: Cc1ncsc1-c1ccc(CNC(=O)[C@@H]2C[C@@H](O)CN2C(=O)[C@@H](NC(=O)COCCOCCOCCOCCOCC(=O)O)C(C)(C)C)cc1]

Linker 16: (S)-19-((2S,4R)-4-Hydroxy-2-((4-(4-methylthiazol-5-yl)benzyl)carbamoyl) pyrrolidine-1-carbonyl)-20,20-dimethyl-17-oxo-3,6,9,12,15-pentaoxa-18-azahenicosanoic acid (496 mg, 54%) as white solid. $^1$H NMR (600 MHz, CD$_3$OD) δ 8.89 (s, 1H), 7.47 (d, J=8.1 Hz, 2H), 7.42 (d, J=8.1 Hz, 2H), 4.69 (s, 1H), 4.59-4.46 (m, 3H), 4.36 (d, J=15.5 Hz, 1H), 4.16-4.00 (m, 4H), 3.87 (d, J=11.0 Hz, 1H), 3.80 (dd, J=11.0, 3.7 Hz, 1H), 3.76-3.53 (m, 16H), 2.48 (s, 3H), 2.22 (dd, J=13.1, 7.6 Hz, 1H), 2.08 (ddd, J=13.3, 9.2, 4.4 Hz, 1H), 1.04 (s, 7H). HRMS (ESI-TOF) m/z: [M+H]$^+$ calculated for C$_{34}$H$_{51}$N$_4$O$_{11}$S, 723.3270; found: 723.3269.

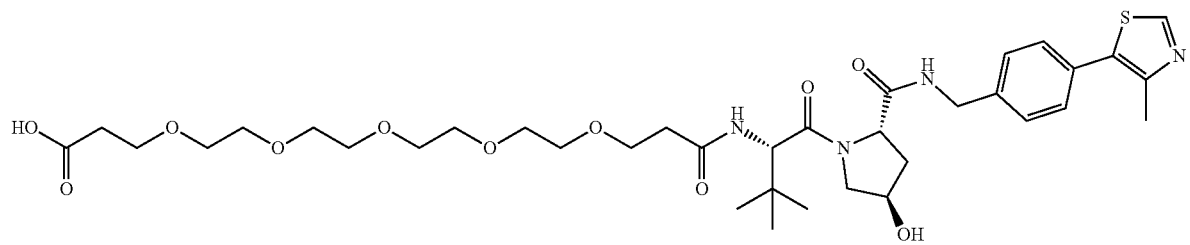 [SMILES: Cc1ncsc1-c1ccc(CNC(=O)[C@@H]2C[C@@H](O)CN2C(=O)[C@@H](NC(=O)CCOCCOCCOCCOCCOCCC(=O)O)C(C)(C)C)cc1]

Linker 17: (S)-21-((2S,4R)-4-Hydroxy-2-((4-(4-methylthiazol-5-yl)benzyl)carbamoyl) pyrrolidine-1-carbonyl)-22,22-dimethyl-19-oxo-4,7,10,13,16-pentaoxa-20-azatricosanoic acid (420 mg, 42%) as white solid. $^1$H NMR (600 MHz, CD$_3$OD) δ 8.89 (s, 1H), 7.47 (d, J=8.0 Hz, 2H), 7.42 (d, J=8.1 Hz, 2H), 4.65 (s, 1H), 4.59-4.51 (m, 2H), 4.49 (s, 1H), 4.35 (d, J=15.5 Hz, 1H), 3.89 (d, J=11.0 Hz, 1H), 3.80 (dd, J=10.9, 3.8 Hz, 1H), 3.77-3.67 (m, 4H), 3.67-3.51 (m, 16H), 2.61-2.42 (m, 7H), 2.24-2.18 (m, 1H), 2.08 (ddd, J=13.2, 9.1, 4.4 Hz, 1H), 1.02 (d, J=14.3 Hz, 9H). HRMS (ESI-TOF) m/z: [M+H]$^+$ calculated for C$_{36}$H$_{55}$N$_4$O$_{11}$S, 751.3583; found: 751.3589.

Example 3

Procedures for the Synthesis of Pomalidomide Linkers

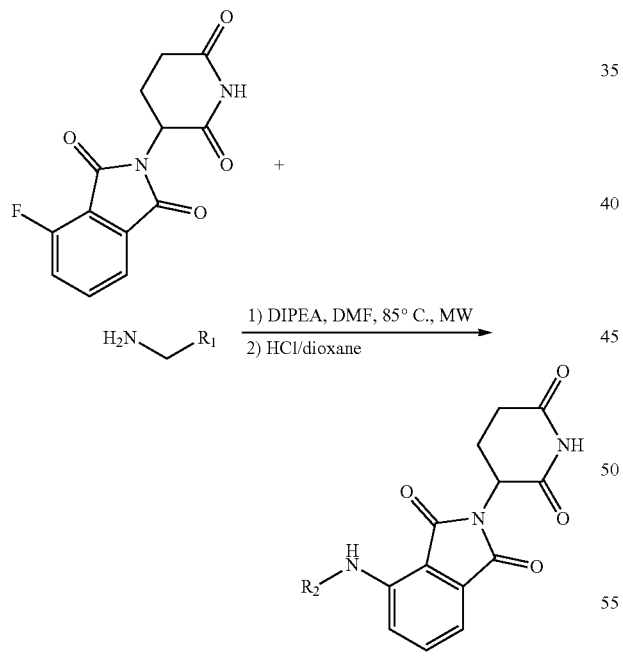

A solution of pomalidomide analogue (1 eq.), amine (1 eq.), and N,N-diisopropylethylamine (1.5 eq.) in DMF (2.0 ml per mmol of pomalidamide) was heated to 85° C. in a microwave reactor for 40 min. After cooling to RT, the reaction was quenched with water and extracted with ethyl acetate (3x). The combined organic phase was dried over anhydrous sodium sulfate and concentrated under reduced pressure. The resulting residue was purified by silica gel chromatography (eluted with hexanes/EtOAc: 0-100%) to give the desired t-Bu ester intermediate as oil. This intermediate was treated with a solution of hydrogen chloride in dioxane (4 M, 5 ml per mmol of pomalidamide) for overnight. After concentration under reduced pressure, the desired acid product was obtained as yellow oil.

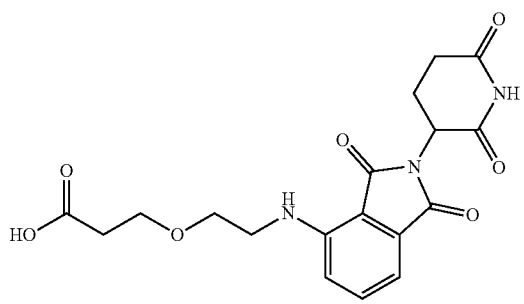

Linker 18: 3-(2-((2-(2,6-Dioxopiperidin-3-yl)-1,3-dioxoisoindolin-4-yl)amino)ethoxy) propanoic acid tert-Butyl 3-(2-aminoethoxy)propanoate (1.0 g, 5.3 mmol) was used to prepare the title compound (500 mg, 24%) according to the above procedures. $^1$H NMR (600 MHz, CD$_3$OD) δ 7.54 (dd, J=8.3, 7.0, 1.2 Hz, 1H), 7.09 (d, 1H), 7.04 (d, J=7.0, 1.1 Hz, 1H), 5.05 (dd, J=12.5, 5.4, 1.2 Hz, 1H), 3.75 (t, J=6.2, 1.2 Hz, 2H), 3.65-3.69 (m, 2H), 3.45-3.49 (m, 2H), 2.88-2.82 (m, 1H), 2.76-2.70 (m, 2H), 2.56 (t, J=6.2, 1.2 Hz, 2H), 2.10 (ddt, J=14.9, 7.6, 3.7, 1.6 Hz, 1H). MS (ESI) m/z 390.2 [M+H]$^+$.

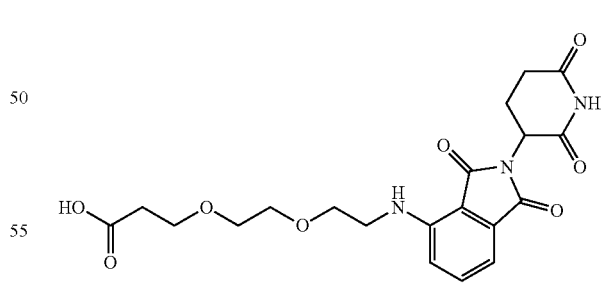

Linker 19: 3-(2-(2-((2-(2,6-Dioxopiperidin-3-yl)-1,3-dioxoisoindolin-4-yl)amino)ethoxy) ethoxy)-propanoic acid tert-Butyl 3-(2-(2-aminoethoxy)ethoxy)propanoate (0.70 g, 3.0 mmol) was used to prepare tert-butyl 3-(2-(2-((2-(2,6-dioxopiperidin-3-yl)-1,3-dioxoisoindolin-4-yl)amino)-ethoxy)ethoxy)propanoate (575 mg, 39%) according to the above procedures. ¹H NMR (600 MHz, CDCl₃) δ 8.13 (s, 1H), 7.53-7.45 (m, 1H), 7.10 (d, J=7.1 Hz, 1H), 6.92 (d, J=8.5 Hz, 1H), 6.49 (t, J=5.6 Hz, 1H), 4.91 (dd, J=12.4, 5.3 Hz, 1H), 3.76-3.69 (m, 4H), 3.67-3.60 (m, 4H), 3.46 (q, J=5.5 Hz, 2H), 2.89 (dt, J=16.8, 3.2 Hz, 1H), 2.84-2.69 (m, 2H), 2.51 (t, J=6.6 Hz, 2H), 2.16-2.08 (m, 1H), 1.44 (s, 9H). MS (ESI) m/z 490.2 [M+H]⁺. The t-Bu ester intermediate was dissolved in formic acid (10 ml) and the resulting solution was stirred at RT overnight. After removal of the solvent under reduced pressure, the tittle compound (512 mg, 100%) was obtained and used for the following reactions without further purification.

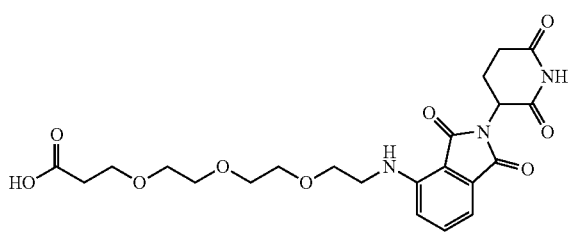 [SMILES: O=C(O)CCOCCOCCOCCNc1cccc2c1C(=O)N(C1CCC(=O)NC1=O)C2=O]

Linker 20: 3-(2-(2-(2-((2-(2,6-Dioxopiperidin-3-yl)-1,3-dioxoisoindolin-4-yl)amino)ethoxy)ethoxy)ethoxy)propanoic acid tert-Butyl 3-(2-(2-(2-aminoethoxy)ethoxy)ethoxy)propanoate (1.0 g, 3.6 mmol) was used to prepare the title compound (240 mg, 10%) according to the above procedures. ¹H NMR (600 MHz, CD₃OD) δ 7.55 (dd, J=8.4, 7.2 Hz, 1H), 7.10 (d, J=8.6 Hz, 1H), 7.05 (d, J=7.1 Hz, 1H), 5.05 (dd, J=12.4, 5.4 Hz, 1H), 3.71 (dt, J=9.4, 5.7 Hz, 4H), 3.66-3.63 (m, 4H), 3.62 (dd, J=6.0, 3.5 Hz, 2H), 3.58 (dd, J=6.1, 3.5 Hz, 2H), 3.50 (t, J=5.3 Hz, 2H), 2.86 (ddd, J=19.1, 14.1, 5.3 Hz, 1H), 2.77-2.66 (m, 2H), 2.52 (t, J=6.3 Hz, 2H), 2.11 (ddt, J=10.3, 5.0 Hz, 1H). MS (ESI) m/z 478.3 [M+H]⁺.

Linker 21: 1-((2-(2,6-Dioxopiperidin-3-yl)-1,3-dioxoisoindolin-4-yl)amino)-3,6,9,12-tetraoxapentadecan-15-oic acid tert-Butyl 1-amino-3,6,9,12-tetraoxapentadecan-15-oate (0.96 g, 3.0 mmol) was used to prepare the t-Bu ester intermediate according to the general procedures. The t-Bu ester intermediate was dissolved in formic acid (10 ml) and the resulting solution was stirred at RT overnight. After removal of the solvent under reduced pressure, the title compound (950 mg, 61%) was obtained and used for the following reactions without further purification. ¹H NMR (600 MHz, CD₃OD) δ 7.55 (t, J=7.8 Hz, 1H), 7.10 (d, J=8.5 Hz, 1H), 7.06 (d, J=7.0 Hz, 1H), 5.05 (dd, J=12.6, 5.3 Hz, 1H), 3.75-3.68 (m, 4H), 3.68-3.55 (m, 12H), 3.50 (t, J=4.9 Hz, 2H), 2.90-2.81 (m, 1H), 2.78-2.66 (m, 2H), 2.52 (t, J=6.0 Hz, 2H), 2.14-2.07 (m, 1H). MS (ESI) m/z 522.2 [M+H]⁺.

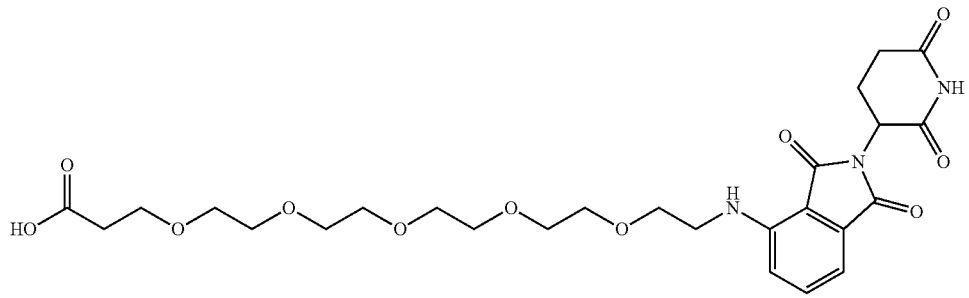

Linker 22: 1-((2-(2,6-Dioxopiperidin-3-yl)-1,3-dioxoisoindolin-4-yl)amino)-3,6,9,12,15-pentaoxaoctadecan-18-oic acid tert-Butyl 1-amino-3,6,9,12,15-pentaoxaoctadecan-18-oate (1.10 g, 3.0 mmol) was used to prepare tert-butyl 1-((2-(2,6-dioxopiperidin-3-yl)-1,3-dioxoisoindolin-4-yl)amino)-3,6,9,12,15-pentaoxaoctadecan-18-oate (1.35 g, 72%) according to the above procedures. ¹H NMR (600 MHz, CDCl₃) δ 8.32 (s, 1H), 7.48 (dd, J=8.5, 7.1 Hz, 1H), 7.10 (d, J=7.1 Hz, 1H), 6.91 (d, J=8.6 Hz, 1H), 6.49 (t, J=5.7 Hz, 1H), 4.91 (dd, J=12.4, 5.3 Hz, 1H), 3.74-3.68 (m, 4H), 3.68-3.63 (m, 12H), 3.63-3.58 (m, 4H), 3.46 (q, J=5.6 Hz, 2H), 2.92-2.85 (m, 1H), 2.83-2.68 (m, 2H), 2.49 (t, J=6.6 Hz, 2H), 2.15-2.08 (m, 1H), 1.43 (s, 9H). MS (ESI) m/z 622.2 [M+H]⁺. The t-Bu ester intermediate was dissolved in formic acid (10 ml) and the resulting solution was stirred at RT overnight. After removal of the solvent under reduced pressure, the tittle compound (1.23 g, 100%) was obtained and used for the following reactions without further purification.

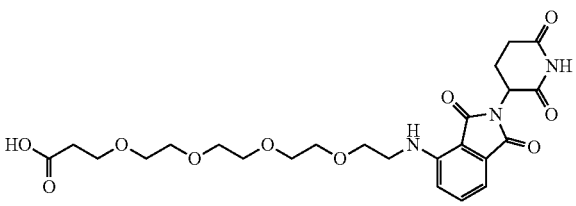 [SMILES: O=C(O)CCOCCOCCOCCOCCNc1cccc2c1C(=O)N(C1CCC(=O)NC1=O)C2=O]

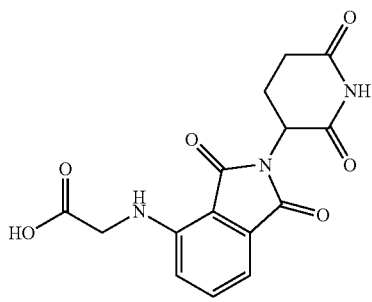 [SMILES: O=C(O)CNc1cccc2c1C(=O)N(C1CCC(=O)NC1=O)C2=O]

Linker 23: (2-(2,6-Dioxopiperidin-3-yl)-1,3-dioxoisoindolin-4-yl)glycine tert-Butyl glycinate (838 mg, 5.0 mmol) was used to prepare the title compound (240 mg, 14%) according to the general procedures. $^1$H NMR (600 MHz, CD$_3$OD) δ 7.57 (dd, J=8.5, 7.1 Hz, 1H), 7.11 (d, J=7.1 Hz, 1H), 6.95 (d, J=8.5 Hz, 1H), 5.07 (dd, J=12.6, 5.5 Hz, 1H), 4.12 (s, 2H), 2.86 (ddd, J=18.0, 14.4, 5.4 Hz, 1H), 2.74-2.67 (m, 2H), 2.15-2.08 (m, 1H). MS (ESI) m/z 332.1 [M+H]$^+$.

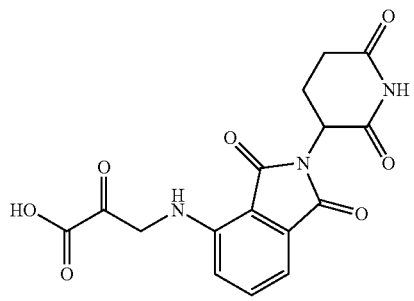 [SMILES: O=C1CCC(N2C(=O)c3cccc(NCC(=O)C(=O)O)c3C2=O)C(=O)N1]

Linker 24: 3-((2-(2,6-Dioxopiperidin-3-yl)-1,3-dioxoisoindolin-4-yl)amino)propanoic acid tert-Butyl 3-aminopropanoate HCl salt (1.0 g, 5.97 mmol) was used to prepare the title compound (700 mg, 4%) according to the above procedures. $^1$H NMR (600 MHz, CD$_3$OD) δ 7.57 (dd, J=8.6, 7.1 Hz, 1H), 7.11 (d, J=8.6 Hz, 1H), 7.06 (d, J=7.1 Hz, 1H), 5.05 (dd, J=12.6, 5.5 Hz, 1H), 3.62 (t, J=6.5 Hz, 2H), 2.88-2.82 (m, 1H), 2.76-2.69 (m, 2H), 2.64 (t, J=6.5 Hz, 2H), 2.13-2.07 (m, 1H). MS (ESI) m/z 346.2 [M+H]$^+$.

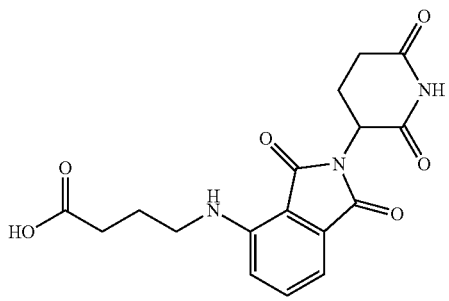 [SMILES: O=C(O)CCCNc1cccc2c1C(=O)N(C1CCC(=O)NC1=O)C2=O]

Linker 25: 4-((2-(2,6-Dioxopiperidin-3-yl)-1,3-dioxoisoindolin-4-yl)amino)butanoic acid tert-Butyl 4-aminobutanoate (1.0 g, 6.2 mmol) was used to prepare the title compound (550 mg, 25%) according to the above procedures. $^1$H NMR (600 MHz, CD$_3$OD) δ 7.55 (dd, J=8.6, 7.1 Hz, 1H), 7.10 (d, J=8.5 Hz, 1H), 7.04 (d, J=7.1 Hz, 1H), 5.05 (dd, J=12.4, 5.5 Hz, 1H), 3.39 (t, J=7.2 Hz, 2H), 2.85-2.82 (m, 1H), 2.76-2.69 (m, 2H), 2.42 (t, J=7.1 Hz, 2H), 2.10 (tq, J=8.0, 3.8 Hz, 1H), 1.94 (dp, J=14.3, 7.0 Hz, 2H). MS (ESI) m/z 360.1 [M+H]+.

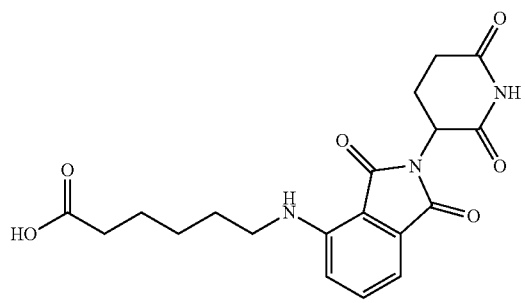 [SMILES: O=C(O)CCCCCNc1cccc2c1C(=O)N(C1CCC(=O)NC1=O)C2=O]

Linker 26: 6-((2-(2,6-Dioxopiperidin-3-yl)-1,3-dioxoisoindolin-4-yl)amino)hexanoic acid tert-Butyl 6-aminohexanoate (1.0 g, 4.47 mmol) was used to prepare the title compound (460 mg, 27%) according to the above procedures. $^1$H NMR (600 MHz, CD$_3$OD) δ 7.54 (dd, J=8.6, 7.1 Hz, 1H), 7.03 (dd, J=7.8, 3.8 Hz, 2H), 5.05 (dd, J=12.5, 5.4 Hz, 1H), 3.33 (t, J=7.1 Hz, 2H), 2.88-2.82 (m, 1H), 2.75-2.67 (m, 2H), 2.31 (t, J=7.4 Hz, 2H), 2.10 (tdd, J=10.1, 5.3, 3.1 Hz, 1H), 1.70-1.64 (m, 4H), 1.46 (dddd, J=13.0, 8.9, 7.1, 4.2 Hz, 2H). MS (ESI) m/z 388.1 [M+H]$^+$.

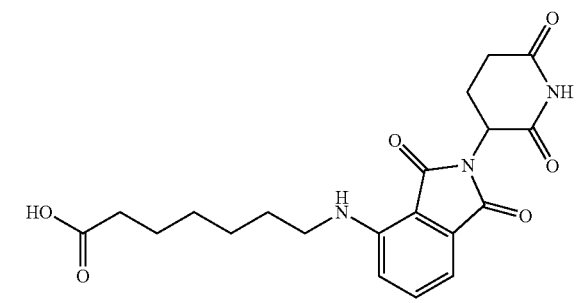 [SMILES: O=C(O)CCCCCCNc1cccc2c1C(=O)N(C1CCC(=O)NC1=O)C2=O]

Linker 27: 7-((2-(2,6-Dioxopiperidin-3-yl)-1,3-dioxoisoindolin-4-yl)amino)heptanoic acid tert-Butyl 7-aminoheptanoate (1.0 g, 4.96 mmol) was used to prepare the title compound (500 mg, 25%) according to the above procedures. $^1$H NMR (600 MHz, CD$_3$OD) δ 7.54 (dd, 1H), 7.03 (dd, J=7.8, 3.7 Hz, 2H), 5.05 (dd, J=12.5, 5.5 Hz, 1H), 3.30-3.33 (m, 2H), 2.90-2.79 (m, 1H), 2.77-2.68 (m, 2H), 2.29 (t, J=7.4 Hz, 2H), 2.13-2.07 (m, 1H), 1.68-1.61 (m, 4H), 1.46-1.40 (m, 4H). MS (ESI) m/z 402.3 [M+H]$^+$.

Linker 28: 8-((2-(2,6-Dioxopiperidin-3-yl)-1,3-dioxoisoindolin-4-yl)amino)octanoic acid
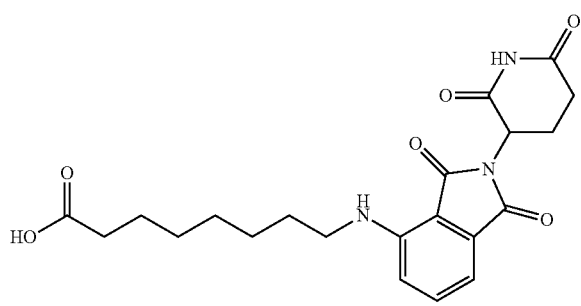 [SMILES: O=C(O)CCCCCCCNc1cccc2c1C(=O)N(C1CCC(=O)NC1=O)C2=O]
tert-Butyl 8-aminooctanoate (1.0 g, 4.6 mmol) was used to prepare the title compound (620 mg, 32%) according to the above procedures. $^1$H NMR (600 MHz, CD$_3$OD) δ 7.53 (dd, J=8.6, 7.0, 1.5 Hz, 1H), 7.08-6.93 (m, 2H), 5.05 (dd, J=12.5, 5.5, 1.5 Hz, 1H), 3.31 (t, 2H), 2.90-2.79 (m, 1H), 2.75-2.66 (m, 2H), 2.28 (t, J=7.5, 1.5 Hz, 2H), 2.13-2.07 (m, 1H), 1.66-1.51 (m, 4H), 1.43-1.33 (m, 6H). MS (ESI) m/z 416.4[M+H]$^+$.
Example 4
Procedures for the Synthesis of Bivalent Compounds
Scheme 1: Synthesis of example 1
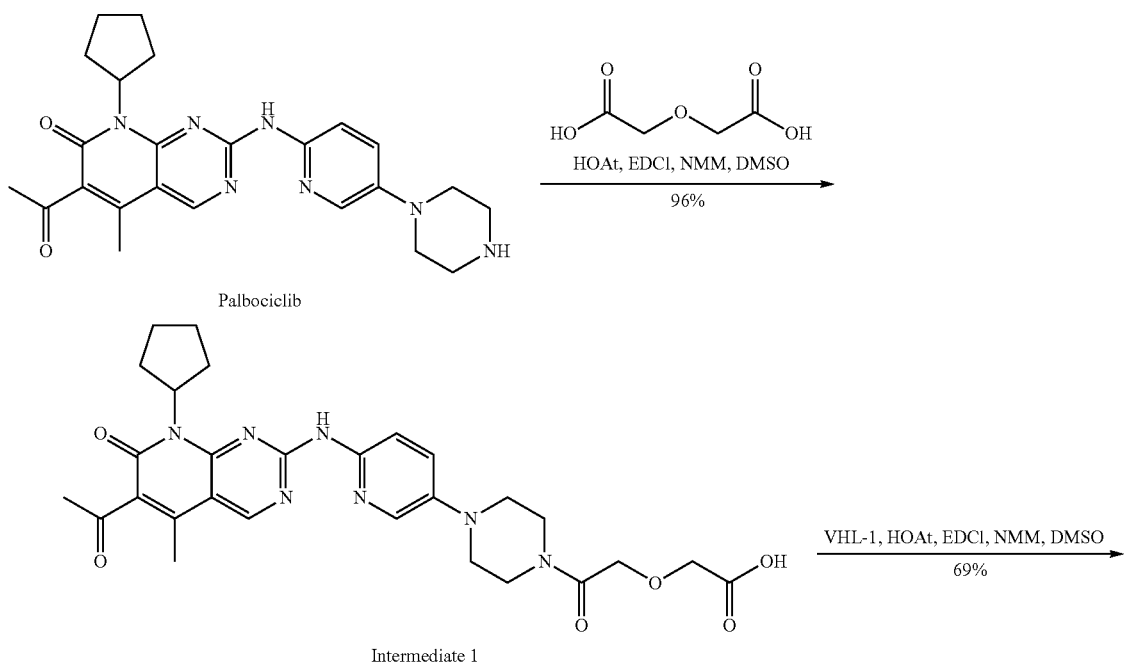
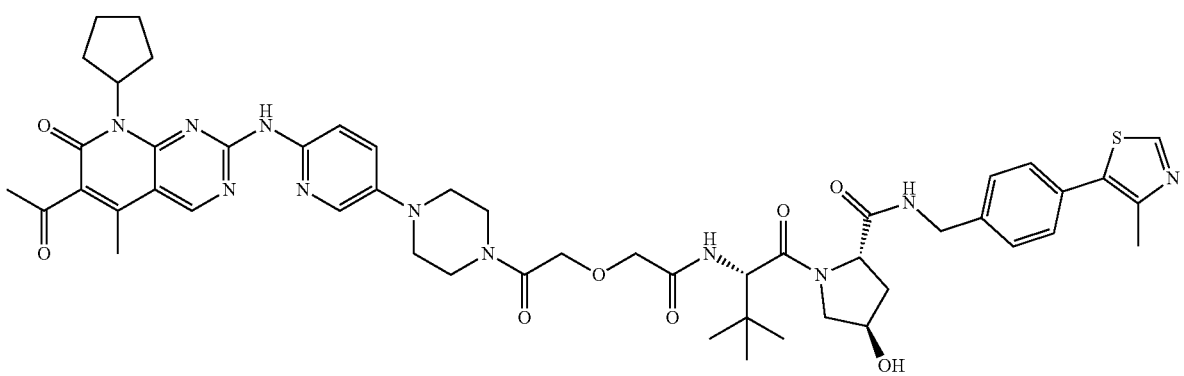
Example 1

2-(2-(4-(6-(((6-Acetyl-8-cyclopentyl-5-methyl-7-oxo-7,8-dihydropyrido[2,3-d]pyrimidin-2-yl)amino)pyridin-3-yl)piperazin-1-yl)-2-oxoethoxy)acetic acid (Intermediate 1)

To a solution of palbociclib (25 mg, 0.0559 mmol) in DMSO (1 ml) and DCM (10 ml) were added NMM (34 mg, 0.335 mmol), 2,2'-oxydiacetic acid (18 mg, 0.135 mmol), HOAt (20 mg, 0.134 mmol), and EDCI (28 mg, 0.134 mmol). The mixture was allowed to stir at room temperature overnight. After palbociclib was consumed, the reaction was concentrated under reduced pressure. The resulting residue was purified by prep-HPLC to yield the product (30 mg, 96%). $^1$H NMR (600 MHz, CD$_3$OD) δ 9.10 (s, 1H), 8.20 (d, J=9.5 Hz, 1H), 7.88 (s, 1H), 7.55 (d, J=9.5 Hz, 1H), 6.00 (p, J=8.9 Hz, 1H), 4.41 (s, 2H), 4.21 (s, 2H), 3.85-3.70 (m, 4H), 3.39-3.26 (m, 4H), 2.49 (s, 3H), 2.43 (s, 3H), 2.35-2.25 (m, 2H), 2.13-2.04 (m, 2H), 1.95-1.85 (m, 2H), 1.74-1.64 (m, 2H). HRMS (ESI-TOF) m/z: [M+H]$^+$ calculated for C$_{28}$H$_{34}$N$_7$O$_6$, 564.2565; found: 564.2560.

(2S,4R)-1-((S)-2-(2-(2-(4-(6-(((6-Acetyl-8-cyclopentyl-5-methyl-7-oxo-7,8-dihydropyrido[2,3-d]pyrimidin-2-yl)amino)pyridin-3-yl)piperazin-1-yl)-2-oxoethoxy)acetamido)-3,3-dimethylbutanoyl)-4-hydroxy-N-(4-(4-methylthiazol-5-yl)benzyl)pyrrolidine-2-carboxamide (compound Example 1)

To a solution of intermediate 1 (30 mg, 0.0553 mmol) in DMSO (1 mL) were added NMM (27 mg, 0.266 mmol), VHL-1 (30 mg, 0.0639 mmol), HOAt (11 mg, 0.0799 mmol), and EDCI (15 mg, 0.0799 mmol). The mixture was allowed to stir at room temperature overnight. After VHL-1 was consumed, the reaction was concentrated under reduced pressure. The resulting residue was purified by prep-HPLC to yield the product (36 mg, 69%) as yellow solid. $^1$H NMR (600 MHz, CD$_3$OD) δ 9.07 (s, 1H), 9.03 (s, 1H), 8.17 (dd, J=2.9, 9.6 Hz, 1H), 7.86 (d, J=2.9 Hz, 1H), 7.52 (d, J=9.6 Hz, 1H), 7.46-7.42 (m, 2H), 7.38 (d, J=8.3 Hz, 2H), 5.99 (p, J=8.9 Hz, 1H), 4.69 (s, 1H), 4.62-4.30 (m, 6H), 4.17 (d, J=15.1 Hz, 1H), 4.10 (d, J=15.0 Hz, 1H), 3.90 (d, J=10.9 Hz, 1H), 3.85-3.74 (m, 3H), 3.72-3.62 (m, 2H), 3.37-3.25 (m, 4H), 2.49 (s, 3H), 2.47 (s, 3H), 2.41 (s, 3H), 2.35-2.21 (m, 3H), 2.14-2.04 (m, 3H), 1.94-1.85 (m, 2H), 1.75-1.63 (m, 2H), 1.06 (s, 9H). HRMS (ESI-TOF) m/z: [M+H]$^+$ calculated for C$_5$H$_{62}$N$_{11}$O$_8$S, 976.4498; found: 976.4492.

Scheme 2: Synthesis of example 2

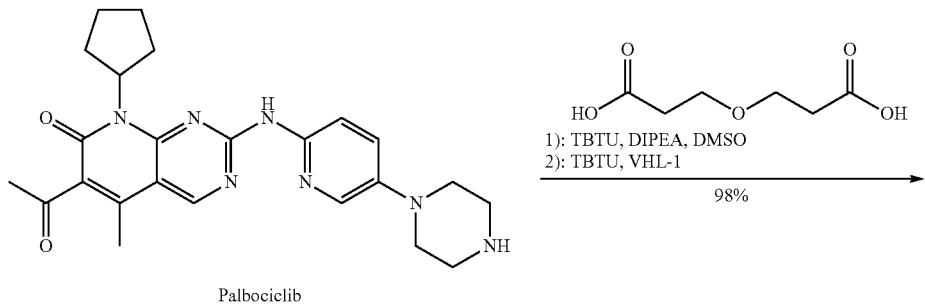

Palbociclib

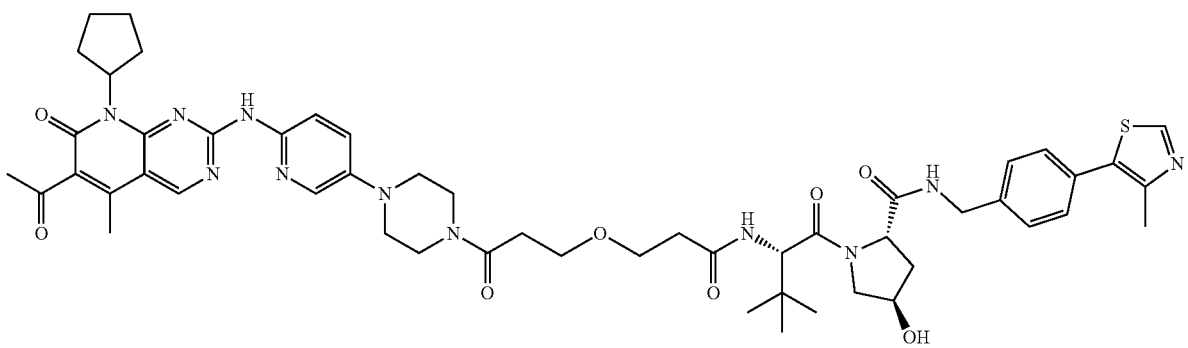

Example 2

(2S,4R)-1-((S)-2-(3-(3-(4-(6-((6-Acetyl-8-cyclopentyl-5-methyl-7-oxo-7,8-dihydropyrido[2,3-d]pyrimidin-2-yl)amino)pyridin-3-yl)piperazin-1-yl)-3-oxopropoxy)propanamido)-3,3-dimethylbutanoyl)-4-hydroxy-N-(4-(4-methylthiazol-5-yl)benzyl)pyrrolidine-2-carboxamide (compound Example 2)

To a solution of palbociclib (53 mg, 0.119 mmol) in DMSO (2 ml) were added DIPEA (76 mg, 0.594 mmol), 3,3'-oxydipropionic acid (25 mg, 0.154 mmol), and TBTU (57 mg, 0.178 mmol). The mixture was allowed to stir at RT overnight, at which time TBTU (57 mg, 0.178 mmol) and VHL-1 (55 mg, 0.119 mmol) were added. The reaction mixture was allowed to stir at RT overnight. After VHL-1 was consumed, the reaction was concentrated under reduced pressure. The resulting residue was purified by prep-HPLC to yield the product (22 mg, 18%) as yellow solid. $^1$H NMR (600 MHz, CD$_3$OD) δ 8.92 (s, 1H), 8.79 (s, 1H), 7.98 (s, 1H), 7.95 (d, J=8.9 Hz, 1H), 7.41 (d, J=8.1 Hz, 1H), 7.37 (d, J=8.0 Hz, 2H), 7.32 (d, J=7.7 Hz, 2H), 5.88 (p, J=9.1 Hz, 1H), 4.66 (s, 1H), 4.56 (t, J=8.4 Hz, 1H), 4.49 (s, 1H), 4.45 (d, J=15.6 Hz, 1H), 4.33 (d, J=15.4 Hz, 1H), 3.88 (d, J=11.1 Hz, 1H), 3.80-3.70 (m, 9H), 3.15 (dt, J=5.1, 29.0 Hz, 4H), 2.73 (d, J=2.7 Hz, 2H), 2.57-2.49 (m, 2H), 2.47 (s, 3H), 2.39 (s, 3H), 2.34-2.25 (m, 5H), 2.24-2.18 (m, 1H), 2.12-2.03 (m, 1H), 2.03-1.95 (m, 2H), 1.89-1.80 (m, 2H), 1.71-1.61 (m, 2H), 1.03 (s, 9H). HRMS (ESI-TOF) m/z: [M+H]$^+$ calculated for C$_{52}$H$_{66}$N$_{11}$O$_8$S, 1004.4811; found: 1004.4813.

The Example 3, 4, 5, 6, 7, 8, 9, and 18 compounds (below) were synthesized according to the procedures for the preparation of the Example 2 compound (above).

(2S,4R)-1-((S)-2-(2-(2-(2-(4-(6-((6-Acetyl-8-cyclopentyl-5-methyl-7-oxo-7,8-dihydropyrido[2,3-d]pyrimidin-2-yl)amino)pyridin-3-yl)piperazin-1-yl)-2-oxoethoxy)ethoxy)acetamido)-3,3-dimethylbutanoyl)-4-hydroxy-N-(4-(4-methylthiazol-5-yl)benzyl)pyrrolidine-2-carboxamide (compound Example 3)

(9 mg, 4%) as yellow solid. $^1$H NMR (600 MHz, CD$_3$OD) δ 9.06 (s, 1H), 8.94 (s, 1H), 8.16 (dd, J=2.9, 9.6 Hz, 1H), 7.82 (d, J=2.9 Hz, 1H), 7.50 (d, J=9.6 Hz, 1H), 7.41 (d, J=8.2 Hz, 2H), 7.38 (d, J=8.2 Hz, 2H), 6.00 (p, J=8.8 Hz, 1H), 4.73 (d, J=9.5 Hz, 1H), 4.57 (dd, J=7.5, 9.5 Hz, 1H), 4.53-4.45 (m, 2H), 4.41-4.31 (m, 3H), 4.06 (d, J=8.3 Hz, 2H), 3.89 (d, J=11.1 Hz, 1H), 3.85-3.70 (m, 9H), 3.37-3.24 (m, 4H), 2.50 (s, 3H), 2.45 (s, 3H), 2.42 (s, 3H), 2.34-2.23 (m, 3H), 2.14-2.05 (m, 3H), 1.94-1.86 (m, 2H), 1.74-1.65 (m, 2H), 1.04 (s, 9H). HRMS (ESI-TOF) m/z: [M+H]$^+$ calculated for C$_{52}$H$_{66}$N$_{11}$O$_9$S, 1020.4760; found: 1020.4769.

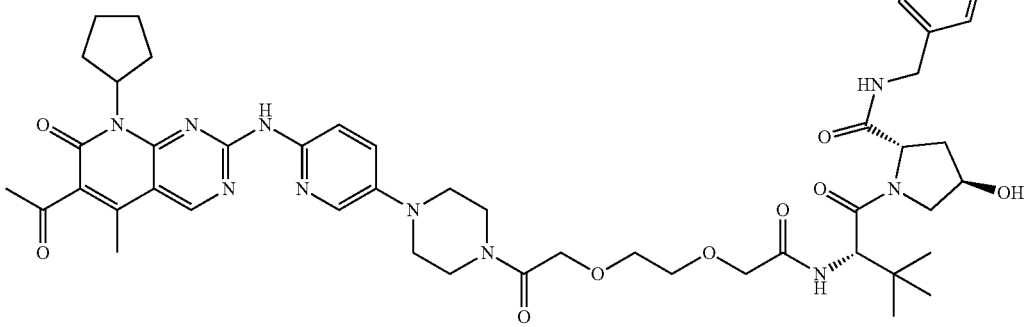

Example 3

Example 4

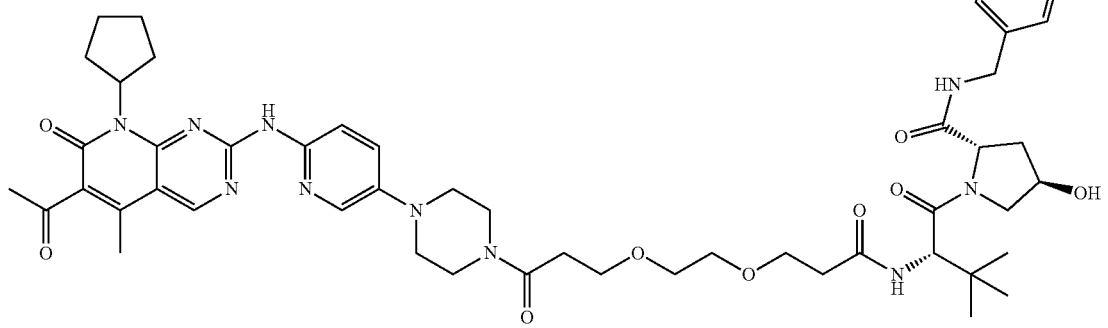

(2S,4R)-1-((S)-2-(3-(2-(3-(4-(6-((6-Acetyl-8-cyclopentyl-5-methyl-7-oxo-7,8-dihydropyrido[2,3-d]pyrimidin-2-yl)amino)pyridin-3-yl)piperazin-1-yl)-3-oxopropoxy)ethoxy)propanamido)-3,3-dimethylbutanoyl)-4-hydroxy-N-(4-(4-methylthiazol-5-yl)benzyl)pyrrolidine-2-carboxamide (compound Example 4)

(13 mg, 11%) as yellow solid. $^1$H NMR (600 MHz, CD$_3$OD) δ 9.09 (s, 1H), 8.98 (s, 1H), 8.20 (dd, J=3.1, 9.6 Hz, 1H), 7.85 (d, J=2.9 Hz, 1H), 7.53 (d, J=9.5 Hz, 1H), 7.46 (d, J=8.0 Hz, 2H), 7.40 (d, J=8.2 Hz, 2H), 6.00 (p, J=8.9 Hz, 1H), 4.64 (s, 1H), 4.60-4.47 (m, 3H), 4.35 (d, J=15.5 Hz, 1H), 3.88 (d, J=11.0 Hz, 1H), 3.82-3.75 (m, 7H), 3.74-3.67 (m, 2H), 3.65-3.57 (m, 5H), 3.33 (t, J=5.4 Hz, 2H), 3.26 (t, J=5.3 Hz, 2H), 2.72 (t, J=6.1 Hz, 2H), 2.56-2.51 (m, 1H), 2.50 (s, 3H), 2.47 (s, 3H), 2.43 (s, 3H), 2.35-2.26 (m, 2H), 2.25-2.20 (m, 1H), 2.14-2.04 (m, 3H), 1.94-1.86 (m, 2H), 1.74-1.66 (m, 2H), 1.03 (s, 9H). HRMS (ESI-TOF) m/z: [M+H]$^+$ calculated for C$_{54}$H$_{70}$N$_{11}$O$_9$S, 1048.5073; found: 1048.5069.

(2S,4R)-1-((S)-14-(4-(6-((6-Acetyl-8-cyclopentyl-5-methyl-7-oxo-7,8-dihydropyrido[2,3-d]pyrimidin-2-yl)amino)pyridin-3-yl)piperazin-1-yl)-2-(tert-butyl)-4,14-dioxo-6,9,12-trioxa-3-azatetradecanoyl)-4-hydroxy-N-(4-(4-methylthiazol-5-yl)benzyl)pyrrolidine-2-carboxamide (compound Example 5)

(15 mg, 17%) as yellow solid. $^1$H NMR (600 MHz, CD$_3$OD) δ 9.08 (s, 1H), 9.07 (s, 1H), 8.18 (dd, J=3.0, 9.6 Hz, 1H), 7.85 (d, J=2.9 Hz, 1H), 7.53 (d, J=9.6 Hz, 1H), 7.46 (d, J=8.1 Hz, 2H), 7.42 (d, J=8.1 Hz, 2H), 6.00 (p, J=8.9 Hz, 1H), 4.69 (s, 1H), 4.60-4.48 (m, 3H), 4.39-4.26 (m, 3H), 4.09-3.96 (m, 2H), 3.88 (d, J=10.9 Hz, 1H), 3.83-3.63 (m, 12H), 3.27 (t, J=5.0 Hz, 4H), 2.49 (s, 3H), 2.48 (s, 3H), 2.42 (s, 3H), 2.34-2.21 (m, 3H), 2.13-2.04 (m, 3H), 1.93-1.86 (m, 2H), 1.72-1.66 (m, 2H), 1.04 (s, 9H). HRMS (ESI-TOF) m/z: [M+H]$^+$ calculated for C$_{54}$H$_{70}$N$_{11}$O$_{10}$S, 1064.5022; found: 1064.5026.

Example 5

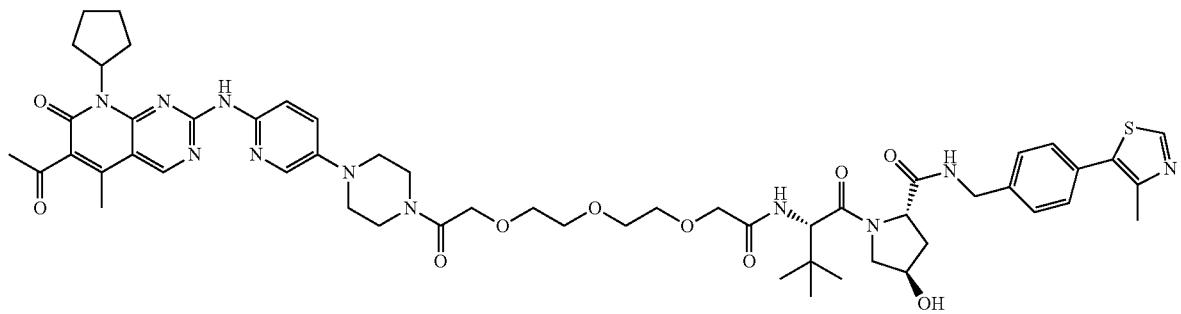

Example 6

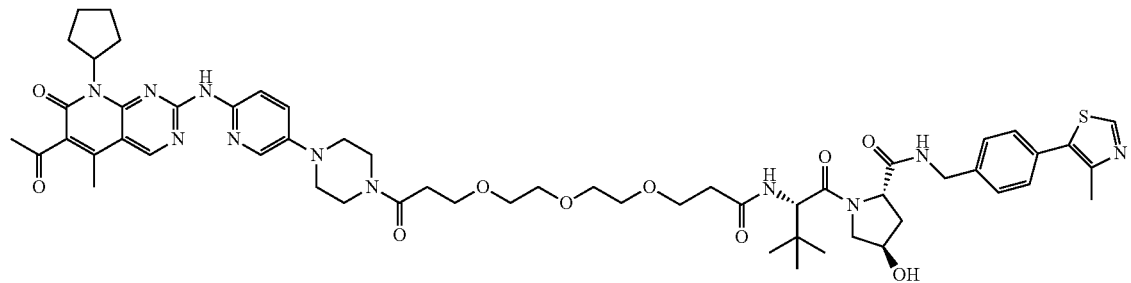

(2S,4R)-1-((S)-16-(4-(6-(((6-Acetyl-8-cyclopentyl-5-methyl-7-oxo-7,8-dihydropyrido[2,3-d]pyrimidin-2-yl)amino)pyridin-3-yl)piperazin-1-yl)-2-(tert-butyl)-4,16-dioxo-7,10,13-trioxa-3-azahexadecanoyl)-4-hydroxy-N-(4-(4-methylthiazol-5-yl)benzyl)pyrrolidine-2-carboxamide (compound Example 6)

(13 mg, 13%) as yellow solid. $^1$H NMR (600 MHz, CD$_3$OD) δ 9.09 (s, 1H), 8.97 (s, 1H), 8.20 (dd, J=3.0, 9.7 Hz, 1H), 7.86 (d, J=3.0 Hz, 1H), 7.53 (d, J=9.7 Hz, 1H), 7.45 (d, J=8.0 Hz, 2H), 7.40 (d, J=8.0 Hz, 2H), 6.01 (p, J=8.8 Hz, 1H), 4.64 (s, 1H), 4.58-4.47 (m, 3H), 4.35 (d, J=15.5 Hz, 1H), 3.88 (d, J=11.0 Hz, 1H), 3.83-3.75 (m, 7H), 3.74-3.65 (m, 2H), 3.64-3.55 (m, 8H), 3.33 (t, J=5.2 Hz, 2H), 3.27 (d, J=7.2 Hz, 2H), 2.71 (t, J=6.2 Hz, 2H), 2.59-2.52 (m, 1H), 2.50 (s, 3H), 2.47 (s, 3H), 2.43 (s, 3H), 2.34-2.26 (m, 2H), 2.24-2.19 (m, 1H), 2.13-2.04 (m, 3H), 1.94-1.86 (m, 2H), 1.74-1.65 (m, 2H), 1.03 (s, 9H). HRMS (ESI-TOF) m/z: [M+H]$^+$ calculated for C$_{56}$H$_{74}$N$_{11}$O$_{10}$S, 1092.5335; found: 1092.5339.

(2S,4R)-1-((S)-19-(4-(6-(((6-Acetyl-8-cyclopentyl-5-methyl-7-oxo-7,8-dihydropyrido[2,3-d]pyrimidin-2-yl)amino)pyridin-3-yl)piperazin-1-yl)-2-(tert-butyl)-4,19-dioxo-7,10,13,16-tetraoxa-3-azanonadecanoyl)-4-hydroxy-N-(4-(4-methylthiazol-5-yl)benzyl)pyrrolidine-2-carboxamide (compound Example 7)

(12 mg, 12%) as yellow solid. $^1$H NMR (600 MHz, CD$_3$OD) δ 9.08 (s, 1H), 8.99 (s, 1H), 8.21 (dd, J=3.0, 9.5 Hz, 1H), 7.87 (d, J=2.9 Hz, 1H), 7.53 (d, J=9.6 Hz, 1H), 7.45 (d, J=8.0 Hz, 2H), 7.40 (d, J=8.1 Hz, 2H), 6.00 (p, J=8.9 Hz, 1H), 4.64 (s, 1H), 4.59-4.47 (m, 3H), 4.35 (d, J=15.5 Hz, 1H), 3.88 (d, J=11.0 Hz, 1H), 3.83-3.75 (m, 7H), 3.75-3.66 (m, 2H), 3.64-3.53 (m, 13H), 3.34 (t, J=5.2 Hz, 2H), 3.28 (t, J=5.3 Hz, 2H), 2.72 (t, J=6.2 Hz, 2H), 2.59-2.52 (m, 1H), 2.50 (s, 3H), 2.47 (s, 3H), 2.43 (s, 3H), 2.35-2.26 (m, 2H), 2.24-2.19 (m, 1H), 2.13-2.04 (m, 3H), 1.94-1.86 (m, 2H), 1.73-1.64 (m, 2H), 1.03 (s, 9H). HRMS (ESI-TOF) m/z: [M+H]$^+$ calculated for C$_{58}$H$_{78}$N$_{11}$O$_{11}$S, 1136.5597; found: 1136.5595.

Example 7

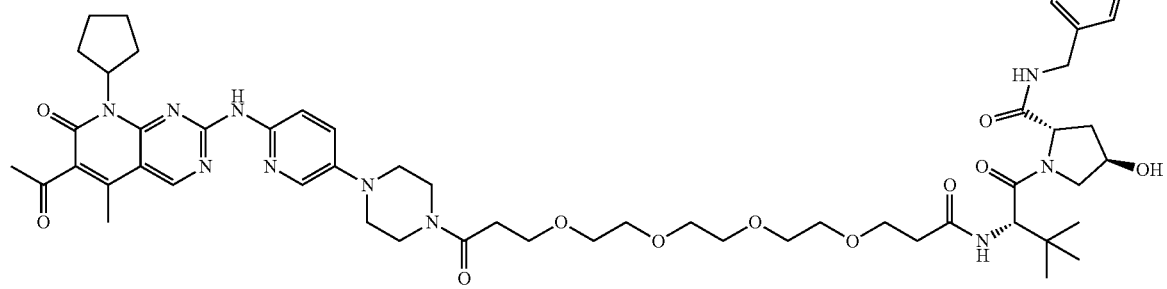

Example 8

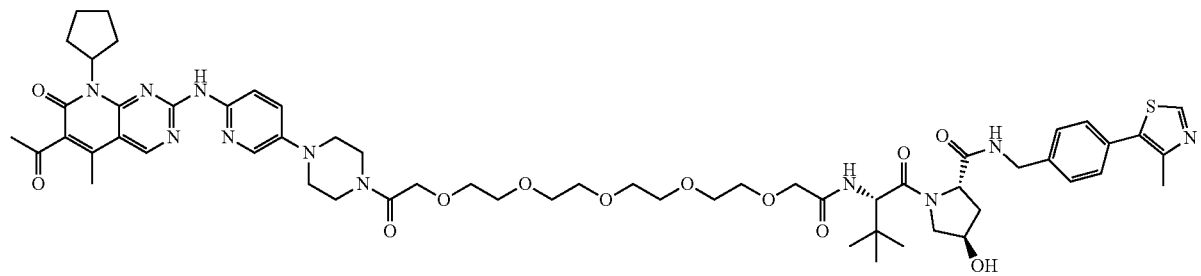

(2S,4R)-1-((S)-20-(4-(6-(((6-Acetyl-8-cyclopentyl-5-methyl-7-oxo-7,8-dihydropyrido[2,3-d]pyrimidin-2-yl)amino)pyridin-3-yl)piperazin-1-yl)-2-(tert-butyl)-4,20-dioxo-6,9,12,15,18-pentaoxa-3-azaicosanoyl)-4-hydroxy-N-(4-(4-methylthiazol-5-yl)benzyl)pyrrolidine-2-carboxamide (compound Example 8)

(6 mg, 7%) as yellow solid. $^1$H NMR (600 MHz, CD$_3$OD) δ 9.08 (s, 1H), 8.93 (s, 1H), 8.20 (dd, J=3.0, 9.6 Hz, 1H), 7.87 (d, J=3.0 Hz, 1H), 7.53 (d, J=9.6 Hz, 1H), 7.44 (d, J=8.0 Hz, 2H), 7.41 (d, J=8.0 Hz, 2H), 6.00 (p, J=8.7 Hz, 1H), 4.69 (s, 1H), 4.59-4.48 (m, 3H), 4.36 (d, J=15.7 Hz, 1H), 4.30 (s, 2H), 4.05 (d, J=15.8 Hz, 1H), 4.00 (d, J=15.5 Hz, 1H), 3.88 (d, J=11.1 Hz, 1H), 3.83-3.72 (m, 5H), 3.72-3.58 (m, 16H), 3.36-3.25 (m, 4H), 2.50 (s, 3H), 2.47 (s, 3H), 2.43 (s, 3H), 2.34-2.27 (m, 2H), 2.26-2.21 (m, 1H), 2.15-2.05 (m, 3H), 1.94-1.86 (m, 2H), 1.73-1.65 (m, 2H), 1.03 (s, 9H). HRMS (ESI-TOF) m/z: [M+H]$^+$ calculated for C$_{58}$H$_{78}$N$_{11}$O$_{12}$S, 1152.5547; found: 1152.5548.

(2S,4R)-1-((S)-22-(4-(6-(((6-Acetyl-8-cyclopentyl-5-methyl-7-oxo-7,8-dihydropyrido[2,3-d]pyrimidin-2-yl)amino)pyridin-3-yl)piperazin-1-yl)-2-(tert-butyl)-4,22-dioxo-7,10,13,16,19-pentaoxa-3-azadocosanoyl)-4-hydroxy-N-(4-(4-methylthiazol-5-yl)benzyl)pyrrolidine-2-carboxamide (compound Example 9)

(25 mg, 19%) as yellow solid. $^1$H NMR (600 MHz, CD$_3$OD) δ 9.09 (s, 1H), 9.06 (s, 1H), 8.21 (dd, J=3.0, 9.6 Hz, 1H), 7.88 (d, J=3.0 Hz, 1H), 7.54 (d, J=9.6 Hz, 1H), 7.46 (d, J=8.1 Hz, 2H), 7.41 (d, J=8.2 Hz, 2H), 6.00 (p, J=8.9 Hz, 1H), 4.64 (s, 1H), 4.60-4.46 (m, 3H), 4.35 (d, J=15.6 Hz, 1H), 3.88 (d, J=10.8 Hz, 1H), 3.84-3.66 (m, 10H), 3.65-3.55 (m, 16H), 3.35 (t, J=5.1 Hz, 2H), 3.28 (t, J=5.3 Hz, 2H), 2.72 (t, J=6.1 Hz, 2H), 2.61-2.53 (m, 1H), 2.49 (s, 3H), 2.48 (s, 3H), 2.42 (s, 3H), 2.34-2.26 (m, 2H), 2.25-2.19 (m, 1H), 2.12-2.03 (m, 3H), 1.94-1.86 (m, 2H), 1.73-1.65 (m, 2H), 1.03 (s, 9H). HRMS (ESI-TOF) m/z: [M+H]$^+$ calculated for C$_{60}$H$_2$N$_{11}$O$_{12}$S, 1180.5860; found: 1180.5859.

Example 9

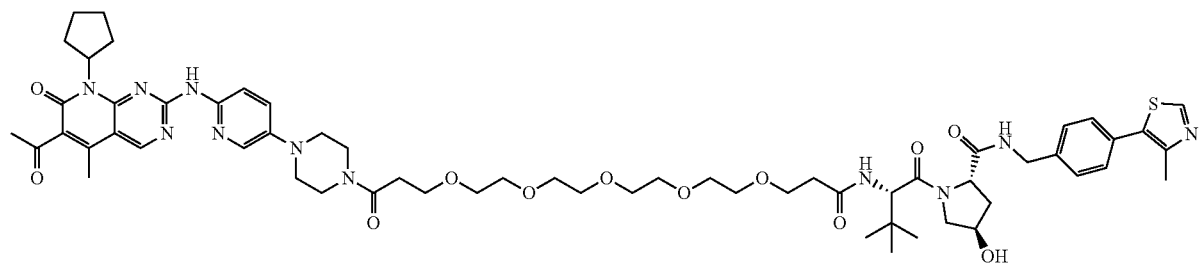

Example 18

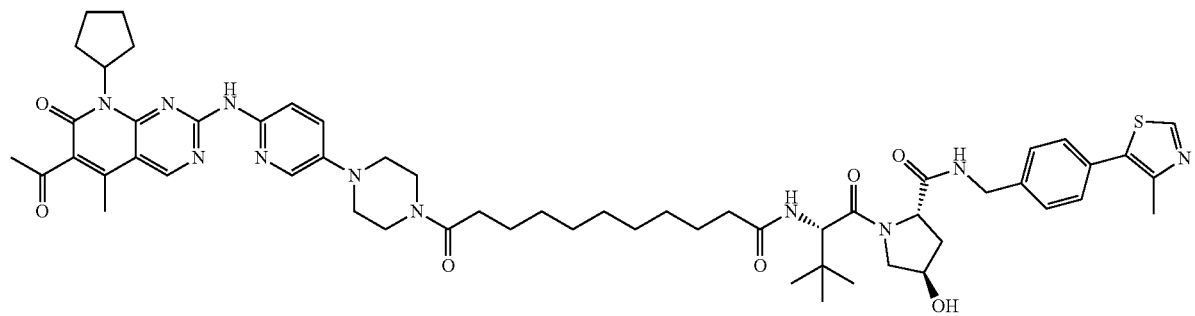

(2S,4R)-1-((S)-2-(11-(4-(6-((6-Acetyl-8-cyclopentyl-5-methyl-7-oxo-7,8-dihydropyrido[2,3-d]pyrimidin-2-yl)amino)pyridin-3-yl)piperazin-1-yl)-11-oxoundecanamido)-3,3-dimethylbutanoyl)-4-hydroxy-N-(4-(4-methylthiazol-5-yl)benzyl)pyrrolidine-2-carboxamide (compound Example 18)

(17 mg, 13%) as yellow solid. $^1$H NMR (600 MHz, CD$_3$OD) δ 9.10 (s, 1H), 8.94 (s, 1H), 8.20 (dd, J=2.9, 9.6 Hz, 1H), 7.86 (d, J=3.0 Hz, 1H), 7.54 (d, J=9.6 Hz, 1H), 7.46 (d, J=8.2 Hz, 2H), 7.41 (d, J=8.1 Hz, 2H), 6.01 (p, J=8.9 Hz, 1H), 4.63 (s, 1H), 4.59-4.46 (m, 3H), 4.35 (d, J=15.5 Hz, 1H), 3.90 (d, J=11.0 Hz, 1H), 3.84-3.72 (m, 5H), 3.36-3.24 (m, 4H), 2.53-2.40 (m, 10H), 2.36-2.18 (m, 5H), 2.15-2.03 (m, 3H), 1.95-1.86 (m, 2H), 1.74-1.53 (m, 6H), 1.42-1.27 (m, 11H), 1.03 (s, 9H). HRMS (ESI-TOF) m/z: [M+H]$^+$ calculated for C$_{57}$H$_{76}$N$_{11}$O$_7$S, 1058.5644; found: 1058.5640.

The Intermediate 2, 3, and 4 and Example 10, 11, and 12 compounds were synthesized according to the procedures for the preparation of the Example 1 compound (above).

Intermediate 2

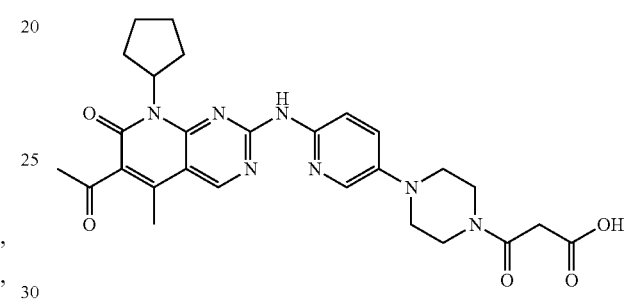

3-(4-(6-((6-Acetyl-8-cyclopentyl-5-methyl-7-oxo-7,8-dihydropyrido[2,3-d]pyrimidin-2-yl)amino)pyridin-3-yl)piperazin-1-yl)-3-oxopropanoic acid (Intermediate 2)

(18 mg, 51%). $^1$H NMR (600 MHz, CD$_3$OD) δ 9.07 (s, 1H), 8.09 (d, J=10.2 Hz, 1H), 7.90 (s, 1H), 7.62 (d, J=9.5 Hz, 1H), 6.06-5.95 (m, 1H), 3.86-3.72 (m, 4H), 3.59 (d, J=9.0 Hz, 2H), 3.40-3.22 (m, 4H), 2.50 (s, 3H), 2.42 (s, 3H), 2.37-2.27 (m, 2H), 2.14-2.03 (m, 2H), 1.95-1.85 (m, 2H), 1.75-1.66 (m, 2H). HRMS (ESI-TOF) m/z: [M+H]$^+$ calculated for C$_{27}$H$_{32}$N$_7$O$_5$, 534.2459; found: 534.2450.

Example 10

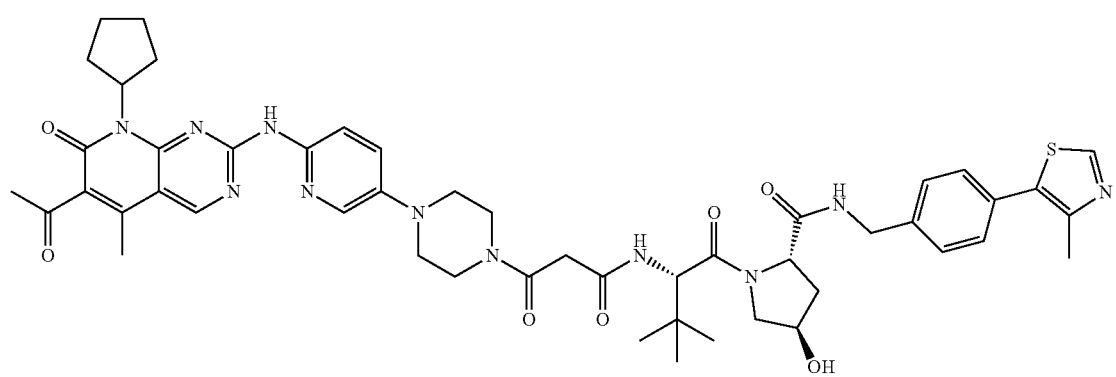

6-Acetyl-8-cyclopentyl-N-(5-(4-(3-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-3-oxopropanoyl)piperazin-1-yl)pyridin-2-yl)-5-methyl-7-oxo-7,8-dihydropyrido[2,3-d]pyrimidin-2-aminium (compound Example 10)

(19 mg, 59%) as yellow solid. $^1$H NMR (600 MHz, CD$_3$OD) δ 9.10 (s, 1H), 9.00 (s, 1H), 8.20 (dd, J=3.0, 9.7 Hz, 1H), 7.86 (d, J=3.0 Hz, 1H), 7.53 (d, J=9.5 Hz, 1H), 7.47 (d, J=8.2 Hz, 2H), 7.41 (d, J=8.3 Hz, 2H), 6.00 (p, J=9.0 Hz, 1H), 4.63 (s, 1H), 4.59-4.43 (m, 4H), 4.37 (d, J=15.5 Hz, 1H), 3.94-3.84 (m, 2H), 3.84-3.68 (m, 5H), 3.41-3.20 (m, 4H), 2.49 (s, 3H), 2.48 (s, 3H), 2.42 (s, 3H), 2.34-2.27 (m, 2H), 2.24-2.18 (m, 1H), 2.13-2.04 (m, 3H), 1.93-1.86 (m, 2H), 1.73-1.66 (m, 2H), 1.06 (s, 9H). HRMS (ESI-TOF) m/z: [M+H]$^+$ calculated for C$_{49}$H$_{60}$N$_{11}$O$_7$S, 946.4392; found: 946.4391.

4-(4-(6-((6-Acetyl-8-cyclopentyl-5-methyl-7-oxo-7,8-dihydropyrido[2,3-d]pyrimidin-2-yl)amino)pyridin-3-yl)piperazin-1-yl)-4-oxobutanoic acid (Intermediate 3)

(27 mg, 88%). $^1$H NMR (600 MHz, CD$_3$OD) δ 9.09 (s, 1H), 8.17 (d, J=9.5 Hz, 1H), 7.88 (s, 1H), 7.57 (d, J=9.6 Hz, 1H), 6.00 (p, J=9.0 Hz, 1H), 3.78 (t, J=5.8 Hz, 4H), 3.35 (t, J=4.9 Hz, 2H), 3.28 (t, J=4.9 Hz, 2H), 2.73 (t, J=6.5 Hz, 2H), 2.64 (t, J=6.5 Hz, 2H), 2.49 (s, 3H), 2.42 (s, 3H), 2.36-2.27 (m, 2H), 2.13-2.04 (m, 2H), 1.95-1.86 (m, 2H), 1.75-1.64 (m, 2H). HRMS (ESI-TOF) m/z: [M+H]$^+$ calculated for C$_{28}$H$_{34}$N$_7$O$_5$, 548.2616; found: 548.2612.

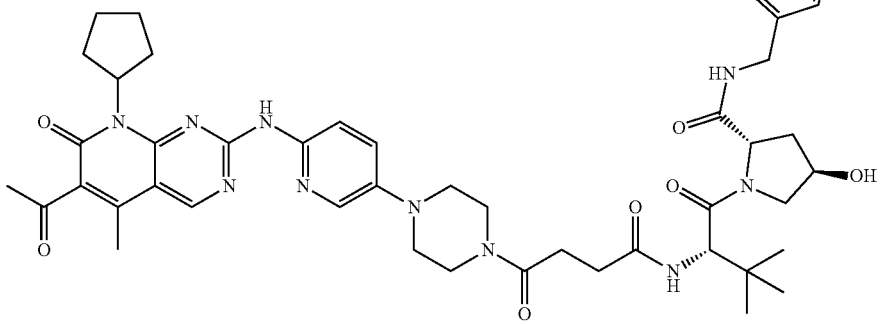

Example 11

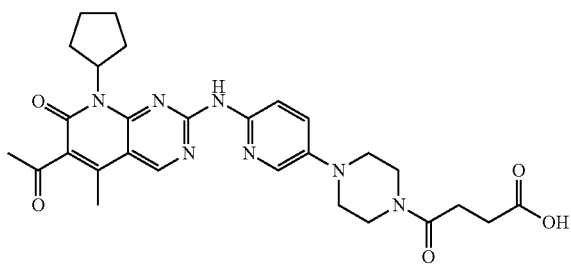

Intermediate 3

(2S,4R)-1-((S)-2-(4-(4-(6-((6-Acetyl-8-cyclopentyl-5-methyl-7-oxo-7,8-dihydropyrido[2,3-d]pyrimidin-2-yl)amino)pyridin-3-yl)piperazin-1-yl)-4-oxobutanamido)-3,3-dimethylbutanoyl)-4-hydroxy-N-(4-(4-methylthiazol-5-yl)benzyl)pyrrolidine-2-carboxamide (compound Example 11)

(32 mg, 68%) as yellow solid. $^1$H NMR (600 MHz, CD$_3$OD) δ 9.09 (s, 1H), 9.01 (s, 1H), 8.20 (dd, J=3.0, 9.6 Hz, 1H), 7.86 (d, J=2.9 Hz, 1H), 7.53 (d, J=9.6 Hz, 1H), 7.46 (d, J=8.1 Hz, 2H), 7.41 (d, J=8.2 Hz, 2H), 6.00 (p, J=8.8 Hz, 1H), 4.61 (s, 1H), 4.58-4.54 (m, 1H), 4.52 (d, J=15.4 Hz, 1H), 4.50-4.47 (m, 1H), 4.36 (d, J=15.5 Hz, 1H), 3.88 (d, J=11.3 Hz, 1H), 3.84-3.70 (m, 5H), 3.34 (t, J=5.1 Hz, 2H), 3.27 (t, J=5.5 Hz, 2H), 2.80-2.62 (m, 3H), 2.60-2.54 (m, 1H), 2.49 (s, 3H), 2.48 (s, 3H), 2.42 (s, 3H), 2.35-2.26 (m, 2H), 2.24-2.19 (m, 1H), 2.13-2.05 (m, 3H), 1.93-1.86 (m, 2H), 1.73-1.66 (m, 2H), 1.03 (s, 9H). HRMS (ESI-TOF) m/z: [M+H]$^+$ calculated for C$_5$H$_{62}$N$_{11}$O$_7$S, 960.4549; found: 960.4545.

Intermediate 4

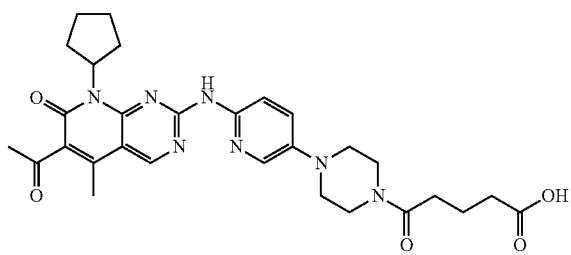

5-(4-(6-(((6-Acetyl-8-cyclopentyl-5-methyl-7-oxo-7,8-dihydropyrido[2,3-d]pyrimidin-2-yl)amino)pyridin-3-yl)piperazin-1-yl)-5-oxopentanoic acid (Intermediate 4)

(30 mg, 96%). $^1$H NMR (600 MHz, CD$_3$OD) δ 9.14 (s, 1H), 8.21 (d, J=9.4 Hz, 1H), 7.92 (s, 1H), 7.56 (d, J=9.3 Hz, 1H), 6.00 (p, J=8.9 Hz, 1H), 4.04 (d, J=13.3 Hz, 2H), 3.77 (t, J=12.2 Hz, 2H), 3.44 (d, J=12.5 Hz, 2H), 3.15 (td, J=3.4, 12.3 Hz, 2H), 2.53 (t, J=7.5 Hz, 2H), 2.49 (s, 3H), 2.43 (s, 3H), 2.40 (t, J=7.3 Hz, 2H), 2.35-2.26 (m, 2H), 2.13-2.05 (m, 2H), 1.95-1.86 (m, 4H), 1.74-1.65 (m, 2H). HRMS (ESI-TOF) m/z: [M+H]$^+$ calculated for C$_{29}$H$_{36}$N$_7$O$_5$, 562.2772; found: 562.2775.

Example 12

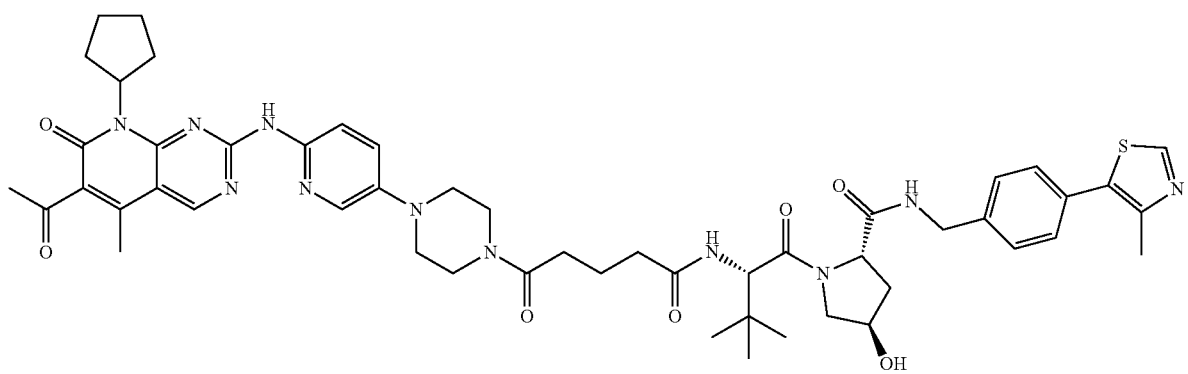

(2S,4R)-1-((S)-2-(5-(4-(6-(((6-Acetyl-8-cyclopentyl-5-methyl-7-oxo-7,8-dihydropyrido[2,3-d]pyrimidin-2-yl)amino)pyridin-3-yl)piperazin-1-yl)-5-oxopentanamido)-3,3-dimethylbutanoyl)-4-hydroxy-N-(4-(4-methylthiazol-5-yl)benzyl)pyrrolidine-2-carboxamide (compound Example 12)

(40 mg, 77%) as yellow solid. $^1$H NMR (600 MHz, CD$_3$OD) δ 9.12 (s, 1H), 9.09 (s, 1H), 8.17 (dd, J=2.9, 9.6 Hz, 1H), 7.86 (d, J=2.9 Hz, 1H), 7.53 (d, J=9.6 Hz, 1H), 7.47 (d, J=7.9 Hz, 2H), 7.41 (d, J=8.3 Hz, 2H), 5.99 (p, J=8.8 Hz, 1H), 4.62 (s, 1H), 4.59-4.49 (m, 3H), 4.37 (d, J=15.6 Hz, 1H), 3.94 (d, J=11.1 Hz, 1H), 3.83-3.71 (m, 6H), 3.34-3.25 (m, 4H), 2.49 (s, 3H), 2.48 (s, 3H), 2.42 (s, 3H), 2.39-2.20 (m, 6H), 2.11-2.05 (m, 3H), 1.95-1.85 (m, 4H), 1.72-1.65 (m, 2H), 1.04 (s, 9H). HRMS (ESI-TOF) m/z: [M+H]$^+$ calculated for C$_{51}$H$_{64}$N$_{11}$O$_7$S, 974.4705; found: 974.4703.

Scheme 3: Synthesis of example 15

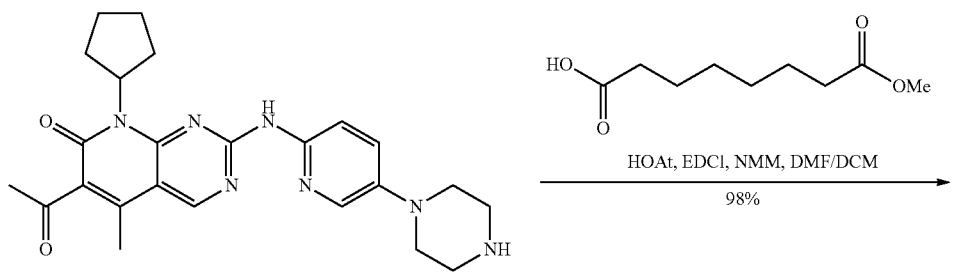

Palbociclib

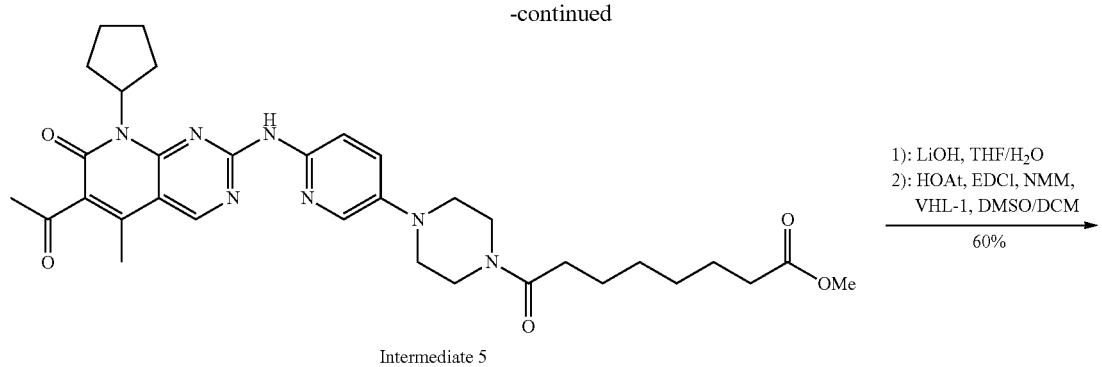

Intermediate 5

1): LiOH, THF/H₂O
2): HOAt, EDCl, NMM, VHL-1, DMSO/DCM
→ 60%

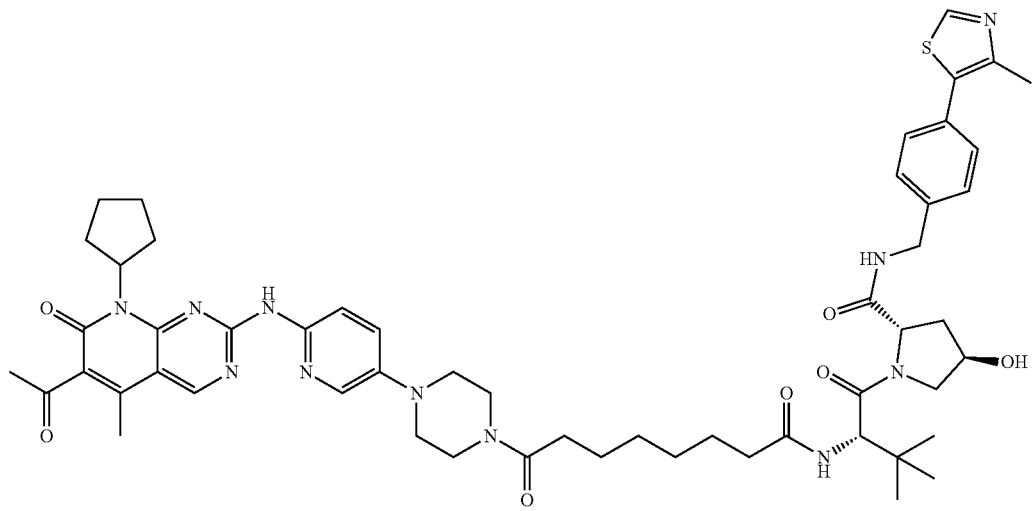

Example 15

Methyl 8-(4-(6-(((6-acetyl-8-cyclopentyl-5-methyl-7-oxo-7,8-dihydropyrido[2,3-d]pyrimidin-2-yl)amino)pyridin-3-yl)piperazin-1-yl)-8-oxooctanoate (Intermediate 5)

To a solution of palbociclib (50 mg, 0.112 mmol) in DMF (5 ml) and DCM (20 ml) were added NMM (34 mg, 0.335 mmol), 8-methoxy-8-oxooctanoic acid (25 mg, 0.134 mmol), HOAt (20 mg, 0.146 mmol), and EDCI (28 mg, 0.146 mmol). The mixture was allowed to stir at RT overnight. After palbociclib was consumed, the reaction was concentrated under reduced pressure. The resulting residue was purified by prep-HPLC to yield the product (69 mg, 98%) as yellow solid. HRMS (ESI-TOF) m/z: [M+H]⁺ calculated for $C_{33}H_{44}N_7O_5$, 618.3398; found: 618.3401.

(2S,4R)-1-((S)-2-(8-(4-(6-(((6-Acetyl-8-cyclopentyl-5-methyl-7-oxo-7,8-dihydropyrido[2,3-d]pyrimidin-2-yl)amino)pyridin-3-yl)piperazin-1-yl)-8-oxooctanamido)-3,3-dimethylbutanoyl)-4-hydroxy-N-(4-(4-methylthiazol-5-yl)benzyl)pyrrolidine-2-carboxamide (compound Example 15)

To a stirring solution of intermediate 5 (69 mg, 0.112 mmol) in THF/H₂O (20 ml/5 ml) was added anhydrous LiOH (6 mg, 0.223 mmol) and the resulting mixture was stirred overnight at RT. The disappearance of starting material was monitored by LC/MS. The reaction mixture was concentrated under reduced pressure and the resulting residue was dissolved in DCM/DMSO (10 ml/3 ml). To the resulting solution were added NMM (13 mg, 0.335 mmol), VHL-1 (57 mg, 0.123 mmol), HOAt (20 mg, 0.145 mmol) and EDCI (28 mg, 0.145 mmol). The mixture was allowed to stir at room temperature overnight. After the starting materials were consumed, the reaction was concentrated under reduced pressure. The resulting residue was purified by prep-HPLC to yield the product (68 mg, 60%) as yellow solid. ¹H NMR (600 MHz, CD₃OD) δ 9.10 (s, 1H), 9.05 (s, 1H), 8.21 (dd, J=3.0, 9.7 Hz, 1H), 7.86 (s, 1H), 7.53 (d, J=9.7 Hz, 1H), 7.47 (d, J=7.9 Hz, 2H), 7.42 (d, J=7.9 Hz, 2H), 6.01 (p, J=8.9 Hz, 1H), 4.63 (s, 1H), 4.59-4.45 (m, 3H), 4.36 (d, J=15.5 Hz, 1H), 3.90 (d, J=11.0 Hz, 1H), 3.84-3.72 (m, 5H), 3.33-3.25 (m, 4H), 2.53-2.40 (m, 10H), 2.36-2.18 (m, 6H), 2.13-2.03 (m, 3H), 1.95-1.85 (m, 2H), 1.74-1.58 (m, 6H), 1.45-1.32 (m, 4H), 1.03 (s, 9H). HRMS (ESI-TOF) m/z: [M+H]⁺ calculated for $C_{54}H_{70}N_{11}O_7S$, 1016.5175; found: 1016.5180.

Scheme 4: Synthesis of example 13

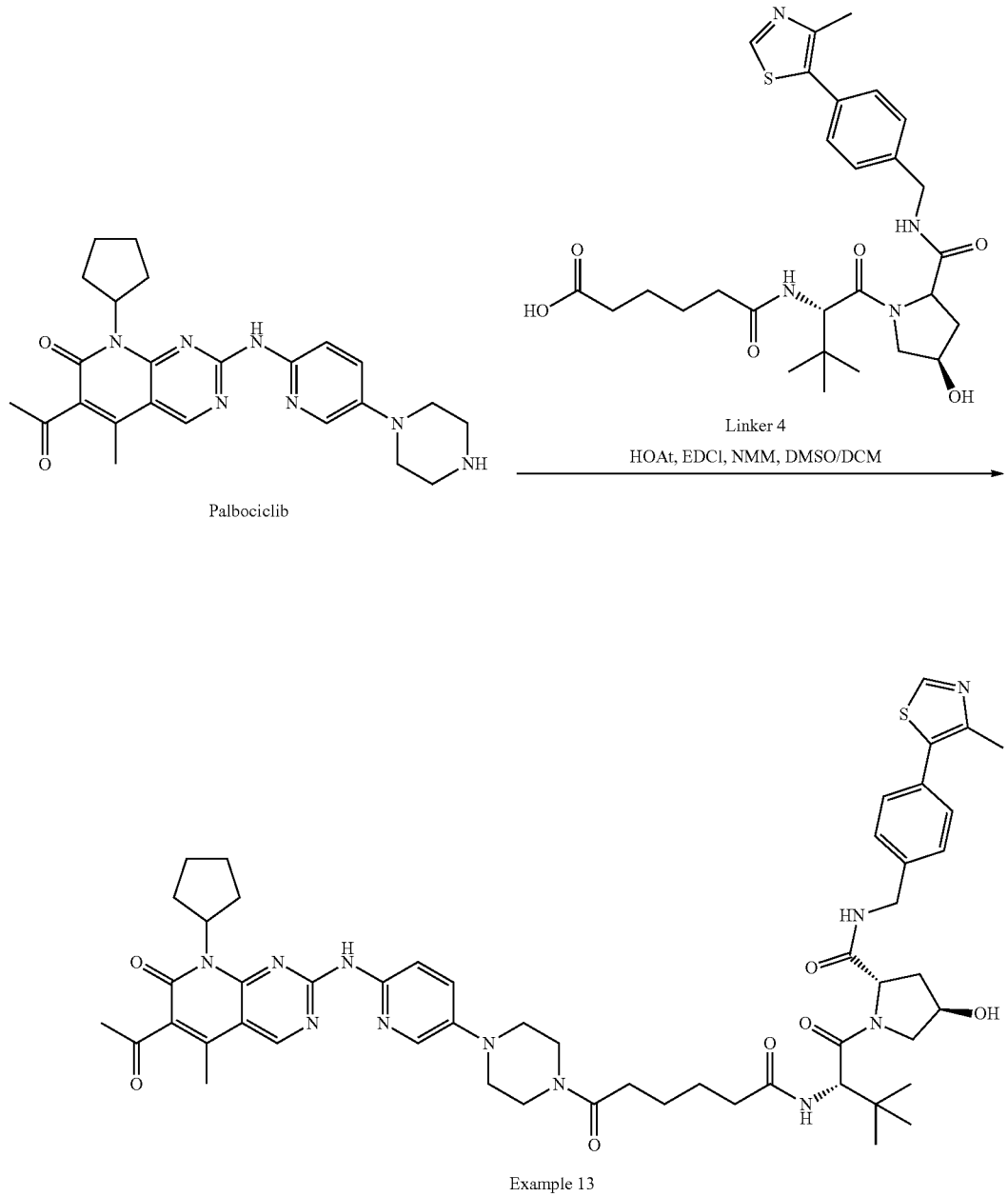

Example 13

(2S,4R)-1-((S)-2-(6-(4-(6-((6-Acetyl-8-cyclopentyl-5-methyl-7-oxo-7,8-dihydropyrido[2,3-d]pyrimidin-2-yl)amino)pyridin-3-yl)piperazin-1-yl)-6-oxohexanamido)-3,3-dimethylbutanoyl)-4-hydroxy-N-(4-(4-methylthiazol-5-yl)benzyl)pyrrolidine-2-carboxamide (compound Example 13)

To a solution of palbociclib (12 mg, 0.0268 mmol) in DMSO (1 mL) and DCM (5 mL) were added NMM (13.6 mg, 0.134 mmol), linker 4 (15 mg, 0.0268 mmol), HOAt (5.5 mg, 0.042 mmol) and EDCI (7.7 mg, 0.042 mmol). The mixture was allowed to stir at rt overnight. After the starting materials were consumed, the reaction was concentrated under reduced pressure. The resulting residue was purified by prep-HPLC to yield the product (24 mg, 81%) as yellow solid. $^1$H NMR (600 MHz, CD$_3$OD) δ 9.09 (s, 1H), 8.95 (s, 1H), 8.19 (dd, J=9.6, 2.9 Hz, 1H), 7.86 (d, J=2.8 Hz, 1H), 7.54 (d, J=9.6 Hz, 1H), 7.46 (d, J=8.2 Hz, 2H), 7.40 (d, J=8.2 Hz, 2H), 6.00 (p, J=8.9 Hz, 1H), 4.63 (s, 1H), 4.60-4.48 (m, 3H), 4.36 (d, J=15.6 Hz, 1H), 3.90 (d, J=11.1 Hz, 1H), 3.83-3.73 (m, 5H), 3.35-3.31 (m, 2H), 3.29-3.25 (m, 2H), 2.50 (s, 3H), 2.47 (s, 3H), 2.43 (s, 3H), 2.36-2.27 (m, 4H), 2.24-2.19 (m, 1H), 2.13-2.05 (m, 3H), 1.94-1.86 (m, 2H), 1.73-1.61 (m, 6H), 1.41-1.24 (m, 2H), 1.04 (s, 9H). HRMS (ESI-TOF) m/z: [M+H]$^+$ calculated for C$_{52}$H$_{66}$N$_{11}$O$_7$S, 988.4862; found: 988.4871.

The Example 14, 16, and 17 compounds were synthesized using the procedures for the preparation of the Example 13 compound (above).

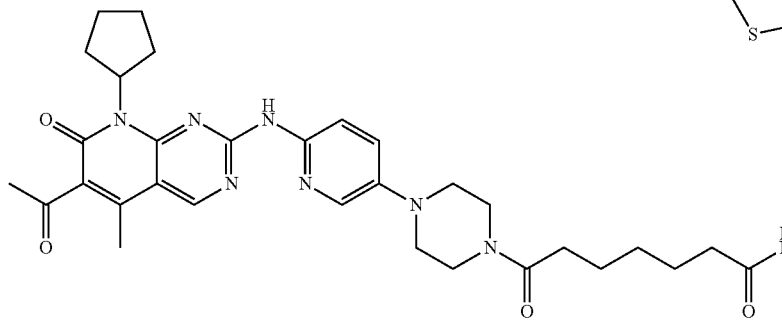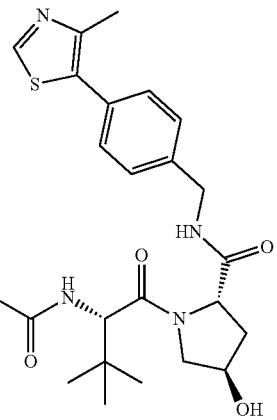

Example 14

(2S,4R)-1-((S)-2-(7-(4-(6-((6-Acetyl-8-cyclopentyl-5-methyl-7-oxo-7,8-dihydropyrido[2,3-d]pyrimidin-2-yl)amino)pyridin-3-yl)piperazin-1-yl)-7-oxoheptanamido)-3,3-dimethylbutanoyl)-4-hydroxy-N-(4-(4-methylthiazol-5-yl)benzyl)pyrrolidine-2-carboxamide (compound Example 14)

(20 mg, 68%) as yellow solid. $^1$H NMR (600 MHz, CD$_3$OD) δ 9.09 (s, 1H), 8.93 (s, 1H), 8.20 (dd, J=9.6, 2.9 Hz, 1H), 7.86 (d, J=2.9 Hz, 1H), 7.53 (d, J=9.6 Hz, 1H), 7.46 (d, J=8.1 Hz, 2H), 7.40 (d, J=8.2 Hz, 2H), 6.01 (p, J=8.8 Hz, 1H), 4.63 (s, 1H), 4.58-4.48 (m, 3H), 4.36 (d, J=15.5 Hz, 1H), 3.90 (d, J=11.1 Hz, 1H), 3.83-3.72 (m, 5H), 3.32 (t, J=5.0 Hz, 2H), 3.28 (t, J=5.0 Hz, 2H), 2.50 (s, 3H), 2.47 (s, 3H), 2.48-2.44 (m, 2H), 2.43 (s, 3H), 2.35-2.24 (m, 4H), 2.24-2.19 (m, 1H), 2.13-2.05 (m, 3H), 1.94-1.86 (m, 2H), 1.74-1.60 (m, 6H), 1.40 (dt, J=8.7, 7.4 Hz, 2H), 1.03 (s, 9H). HRMS (ESI-TOF) m/z: [M+H]$^+$ calculated for C$_{53}$H$_{68}$N$_{11}$O$_7$S, 1002.5018; found: 1002.5019.

(2S,4R)-1-((S)-2-(9-(4-(6-((6-Acetyl-8-cyclopentyl-5-methyl-7-oxo-7,8-dihydropyrido[2,3-d]pyrimidin-2-yl)amino)pyridin-3-yl)piperazin-1-yl)-9-oxononanamido)-3,3-dimethylbutanoyl)-4-hydroxy-N-(4-(4-methylthiazol-5-yl)benzyl)pyrrolidine-2-carboxamide (compound Example 16)

(18 mg, 63%) as yellow solid. $^1$H NMR (600 MHz, CD$_3$OD) δ 9.10 (s, 1H), 9.00 (s, 1H), 8.20 (dd, J=9.6, 2.8 Hz, 1H), 7.86 (d, J=2.8 Hz, 1H), 7.54 (d, J=9.6 Hz, 1H), 7.46 (d, J=8.1 Hz, 2H), 7.41 (d, J=8.1 Hz, 2H), 6.00 (p, J=8.8 Hz, 1H), 4.63 (s, 1H), 4.60-4.47 (m, 3H), 4.36 (d, J=15.5 Hz, 1H), 3.90 (d, J=11.0 Hz, 1H), 3.82-3.72 (m, 5H), 3.34-3.23 (m, 4H), 2.50 (s, 3H), 2.48 (s, 3H), 2.48-2.44 (m, 2H), 2.43 (s, 3H), 2.34-2.18 (m, 5H), 2.13-2.04 (m, 3H), 1.94-1.85 (m, 2H), 1.73-1.57 (m, 6H), 1.41-1.30 (m, 6H), 1.03 (s, 9H). HRMS (ESI-TOF) m/z: [M+H]$^+$ calculated for C$_{55}$H$_{72}$N$_{11}$O$_7$S, 1030.5331; found: 1030.5335.

Example 16

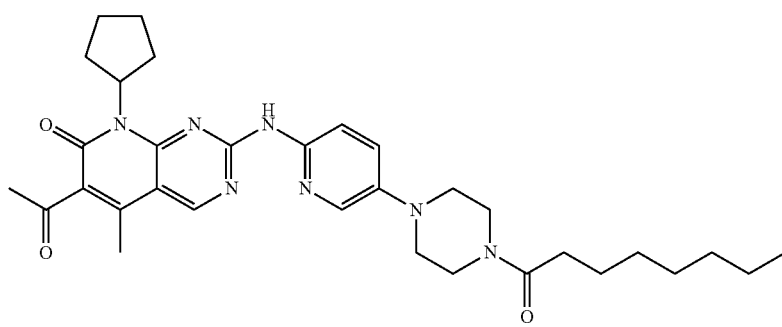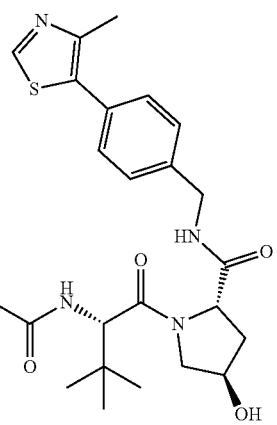

Example 17

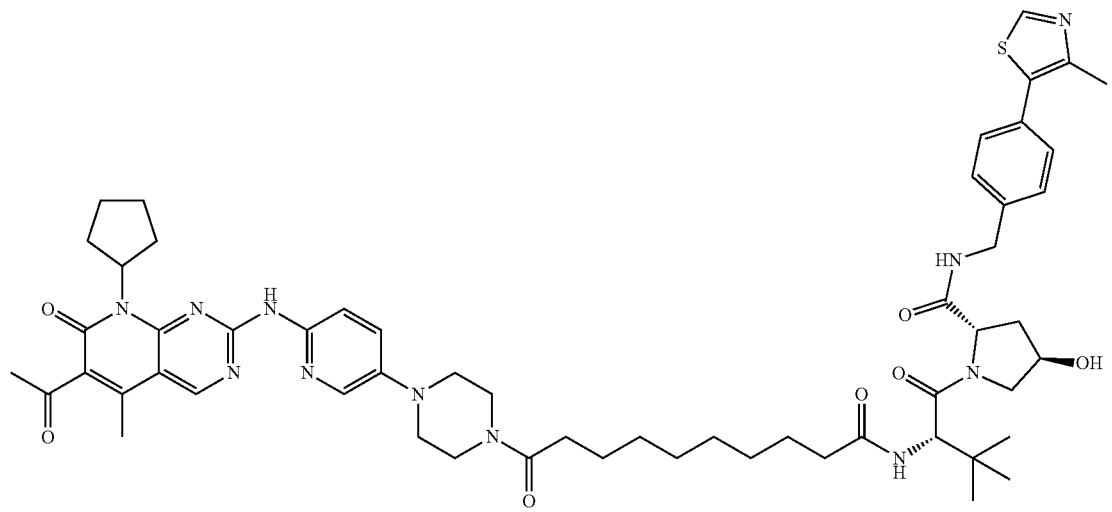

(2S,4R)-1-((S)-2-(10-(4-(6-((6-Acetyl-8-cyclopentyl-5-methyl-7-oxo-7,8-dihydropyrido[2,3-d]pyrimidin-2-yl)amino)pyridin-3-yl)piperazin-1-yl)-10-oxodecanamido)-3,3-dimethylbutanoyl)-4-hydroxy-N-(4-(4-methylthiazol-5-yl)benzyl)pyrrolidine-2-carboxamide (compound Example 17)

(18 mg, 64%) as yellow solid. $^1$H NMR (600 MHz, CD$_3$OD) δ 9.09 (s, 1H), 8.93 (s, 1H), 8.19 (dd, J=9.6, 2.9 Hz, 1H), 7.87 (d, J=2.9 Hz, 1H), 7.54 (d, J=9.6 Hz, 1H), 7.46 (d, J=8.1 Hz, 2H), 7.41 (d, J=8.2 Hz, 2H), 6.00 (p, J=8.8 Hz, 1H), 4.63 (s, 1H), 4.60-4.47 (m, 3H), 4.35 (d, J=15.5 Hz, 1H), 3.90 (d, J=11.0 Hz, 1H), 3.83-3.70 (m, 5H), 3.36-3.23 (m, 4H), 2.50 (s, 3H), 2.47 (s, 3H), 2.48-2.44 (m, 2H), 2.43 (s, 3H), 2.34-2.19 (m, 5H), 2.12-2.05 (m, 3H), 1.93-1.86 (m, 2H), 1.73-1.66 (m, 2H), 1.65-1.56 (m, 4H), 1.40-1.28 (m, 8H), 1.03 (s, 9H). HRMS (ESI-TOF) m/z: [M+H]$^+$ calculated for C$_{56}$H$_{74}$N$_{11}$O$_7$S, 1044.5488; found: 1044.5487.

Scheme 5: Synthesis of example 21

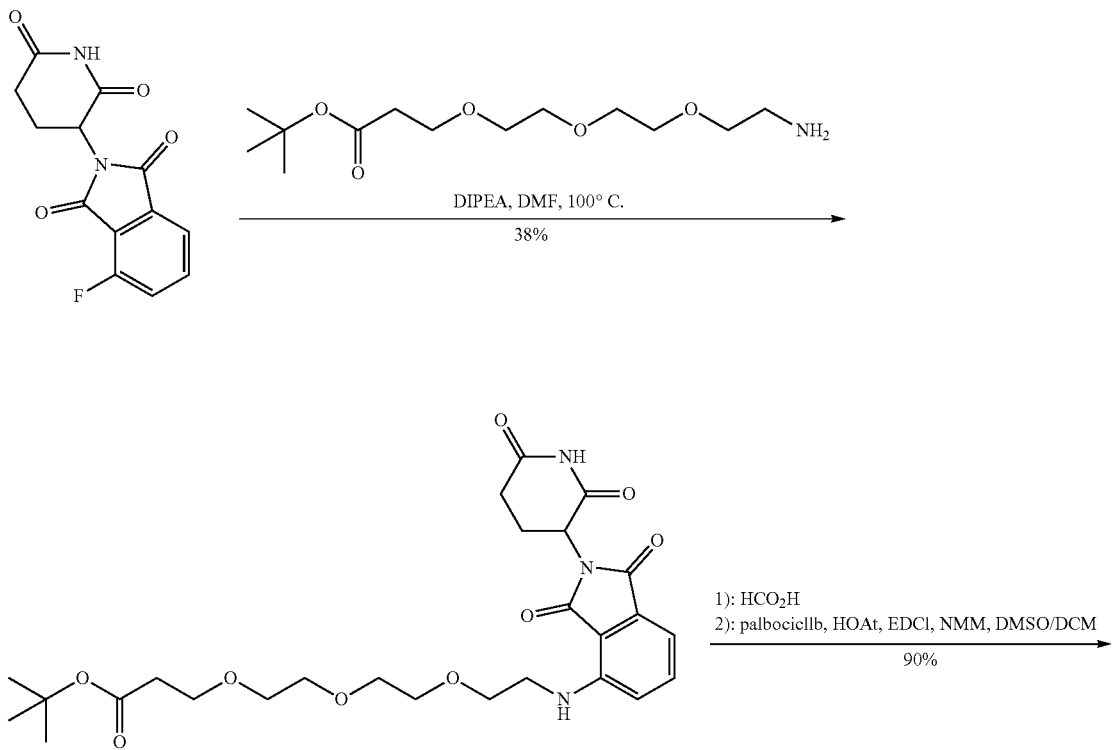

Intermediate 6

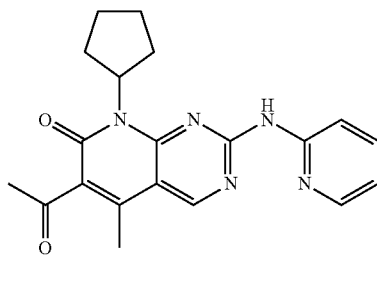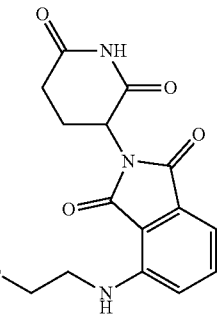

Example 21 tert-Butyl 3-(2-(2-(2-((2-(2,6-dioxopiperidin-3-yl)-1,3-dioxoisoindolin-4-yl)amino)ethoxy) ethoxy) ethoxy)propanoate (Intermediate 6)

A solution of 2-(2,6-dioxopiperidin-3-yl)-4-fluoroisoindoline-1,3-dione (100 mg, 0.362 mmol), tert-butyl 3-(2-(2-(2-aminoethoxy)ethoxy) ethoxy)propanoate (100 mg, 0.362 mmol) and DIPEA (0.5 ml) in DMF (5 ml) was heated at 100° C. overnight. After the starting materials were consumed, the reaction was concentrated under reduced pressure. The resulting residue was purified by prep-HPLC to yield the product (72 mg, 37%) as yellow solid. $^1$H NMR (600 MHz, CD$_3$OD) δ 7.55 (dd, J=7.1, 8.6 Hz, 1H), 7.10 (d, J=8.5 Hz, 1H), 7.05 (d, J=7.0 Hz, 1H), 5.06 (dd, J=5.4, 12.4 Hz, 1H), 4.10 (q, J=7.1 Hz, 1H), 3.72 (t, J=5.3 Hz, 2H), 3.69-3.59 (m, 8H), 3.59-3.55 (m, 2H), 3.50 (t, J=5.3 Hz, 2H), 2.91-2.82 (m, 1H), 2.78-2.68 (m, 2H), 2.45 (t, J=6.2 Hz, 2H), 1.43 (s, 9H). HRMS (ESI-TOF) m/z: [M+H]$^+$ calculated for C$_{26}$H$_{36}$N$_3$O$_9$, 534.2446; found: 534.2459.

4-((2-(2-(2-(3-(4-(6-((6-Acetyl-8-cyclopentyl-5-methyl-7-oxo-7,8-dihydropyrido[2,3-d]pyrimidin-2-yl)amino)pyridin-3-yl)piperazin-1-yl)-3-oxopropoxy)ethoxy)ethoxy)ethyl) amino)-2-(2,6-dioxopiperidin-3-yl)isoindoline-1,3-dione (compound Example 21)

A solution of intermediate 6 (20 mg, 0.0308 mmol) in HCO$_2$H (5 mL) was stirred overnight at RT. The reaction was concentrated under reduced pressure and the resulting residue was dissolved in DCM/DMSO (10 ml/2 ml). To the resulting solution were added palbociclib (13.7 mg, 0.0308 mmol), NMM (16 mg, 0.154 mmol), HOAt (5.4 mg, 0.0399 mmol), and EDCI (7.6 mg, 0.0399 mmol). The reaction mixture was allowed to stir at RT overnight. After palbociclib was consumed, the reaction was concentrated under reduced pressure. The resulting residue was purified by prep-HPLC to yield the product (25 mg, 90%) as yellow solid. $^1$H NMR (600 MHz, CD$_3$OD) δ 8.98 (s, 1H), 8.13 (d, J=9.7 Hz, 1H), 7.72 (d, J=2.9 Hz, 1H), 7.44-7.35 (m, 2H), 6.94 (d, J=8.6 Hz, 1H), 6.77 (d, J=7.1 Hz, 1H), 6.03-5.93 (m, 1H), 5.09 (dd, J=5.5, 12.7 Hz, 1H), 3.87-3.75 (m, 8H), 3.67 (t, J=5.2 Hz, 2H), 3.65-3.58 (m, 9H), 3.41-3.37 (m, 2H), 2.92-2.84 (m, 1H), 2.79-2.63 (m, 4H), 2.52 (s, 3H), 2.42 (s, 3H), 2.36-2.28 (m, 2H), 2.13-2.07 (m, 4H), 1.97-1.88 (m, 2H), 1.75-1.67 (m, 2H). HRMS (ESI-TOF) m/z: [M+H]$^+$ calculated for C$_{46}$H$_{55}$N$_{10}$O$_{10}$, 907.4097; found: 907.4095.

The Example 19, 20, 22, 23, 24, 25, 26, 27, 28, and 29 compounds were synthesized according to the procedures for the preparation of the Example 21 compound (above).

Example 19

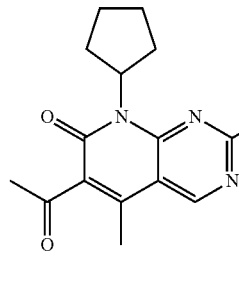

4-((2-(3-(4-(6-((6-Acetyl-8-cyclopentyl-5-methyl-7-oxo-7,8-dihydropyrido[2,3-d]pyrimidin-2-yl)amino)pyridin-3-yl)piperazin-1-yl)-3-oxopropoxy)ethyl)amino)-2-(2,6-dioxopiperidin-3-yl)isoindoline-1,3-dione (compound Example 19)

(28 mg, 88%) as yellow solid. $^1$H NMR (600 MHz, CD$_3$OD) δ 9.08 (s, 1H), 7.99 (dd, J=9.6, 2.8 Hz, 1H), 7.64 (d, J=2.8 Hz, 1H), 7.44 (dd, J=8.3, 7.2 Hz, 1H), 7.30 (d, J=9.6 Hz, 1H), 6.96 (d, J=8.6 Hz, 1H), 6.80 (d, J=7.0 Hz, 1H), 6.02 (p, J=8.9 Hz, 1H), 5.07 (dd, J=12.8, 5.6 Hz, 1H), 3.99-3.79 (m, 4H), 3.79-3.61 (m, 4H), 3.48-3.36 (m, 2H), 3.30-3.24 (m, 1H), 3.23-3.13 (m, 2H), 3.13-3.05 (m, 1H), 2.90-2.77 (m, 2H), 2.76-2.70 (m, 1H), 2.70-2.60 (m, 2H), 2.51 (s, 3H), 2.45 (s, 3H), 2.37-2.27 (m, 2H), 2.15-2.04 (m, 3H), 1.96-1.87 (m, 2H), 1.75-1.66 (m, 2H). HRMS (ESI-TOF) m/z: [M+H]$^+$ calculated for $C_{42}H_{47}N_{10}O_8$, 819.3573; found: 819.3573.

Example 20

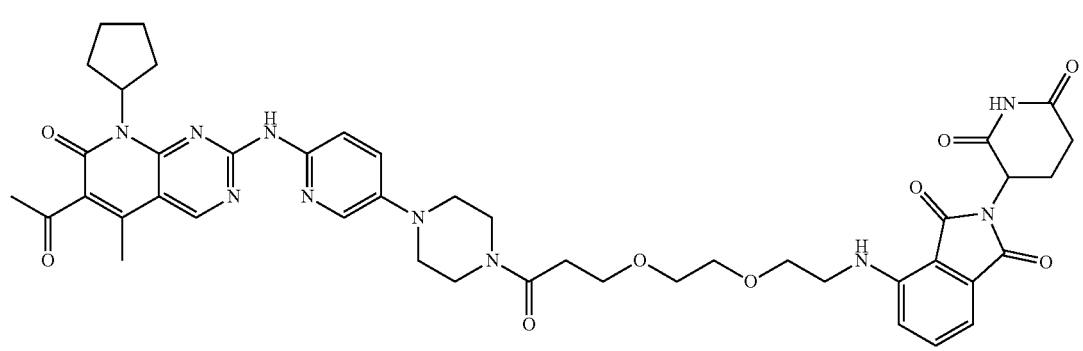

4-((2-(2-(3-(4-(6-(((6-Acetyl-8-cyclopentyl-5-methyl-7-oxo-7,8-dihydropyrido[2,3-d]pyrimidin-2-yl) amino)pyridin-3-yl)piperazin-1-yl)-3-oxopropoxy) ethoxy)ethyl)amino)-2-(2,6-dioxopiperidin-3-yl) isoindoline-1,3-dione (compound Example 20)

(22 mg, 73%) as yellow solid. $^1$H NMR (600 MHz, CD$_3$OD) δ 8.99 (s, 1H), 8.08 (dd, J=9.6, 2.8 Hz, 1H), 7.68 (d, J=2.6 Hz, 1H), 7.40 (dd, J=8.4, 7.2 Hz, 1H), 7.37 (d, J=9.6 Hz, 1H), 6.94 (d, J=8.6 Hz, 1H), 6.72 (d, J=7.1 Hz, 1H), 5.99 (p, J=8.9 Hz, 1H), 5.08 (dd, J=12.8, 5.6 Hz, 1H), 3.86-3.70 (m, 6H), 3.69-3.61 (m, 6H), 3.41-3.31 (m, 4H), 3.26-3.17 (m, 2H), 2.92-2.82 (m, 1H), 2.78-2.63 (m, 4H), 2.51 (s, 3H), 2.43 (s, 3H), 2.36-2.28 (m, 2H), 2.13-2.07 (m, 3H), 1.96-1.87 (m, 2H), 1.74-1.66 (m, 2H). HRMS (ESI-TOF) m/z: [M+H]$^+$ calculated for $C_{44}H_{51}N_{10}O_9$, 863.3835; found: 863.3842.

Example 22

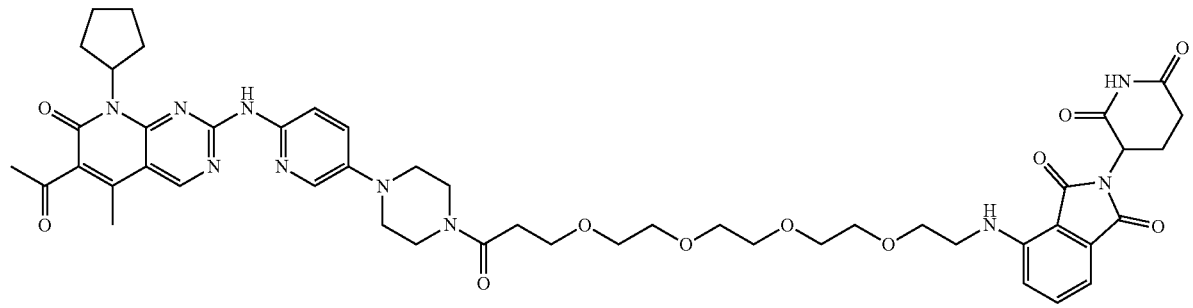

4-((15-(4-(6-(((6-Acetyl-8-cyclopentyl-5-methyl-7-oxo-7,8-dihydropyrido[2,3-d]pyrimidin-2-yl)amino) pyridin-3-yl)piperazin-1-yl)-15-oxo-3,6,9,12-tetraoxapentadecyl)amino)-2-(2,6-dioxopiperidin-3-yl) isoindoline-1,3-dione (compound Example 22)

(34 mg, 85%) as yellow solid. $^1$H NMR (600 MHz, CD$_3$OD) δ 8.97 (s, 1H), 8.17 (d, J=9.6 Hz, 1H), 7.75 (s, 1H), 7.44 (d, J=9.6 Hz, 1H), 7.39 (t, J=7.8 Hz, 1H), 6.92 (d, J=8.5 Hz, 1H), 6.80 (d, J=7.0 Hz, 1H), 5.96 (p, J=8.7 Hz, 1H), 5.07 (dd, J=12.8, 5.4 Hz, 1H), 3.87-3.73 (m, 6H), 3.70-3.51 (m, 14H), 3.42-3.32 (m, 4H), 3.30-3.22 (m, 2H), 2.91-2.83 (m, 1H), 2.78-2.59 (m, 4H), 2.50 (s, 3H), 2.39 (s, 3H), 2.34-2.24 (m, 2H), 2.15-2.03 (m, 3H), 1.95-1.86 (m, 2H), 1.74-1.64 (m, 2H). HRMS (ESI-TOF) m/z: [M+H]$^+$ calculated for $C_{48}H_{59}N_{10}O_{11}$, 951.4359; found: 951.4353.

Example 23

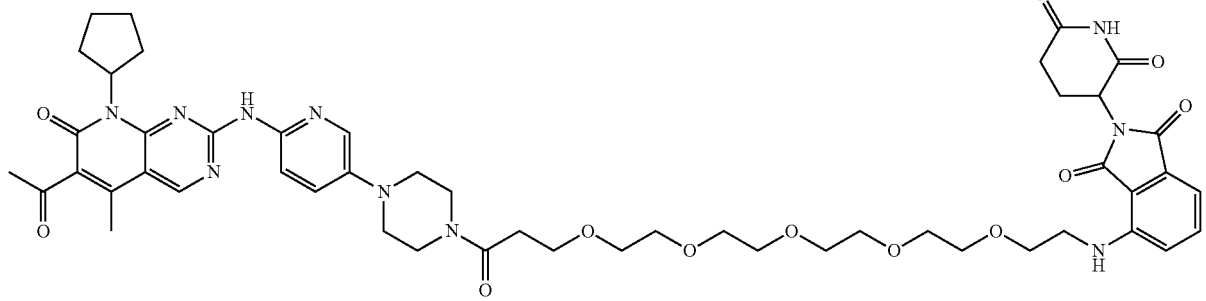

4-((18-(4-(6-(((6-Acetyl-8-cyclopentyl-5-methyl-7-oxo-7,8-dihydropyrido[2,3-d]pyrimidin-2-yl)amino)pyridin-3-yl)piperazin-1-yl)-18-oxo-3,6,9,12,15-pentaoxaoctadecyl)amino)-2-(2,6-dioxopiperidin-3-yl)isoindoline-1,3-dione (compound Example 23)

(18 mg, 51%) as yellow solid. $^1$H NMR (600 MHz, CD$_3$OD) δ 9.03-8.97 (m, 1H), 8.20 (dd, J=9.6, 2.9 Hz, 1H), 7.78 (d, J=2.9 Hz, 1H), 7.45 (d, J=9.7 Hz, 1H), 7.43 (dd, J=8.5, 7.2 Hz, 1H), 6.97 (d, J=8.6 Hz, 1H), 6.85 (d, J=7.0 Hz, 1H), 5.97 (p, J=8.8 Hz, 1H), 5.06 (dd, J=12.8, 5.5 Hz, 1H), 3.84-3.78 (m, 4H), 3.77 (t, J=6.0 Hz, 2H), 3.68 (t, J=5.1 Hz, 2H), 3.66-3.53 (m, 16H), 3.44-3.38 (m, 2H), 3.37-3.32 (m, 2H), 3.29-3.22 (m, 2H), 2.90-2.82 (m, 1H), 2.77-2.62 (m, 4H), 2.51 (s, 3H), 2.41 (s, 3H), 2.34-2.26 (m, 2H), 2.13-2.05 (m, 3H), 1.95-1.87 (m, 2H), 1.74-1.65 (m, 2H). HRMS (ESI-TOF) m/z: [M+H]$^+$ calculated for C$_{50}$H$_{63}$N$_{10}$O$_{12}$, 995.4621; found: 995.4628.

Example 24

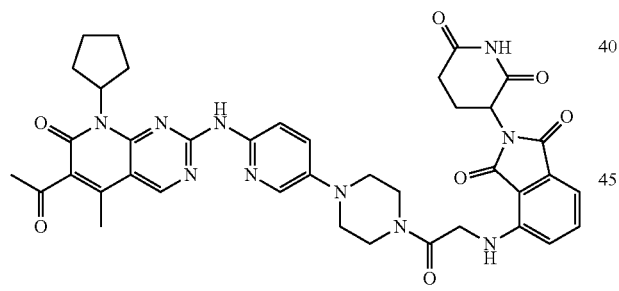

4-((2-(4-(6-(((6-Acetyl-8-cyclopentyl-5-methyl-7-oxo-7,8-dihydropyrido[2,3-d]pyrimidin-2-yl)amino)pyridin-3-yl)piperazin-1-yl)-2-oxoethyl)amino)-2-(2,6-dioxopiperidin-3-yl)isoindoline-1,3-dione (compound Example 24)

(28 mg, 72%) as yellow solid. $^1$H NMR (600 MHz, CD$_3$OD) δ 9.08 (s, 1H), 8.21 (dd, J=9.6, 2.8 Hz, 1H), 7.86 (d, J=2.8 Hz, 1H), 7.55-7.50 (m, 2H), 7.03 (d, J=7.0 Hz, 1H), 6.99 (d, J=8.5 Hz, 1H), 6.04-5.97 (m, 1H), 5.08 (dd, J=12.7, 5.5 Hz, 1H), 4.24 (s, 2H), 3.88-3.73 (m, 4H), 3.42-3.31 (m, 4H), 2.92-2.82 (m, 1H), 2.80-2.67 (m, 2H), 2.50 (s, 3H), 2.43 (s, 3H), 2.35-2.27 (m, 2H), 2.15-2.06 (m, 3H), 1.94-1.87 (m, 2H), 1.73-1.66 (m, 2H). HRMS (ESI-TOF) m/z: [M+H]$^+$ calculated for C$_{39}$H$_{41}$N$_{10}$O$_7$, 761.3154; found: 761.3150.

Example 25

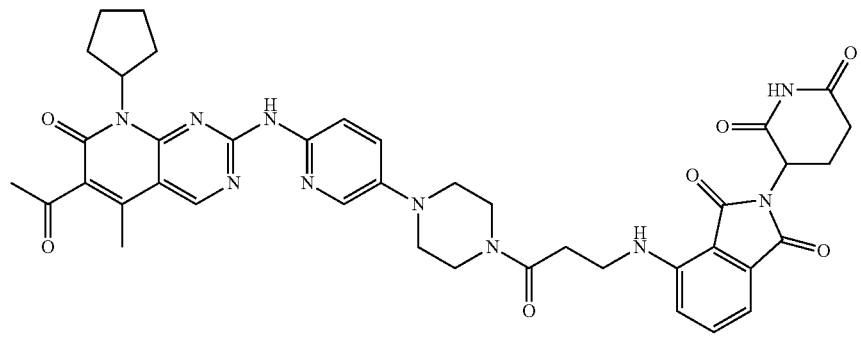

4-((3-(4-(6-(((6-Acetyl-8-cyclopentyl-5-methyl-7-oxo-7,8-dihydropyrido[2,3-d]pyrimidin-2-yl)amino)pyridin-3-yl)piperazin-1-yl)-3-oxopropyl)amino)-2-(2,6-dioxopiperidin-3-yl)isoindoline-1,3-dione (compound Example 25)

(26 mg, 67%) as yellow solid. $^1$H NMR (600 MHz, CD$_3$OD) δ 9.07 (s, 1H), 8.13 (dd, J=9.6, 2.9 Hz, 1H), 7.77 (d, J=2.9 Hz, 1H), 7.52 (dd, J=8.5, 7.1 Hz, 1H), 7.49 (d, J=9.6 Hz, 1H), 7.09 (d, J=8.6 Hz, 1H), 6.95 (d, J=7.0 Hz, 1H), 6.00 (p, J=8.9 Hz, 1H), 5.03 (dd, J=12.7, 5.5 Hz, 1H), 3.76 (dt, J=10.3, 4.7 Hz, 4H), 3.68 (t, J=6.1 Hz, 2H), 3.18 (br. s, 4H), 2.88-2.80 (m, 1H), 2.79 (td, J=5.9, 1.9 Hz, 2H), 2.75-2.62 (m, 2H), 2.50 (s, 3H), 2.42 (s, 3H), 2.34-2.26 (m, 2H), 2.13-2.03 (m, 3H), 1.94-1.86 (m, 2H), 1.73-1.64 (m, 2H). HRMS (ESI-TOF) m/z: [M+H]$^+$ calculated for C$_{40}$H$_{43}$N$_{10}$O$_7$, 775.3311; found: 775.3316.

Example 26

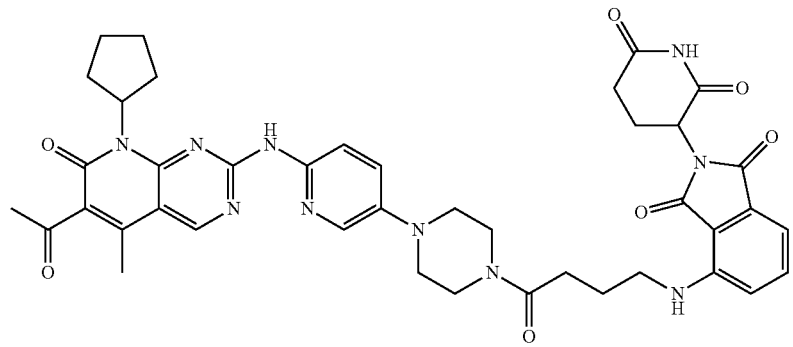

4-((4-(4-(6-(((6-Acetyl-8-cyclopentyl-5-methyl-7-oxo-7,8-dihydropyrido[2,3-d]pyrimidin-2-yl)amino)pyridin-3-yl)piperazin-1-yl)-4-oxobutyl)amino)-2-(2,6-dioxopiperidin-3-yl)isoindoline-1,3-dione (compound Example 26)

(17 mg, 45%) as yellow solid. $^1$H NMR (600 MHz, CD$_3$OD) δ 9.09 (s, 1H), 8.13 (dd, J=9.6, 2.9 Hz, 1H), 7.79 (d, J=2.8 Hz, 1H), 7.54-7.45 (m, 2H), 7.08 (d, J=8.6 Hz, 1H), 6.92 (d, J=7.0 Hz, 1H), 6.00 (p, J=8.8 Hz, 1H), 5.05 (dd, J=12.7, 5.5 Hz, 1H), 3.80-3.70 (m, 4H), 3.41 (td, J=6.5, 1.3 Hz, 2H), 3.25-3.16 (m, 4H), 2.90-2.82 (m, 1H), 2.77-2.65 (m, 2H), 2.58 (t, J=6.9 Hz, 2H), 2.50 (s, 3H), 2.43 (s, 3H), 2.35-2.27 (m, 2H), 2.13-2.06 (m, 3H), 2.00 (p, J=6.7 Hz, 2H), 1.95-1.86 (m, 2H), 1.70 (dt, J=10.1, 8.6 Hz, 2H). HRMS (ESI-TOF) m/z: [M+H]$^+$ calculated for C$_{41}$H$_{45}$N$_{10}$O$_7$, 789.3467; found: 789.3474.

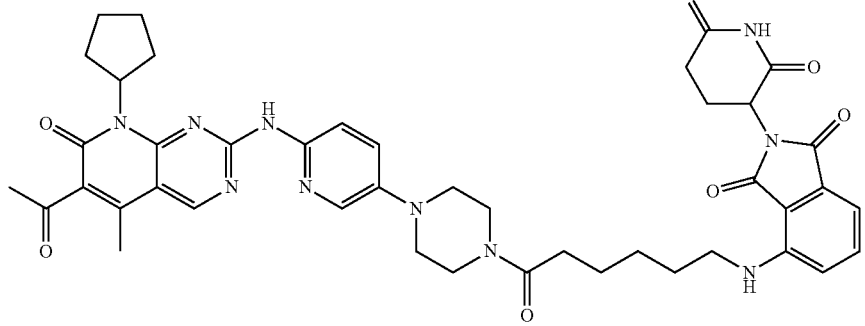

Example 27

4-((6-(4-(6-(((6-Acetyl-8-cyclopentyl-5-methyl-7-oxo-7,8-dihydropyrido[2,3-d]pyrimidin-2-yl)amino)pyridin-3-yl)piperazin-1-yl)-6-oxohexyl)amino)-2-(2,6-dioxopiperidin-3-yl)isoindoline-1,3-dione (compound Example 27)

(24 mg, 66%) as yellow solid. $^1$H NMR (600 MHz, CD$_3$OD) δ 9.09 (s, 1H), 8.13 (dd, J=9.6, 2.9 Hz, 1H), 7.78 (d, J=2.8 Hz, 1H), 7.52-7.46 (m, 2H), 7.02 (d, J=8.6 Hz, 1H), 6.90 (d, J=7.0 Hz, 1H), 6.01 (p, J=8.8 Hz, 1H), 5.04 (dd, J=12.7, 5.5 Hz, 1H), 3.83-3.69 (m, 4H), 3.36-3.29 (m, 2H), 3.27-3.16 (m, 4H), 2.85 (ddd, J=17.5, 13.9, 5.4 Hz, 1H), 2.76-2.62 (m, 2H), 2.54-2.45 (m, 5H), 2.43 (s, 3H), 2.36-2.27 (m, 2H), 2.14-2.04 (m, 3H), 1.95-1.86 (m, 2H), 1.75-1.63 (m, 6H), 1.54-1.44 (n, 2H). HRMS (ESI-TOF) m/z: [M+H]$^+$ calculated for C$_{43}$H$_{49}$N$_{10}$O$_7$, 817.3780; found: 817.3773.

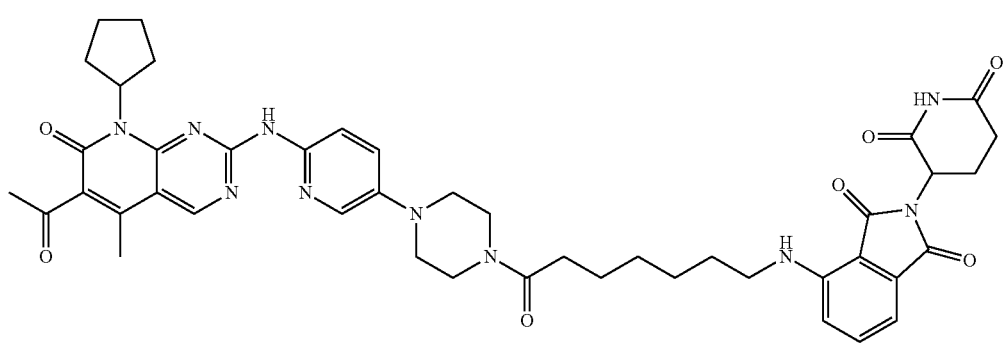

Example 28

4-((7-(4-(6-(((6-Acetyl-8-cyclopentyl-5-methyl-7-oxo-7,8-dihydropyrido[2,3-d]pyrimidin-2-yl)amino)pyridin-3-yl)piperazin-1-yl)-7-oxoheptyl)amino)-2-(2,6-dioxopiperidin-3-yl)isoindoline-1,3-dione (compound Example 28)

(26 mg, 74%) as yellow solid. $^1$H NMR (600 MHz, CD$_3$OD) δ 9.07 (s, 1H), 8.16 (dd, J=9.7, 2.9 Hz, 1H), 7.80 (d, J=2.8 Hz, 1H), 7.55-7.45 (m, 2H), 7.00 (d, J=8.6 Hz, 1H), 6.93 (d, J=7.1 Hz, 1H), 6.00 (p, J=8.9 Hz, 1H), 5.04 (dd, J=12.8, 5.5 Hz, 1H), 3.82-3.69 (m, 4H), 3.32-3.20 (m, 6H), 2.84 (ddd, J=17.8, 14.1, 5.3 Hz, 1H), 2.77-2.63 (m, 2H), 2.50 (s, 3H), 2.46 (t, J=7.4 Hz, 2H), 2.42 (s, 3H), 2.35-2.25 (m, 2H), 2.13-2.05 (m, 3H), 1.95-1.85 (m, 2H), 1.74-1.60 (m, 6H), 1.50-1.39 (m, 4H). HRMS (ESI-TOF) m/z: [M+H]$^+$ calculated for C$_{44}$H$_{51}$N$_{10}$O$_7$, 831.3937; found: 831.3929.

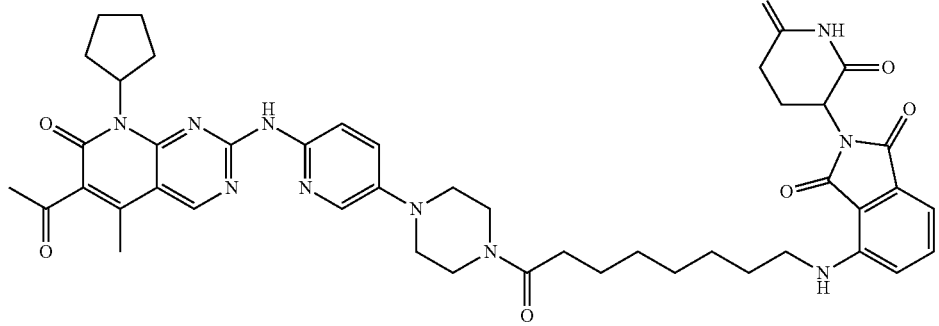

Example 29

4-((8-(4-(6-(((6-Acetyl-8-cyclopentyl-5-methyl-7-oxo-7,8-dihydropyrido[2,3-d]pyrimidin-2-yl)amino)pyridin-3-yl)piperazin-1-yl)-8-oxooctyl)amino)-2-(2,6-dioxopiperidin-3-yl)isoindoline-1,3-dione (compound Example 29)

(23 mg, 66%) as yellow solid. $^1$H NMR (600 MHz, CD$_3$OD) δ 9.07 (s, 1H), 8.16 (dd, J=9.6, 2.9 Hz, 1H), 7.82 (d, J=2.8 Hz, 1H), 7.54-7.48 (m, 2H), 7.01 (d, J=8.6 Hz, 1H), 6.95 (d, J=7.1 Hz, 1H), 6.01 (p, J=8.8 Hz, 1H), 5.05 (dd, J=12.8, 5.5 Hz, 1H), 3.82-3.71 (m, 4H), 3.33-3.22 (m, 6H), 2.85 (ddd, J=17.7, 14.1, 5.3 Hz, 1H), 2.76-2.64 (m, 2H), 2.50 (s, 3H), 2.46 (t, J=7.4 Hz, 2H), 2.43 (s, 3H), 2.32 (td, J=15.4, 7.8 Hz, 2H), 2.14-2.04 (m, 3H), 1.95-1.86 (m, 2H), 1.74-1.60 (m, 6H), 1.50-1.36 (m, 6H). HRMS (ESI-TOF) m/z: [M+H]$^+$ calculated for C$_{45}$H$_{53}$N$_{10}$O$_7$, 845.4093; found: 845.4101.

Scheme 6: Synthesis of example 30

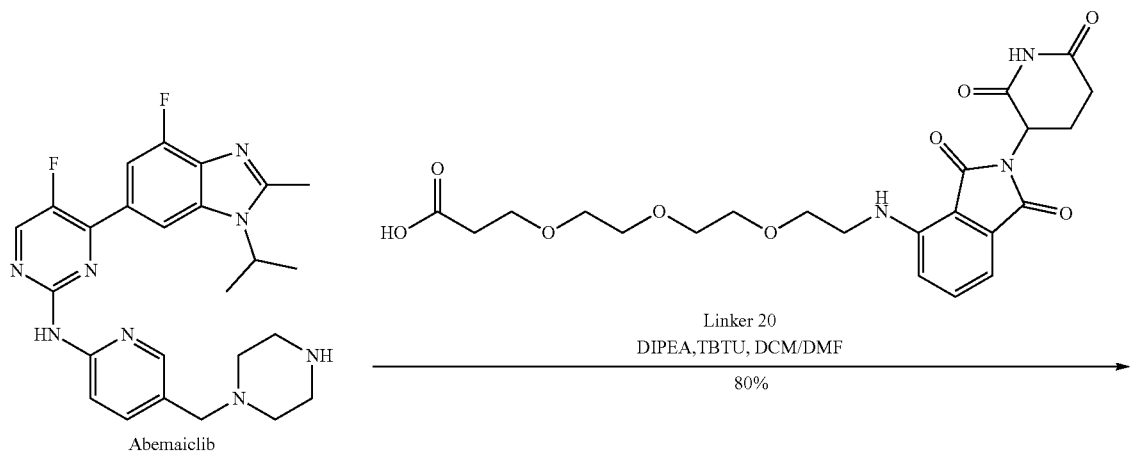

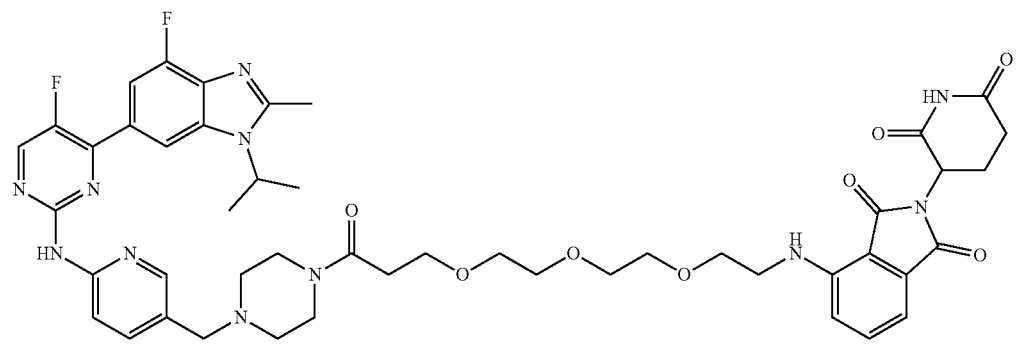

Example 30

2-(2,6-Dioxopiperidin-3-yl)-4-((2-(2-(2-(3-(4-((6-((5-fluoro-4-(4-fluoro-1-isopropyl-2-methyl-1H-benzo[d]imidazol-6-yl)pyrimidin-2-yl)amino)pyridin-3-yl)methyl)piperazin-1-yl)-3-oxopropoxy)ethoxy)ethyl)amino)isoindoline-1,3-dione (compound Example 30)

To a solution of linker 20 (32 mg, 0.07 mmol) and abemaiclib (24 mg, 0.05 mmol) in CH$_2$Cl$_2$ (4 ml) and DMF (1 ml) were added DIEA (17 μl, 0.1 mmol) and TBTU (22 mg, 0.07 mmol). The reaction was stirred at RT for 1 h before being concentrated under reduced pressure. The resulting residue was purified by prep-HPLC to provide the title compound (37 mg, 80% over 2 steps). $^1$H NMR (600 MHz, CD$_3$OD) δ 8.52 (d, J=3.6 Hz, 1H), 8.32 (d, J=8.4 Hz, 1H), 8.28 (s, 1H), 8.24 (s, 1H), 7.80-7.78 (m, 2H), 7.49 (t, J=7.8 Hz, 1H), 7.02 (dd, J=6.6 Hz, J=3.0 Hz, 1H), 6.98 (d, J=8.4 Hz, 1H), 5.00 (dd, J=12.6 Hz, J=6.0 Hz, 1H), 3.75 (t, J=6.0 Hz, 2H), 3.71 (t, J=5.4 Hz, 2H), 3.66-3.60 (m, 14H), 3.46 (t, J=5.4 Hz, 2H), 2.88-2.73 (m, 4H), 2.70 (s, 3H), 2.64 (t, J=6.0 Hz, 2H), 2.65-2.50 (m, 4H), 2.12-2.10 (m, 1H), 1.74 (d, J=6.6 Hz, 6H). HRMS (ESI-TOF) m/z: [M+H]$^+$ calculated for C$_{47}$H$_{54}$F$_2$N$_{11}$O$_8$, 938.4119; found: 938.4148.

Scheme 7: Synthesis of example 31

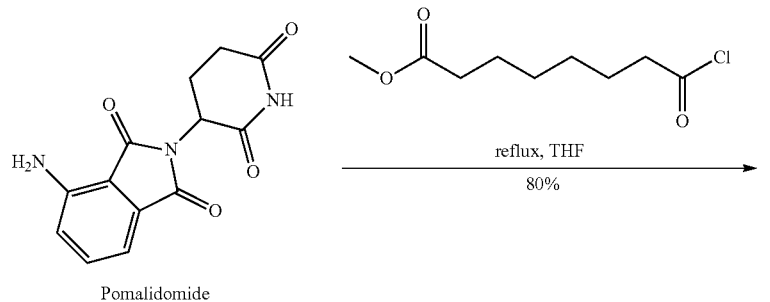

Pomalidomide

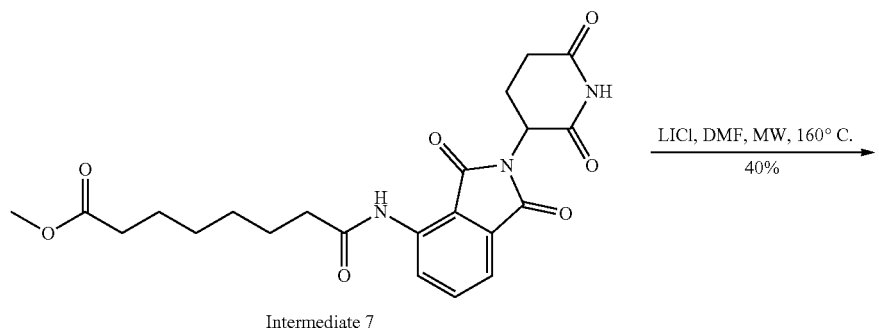

Intermediate 7

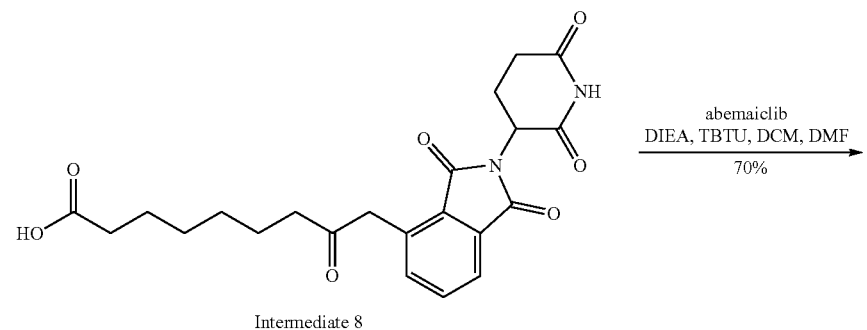

Intermediate 8

-continued

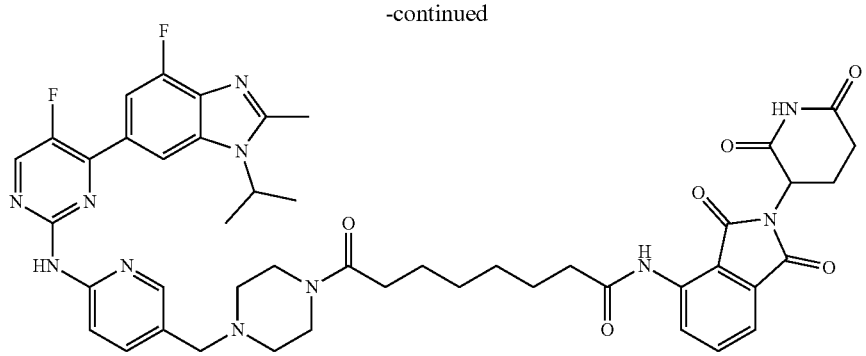

Example 31

N-(2-(2,6-Dioxopiperidin-3-yl)-1,3-dioxoisoindolin-4-yl)-8-(4-(((6-((5-fluoro-4-(4-fluoro-1-isopropyl-2-methyl-1H-benzo[d]imidazol-6-yl)pyrimidin-2-yl)amino)pyridin-3-yl)methyl)piperazin-1-yl)-8-oxooctanamide (compound Example 31)

Methyl 8-chloro-8-oxooctanoate (30 mg, 0.15 mmol) and pomalidomide (40 mg, 0.15 mmol) were dissolved in THF (5 ml). The resulting solution was heated at reflux for 3 h before the solvent was evaporated under reduced pressure. The residue was purified by prep-HPLC to provide intermediate 7 (53 mg, 0.12 mmol) as yellow oil. A solution of intermediate 7 (53 mg, 0.12 mmol) in DMF (1 ml) was treated with LiCl (25 mg, 0.6 mmol) at 160° C. in microwave reactor for 2 h. After being cooled to RT, the reaction mixture was poured into water (5 mL) and extracted with DCM (3×5 ml). The organic phase was combined, dried over $Na_2SO_4$, and concentrated. The resulting residue was purified by prep-HPLC to provide intermediate 8 (21 mg, 40%) as yellow oil. To a solution of intermediate 8 (21 mg, 0.05 mmol) and abemaiclib (19 mg, 0.04 mmol) in $CH_2Cl2$ (4 ml) and DMF (1 ml) were added DIEA (17 μl, 0.1 mmol) and TBTU (15 mg, 0.05 mmol). The reaction was stirred at RT for 1 h before being concentrated under reduced pressure. The resulting residue was purified by prep-HPLC to provide the title compound (25 mg, 70%). $^1$H NMR (600 MHz, $CDCl_3$) δ 9.47 (s, 1H), 8.95 (s, 1H), 8.86 (d, J=8.4 Hz, 1H), 8.50-8.49 (m, 2H), 8.28 (s, 1H), 8.23 (s, 1H), 7.84 (d, J=12.0 Hz, 1H), 7.75-7.73 (m, 2H), 7.58 (d, J=7.2 Hz, 1H), 5.02-4.99 (m, 1H), 4.79-4.74 (m, 1H), 3.86-3.85 (m, 1H), 3.61 (d, J=12.6 Hz, 1H), 3.52-3.33 (m, 3H), 3.41-3.37 (m, 1H), 3.03-3.01 (m, 1H), 2.89-2.81 (m, 2H), 2.72 (s, 3H), 2.63-2.56 (m, 1H), 2.53-2.37 (m, 4H), 2.36-2.28 (m, 3H), 2.25-2.18 (m, 1H), 1.86-1.78 (m, 2H), 1.74 (d. J=6.6 Hz, 6H), 1.70-1.60 (m, 2H), 1.46-1.35 (5H). HRMS (ESI-TOF) m/z: [M+H]$^+$ calculated for $C_{46}H_{50}F_2N_{11}O_6$, 890.3908; found: 890.3931.

Scheme 8: Synthesis of example 32

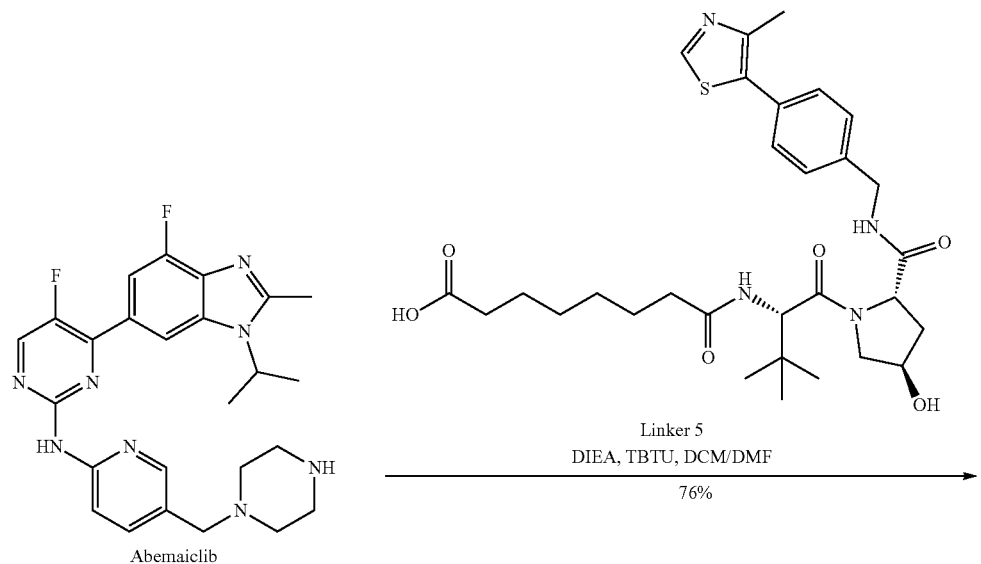

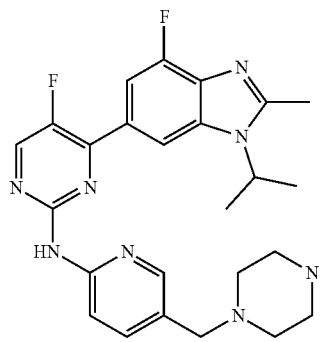
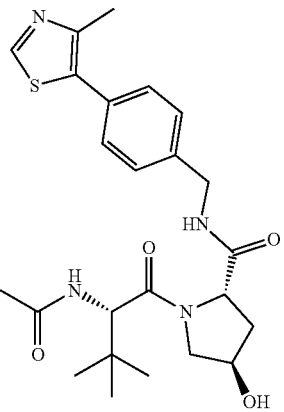

Example 32

(2S,4R)-1-((S)-2-(8-(4-((6-((5-Fluoro-4-(4-fluoro-1-isopropyl-2-methyl-1H-benzo[d]imidazol-6-yl)pyrimidin-2-yl)amino)pyridin-3-yl)methyl)piperazin-1-yl)-8-oxooctanamido)-3,3-dimethylbutanoyl)-4-hydroxy-N-(4-(4-methylthiazol-5-yl)benzyl)pyrrolidine-2-carboxamide (compound Example 32)

To a solution of linker 5 (29 mg, 0.05 mmol) and abemaiclib (19 mg, 0.04 mmol) in $CH_2Cl2$ (4 ml) and DMF (1 ml) were added DIEA (17 μl, 0.1 mmol) and TBTU (15 mg, 0.05 mmol). The reaction was stirred at RT for 1 h before being concentrated under reduced pressure. The resulting residue was purified by prep-HPLC to provide the Example 32 compound (31 mg, 76% over 2 steps). $^1$H NMR (600 MHz, $CD_3OD$) δ 8.88 (s, 1H), 8.55 (d, J=3.6 Hz, 1H), 8.36-8.35 (m, 2H), 8.25 (s, 1H), 7.86 (d, J=9.0 Hz, 1H), 7.81-7.78 (m, 2H), 7.48-7.41 (m, 3H), 4.66-4.51 (m, 4H), 4.36 (d, J=8.4 Hz, 1H), 3.91 (d, J=10.8 Hz, 1H), 3.81 (dd, J=10.8 Hz, 3.6 Hz, 1H), 3.66-3.54 (m, 7H), 2.71 (s, 3H), 2.51-2.48 (m, 6H), 2.40 (t, J=7.8 Hz, 2H), 2.34-2.21 (m, 3H), 2.12-2.06 (m, 1H), 1.73 (d, J=6.6 Hz, 6H), 1.63-1.60 (m, 4H), 1.37-1.27 (m, 5H), 1.05 (s, 9H). HRMS (ESI-TOF) m/z: [M+H]$^+$ calculated for $C_{55}H_{69}F_2N_{12}O_5S$, 1047.5197; found: 1047.5192.

Scheme 9: synthesis of example 33

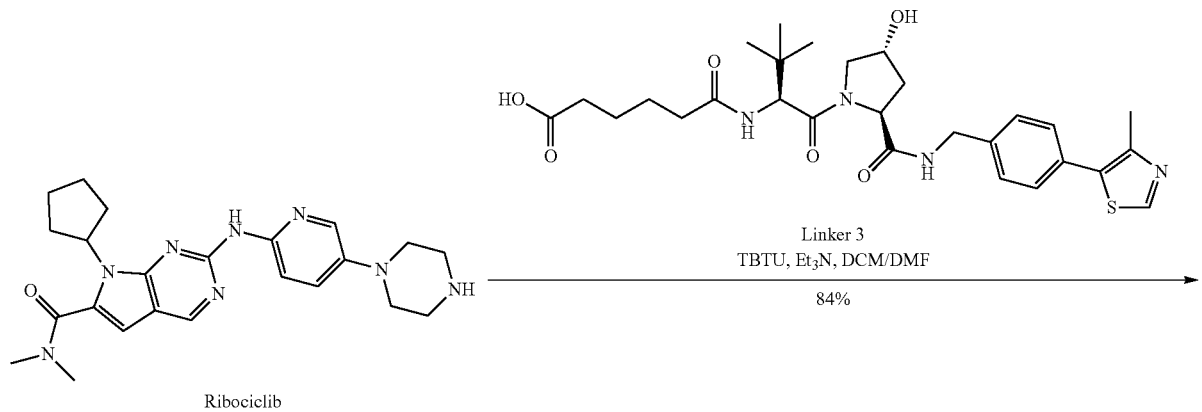

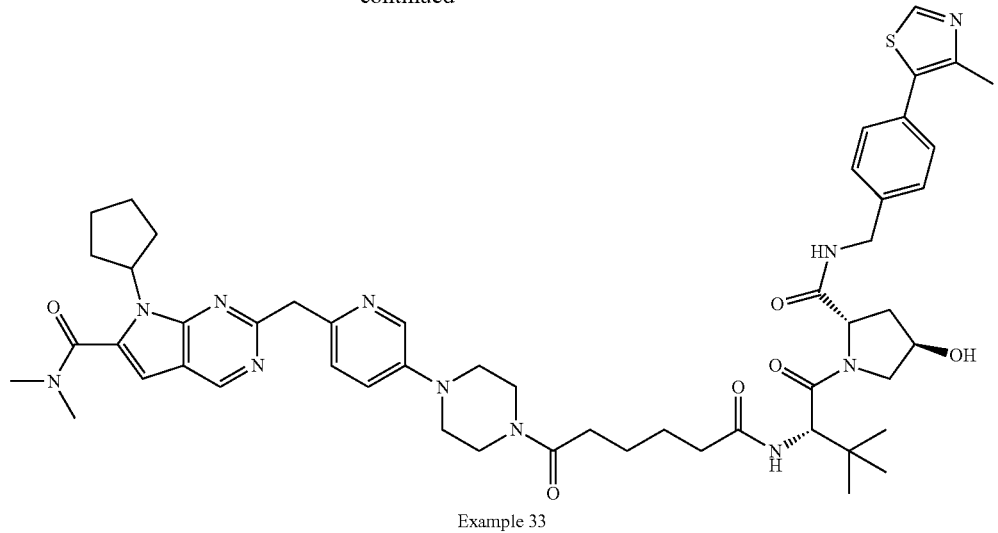

Example 33

7-Cyclopentyl-2-((5-(4-(6-(((S)-1-((2S,4R)-4-hydroxy-2-((4-(4-methylthiazol-5-yl)benzyl) carbamoyl)pyrrolidin-1-yl)-3,3-dimethyl-1-oxobutan-2-yl) amino)-6-oxohexanoyl)piperazin-1-yl)pyridin-2-yl) amino)-N,N-dimethyl-7H-pyrrolo[2,3-d]pyrimidine-6-carboxamide (compound Example 33)

To a solution of ribociclib (9 mg, 0.021 mmol) and linker 3 (14 mg, 0.025 mmol) in DCM/DMF (1:1, 2 ml) were added triethylamine (17 μl, 0.12 mmol) and TBTU (8 mg, 0.025 mmol). The reaction was stirred at RT for 1 h before being concentrated under reduced pressure. The resulting residue was dissolved in MeOH, and purified by prep-HPLC to yield the product (19 mg, 84%) as yellow solid. $^1$H NMR (600 MHz, CD$_3$OD) of major isomer (rotamer ratio 6:1) δ 9.02 (s, 1H), 8.97 (s, 1H), 8.08 (dd, J=9.6, 2.4 Hz, 1H), 7.87 (d, J=2.4 Hz, 1H), 7.48 (d, J=7.8 Hz, 2H), 7.45 (d, J=10.2 Hz, 1H), 7.43 (d, J=8.4 Hz, 1H), 6.82 (s, 1H), 4.86-4.80 (m, 1H), 4.65 (s, 1H), 4.62-4.52 (m, 3H), 4.38 (d, J=16.8 Hz, 1H), 3.93 (d, J=10.8 Hz, 1H), 3.84-3.76 (m, 5H), 3.29 (t, J=4.8 Hz, 2H), 3.24 (t, J=4.8 Hz, 2H), 3.19 (s, 3H), 3.17 (s, 3H), 2.52-2.47 (m, 7H), 2.39-2.30 (m, 3H), 2.14-2.08 (m, 5H), 1.77-1.64 (m, 6H), 1.06 (s, 9H); HRMS(ESI-TOF) m/z: [M+H]$^+$ calculated for C$_{51}$H$_{67}$N$_{12}$O$_6$S, 975.5022, found 975.5024.

The Example 34, 35, and 36 compounds were synthesized according to the procedures for the preparation of the Example 33 compound (above).

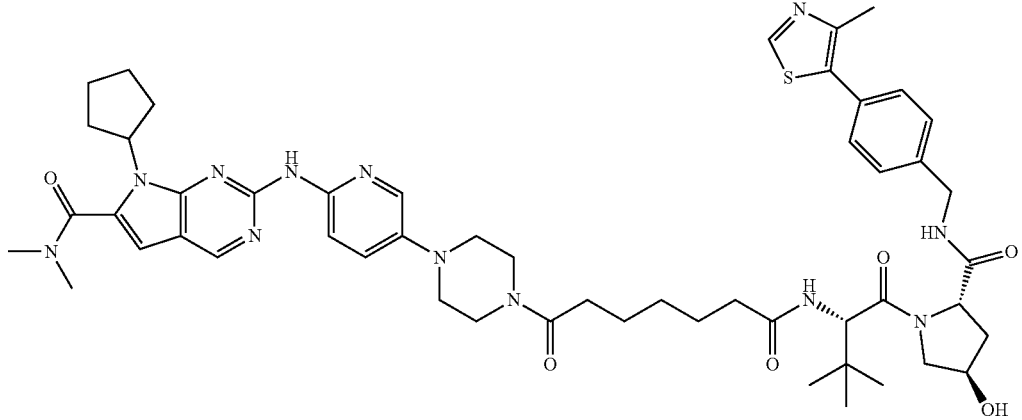

Example 34

7-Cyclopentyl-2-((5-(4-(7-(((S)-1-((2S,4R)-4-hydroxy-2-((4-(4-methylthiazol-5-yl)benzyl) carbamoyl)pyrrolidin-1-yl)-3,3-dimethyl-1-oxobutan-2-yl) amino)-7-oxoheptanoyl) piperazin-1-yl)pyridin-2-yl) amino)-N,N-dimethyl-7H-pyrrolo[2,3-d]pyrimidine-6-carboxamide (compound Example 34)

(17 mg, 83%) as yellow solid. $^1$H NMR (600 MHz, CD$_3$OD) of major isomer (rotamer ratio 7:2) δ 9.03 (s, 1H), 8.97 (s, 1H), 8.08 (dd, J=9.6, 2.4 Hz, 1H), 7.88 (d, J=2.4 Hz, 1H), 7.49 (d, J=8.4 Hz, 2H), 7.46-7.43 (m, 3H), 6.82 (s, 1H), 4.86-4.80 (m, 1H), 4.66 (s, 1H), 4.61-4.51 (m, 3H), 4.39 (d, J=14.4 Hz, 1H), 3.93 (d, J=10.8 Hz, 1H), 3.84-3.77 (m, 5H), 3.29 (t, J=4.8 Hz, 2H), 3.24 (t, J=4.8 Hz, 2H), 3.19 (s, 3H), 3.17 (s, 3H), 2.51-2.47 (m, 7H), 2.37-2.23 (m, 3H), 2.16-2.08 (m, 5H), 1.79-1.73 (m, 2H), 1.70-1.63 (m, 4H), 1.45-1.39 (m, 2H), 1.06 (s, 9H). HRMS(ESI-TOF) m/z: [M+H]$^+$ calculated for $C_{52}H_{69}N_{12}O_6S$, 989.5178, found 989.5180.

Example 35

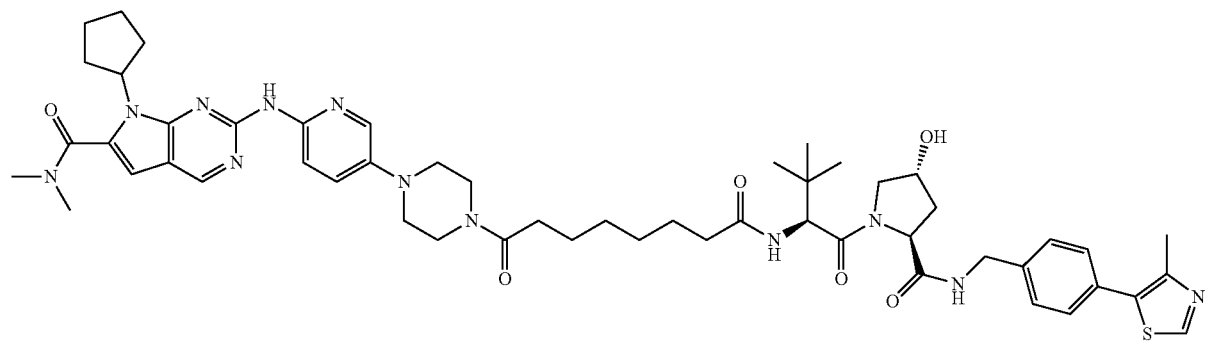

7-Cyclopentyl-2-((5-(4-(8-(((S)-1-((2S,4R)-4-hydroxy-2-((4-(4-methylthiazol-5-yl)benzyl) carbamoyl)pyrrolidin-1-yl)-3,3-dimethyl-1-oxobutan-2-yl) amino)-8-oxooctanoyl)piperazin-1-yl)pyridin-2-yl) amino)-N,N-dimethyl-7H-pyrrolo[2,3-d]pyrimidine-6-carboxamide (compound Example 35)

(25 mg, 98%) as yellow solid. $^1$H NMR (600 MHz, CD$_3$OD) of major isomer rotamer ration 8:1) δ 9.02 (s, 1H), 8.97 (s, 1H), 8.08 (dd, J=9.6, 2.4 Hz, 1H), 7.87 (d, J=2.4 Hz, 1H), 7.49 (d, J=8.4 Hz, 2H), 7.50 (d, J=11.2 Hz, 1H), 7.43 (d, J=8.4 Hz, 2H), 6.82 (s, 1H), 4.86-4.79 (m, 1H), 4.66 (s, 1H), 4.62-4.52 (m, 3H), 4.38 (d, J=15.6 Hz, 1H), 3.93 (d, J=10.8 Hz, 1H), 3.84-3.77 (m, 5H), 3.29-3.28 (m, 2H), 3.24-3.22 (m, 2H), 3.19 (s, 3H), 3.17 (s, 3H), 2.50 (s, 3H), 2.49-2.47 (m, 4H), 2.36-2.32 (m, 3H), 2.16-2.08 (m, 5H), 1.80-1.72 (m, 2H), 1.69-1.62 (m, 4H), 1.46-1.36 (m, 4H), 1.06 (s, 9H). HRMS(ESI-TOF) m/z: [M+H]$^+$ calculated for $C_{53}H_{71}N_{12}O_6S$, 1003.5335, found 1003.5361.

7-Cyclopentyl-2-((5-(4-(3-(3-(((S)-1-((2S,4R)-4-hydroxy-2-((4-(4-methylthiazol-5-yl)benzyl) carbamoyl)pyrrolidin-1-yl)-3,3-dimethyl-1-oxobutan-2-yl)amino)-3-oxopropoxy) propanoyl)piperazin-1-yl) pyridin-2-yl)amino)-N,N-dimethyl-7H-pyrrolo[2,3-d]pyrimidine-6-carboxamide (compound Example 36)

(17 mg, 74%) as yellow solid. $^1$H NMR (600 MHz, CD$_3$OD) of major isomer (rotamer ration 7:2) δ 9.04 (s, 1H), 8.96 (s, 1H), 8.07 (dd, J=9.6, 2.4 Hz, 1H), 7.85 (d, J=2.4 Hz, 1H), 7.45 (d, J=9.0 Hz, 2H), 7.43 (d, J=9.6 Hz, 1H), 7.40 (d, J=8.4 Hz, 2H), 6.81 (s, 1H), 4.85-4.79 (m, 1H), 4.70 (s, 1H), 4.58 (t, J=8.4 Hz, 1H), 4.54-4.51 (m, 1H), 4.49 (d, J=15.6 Hz, 1H), 4.38 (d, J=14.4 Hz, 1H), 3.93 (d, J=10.8 Hz, 1H), 3.84-3.78 (m, 7H), 3.74 (t, J=6.0 Hz, 2H), 3.28-3.22 (m, 4H), 3.19 (s, 3H), 3.17 (s, 3H), 2.81-2.71 (m, 2H), 2.60-2.48 (m, 7H), 2.28-2.25 (m, 1H), 2.16-2.08 (m, 5H), 1.79-1.72 (m, 2H), 1.07 (s, 9H). HRMS(ESI-TOF) m/z: [M+H]$^+$ calculated for $C_{51}H_{67}N_{12}O_7S$, 991.4971, found 991.4975.

Example 36

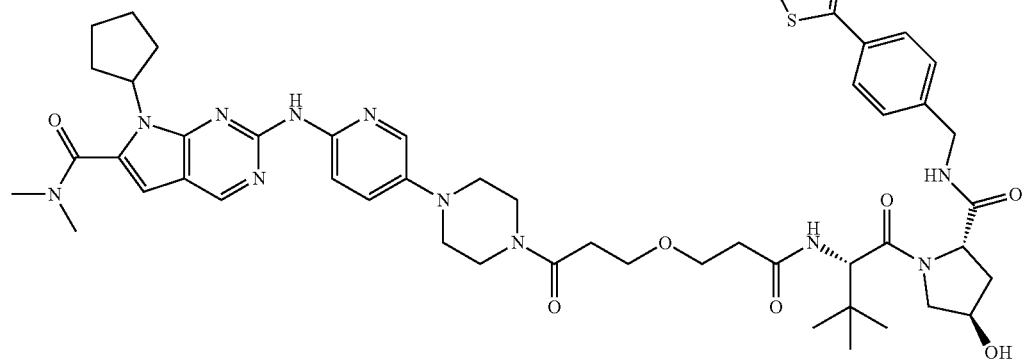

Scheme 10: synthesis of example 37

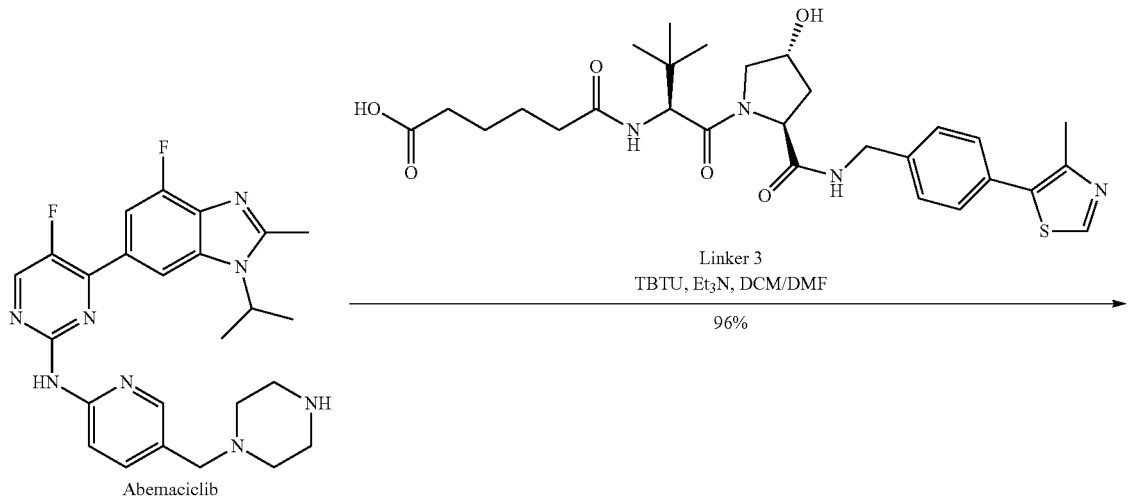

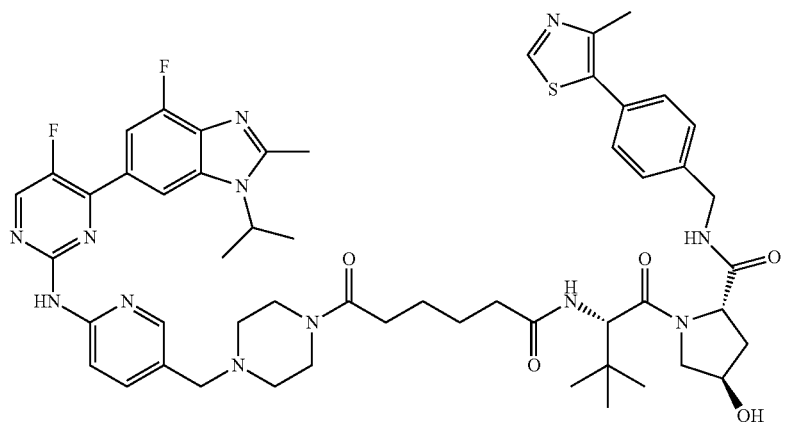

Example 37

(2S,4R)-1-((S)-2-(6-(4-((6-((5-Fluoro-4-(4-fluoro-1-isopropyl-2-methyl-1H-benzo[d]imidazol-6-yl)pyrimidin-2-yl)amino)pyridin-3-yl)methyl)piperazin-1-yl)-6-oxohexanamido)-3,3-dimethylbutanoyl)-4-hydroxy-N-(4-(4-methylthiazol-5-yl)benzyl) pyrrolidine-2-carboxamide (compound Example 37)

To a solution of abemaciclib (13 mg, 0.028 mmol) and linker 3 (18 mg, 0.032 mmol) in DCM/DMF (1:1, 2 ml) were added triethylamine (17 µl, 0.12 mmol) and TBTU (10 mg, 0.031 mmol). The reaction was stirred at RT for 1 h before being concentrated under reduced pressure. The resulting residue was dissolved in MeOH and purified by prep-HPLC to yield the desired product (31 mg, 96%) as white solid. $^1$H NMR (CD$_3$OD, 600 MHz) (1H buried in solvent peak) 9.13 (s, 1H), 8.85 (d, J=3.6 Hz, 1H), 8.57 (d, J=11.4 Hz, 1H), 8.36 (d, J=8.4 Hz, 1H), 8.14 (d, J=10.8 Hz, 1H), 7.86 (d, J=8.4 Hz, 1H), 7.50 (d, J=8.4 Hz, 2H), 7.44 (d, J=7.8 Hz, 2H), 5.15-5.10 (m, 1H), 4.65 (s, 1H), 4.62-4.51 (m, 5H), 4.39 (d, J=15.6 Hz, 1H), 3.93-3.82 (m, 6H), 3.41-3.33 (m, 4H), 2.94 (s, 3H), 2.51-2.45 (m, 5H), 2.39-2.29 (m, 2H), 2.26-2.23 (m, 1H), 2.12-2.08 (m, 1H), 1.82 (d, J=6.0 Hz, 6H), 1.72-1.62 (m, 4H), 1.06 (s, 9H). HRMS (ESI-TOF) m/z: [M+H]$^+$ calculated for C$_{53}$H$_{65}$F$_2$N$_{12}$O$_5$S [M+H]$^+$, 1019.4884, found 1019.4881.

The Example 38 compound was synthesized according to the procedures for the preparation of the Example 37 compound (above).

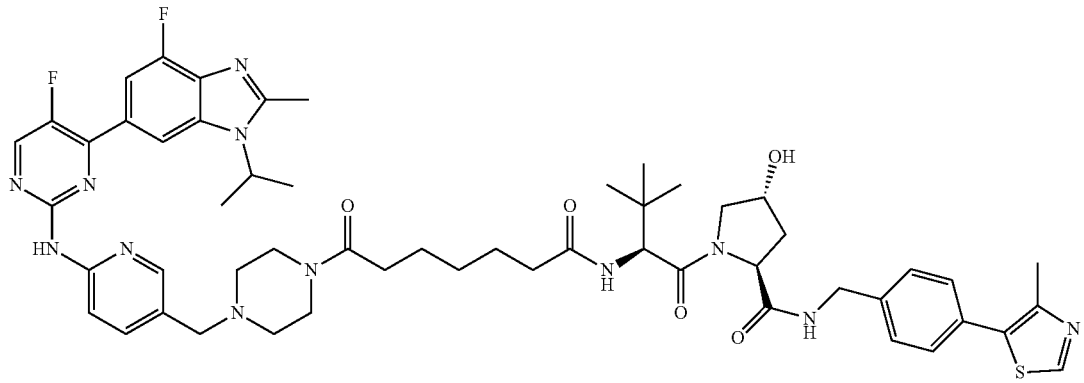

Example 38

(2S,4R)-1-((S)-2-(7-(4-((6-((5-Fluoro-4-(4-fluoro-1-isopropyl-2-methyl-1H-benzo[d]imidazol-6-yl)pyrimidin-2-yl)amino)pyridin-3-yl)methyl)piperazin-1-yl)-7-oxoheptanamido)-3,3-dimethylbutanoyl)-4-hydroxy-N-(4-(4-methylthiazol-5-yl)benzyl)pyrrolidine-2-carboxamide (compound Example 38)

(24 mg, 98%) as white solid. $^1$H NMR (CD$_3$OD, 600 MHz) (1H buried in solvent peak) δ 9.11 (s, 1H), 8.85 (d, J=3.6 Hz, 1H), 8.56 (d, J=9.6 Hz, 1H), 8.35 (d, J=8.4 Hz, 1H), 8.14 (d, J=10.8 Hz, 1H), 7.87 (d, J=8.4 Hz, 1H), 7.50 (d, J=7.2 Hz, 2H), 7.44 (d, J=9.0 Hz, 2H), 5.14-5.10 (m, 1H), 4.66 (s, 1H), 4.62-4.51 (m, 5H), 4.39 (d, J=15.6 Hz, 1H), 3.94-3.82 (m, 6H), 3.46-3.30 (m, 4H), 2.95 (s, 3H), 2.51 (s, 3H), 2.47 (t, J=7.8 Hz, 2H), 2.36-2.23 (m, 3H), 2.13-2.08 (m, 1H), 1.82 (d, J=6.0 Hz, 6H), 1.69-1.62 (m, 4H), 1.41-1.39 (m, 2H), 1.06 (s, 9H). HRMS(ESI-TOF) m/z: [M+H]$^+$ calculated for $C_{54}H_{67}F_2N_{12}O_5S$, 1033.5041, found 1033.5053.

Scheme 11: synthesis of example 39

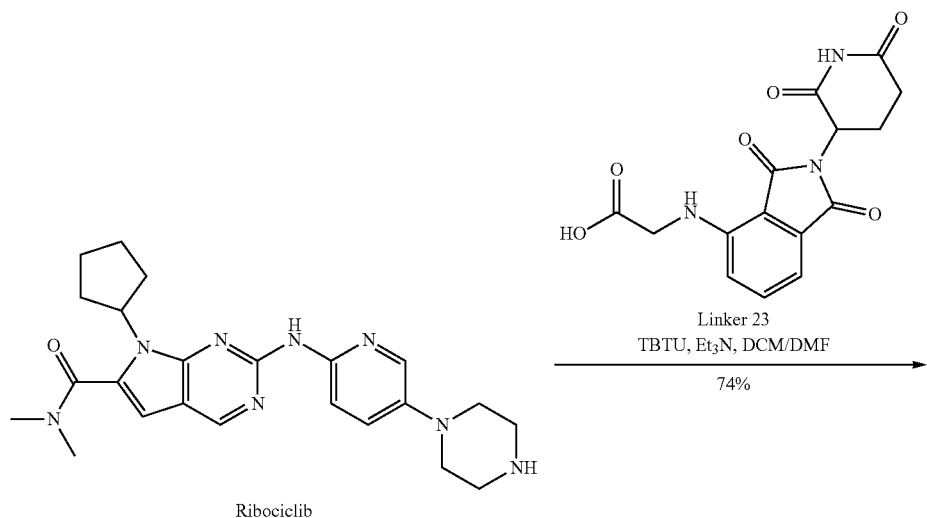

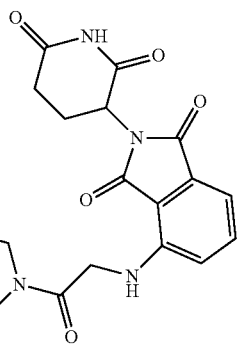

Example 39

7-Cyclopentyl-2-((5-(4-((2-(2,6-dioxopiperidin-3-yl)-1,3-dioxoisoindolin-4-yl)glycyl) piperazin-1-yl) pyridin-2-yl)amino)-N,N-dimethyl-7H-pyrrolo[2,3-d]pyrimidine-6-carboxamide (compound Example 39)

To a solution of ribociclib (12 mg, 0.027 mmol) and linker 23 (11 mg, 0.034 mmol) in DCM/DMF (1:1, 2 ml) were added triethylamine (17 µl, 0.12 mmol) and TBTU (12 mg, 0.038 mmol). The reaction solution was stirred at RT for 1 h before being concentrated under reduced pressure. The resulting residue was dissolved in MeOH and purified by prep-HPLC to yield the desired product (15 mg, 74%) as yellow solid. $^1$H NMR (CD$_3$OD, 600 MHz) δ 8.86 (s, 1H), 7.89 (dd, J=8.4, 2.4 Hz, 1H), 7.82 (d, J=2.4 Hz, 1H), 7.52-7.49 (m, 2H), 7.08 (d, J=7.2 Hz, 1H), 6.90 (d, J=8.4 Hz, 1H), 6.65 (s, 1H), 4.96-4.93 (m, 1H), 4.78-4.72 (m, 1H), 4.17 (s, 2H), 3.85-3.83 (m, 2H), 3.72-3.72 (m, 2H), 3.30-3.28 (m, 2H), 3.23-3.21 (m, 2H), 3.18 (s, 3H), 3.15 (s, 3H), 2.84-2.73 (m, 3H), 2.46-2.40 (m, 2H), 2.15-2.02 (m, 5H), 1.75-1.67 (m, 2H). HRMS(ESI-TOF) m/z: [M+H]$^+$ calculated for C$_{38}$H$_{41}$N$_{11}$O$_6$, 748.3314, found 748.3391.

Scheme 12: synthesis of example 40

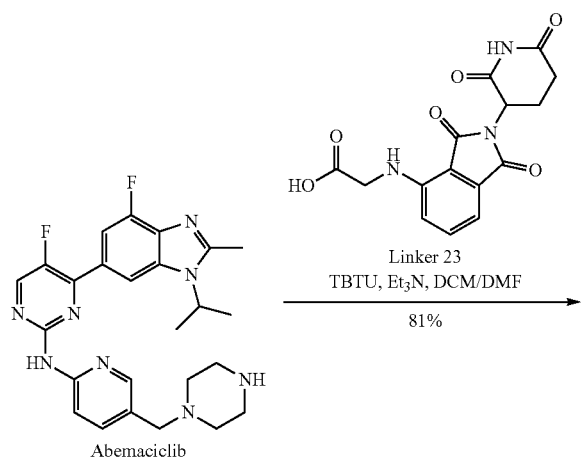

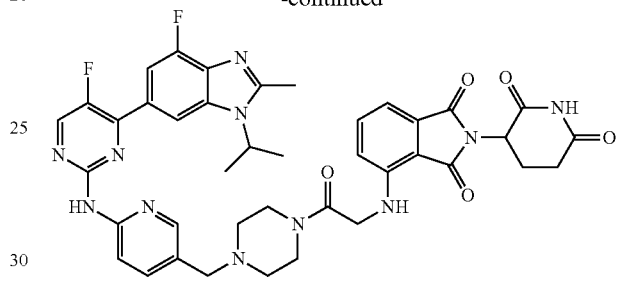

Example 40

2-(2,6-Dioxopiperidin-3-yl)-4-((2-(4-((6-((5-fluoro-4-(4-fluoro-1-isopropyl-2-methyl-1H-benzo[d]imidazol-6-yl)pyrimidin-2-yl)amino)pyridin-3-yl) methyl)piperazin-1-yl)-2-oxoethyl)amino) isoindoline-1,3-dione (compound Example 40)

To a solution of abemaciclib (12 mg, 0.025 mmol) and compound 23 (10 mg, 0.032 mmol) in DCM/DMF (1:1, 2 ml) were added triethylamine (17 µl, 0.12 mmol) and TBTU (11 mg, 0.034 mmol). The reaction was stirred at RT for 1 h before being concentrated under reduced pressure. The resulting residue was dissolved in MeOH and purified by prep-HPLC to yield the desired product (16 mg, 81%) as yellow solid. $^1$H NMR (CD$_3$OD, 600 MHz) δ 8.59 (d, J=2.4 Hz, 1H), 8.44 (s, 1H), 8.30 (s, 1H), 8.13 (s, 2H), 7.89 (d, J=10.8 Hz, 1H), 7.36 (t, J=7.2 Hz, 1H), 6.98 (d, J=7.2 Hz, 1H), 6.75 (d, J=8.4 Hz, 1H), 4.95-4.92 (m, 1H), 4.89-4.84 (m, 1H), 4.29 (s, 2H), 4.04 (s, 2H), 3.98-3.74 (m, 4H), 3.31-3.20 (m, 4H), 3.18 (s, 3H), 2.85-2.69 (m, 6H), 2.13-2.11 (m, 1H), 1.73 (d, J=7.8 Hz, 6H); HRMS(ESI-TOF) m/z: [M+H]$^+$ calculated for C$_{38}$H$_{41}$N$_{11}$O$_6$, 792.3176, found 792.3180.

Scheme 13: Synthesis of example 41

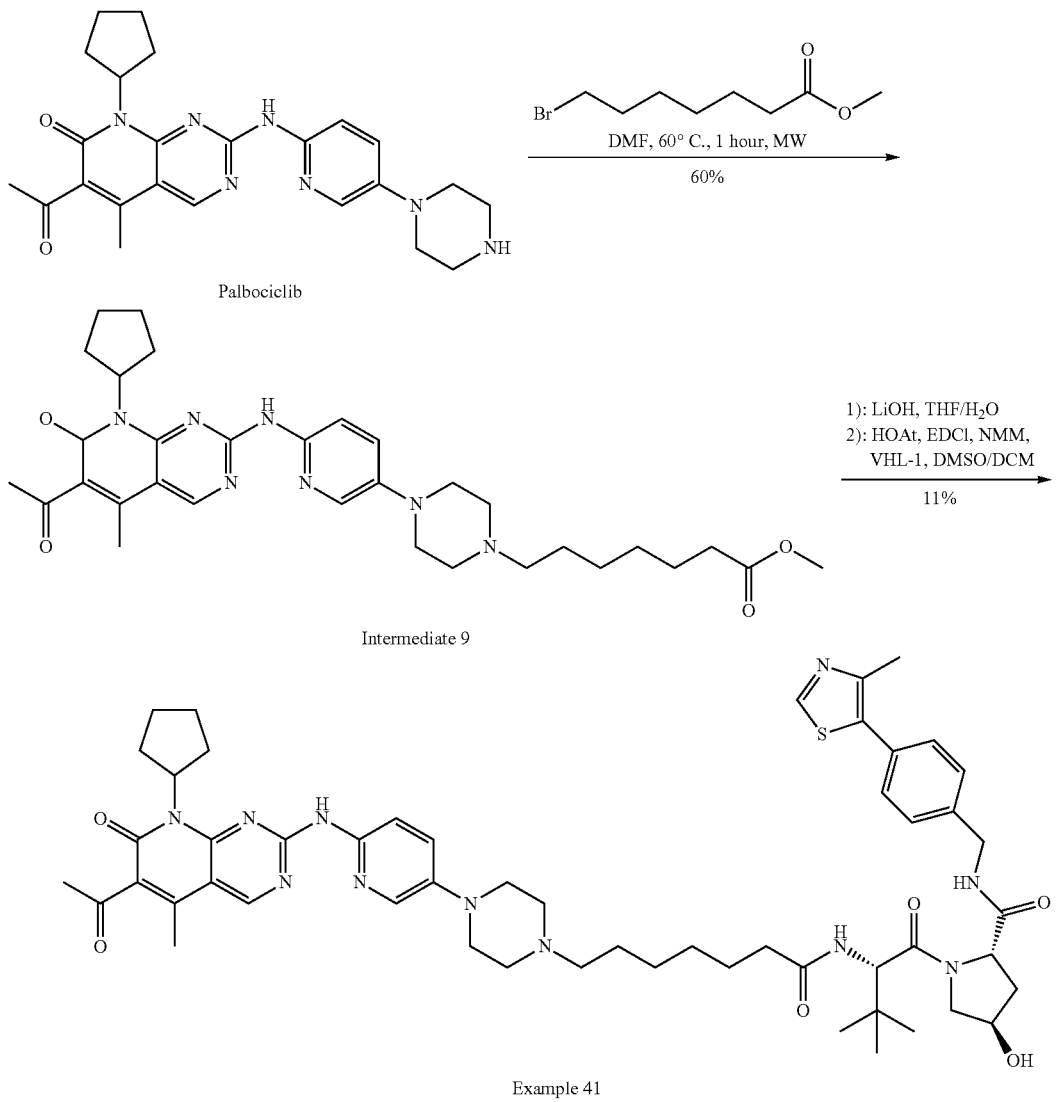

Methyl 7-(4-(6-(((6-acetyl-8-cyclopentyl-5-methyl-7-oxo-7,8-dihydropyrido[2,3-d]pyrimidin-2-yl)amino)pyridin-3-yl)piperazin-1-yl)heptanoate (Intermediate 9)

A solution of palbociclib (50 mg, 0.112 mmol), methyl 7-bromoheptanoate (75 mg, 0.335 mmol) and K$_2$CO$_3$ (46 mg, 0.335 mmol) in DMF (5 ml) was heated at 60° C. in a microwave reactor for 1 h. After being cooled to RT, the reaction mixture was filtered and concentrated, and the resulting residue was purified by prep-HPLC to yield the title compound (40 mg, 60%) as yellow solid. $^1$H NMR (600 MHz, CD$_3$OD) δ 9.10 (s, 1H), 8.21 (dd, J=9.6, 2.7 Hz, 1H), 7.98 (d, J=2.5 Hz, 1H), 7.59 (d, J=9.6 Hz, 1H), 5.99 (p, J=8.8 Hz, 1H), 3.93 (s, 2H), 3.75 (s, 2H), 3.65 (s, 3H), 3.38-3.16 (m, 6H), 2.49 (s, 3H), 2.42 (s, 3H), 2.37-2.25 (m, 4H), 2.13-2.03 (m, 2H), 1.94-1.86 (m, 2H), 1.85-1.78 (m, 2H), 1.72-1.59 (m, 4H), 1.47-1.36 (m, 4H). HRMS (ESI-TOF) m/z: [M+H]$^+$ calculated for C$_{32}$H$_{44}$N$_7$O$_4$, 590.3449; found: 590.3446.

(2S,4R)-1-((S)-2-(7-(4-(6-(((6-Acetyl-8-cyclopentyl-5-methyl-7-oxo-7,8-dihydropyrido[2,3-d]pyrimidin-2-yl)amino)pyridin-3-yl)piperazin-1-yl)heptanamido)-3,3-dimethylbutanoyl)-4-hydroxy-N-(4-(4-methylthiazol-5-yl)benzyl)pyrrolidine-2-carboxamide (compound Example 41)

To a stirring solution of intermediate 9 (40 mg, 0.0678 mmol) in THF/H$_2$O (10 ml/2 ml) was added anhydrous LiOH (3.3 mg, 0.136 mmol). After the reaction mixture was stirred overnight at RT, the reaction mixture was concentrated under reduced pressure and the resulting residue was dissolved in DCM/DMSO (5 ml/1 ml). To the resulting solution were added NMM (68 mg, 0.678 mmol), VHL-1 (32 mg, 0.0678 mmol), HOAt (14 mg, 0.102 mmol), and EDCI (19.5 mg, 0.102 mmol). After the mixture was stirred at RT overnight, the reaction was concentrated. The resulting residue was purified by prep-HPLC to yield the title compound (8 mg, 11%) as yellow solid. $^1$H NMR (600 MHz, CD$_3$OD) δ 9.10 (s, 1H), 8.98 (s, 1H), 8.20 (dd, J=9.5, 2.6 Hz, 1H), 7.97 (d, J=2.4 Hz, 1H), 7.58 (d, J=9.5 Hz, 1H), 7.47 (d, J=8.2 Hz, 2H), 7.42 (d, J=8.0 Hz, 2H), 6.05-5.96 (m, 1H), 4.64 (s, 1H), 4.58-4.47 (m, 3H), 4.37 (d, J=15.5 Hz, 1H), 3.99-3.84 (m, 3H), 3.84-3.79 (m, 1H), 3.80-3.66 (m, 2H), 3.34-3.18 (m, 6H), 2.50 (s, 3H), 2.48 (s, 3H), 2.43 (s, 3H), 2.36-2.26 (m, 4H), 2.23 (dd, J=13.1, 7.6 Hz, 1H), 2.14-2.05 (m, 3H), 1.94-1.86 (m, 2H), 1.84-1.75 (m, 2H), 1.74-1.61 (m, 4H), 1.48-1.38 (m, 4H), 1.04 (s, 9H). HRMS (ESI-TOF) m/z: [M+H]$^+$ calculated for $C_{53}H_{70}N_{11}O_6S$, 988.5226; found: 988.5226.

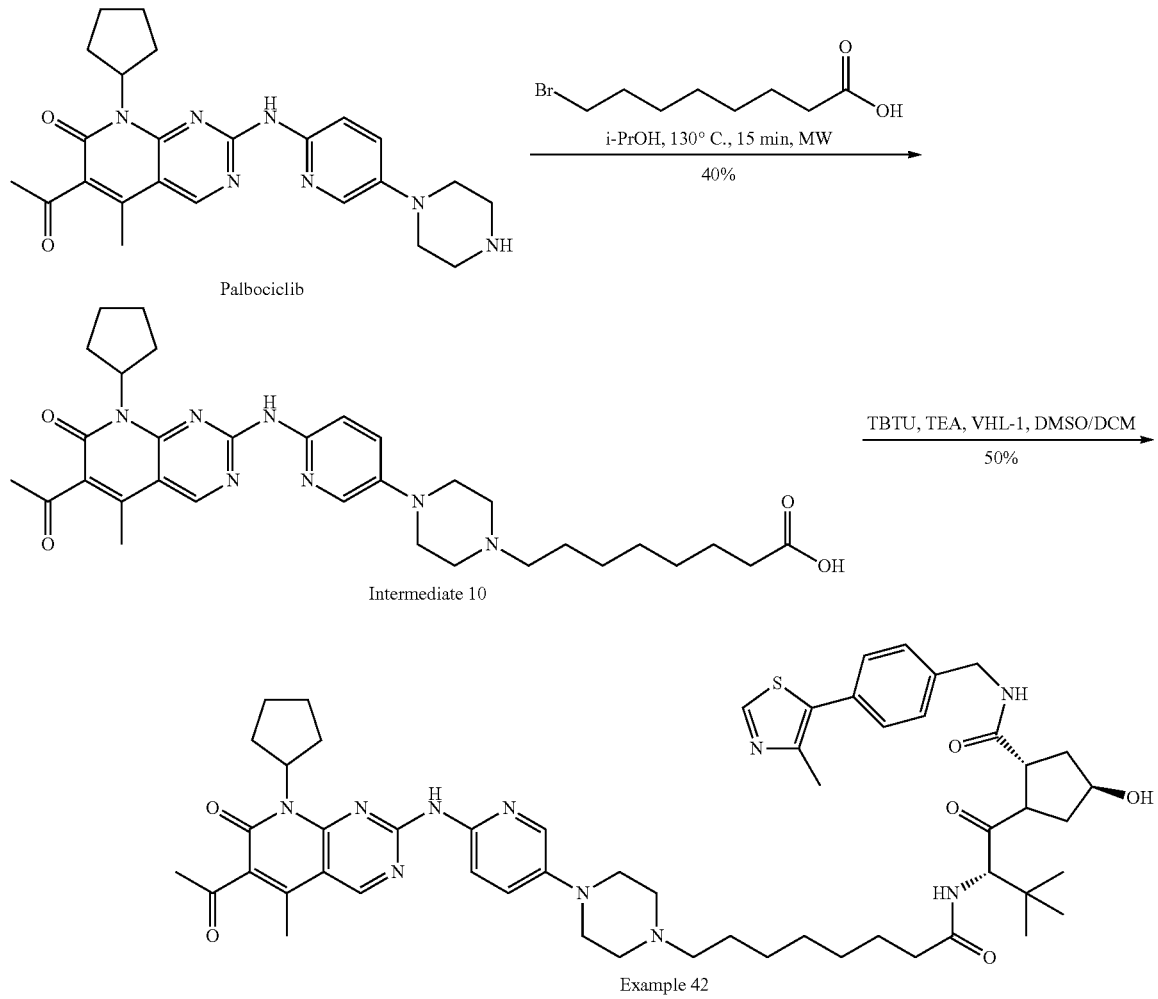

Scheme 14: Synthesis of example 42

(2S,4R)-1-((S)-2-(8-(4-(6-((6-Acetyl-8-cyclopentyl-5-methyl-7-oxo-7,8-dihydropyrido[2,3-d]pyrimidin-2-yl)amino)pyridin-3-yl)piperazin-1-yl)octanamido)-3,3-dimethylbutanoyl)-4-hydroxy-N-(4-(4-methylthiazol-5-yl)benzyl)pyrrolidine-2-carboxamide (example 42)

A solution of palbociclib (45 mg, 0.1 mmol), 8-bromooctanoic acid (64 mg, 0.28 mmol) and TEA (0.05 mL, 0.36 mmol) in i-PrOH (1 ml) was heated at 130° C. in a microwave reactor for 15 min. After being cooled to RT, the reaction mixture was concentrated, and the resulting residue was purified by prep-HPLC to yield the intermediate 10 (24 mg, 40%) as yellow solid. To a stirring solution of intermediate 10 (24 mg, 0.04 mmol) in DCM/DMSO (5 ml/1 ml) were added TEA (0.05 mL, 0.36 mmol), VHL-1 (20 mg, 0.043 mmol), and TBTU (12 mg, 0.038 mmol). After the mixture was stirred at RT overnight, the reaction was concentrated. The resulting residue was purified by prep-HPLC to yield the title compound (20 mg, 50%) as yellow solid. $^1$H NMR (600 MHz, CD$_3$OD) δ 9.13 (s, 1H), 9.07 (s, 1H), 8.23 (dd, J=9.6, 3.0 Hz, 1H), 8.00 (d, J=2.8 Hz, 1H), 7.60 (d, J=9.6 Hz, 1H), 7.50 (d, J=8.1 Hz, 2H), 7.45 (d, J=8.2 Hz, 2H), 6.03 (p, J=8.7 Hz, 1H), 4.67 (s, 1H), 4.60-4.53 (m, 3H), 4.40 (d, J=15.5 Hz, 1H), 3.96-3.71 (m, 6H), 3.30-3.20 (m, 6H), 2.52 (s, 3H), 2.51 (s, 3H), 2.45 (s, 3H), 2.37-2.24 (m, 5H), 2.17-2.03 (m, 3H), 1.97-1.87 (m, 2H), 1.84-1.80 (m, 2H), 1.77-1.60 (m, 4H), 1.50-1.33 (m, 6H), 1.05 (s, 9H). HRMS (ESI-TOF) m/z: [M+H]$^+$ calculated for $C_{54}H_{72}N_{11}O_6S$, 1002.5389; found: 1002.5390.

Scheme 15: Synthesis of example 43

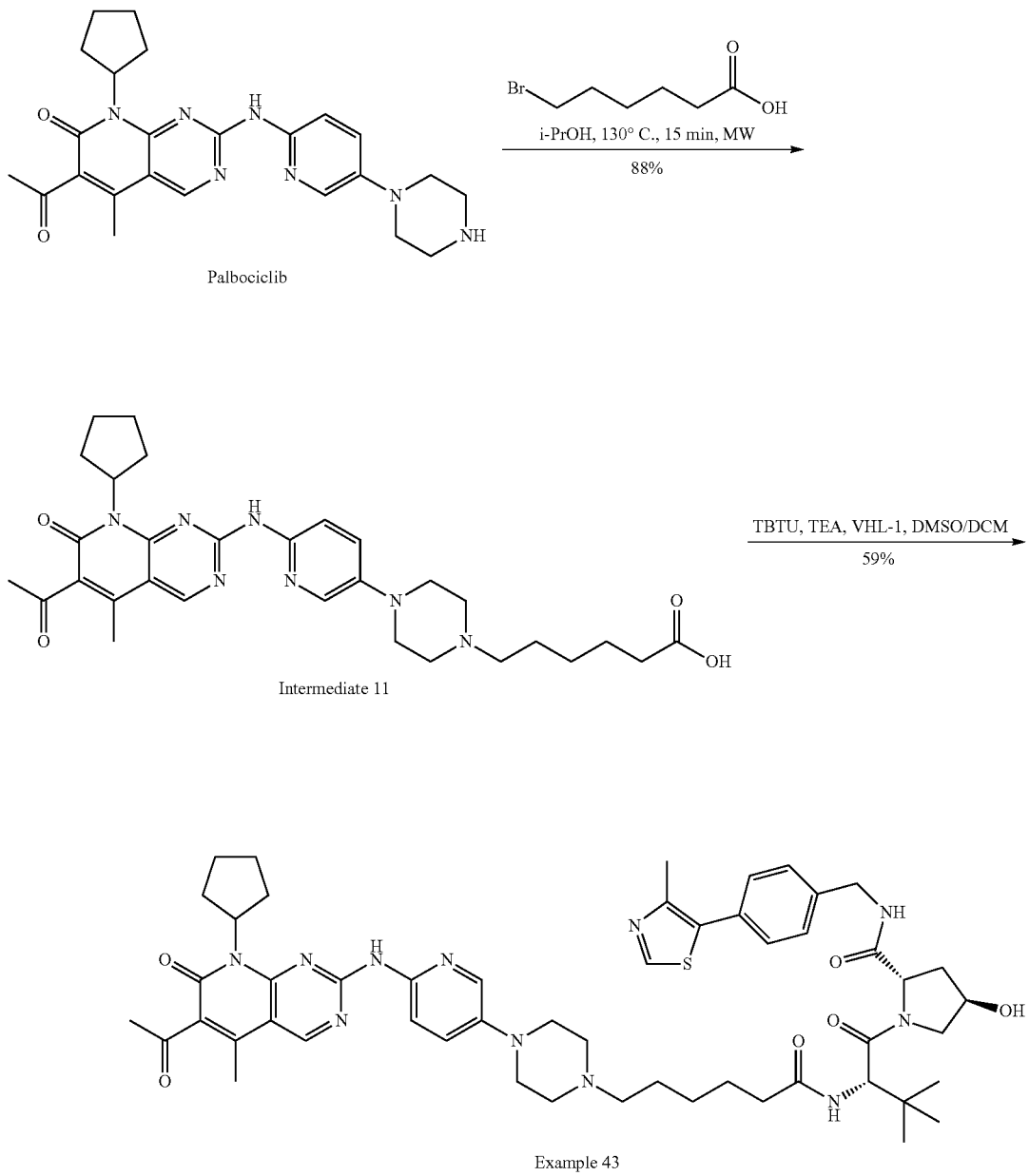

(2S,4R)-1-((S)-2-(6-(4-(6-((6-Acetyl-8-cyclopentyl-5-methyl-7-oxo-7,8-dihydropyrido[2,3-d]pyrimidin-2-yl)amino)pyridin-3-yl)piperazin-1-yl)hexanamido)-3,3-dimethylbutanoyl)-4-hydroxy-N-(4-(4-methylthiazol-5-yl)benzyl)pyrrolidine-2-carboxamide (example 43)

A solution of palbociclib (40 mg, 0.09 mmol), 6-bromohexanoic acid (55 mg, 0.28 mmol) and TEA (0.05 mL, 0.36 mmol) in i-PrOH (1 ml) was heated at 130° C. in a microwave reactor for 15 min. After being cooled to RT, the reaction mixture was concentrated, and the resulting residue was purified by prep-HPLC to yield the intermediate 11 (44 mg, 88%) as yellow solid. To a stirring solution of intermediate 11 (44 mg, 0.065 mmol) in DCM/DMSO (5 ml/1 ml) were added TEA (0.05 mL, 0.36 mmol), VHL-1 (34 mg, 0.073 mmol), and TBTU (22 mg, 0.070 mmol). After the mixture was stirred at RT overnight, the reaction was concentrated. The resulting residue was purified by prep-HPLC to yield the title compound (37 mg, 59%) as yellow solid. $^1$H NMR (600 MHz, CD$_3$OD) δ 9.12 (s, 1H), 9.12 (s, 1H), 8.23 (dd, J=9.8, 2.4 Hz, 1H), 8.00 (d, J=2.7 Hz, 1H), 7.60 (d, J=9.6 Hz, 1H), 7.49 (d, J=7.8 Hz, 2H), 7.44 (d, J=8.1 Hz, 2H), 6.02 (p, J=8.8 Hz, 1H), 4.67 (s, 1H), 4.62-4.49 (m, 3H), 4.40 (d, J=15.5 Hz, 1H), 3.96-3.71 (m, 6H), 3.30-3.20 (m, 6H), 2.52 (s, 3H), 2.51 (s, 3H), 2.45 (s, 3H), 2.40-2.21 (m, 5H), 2.16-2.05 (m, 3H), 1.97-1.88 (m, 2H), 1.88-1.78 (m, 2H), 1.72-1.67 (m 4H), 1.49-1.40 (m, 2H), 1.07 (s, 9H). HRMS (ESI-TOF) m/z: [M+H]$^+$ calculated for C$_{52}$H$_{68}$N$_{11}$O$_6$S, 974.5069; found: 974.5069.

Scheme 16: Synthesis of example 44

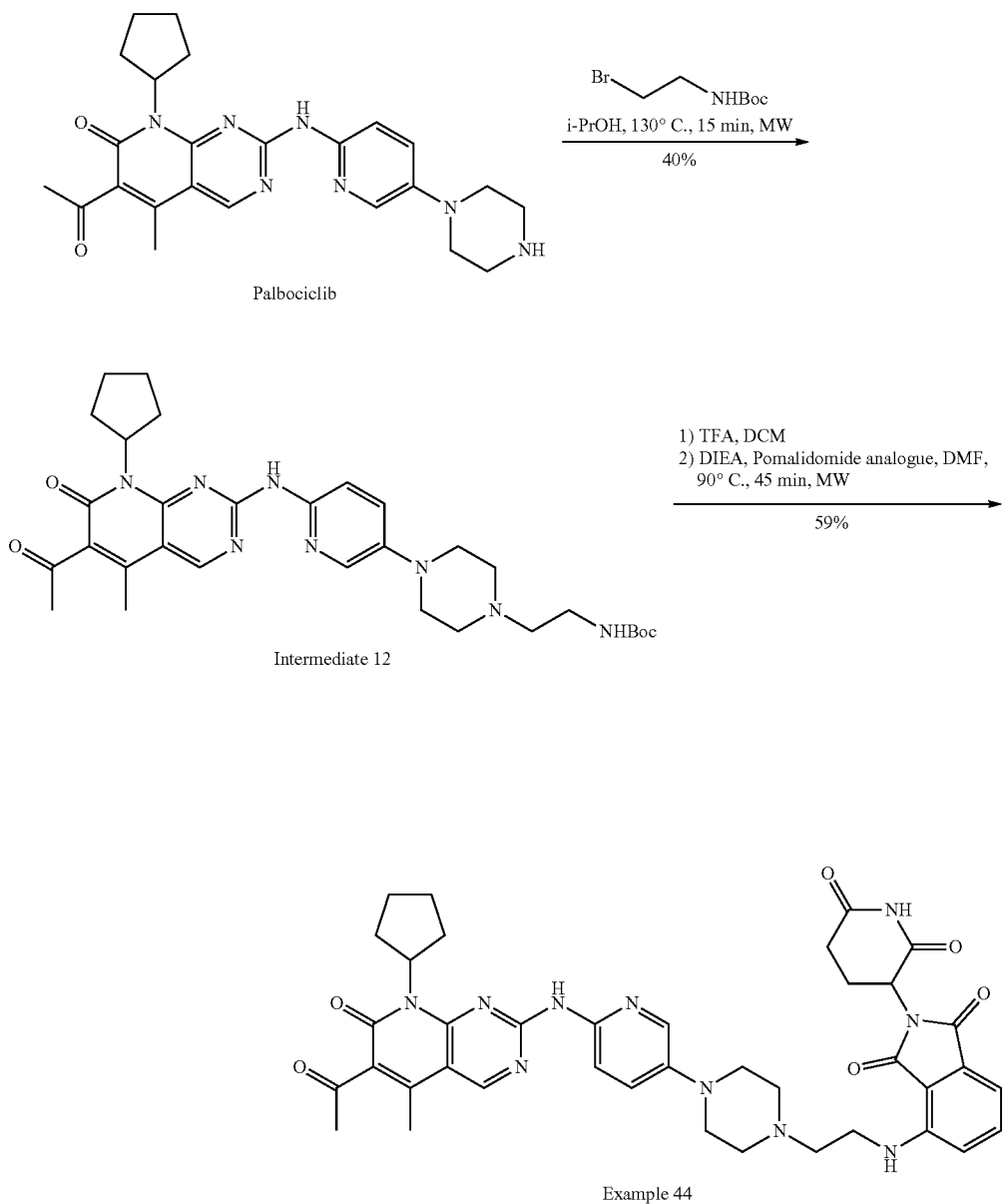

Example 44

4-((2-(4-(6-(((6-Acetyl-8-cyclopentyl-5-methyl-7-oxo-7,8-dihydropyrido[2,3-d]pyrimidin-2-yl)amino)pyridin-3-yl)piperazin-1-yl)ethyl)amino)-2-(2,6-dioxopiperidin-3-yl)isoindoline-1,3-dione (example 44)

A solution of palbociclib (45 mg, 0.1 mmol), tert-butyl (2-bromoethyl)carbamate (69 mg, 0.31 mmol) and TEA (0.05 mL, 0.36 mmol) in i-PrOH (1 ml) was heated at 130° C. in a microwave reactor for 15 min. After being cooled to RT, the reaction mixture was concentrated. The resulting residue was purified by prep-HPLC to yield the intermediate 12 (24 mg, 40%) as yellow solid. To a stirring solution of intermediate 12 (24 mg, 0.04 mmol) in DCM (2 mL) was added TFA (1 mL). The mixture was stirred at RT and the reaction progress was monitored by LC/MS. After completion of the reaction, the reaction solution was concentrated, and the resulting residue was dissolved in DMF (1 ml). To this solution were added TEA (0.05 mL, 0.36 mmol) and pomalidomide analogue (17 mg, 0.06 mmol). The resulting mixture was heated at 90° C. in a microwave reactor for 45 min. After being cooled to RT, the reaction mixture was concentrated, and the resulting residue was purified by prep-HPLC to yield the title compound (4 mg, 13%) as yellow solid. $^1$H NMR (600 MHz, CD$_3$OD) δ 9.10 (s, 1H), 8.14 (dd, J=9.5, 2.7 Hz, 1H), 8.01 (d, J=2.8 Hz, 1H), 7.70-7.65 (m, 2H), 7.22 (d, J=7.8 Hz, 1H), 7.21 (d, J=6.6 Hz, 1H), 6.02 (p, J=8.9 Hz, 1H), 5.11 (dd, J=12.5, 5.5 Hz, 1H), 3.90 (t, J=6.2 Hz, 2H), 3.63 (br, 8H), 3.55 (t, J=6.1 Hz, 2H), 2.94-2.86 (m, 1H), 2.80-2.65 (m, 2H), 2.52 (s, 3H), 2.43 (s, 3H), 2.38-2.26 (m, 42H), 2.17-2.05 (m, 3H), 1.99-1.84 (m, 2H), 1.77-1.64 (m, 2H). HRMS (ESI-TOF) m/z: [M+H]$^+$ calculated for C$_{39}$H$_{43}$N$_{10}$O$_6$, 747.3362; found: 747.3342.

Scheme 17: Synthesis of example 45

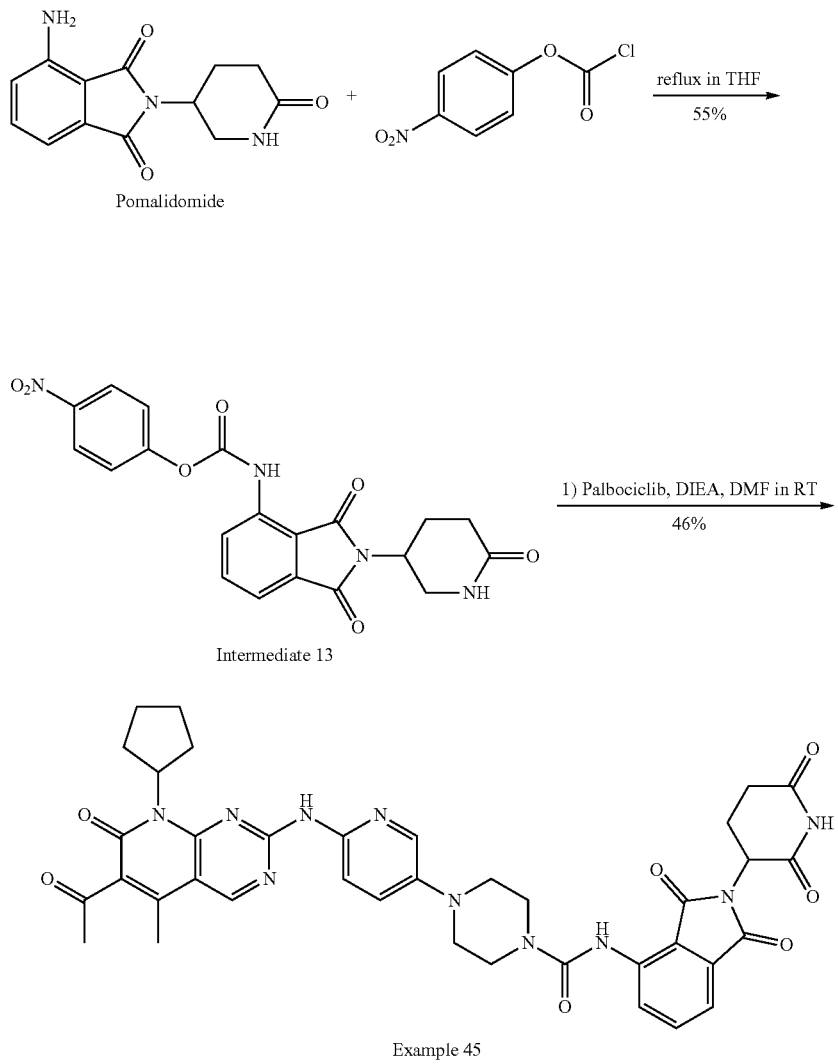

Example 45

4-(6-(((6-Acetyl-8-cyclopentyl-5-methyl-7-oxo-7,8-dihydropyrido[2,3-d]pyrimidin-2-yl)amino)pyridin-3-yl)-N-(2-(2,6-dioxopiperidin-3-yl)-1,3-dioxoisoindolin-4-yl)piperazine-1-carboxamide (example 45)

A solution of pomalidomide (278 mg, 1 mmol), 4-nitrophenyl carbonochloridate (307 mg, 1.52 mmol) in THF (5 ml) was heated at reflux overnight. After being cooled to RT, the reaction mixture was concentrated. The resulting residue was washed with ethyl acetate, dried over NaSO₄, and concentrated to yield the intermediate 13 (240 mg, 55%) as yellow solid. To a stirring solution of intermediate 13 (19 mg, 0.043 mmol) in DMF (1 mL) were added DIEA (0.014 mL, 0.1 mmol) and palbociclib (18 mg, 0.041 mmol). The mixture was stirred at RT overnight, before being concentrated. The resulting residue was purified by prep-HPLC to yield the title compound (14 mg, 46%) as yellow solid. $^1$H NMR (600 MHz, CD$_3$OD) δ 9.07 (s, 1H), 8.56 (d, J=8.5 Hz, 1H), 8.10 (dd, J=9.6, 2.6 Hz, 1H), 7.78-7.70 (m, 1H), 7.64 (d, J=8.8 Hz, 1H), 7.51 (d, J=7.3 Hz, 1H), 5.97 (p, J=8.9 Hz, 1H), 5.07 (dd, J=12.5, 5.5 Hz, 1H), 3.86-3.79 (m, 4H), 3.45-3.40 (m, 4H), 2.89-2.72 (m, 3H), 2.54 (s, 3H), 2.44 (s, 3H), 2.33-2.27 (m, 2H), 2.22-2.15 (m, 1H), 2.11-2.06 (m, 2H), 1.96-1.86 (m, 2H), 1.73-1.59 (m, 2H). HRMS (ESI-TOF) m/z: [M+H]⁺ calculated for C$_{38}$H$_{39}$N$_{10}$O$_7$, 747.2998; found: 747.2970.

Scheme 18: Synthesis of example 46

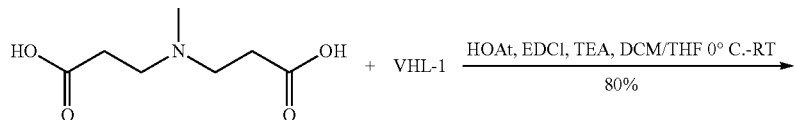

-continued

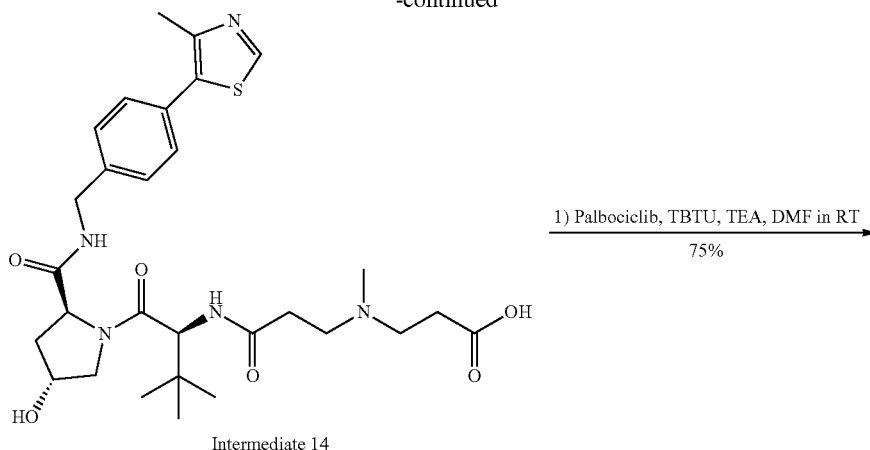

Intermediate 14

1) Palbociclib, TBTU, TEA, DMF in RT
75%

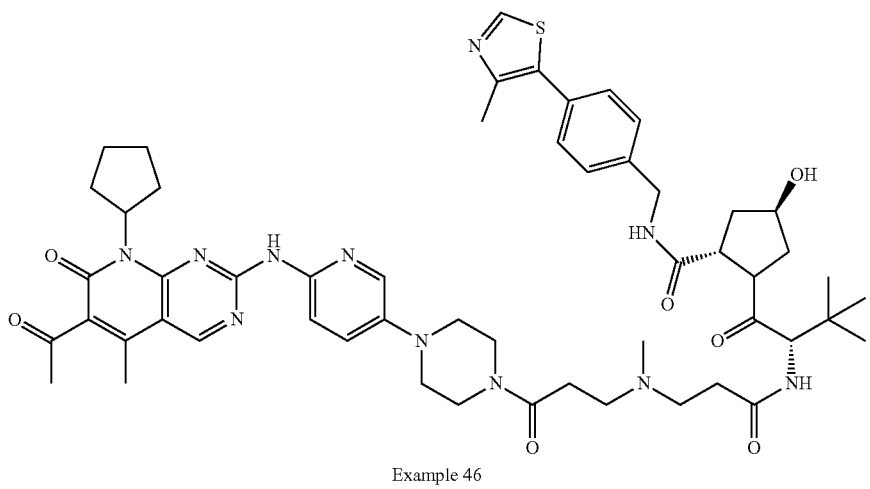

Example 46

3-((3-(((S)-1-((2S,4R)-4-Hydroxy-2-((4-(4-methyl-thiazol-5-yl)benzyl)carbamoyl)pyrrolidin-1-yl)-3,3-dimethyl-1-oxobutan-2-yl)amino)-3-oxopropyl)(methyl)amino)propanoic acid (intermediate 14)

To a solution of 3,3'-(methylazanediyl)dipropionic acid (700 mg, 4 mmol) in DMSO/THF (1:1, 10 ml) were added VHL-1 (472 mg, 1 mmol), triethylamine (0.5 ml, 3.5 mmol), HOAt (173 mg, 1.3 mmol), and EDCI (242 mg, 1.3 mmol) sequentially at 0° C. The resulting solution was stirred for 2 h at 0° C., before being warmed to room temperature (RT). After being stirred overnight at RT, the reaction was quenched with water, and concentrated under reduced pressure. The resulting residue was purified by reverse-phase chromatography to yield the title compound (470 mg, 80%) as white solid. $^1$H NMR (600 MHz, CD$_3$OD) δ 8.93 (s, 1H), 7.49 (d, J=8.7 Hz, 2H), 7.44 (d, J=8.1 Hz, 2H), 4.61-4.54 (m, 4H), 4.37 (d, J=15.4 Hz, 1H), 3.98 (d, J=11.0 Hz, 1H), 3.82 (dd, J=10.9, 3.8 Hz, 1H), 3.37 (s, 4H), 2.92 (s, 3H), 2.87 (dt, J=18.1, 6.5 Hz, 4H), 2.50 (s, 3H), 2.28-2.22 (m, 1H), 2.16-2.09 (m, 1H), 1.08 (s, 9H).

(2S,4R)-1-((S)-2-(3-((3-(4-(6-((6-Acetyl-8-cyclopentyl-5-methyl-7-oxo-7,8-dihydropyrido[2,3-d]pyrimidin-2-yl)amino)pyridin-3-yl)piperazin-1-yl)-3-oxopropyl)(methyl)amino)propanamido)-3,3-dimethylbutanoyl)-4-hydroxy-N-(4-(4-methylthiazol-5-yl)benzyl)pyrrolidine-2-carboxamide (example 46)

To a stirring solution of intermediate 14 (22 mg, 0.031 mmol) in DMF (1 ml) were added TEA (0.015 mL, 0.11 mmol), palbociclib (13.1 mg, 0.029 mmol), and TBTU (11.3 mg, 0.035 mmol). The mixture was stirred at RT overnight before being concentrated. The resulting residue was purified by prep-HPLC to yield the title compound (22 mg, 75%) as yellow solid. $^1$H NMR (600 MHz, CD$_3$OD) δ 9.11 (s, 1H), 8.92 (s, 1H), 8.19 (d, J=7.9 Hz, 1H), 7.93 (d, J=2.7 Hz, 1H), 7.59 (d, J=9.6 Hz, 1H), 7.47 (d, J=7.8 Hz, 2H), 7.42 (d, J=8.1 Hz, 2H), 6.03 (p, J=8.8 Hz, 1H), 4.65-4.49 (m, 4H), 4.38 (d, J=15.5 Hz, 1H), 3.97 (d, J=10.8 Hz, 1H), 3.90-3.64 (m, 5H), 3.64-3.51 (m, 2H), 3.43-3.36 (m, 4H), 3.10-3.02 (m, 2H), 2.93 (s, 3H), 2.93-2.85 (m, 4H), 2.52 (s, 3H), 2.49 (s, 3H), 2.45 (s, 3H), 2.37-2.29 (m, 2H), 2.29-2.20 (m, 1H), 2.16-2.07 (m, 3H), 1.97-1.88 (m, 2H), 1.76-1.66 (m, 2H), 1.07 (d, J=10.7 Hz, 9H). HRMS (ESI-TOF) m/z: [M+H]$^+$ calculated for C$_{53}$H$_{69}$N$_{12}$O$_7$S, 1017.5127; found: 1017.5013.

Scheme 18: Synthesis of example 47

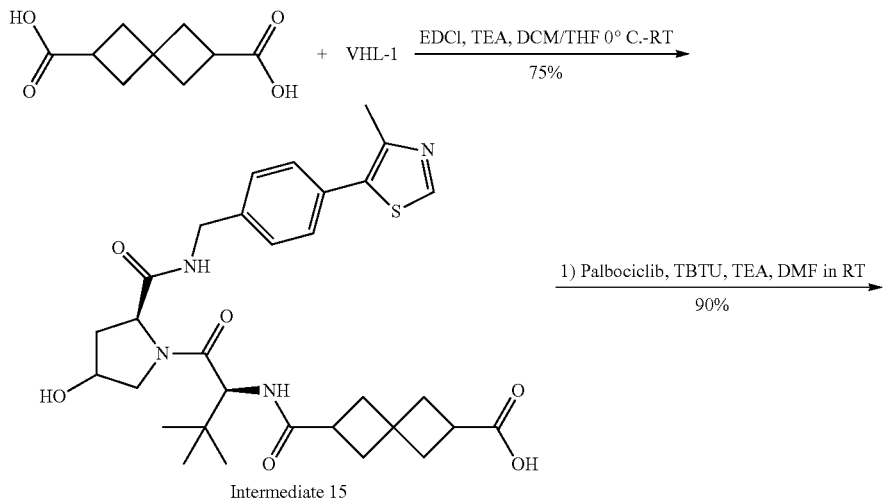

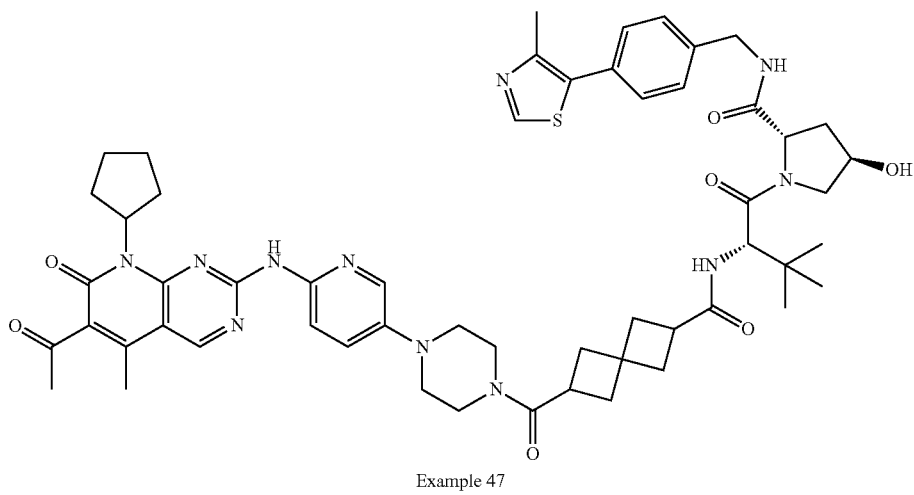

Example 47

(2S,4R)-1-((S)-2-(6-(4-(6-((6-Acetyl-8-cyclopentyl-5-methyl-7-oxo-7,8-dihydropyrido[2,3-d]pyrimidin-2-yl)amino)pyridin-3-yl)piperazine-1-carbonyl)spiro[3.3]heptane-2-carboxamido)-3,3-dimethylbutanoyl)-4-hydroxy-N-(4-(4-methylthiazol-5-yl)benzyl)pyrrolidine-2-carboxamide (example 47)

To a solution of spiro[3.3]heptane-2,6-dicarboxylic acid (250 mg, 1.36 mmol) in DCM/THF (1:1, 5 ml) were added VHL-1 (218 mg, 0.47 mmol), triethylamine (0.21 ml, 1.4 mmol), and EDCI (112 mg, 0.59 mmol) sequentially at 0° C. The resulting solution was stirred for 2 h at 0° C., before being warmed to room temperature (RT). After stirring overnight at RT, the reaction was quenched with water, and concentrated under reduced pressure. The resulting residue was purified by reverse-phase chromatography to yield the intermediate 15 (210 mg, 75%) as white solid. To a stirring solution of intermediate 15 (19 mg, 0.031 mmol) in DMF (1 ml) were added TEA (0.01 mL, 0.07 mmol), palbociclib (12.7 mg, 0.028 mmol), and TBTU (14.2 mg, 0.044 mmol). The mixture was stirred at RT overnight before being concentrated. The resulting residue was purified by prep-HPLC to yield the title compound (26 mg, 90%) as yellow solid. $^1$H NMR (600 MHz, CD$_3$OD) δ 9.11 (s, 1H), 8.97 (s, 1H), 8.21 (dd, J=9.6, 3.0 Hz, 1H), 7.88 (d, J=2.4 Hz, 1H), 7.57 (d, J=9.6 Hz, 1H), 7.48 (dd, J=8.0, 1.6 Hz, 2H), 7.45-7.42 (m, 2H), 6.02 (p, J=8.8 Hz, 1H), 4.69-4.62 (m, 1H), 4.62-4.47 (m, 3H), 4.41-4.27 (m, 1H), 3.92 (dd, J=11.0, 4.4 Hz, 1H), 3.86-3.70 (m, 3H), 3.71-3.56 (m, 2H), 3.37-3.22 (m, 6H), 3.17-3.03 (m, 1H), 2.52 (s, 3H), 2.50 (s, 3H), 2.45 (s, 3H), 2.40-2.04 (m, 13H), 1.96-1.88 (m, 2H), 1.76-1.68 (m, 2H), 1.04 (d, J=3.4 Hz, 9H). HRMS (ESI-TOF) m/z: [M+H]$^+$ calculated for C$_{55}$H$_{68}$N$_{11}$O$_7$S, 1026.5018; found: 1026.4985.

Scheme 19: Synthesis of example 48

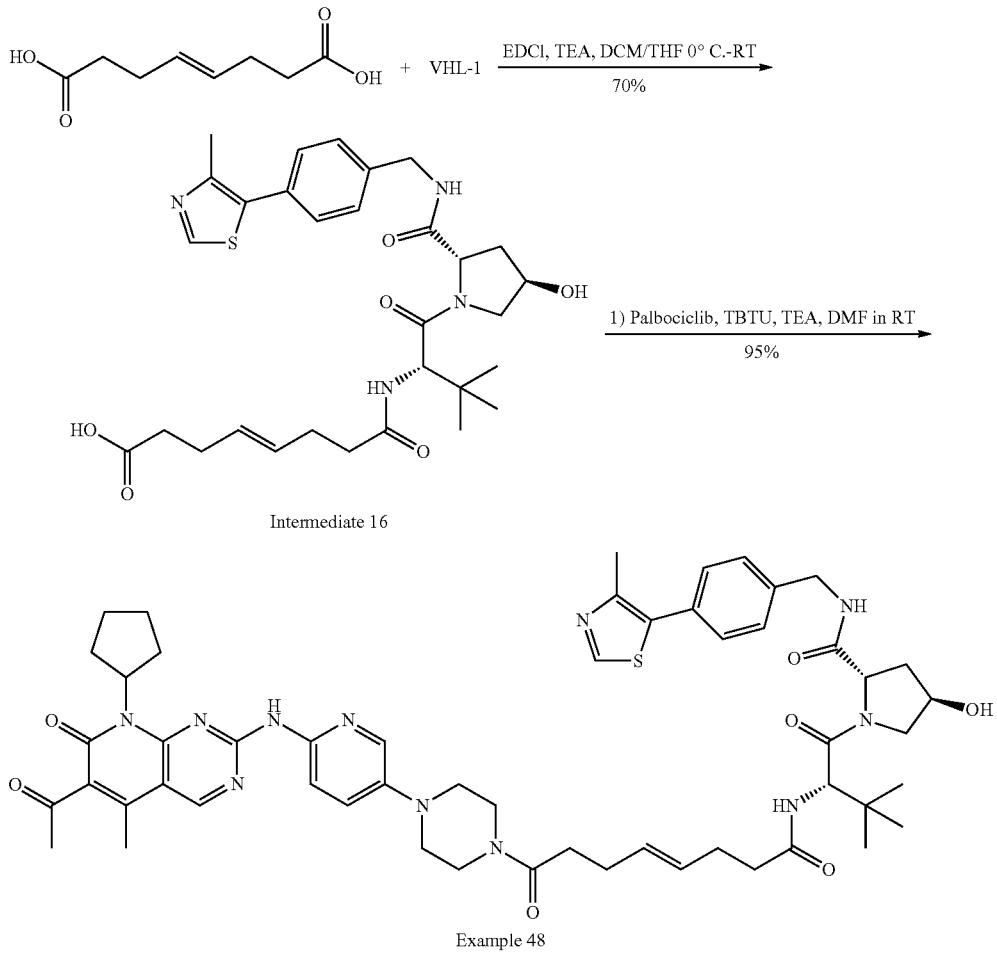

(2S,4R)-1-((S)-2-((E)-8-(4-(6-(((6-Acetyl-8-cyclopentyl-5-methyl-7-oxo-7,8-dihydropyrido[2,3-d]pyrimidin-2-yl)amino)pyridin-3-yl)piperazin-1-yl)-8-oxooct-4-enamido)-3,3-dimethylbutanoyl)-4-hydroxy-N-(4-(4-methylthiazol-5-yl)benzyl)pyrrolidine-2-carboxamide (example 48)

To a solution of (E)-oct-4-enedioic acid (250 mg, 1.45 mmol) in THF (5 ml) were added VHL-1 (239 mg, 0.51 mmol), triethylamine (0.21 ml, 1.4 mmol), and EDCI (104 mg, 0.54 mmol) sequentially at 0° C. The resulting solution was stirred for 2 h at 0° C., before being warmed to room temperature (RT). After stirring overnight at RT, the reaction was quenched with water and concentrated under reduced pressure. The resulting residue was purified by reverse-phase chromatography to yield the intermediate 16 (208 mg, 70%) as white solid. To a stirring solution of intermediate 16 (19 mg, 0.032 mmol) in DMF (1 ml) were added TEA (0.01 mL, 0.07 mmol), palbociclib (11.1 mg, 0.025 mmol), and TBTU (10.4 mg, 0.032 mmol). The mixture was stirred at RT overnight before being concentrated. The resulting residue was purified by prep-HPLC to yield the title compound (24 mg, 95%) as yellow solid. $^1$H NMR (600 MHz, CD$_3$OD) δ 9.12 (s, 1H), 9.00 (s, 1H), 8.21 (dd, J=9.6, 2.9 Hz, 1H), 7.88 (d, J=2.8 Hz, 1H), 7.56 (d, J=9.6 Hz, 1H), 7.49 (d, J=8.1 Hz, 2H), 7.43 (d, J=8.1 Hz, 2H), 6.03 (p, J=8.8 Hz, 1H), 5.61-5.50 (m, 2H), 4.66 (s, 1H), 4.60-4.48 (m, 3H), 4.37 (dd, J=15.3, 8.6 Hz, 1H), 3.92 (d, J=11.0 Hz, 1H), 3.83-3.77 (m, 5H), 3.31-3.25 (m, 3H), 2.54 (t, J=7.8 Hz, 2H), 2.51 (s, 3H), 2.49 (s, 3H), 2.45 (s, 3H), 2.40-2.28 (m, 9H), 2.26-2.23 (m, 1H), 2.16-2.07 (m, 3H), 1.96-1.87 (m, 2H), 1.76-1.66 (m, 2H), 1.04 (s, 9H). HRMS (ESI-TOF) m/z: [M+H]$^+$ calculated for C$_{54}$H$_{68}$N$_{11}$O$_7$S, 1014.5018; found: 1014.5011.

Scheme 20: Synthesis of example 49

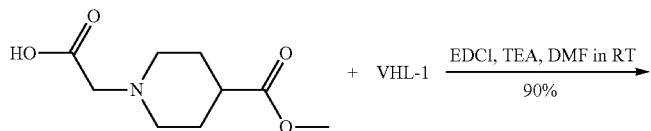

-continued

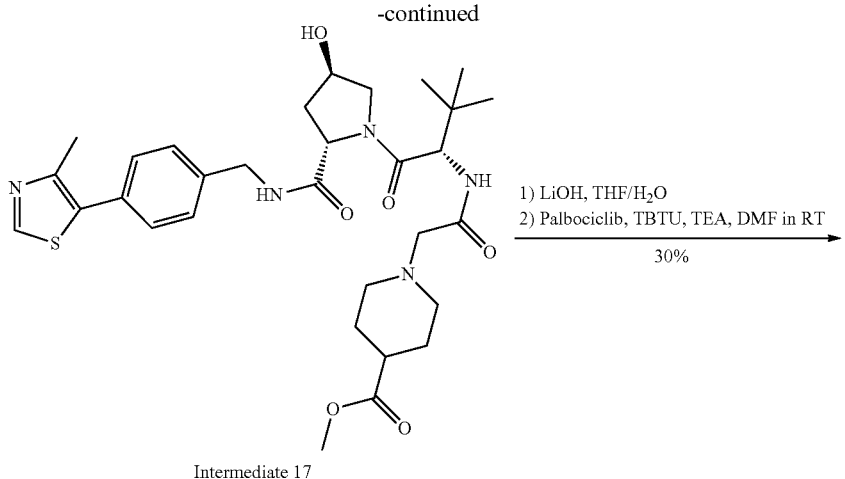

Intermediate 17

1) LiOH, THF/H₂O
2) Palbociclib, TBTU, TEA, DMF in RT

30%

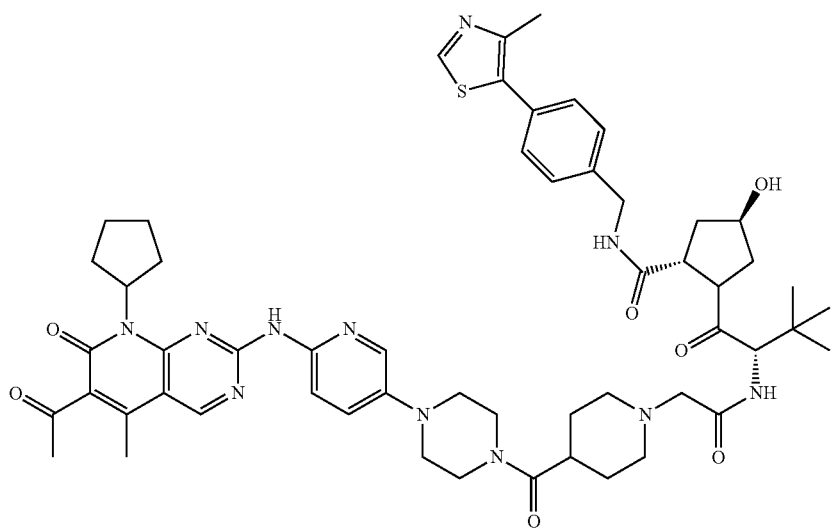

Example 49

(2S,4R)-1-((S)-2-(2-(4-(4-(6-((6-Acetyl-8-cyclopentyl-5-methyl-7-oxo-7,8-dihydropyrido[2,3-d]pyrimidin-2-yl)amino)pyridin-3-yl)piperazine-1-carbonyl)piperidin-1-yl)acetamido)-3,3-dimethylbutanoyl)-4-hydroxy-N-(4-(4-methylthiazol-5-yl)benzyl)pyrrolidine-2-carboxamide (example 49)

To a solution of 2-(4-(methoxycarbonyl)piperidin-1-yl) acetic acid (300 mg, 1.5 mmol) in DMF (10 ml) were added VHL-1 (715 mg, 1.5 mmol), triethylamine (1.07 ml, 7.7 mmol), and TBTU (513 mg, 1.6 mmol) sequentially at RT. After being stirred overnight at RT, the reaction was quenched with water and concentrated under reduced pressure, the resulting residue was purified by reverse-phase chromatography to yield the intermediate 17 (552 mg, 90%) as white solid. To a stirring solution of intermediate 17 (52 mg, 0.085 mmol) in THF/H₂O (5:1, 3 ml) was added anhydrous LiOH (3.3 mg, 0.136 mmol). The resulting mixture was stirred overnight at RT before being concentrated under reduced pressure. The resulting residue was dissolved in DMF (1 ml). To the resulting solution, TEA (0.015 mL, 0.11 mmol), palbociclib (13.3 mg, 0.030 mmol), and TBTU (14 mg, 0.044 mmol) were added. After the mixture was stirred at RT overnight, the reaction was concentrated. The resulting residue was purified by prep-HPLC to yield the title compound (25 mg, 30%) as yellow solid. $^1$H NMR (600 MHz, CD$_3$OD) δ 9.12 (s, 1H), 8.97 (s, 1H), 8.22 (dd, J=10.1, 3.0 Hz, 1H), 7.91 (d, J=3.0 Hz, 1H), 7.58 (dd, J=9.6, 5.5 Hz, 1H), 7.50 (d, J=8.0 Hz, 2H), 7.43 (d, J=8.2 Hz, 2H), 6.03 (p, J=8.8 Hz, 1H), 4.69-4.65 (m, 1H), 4.61-4.54 (m, 3H), 4.38 (d, J=15.5 Hz, 1H), 4.13-3.90 (m, 3H), 3.90-3.76 (m, 5H), 3.72-3.64 (m, 2H), 3.40-3.32 (m, 2H), 3.30-3.28 (m, 2H), 3.15 (br, 2H), 2.52 (s, 3H), 2.50 (s, 3H), 2.45 (s, 3H), 2.37-2.29 (m, 2H), 2.29-2.23 (m, 1H), 2.16-1.99 (m, 9H), 1.98-1.88 (m, 2H), 1.77-1.65 (m, 2H), 1.09 (s, 9H). HRMS (ESI-TOF) m/z: [M+H]⁺ calculated for C$_{54}$H$_{69}$N$_{12}$O$_7$S, 1029.5127; found: 1029.5048.

Scheme 21: Synthesis of example 50

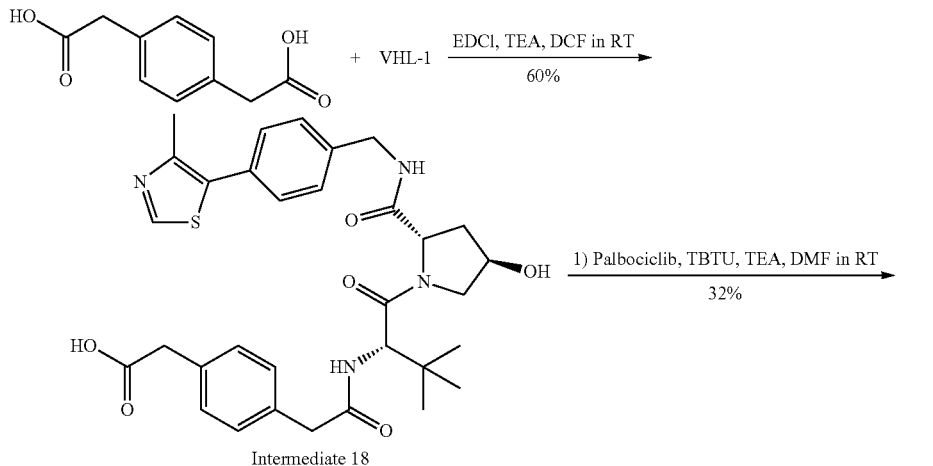

Intermediate 18

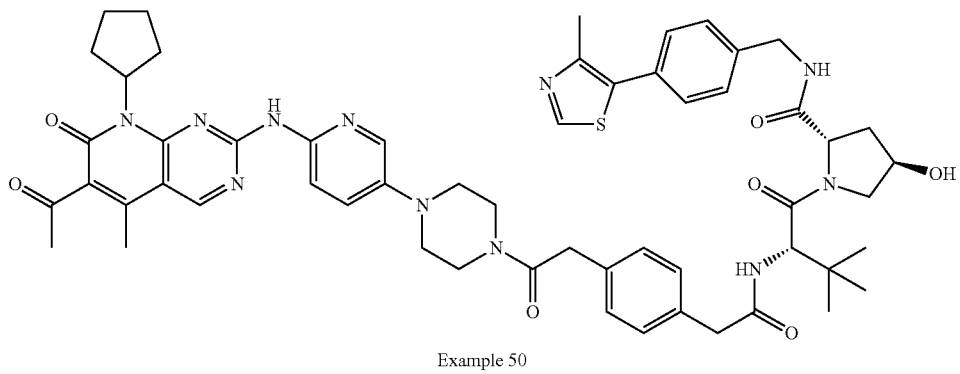

Example 50

(2S,4R)-1-((S)-2-(2-(4-(2-(4-(6-(((6-Acetyl-8-cyclopentyl-5-methyl-7-oxo-7,8-dihydropyrido[2,3-d]pyrimidin-2-yl)amino)pyridin-3-yl)piperazin-1-yl)-2-oxoethyl)phenyl)acetamido)-3,3-dimethylbutanoyl)-4-hydroxy-N-(4-(4-methylthiazol-5-yl)benzyl)pyrrolidine-2-carboxamide (example 50)

To a solution of 2,2'-(1,4-phenylene)diacetic acid (414 mg, 2.13 mmol) in THF (10 ml) were added VHL-1 (217 mg, 0.47 mmol), triethylamine (0.21 ml, 1.4 mmol), and EDCI (110 mg, 0.58 mmol) sequentially at 0° C. The resulting solution was stirred for 2 h at 0° C., before being warmed to room temperature (RT). After stirring overnight at RT, the reaction was quenched with water and concentrated under reduced pressure. The resulting residue was purified by reverse-phase chromatography to yield the intermediate 18 (170 mg, 60%) as white solid. To a stirring solution of intermediate 18 (20 mg, 0.033 mmol) in DMF (1 ml) were added TEA (0.015 mL, 0.11 mmol), palbociclib (12 mg, 0.027 mmol), and TBTU (12.2 mg, 0.038 mmol). After the mixture was stirred at RT overnight, the reaction was concentrated under reduced pressure. The resulting residue was purified by prep-HPLC to yield the title compound (9 mg, 32%) as yellow solid. $^1$H NMR (600 MHz, CD$_3$OD) δ 9.08 (s, 1H), 8.95 (s, 1H), 8.15 (dd, J=9.7, 2.8 Hz, 1H), 7.78 (d, J=2.6 Hz, 1H), 7.51 (d, J=11.4 Hz, 1H), 7.46-7.38 (m, 4H), 7.34-7.25 (m, 4H), 6.06-5.97 (m, 1H), 4.66-4.61 (m, 1H), 4.59-4.46 (m, 3H), 4.38-4.32 (m, 1H), 3.92-3.83 (m, 3H), 3.81-3.70 (m, 4H), 3.64 (d, J=14.4 Hz, 1H), 3.58 (d, J=14.7 Hz, 1H), 3.24-3.18 (m, 1H), 3.16-3.09 (m, 1H), 3.08-3.02 (m, 1H), 2.52 (s, 3H), 2.49 (s, 3H), 2.44 (s, 3H), 2.37-2.31 (m, 2H), 2.26-2.20 (m, 1H), 2.15-2.08 (m, 3H), 1.96-1.87 (m, 2H), 1.76-1.68 (m, 2H), 0.97 (s, 9H). HRMS (ESI-TOF) m/z: [M+H]$^+$ calculated for C$_{56}$H$_{66}$N$_{11}$O$_7$S, 1036.4862; found: 1036.4860.

Scheme 22: Synthesis of example 51

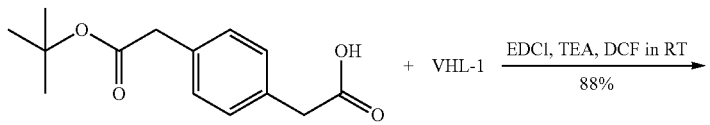

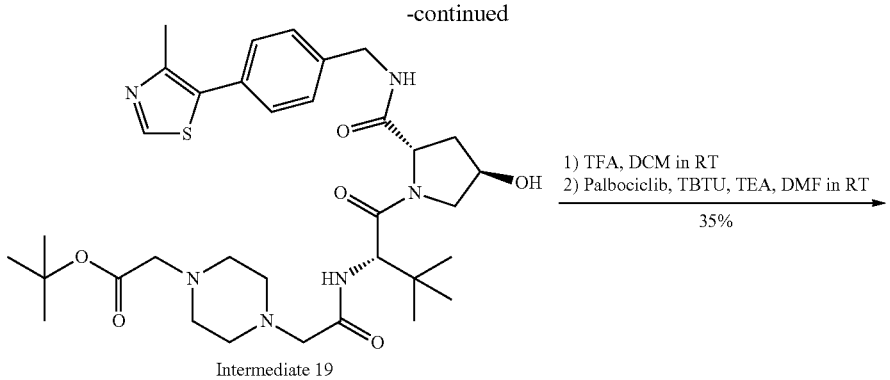

Intermediate 19

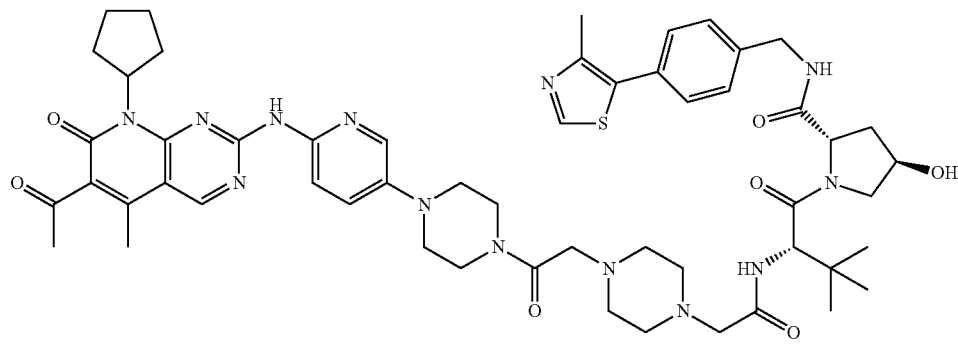

Example 51

(2S,4R)-1-((S)-2-(2-(4-(2-(4-(6-((6-Acetyl-8-cyclopentyl-5-methyl-7-oxo-7,8-dihydropyrido[2,3-d]pyrimidin-2-yl)amino)pyridin-3-yl)piperazin-1-yl)-2-oxoethyl)piperazin-1-yl)acetamido)-3,3-dimethylbutanoyl)-4-hydroxy-N-(4-(4-methylthiazol-5-yl)benzyl)pyrrolidine-2-carboxamide (example 51)

To a solution of 2-(4-(2-(tert-butoxy)-2-oxoethyl)piperazin-1-yl)acetic acid (340 mg, 0.7 mmol) in DMF (5 ml) were added VHL-1 (277 mg, 0.6 mmol), triethylamine (0.7 ml, 5 mmol), and EDCI (224 mg, 1.2 mmol) sequentially at RT. After being stirred overnight at RT, the reaction was quenched with water, and concentrated under reduced pressure. The resulting residue was purified by reverse-phase chromatography to yield the intermediate 17 (350 mg, 88%) as white solid. To a stirring solution of intermediate 19 (15 mg, 0.023 mmol) in DCM (1 ml) was added TFA (1 mL). The resulting mixture was stirred at RT. The disappearance of starting material was monitored by LC/MS. The reaction mixture was concentrated under reduced pressure and the resulting residue was dissolved in DMF (1 ml). To the resulting solution, TEA (0.015 mL, 0.11 mmol), palbociclib (8.3 mg, 0.019 mmol), and TBTU (7 mg, 0.022 mmol) were added. The mixture was stirred at RT overnight before being concentrated. The resulting residue was purified by prep-HPLC to yield the title compound (7 mg, 35%) as yellow solid. $^1$H NMR (600 MHz, CD$_3$OD) δ 9.13 (s, 1H), 8.99 (s, 1H), 8.24 (dd, J=9.6, 2.4 Hz, 1H), 7.93 (s, 1H), 7.59 (d, J=9.6 Hz, 1H), 7.49 (d, J=8.4 Hz, 2H), 7.45 (d, J=8.2 Hz, 2H), 6.08-5.98 (m, 1H), 4.69 (s, 1H), 4.61-4.50 (m, 3H), 4.44-4.38 (m, 1H), 4.25 (s, 2H), 3.92 (d, J=11.1 Hz, 1H), 3.88-3.79 (m, 3H), 3.68 (br, 2H), 3.50-3.37 (m, 8H), 3.37-3.34 (m, 2H), 3.06 (br, 4H), 2.53 (s, 2H), 2.51 (s, 2H), 2.46 (s, 3H), 2.37-2.25 (m, 3H), 2.17-2.07 (m, 3H), 1.97-1.87 (m, 2H), 1.76-1.69 (m, 2H), 1.07 (s, 9H). HRMS (ESI-TOF) m/z: [M+H]$^+$ calculated for C$_{54}$H$_{70}$N$_{13}$O$_7$S, 1044.5236; found: 1044.5226.

Scheme 23: Synthesis of example 52

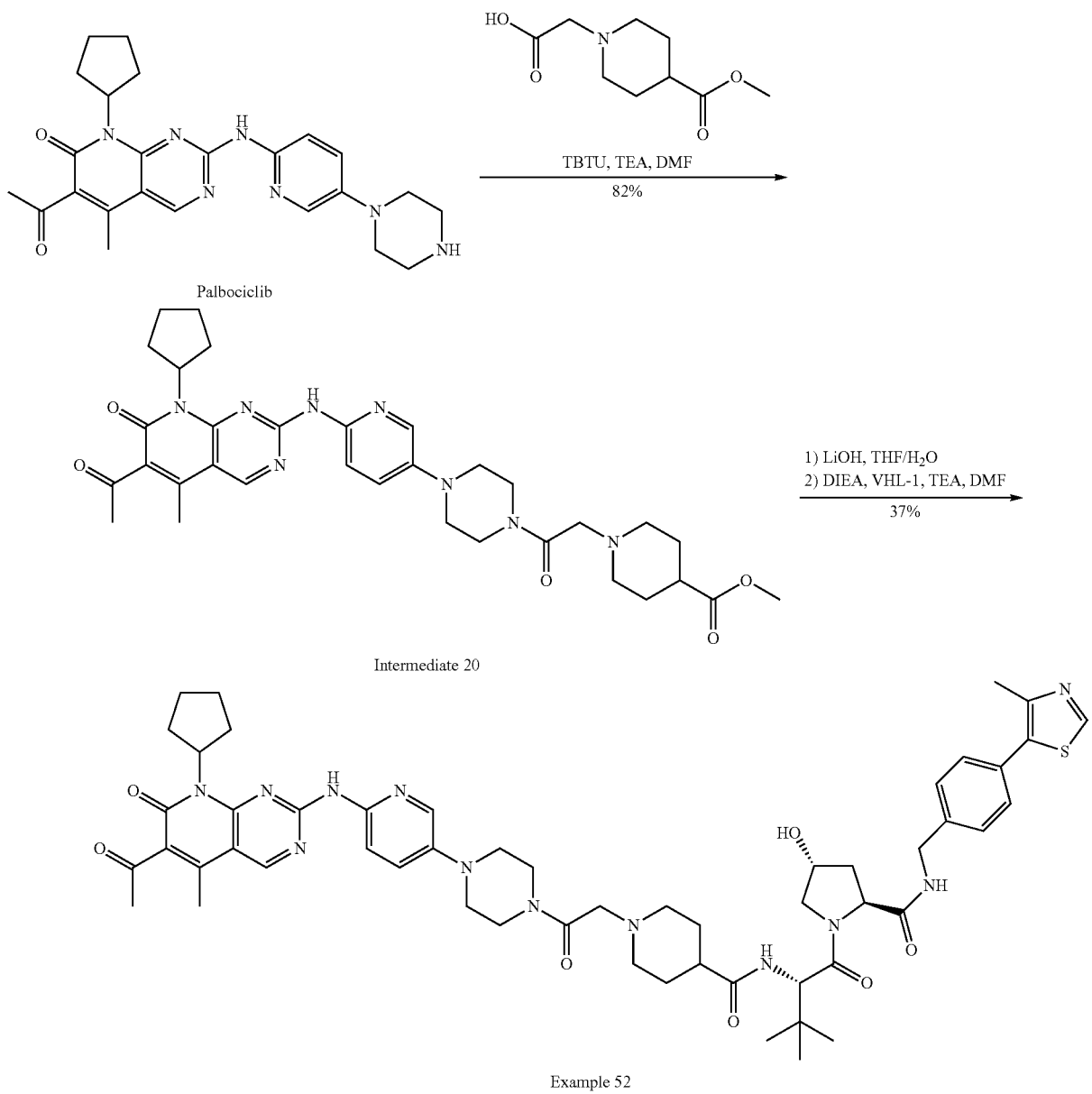

1-(2-(4-(6-(((6-Acetyl-8-cyclopentyl-5-methyl-7-oxo-7,8-dihydropyrido[2,3-d]pyrimidin-2-yl)amino)pyridin-3-yl)piperazin-1-yl)-2-oxoethyl)-N—((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)piperidine-4-carboxamide (example 52)

A solution of palbociclib (43 mg, 0.096 mmol) in DMF were added 2-(4-(methoxycarbonyl)piperidin-1-yl)acetic acid (20 mg, 0.1 mmol), TEA (0.035 mL, 0.25 mmol), and TBTU (42 mg, 0.13 mmol) sequentially at RT. After being stirred overnight at RT, the reaction was quenched with water. After concentration under reduced pressure, the resulting residue was purified by reverse-phase chromatography to yield the intermediate 20 (50 mg, 82%) as white solid. To a stirring solution of intermediate 20 (50 mg, 0.079 mmol) in THF/H$_2$O (5:1, 3 mL) was added anhydrous LiOH (6 mg, 0.025 mmol). The mixture was stirred at RT and the reaction progress was monitored by LC/MS. After total consumption of intermediate 20, the reaction was concentrated. The resulting residue was dissolved in DMF (1 ml). To the solution were added TEA (0.02 mL, 0.14 mmol), VHL-1 (26 mg, 0.055 mmol), and TBTU (16 mg, 0.05 mmol). The reaction mixture was stirred at RT overnight before being concentrated. The resulting residue was purified by prep-HPLC to yield the title compound (30 mg, 37%) as yellow solid. $^1$H NMR (600 MHz, CD$_3$OD) δ 9.15 (s, 1H), 9.13 (s, 1H), 8.24 (dd, J=9.6, 2.7 Hz, 1H), 7.93 (d, J=2.2 Hz, 1H), 7.58 (d, J=9.6 Hz, 1H), 7.51 (d, J=8.1 Hz, 2H), 7.46 (d, J=8.2 Hz, 2H), 6.03 (p, J=8.8 Hz, 1H), 4.65 (d, J=8.3 Hz, 1H), 4.62-4.51 (m, 3H), 4.42-4.32 (m, 3H), 3.91 (d, J=9.6 Hz, 1H), 3.87-3.82 (m, 3H), 3.79-3.70 (m, 1H), 3.65 (br, 2H), 3.50 (br, 1H), 3.40 (br, 2H), 3.37-3.34 (m, 3H), 3.20-3.07 (m, 1H), 2.74 (br, 1H), 2.52 (s, 3H), 2.52 (s, 3H), 2.45 (s, 3H), 2.36-2.24 (m, 3H), 2.21-2.03 (m, 7H), 1.97-1.88 (m, 2H), 1.77-1.64 (m, 2H), 1.07 (s, 9H). HRMS (ESI-TOF) m/z: [M+H]$^+$ calculated for $C_{54}H_{69}N_{12}O_7S$, 1029.5127; found: 1029.5106.

Scheme 24: Synthesis of example 53

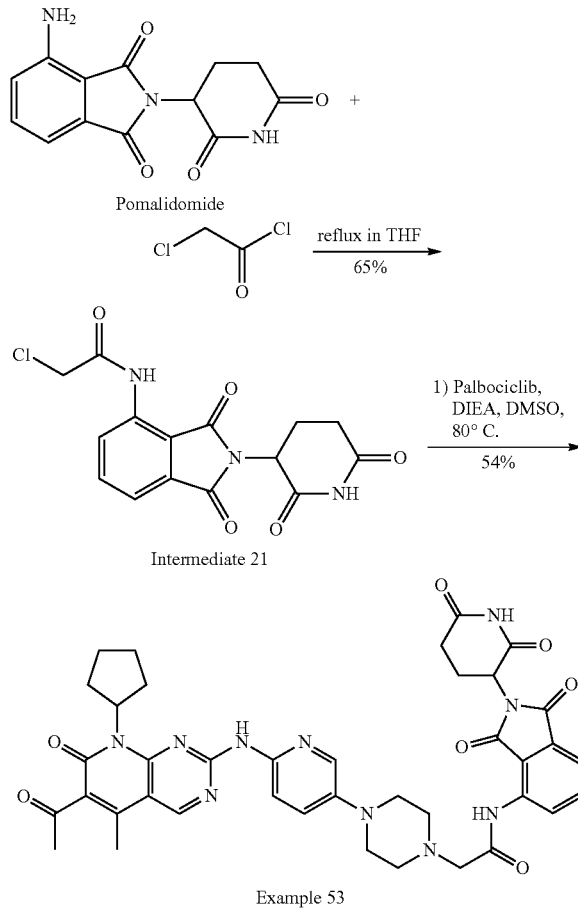

Example 53

2-(4-(6-(((6-Acetyl-8-cyclopentyl-5-methyl-7-oxo-7,8-dihydropyrido[2,3-d]pyrimidin-2-yl)amino)pyridin-3-yl)piperazin-1-yl)-N-(2-(2,6-dioxopiperidin-3-yl)-1,3-dioxoisoindolin-4-yl)acetamide (example 53)

A solution of pomalidomide (90 mg, 0.33 mmol) and 2-chloroacetyl chloride (0.026 mL, 0.33 mmol) in THF (2 ml) was heated at reflux overnight. After being cooled to RT, the reaction mixture was concentrated, and the resulting residue was washed with ethyl acetate to yield the intermediate 21 (75 mg, 65%) as yellow solid. To a stirring solution of intermediate 13 (36 mg, 0.082 mmol) in DMSO (1 mL) were added DIEA (0.043 mL, 0.24 mmol) and palbociclib (39 mg, 0.087 mmol). The mixture was heated at 80° C. After the starting materials were consumed, the reaction was concentrated under reduced pressure. The resulting residue was purified by prep-HPLC to yield the title compound (36 mg, 54%) as yellow solid. $^1$H NMR (600 MHz, CDCl$_3$) δ 11.19 (s, 1H), 8.89 (d, J=8.5 Hz, 1H), 8.81 (s, 1H), 8.20 (d, J=9.1 Hz, 1H), 8.14 (d, J=2.8 Hz, 1H), 7.71 (t, J=4.2 Hz, 1H), 7.55 (d, J=7.3 Hz, 1H), 7.38 (dd, J=9.1, 2.9 Hz, 1H), 5.87 (p, J=9.0 Hz, 1H), 4.94 (dd, J=12.7, 5.3 Hz, 1H), 3.39 (br, 4H), 3.34 (AB, J$_{ab}$=17.4 Hz, 1H), 3.27 (AB, J$_{ab}$=17.4 Hz, 1H), 2.92-2.73 (m, 8H), 2.54 (s, 3H), 2.40-2.29 (m, 4H), 2.14-2.09 (m, 1H), 2.08-2.00 (m, 2H), 1.90-1.81 (m, 2H), 1.70-1.59 (m, 2H). HRMS (ESI-TOF) m/z: [M+H]$^+$ calculated for $C_{39}H_{41}N_{10}O_7$, 761.3154; found: 761.3157.

Synthesis of various linkers of pomalidomide analogues.

Scheme 25: Synthesis of Linker 29 and 30

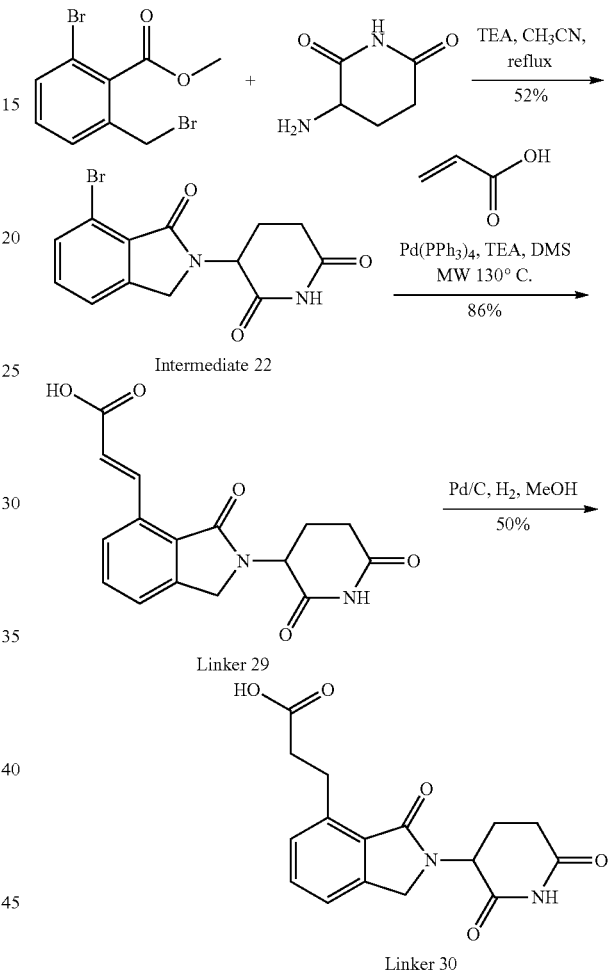

3-(7-Bromo-1-oxoisoindolin-2-yl)piperidine-2,6-dione (intermediate 22)

A solution of methyl 2-bromo-6-(bromomethyl)benzoate (970 mg, 3.16 mmol), 3-aminopiperidine-2,6-dione (667 mg, 4.06 mmol) and TEA (0.62 mL, 4.4 mmol) in CH$_3$CN (10 mL) was heated at reflux for 16 h. After being cooled to RT, the reaction was concentrated. To the resulting residue were added ethyl acetate (10 mL) and H$_2$O (10 mL). After filtration, the solid was collected and dried to yield the title compound (534 mg, 54%) as purple solid.

(E)-3-(2-(2,6-Dioxopiperidin-3-yl)-3-oxoisoindolin-4-yl)acrylic acid (linker 29)

A solution of intermediate 22 (46 mg, 0.14 mmol), acrylic acid (0.02 mL, 0.29 mmol), tetrakis(triphenylphosphine)

palladium (23.3 mg, 0.02 mmol) and TEA (0.02 mL, 0.14 mmol) in DMSO (1 mL) was heated in a microwave reactor at 130° C. for 30 min. After being cooled to RT, the mixture was filtered. The solution was concentrated and purified by prep-HPLC to yield the title compound (38 mg, 86%) as yellow solid. $^1$H NMR (600 MHz, DMSO-d$_6$) δ 12.51 (sbr, 1H), 11.03 (s, 1H), 8.87 (d, J=16.2 Hz, 1H), 7.98 (t, J=6.0 Hz, 1H), 7.64 (d, J=4.7 Hz, 2H), 6.69 (d, J=16.3 Hz, 1H), 5.10 (dd, J=13.3, 5.1 Hz, 1H), 4.47 (d, J=17.4 Hz, 1H), 4.35 (d, J=17.4 Hz, 1H), 2.98-2.86 (m, 1H), 2.62 (d, J=17.1 Hz, 1H), 2.42 (qd, J=13.2, 4.5 Hz, 1H), 2.07-1.99 (m, 1H).

3-(2-(2,6-Dioxopiperidin-3-yl)-3-oxoisoindolin-4-yl)propanoic acid (linker 30)

A mixture of linker 29 (20 mg, 0.064 mmol) and Pd/C (5 mg) in MeOH/DMSO (1:1, 2 mL) was stirred for 16 h under H$_2$ atmosphere. After removal of Pd/C through filtration, the solution was concentrated under reduced pressure. The resulting residue was purified by prep-HPLC to yield the title compound (11 mg, 50%) as yellow solid. $^1$H NMR (600 MHz, DMSO-d$_6$) δ 10.99 (br, 2H), 7.55-7.47 (m, 1H), 7.43 (d, J=7.5 Hz, 1H), 7.31 (d, J=7.7 Hz, 1H), 5.13-5.03 (m, 1H), 4.41 (dd, J=16.8, 8.8 Hz, 1H), 4.30 (dd, J=16.8, 8.8 Hz, 1H), 3.33-3.27 (m, 2H), 2.97-3.84 (m, 1H), 2.63-2.55 (m, 3H), 2.43-2.38 (m, 1H), 2.06-1.98 (m, 1H).

Scheme 26: Synthesis of Linker 31

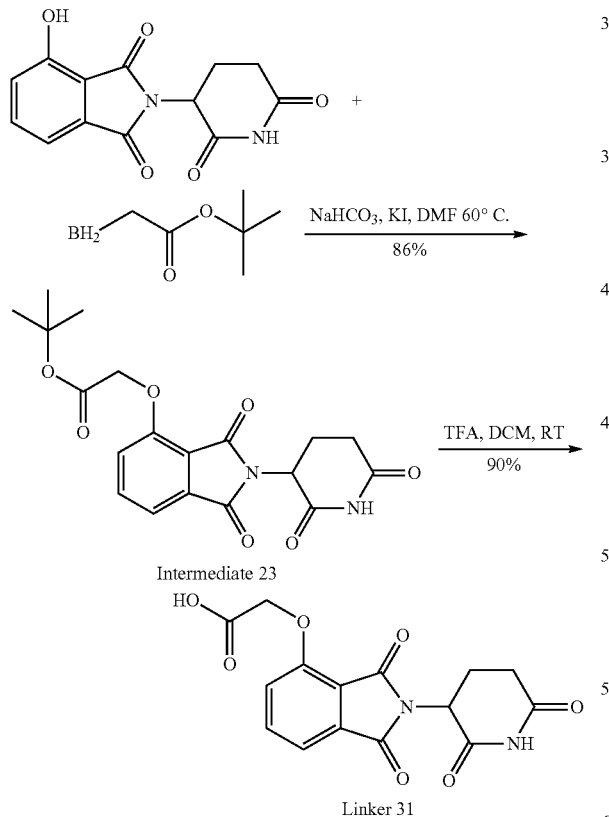

Linker 31

2-((2-(2,6-Dioxopiperidin-3-yl)-1,3-dioxoisoindolin-4-yl)oxy)acetic acid (linker 31)

A round bottom flash was charged with 2-(2,6-dioxopiperidin-3-yl)-4-hydroxyisoindoline-1,3-dione (68 mg, 0.25 mmol), DMF (2 mL), tert-butyl-2-bromo acetate ester (0.045 mL, 0.3 mmol), sodium bicarbonate (49 mg, 0.058 mmol), and potassium iodide (10 mg, 0.06 mmol). The reaction mixture was heated at 60° C. overnight. After being cooled to RT, the insoluble solid was removed by filtration. The solution was collected and concentrated. The resulting residue was purified by reverse-ISCO to yield intermediated 23 (83 mg, 86%). Intermediate 23 (83 mg, 0.21 mmol) was dissolved in DCM/TFA (2:1, 3 mL). After the reaction was stirred for 3 h at RT, the solvent was removed to yield the title compound (60 mg, 90%) as white solid. $^1$H NMR (600 MHz, DMSO-d$_6$) δ 11.11 (br, 2H), 7.82-7.77 (m, 1H), 7.48 (d, J=7.2 Hz, 1H), 7.40 (d, J=8.6 Hz, 1H), 5.11 (ddd, J=12.8, 5.4, 1.2 Hz, 1H), 5.00 (s, 2H), 2.95-2.80 (m, 1H), 2.63-2.53 (m, 2H), 2.08-2.00 (m, 1H).

Scheme 27: Synthesis of Linker 32

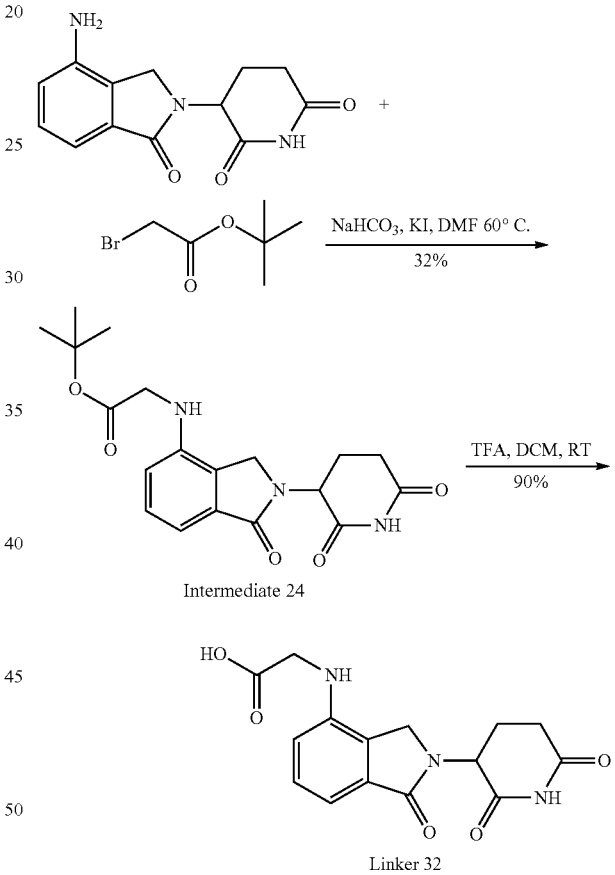

Linker 32

(2-(2,6-Dioxopiperidin-3-yl)-1-oxoisoindolin-4-yl)glycine (linker 32)

The title compound was synthesized using the same procedures for the preparation of linker 31. $^1$H NMR (600 MHz, DMSO-d$_6$) δ 12.66 (br, 1H), 11.03 (s, 1H), 7.29 (t, J=7.7 Hz, 1H), 6.99 (d, J=7.4 Hz, 1H), 6.66 (d, J=8.0 Hz, 1H), 5.13 (dd, J=13.3, 4.9 Hz, 1H), 4.27 (d, J=17.0 Hz, 1H), 4.18 (d, J=17.4 Hz, 1H), 3.93 (s, 2H), 2.98-2.84 (m, 1H), 2.63 (d, J=17.0 Hz, 1H), 2.34 (qd, J=13.2, 4.1 Hz, 1H), 2.08-1.97 (m, 1H).

Scheme 28: Synthesis of Linker 33

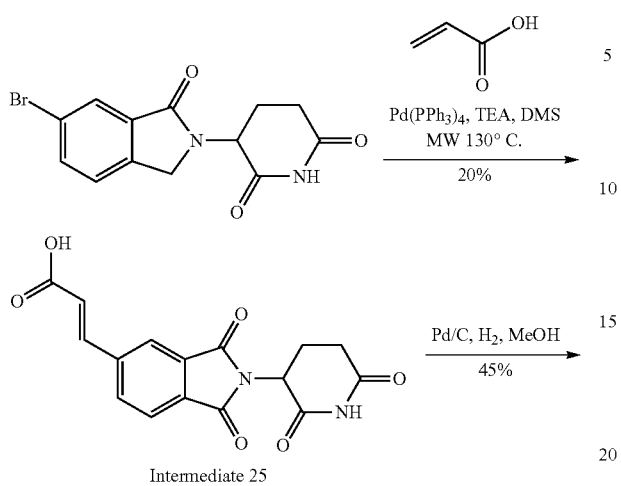

3-(2-(2,6-Dioxopiperidin-3-yl)-1,3-dioxoisoindolin-5-yl)propanoic acid (linker 33)

The title compound was synthesized using the same procedures for the preparation of linker 30. $^1$H NMR (600 MHz, DMSO-d$_6$) δ 11.15 (br, 2H), 7.85 (d, J=7.7 Hz, 1H), 7.82 (s, 1H), 7.76 (d, J=7.7 Hz, 1H), 5.14 (dd, J=12.9, 5.4 Hz, 1H), 3.02 (t, J=7.4 Hz, 2H), 2.93-2.84 (m, 1H), 2.65 (t, J=7.5 Hz, 2H), 2.60-2.53 (m, 2H), 2.08-2.04 (m, 1H).

Scheme 29: Synthesis of Linker 34

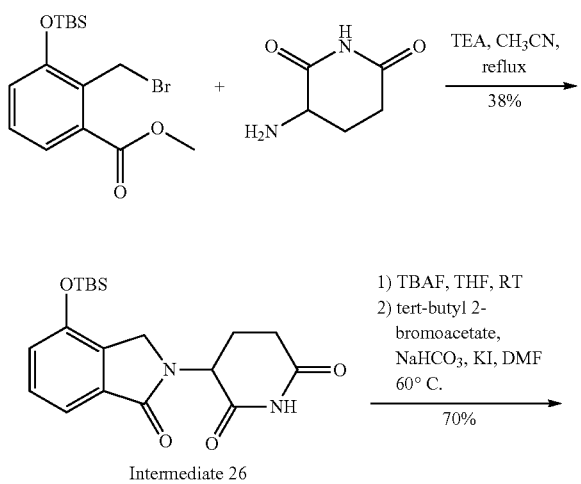

3-(4-((tert-Butyldimethylsilyl)oxy)-1-oxoisoindolin-2-yl)piperidine-2,6-dione (intermediate 26)

The title compound was synthesized using the same procedures for the preparation of intermediate 22 (38%). $^1$H NMR (600 MHz, DMSO-d$_6$) δ 10.98 (s, 1H), 7.44 (t, J=7.7 Hz, 1H), 7.36 (d, J=7.4 Hz, 1H), 7.11 (d, J=7.9 Hz, 1H), 5.11 (dd, J=13.2, 4.8 Hz, 1H), 4.34 (d, J=17.3 Hz, 1H), 4.25 (d, J=17.2 Hz, 1H), 2.96-2.82 (m, 1H), 2.66-2.53 (m, 2H), 2.02-1.96 (m, 1H), 0.99 (s, 9H), 0.26 (s, 6H).

2-((2-(2,6-Dioxopiperidin-3-yl)-1-oxoisoindolin-4-yl)oxy)acetic acid (linker 34)

The title compound was synthesized using the same procedures for the preparation of linker 31. $^1$H NMR (600 MHz, DMSO-d$_6$) δ 11.00 (s, 1H), 7.47 (t, J=7.8 Hz, 1H), 7.36 (d, J=8.6 Hz, 1H), 7.17 (d, J=8.2 Hz, 1H), 5.19-5.05 (m, 2H), 4.84 (s, 2H), 4.41 (d, J=17.4 Hz, 1H), 4.28 (d, J=17.3 Hz, 1H), 3.00-2.84 (m, 1H), 2.63-2.58 (m, 1H), 2.49-2.38 (m, 1H), 2.04-1.92 (m, 1H).

Scheme 30: Synthesis of Linker 35

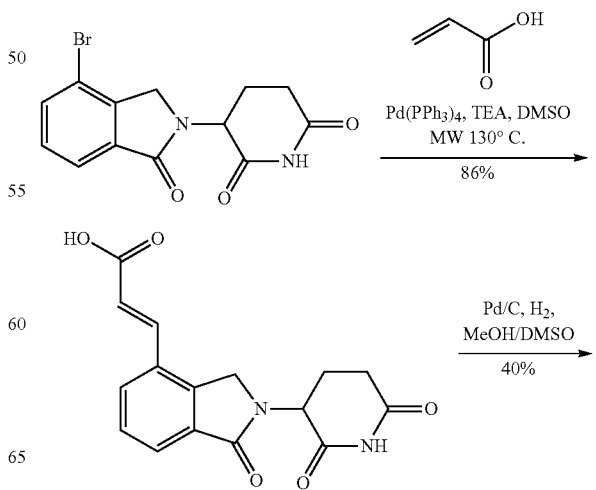

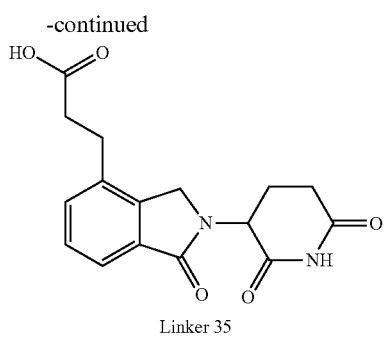

Linker 35

3-(2-(2,6-Dioxopiperidin-3-yl)-1-oxoisoindolin-4-yl)propanoic acid (linker 35)

The title compound was synthesized using the same procedures for the preparation of linker 30. $^1$H NMR (600 MHz, DMSO-d$_6$) δ 12.23 (br, 1H), 11.01 (s, 1H), 7.59 (d, J=7.1 Hz, 1H), 7.51-7.46 (m, 2H), 5.14 (dd, J=13.3, 5.1 Hz, 1H), 4.51 (d, J=17.0 Hz, 1H), 4.36 (d, J=17.1 Hz, 1H), 2.97-2.83 (m, 3H), 2.67-2.58 (m, 3H), 2.49-2.39 (m, 1H), 2.05-1.99 (m, 1H).

Scheme 31: Synthesis of Linker 36

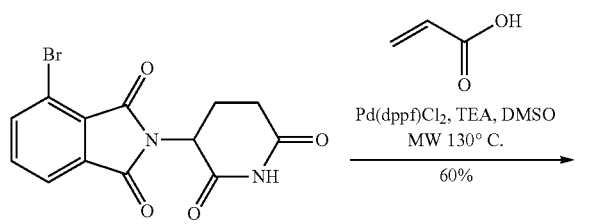

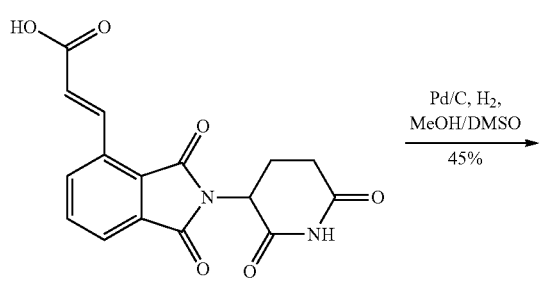

Linker 36

3-(2-(2,6-Dioxopiperidin-3-yl)-1,3-dioxoisoindolin-4-yl)propanoic acid (linker 36)

The title compound was synthesized using the same procedures for the preparation of linker 30. $^1$H NMR (600 MHz, DMSO-d$_6$) δ 11.15 (br, 2H), 7.79-7.73 (m, 3H), 5.14 (dd, J=12.9, 5.4 Hz, 1H), 3.27 (t, J=7.2 Hz, 2H), 2.95-2.83 (m, 1H), 2.67-2.52 (m, 4H), 2.12-2.01 (m, 1H).

The example 54-61 compounds were synthesized using the same procedures for the preparation of the example 40 compound with linkers 29-36.

example 54

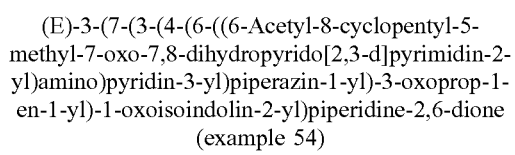

(E)-3-(7-(3-(4-(6-((6-Acetyl-8-cyclopentyl-5-methyl-7-oxo-7,8-dihydropyrido[2,3-d]pyrimidin-2-yl)amino)pyridin-3-yl)piperazin-1-yl)-3-oxoprop-1-en-1-yl)-1-oxoisoindolin-2-yl)piperidine-2,6-dione (example 54)

(52 mg, 58%) as yellow solid. $^1$H NMR (600 MHz, CD$_3$OD) δ 9.08 (s, 1H), 8.74 (d, J=15.7 Hz, 1H), 8.17 (dd, J=9.7, 2.7 Hz, 1H), 7.90 (d, J=2.7 Hz, 1H), 7.84 (d, J=7.7 Hz, 1H), 7.62-7.54 (m, 2H), 7.51 (d, J=7.5 Hz, 1H), 7.27 (d, J=15.7 Hz, 1H), 5.98 (p, J=8.8 Hz, 1H), 5.13 (dd, J=12.6, 5.4 Hz, 1H), 4.47 (AB, J$_{ab}$=16.8 Hz, 1H), 4.43 (AB, J$_{ab}$=16.8 Hz, 1H), 3.97 (br, 2H), 3.90 (br, 2H), 3.28 (br, 2H), 3.34 (br, 2H), 2.87-2.75 (m, 1H), 2.52 (s, 3H), 2.50-2.44 (m, 1H), 2.43 (s, 3H), 2.35-2.25 (m, 2H), 2.25-2.15 (m, 2H), 2.14-2.03 (m, 3H), 1.94-1.86 (m, 2H), 1.73-1.64 (m, 2H). HRMS (ESI-TOF) m/z: [M+H]$^+$ calculated for C$_{40}$H$_{42}$N$_9$O$_6$, 744.3253; found: 744.3274.

example 55

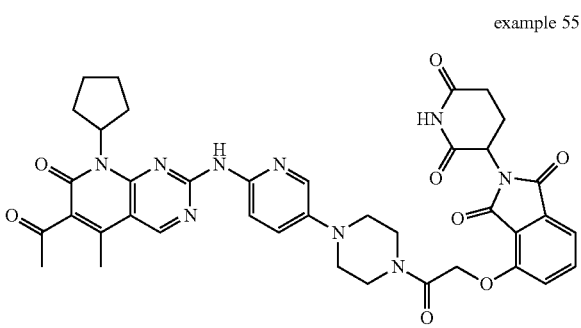

4-(2-(4-(6-(((6-Acetyl-8-cyclopentyl-5-methyl-7-oxo-7,8-dihydropyrido[2,3-d]pyrimidin-2-yl)amino)pyridin-3-yl)piperazin-1-yl)-2-oxoethoxy)-2-(2,6-dioxopiperidin-3-yl)isoindoline-1,3-dione (example 55)

(27 mg, 51%) as yellow solid. $^1$H NMR (600 MHz, CD$_3$OD) δ 9.11 (s, 1H), 8.19 (d, J=8.6 Hz, 1H), 7.88 (br, 1H), 7.76 (t, J=7.9 Hz, 1H), 7.57 (d, J=7.9 Hz, 1H), 7.49 (d, J=7.2 Hz, 1H), 7.41 (d, J=8.5 Hz, 1H), 6.06-5.96 (m, 1H), 5.22-5.15 (m, 2H), 5.12 (dd, J=12.7, 5.4 Hz, 1H), 3.93-3.76 (m, 4H), 3.45-3.24 (m, 4H), 2.95-2.69 (m, 3H), 2.53 (s, 3H), 2.45 (s, 3H), 2.37-2.27 (m, 2H), 2.20-2.05 (m, 3H), 1.96-1.87 (m, 2H), 1.77-1.62 (m, 2H). HRMS (ESI-TOF) m/z: [M+H]$^+$ calculated for C$_{39}$H$_{40}$N$_9$O$_8$, 762.2994; found: 762.3008.

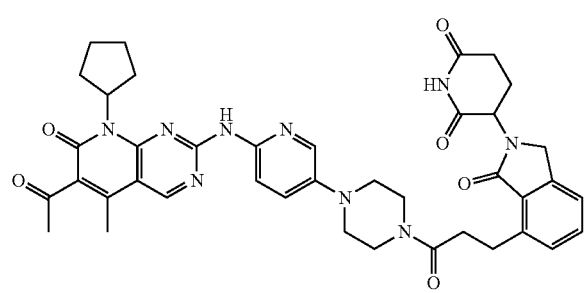

example 56

3-(7-(3-(4-(6-(((6-Acetyl-8-cyclopentyl-5-methyl-7-oxo-7,8-dihydropyrido[2,3-d]pyrimidin-2-yl)amino)pyridin-3-yl)piperazin-1-yl)-3-oxopropyl)-1-oxoisoindolin-2-yl)piperidine-2,6-dione (example 56)

(9 mg, 48%) as yellow solid. $^1$H NMR (600 MHz, CD$_3$OD) δ 8.81 (s, 1H), 7.73-7.65 (m, 2H), 7.63 (s, 1H), 7.31 (t, J=7.5 Hz, 1H), 7.18 (d, J=7.4 Hz, 1H), 7.13 (d, J=7.4 Hz, 1H), 5.75-5.70 (m, 1H), 4.93 (dd, J=13.2, 5.1 Hz, 1H), 3.69-3.48 (m, 4H), 3.31-3.21 (m, 1H), 3.21-3.09 (m, 3H), 3.07-3.00 (m, 2H), 2.99-2.77 (m, 2H), 2.76-2.63 (m, 3H), 2.63-2.54 (m, 1H), 2.34 (s, 3H), 2.28-2.16 (m, 4H), 2.15-2.02 (m, 3H), 1.94-1.85 (m, 2H), 1.75-1.65 (m, 2H), 1.55-1.44 (m, 2H). HRMS (ESI-TOF) m/z: [M+H]$^+$ calculated for C$_{40}$H$_{44}$N$_9$O$_6$, 746.3409; found: 746.3427.

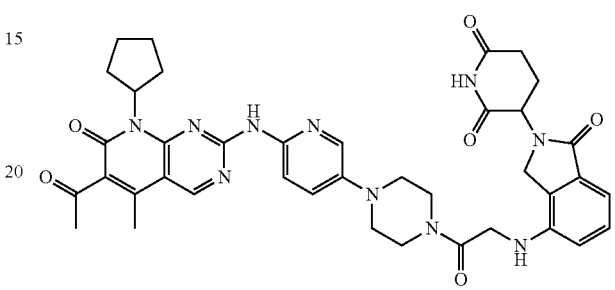

example 57

3-(4-((2-(4-(6-(((6-Acetyl-8-cyclopentyl-5-methyl-7-oxo-7,8-dihydropyrido[2,3-d]pyrimidin-2-yl)amino)pyridin-3-yl)piperazin-1-yl)-2-oxoethyl)amino)-1-oxoisoindolin-2-yl)piperidine-2,6-dione (example 57)

(39 mg, 80%) $^1$H NMR (600 MHz, CD$_3$OD) δ 9.07 (s, 1H), 8.09 (d, J=9.5 Hz, 1H), 7.89 (s, 1H), 7.61 (d, J=8.7 Hz, 1H), 7.34 (t, J=7.6 Hz, 1H), 7.16 (d, J=7.4 Hz, 1H), 6.79 (d, J=7.9 Hz, 1H), 5.96 (p, J=8.7 Hz, 1H), 5.14 (dd, J=13.2, 4.1 Hz, 1H), 4.37 (s, 2H), 4.18-4.06 (m, 2H), 3.85-3.79 (m, 4H), 3.38-3.22 (m, 4H), 2.90-2.76 (m, 2H), 2.56-2.48 (m, 3H), 2.49-2.38 (m, 4H), 2.27 (t, J=18.1 Hz, 2H), 2.24-2.14 (m, 1H), 2.09 (s, 2H), 1.90 (s, 2H), 1.68 (d, J=3.0 Hz, 2H). HRMS (ESI-TOF) m/z: [M+H]$^+$ calculated for C$_{39}$H$_{43}$N$_{10}$O$_6$, 747.3362; found: 747.3370.

example 58

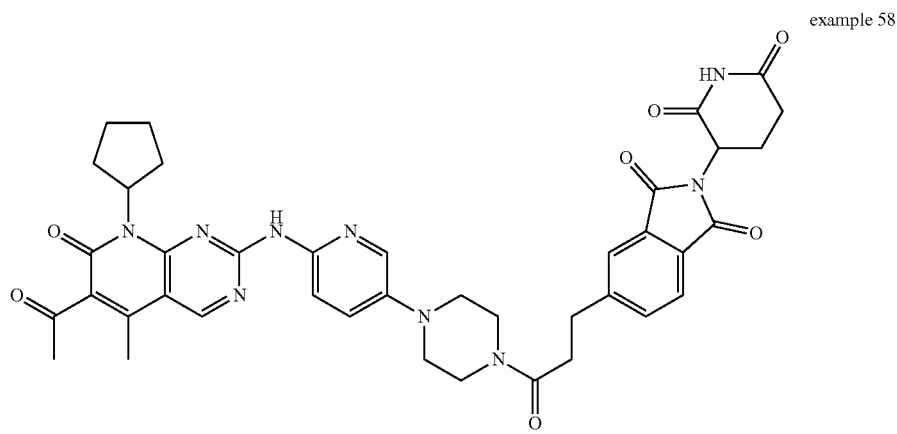 [SMILES: CC(=O)c1c(C)c2cnc(Nc3ccc(N4CCN(C(=O)CCc5ccc6c(c5)C(=O)N(C5CCC(=O)NC5=O)C6=O)CC4)cn3)nc2n(C2CCCC2)c1=O]

5-(3-(4-(6-(((6-Acetyl-8-cyclopentyl-5-methyl-7-oxo-7,8-dihydropyrido[2,3-d]pyrimidin-2-yl)amino)pyridin-3-yl)piperazin-1-yl)-3-oxopropyl)-2-(2,6-dioxopiperidin-3-yl)isoindoline-1,3-dione (example 58)

(4 mg, 33%). ¹H NMR (600 MHz, CD₃OD) δ 9.04 (s, 1H), 7.99-7.96 (m, 1H), 7.85 (s, 1H), 7.82-7.78 (m, 1H), 7.74-7.70 (m, 1H), 7.67-7.63 (m, 1H), 6.31 (s, 1H), 5.99-5.93 (m, 1H), 5.04 (dd, J=11.8, 6.0 Hz, 1H), 3.87-3.63 (m, 4H), 3.26-3.01 (m, 5H), 2.88-2.72 (m, 4H), 2.54 (s, 3H), 2.43 (s, 3H), 2.35-2.22 (m, 2H), 2.19-2.10 (m, 1H), 2.08-2.04 (m, 2H), 1.92-1.87 (m, 2H), 1.74-1.63 (m, 2H), 1.30-1.26 (m, 2H). HRMS (ESI-TOF) m/z: [M+H]⁺ calculated for $C_{40}H_{42}N_9O_7$, 760.3202; found: 760.3226.

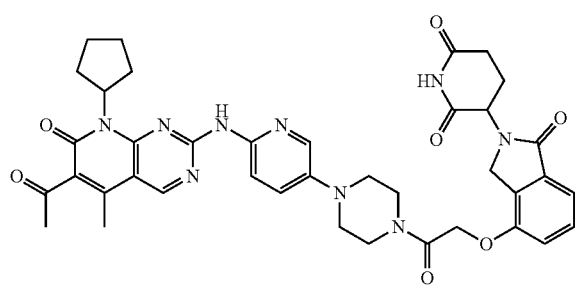

3-(4-(2-(4-(6-(((6-Acetyl-8-cyclopentyl-5-methyl-7-oxo-7,8-dihydropyrido[2,3-d]pyrimidin-2-yl)amino)pyridin-3-yl)piperazin-1-yl)-2-oxoethoxy)-1-oxoisoindolin-2-yl)piperidine-2,6-dione (example 59)

(43 mg, 90%) ¹H NMR (600 MHz, CD₃OD) δ 9.09 (s, 1H), 8.14 (dd, J=9.7, 2.8 Hz, 1H), 7.89 (d, J=2.5 Hz, 1H), 7.59 (d, J=9.6 Hz, 1H), 7.48-7.40 (m, 2H), 7.15 (d, J=8.0 Hz, 1H), 5.98 (p, J=8.8 Hz, 1H), 5.15 (dd, J=13.3, 5.1 Hz, 1H), 5.03 (AB, J$_{ab}$=14.4 Hz, 1H), 4.99 (AB, J$_{ab}$=14.4 Hz, 1H), 4.53 (AB, J$_{ab}$=17.4 Hz, 1H), 4.49 (AB, J$_{ab}$=17.4 Hz, 1H), 3.90-3.67 (m, 4H), 3.42-3.20 (m, 4H), 2.96-2.73 (m, 2H), 2.54 (s, 3H), 2.52-2.47 (m, 1H), 2.44 (s, 3H), 2.34-2.28 (m, 2H), 2.26-2.16 (m, 1H), 2.12-2.05 (m, 2H), 1.96-1.83 (m, 2H), 1.74-1.59 (m, 2H). HRMS (ESI-TOF) m/z: [M+H]⁺ calculated for $C_{39}H_{49}N_9O_7$, 748.3202; found: 748.3236.

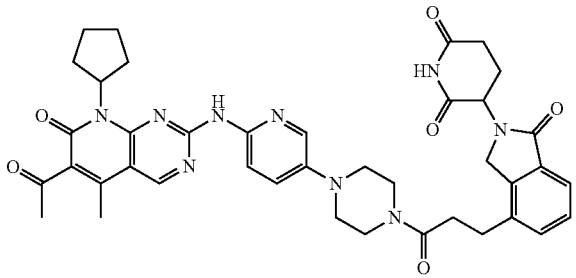

3-(4-(3-(4-(6-(((6-Acetyl-8-cyclopentyl-5-methyl-7-oxo-7,8-dihydropyrido[2,3-d]pyrimidin-2-yl)amino)pyridin-3-yl)piperazin-1-yl)-3-oxopropyl)-1-oxoisoindolin-2-yl)piperidine-2,6-dione (example 60)

(15 mg, 75%). ¹H NMR (600 MHz, CD₃OD) δ 9.12 (s, 1H), 8.11 (dd, J=9.7, 2.9 Hz, 1H), 7.79 (d, J=2.8 Hz, 1H), 7.65 (d, J=4.8 Hz, 1H), 7.58-7.52 (m, 2H), 7.49 (t, J=7.5 Hz, 1H), 6.01 (p, J=8.9 Hz, 1H), 5.17 (dd, J=13.3, 5.2 Hz, 1H), 4.56 (q, J=16.9 Hz, 2H), 3.83-3.72 (m, 2H), 3.63 (t, J=5.1 Hz, 2H), 3.22-3.13 (m, 2H), 3.08 (t, J=7.1 Hz, 2H), 3.03-2.97 (m, 1H), 2.94-2.82 (m, 5H), 2.59-2.49 (m, 4H), 2.45 (s, 3H), 2.35-2.29 (m, 2H), 2.27-2.16 (m, 1H), 2.14-2.04 (m, 2H), 1.95-1.83 (m, 2H), 1.75-1.63 (m, 2H). HRMS (ESI-TOF) m/z: [M+H]⁺ calculated for $C4H_{44}N_9O_6$, 746.3409; found: 746.3382.

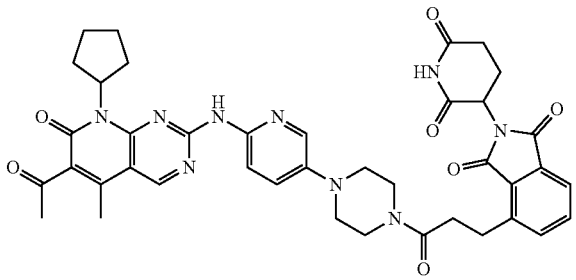

4-(3-(4-(6-(((6-Acetyl-8-cyclopentyl-5-methyl-7-oxo-7,8-dihydropyrido[2,3-d]pyrimidin-2-yl)amino)pyridin-3-yl)piperazin-1-yl)-3-oxopropyl)-2-(2,6-dioxopiperidin-3-yl)isoindoline-1,3-dione (example 61)

(17 mg, 43%). ¹H NMR (600 MHz, CD₃OD) δ 9.10 (s, 1H), 8.14 (d, J=9.4 Hz, 1H), 7.86 (s, 1H), 7.81-7.65 (m, 3H), 7.59 (d, J=9.5 Hz, 1H), 6.00 (p, J=8.8 Hz, 1H), 5.13 (dd, J=12.5, 5.3 Hz, 1H), 3.82-3.74 (m, 4H), 3.47-3.37 (m, 2H), 3.31-3.20 (m, 4H), 2.92-2.69 (m, 5H), 2.54 (s, 3H), 2.45 (s, 3H), 2.39-2.26 (m, 2H), 2.22-2.16 (m, 1H), 2.14-2.06 (m, 2H), 1.96-1.86 (m, 2H), 1.76-1.65 (m, 2H). HRMS (ESI-TOF) m/z: [M+H]⁺ calculated for $C_{40}H_{42}N_9O_7$, 760.3202; found: 760.3210.

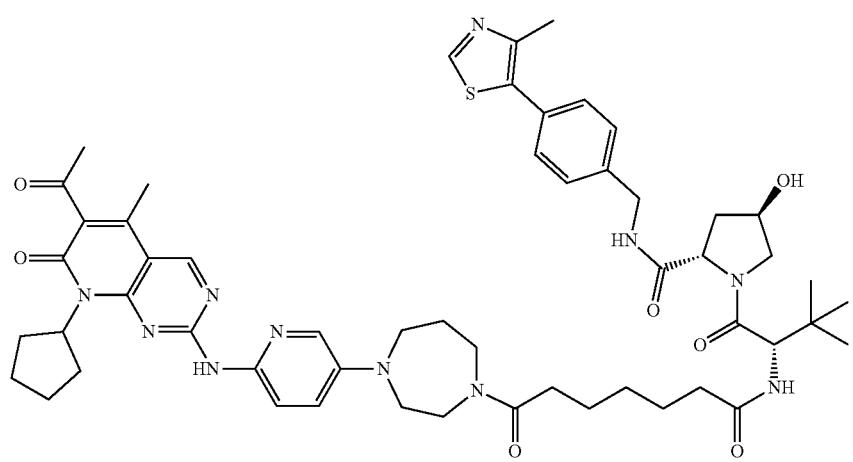

example 62

(2S,4R)-1-((S)-2-(7-(4-(6-((6-Acetyl-8-cyclopentyl-5-methyl-7-oxo-7,8-dihydropyrido[2,3-d]pyrimidin-2-yl)amino)pyridin-3-yl)-1,4-diazepan-1-yl)-7-oxo-heptanamido)-3,3-dimethylbutanoyl)-4-hydroxy-N-(4-(4-methylthiazol-5-yl)benzyl)pyrrolidine-2-carboxamide (example 62)

The title compound was synthesized using the same procedures for the preparation of the example 40 compound with linker 4 (9 mg, 74%) as white solid. $^1$H NMR (600 MHz, CD$_3$OD) δ 9.10 (s, 1H), 9.01 (s, 1H), 8.06-8.01 (m, 1H), 7.80-7.75 (m, 1H), 7.55-7.41 (m, 5H), 6.06-5.98 (m, 1H), 4.66-4.49 (m, 5H), 4.38 (dd, J=15.4, 4.1 Hz, 1H), 3.93-3.77 (m, 5H), 3.77-3.54 (m, 4H), 2.52 (s, 3H), 2.50 (s, 3H), 2.45 (s, 3H), 2.40-2.05 (m, 9H), 2.00-1.88 (m, 4H), 1.76-1.46 (m, 6H), 1.40-1.23 (m, 3H), 1.06-1.01 (m, 9H). HRMS (ESI-TOF) m/z: [M+H]$^+$ calculated for C$_{54}$H$_{70}$N$_{11}$O$_7$S, 1016.5175; found: 1016.5166.

example 63

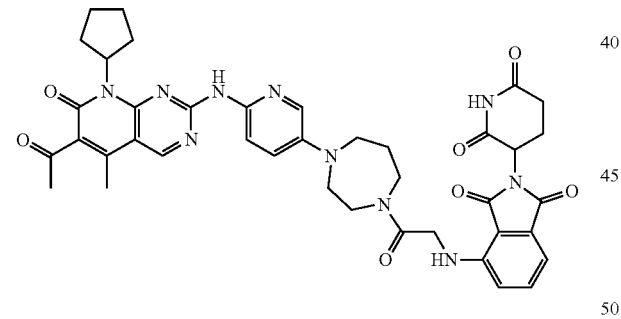

4-((2-(4-(6-((6-Acetyl-8-cyclopentyl-5-methyl-7-oxo-7,8-dihydropyrido[2,3-d]pyrimidin-2-yl)amino)pyridin-3-yl)-1,4-diazepan-1-yl)-2-oxoethyl)amino)-2-(2,6-dioxopiperidin-3-yl)isoindoline-1,3-dione (example 63)

The title compound was synthesized using the same procedures for the preparation of the example 40 compound with linker 24 (4 mg, 44%) as yellow solid. Rotamer (3:2) major one $^1$H NMR (600 MHz, CD$_3$OD) δ 9.02 (s, 1H), 7.81 (dd, J=9.6, 3.0 Hz, 1H), 7.51 (d, J=2.9 Hz, 1H), 7.37-7.33 (m, 2H), 6.92 (d, J=8.6 Hz, 1H), 6.87 (d, J=7.8 Hz, 1H), 6.06-6.00 (m, 1H), 5.05 (dd, J=12.8, 5.5 Hz, 1H), 4.24 (d, J=16.2 Hz, 1H), 4.16-4.14 (m, 1H), 3.96-3.79 (m, 4H), 3.74-3.65 (m, 4H), 2.90-2.63 (m, 4H), 2.54 (s, 3H), 2.44 (s, 3H), 2.40-2.28 (m, 2H), 2.16-2.06 (m, 2H), 1.98-1.87 (m, 4H), 1.78-1.65 (m, 2H). HRMS (ESI-TOF) m/z: [M+H]$^+$ calculated for C$_4$H$_{43}$N$_{10}$O$_7$, 775.3311; found: 775.3314.

Scheme 32: synthesis of example 64

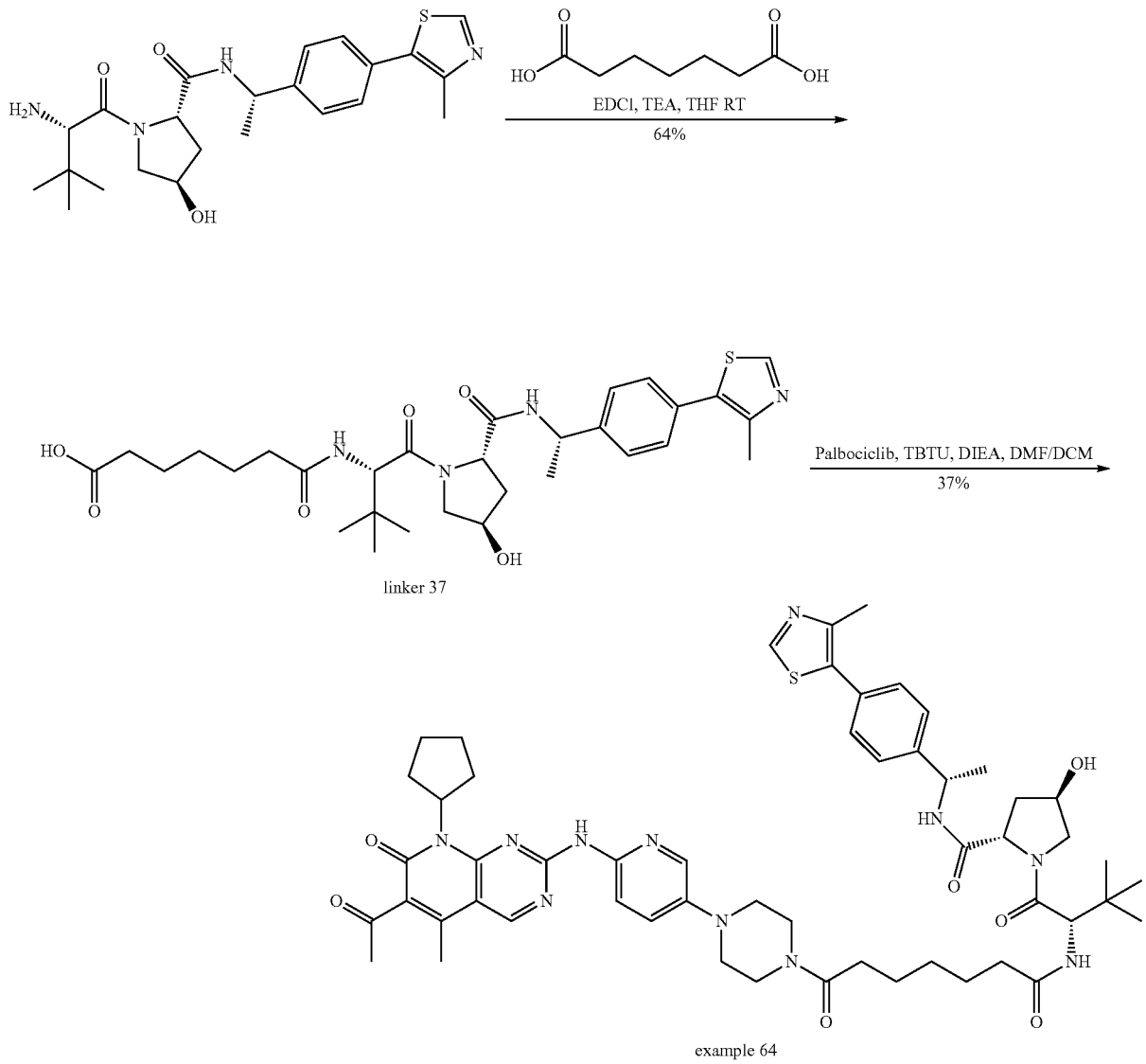

linker 37 example 64

7-(((S)-1-((2S,4R)-4-Hydroxy-2-(((S)-1-(4-(4-methylthiazol-5-yl)phenyl)ethyl)carbamoyl)pyrrolidin-1-yl)-3,3-dimethyl-1-oxobutan-2-yl)amino)-7-oxoheptanoic acid (linker 37)

The title compound was synthesis using the same procedures for the preparation of linker 1 (22 mg, 64%). $^1$H NMR (600 MHz, CD$_3$OD) δ 9.23 (s, 1H), 7.48 (dd, J=12.0, 7.3 Hz, 4H), 5.06-5.00 (m, 1H), 4.64 (s, 1H), 4.59 (t, J=8.4 Hz, 1H), 4.46-4.42 (m, 1H), 3.91 (d, J=11.1 Hz, 1H), 3.77 (dd, J=11.0, 4.0 Hz, 1H), 2.53 (s, 3H), 2.35-2.26 (m, 4H), 2.24-2.16 (m, 1H), 1.99-1.94 (m, 1H), 1.67-1.62 (m, 4H), 1.52 (d, J=7.2 Hz, 3H), 1.45-1.34 (m, 2H), 1.06 (s, 9H).

(2S,4R)-1-((S)-2-(7-(4-(6-((6-Acetyl-8-cyclopentyl-5-methyl-7-oxo-7,8-dihydropyrido[2,3-d]pyrimidin-2-yl)amino)pyridin-3-yl)piperazin-1-yl)-7-oxoheptanamido)-3,3-dimethylbutanoyl)-4-hydroxy-N—((S)-1-(4-(4-methylthiazol-5-yl)phenyl)ethyl)pyrrolidine-2-carboxamide (example 64)

The title compound was synthesized using the same procedures for the preparation of the example 40 compound with linker 37 (15 mg, 37%). $^1$H NMR (600 MHz, CD$_3$OD) δ 9.12 (s, 1H), 8.98 (s, 1H), 8.23 (dd, J=9.6, 2.9 Hz, 1H), 7.90 (d, J=2.6 Hz, 1H), 7.57 (d, J=9.5 Hz, 1H), 7.45 (q, J=8.3 Hz, 4H), 6.03 (p, J=8.8 Hz, 1H), 5.02 (q, J=6.6 Hz, 1H), 4.66 (s, 1H), 4.60 (t, J=7.7 Hz, 1H), 4.46 (br, 1H), 3.90 (d, J=11.0 Hz, 1H), 3.85-3.74 (m, 5H), 3.39-3.34 (m, 2H), 3.33-3.30 (m, 2H), 2.52 (s, 3H), 2.50 (s, 3H), 2.45 (s, 3H), 2.39-2.26 (m, 5H), 2.26-2.18 (m, 1H), 2.14-2.09 (m, 2H), 2.01-1.88 (m, 3H), 1.76-1.62 (m, 7H), 1.51 (d, J=6.6 Hz, 3H), 1.46-1.41 (m, 2H), 1.06 (s, 9H). HRMS (ESI-TOF) m/z: [M+H]$^+$ calculated for C$_{54}$H$_{70}$N$_{11}$O$_7$S, 1016.5175; found: 1016.5154.

Scheme 33: synthesis of example 65

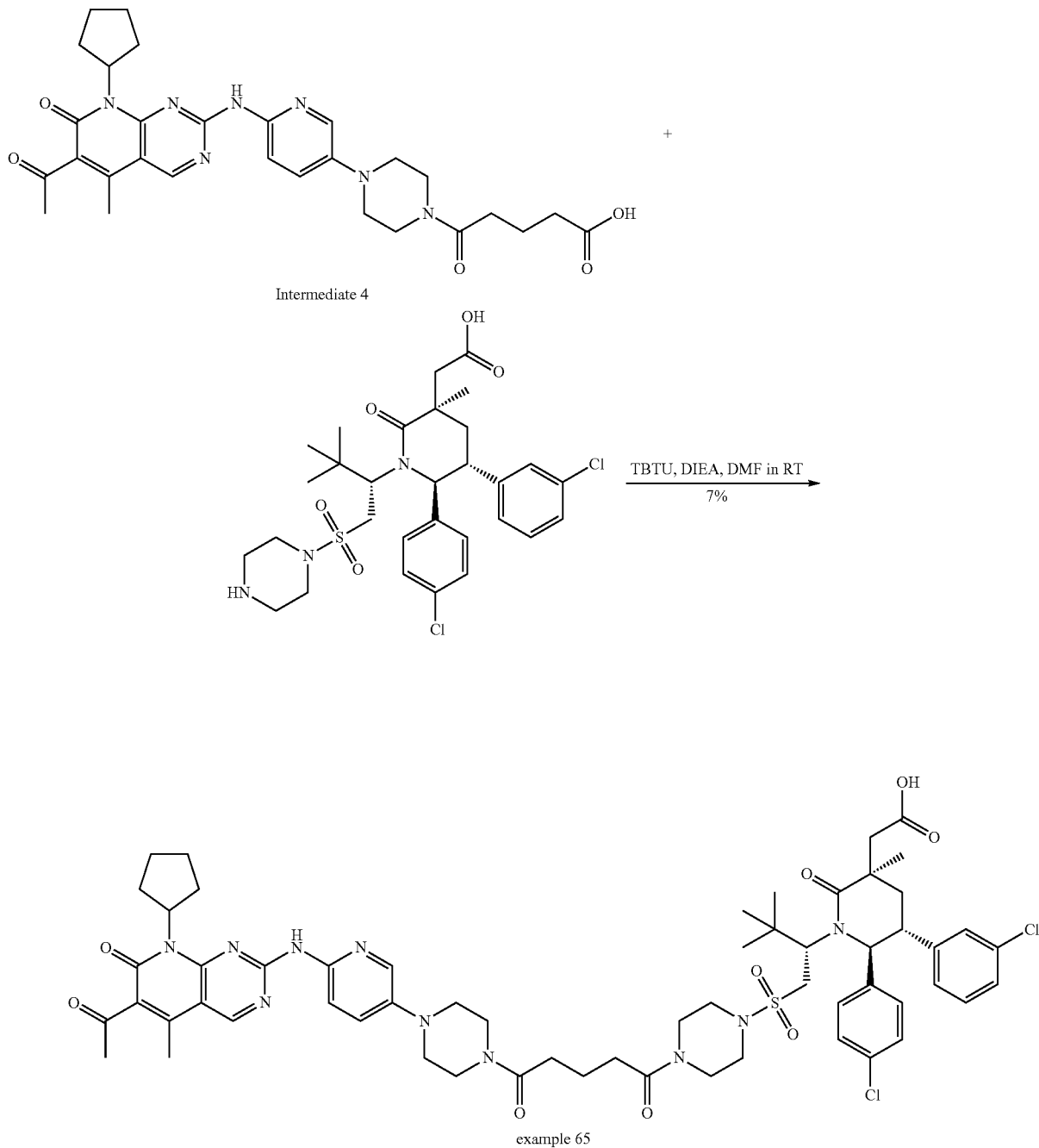

example 65

2-((3R,5R,6S)-1-((S)-1-((4-(5-(4-(6-(((6-Acetyl-8-cyclopentyl-5-methyl-7-oxo-7,8-dihydropyrido[2,3-d]pyrimidin-2-yl)amino)pyridin-3-yl)piperazin-1-yl)-5-oxopentanoyl)piperazin-1-yl)sulfonyl)-3,3-dimethylbutan-2-yl)-5-(3-chlorophenyl)-6-(4-chlorophenyl)-3-methyl-2-oxopiperidin-3-yl)acetic acid (example 65)

The title compound was synthesized using the same procedures for the preparation of the example 15 compound (4 mg, 7%). $^1$H NMR (600 MHz, CD$_3$OD) δ 9.13 (s, 1H), 8.24 (dd, J=9.6, 2.8 Hz, 1H), 7.89 (d, J=2.8 Hz, 1H), 7.79 (br, 1H), 7.57 (d, J=9.6 Hz, 1H), 7.47 (br, 1H), 7.19 (br, 1H), 7.16-7.07 (m, 3H), 7.07 (br, 1H), 7.02 (d, J=7.4 Hz, 1H), 6.08-5.98 (m, 1H), 5.09 (d, J=11.2 Hz, 1H), 3.96 (dd, J=13.6, 11.5 Hz, 1H), 3.87-3.67 (m, 8H), 3.55 (dd, J=11.4, 2.2 Hz, 1H), 3.43-3.36 (m, 9H), 3.03 (d, J=13.4 Hz, 1H), 2.94 (dd, J=13.6, 2.2 Hz, 1H), 2.66 (d, J=13.5 Hz, 1H), 2.56 (dd, J=13.6, 7.0 Hz, 4H), 2.53 (s, 3H), 2.46 (s, 3H), 2.89-2.35 (m, 3H), 2.16-2.08 (m, 3H), 2.01-1.90 (m, 4H), 1.72 (dd, J=10.5, 5.4 Hz, 2H), 1.40 (s, 3H), 0.73 (s, 9H). HRMS (ESI-TOF) m/z: [M+H]$^+$ calculated for C$_{59}$H$_{73}$Cl2N$_{10}$O$_9$S, 1167.4654; found: 1167.4653.

Scheme 34: synthesis of example 66

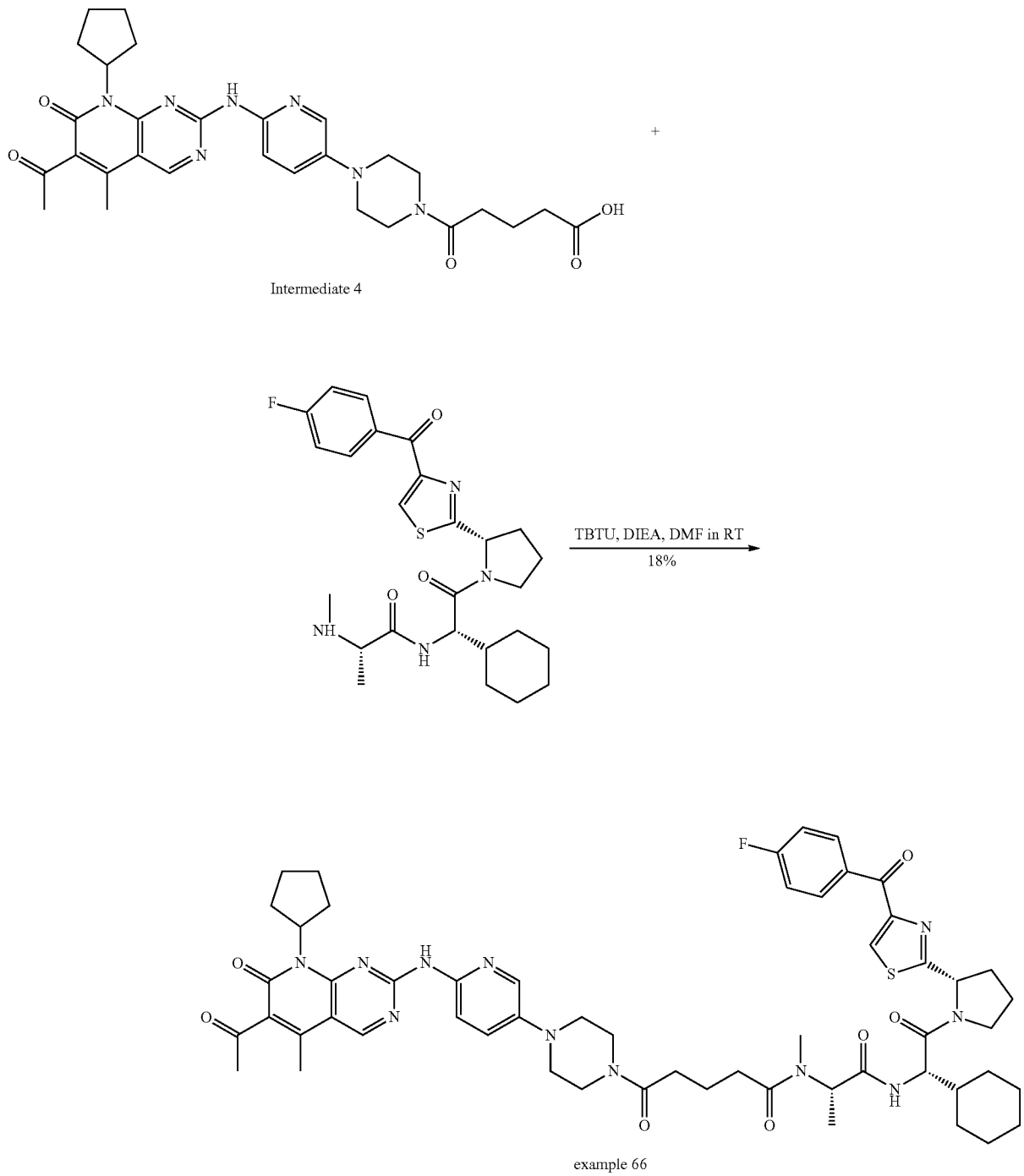

5-(4-(6-((6-Acetyl-8-cyclopentyl-5-methyl-7-oxo-7,8-dihydropyrido[2,3-d]pyrimidin-2-yl)amino)pyridin-3-yl)piperazin-1-yl)-N—((S)-1-(((S)-1-cyclohexyl-2-((S)-2-(4-(4-fluorobenzoyl)thiazol-2-yl)pyrrolidin-1-yl)-2-oxoethyl)amino)-1-oxopropan-2-yl)-N-methyl-5-oxopentanamide (example 66)

The title compound was synthesized using the same procedures for the preparation of the example 15 compound (9 mg, 18%). Rotamer (4:3) major one $^1$H NMR (600 MHz, CD$_3$OD) δ 9.10 (s, 1H), 8.41-8.15 (m, 3H), 7.88 (d, J=8.4 Hz, 1H), 7.83 (s, 1H), 7.56-7.50 (m, 1H), 7.30-7.20 (m, 2H), 6.08-6.00 (m, 1H), 5.46 (d, J=7.8 Hz, 1H), 5.17-5.13 (m, 1H), 4.58-4.52 (m, 1H), 4.28-4.23 (m, 1H), 3.85-3.69 (m, 5H), 3.36-3.19 (m, 4H), 2.88 (s, 3H), 2.56-2.25 (m, 12H), 2.21-2.06 (m, 4H), 2.01-1.66 (m, 11H), 1.35 (d, J=7.1 Hz, 4H), 1.34-0.84 (m, 7H). HRMS (ESI-TOF) m/z: [M+H]$^+$ calculated for C$_{55}$H$_{67}$FN$_{11}$O$_7$S. 1044.4924; found: 1044.4940.

Scheme 35: synthesis of example 67

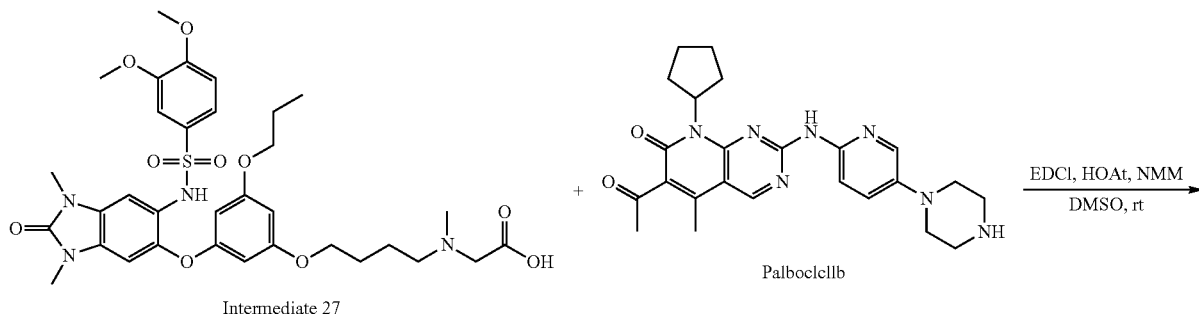

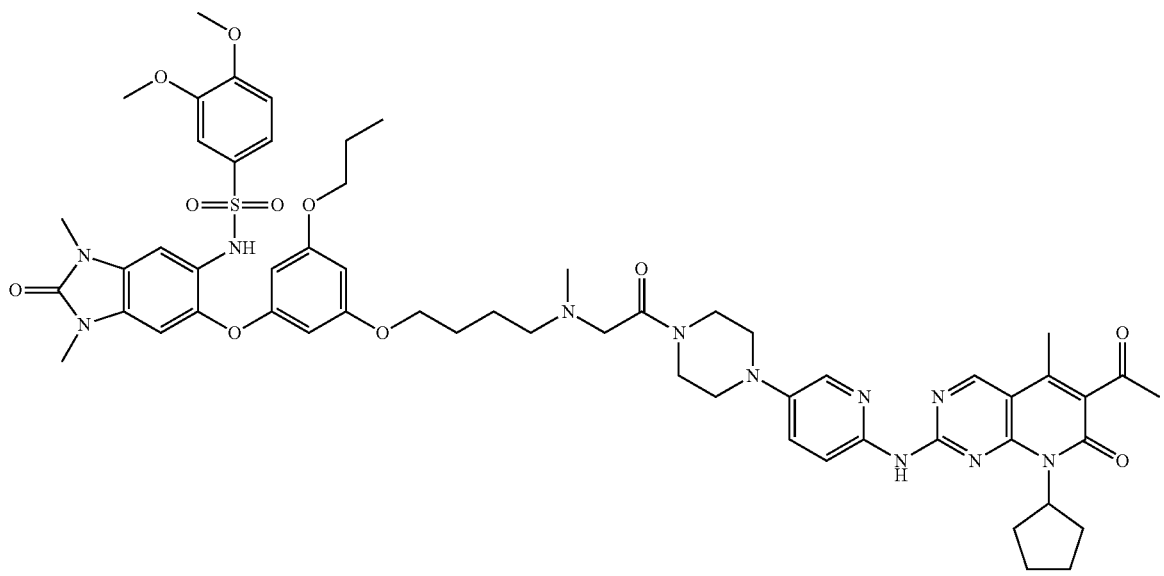

example 67

N-(6-(3-(4-((2-(4-(6-(((6-Acetyl-8-cyclopentyl-5-methyl-7-oxo-7,8-dihydropyrido[2,3-d]pyrimidin-2-yl)amino)pyridin-3-yl)piperazin-1-yl)-2-oxoethyl)(methyl)amino)butoxy)-5-propoxyphenoxy)-1,3-dimethyl-2-oxo-2,3-dihydro-1H-benzo[d]imidazol-5-yl)-3,4-dimethoxybenzenesulfonamide (example 67)

To a solution of intermediate 27 (10 mg, 0.01 mmol), HOAt (1-hydroxy-7-azabenzo-triazole) (4.3 mg, 0.03 mmol), and intermediate 2 (5 mg, 0.01 mmol) in DMSO (1 mL) were added NMM (14 μL, 0.13 mmol) and EDCI (6.05 mg, 0.03 mmol) at room temperature. After being stirred overnight at room temperature, the mixture was purified by preparative HPLC (10%-100% methanol/0.1% TFA in H$_2$O) to afford example 67 as white solid (6 mg, 54%). $^1$H NMR (600 MHz, CD$_3$OD) δ 9.07 (s, 1H), 8.15 (dd, J=10.0, 2.7 Hz, 1H), 7.83 (s, 1H), 7.51 (d, J=9.6 Hz, 1H), 7.29 (s, 1H), 7.18 (dd, J=8.5, 2.2 Hz, 1H), 7.13 (d, J=2.1 Hz, 1H), 6.77 (d, J=8.5 Hz, 1H), 6.59 (s, 1H), 6.14 (s, 1H), 6.04-5.97 (m, 1H), 5.72 (t, J=2.1 Hz, 1H), 5.61 (t, J=2.1 Hz, 1H), 4.52-4.25 (m, 2H), 3.97-3.83 (m, 4H), 3.82-3.78 (m, 3H), 3.75 (t, J=6.5 Hz, 2H), 3.60 (s, 6H), 3.39 (s, 5H), 3.24 (s, 6H), 2.99 (s, 3H), 2.50 (s, 3H), 2.43 (s, 3H), 2.31 (dt, J=15.7, 8.4 Hz, 2H), 2.09 (dq, J=12.3, 7.0 Hz, 2H), 2.02-1.87 (m, 4H), 1.83 (p, J=6.8 Hz, 2H), 1.76-1.65 (m, 4H), 1.00 (t, J=7.4 Hz, 3H). HRMS (ESI-TOF) m/z: [M+H]$^+$ calcd for C$_{57}$H$_{70}$N$_{11}$O$_{11}$S$^+$, 1116.4971; found, 1116.4961.

example 68

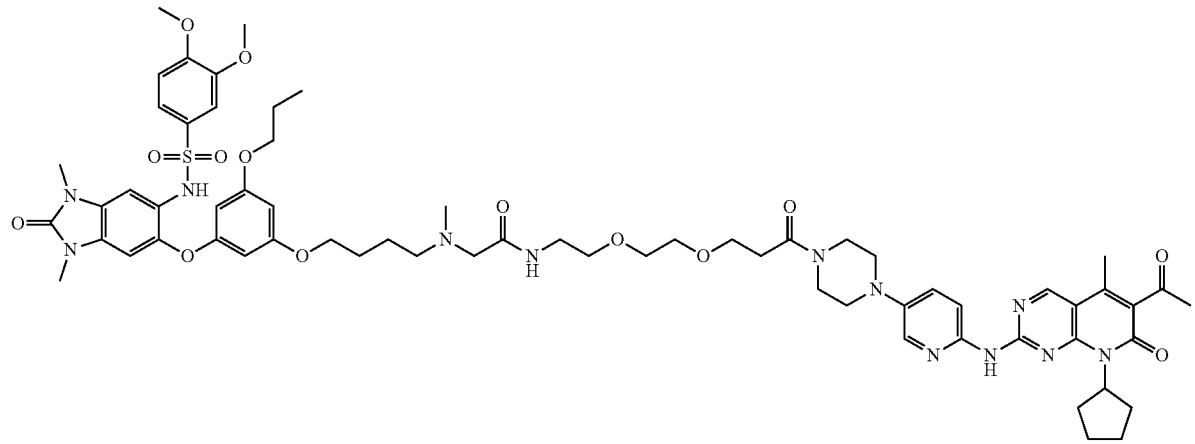

N-(2-(2-(3-(4-(6-(((6-Acetyl-8-cyclopentyl-5-methyl-7-oxo-7,8-dihydropyrido[2,3-d]pyrimidin-2-yl)amino)pyridin-3-yl)piperazin-1-yl)-3-oxopropoxy)ethoxy)ethyl)-2-((4-(3-((6-(((3,4-dimethoxyphenyl)sulfonamido)-1,3-dimethyl-2-oxo-2,3-dihydro-1H-benzo[d]imidazol-5-yl)oxy)-5-propoxyphenoxy)butyl)(methyl)amino)acetamide (example 68)

The title compound was synthesized using the same procedures for the preparation of the example 67 compound as white solid (7 mg, 55%). $^1$H NMR (600 MHz, CD$_3$OD) δ 9.05 (s, 1H), 8.16 (dd, J=9.7, 2.9 Hz, 1H), 7.84 (d, J=2.9 Hz, 1H), 7.52 (d, J=9.5 Hz, 1H), 7.29 (s, 1H), 7.17 (dd, J=8.5, 2.1 Hz, 1H), 7.12 (d, J=2.1 Hz, 1H), 6.78 (d, J=8.5 Hz, 1H), 6.60 (s, 1H), 6.14 (d, J=2.7 Hz, 1H), 6.00 (p, J=8.9 Hz, 1H), 5.73 (d, J=2.3 Hz, 1H), 5.62 (d, J=2.4 Hz, 1H), 3.96 (d, J=45.2 Hz, 2H), 3.86 (t, J=5.9 Hz, 2H), 3.82-3.71 (m, 14H), 3.59 (d, J=3.9 Hz, 7H), 3.54 (t, J=5.3 Hz, 2H), 3.45-3.37 (m, 5H), 3.28-3.22 (m, 6H), 2.95 (d, J=1.1 Hz, 3H), 2.72 (t, J=6.2 Hz, 2H), 2.50 (d, J=1.1 Hz, 3H), 2.42 (s, 3H), 2.31 (dt, J=15.2, 7.6 Hz, 2H), 2.09 (s, 2H), 1.92 (dt, J=15.9, 8.2 Hz, 4H), 1.82 (p, J=6.3 Hz, 2H), 1.71 (dq, J=20.6, 6.3, 5.6 Hz, 4H), 1.00 (dd, J=7.9, 6.8 Hz, 3H). HRMS (ESI-TOF) m/z: [M+H]$^+$ calcd for C$_{64}$H$_{83}$N$_{12}$O$_{14}$S$^+$, 1275.5867; found, 1275.5887.

N-(15-(4-(6-(((6-Acetyl-8-cyclopentyl-5-methyl-7-oxo-7,8-dihydropyrido[2,3-d]pyrimidin-2-yl)amino)pyridin-3-yl)piperazin-1-yl)-15-oxo-3,6,9,12-tetraoxapentadecyl)-2-((4-(3-((6-((6-((3,4-dimethoxyphenyl)sulfonamido)-1,3-dimethyl-2-oxo-2,3-dihydro-1H-benzo[d]imidazol-5-yl)oxy)-5-propoxyphenoxy)butyl)(methyl)amino)acetamide (example 69)

The title compound was synthesized using the same procedures for the preparation of the example 67 compound as white solid (6 mg, 44%). $^1$H NMR (600 MHz, CD$_3$OD) δ 9.06 (d, J=1.2 Hz, 1H), 8.17 (dd, J=9.6, 3.0 Hz, 1H), 7.85 (d, J=2.9 Hz, 1H), 7.53 (d, J=9.6 Hz, 1H), 7.31 (d, J=1.2 Hz, 1H), 7.18 (dd, J=8.5, 1.9 Hz, 1H), 7.13 (d, J=2.0 Hz, 1H), 6.78 (d, J=8.5 Hz, 1H), 6.60 (d, J=1.2 Hz, 1H), 6.20-6.11 (m, 1H), 6.05-5.92 (m, 1H), 5.75 (d, J=2.3 Hz, 1H), 5.63-5.41 (m, 1H), 3.97 (d, J=43.7 Hz, 2H), 3.88-3.84 (m, 2H), 3.83-3.68 (m, 13H), 3.62-3.56 (m, 14H), 3.54 (t, J=5.3 Hz, 2H), 3.45-3.38 (m, 5H), 3.35-3.19 (m, 8H), 2.95 (d, J=1.3 Hz, 3H), 2.72 (t, J=6.2 Hz, 2H), 2.50 (d, J=1.3 Hz, 3H), 2.42 (d, J=1.2 Hz, 3H), 2.30 (d, J=9.6 Hz, 2H), 2.09 (s, 2H), 1.95-1.87 (m, 4H), 1.82 (q, J=7.1, 6.7 Hz, 2H), 1.72 (dq, J=20.9, 7.2 Hz, 4H), 1.01 (td, J=7.4, 1.2 Hz, 3H). HRMS (ESI-TOF) m/z: [M+H]$^+$ calcd for C$_{68}$H$_{91}$N$_{12}$O$_{16}$S$^+$, 1363.6391; found, 1363.6387.

example 69

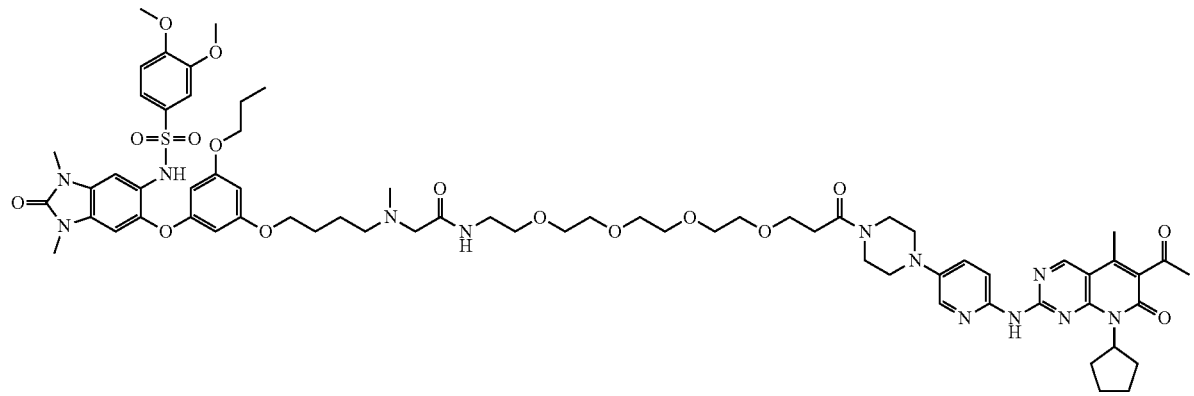

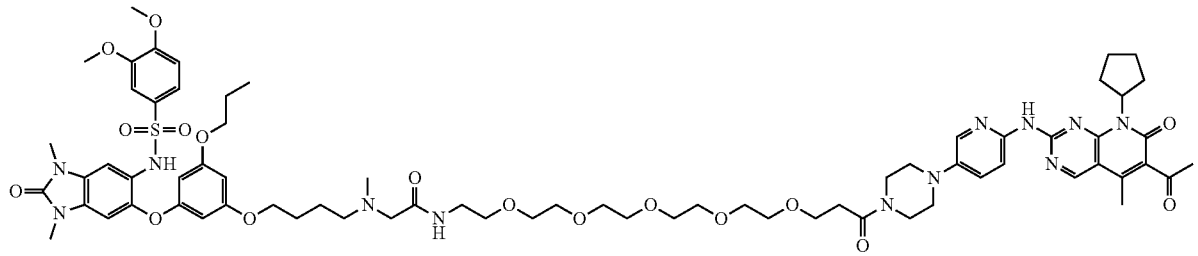

example 70

N-(18-(4-(6-(((6-Acetyl-8-cyclopentyl-5-methyl-7-oxo-7,8-dihydropyrido[2,3-d]pyrimidin-2-yl)amino)pyridin-3-yl)piperazin-1-yl)-18-oxo-3,6,9,12,15-pentaoxaoctadecyl)-2-((4-(3-((6-(((3,4-dimethoxyphenyl)sulfonamido)-1,3-dimethyl-2-oxo-2,3-dihydro-1H-benzo[d]imidazol-5-yl)oxy)-5-propoxyphenoxy)butyl)(methyl)amino)acetamide (example 70)

The title compound was synthesized using the same procedures for the preparation of the example 67 compound as white solid (9 mg, 64%). $^1$H NMR (600 MHz, CD$_3$OD) δ 9.09-9.04 (m, 1H), 8.18 (dd, J=9.6, 2.9 Hz, 1H), 7.86 (d, J=2.9 Hz, 1H), 7.53 (d, J=9.6 Hz, 1H), 7.31 (d, J=0.9 Hz, 1H), 7.18 (dd, J=8.4, 1.9 Hz, 1H), 7.13 (d, J=2.2 Hz, 1H), 6.78 (d, J=8.5 Hz, 1H), 6.60 (d, J=0.9 Hz, 1H), 6.15 (d, J=2.3 Hz, 1H), 6.00 (p, J=8.9 Hz, 1H), 5.75 (d, J=2.3 Hz, 1H), 5.61 (d, J=2.5 Hz, 1H), 3.97 (d, J=42.8 Hz, 2H), 3.86 (t, J=5.9 Hz, 2H), 3.83-3.73 (m, 13H), 3.63-3.56 (m, 18H), 3.54 (t, J=5.3 Hz, 2H), 3.48-3.38 (m, 5H), 3.36-3.21 (m, 8H), 2.95 (d, J=1.0 Hz, 3H), 2.72 (t, J=6.2 Hz, 2H), 2.50 (d, J=1.0 Hz, 3H), 2.42 (s, 3H), 2.31 (dd, J=12.5, 7.3 Hz, 2H), 2.09 (s, 2H), 1.96-1.88 (m, 4H), 1.82 (q, J=7.2, 6.6 Hz, 2H), 1.72 (dq, J=25.3, 6.3, 5.6 Hz, 4H), 1.07-0.88 (m, 3H). HRMS (ESI-TOF) m/z: [M+H]$^+$ calcd for C$_{70}$H$_{94}$N$_{12}$O$_{17}$S$^+$, 1407.6653; found, 1407.6628.

N-(2-(4-(6-(((6-Acetyl-8-cyclopentyl-5-methyl-7-oxo-7,8-dihydropyrido[2,3-d]pyrimidin-2-yl)amino)pyridin-3-yl)piperazin-1-yl)-2-oxoethyl)-2-((4-(3-(((6-(((3,4-dimethoxyphenyl)sulfonamido)-1,3-dimethyl-2-oxo-2,3-dihydro-H-benzo[d]imidazol-5-yl)oxy)-5-propoxyphenoxy)butyl)(methyl)amino)acetamide (example 71)

The title compound was synthesized using the same procedures for the preparation of the example 67 compound as white solid (7 mg, 60%). $^1$H NMR (600 MHz, CD$_3$OD) δ 9.08 (s, 1H), 8.13 (d, J=9.6 Hz, 1H), 7.84 (s, 1H), 7.54 (d, J=9.6 Hz, 1H), 7.32 (d, J=1.6 Hz, 1H), 7.18 (d, J=8.5 Hz, 1H), 7.13 (d, J=1.9 Hz, 1H), 6.78 (dd, J=8.6, 1.6 Hz, 1H), 6.62 (d, J=1.6 Hz, 1H), 6.14 (d, J=2.0 Hz, 1H), 6.01 (t, J=8.8 Hz, 1H), 5.73 (d, J=2.1 Hz, 1H), 5.64 (d, J=2.1 Hz, 1H), 4.23 (d, J=37.0 Hz, 2H), 4.08 (d, J=31.5 Hz, 2H), 3.87 (t, J=5.9 Hz, 2H), 3.82-3.68 (m, 10H), 3.60 (d, J=1.6 Hz, 3H), 3.41 (d, J=1.6 Hz, 3H), 3.25 (d, J=1.6 Hz, 8H), 2.98 (d, J=1.6 Hz, 3H), 2.50 (d, J=1.6 Hz, 3H), 2.43 (d, J=1.7 Hz, 3H), 2.31 (d, J=9.0 Hz, 2H), 2.09 (s, 2H), 1.93 (dd, J=16.5, 9.0 Hz, 4H), 1.83 (d, J=7.2 Hz, 2H), 1.73 (dt, J=19.8, 9.9 Hz, 4H), 1.00 (td, J=7.4, 1.7 Hz, 3H). HRMS (ESI-TOF) m/z: [M+H]$^+$ calcd for C$_{59}$H$_{73}$N$_{12}$O$_{12}$S$^+$, 1173.5186; found, 1173.5195.

example 71

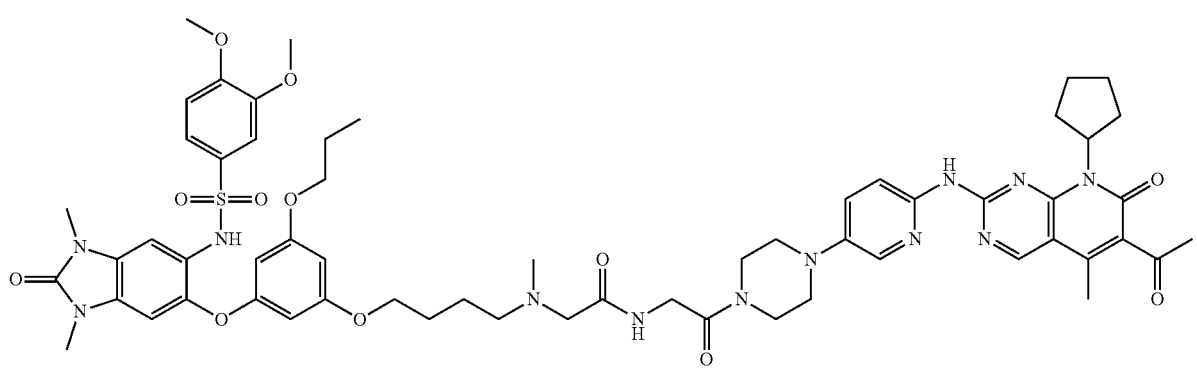

example 72

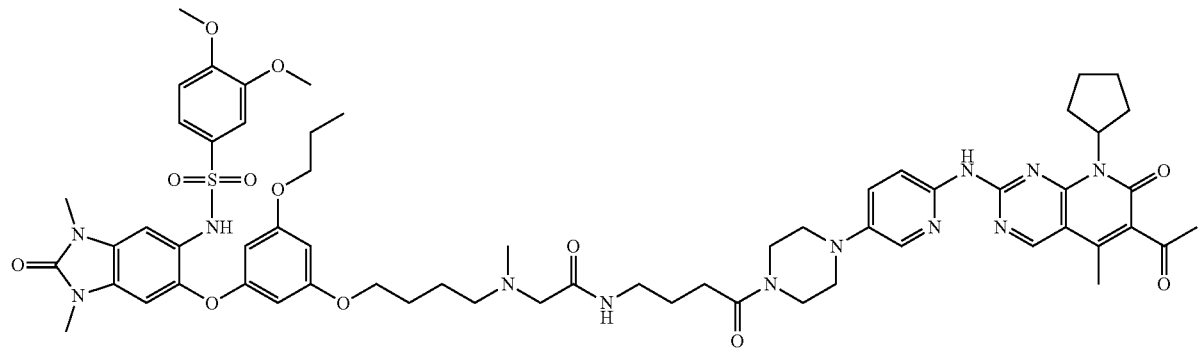

N-(4-(4-(6-(((6-Acetyl-8-cyclopentyl-5-methyl-7-oxo-7,8-dihydropyrido[2,3-d]pyrimidin-2-yl)amino)pyridin-3-yl)piperazin-1-yl)-4-oxobutyl)-2-((4-(3-((6-((3,4-dimethoxyphenyl)sulfonamido)-1,3-dimethyl-2-oxo-2,3-dihydro-1H-benzo[d]imidazol-5-yl)oxy)-5-propoxyphenoxy)butyl)(methyl)amino)acetamide (example 72)

The title compound was synthesized using the same procedures for the preparation of the example 67 compound as white solid (7 mg, 58%). $^1$H NMR (600 MHz, CD$_3$OD) δ 9.07 (s, 1H), 8.14 (dd, J=9.5, 2.9 Hz, 1H), 7.84 (s, 1H), 7.54 (d, J=9.5 Hz, 1H), 7.31 (s, 1H), 7.18 (d, J=8.5 Hz, 1H), 7.13 (d, J=2.2 Hz, 1H), 6.78 (d, J=8.5 Hz, 1H), 6.61 (s, 1H), 6.14 (d, J=2.5 Hz, 1H), 6.00 (p, J=8.9 Hz, 1H), 5.74 (s, 1H), 5.62 (d, J=2.5 Hz, 1H), 3.98 (d, J=50.2 Hz, 2H), 3.86 (t, J=5.9 Hz, 2H), 3.80 (s, 3H), 3.78-3.66 (m, 7H), 3.61 (s, 3H), 3.41 (d, J=1.1 Hz, 3H), 3.31-3.18 (m, 10H), 2.95 (s, 3H), 2.52-2.46 (m, 5H), 2.42 (s, 3H), 2.31 (q, J=9.1, 7.5 Hz, 2H), 2.09 (s, 2H), 1.94-1.88 (m, 4H), 1.83 (dt, J=14.3, 7.4 Hz, 4H), 1.76-1.66 (m, 4H), 1.00 (t, J=7.4 Hz, 3H). HRMS (ESI-TOF) m/z: [M+H]$^+$ calcd for C$_{61}$H$_{77}$N$_{12}$1$_2$S$^+$, 1201.5499; found, 1201.5489.

N-(2-(3-(4-(6-(((6-Acetyl-8-cyclopentyl-5-methyl-7-oxo-7,8-dihydropyrido[2,3-d]pyrimidin-2-yl)amino)pyridin-3-yl)piperazin-1-yl)-3-oxopropoxy)ethyl)-2-((4-(3-((6-((3,4-dimethoxyphenyl)sulfonamido)-1,3-dimethyl-2-oxo-2,3-dihydro-1H-benzo[d]imidazol-5-yl)oxy)-5-propoxyphenoxy)butyl)(methyl)amino)acetamide (example 73)

The title compound was synthesized using the same procedures for the preparation of the example 67 compound as white solid (8 mg, 65%). $^1$H NMR (600 MHz, CD$_3$OD) δ 9.05 (s, 1H), 8.10 (d, J=9.6 Hz, 1H), 7.84 (s, 1H), 7.56 (d, J=9.4 Hz, 1H), 7.34-7.26 (m, 1H), 7.18 (d, J=8.4 Hz, 1H), 7.13 (d, J=1.7 Hz, 1H), 6.84-6.72 (m, 1H), 6.67-6.50 (m, 1H), 6.14 (s, 1H), 6.00 (p, J=8.9 Hz, 1H), 5.74 (s, 1H), 5.63 (s, 1H), 3.99 (s, 2H), 3.86 (t, J=5.8 Hz, 2H), 3.83-3.72 (m, 15H), 3.60 (d, J=1.1 Hz, 3H), 3.56 (t, J=5.4 Hz, 2H), 3.40 (d, J=1.1 Hz, 4H), 3.26-3.22 (m, 5H), 2.96 (d, J=1.2 Hz, 3H), 2.70 (t, J=5.9 Hz, 2H), 2.50 (d, J=1.2 Hz, 3H), 2.42 (d, J=1.2 Hz, 3H), 2.31 (dd, J=12.5, 7.3 Hz, 2H), 2.09 (s, 3H), 1.93 (dt, J=16.9, 8.3 Hz, 4H), 1.86-1.79 (m, 2H), 1.72 (dt, J=19.2, 9.6 Hz, 4H), 1.00 (td, J=7.5, 1.2 Hz, 3H). HRMS (ESI-TOF) m/z: [M+H]$^+$ calcd for C$_{62}$H$_{79}$N$_{12}$O$_{13}$S$^+$, 1231.5605; found, 1231.5621.

example 73

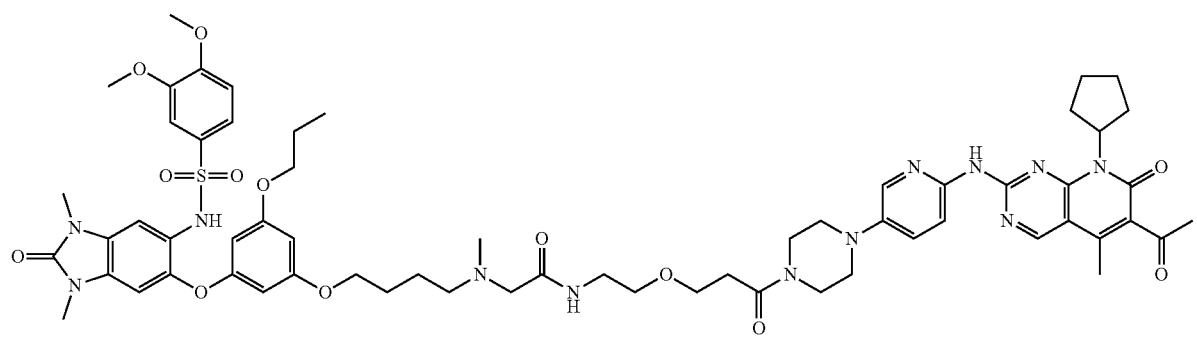

example 74

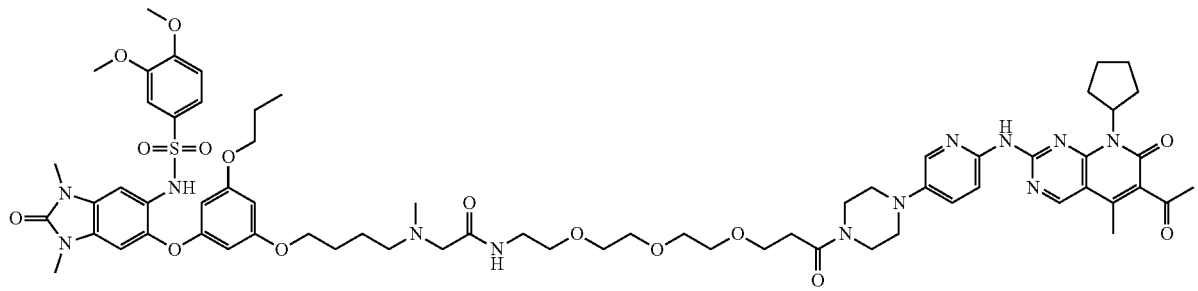

N-(2-(2-(2-(3-(4-(6-(((6-Acetyl-8-cyclopentyl-5-methyl-7-oxo-7,8-dihydropyrido[2,3-d]pyrimidin-2-yl)amino)pyridin-3-yl)piperazin-1-yl)-3-oxopropoxy)ethoxy)ethoxy)ethyl)-2-((4-(3-((6-(((3,4-dimethoxyphenyl)sulfonamido)-1,3-dimethyl-2-oxo-2,3-dihydro-1H-benzo[d]imidazol-5-yl)oxy)-5-propoxyphenoxy)butyl)(methyl)amino)acetamide (example 74)

The title compound was synthesized using the same procedures for the preparation of the example 67 compound as white solid (8 mg, 61%). $^1$H NMR (600 MHz, CD$_3$OD) δ 9.06 (s, 1H), 8.16 (dd, J=9.6, 2.9 Hz, 1H), 7.85 (s, 1H), 7.53 (d, J=9.6 Hz, 1H), 7.30 (s, 1H), 7.18 (dd, J=8.5, 2.1 Hz, 1H), 7.12 (d, J=2.1 Hz, 1H), 6.78 (d, J=8.4 Hz, 1H), 6.60 (s, 1H), 6.14 (d, J=2.6 Hz, 1H), 6.00 (p, J=9.0 Hz, 1H), 5.74 (d, J=2.4 Hz, 1H), 5.61 (d, J=2.5 Hz, 1H), 3.98 (d, J=36.9 Hz, 2H), 3.85 (t, J=5.9 Hz, 2H), 3.82-3.70 (m, 13H), 3.63-3.52 (m, 15H), 3.45-3.36 (m, 5H), 3.29-3.19 (m, 5H), 2.95 (d, J=1.1 Hz, 3H), 2.72 (t, J=6.2 Hz, 2H), 2.50 (d, J=1.2 Hz, 3H), 2.42 (s, 3H), 2.30 (d, J=9.4 Hz, 2H), 2.09 (s, 2H), 1.92 (q, J=8.3, 7.9 Hz, 4H), 1.81 (p, J=6.3 Hz, 2H), 1.71 (ddd, J=23.2, 12.4, 6.2 Hz, 4H), 1.00 (t, J=7.4 Hz, 3H). HRMS (ESI-TOF) m/z: [M+H]$^+$ calcd for C$_{66}$H$_{87}$N$_{12}$O$_{15}$S$^+$, 1319.6129; found, 1319.6132.

N-(3-(4-(6-(((6-Acetyl-8-cyclopentyl-5-methyl-7-oxo-7,8-dihydropyrido[2,3-d]pyrimidin-2-yl)amino)pyridin-3-yl)piperazin-1-yl)-3-oxopropyl)-2-((4-(3-((6-(((3,4-dimethoxyphenyl)sulfonamido)-1,3-dimethyl-2-oxo-2,3-dihydro-H-benzo[d]imidazol-5-yl)oxy)-5-propoxyphenoxy)butyl)(methyl)amino) acetamide (example 75)

The title compound was synthesized using the same procedures for the preparation of the example 67 compound as white solid (9 mg, 76%). $^1$H NMR (600 MHz, CD$_3$OD) δ 9.07 (s, 1H), 8.15 (dd, J=9.6, 2.9 Hz, 1H), 7.82 (d, J=2.9 Hz, 1H), 7.52 (d, J=9.5 Hz, 1H), 7.30 (d, J=1.2 Hz, 1H), 7.17 (dd, J=8.4, 2.0 Hz, 1H), 7.12 (d, J=2.2 Hz, 1H), 6.77 (d, J=8.4 Hz, 1H), 6.60 (d, J=1.2 Hz, 1H), 6.14 (t, J=1.9 Hz, 1H), 6.01 (p, J=8.9 Hz, 1H), 5.74 (t, J=1.9 Hz, 1H), 5.61 (t, J=1.9 Hz, 1H), 3.96 (d, J=48.7 Hz, 2H), 3.86 (t, J=5.9 Hz, 2H), 3.80 (d, J=1.3 Hz, 3H), 3.76 (t, J=6.6 Hz, 6H), 3.69 (t, J=5.2 Hz, 2H), 3.60 (d, J=1.2 Hz, 5H), 3.40 (d, J=1.3 Hz, 3H), 3.30-3.21 (m, 7H), 2.95 (d, J=1.2 Hz, 3H), 2.68 (t, J=6.4 Hz, 2H), 2.51 (d, J=1.2 Hz, 3H), 2.43 (d, J=1.2 Hz, 3H), 2.37-2.27 (m, 2H), 2.10 (s, 2H), 1.91 (q, J=8.1 Hz, 4H), 1.86-1.79 (m, 2H), 1.72 (dq, J=14.0, 7.1 Hz, 4H), 1.00 (td, J=7.4, 1.2 Hz, 3H). HRMS (ESI-TOF) m/z: [M+H]$^+$ calcd for C$_{57}$H$_{70}$N$_{11}$O$_{11}$S$^+$, 1187.5343; found, 1187.5355.

example 75

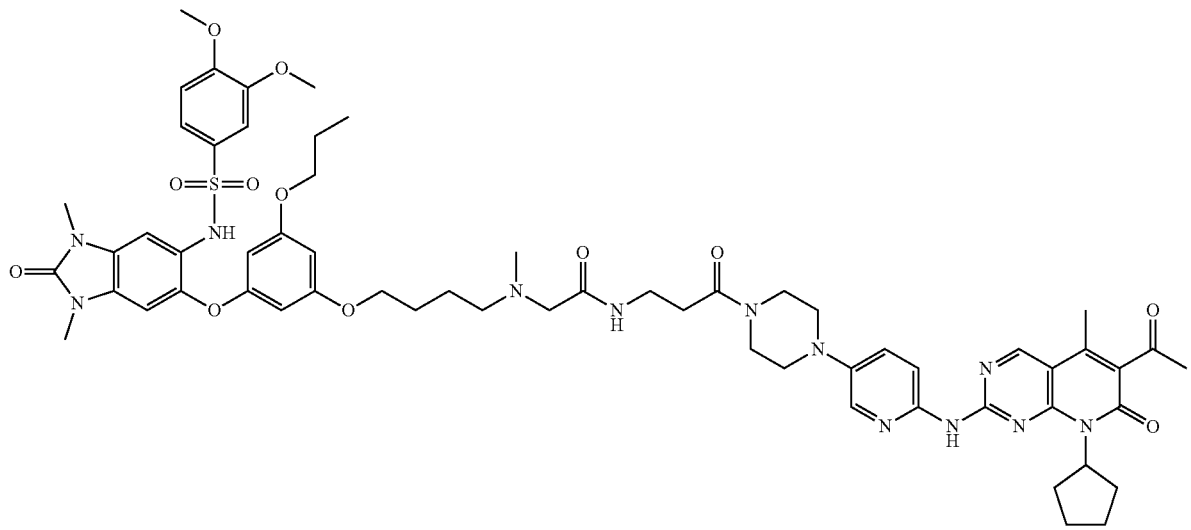

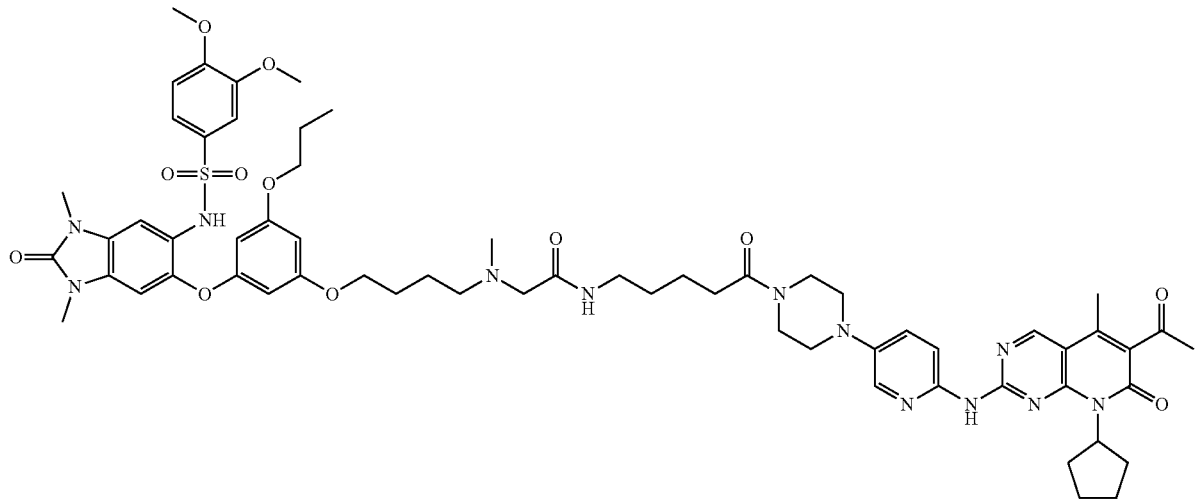

example 76

N-(5-(4-(6-(((6-Acetyl-8-cyclopentyl-5-methyl-7-oxo-7,8-dihydropyrido[2,3-d]pyrimidin-2-yl)amino)pyridin-3-yl)piperazin-1-yl)-5-oxopentyl)-2-((4-(3-((6-((3,4-dimethoxyphenyl)sulfonamido)-1,3-dimethyl-2-oxo-2,3-dihydro-H-benzo[d]imidazol-5-yl)oxy)-5-propoxyphenoxy)butyl)(methyl)amino)acetamide (example 76)

The title compound was synthesized using the same procedures for the preparation of the example 67 compound as white solid (5 mg, 41%). $^1$H NMR (600 MHz, CD$_3$OD) δ 9.08 (d, J=1.2 Hz, 1H), 8.17 (dd, J=9.6, 2.9 Hz, 1H), 7.83 (d, J=2.9 Hz, 1H), 7.52 (d, J=9.5 Hz, 1H), 7.31 (d, J=1.2 Hz, 1H), 7.18 (dd, J=8.5, 2.0 Hz, 1H), 7.13 (d, J=2.0 Hz, 1H), 6.78 (dd, J=8.5, 1.2 Hz, 1H), 6.61 (d, J=1.1 Hz, 1H), 6.14 (t, J=2.0 Hz, 1H), 6.01 (p, J=8.9 Hz, 1H), 5.73 (t, J=2.0 Hz, 1H), 5.62 (t, J=2.0 Hz, 1H), 4.07-3.93 (m, 2H), 3.86 (t, J=5.9 Hz, 2H), 3.80 (d, J=1.2 Hz, 3H), 3.79-3.68 (m, 10H), 3.60 (d, J=1.2 Hz, 3H), 3.40 (d, J=1.2 Hz, 3H), 3.34-3.23 (m, 7H), 2.95 (d, J=1.3 Hz, 3H), 2.50 (d, J=1.3 Hz, 3H), 2.48-2.38 (m, 5H), 2.31 (q, J=9.0, 7.5 Hz, 2H), 2.10 (s, 2H), 1.92 (dt, J=15.5, 7.9 Hz, 4H), 1.82 (p, J=6.3 Hz, 2H), 1.72 (dq, J=20.1, 6.3, 5.5 Hz, 4H), 1.61 (dq, J=28.9, 7.8 Hz, 4H), 1.00 (td, J=7.5, 1.3 Hz, 3H). HRMS (ESI-TOF m/z: [M+H]$^+$ calcd for C$_{62}$H$_{79}$N$_{12}$O$_{12}$S$^+$, 1215.5656; found, 1215.5637.

N-(6-(4-(6-(((6-Acetyl-8-cyclopentyl-5-methyl-7-oxo-7,8-dihydropyrido[2,3-d]pyrimidin-2-yl)amino)pyridin-3-yl)piperazin-1-yl)-6-oxohexyl)-2-((4-(3-((6-((3,4-dimethoxyphenyl)sulfonamido)-1,3-dimethyl-2-oxo-2,3-dihydro-1H-benzo[d]imidazol-5-yl)oxy)-5-propoxyphenoxy)butyl)(methyl)amino)acetamide (example 77)

The title compound was synthesized using the same procedures for the preparation of the example 67 compound as white solid (6 mg, 41%). $^1$H NMR (600 MHz, CD$_3$OD) δ 9.07 (s, 1H), 8.16 (d, J=9.6 Hz, 1H), 7.85 (s, 1H), 7.53 (d, J=9.5 Hz, 1H), 7.31 (d, J=1.2 Hz, 1H), 7.18 (dd, J=8.5, 1.9 Hz, 1H), 7.13 (d, J=2.1 Hz, 1H), 6.78 (d, J=8.4 Hz, 1H), 6.61 (d, J=1.2 Hz, 1H), 6.14 (t, J=1.9 Hz, 1H), 6.05-5.93 (m, 1H), 5.74 (t, J=1.9 Hz, 1H), 5.62 (t, J=1.9 Hz, 1H), 3.96 (d, J=46.5 Hz, 2H), 3.86 (t, J=5.9 Hz, 2H), 3.81 (d, J=1.3 Hz, 3H), 3.79-3.69 (m, 10H), 3.60 (d, J=1.3 Hz, 3H), 3.41 (d, J=1.3 Hz, 3H), 3.25 (d, J=1.3 Hz, 7H), 2.95 (d, J=1.3 Hz, 3H), 2.50 (d, J=1.3 Hz, 3H), 2.43 (d, J=6.8 Hz, 5H), 2.31 (q, J=9.0, 7.5 Hz, 2H), 2.09 (s, 2H), 1.92 (dt, J=15.7, 8.0 Hz, 4H), 1.82 (q, J=7.1, 6.6 Hz, 2H), 1.73 (ddt, J=16.9, 10.7, 6.1 Hz, 4H), 1.59 (dp, J=38.0, 7.4 Hz, 4H), 1.38 (p, J=7.8 Hz, 2H), 1.01 (td, J=7.4, 1.3 Hz, 3H). HRMS (ESI-TOF) m/z: [M+H]$^+$ calcd for C$_{63}$H$_{80}$N$_{12}$O$_{12}$S$^+$, 1229.5812; found, 1229.5802.

example 77

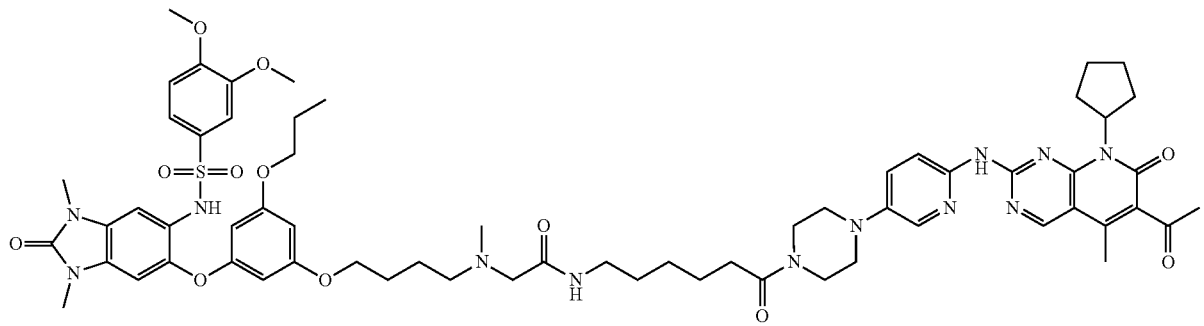

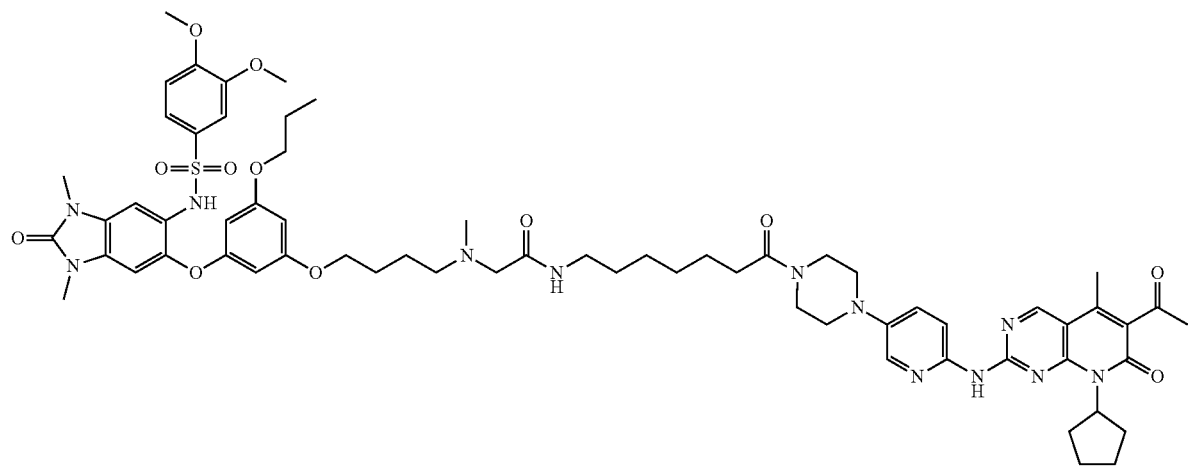

example 78

N-(7-(4-(6-(((6-Acetyl-8-cyclopentyl-5-methyl-7-oxo-7,8-dihydropyrido[2,3-d]pyrimidin-2-yl)amino)pyridin-3-yl)piperazin-1-yl)-7-oxoheptyl)-2-((4-(3-((6-(((3,4-dimethoxyphenyl)sulfonamido)-1,3-dimethyl-2-oxo-2,3-dihydro-1H-benzo[d]imidazol-5-yl)oxy)-5-propoxyphenoxy)butyl)(methyl)amino)acetamide (example 78)

The title compound was synthesized using the same procedures for the preparation of the example 67 compound as white solid (8 mg, 64%). $^1$H NMR (600 MHz, CD$_3$OD) δ 9.08 (s, 1H), 8.18 (d, J=9.5 Hz, 1H), 7.85 (s, 1H), 7.53 (d, J=9.5 Hz, 1H), 7.32 (s, 1H), 7.22-7.16 (m, 1H), 7.13 (d, J=2.1 Hz, 1H), 6.78 (d, J=8.5 Hz, 1H), 6.61 (s, 1H), 6.14 (t, J=1.9 Hz, 1H), 6.00 (p, J=8.9 Hz, 1H), 5.74 (t, J=1.9 Hz, 1H), 5.61 (d, J=1.8 Hz, 1H), 3.96 (d, J=44.8 Hz, 2H), 3.85 (t, J=5.8 Hz, 2H), 3.82-3.67 (m, 13H), 3.60 (d, J=1.3 Hz, 3H), 3.41 (d, J=1.2 Hz, 3H), 3.26 (dd, J=10.4, 3.4 Hz, 7H), 2.94 (d, J=1.3 Hz, 3H), 2.50 (d, J=1.3 Hz, 3H), 2.43 (d, J=5.7 Hz, 5H), 2.36-2.29 (m, 2H), 2.09 (s, 2H), 1.92 (p, J=7.6 Hz, 4H), 1.81 (p, J=6.4 Hz, 2H), 1.72 (dq, J=19.2, 6.7 Hz, 4H), 1.59 (d, J=6.9 Hz, 2H), 1.53 (t, J=6.9 Hz, 2H), 1.36 (s, 4H), 1.03-0.89 (m, 3H). HRMS (ESI-TOF) m/z: [M+H]$^+$ calcd for C$_{64}$H$_{83}$N$_{12}$O$_{12}$S$^+$, 1243.5969; found, 1243.5967.

example 79

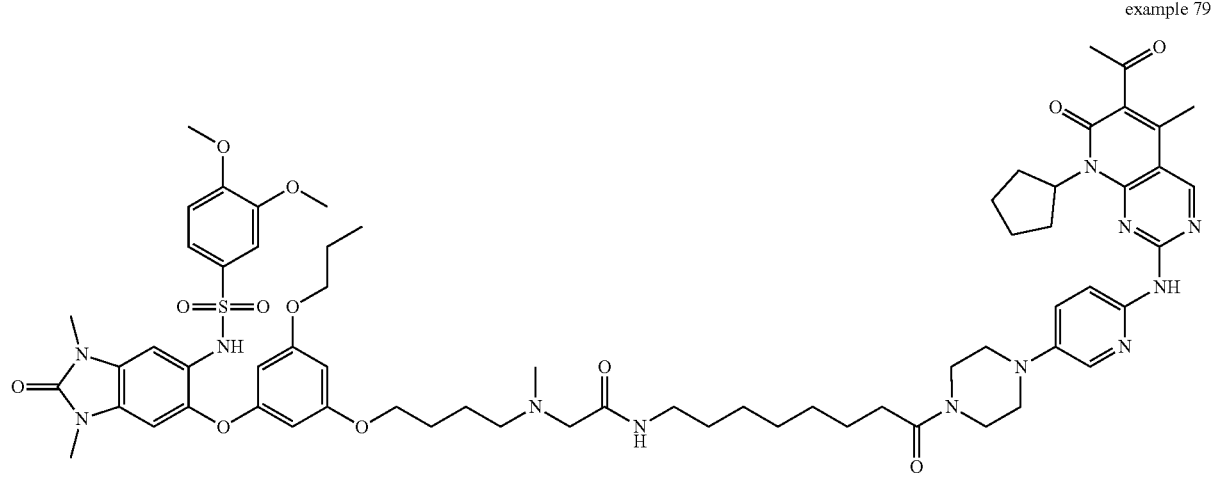 [SMILES: CCCOc1cc(OCCCCN(C)CC(=O)NCCCCCCCC(=O)N2CCN(c3ccc(Nc4ncc5c(C)c(C(C)=O)c(=O)n(C6CCCC6)c5n4)nc3)CC2)cc(Oc2cc3c(cc2NS(=O)(=O)c2ccc(OC)c(OC)c2)n(C)c(=O)n3C)c1]

313

N-(8-(4-(6-(((6-Acetyl-8-cyclopentyl-5-methyl-7-oxo-7,8-dihydropyrido[2,3-d]pyrimidin-2-yl)amino)pyridin-3-yl)piperazin-1-yl)-8-oxooctyl)-2-((4-(3-((6-((3,4-dimethoxyphenyl)sulfonamido)-1,3-dimethyl-2-oxo-2,3-dihydro-1H-benzo[d]imidazol-5-yl)oxy)-5-propoxyphenoxy)butyl)(methyl)amino)acetamide (example 79)

The title compound was synthesized using the same procedures for the preparation of the example 67 compound as white solid (8 mg, 64%). $^1$H NMR (600 MHz, CD$_3$OD) δ 9.08 (s, 1H), 8.19 (dd, J=9.6, 2.9 Hz, 1H), 7.85 (d, J=2.9 Hz, 1H), 7.52 (d, J=9.6 Hz, 1H), 7.32 (s, 1H), 7.18 (dd, J=8.4, 2.1 Hz, 1H), 7.14 (d, J=2.1 Hz, 1H), 6.78 (d, J=8.4 Hz, 1H), 6.61 (s, 1H), 6.14 (d, J=2.4 Hz, 1H), 6.01 (p, J=8.9 Hz, 1H), 5.75 (d, J=2.4 Hz, 1H), 5.60 (d, J=2.4 Hz, 1H), 3.96 (d, J=48.0 Hz, 2H), 3.85 (t, J=5.9 Hz, 2H), 3.83-3.69 (m, 13H), 3.61 (d, J=1.0 Hz, 3H), 3.41 (d, J=1.0 Hz, 3H), 3.28-3.21 (m, 7H), 2.94 (d, J=1.1 Hz, 3H), 2.50 (d, J=1.0 Hz, 3H), 2.43 (q, J=3.4 Hz, 5H), 2.31 (dd, J=12.5, 7.5 Hz, 2H), 2.10 (s, 2H), 1.96-1.87 (m, 4H), 1.82 (q, J=7.1, 6.6 Hz, 2H), 1.78-1.66 (m, 4H), 1.59 (d, J=7.4 Hz, 2H), 1.56-1.48 (m, 2H), 1.34 (s, 6H), 1.03-0.90 (m, 3H). HRMS (ESI-TOF) m/z: [M+H]$^+$ calcd for C$_{65}$H$_{85}$N$_{12}$O$_{12}$S$^+$, 1257.6125; found, 1257.6103.

Scheme 36: synthesis of example 126

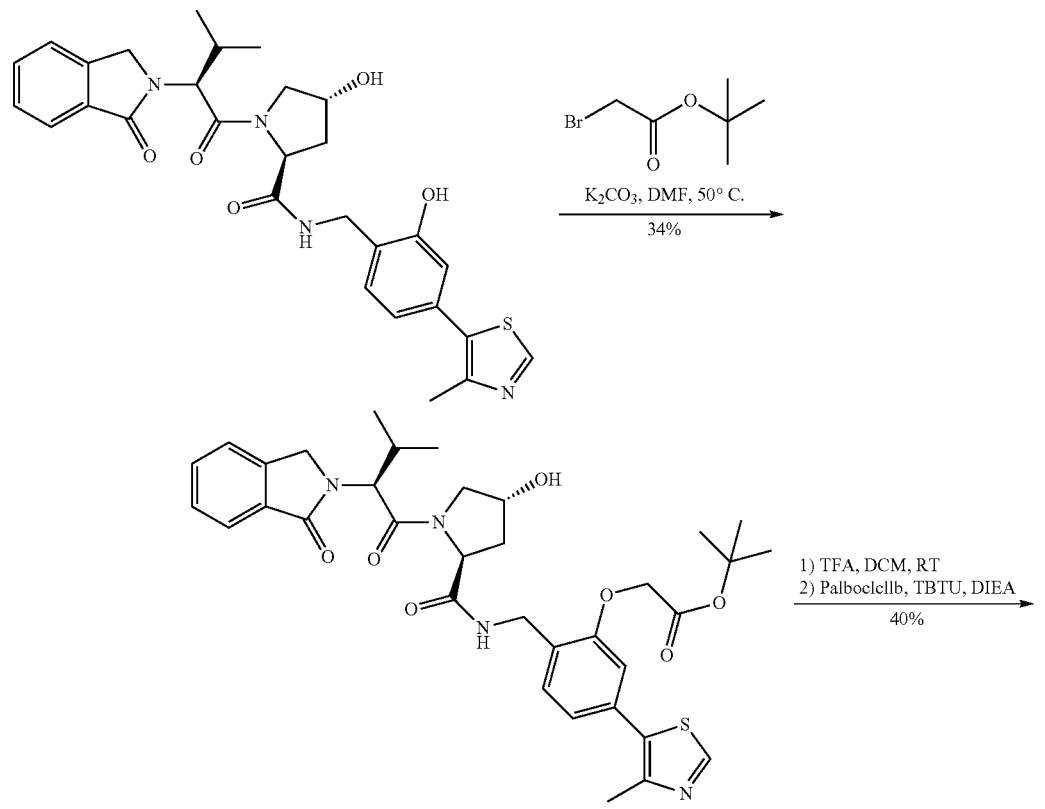

Intermediate 28

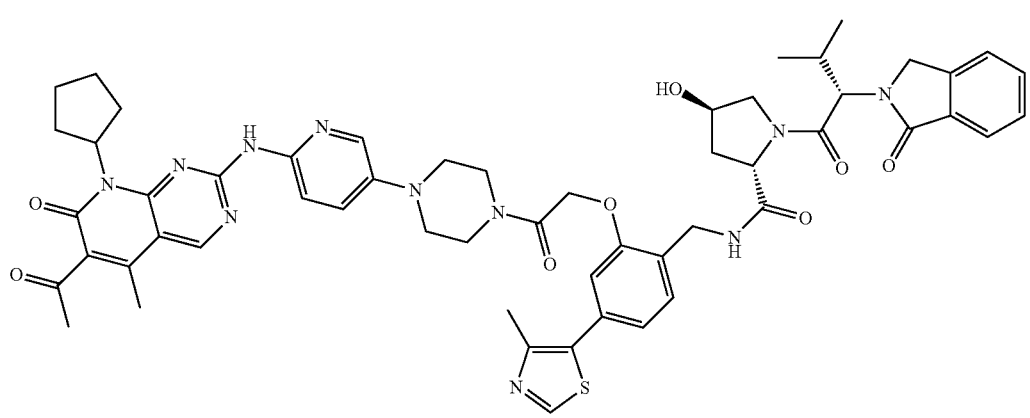

example 126 tert-Butyl 2-(2-(((2S,4R)-4-hydroxy-1-((S)-3-methyl-2-(1-oxoisoindolin-2-yl)butanoyl)pyrrolidine-2-carboxamido)methyl)-5-(4-methylthiazol-5-yl)phenoxy)acetate (intermediate 28)

To a solution of (2S,4R)-4-hydroxy-N-(2-hydroxy-4-(4-methylthiazol-5-yl)benzyl)-1-((S)-3-methyl-2-(1-oxoisoindolin-2-yl)butanoyl)pyrrolidine-2-carboxamide (124 mg, 0.23 mmol) in DMF (2 mL) were added $K_2CO_3$ (130 mg, 0.94 mmol) and tert-butyl-2-bromo-acetate ester (0.037 mmL, 0.25 mmol). The mixture was stirred at 50° C. for 18 h. After cooling to RT, the mixture was filtered to remove the unsolvable materials. The filtrate was concentrated under reduce pressure. The resulting residue was purified by prep-HPLC to yield the title compound (52 mg, 34%) as brown oil. $^1$H NMR (600 MHz, $CD_3OD$) δ 9.10 (s, 1H), 7.80 (d, J=7.8 Hz, 1H), 7.67-7.57 (m, 2H), 7.56-7.47 (m, 2H), 7.11 (d, J=7.9 Hz, 1H), 6.98 (s, 1H), 4.88-4.85 (m, 1H), 4.78 (s, 2H), 4.68-4.46 (m, 6H), 3.99 (d, J=11.2 Hz, 1H), 3.91 (d, J=11.1 Hz, 1H), 2.53 (s, 3H), 2.50-2.40 (m, 1H), 2.27-2.18 (m, 1H), 2.15-2.05 (m, 1H), 1.50 (s, 9H), 1.04 (d, J=6.6 Hz, 3H), 0.84 (d, J=6.6 Hz, 3H).

(2S,4R)—N-(2-(2-(4-(6-((6-Acetyl-8-cyclopentyl-5-methyl-7-oxo-7,8-dihydropyrido[2,3-d]pyrimidin-2-yl)amino)pyridin-3-yl)piperazin-1-yl)-2-oxoethoxy)-4-(4-methylthiazol-5-yl)benzyl)-4-hydroxy-1-((S)-3-methyl-2-(1-oxoisoindolin-2-yl)butanoyl)pyrrolidine-2-carboxamide (example 126)

Intermediate 28 (52 mg, 0.078 mmol) was dissolved in DCM/TFA (2:1, 3 mL). The solution was stirred at RT for 3 h before being concentrated. The residue was dissolved in DCM/DMF (3:1, 2 mL). To the resulting solution were added palbociclib (33 mg, 0.074 mmol), TBTU (25 mg, 0.076 mmol), and DIEA (0.04 mL, 0.24 mmol). The reaction mixture was stirred at RT for 18 h. After concentration, the resulting residue was purified by prep-HPLC to yield the title compound (32 mg, 40%) as yellow solid. $^1$H NMR (600 MHz, Methanol-$d_4$) δ 9.07 (s, 1H), 8.96 (s, 1H), 8.18 (dd, J=9.7, 2.9 Hz, 1H), 7.89 (d, J=2.9 Hz, 1H), 7.74 (d, J=7.6 Hz, 1H), 7.58 (t, J=7.5 Hz, 1H), 7.55 (d, J=9.6 Hz, 1H), 7.51 (d, J=7.7 Hz, 1H), 7.48-7.44 (m, 2H), 7.12-7.07 (m, 2H), 5.99 (p, J=8.9 Hz, 1H), 5.14-5.00 (m, 2H), 4.88 (d, J=11.2 Hz, 1H), 4.62-4.41 (m, 6H), 4.02 (d, J=11.1 Hz, 1H), 3.96 (dd, J=11.1, 3.9 Hz, 1H), 3.91-3.83 (m, 4H), 3.39-3.30 (m, 4H), 2.53 (s, 3H), 2.52 (s, 3H), 2.44 (s, 3H), 2.43-2.38 (m, 1H), 2.37-2.23 (m, 3H), 2.16-2.05 (m, 3H), 1.98-1.85 (m, 2H), 1.76-1.66 (m, 2H), 1.03 (d, J=6.5 Hz, 3H), 0.83 (d, J=6.6 Hz, 3H). HRMS (ESI-TOF) m/z: $[M+H]^+$ calcd for $C_{55}H_{62}N_{11}O_8S^+$, 1036.4498; found, 1036.4508.

Materials and Methods:

General Chemistry Methods

HPLC spectra for all compounds were acquired using an Agilent 1200 Series system with DAD detector. Chromatography was performed on a 2.1×150 mm Zorbax 300SB-C18 5 μm column with water containing 0.1% formic acid as solvent A and acetonitrile containing 0.1% formic acid as solvent B at a flow rate of 0.4 ml/min. The gradient program was as follows: 1% B (0-1 min), 1-99% B (1-4 min), and 99% B (4-8 min). High-resolution mass spectra (HRMS) data were acquired in positive ion mode using an Agilent G1969A API-TOF with an electrospray ionization (ESI) source. Nuclear Magnetic Resonance (NMR) spectra were acquired on a Bruker DRX-600 spectrometer with 600 MHz for proton ($^1$H NMR) and 150 MHz for carbon ($^{13}$C NMR); chemical shifts are reported in (δ). Preparative HPLC was performed on Agilent Prep 1200 series with UV detector set to 254 nm. Samples were injected onto a Phenomenex Luna 75×30 mm, 5 μm, $C_{18}$ column at room temperature. The flow rate was 40 ml/min. A linear gradient was used with 10% (or 50%) of MeOH (A) in $H_2O$ (with 0.1% TFA) (B) to 100% of MeOH (A). HPLC was used to establish the purity of target compounds. All final compounds had >95% purity using the HPLC methods described above.

Cell Culture

Breast cancer cell lines (MCF7, T47D, and ZR-75-1) and melanoma cell lines (A375, SK-MEL-2, SK-MEL-30, and WM1382) were cultured in the presence of DMEM or RPMI supplemented with 10% FBS in the presence of penicillin and streptomycin.

Cell Viability Assay

Cells were cultured for 7-11 days in the presence of different compounds. Media with compound was replenished every two days. At the end of the experiment, media was aspirated and viable cells were stained with 0.5% crystal violet dye.

BrdU Cell Proliferation Assay

BrdU incorporation was measured using a BrdU cell proliferation kit (Millipore) according to the manufacturer's instructions. Briefly, ER+ or melanoma cells were seeded at $1*10^5$ cells/ml in 96-well plates. The following day, cultured cells were treated with different concentrations of abemaciclib or palbociclib for 12 h, followed by incubation with BrdU labeling solution for 4 h. BrdU absorbance was measured with a spectrophotometer microplate reader at a dual wavelength of 450/550 nm. The measured absorbance reflected the degree of cell proliferation. Each group was cultured in triplicate.

Quantitative Real-Time PCR Analysis

Cells were treated with CDK4/6i for 24 h, and total RNA was extracted using an RNeasy Mini kit (Qiagen). Complementary DNA (cDNA) was synthesized with a SuperScript III First Strand Synthesis System (Thermo Fisher). Quantitative real-time PCR was performed using a Fast SYBR Green Master Mix with an ABI-7500 Fast Real-Time PCR System. Samples were normalized using the housekeeping gene GAPDH. Differences in expression were calculated using the ΔΔCT method.

The following primer sequences were used in PCR analyses:

```
GAPDH:
                                      (SEQ ID NO: 1)
F: 5'-ACAACTTTGGTATCGTGGAAGG-3';

(SEQ ID NO: 2)
R: 5'-GCCATCACGCCACAGTTTC-3'

CDK4:
                                      (SEQ ID NO: 3)
F: 5'-CTGGTGTTTGAGCATGTAGACC-3';

(SEQ ID NO: 4)
R: 5'-GATCCTTGATCGTTTCGGCTG-3'

CDK6:
                                      (SEQ ID NO: 5)
F: 5'-TCTTCATTCACACCGAGTAGTGC-3';

(SEQ ID NO: 6)
R: 5'-TGAGGTTAGAGCCATCTGGAAA-3'

CCNA2:
                                      (SEQ ID NO: 7)
F: 5'-CGCTGGCGGTACTGAAGTC-3';
```

```
                                                   (SEQ ID NO: 8)
R:  5'-GAGGAACGGTGACATGCTCAT-3'

PLK1:
                                                   (SEQ ID NO: 9)
F:  5'-CACCAGCACGTCGTAGGATTC-3';

(SEQ ID NO: 10)
R:  5'-CCGTAGGTAGTATCGGGCCTC-3'
```

Western Blot Assay

Protein concentrations were determined by BCA from cell lysates and equal amounts of protein are loaded to a Bis-Tris 4-12% gel. Gels were run at 80 V for 4 h using 1× running buffer (25 mM Tris, pH 8.3, 1.92 M glycine, 0.1% SDS). Proteins were transferred to a nitrocellulose membrane for 2 h at 100 V using transfer buffer (25 mM Tris, pH 8.3, 1.92 M glycine, 20% methanol). Ponceau S staining (0.1% Ponceau S, 1% acetic acid) was used to confirm transfer of proteins to the membrane followed by blocking of the membrane for 30 min at room temperature using blocking buffer (5% dry nonfat milk, 0.1% Tween, 0.02% sodium azide in TBS). The blocked membrane is incubated with primary antibodies (1:1000 dilution) in blocking buffer at 4° C. overnight. When primary phosphor-antibodies were used, then the membrane is incubated with 5% BSA instead of milk. The membrane was washed three times, 10 min each, with wash buffer (0.1% Tween in TBS) followed by incubation with secondary HRP conjugated antibody (1:5000 dilution) in 2.5% dry nonfat milk, 0.1% Tween in TBS for 1 h at room temperature. The membrane was washed three times, 10 min each, with wash buffer (0.1% Tween in TBS). Membranes are incubated with ECL for 1 min and proteins are detected after exposure to a blue autoradiographic film.

Example 5

CDK4/6 Inhibitors Fail to Suppress CDK4/6 Activity at High Concentrations

MCF7, T47D, or ZR-75-1 breast cancer cells were treated with 0, 0.1, 0.3, 1, 3, 10, or M palbociclib (PB) or abemaciclib (AB) for 24 h, then lysed and immunoblotted with antibodies to phospho-Rb, PLK1, cyclin A, and total Rb and actin (as controls) (FIG. 1, panels A and B). Similarly, SK-MEL-2, SK-MEL-30, or MCF7 melanoma cells were treated with 0, 0.1, 0.3, 1, 3, 10, or 30 μM palbociclib (PB), abemaciclib (AB), or 219476 for 24 h, then lysed and immunoblotted with antibodies to phospho-Rb, PLK1, cyclin A, and total Rb and actin (as controls) (FIG. 1, panels C, D, and E). The results indicated that all three CDK4/6 inhibitors tested only had a narrow window of activity. As expected, they failed to suppress CDK4/6 activity (as evidenced by Rb phosphorylation (pRb level)) in breast cancer or melanoma cells when administered at low concentrations; surprisingly, they also failed to suppress CDK4/6 activity when administered at high concentrations (e.g., a concentration ≥about 10 μM).

Example 6

CDK4/6 Inhibitors Increase Expression of PLK1 and Cyclin a mRNA

Figure 2:
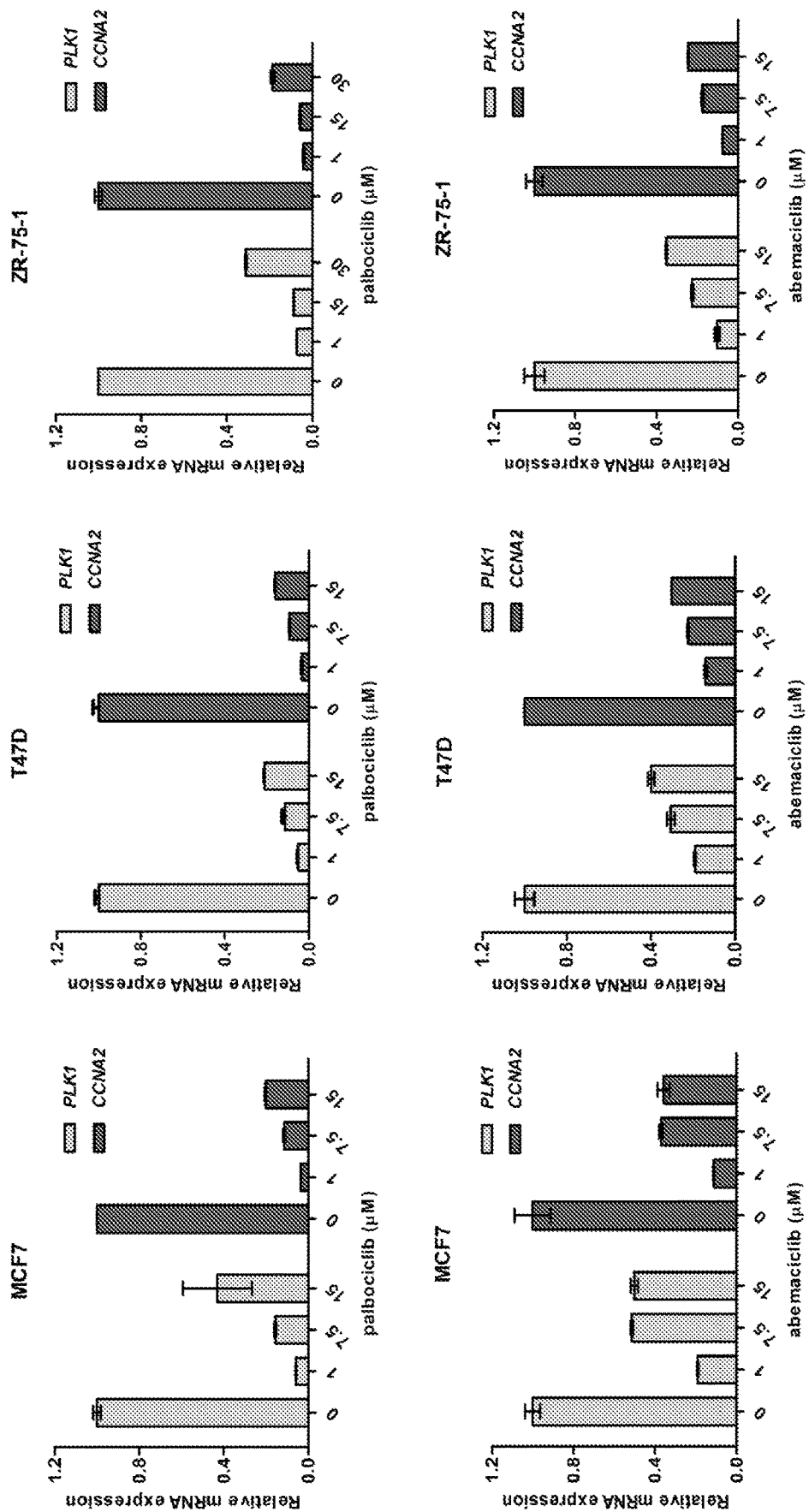
FIG. 2 is a series of bar graphs showing the effect of various CDK4/6 inhibitors on PLK1 and cyclin A (CCNA2) mRNA levels in indicated breast cancer cells at different concentrations.
Figure 3:
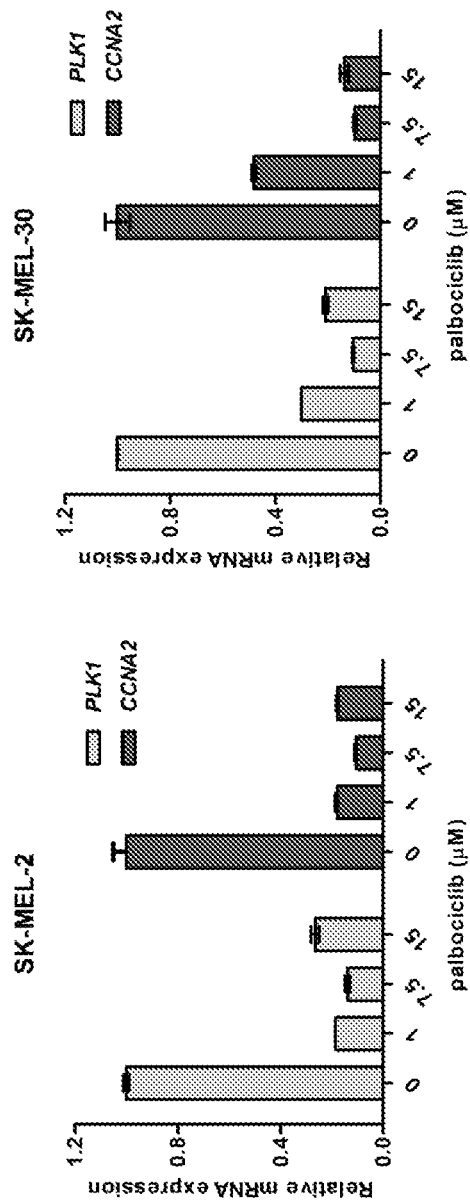
FIG. 3 is a series of bar graphs showing the effect of PB on PLK1 and cyclin A (CCNA2) mRNA levels in melanoma cancer cells at different concentrations.

MCF7, T47D, or ZR-75-1 breast cancer cells or SK-MEL-2 or SK-MEL-30 melanoma cells were treated with 0, 1, 7.5, 15, or 30 μM palbociclib or abemaciclib for 24 h, then lysed and subjected to PCR analysis of expression of the Rb/E2F downstream targets PLK1 and cyclin A (CCNA2). Neither palbociclib nor abemaciclib suppressed expression of PLK1 or cyclin A at the mRNA level; in fact, there was a positive correlation between increased inhibitor concentration and increased gene expression (FIGS. 2 and 3). This data suggests a mechanistic explanation for the failure of CDK4/6 inhibitors to suppress CDK4/6 activity when administered at high concentrations.

Example 7

Figure 4:
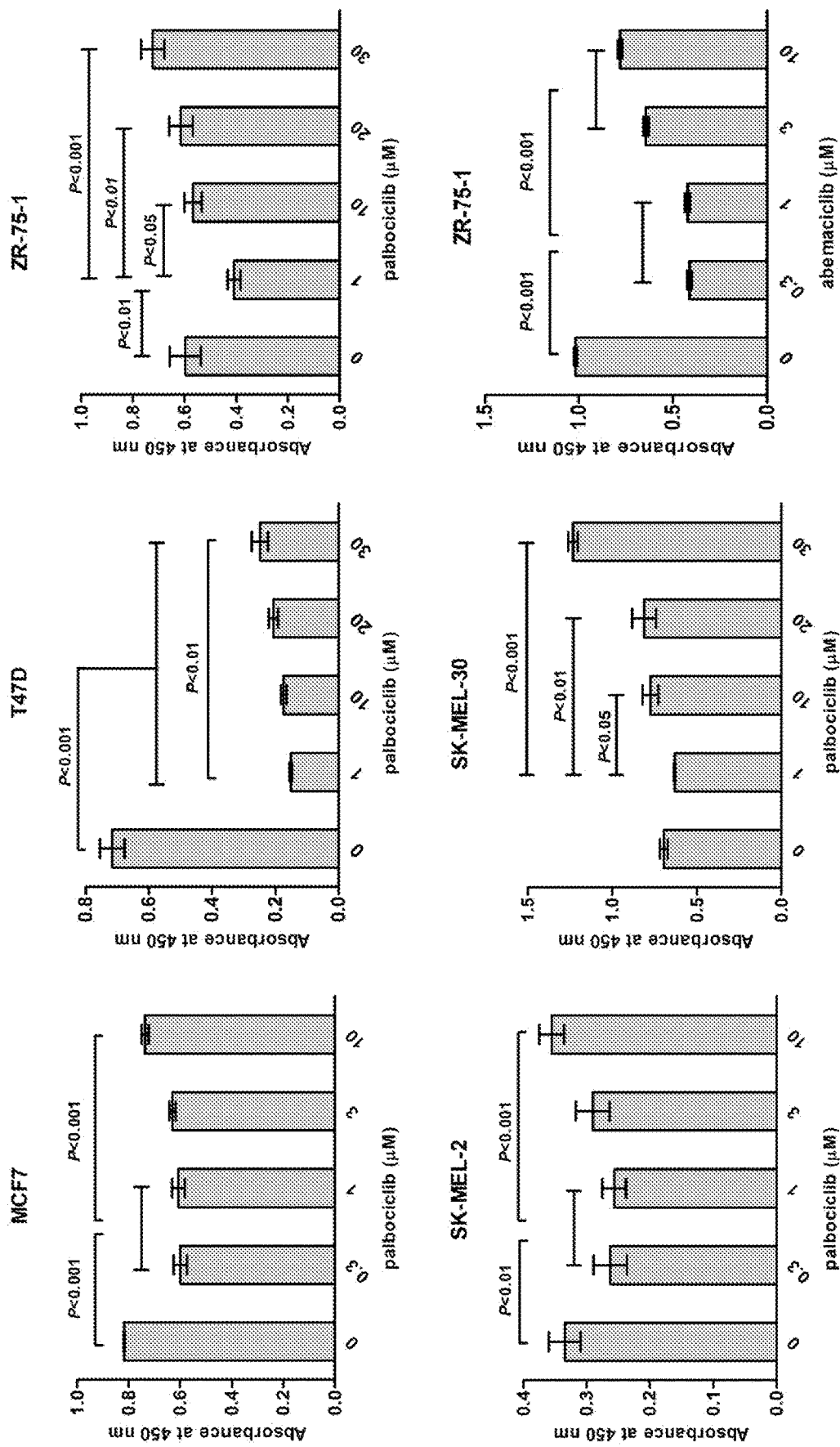
FIG. 4 is a series of bar graphs showing the effect of various CDK4/6 inhibitors on cell cycle progression at different concentrations.

CDK4/6 Inhibitors Suppress Cell Proliferation Less Effectively at High Concentrations MCF7, T47D, or ZR-75-1 breast cancer cells or SK-MEL-2 or SK-MEL-30 melanoma cells were treated with 0, 0.3, 1, 3, 10, 20, or 30 μM palbociclib or abemaciclib for 16 h; cell cycle progression through S phase was determined using the BrdU incorporation assay. Consistent with the results in Examples 5 and 6 (above), the results indicated that there was an inverse correlation between increased inhibitor concentration and suppression of cell cycle progression (FIG. 4).

Example 8

CDK4/6 Inhibitors Increase Expression of CDK4/6

Figure 5:
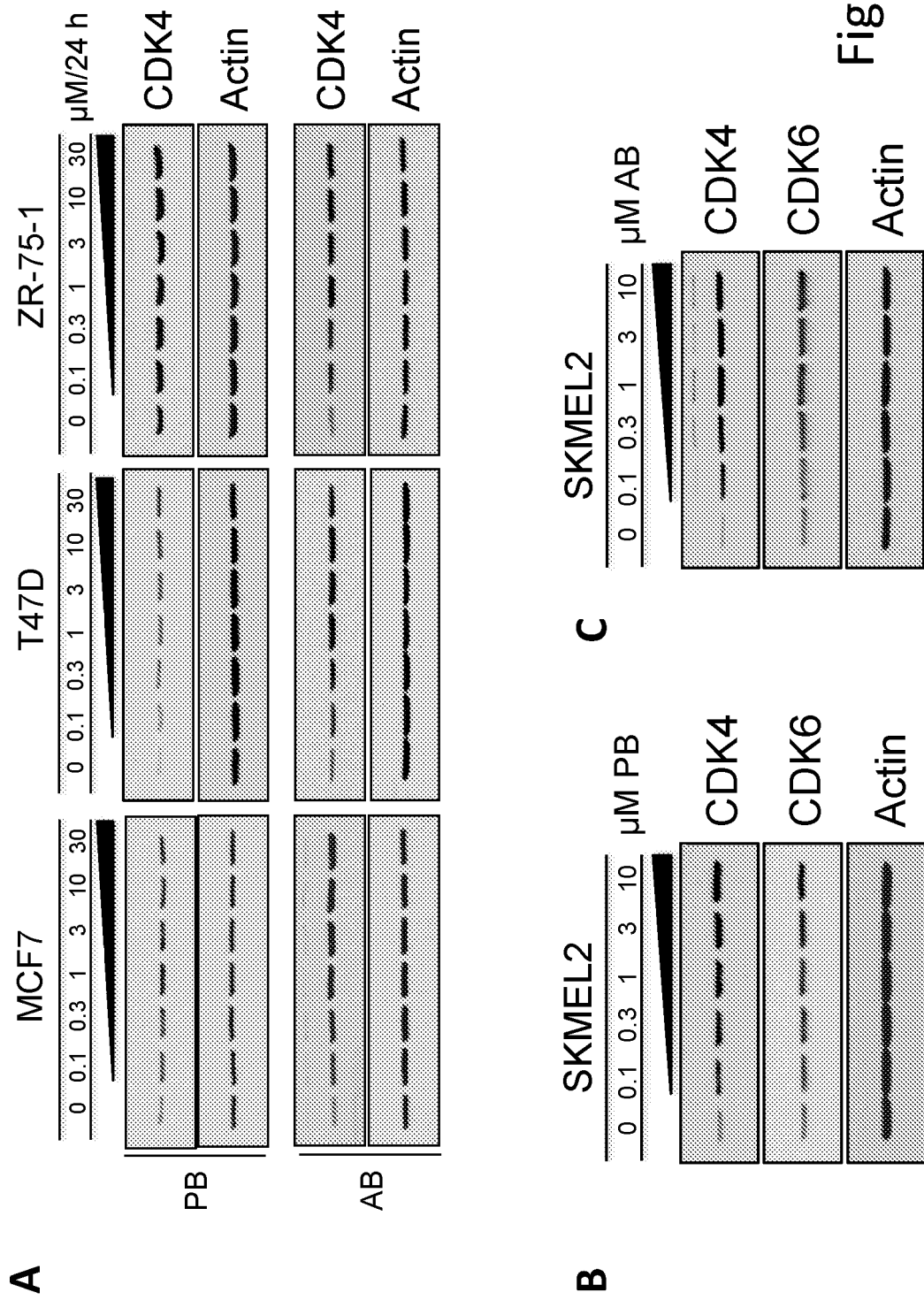
FIG. 5 is a series of Western blots showing the effect of various CDK4/6 inhibitors on CDK4 or CDK6 expression at different concentrations. PB- or AB-treated breast cancer cells (A); PB-treated melanoma cells (B); AB-treated melanoma cells (C).
Figure 6:
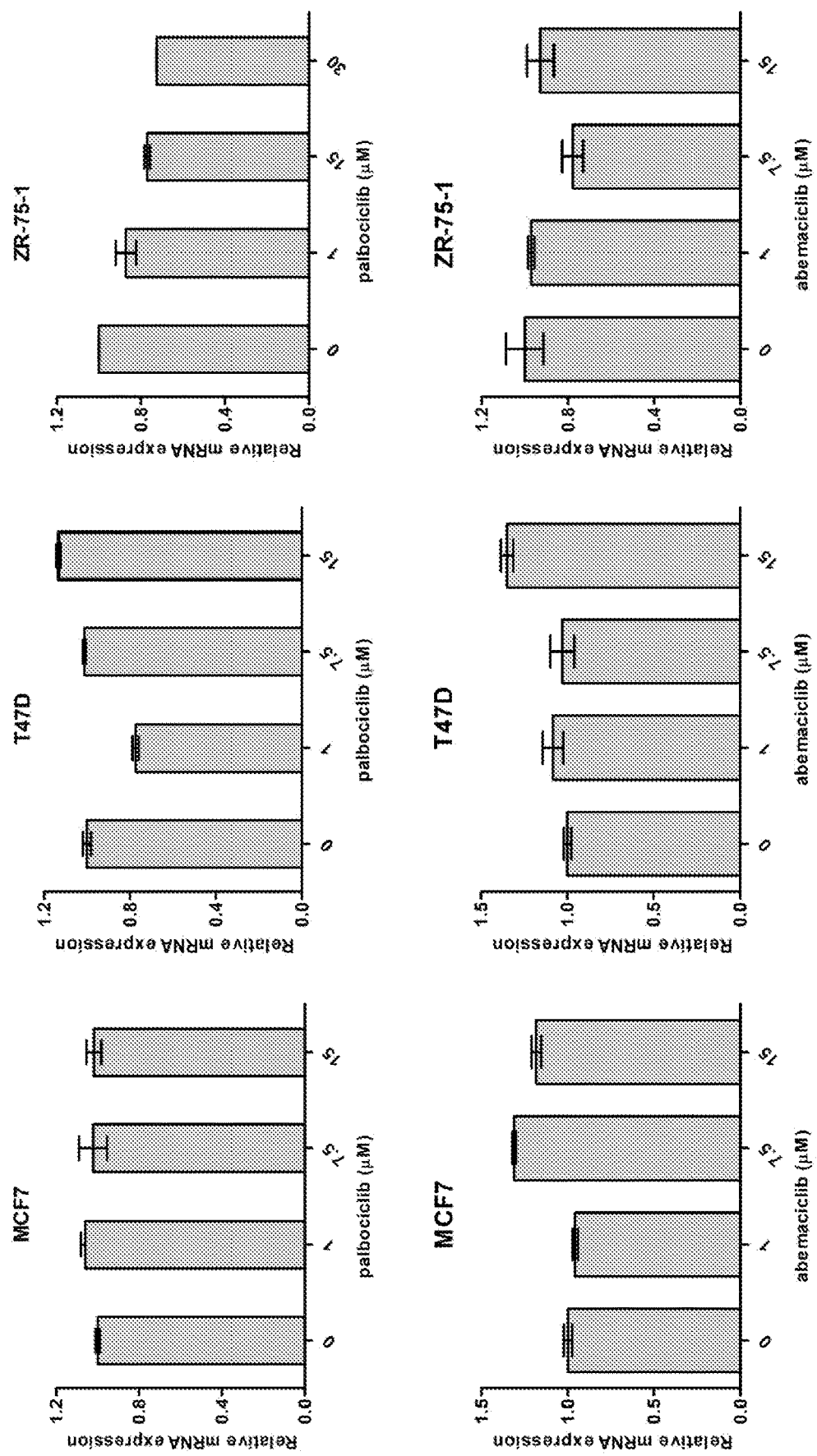
FIG. 6 is a series of bar graphs showing the effect of various CDK4/6 inhibitors on CDK4 mRNA levels at different concentrations.

MCF7, T47D, or ZR-75-1 breast cancer cells or SK-MEL-2 melanoma cells were treated with 0, 0.1, 0.3, 1, 3, 10, or 30 μM palbociclib or abemaciclib for 24 h, then lysed and immunoblotted with antibodies to CDK4, CDK6, and actin. The results indicated that, despite the CDK4/6 inhibitors' ability to inhibit the activity of CDK4 and CDK6, the inhibitors actually upregulate the expression of both CDK4 and CDK6, with a positive correlation between increased inhibitor concentration and increased CDK4/6 expression (FIG. 5, panels A-C). This data suggests a mechanistic explanation for the positive correlation between CDK4/6 inhibitor concentration and increased expression of PLK1 and cyclin A mRNA.

MCF7, T47D, or ZR-75-1 breast cancer cells were treated with 0, 1, 7.5, 15, or 30 μM palbociclib or abemaciclib for 24 h, then lysed and subjected to PCR analysis of expression of CDK4. The CDK4/6 inhibitors did not upregulate the expression of CDK4 mRNA (FIG. 6), indicating that the CDK4/6 inhibitors increase CDK4/6 protein expression by inhibiting protein degradation (instead of by increasing transcription or extending mRNA half-life).

Figure 7:
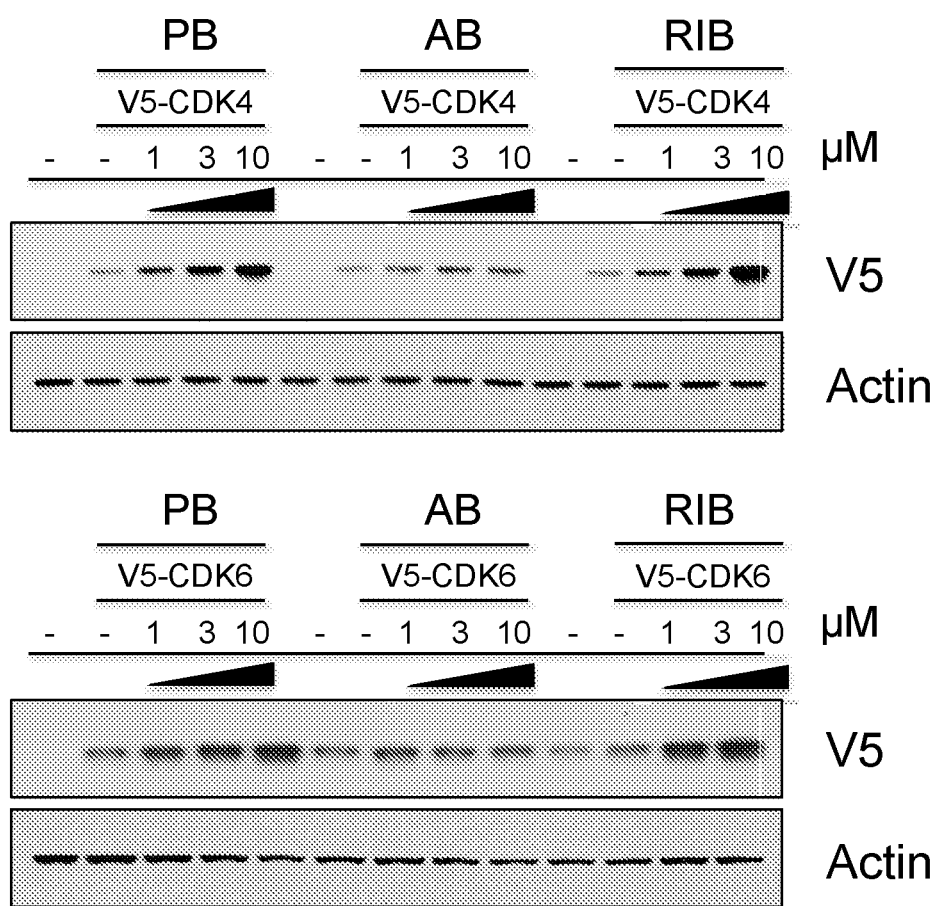
FIG. 7 is a series of Western blots showing the effect of various CDK4/6 inhibitors on ectopically expressed of V5-tagged CDK4 or CDK6 at different concentrations.

To confirm the above findings, 293H cells ectopically expressing V5-tagged CDK4 or V5-tagged CDK6 were treated with 1, 3, or 10 μM palbociclib (PB), abemaciclib (AB), or ribociclib (RIB) for 24 h, then lysed and immunoblotted with antibodies to V5 (to detect V5-tagged CDK4 or CDK6) and actin. Consistent with FIG. 5, all three CDK4/6 inhibitors examined upregulated the expression of V5-tagged CDK4 and CDK6 (FIG. 7).

Example 9

CDK4/6 Inhibitors Prevent Ubiquitination of CDK4

Figure 8:
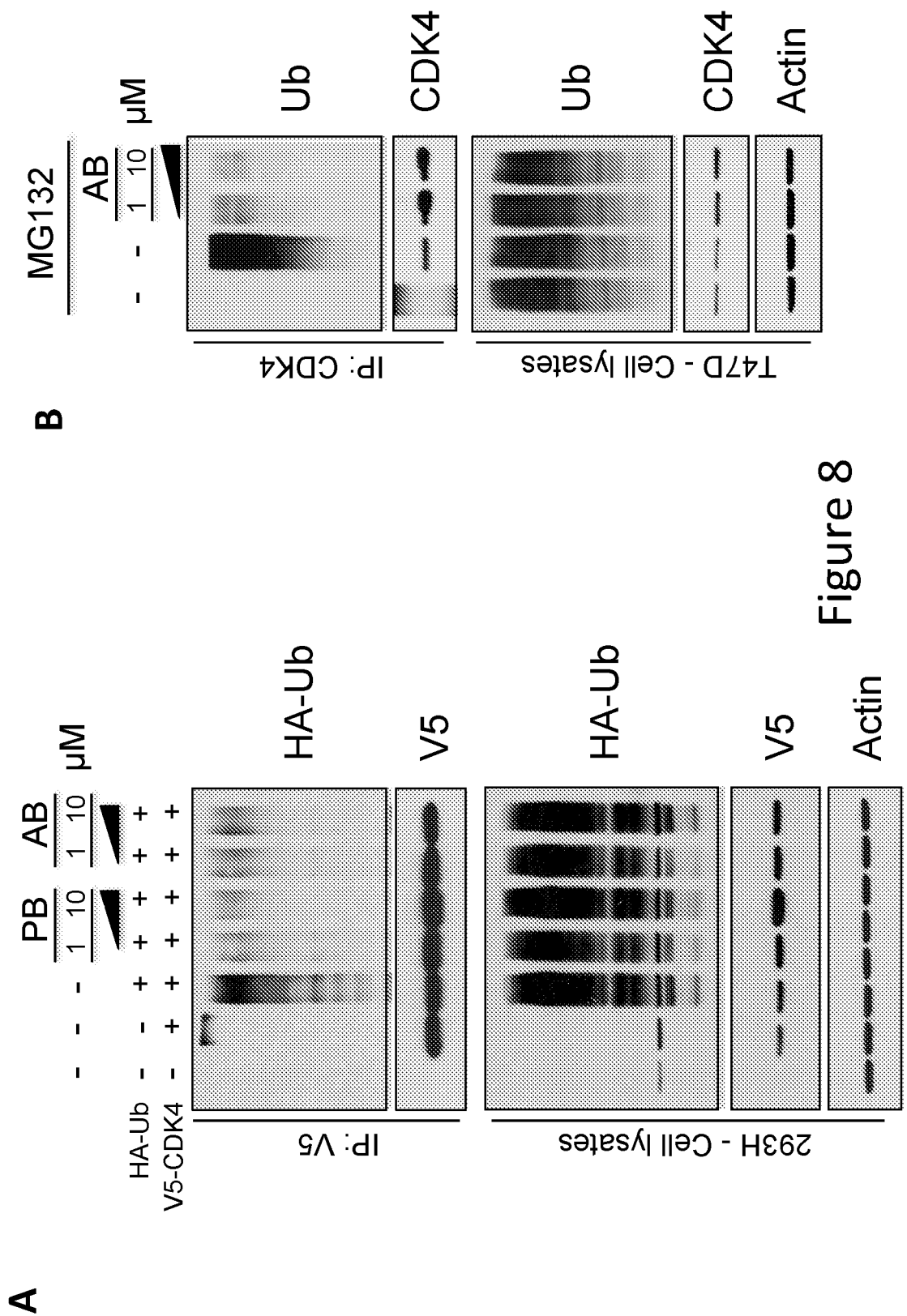
FIG. 8 is a series of pull-down assays showing the effect of various CDK4/6 inhibitors on the ubiquitination of either ectopically expressed (A), or endogenous (B) CDK4 at different concentrations.

293H cells ectopically co-expressing V5-tagged CDK4 and HA-tagged ubiquitin were treated with 1 or 10 μM palbociclib or abemaciclib for 24 h, then lysed and either 1) subjected to immunoprecipitation with a V5 antibody (to pull down V5-tagged CDK4) followed by immunoblotting for HA (to detect HA-tagged ubiquitin), or 2) directly immunoblotted with antibodies to V5, HA, and actin. The data indicated that CDK4/6 inhibitors inhibit the ubiquitination of CDK4, thus protecting it from degradation and inducing elevated cellular levels of CDK4 (FIG. 8, panel A).

T47D breast cancer cells were treated with the proteasome inhibitor MG132 for 24 h in the presence or absence of 1 or 10 µM abemaciclib, then lysed and either 1) subjected to immunoprecipitation with a CDK4 antibody followed by immunoblotting for ubiquitin, or 2) directly immunoblotted with antibodies to ubiquitin, CDK4, and actin. Consistent with the results above for V5-tagged CDK4, the data indicated that CDK4/6 inhibitors inhibit the ubiquitination of native CDK4 (FIG. 8, panel B).

Example 10

Figure 9:
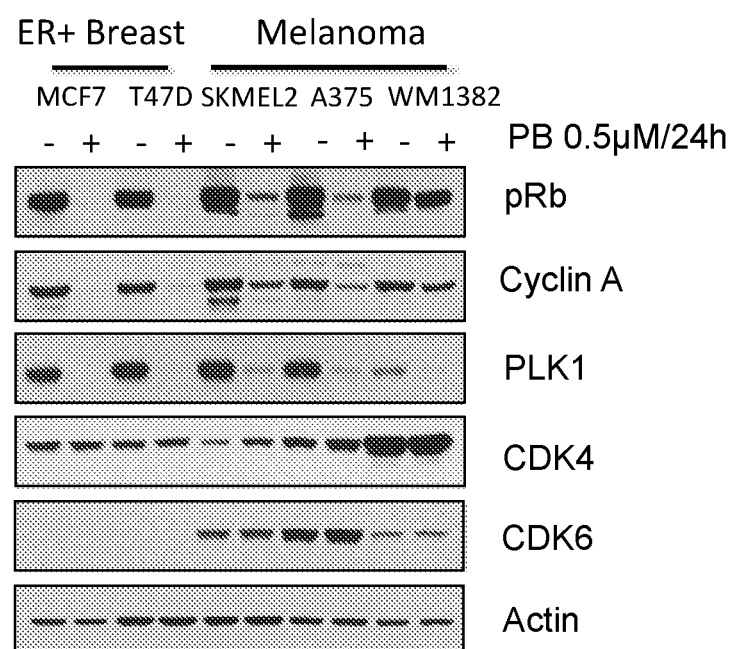
FIG. 9 is a series of Western blots showing the efficacy of palbociclib in inhibiting Rb phosphorylation in ER+ breast cancer cells, palbociclib-resistant ER+ breast cancer cells (a) and melanoma cells (b).

Increased CDK4/6 Expression is Associated with Decreased CDK4/6 Inhibitor Efficacy MCF7 breast cancer cells resistant to palbociclib (MCF7-PBR) were generated by treating MCF7 cells with 1 µM palbociclib for 12 weeks. MCF7-PBR cells were then treated with 1, 3, or 10 µM palbociclib (PB) for 24 h, then lysed and immunoblotted with antibodies to phospho-Rb (pRB), Rb (RB), PLK1, cyclin A, CDK2, CDK6, and actin (FIG. 9). These results confirmed the resistance of the MCF7-PBR cells to palbociclib and demonstrated that this resistance is associated with elevated expression of CDK6 (compare CDK6 levels in the MCF7 lane with CDK6 levels in any of the MCF7-PBR lanes, noting that the actin control indicates equal amounts of total protein in the MCF7 and MCF7-PBR lanes).

Example 11

Palbociclib Suppresses Rb Phosphorylation More Effectively in ER+ Breast Cancer Cells MCF7 or T47D breast cancer cells or SK-MEL-2, A375, or WM1382 melanoma cells were treated with or without 0.5 µM palbociclib for 24 h, then lysed and immunoblotted with antibodies to phospho-Rb (pRb), cyclin A, PLK1, CDK4, CDK6, and actin (FIG. 9). The results indicated that palbociclib suppresses Rb phosphorylation more effectively in ER+ breast cancer cells than melanoma cells.

Example 12

Figure 10:
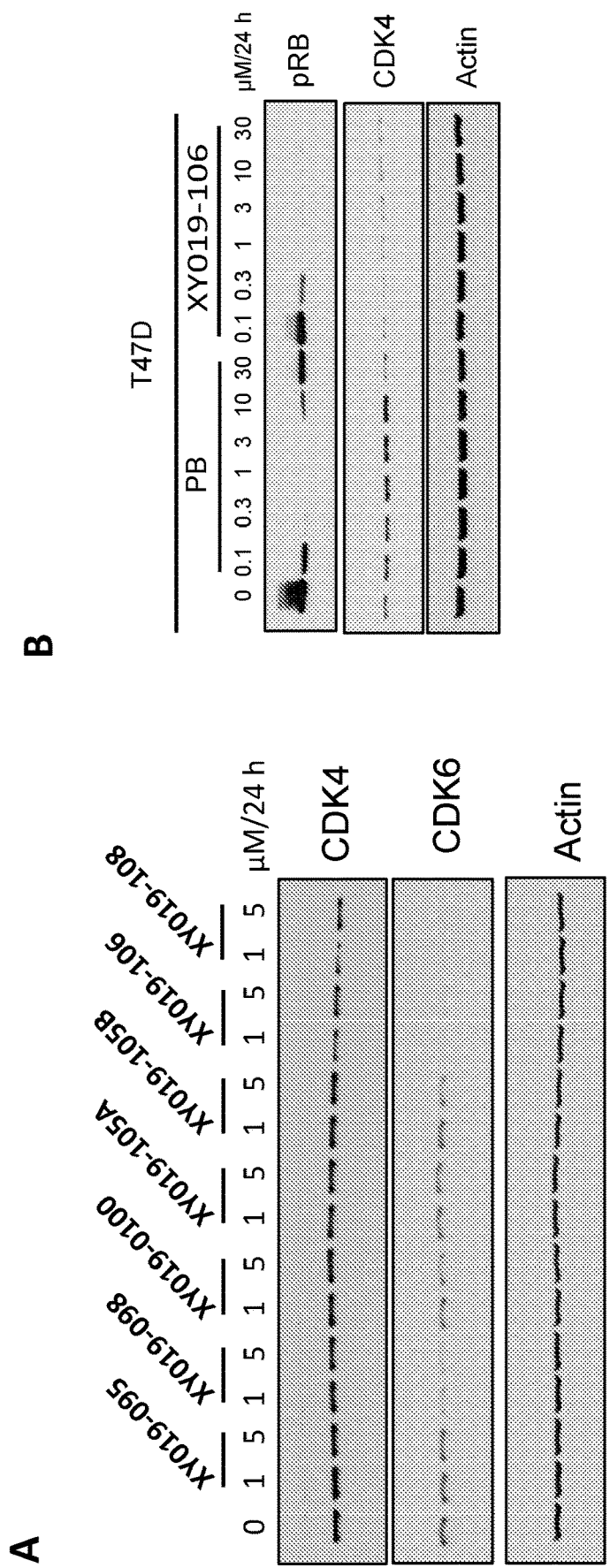
FIG. 10 is a series of Western blots showing the efficacy of various CDK4/6 degraders in inhibiting CDK4/6 activity and suppressing CDK4/6 expression in either MCF7 (A) or T47D (B) breast cancer cells.

CDK4/6 Degraders/Disruptors Inhibit CDK4/6 Activity and Suppress CDK4/6 Expression MCF7 breast cancer cells were treated with 1 or 5 µM XY019-095, XY019-098, XY019-0100, XY019-105A, XY019-105B, XY019-106, or XY019-108 for 24 h, then lysed and immunoblotted with antibodies to CDK4, CDK6, and actin (FIG. 10, panel A). The results indicated that XY019-098, XY019-106, and XY019-108 were especially effective in suppressing CDK4/6 expression even at 1 µM; this effect did not diminish at 5 µM. T47D breast cancer cells were treated with 0.1, 0.3, 1, 3, 10, or 30 µM XY019-106 for 24 h, then lysed and immunoblotted with antibodies to phospho-Rb (pRB), CDK4, and actin (FIG. 10, panel B). The results showed that XY019-106 both suppresses CDK4 expression and inhibit CDK4 activity (as evidenced by decreased Rb phosphorylation), with significant effects at concentrations as low as 0.3 µM. Further, unlike CDK4/6 inhibitors such as palbociclib, XY019-106 inhibited Rb phosphorylation even when administered at high concentrations (e.g., at concentrations as high as 30 µM).

Figure 11:
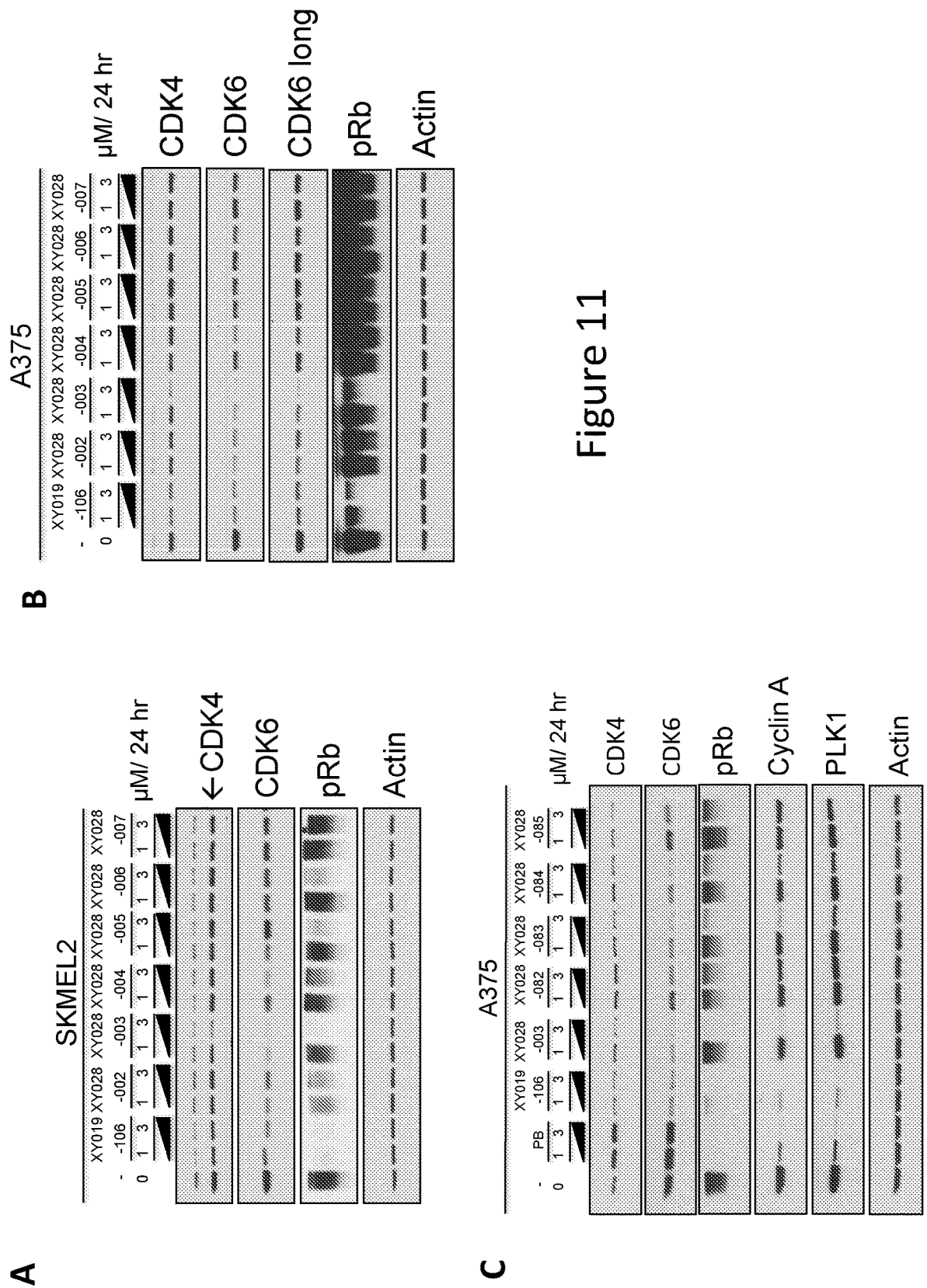
FIG. 11 is a series of Western blots (A, B, and C) showing the efficacy of various CDK4/6 degraders with different linkers in inhibiting CDK4/6 activity and suppressing CDK4/6 expression in melanoma cells.

SK-MEL-2 or A375 melanoma cells (FIG. 11, panels A and B) were treated with 1 or 3 M XY019-106, XY028-002, XY028-003, XY028-004, XY028-005, XY028-006, or XY028-007 for 24 h, then lysed and immunoblotted with antibodies to CDK4, CDK6, phospho-Rb (pRb), and actin. Similarly, A375 melanoma cells were treated with 1 or 3 µM palbociclib (PB), XY019-106, XY028-003, XY028-082, XY028-083, XY028-084, or XY028-085 for 24 h, then lysed and immunoblotted with antibodies to CDK6, CDK4, phospho-Rb (pRb), cyclin A, PLK1, and actin (FIG. 11, panel C).

The results confirmed the efficacy of CDK4/6 degraders/disruptors, particularly XY019-106 and XY028-003, in inhibiting both CDK4/6 expression and CDK4/6 activity (as evidenced by decreased Rb phosphorylation).

Figure 12:
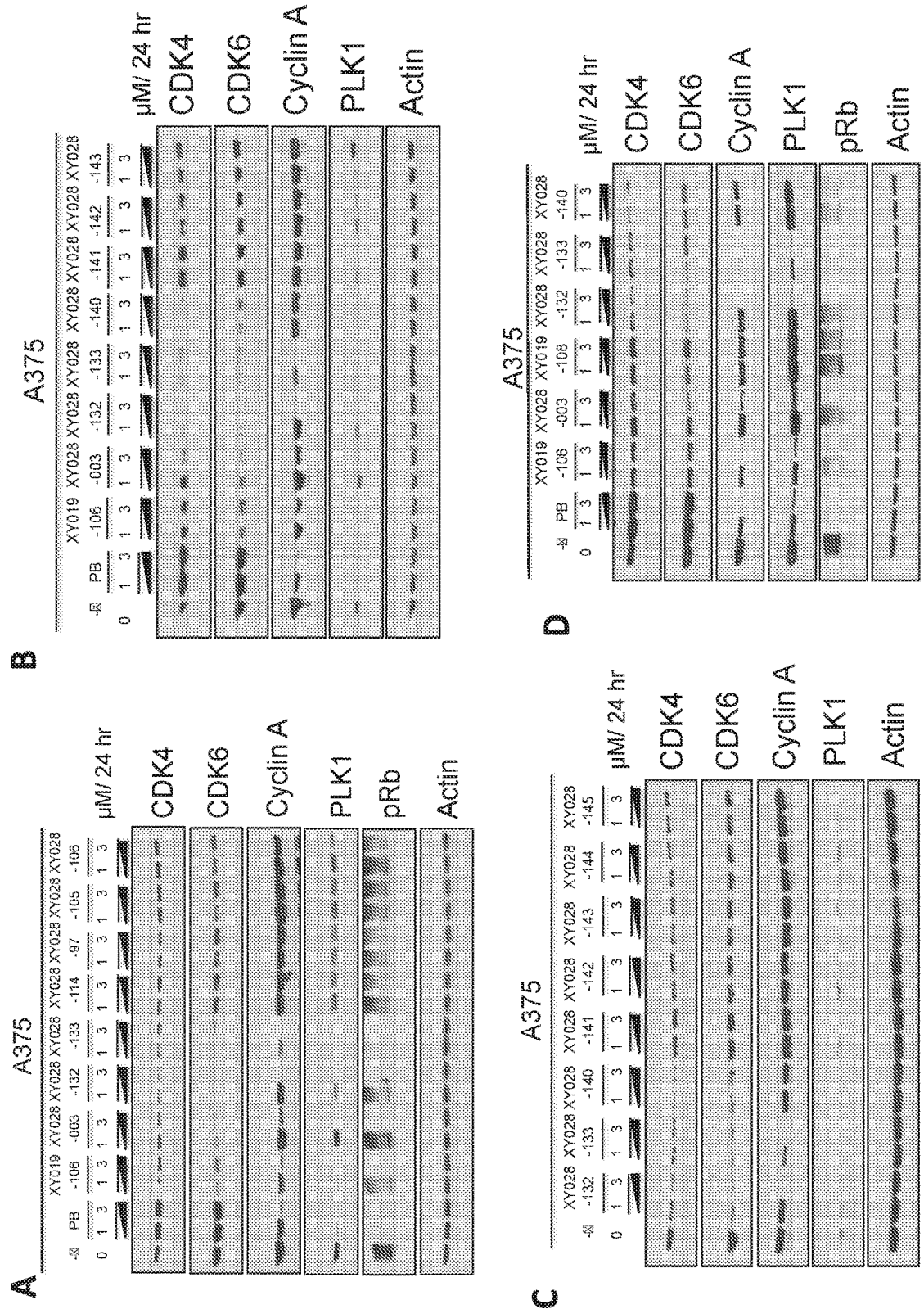
FIG. 12 is a series of Western blots (A, B, C, and D) showing the efficacy of various CDK4/6 degraders with different linkers in inhibiting CDK4/6 activity and suppressing CDK4/6 expression in melanoma cells.
Figure 13:
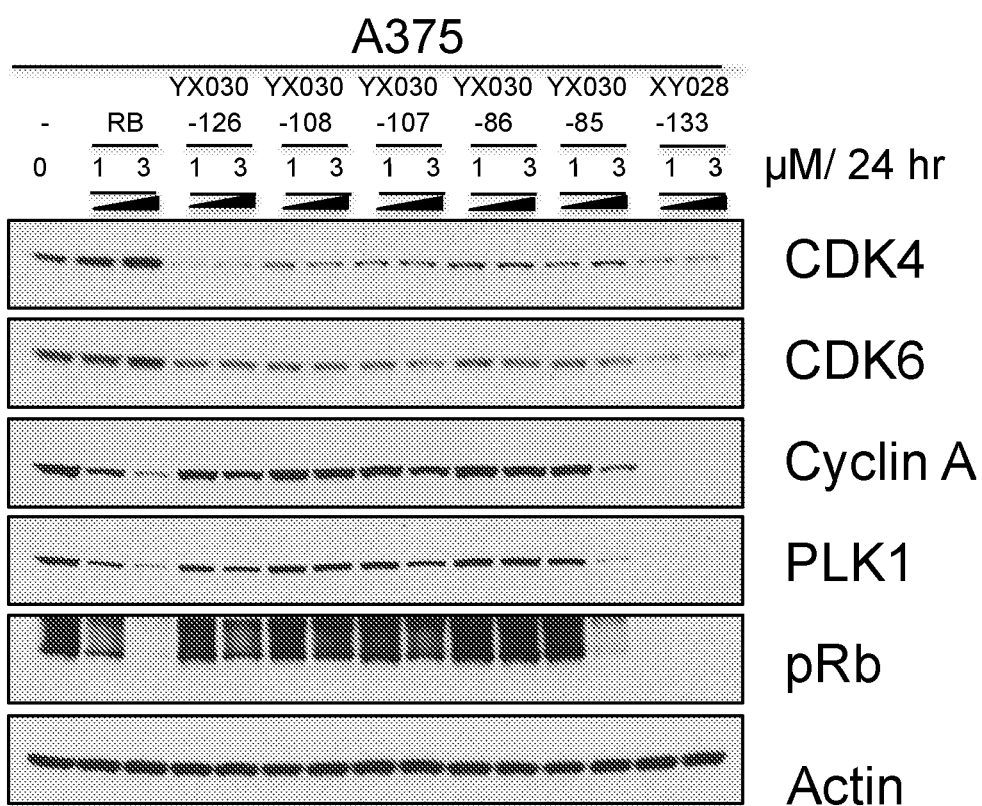
FIG. 13 is a series of Western blots showing the effect of various CDK4/6 degraders in inhibiting CDK4/6 activity and suppressing CDK4/6 expression in melanoma cells.
Figure 14:
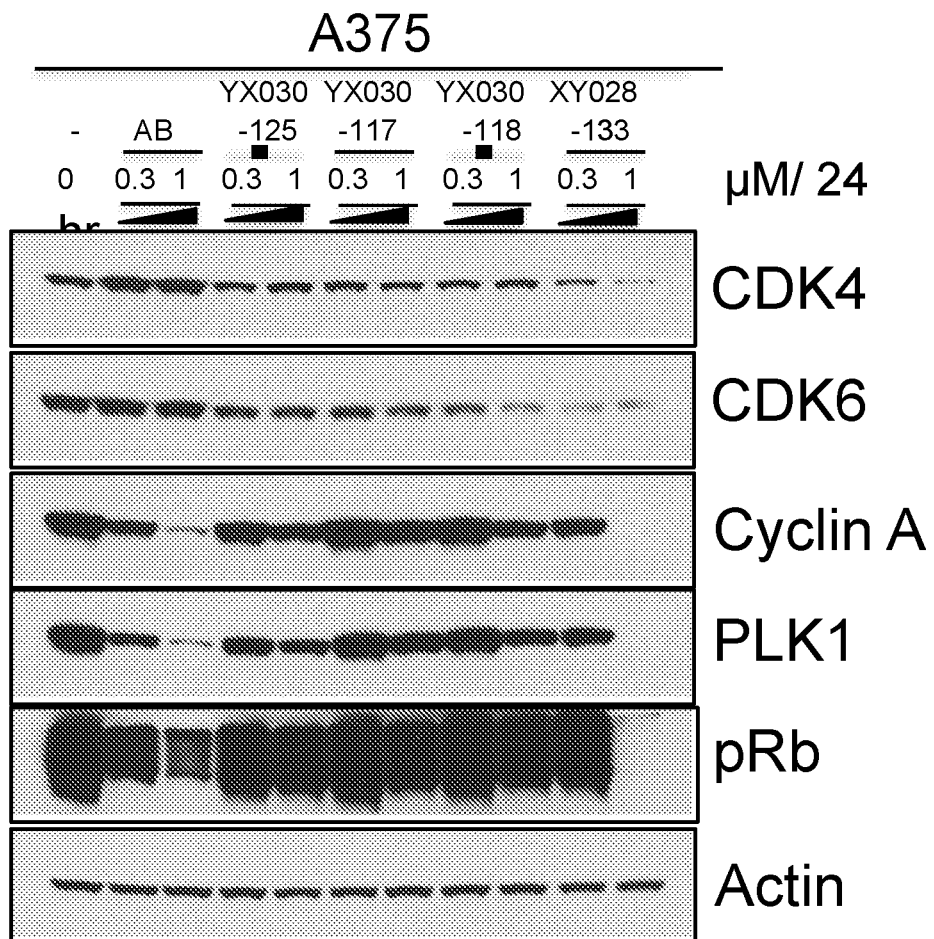
FIG. 14 is a series of Western blots showing the effect of various CDK4/6 degraders in inhibiting CDK4/6 activity and suppressing CDK4/6 expression in melanoma cells.
Figure 15:
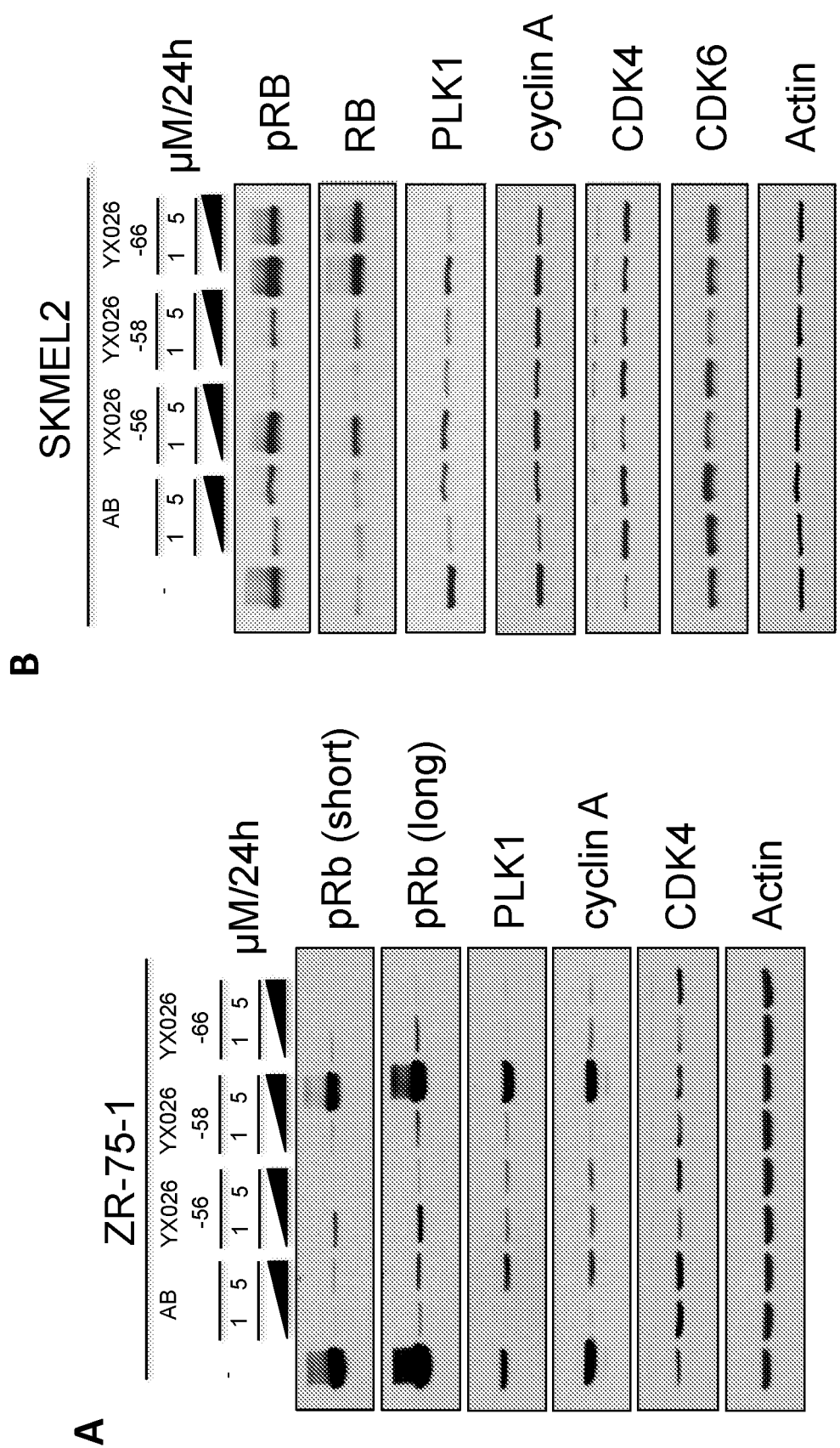
FIG. 15 is a series of Western blots showing the effect of various CDK4/6 degraders in inhibiting CDK4/6 activity and suppressing CDK4/6 expression in breast cancer (A) and melanoma (B) cells.

A375 melanoma cells (FIG. 12, panel A) were treated with 1 or 3 µM palbociclib (PB), XY019-106, XY028-003, XY028-132, XY028-133, XY028-114, XY028-097, XY028-105, or XY028-106 for 24 h, then lysed and immunoblotted with antibodies to CDK4, CDK6, phospho-Rb (pRb), and actin. Similarly, A375 melanoma cells were treated with 1 or 3 µM palbociclib (PB), XY019-106, XY028-003, XY028-132, XY028-133, XY028-140, XY028-141, XY028-142, or XY028-143 for 24 h, then lysed and immunoblotted with antibodies to CDK6, CDK4, phospho-Rb (pRb), cyclin A, PLK1, and actin (FIG. 12, panel B). Similarly, A375 melanoma cells were treated with 1 or 3 µM XY028-132, XY028-133, XY028-140, XY028-141, XY028-142, XY028-143, XY028-144, or XY028-145 for 24 h, then lysed and immunoblotted with antibodies to CDK6, CDK4, cyclin A, PLK1, and actin (FIG. 12, panel C). Similarly, A375 melanoma cells were treated with 1 or 3 µM palbociclib (PB), XY019-106, XY028-103, XY028-108, XY028-132, XY028-133, or XY028-140 for 24 h, then lysed and immunoblotted with antibodies to CDK6, CDK4, phospho-Rb (pRb), cyclin A, PLK1, and actin (FIG. 12, panel D).

The results confirmed the efficacy of CDK4/6 degraders, particularly XY028-133, XY028-140, XY019-106 and XY028-003, in inhibiting both CDK4/6 expression and CDK4/6 activity (as evidenced by decreased Rb phosphorylation).

A375 melanoma cells (FIG. 13) were treated with 1 or 3 µM Ribociclib (RB), YX030-126, YX030-108, YX030-107, YX030-086, YX030-085 or XY028-133 for 24 h, then lysed and immunoblotted with antibodies to CDK4, CDK6, cyclin A, PLK1, phospho-Rb (pRb), and actin.

The results demonstrated that ribociclib-based CDK4/6 degraders, in particular YX-085, are likewise effective in inhibiting both CDK4/6 expression and CDK4/6 activity (as evidenced by decreased Rb phosphorylation).

A375 melanoma cells (FIG. 14) were treated with 1 or 3 µM Abemaciclib (AB), YX030-125, YX030-117, YX030-118 or XY028-133 for 24 h, then lysed and immunoblotted with antibodies to CDK4, CDK6, cyclin A, PLK1, phospho-Rb (pRb), and actin.

ZR-75-1 breast cancer cells (FIG. 15, panel A) or SK-MEL-2 melanoma cells (FIG. 15, panel B) were treated with 1 or 5 µM abemaciclib (AB), YX26-56, YX26-58, or YX26-66 for 24 h, then lysed and immunoblotted with antibodies to phospho-Rb (pRb), total Rb, PLK1, cyclin A, CDK4, CDK6, and actin. The results demonstrated that ademaciclib-based CDK4/6 degraders/disruptors are likewise effective in inhibiting both CDK4/6 expression and CDK4/6 activity (as evidenced by decreased Rb phosphorylation).

Figure 16:
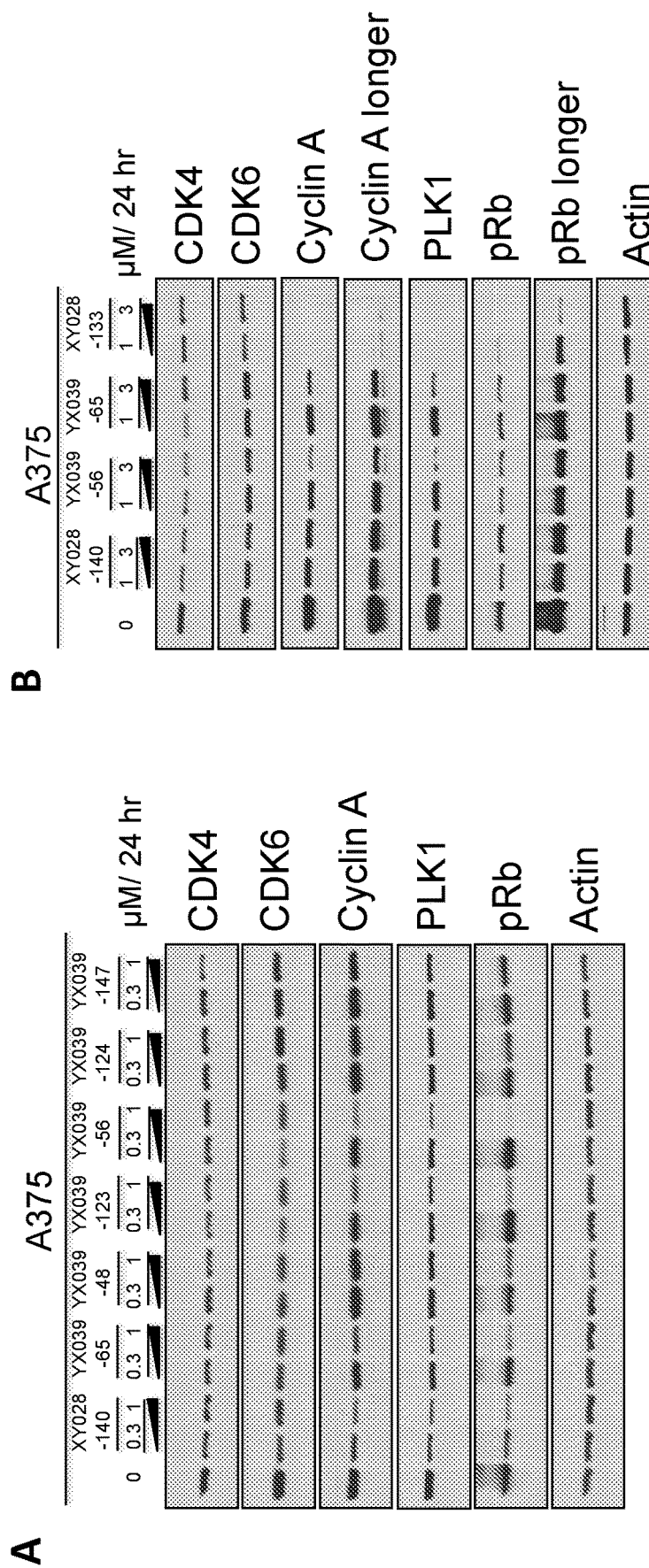
FIG. 16 is a series of Western blots (A and B) showing the effect of various CDK4/6 degraders in inhibiting CDK4/6 activity and suppressing CDK4/6 expression in melanoma cells.
Figure 17:
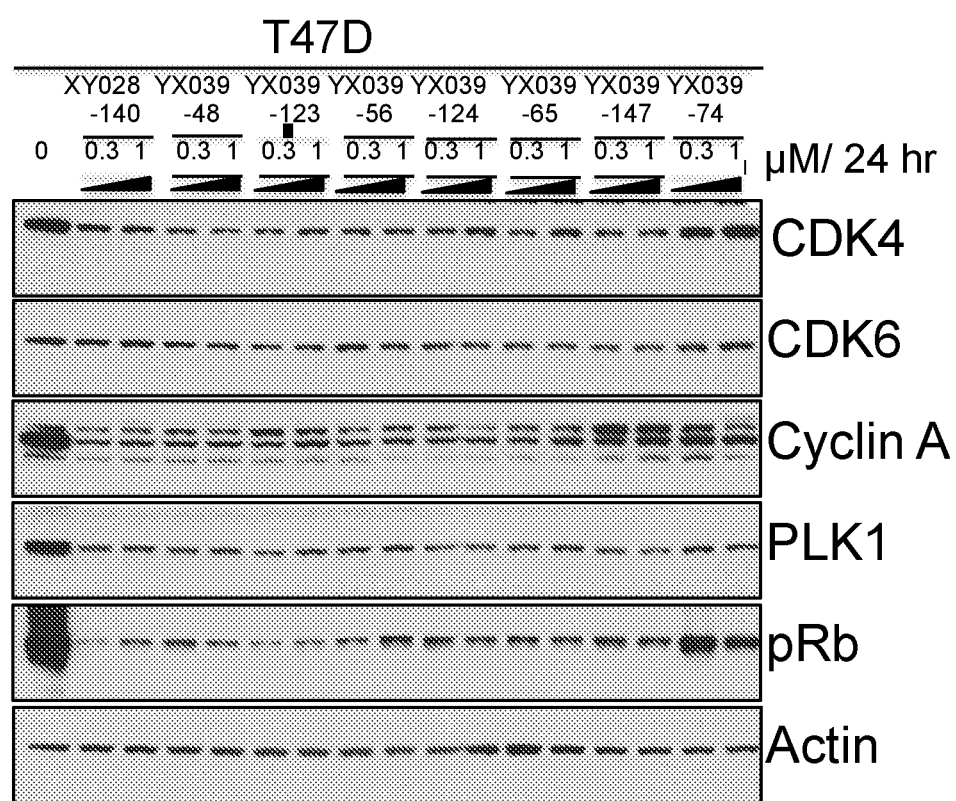
FIG. 17 is a series of Western blots showing the effect of various CDK4/6 degraders in inhibiting CDK4/6 activity and suppressing CDK4/6 expression in breast cancer cells.
Figure 18:
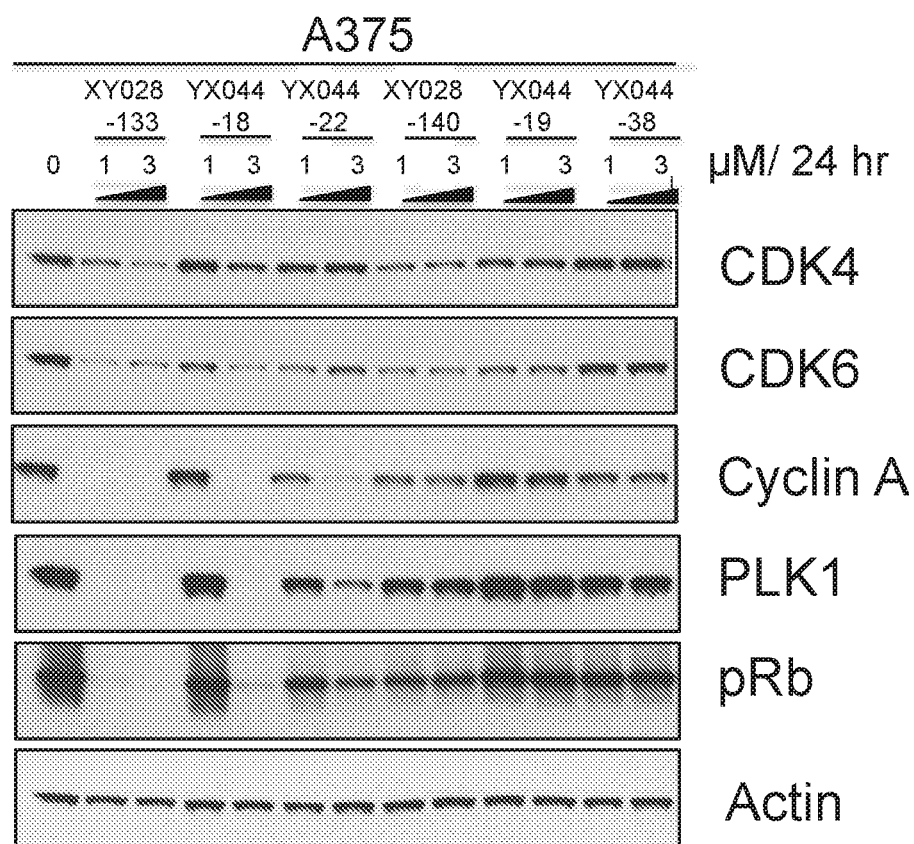
FIG. 18 is a series of Western blots showing the effect of various CDK4/6 degraders in inhibiting CDK4/6 activity and suppressing CDK4/6 expression in melanoma cells.
Figure 19:
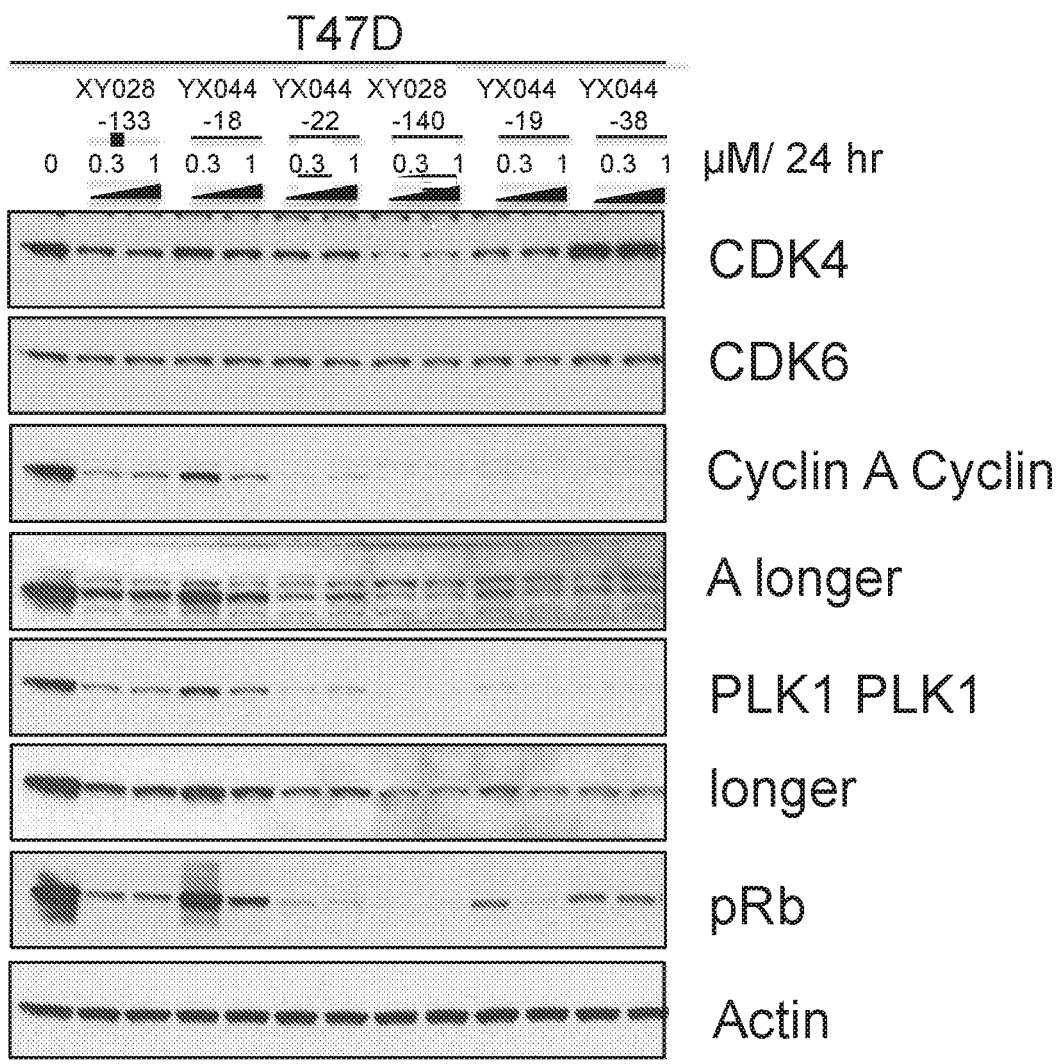
FIG. 19 is a series of Western blots showing the effect of various CDK4/6 degraders in inhibiting CDK4/6 activity and suppressing CDK4/6 expression in breast cancer cells.
Figure 20:
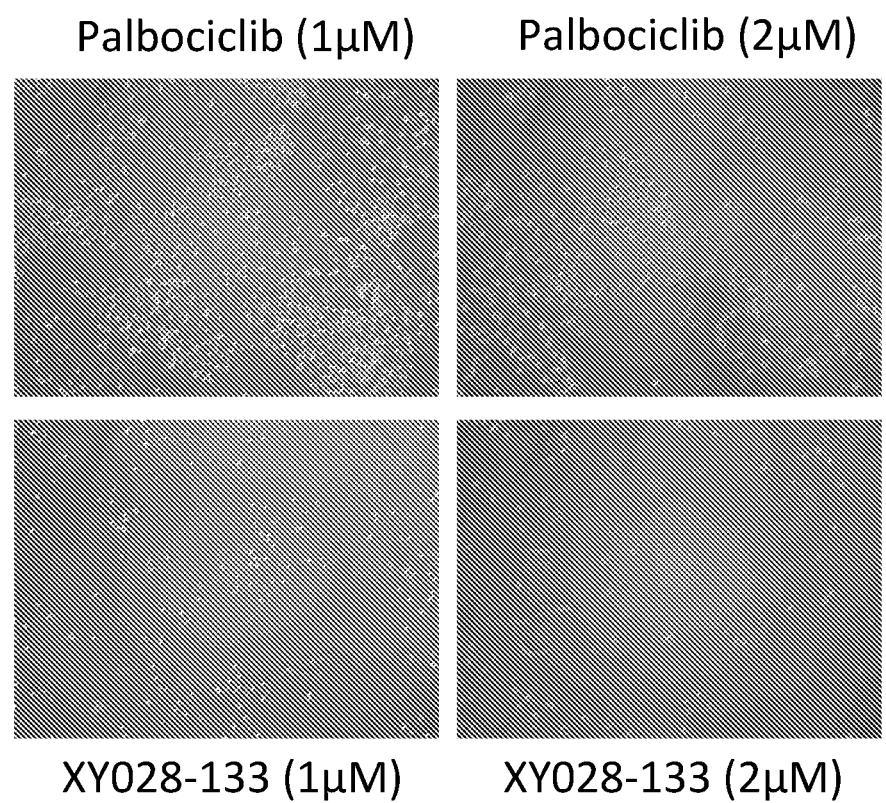
FIG. 20 is a series of images showing the effect of the CDK4/6 degrader XY028-133 in suppressing cell proliferation of melanoma cells.
Figure 21:
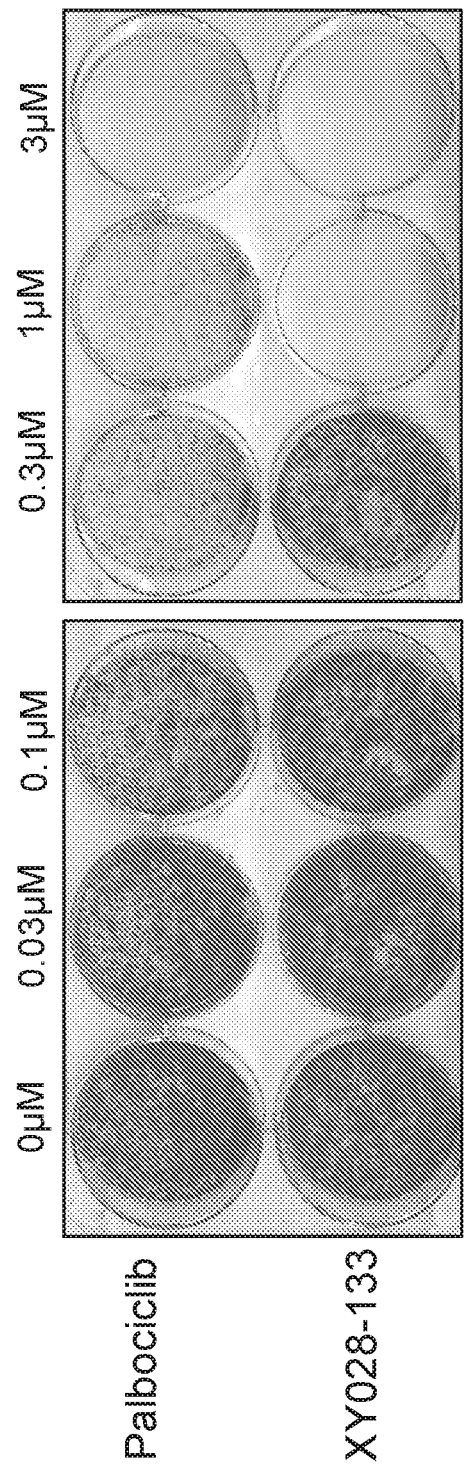
FIG. 21 is a series of clonogenic assays showing the effect of the CDK4/6 degrader XY028-133 in suppressing cell proliferation of melanoma cells.
Figure 22:
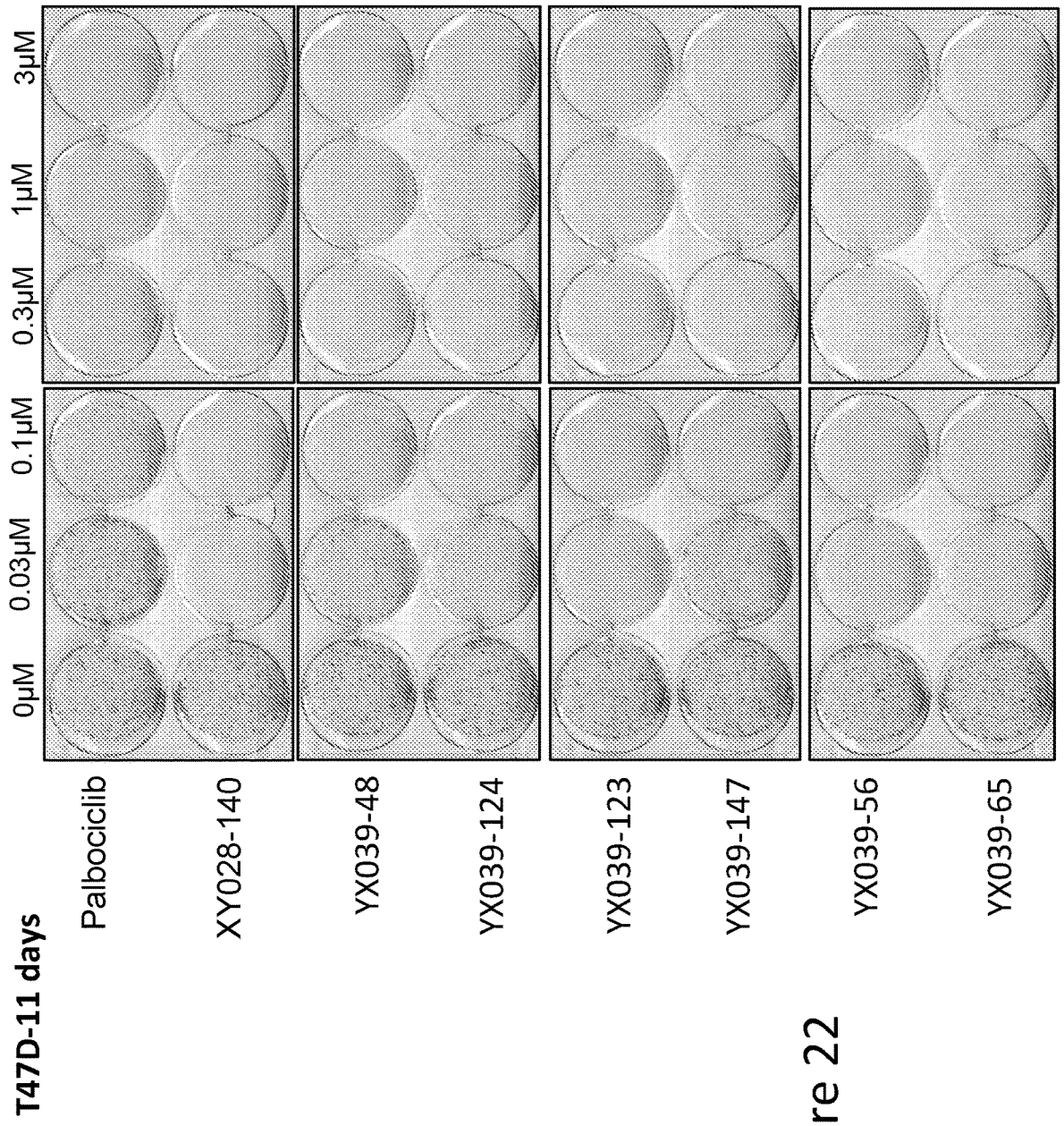
FIG. 22 is a series of clonogenic assays showing the effect of various CDK4/6 degraders in suppressing cell proliferation of breast cancer cells.
Figure 23:
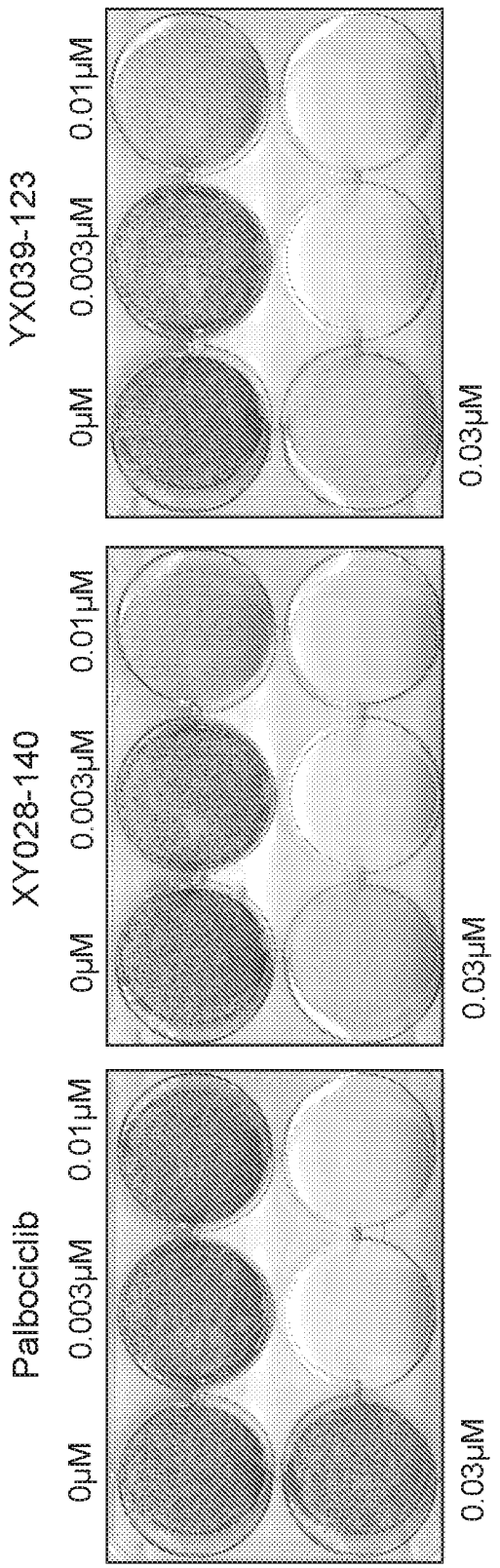
FIG. 23 is a series of clonogenic assays showing the effect of various CDK4/6 degraders in suppressing cell proliferation of breast cancer cells.
Figure 23:
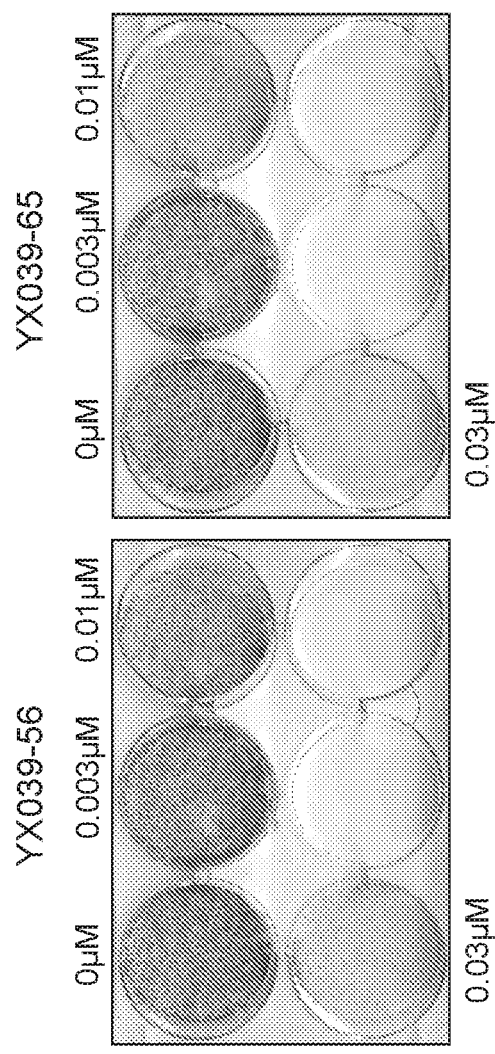

A375 melanoma cells (FIG. 16, panel A) were treated with 0.3 or 1 µM XY028-140, YX039-65, YX039-48, YX039-123, YX039-56, YX039-124 or YX039-147 for 24 h. A375 melanoma cells were treated with 1 or 3 µM XY028-140, YX039-56, YX039-65 or XY028-133 (FIG. 16, panel B). Cells were lysed and immunoblotted with antibodies to phospho-Rb (pRb), total Rb, PLK1, cyclin A, CDK4, CDK6, and actin. The results confirmed the efficacy of CDK4/6 degraders, particularly XY028-133 in inhibiting both CDK4/6 expression and CDK4/6 activity (as evidenced by decreased Rb phosphorylation).

T47D breast cancer cells (FIG. 17) were treated with 0.3 or 1 µM XY028-140, YX039-48, YX039-123, YX039-56, YX039-124, YX039-65, YX039-147 or YX039-74 for 24 h, then lysed and immunoblotted with antibodies to phospho-Rb (pRb), total Rb, PLK1, cyclin A, CDK4, CDK6, and actin. The results confirmed the efficacy of CDK4/6 degraders, particularly XY028-140 and YX039-123, in inhibiting both CDK4/6 expression and CDK4/6 activity (as evidenced by decreased Rb phosphorylation).

A375 melanoma cells (FIG. 18) were treated with 1 or 3 µM XY028-133, YX044-18, YX044-22, XY028-140, YX044-19 or YX044-38 for 24 h, then lysed and immunoblotted with antibodies to phospho-Rb (pRb), total Rb, PLK1, cyclin A, CDK4, CDK6, and actin. The results confirmed the efficacy of CDK4/6 degraders, particularly XY028-133 and YX044-18, in inhibiting both CDK4/6 expression and CDK4/6 activity (as evidenced by decreased Rb phosphorylation).

T47D breast cancer cells (FIG. 19) were treated with 0.3 or 1 µM XY028-133, YX044-18, YX044-22, XY028-140, YX044-19 or YX044-38 for 24 h, then lysed and immunoblotted with antibodies to phospho-Rb (pRb), total Rb, PLK1, cyclin A, CDK4, CDK6, and actin. The results confirmed the efficacy of CDK4/6 degraders, particularly XY028-140 and YX044-22 and YX044-19, in inhibiting both CDK4/6 expression and CDK4/6 activity (as evidenced by decreased Rb phosphorylation).

Example 13

CDK4/6 Degraders/Disruptors Inhibit Cancer Cell Proliferation

A375 melanoma cells (FIG. 20) were treated with 1 or 2 µM palbociclib or XY028-133 for 7 days. Bright field imaging indicated that XY028-133 was more effective in inhibiting cancer cell proliferation than palbociclib at the same concentration in melanoma cells.

A375 melanoma cells (FIG. 21) were treated with 0.03, 0.1, 0.3, 1, or 3 µM palbociclib or XY028-133 for 11 days. Crystal violet staining indicated that XY028-133 was more effective in inhibiting cancer cell proliferation than palbociclib at 1 and 3 µM in melanoma cells.

T47D breast cancer cells (FIG. 22) were treated with 0.03, 0.1, 0.3, 1, or 3 µM palbociclib, XY028-140, YX039-48, YX039-124, YX039-123, YX039-147, YX039-56, or YX039-65 for 11 days. Crystal violet staining indicated that CDK4/6 degraders and particularly XY028-140, YX039-123, YX039-56, and YX039-65 inhibited cancer cell proliferation more effective that palbociclib at the same concentration in breast cancer cells.

T47D breast cancer cells (FIG. 23) were treated with 0.003, 0.01, or 0.03 µM palbociclib, XY028-140, YX039-123, YX039-56, or YX039-65 for 11 days. Crystal violet staining indicated that CDK4/6 degraders inhibited cancer cell proliferation more effective that palbociclib at the same concentration in breast cancer cells.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

REFERENCES

Bondeson, D. P., A. Mares, I. E. Smith, E. Ko, S. Campos, A. H. Miah, K. E. Mulholland, N. Routly, D. L. Buckley, J. L. Gustafson, N. Zinn, P. Grandi, S. Shimamura, G. Bergamini, M. Faelth-Savitski, M. Bantscheff, C. Cox, D. A. Gordon, R. R. Willard, J. J. Flanagan, L. N. Casillas, B. J. Votta, W. den Besten, K. Famm, L. Kruidenier, P. S. Carter, J. D. Harling, I. Churcher and C. M. Crews (2015). "Catalytic in vivo protein knockdown by small-molecule PROTACs." Nat Chem Biol 11(8): 611-617.

Buckley, D. L. and C. M. Crews (2014). "Small-molecule control of intracellular protein levels through modulation of the ubiquitin proteasome system." Angew Chem Int Ed Engl 53(9): 2312-2330.

Buckley, D. L., J. L. Gustafson, I. Van Molle, A. G. Roth, H. S. Tae, P. C. Gareiss, W. L. Jorgensen, A. Ciulli and C. M. Crews (2012). "Small-molecule inhibitors of the interaction between the E3 ligase VHL and HIF1alpha." Angew Chem Int Ed Engl 51(46): 11463-11467. Buckley, D. L., K. Raina, N. Darricarrere, J. Hines, J. L. Gustafson, I. E. Smith, A. H. Miah, J. D. Harling and C. M. Crews (2015). "HaloPROTACS: Use of Small Molecule PROTACs to Induce Degradation of HaloTag Fusion Proteins." ACS Chem Biol 10(8): 1831-1837.

Buckley, D. L., I. Van Molle, P. C. Gareiss, H. S. Tae, J. Michel, D. J. Noblin, W. L. Jorgensen, A. Ciulli and C. M. Crews (2012). "Targeting the von Hippel-Lindau E3 ubiquitin ligase using small molecules to disrupt the VHL/HIF-1alpha interaction." J Am Chem Soc 134(10): 4465-4468.

Burkhart, D. L. and J. Sage (2008). "Cellular mechanisms of tumour suppression by the retinoblastoma gene." Nat Rev Cancer 8(9): 671-682.

Chamberlain, P. P., A. Lopez-Girona, K. Miller, G. Carmel, B. Pagarigan, B. Chie-Leon, E. Rychak, L. G. Corral, Y. J. Ren, M. Wang, M. Riley, S. L. Delker, T. Ito, H. Ando, T. Mori, Y. Hirano, H. Handa, T. Hakoshima, T. O. Daniel and B. E. Cathers (2014). "Structure of the human Cereblon-DDB1-lenalidomide complex reveals basis for responsiveness to thalidomide analogs." Nat Struct Mol Biol 21(9): 803-809.

Finn, R. S., J. P. Crown, I. Lang, K. Boer, I. M. Bondarenko, S. O. Kulyk, J. Ettl, R. Patel, T. Pinter, M. Schmidt, Y. Shparyk, A. R. Thummala, N. L. Voytko, C. Fowst, X. Huang, S. T. Kim, S. Randolph and D. J. Slamon (2015). "The cyclin-dependent kinase 4/6 inhibitor palbociclib in combination with letrozole versus letrozole alone as first-line treatment of oestrogen receptor-positive, HER2-negative, advanced breast cancer (PALOMA-1/TRIO-18): a randomised phase 2 study." Lancet Oncol 16(1): 25-35.

Fischer, E. S., K. Bohm, J. R. Lydeard, H. Yang, M. B. Stadler, S. Cavadini, J. Nagel, F. Serluca, V. Acker, G. M. Lingaraju, R. B. Tichkule, M. Schebesta, W. C. Forrester, M. Schirle, U. Hassiepen, J. Ottl, M. Hild, R. E. Beckwith, J. W. Harper, J. L. Jenkins and N. H. Thoma (2014). "Structure of the DDB1-CRBN E3 ubiquitin ligase in complex with thalidomide." *Nature* 512(7512): 49-53.

Galdeano, C., M. S. Gadd, P. Soares, S. Scaffidi, I. Van Molle, I. Birced, S. Hewitt, D. M. Dias and A. Ciulli (2014). "Structure-guided design and optimization of small molecules targeting the protein-protein interaction between the von Hippel-Lindau (VHL) E3 ubiquitin ligase and the hypoxia inducible factor (HIF) alpha subunit with in vitro nanomolar affinities." *J Med Chem* 57(20): 8657-8663.

Hamilton, E. and J. R. Infante (2016). "Targeting CDK4/6 in patients with cancer." *Cancer Treat Rev* 45: 129-138.

Herrera-Abreu, M. T., M. Palafox, U. Asghar, M. A. Rivas, R. J. Cutts, I. Garcia-Murillas, A. Pearson, M. Guzman, O. Rodriguez, J. Grueso, M. Bellet, J. Cortes, R. Elliott, S. Pancholi, J. Baselga, M. Dowsett, L. A. Martin, N. C. Turner and V. Serra (2016). "Early Adaptation and Acquired Resistance to CDK4/6 Inhibition in Estrogen Receptor-Positive Breast Cancer." *Cancer Res* 76(8): 2301-2313.

Ito, T., H. Ando, T. Suzuki, T. Ogura, K. Hotta, Y. Imamura, Y. Yamaguchi and H. Handa (2010). "Identification of a primary target of thalidomide teratogenicity." *Science* 327(5971): 1345-1350.

Lai, A. C., M. Toure, D. Hellerschmied, J. Salami, S. Jaime-Figueroa, E. Ko, J. Hines and C. M. Crews (2016). "Modular PROTAC Design for the Degradation of Oncogenic BCR-ABL." *Angew Chem Int Ed Engl* 55(2): 807-810.

Lim, J. S., N. C. Turner and T. A. Yap (2016). "CDK4/6 Inhibitors: Promising Opportunities beyond Breast Cancer." *Cancer Discov* 6(7): 697-699.

Lu, J., Y. Qian, M. Altieri, H. Dong, J. Wang, K. Raina, J. Hines, J. D. Winkler, A. P. Crew, K. Coleman and C. M. Crews (2015). "Hijacking the E3 Ubiquitin Ligase Cereblon to Efficiently Target BRD4." *Chem Biol* 22(6): 755-763.

Matsushime, H., M. E. Ewen, D. K. Strom, J. Y. Kato, S. K. Hanks, M. F. Roussel and C. J. Sherr (1992). "Identification and properties of an atypical catalytic subunit (p34PSK-J3/cdk4) for mammalian D type G1 cyclins." *Cell* 71(2): 323-334.

Meyerson, M. and E. Harlow (1994). "Identification of G1 kinase activity for cdk6, a novel cyclin D partner." *Mol Cell Biol* 14(3): 2077-2086.

Sherr, C. J., D. Beach and G. I. Shapiro (2016). "Targeting CDK4 and CDK6: From Discovery to Therapy." *Cancer Discov* 6(4): 353-367.

Turner, N. C., J. Ro, F. Andre, S. Loi, S. Verma, H. Iwata, N. Harbeck, S. Loibl, C. Huang Bartlett, K. Zhang, C. Giorgetti, S. Randolph, M. Koehler, M. Cristofanilli and P. S. Group (2015). "Palbociclib in Hormone-Receptor-Positive Advanced Breast Cancer." *N Engl J Med* 373(3): 209-219.

Winter, G. E., D. L. Buckley, J. Paulk, J. M. Roberts, A. Souza, S. Dhe-Paganon and J. E. Bradner (2015). "Phthalimide conjugation as a strategy for in vivo target protein degradation." *Science* 348(6241): 1376-1381.

Xie, T., S. M. Lim, K. D. Westover, M. E. Dodge, D. Ercan, S. B. Ficarro, D. Udayakumar, D. Gurbani, H. S. Tae, S. M. Riddle, T. Sim, J. A. Marto, P. A. Janne, C. M. Crews and N. S. Gray (2014). "Pharmacological targeting of the pseudokinase Her3." *Nat Chem Biol* 10(12): 1006-1012.

Yu, Q., E. Sicinska, Y. Geng, M. Ahnstrom, A. Zagozdzon, Y. Kong, H. Gardner, H. Kiyokawa, L. N. Harris, O. Stal and P. Sicinski (2006). "Requirement for CDK4 kinase function in breast cancer." *Cancer Cell* 9(1): 23-32.

Zengerle, M., K. H. Chan and A. Ciulli (2015). "Selective Small Molecule Induced Degradation of the BET Bromodomain Protein BRD4." *ACS Chem Biol* 10(8): 1770-1777.

What is claimed is:

1. A bivalent compound comprising a cyclin-dependent kinase 4/6 (CDK4/6) ligand (PI) conjugated to a degradation/disruption tag (EL) through a linker (Linker), wherein PI has the structure of Formula II,

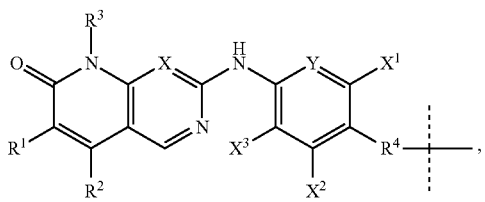

Formula II wherein $X^1$, $X^2$, and $X^3$ are independently hydrogen, halogen, C1-C8 alkyl, C1-C8 alkoxy, C1-C8 alkoxyalkyl, $NR^5R^6$, CN, $NO_2$, $COR^5$, $CO_2R^5$, $CONR^5R^6$, or $NR^5COR^6$;

$R^1$ is hydrogen, halogen, C1-C8 alkyl, C1-C8 alkoxy, C1-C8 alkoxyalkyl, C1-C8 haloalkyl, C1-C8 hydroxyalkyl, C3-C7 cycloalkyl, C3-C7 heterocyclyl, C2-C8 alkenyl, C2-C8 alkynyl, $OR^5$, $SR^5$, $NR^5R^6$, CN, $NO_2$, $(CR^5R^6)mNR^7R^8$, $(CR^5R^6)mC(O)R^7$, $COR^5$, $CO_2R^5$, $CONR^5R^6$, $NR^5COR^6$, $NR^5SOR^6$, $NR^5SO_2R^6$, $SOR^5$, $SO_2R^5$, $SO_2NR^5R^6$, $(CR^5R^6)$m-aryl, or $(CR^5R^6)$m-heteroaryl, wherein m is 0-8;

$R^2$ is hydrogen, halogen, C1-C8 alkyl, C1-C8 alkoxy, C3-C7 cycloalkyl, or C3-C7 heterocyclyl;

$R^3$ is hydrogen, aryl, C1-C8 alkyl, C1-C8 alkoxy, C3-C7 cycloalkyl, or C3-C7 heterocyclyl;

$R^4$ is piperazine-1,4-diyl;

$R^5$, $R^6$, $R^7$, and $R^8$ are independently hydrogen, C1-C8 alkyl, C2-C8 alkenyl, C2-C8 alkynyl, arylalkyl, cycloalkyl, heterocycloalkyl, aryl, heteroaryl, or heteroarylalkyl;

optionally, $R^1$ and $R^2$, $R^5$ and $R^6$, or $R^7$ and $R^8$ independently form 4-8 membered cycloalkyl or heterocyclyl rings; and X and Y are independently $CR^5R^6$ or N;

EL has the structure of Formula VII:

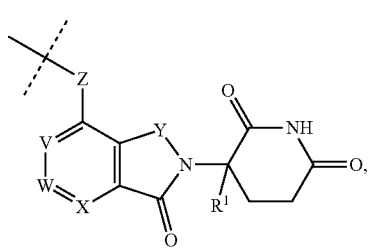

Formula VII wherein V', W', and X' are independently $CR^{2'}$ or N;

Y' is CO or $CH_2$;

Z' is $CH_2$, NH, or O;

$R^{1'}$ is hydrogen, methyl, or fluoro; and $R^{2'}$ is hydrogen, halogen, or C1-C5 alkyl; and Linker has the structure of Formula A:

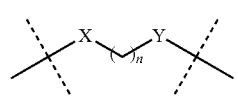

Formula A wherein X" is bound to PI and is C=O;

Y" is bound to EL and is $CH_2$; and n" is 0-15;

or Linker has the structure of Formula B:

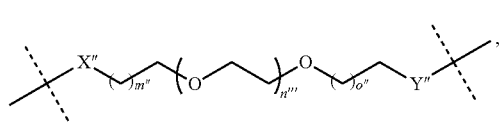

Formula B wherein X" is bound to PI and is C=O;

Y" is bound to EL and is $CH_2$;

m" is 0-15;

n'" is 0-6; and o" is 0-15, and enantiomers and pharmaceutically acceptable salts thereof.

2. The bivalent compound of claim 1, wherein the CDK4/6 ligand (PI) is:

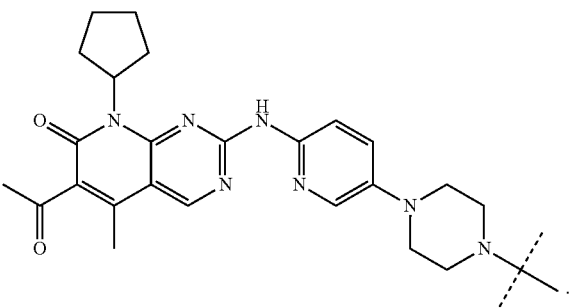

3. The bivalent compound of claim 1, wherein the degradation/disruption tag is selected from the group consisting of

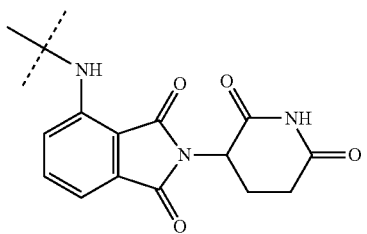

Formula XIV

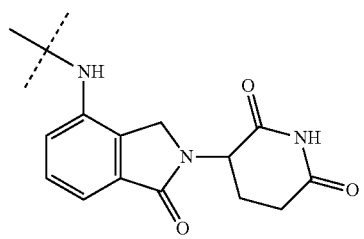

Formula XV

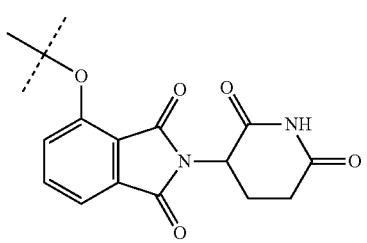

Formula XVI

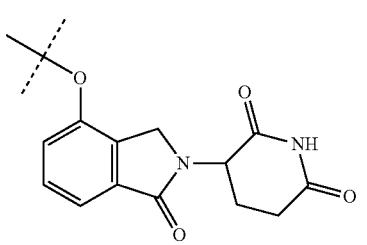

Fromula XVII

-continued

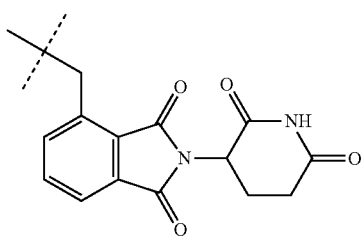

Formula XVIII

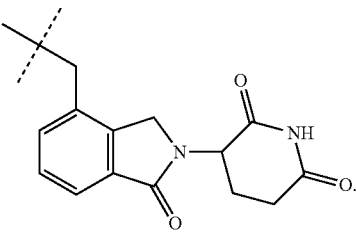

Formula XIX

4. The bivalent compound of claim 1, wherein $X^1$, $X^2$, and $X^3$ are H.

5. The bivalent compound of claim 1, wherein X is N.

6. The bivalent compound of claim 1, wherein Y is N.

7. The bivalent compound of claim 1, wherein $R^1$ is acetyl.

8. The bivalent compound of claim 1, wherein $R^2$ is methyl.

9. The bivalent compound of claim 1, wherein $R^3$ is cyclopentyl.

10. The bivalent compound of claim 1, wherein V', W', and X' are CH.

11. The bivalent compound of claim 1, wherein Y' is CO.

12. The bivalent compound of claim 1, wherein Y' is $CH_2$.

13. The bivalent compound of claim 1, wherein Z' is NH.

14. The bivalent compound of claim 1, wherein $R^{1'}$ is H.

15. Bivalent compound XY028-140.

* * * * *

SEQUENCE LISTING

```
<160> NUMBER OF SEQ ID NOS: 10

<210> SEQ ID NO 1
<211> LENGTH: 22
<212> TYPE: DNA
<213> ORGANISM: Artificial Sequence
<220> FEATURE:
<223> OTHER INFORMATION: Amplification Primer

<400> SEQUENCE: 1
acaactttgg tatcgtggaa gg                                                  22

<210> SEQ ID NO 2
<211> LENGTH: 19
<212> TYPE: DNA
<213> ORGANISM: Artificial Sequence
<220> FEATURE:
<223> OTHER INFORMATION: Amplification Primer

<400> SEQUENCE: 2
gccatcacgc cacagtttc                                                     19

<210> SEQ ID NO 3
<211> LENGTH: 22
<212> TYPE: DNA
<213> ORGANISM: Artificial Sequence
```

```
<220> FEATURE:
<223> OTHER INFORMATION: Amplification Primer

<400> SEQUENCE: 3
ctggtgtttg agcatgtaga cc                                                22

<210> SEQ ID NO 4
<211> LENGTH: 21
<212> TYPE: DNA
<213> ORGANISM: Artificial Sequence
<220> FEATURE:
<223> OTHER INFORMATION: Amplification Primer

<400> SEQUENCE: 4
gatccttgat cgtttcggct g                                                 21

<210> SEQ ID NO 5
<211> LENGTH: 23
<212> TYPE: DNA
<213> ORGANISM: Artificial Sequence
<220> FEATURE:
<223> OTHER INFORMATION: Amplification Primer

<400> SEQUENCE: 5
tcttcattca caccgagtag tgc                                               23

<210> SEQ ID NO 6
<211> LENGTH: 22
<212> TYPE: DNA
<213> ORGANISM: Artificial Sequence
<220> FEATURE:
<223> OTHER INFORMATION: Amplification Primer

<400> SEQUENCE: 6
tgaggttaga gccatctgga aa                                                22

<210> SEQ ID NO 7
<211> LENGTH: 19
<212> TYPE: DNA
<213> ORGANISM: Artificial Sequence
<220> FEATURE:
<223> OTHER INFORMATION: Amplification Primer

<400> SEQUENCE: 7
cgctggcggt actgaagtc                                                    19

<210> SEQ ID NO 8
<211> LENGTH: 21
<212> TYPE: DNA
<213> ORGANISM: Artificial Sequence
<220> FEATURE:
<223> OTHER INFORMATION: Amplification Primer

<400> SEQUENCE: 8
gaggaacggt gacatgctca t                                                 21

<210> SEQ ID NO 9
<211> LENGTH: 21
<212> TYPE: DNA
<213> ORGANISM: Artificial Sequence
<220> FEATURE:
<223> OTHER INFORMATION: Amplification Primer

<400> SEQUENCE: 9
caccagcacg tcgtaggatt c                                                 21
```

```
<210> SEQ ID NO 10
<211> LENGTH: 21
<212> TYPE: DNA
<213> ORGANISM: Artificial Sequence
<220> FEATURE:
<223> OTHER INFORMATION: Amplification Primer

<400> SEQUENCE: 10
ccgtaggtag tatcgggcct c                                           21
```